US010174062B2

(12) United States Patent
Tian et al.

(10) Patent No.: US 10,174,062 B2
(45) Date of Patent: Jan. 8, 2019

(54) ACTIVATORS OF GLUCOKINASE

(71) Applicant: Metabasis Therapeutics, Inc., San Diego, CA (US)

(72) Inventors: Feng Tian, Fairfax, VA (US); Qun Dang, Westfield, NJ (US); G. Sridhar Prasad, San Diego, CA (US); Wenyu Li, San Diego, CA (US); Brett C. Bookser, San Diego, CA (US); Nicholas Brian Raffaele, San Diego, CA (US); Mark D. Erion, Del Mar, CA (US)

(73) Assignee: Metabasis Therapeutics, Inc., San Diego, CA (US)

( * ) Notice: Subject to any disclaimer, the term of this patent is extended or adjusted under 35 U.S.C. 154(b) by 0 days.

(21) Appl. No.: 15/384,226

(22) Filed: Dec. 19, 2016

(65) Prior Publication Data
US 2017/0096440 A1    Apr. 6, 2017

Related U.S. Application Data

(63) Continuation of application No. 14/585,073, filed on Dec. 29, 2014, now Pat. No. 9,522,926, which is a continuation of application No. 13/115,647, filed on May 25, 2011, now Pat. No. 8,940,927, which is a continuation of application No. 12/673,743, filed as application No. PCT/US2008/073026 on Aug. 13, 2008, now abandoned.

(60) Provisional application No. 60/955,522, filed on Aug. 13, 2007.

(51) Int. Cl.
| C07D 213/81 | (2006.01) |
| A61K 31/44 | (2006.01) |
| C07F 9/6558 | (2006.01) |
| C07F 9/58 | (2006.01) |
| C07F 9/653 | (2006.01) |
| C07F 9/6539 | (2006.01) |
| C07F 9/6571 | (2006.01) |
| C07F 9/6512 | (2006.01) |
| C07F 9/6561 | (2006.01) |
| C07F 9/6509 | (2006.01) |
| C07F 9/6541 | (2006.01) |

(52) U.S. Cl.
CPC ......... *C07F 9/65586* (2013.01); *A61K 31/44* (2013.01); *C07D 213/81* (2013.01); *C07F 9/58* (2013.01); *C07F 9/587* (2013.01); *C07F 9/653* (2013.01); *C07F 9/6512* (2013.01); *C07F 9/6539* (2013.01); *C07F 9/6541* (2013.01); *C07F 9/65122* (2013.01); *C07F 9/65395* (2013.01); *C07F 9/65397* (2013.01); *C07F 9/65583* (2013.01); *C07F 9/65616* (2013.01); *C07F 9/650952* (2013.01); *C07F 9/650964* (2013.01); *C07F 9/657181* (2013.01)

(58) Field of Classification Search
CPC .............................. C07D 213/81; A61K 31/44
USPC .................................... 546/22; 514/277, 337
See application file for complete search history.

(56) References Cited

U.S. PATENT DOCUMENTS

| 3,524,846 | A | 8/1970 | Moffatt et al. |
| 3,536,809 | A | 10/1970 | Applezweig |
| 3,598,123 | A | 8/1971 | Zaffaroni |
| 3,845,770 | A | 11/1974 | Theeuwes et al. |
| 3,916,899 | A | 11/1975 | Theeuwes et al. |
| 4,008,719 | A | 2/1977 | Theeuwes et al. |
| 4,026,709 | A | 5/1977 | Piller et al. |
| 4,822,780 | A | 4/1989 | Tsuda et al. |
| 5,059,595 | A | 10/1991 | Le Grazie |
| 5,073,543 | A | 12/1991 | Marshall et al. |
| 5,120,548 | A | 6/1992 | McClelland et al. |
| 5,157,027 | A | 10/1992 | Biller et al. |
| 5,354,556 | A | 10/1994 | Sparks et al. |
| 5,591,767 | A | 1/1997 | Mohr et al. |
| 5,639,476 | A | 6/1997 | Oshlack et al. |
| 5,674,533 | A | 10/1997 | Santus et al. |
| 5,733,566 | A | 3/1998 | Lewis |
| 6,132,420 | A | 10/2000 | Dionne et al. |
| 6,245,357 | B1 | 6/2001 | Edren et al. |
| 6,270,787 | B1 | 8/2001 | Ayer |

(Continued)

FOREIGN PATENT DOCUMENTS

| CN | 1516705 A | 7/2004 |
| CN | 1326459 A | 7/2007 |

(Continued)

OTHER PUBLICATIONS

Canadian Office Action re CA Application No. 2,695,583, dated Jul. 16, 2013.

(Continued)

*Primary Examiner* — Venkataraman Balasubramanian
(74) *Attorney, Agent, or Firm* — Knobbe, Martens, Olson & Bear LLP

(57) ABSTRACT

The present invention provides for novel compounds of Formulas I and II and pharmaceutically acceptable salts and co-crystals thereof which have glucokinsae activator activity. The present invention further provides for pharmaceutical compositions comprising the same as well as methods of treating, preventing, delaying the time to onset or reducing the risk for the development or progression of a disease or condition for which one or more glucokinase activator is indicated, including Type 1 and 2 diabetes, impaired glucose tolerance, insulin resistance and hyperglycemia. The present invention also provides for processes of making the compounds of Formulas I and II, including salts and co-crystals thereof, and pharmaceutical compositions comprising the same.

35 Claims, No Drawings

(56) References Cited

U.S. PATENT DOCUMENTS

| | | | |
|---|---|---|---|
| 6,283,953 | B1 | 9/2001 | Ayer et al. |
| 6,287,295 | B1 | 9/2001 | Chen et al. |
| 6,333,050 | B2 | 12/2001 | Wong et al. |
| 6,342,249 | B1 | 1/2002 | Wong et al. |
| 6,365,185 | B1 | 4/2002 | Ritschel et al. |
| 6,368,626 | B1 | 4/2002 | Bhatt et al. |
| 6,375,978 | B1 | 4/2002 | Kleiner et al. |
| 6,919,322 | B2 | 7/2005 | Bookser et al. |
| 7,303,739 | B2 | 12/2007 | Erion et al. |
| 7,371,739 | B2 | 5/2008 | Bookser et al. |
| 7,572,775 | B2 | 8/2009 | Wakabayashi et al. |
| 8,940,927 | B2 | 1/2015 | Tian et al. |

FOREIGN PATENT DOCUMENTS

| | | |
|---|---|---|
| CN | 101821276 | 9/2010 |
| EP | 0 273 444 | 5/1993 |
| EP | 0 632 048 B1 | 3/2001 |
| EP | 2 185 570 | 3/2014 |
| JP | 50-048922 | 5/1955 |
| JP | 61-151199 | 7/1986 |
| JP | 2007-519618 | 7/2007 |
| JP | 2010-529203 | 8/2010 |
| JP | 5572549 | 7/2014 |
| WO | WO 1990/08155 | 7/1990 |
| WO | WO 1990/10636 | 9/1990 |
| WO | WO 1991/19721 | 12/1991 |
| WO | WO 2004/076420 | 10/2004 |
| WO | WO 2005/056530 | 6/2005 |
| WO | WO 2006/040940 | 4/2006 |
| WO | WO 2008/005964 | 1/2008 |
| WO | WO 2008/154563 | 12/2008 |
| WO | WO 2009/023718 | 2/2009 |

OTHER PUBLICATIONS

Chinese Second Office Action, re CN Application No. 200880111311. 8, dated Dec. 19, 2012.
Chinese Third Office Action, re CN Application No. 200880111311. 8, dated Aug. 21, 2013.
Chinese Fourth Office Action and Search Report, re CN Application No. 200880111311.8, dated Apr. 10, 2014.
European Examination Report re EP Application No. 08 827 446.9, dated Nov. 12, 2012.
Japanese Office Action, re JP Application No. 2010-521136, dated Jul. 23, 2013.
Japanese Office Action (Final), re JP Application No. 2010-521136, dated Dec. 17, 2013.
PCT International Written Opinion re PCT Application No. PCT/US2008/073026, dated Feb. 24, 2009.
PCT International Preliminary Report on Patentability re PCT Application No. PCT/US2008/073026, dated Feb. 16, 2010.
PCT International Search Report re PCT Application No. PCT/US2008/073026, dated Feb. 24, 2009.
Abrunhosa-Thomasetal., "Alkylation of H-Phosphinate Esters under Basic Conditions," JOrg.Chern., 72:2851-2856 (2007).
Alexander e tal., "Preparation of 9-(2-Phosphonomethoxyethyl) Adenine Esters as Potential Prodrugs," Collect. Czech.Chern. Cornrnun., 59:1853-1869 (1994).
Baddiley et al., "Structure of Coenzyme A," Nature, 171:76 (1953).
Banker et al., "Modern Pharmaceutices, 3ed.", Marcel Dekker, New York, 1996, pp. 451 and 596.
Benzaria et al., "Synthesis, in Vitro Antiviral Evaluation, and Stability Studies of Bis(S-acyl-2-thioethyl) Ester Derivatives of 9-[2-(Phosphonomethoxy)ethyl] adenine (PMEA) as Potential PMEA Prodrugs with Improved Oral Bioavailability," J. Med. Chem. 39(25):4958-4965 (1996).
Bhattacharya et al., "The Michaelis-Arbuzov Rearrangement," Chem. Rev., 81:415-430 (1981).
Blackburn et al., "Specific Dealkylation of Phosphonate Esters using Iodotrimcthylsilanc," J. Chem. Soc. , Chem. Commun. 870-871 (1978).

Boyd et al., "Facile Synthesis of Functionalised Phenylphosphinic Acid Derivatives," Tetrahedron Letters, 37(10):1651-1654 (1996).
Boyd et al., "Synthesis of γ-Keto-substituted Phosphinic Acids from Bis(trimethylsilyl)phosphonite and $_\alpha$,β-Unsaturated Ketones, "Tetrahedron Letters, 33(6):813-816 (1992).
Bravo-Altamirano et al., "Palladium-catalyzed phosphorus-carbon bond formation: cross-coupling reactions of alkyl phosphinates with aryl, heteroaryl, alkenyl, benzylic, and allylic halides and triflates, "Tetrahedron. 61:6315-6329 (2005).
Brechbühler et al., "Die Reaktion von Carbonsauren mit Acetalen des N, N-Dimethylformmids: eine Veresterungsmethode," Helv. Chim. Acta. 48(7):1746-1771 (1965).
Campagne, J.-M. et al., "Synthesis of Mixed Phosphonate Diester Analogues of Dipeptides using BOP or PyBOP Reagents," Tetrahedron Left. 34(42), 6743-6744, Pergamon Press Ltd. (1993).
Campbell, DA, "The Synthesis of Phosphonate Esters, an Extension of the Mitsunobu Reaction," J. Org. Chem. 57,6331-6335, American Chemical Society (1992).
Casara, P.J. et al., Synthesis of Acid Stable 5'-O-Fluoromethyl Phosphonates of Nucleosides. Evaluation as Inhibitors of Reverse Transcriptase, Bioorg. Med. Chem. Left. 2(2), 145-148, Pergamon Press pic. (1992).
Cohen et al., "The development and therapeutic potential of protein kinase inhibitors", Current Opinion in Chemical Biology, 3, 459-465 (1999).
Coppi et al., "Lewis Acid Mediated Condensation of Alkenols and Aldehydes. A Selective Synthesis of Tetrahydropyrans and Oxepanes," J. Org. Chern. 53(4) 911-913 (1988).
Corey et al., "Synthesis of 6,9α-Oxido-11a, 15a-Dihydroxyprosta-(E)5, (E)13-Dienoic Acid, an Isomer of PGI2 (Vane's PGX)," Tetrahedron Letters, 40:3529-3532 (1977).
Cristau et al.. "Synthesis of New Arylhydroxymethylphosphinic Acids and Derivatives,"Synthesis, (14):2216-2220.
Curran et al., "Thermolysis ofbis[2-[(trimethylsilyl)oxy]prop-2-yl] furoxan (TOP-furoxan). The First Practical Method for Intermolecular Cycloaddition of an in Situ Generated Nitrile Oxide with 1, 2-Di- and Trisubstituted Olefins," J. Am. Chem. Soc. 107(21):6023-6028 (1985).
Danishefsky et al., "Derivatives of 1-Methoxy-3-trimethy1si1y10xy-1,3-butadiene for Diels-Alder Reactions, "J. Am. Chem. Soc., 101:7001-7008 (1979).
DeLambert et al., "N-Phosphonomethyl Dipeptides and Their Phosphonate Prodrugs, a New Generation of Neutral Endopeptidase (NEP, TIC3.4.24.11) Inhibitors," J. Med. Chem. 37(7):498-511 (1994).
Deng et al., "Total Synthesis of Anti-HIV Agent Chloropeptin I," J. Am. Chem. Soc., 125:9032-9034 (2003).
Deng et al., "Cul-Catalyzed Coupling Reactions of Aryl Iodides and Bromides withThiols Promoted by Amino Acid Ligands," Synlett, 2004 (7):1254-1258 (2004).
Dermer et al., "Another Anniversary for the War on Cancer", Bio/Technology vol. 12, 320, Mar. 1994.
DeRoos et al., "The Preparation of Some Iso-Propyl p-Nitrophenyl Alkylphosphonates, " Recl. Trav. Chim. Pays-Bas. 78:59-66 (1959).
Egron et al., "Synthesis and Anti-HIV Activity of Some S-Acyl-2-thioethyl (SATE) Phosphoramidate Derivatives of3'-Acido-2' 3'-dideoxythymidine," Nucleosides & Nucleotides 18(4):981-982 (1999).
Elhaddadi et al., "A Convenient Synthesis of Alkyl and Dialkyl 1-benzyloxyamino alkyl phosphonates and phosphinates," Phosphorus, Sulfur and Silicon 54:143-150 (1990).
Elliott, RL. et al., "Synthesis and Biological Evaluation of Phosphonamidate Peptide Inhibitors of Enkephalinase and Angiotensin-Converting Enzyme," J. Med. Chem. 28: 1208-1216, American Chemical Society (1985).
Farquhar et al., "Biologically Reversible Phosphate-Protective Groups," J. Pharm. Sci. 72(3):324-325 (1983).
Ferres, "Pro-Drugs of B-Lactam Antibiotics," Drugs of Today 19(9):499-538 (1983).
Ferro et al., "N-G;ycosyl phosphonamidates: potential transition-state analogue inhibitors of glycopeptidases," Can. J. Chem., 76(3):313-318 (1998).

(56) References Cited

OTHER PUBLICATIONS

Freed et al., "Evidence for Acyloxmethyl Esters of Pyrimidine 5'-Deoxyribonucleotides as Extracellular Sources of Active 5'-Deoxyribonucleotides in Cultured Cells," Biochem. Pharmac. 38:3193-3198 (1989).
Freshney et al., "Culture of Animal Cells", A Manual of Basic Technique, Alan R. Liss, Inc. (1983).
Gallagher et al., "Mono-and Dialkylation of Isopropyl Phosphinate—A Simple Preparation of Alkylphosphinate Esters," Phosphorus, Sulfur, and Silicon and the Related Elements, 115:255-259 (1996).
Gobec et al., "Phosphonate inhibitors of antigen 85C, a crucial enzyme involved in the biosynthesis of the *Mycobacterium tuberculosis* cell wall," Bioorganic & Medicinal Chemistry Letters, 14:3559-3562 (2004).
Gupta et al., "An Improved Synthesis of Vinylic Phosphonates from Ketones," Synth. Commun. 10(4):299-304 (1980).
Han et al., "Retention of Configuration on the Oxidative Addition of P—H Bond to Platinum (0) Complexes: The First Straightforward Synthesis of Enantiomerically Pure P-Chiral Alkenylphosphinates via Palladium-Catalyzed Stereospecific Hydrophosphinylation of Alkynes," J. Am. Chem. Soc., 124:3842-3843 (2002).
Hartung et al., "Hydrogenolysis of Benzyl Groups Attached to Oxygen, Nitrogen, or Sulfur," Org. React., VII:263-288 (1953).
Hoffman, "A Simple Efficient Synthesis of Dibenzyl and Di-p-nitrobenzyl 1-Hydroxyalkanephosphonates," Synthesis 1988(1):62-64 (1988).
Hughes, "Progress in the Mitsunobu Reaction. A Review." Org. Prep. Proceed. Int., 28:127-164 (1996).
Huo, "Highly Efficient, General Procedure for the Preparation of Alkylzinc Reagents from Unactivated Alkyl Bromides and Chlorides," Organic Letters, 5(4):423-425 (2003).
Inanaga et al., "A Rapid Esterification by Means of Mixed Anydride and Its Application to Large-ring Lactonization," Bulletin of the Chemical Society of Japan 52(7):1989-1993 (1979).
Iynedjian, P.B., "Molecular Physiology of Mammalian Glucokinase", Celluar and Molecular Life Sciences, 66; 27-42 (2009).
Khamnei, S. et al., "Neighboring Group Catalysis in the Design of Nucleotide Prodrugs," J. Med. Chem. 39, 4109-4115, American Chemical Society (1996).
Kim et al., "Novel Synthesis of Desymmetrized Resorcinol Derivatives: Aryl Fluoride Displacement on Deactivated Substrates," J. Org. Chem., 71:2170-2172 (2006).
Kim et al., "Synthesis of Tunichromes Mm-1 and Mm-2, Blood Pigments of the Iron-Assimilating Tunicate, Molgula Manhattensis," Tetrahedron Letters, 31(49):7119-7122 (1990).
Kwong et al., "A General, Efficient, and Inexpensive Catalyst System for the Coupling of Aryl Iodides and Thiols," Organic Letters, 4(20):3517-3520 (2002).
Lapeyre et al., "Synthesis of phosphonocinnamic thioesters, substrate analogues of cinnamoyl-CoA reductase, a key enzyme in the lignification process," Tetrahedron Letters, 44:2445-2447 (2003).q.
Latour et al., "Simple Syntheses of 2-Hydroxymethy-1, 3-propanediol and Related Compounds," Synthesis 1987(8):742-745 (1987).
Lejczak et al., Transcstcrification ofDiphenyl Phosphonates Using the Potassium Fluoride/Crown Ether/Alcohol System; Part 2. The Use of Diphenyl 1-Aminoalkanephosphonates in Phosphonopeptide Synthesis 1982(5):412-414 (1982).
Lotz et al., "Diastereoselective Synthesis of the Carbacephem Framework," J. Org. Chem. 58:618-625 (1993).
Ma et al., "Asymmetric Strecker-Type Reaction of a-Aryl Ketones. Synthesis of (S)-aM4CPG, (S)-AIDA, and (S)-APICA, theAntagonists of Metabotropic Glutamate Receptors," J. Org. Chem., 64:120-125 (1999).
Ma et al., "Synthesis of (S)-a-Cyclopropyl-4-phosphonophenylglycine," J. Org. Chem., 66:348-350 (2001).
Mano et al., "Efficient Synthesis of 4-(3-Fluoro-5-{[4-(2-methyl-1H-imidazol-l-yl)benzyl]-oxy}phenyl)tetrahydro-2H-pyran-4-carboxamide, a Novel 5-Lipoxygenase Inhibitor," Synthesis, 2004(16):2625-2628 (2004).

Martin et al., "Synthesis and Antiviral Activity of Various Esters of 9-[(1 ,3-Dihydroxy-2-propoxy)methyl]guanine," J. Pharm. Sci. 76(2):180-184 (1987).
Martorell et al., "Direct Palladium-Catalyzed Phosphinylation of Aryl Triflates with Secondary Phosphines. Its Scope and Limitations: The Synthesis of Optically Active Carboxylated2-(Diphenylphosphino)-1,1'-binaphthalenes," J. Org. Chem., 63:3463-3467 (1998).
McGuigan, C. et al., "Kinase Bypass: A New Strategy for Anti-HIV Drug Design," Bioorganic & Medicinal Chemistry Letters 3(6): 1207-1210, Pergamon Press Ltd. (1993).
McHale et al., "Tocopherols. PartIV. Synthesis of 5-Methyltocol," J. Chem. Soc., 1959:3358-3361 (1959).
McKenna et al., "The facile dealkylation of phosphonic acid dialkyl esters by bromotrimcthylsilanc," Tetrahedron Lett. 2:155-158 (1977).
Meier, C. et al., "Cyclic Saligenyl Phosphotriesters of 2',3'-Dideoxy-2',3'-didehydrothymidine (d4T)—A New Pro-Nucleotide Approach," Bioorganic Med. Chem. Lett. 7(2), 99-104, Elsevier Science Ltd. (1997).
Mitchell, A.G. et al., "Bioreversible Protection for the Phospho Group: Bioactivation of the Di(4-acyloxybenzyl) and Mono(4-acyloxybenzyl) Phosphoesters of Methylphosphonate and Phosphonacetate," J. Chem. Soc. Perkin Trans. 1 38:2345-2353, Chemical Society, London (1992).
Mitsunobu, O., "The Use of Diethyl Azodicarboxylate and Triphenylphosphine in Synthesis and Transformation of Natural Products," Synthesis 1-28, Georg Thieme Verlag (1981).
Miyaura et al., "Palladium-Catalyzed Cross-Coupling Reactions of Organoboron Compounds," Chem. Rev., 95:2457-2483 (1995).
Montchamp et al., "Double Arbuzov Reaction of in Situ Generated Bis(trimethylsiloxy)phosphine with Dielectrophiles: Methodology for the Synthesis of Cyclic Phosphinic Acids," J. Org. Chem., 60:6076-6081 (1995).
Montchamp, "Recent advances in phosphorus-carbon bond formation: synthesis of H-phosphinic acid derivatives from hypophosphorous compounds," J. Orgnomet. Chem., 690:2388-2406 (2005).
Moriarty et al., "Diphenyl Methylphosphonate as a Phosphonylation Reagent with High Diastereoselectivity at Phosphorus," Tetrahedron Lett. 38(15):2597-2600 (1997).
Morise et al., "New syntheses of 1-chloroalkylphosphinates," J. Chem. Soc. Perkin Trans. /,17:2179-2186 (1996).
Mu et al., "Design and Synthesis of Chiral and Racemic Phosphonate-Based Haptens for the Induction of Aldolase Catalytic Antibodies," Bioorg. Med. Chem.. 5(7):1327-1337 (1997).
Mu et al., "Manganese(III) Acetate Promoted Regioselective Phosphonation of Heteroaryl Compounds," Organic Letters, 8(23):5291-5293 (2006).
Mukalyama et al., "Synthesis of Oligothymidylates and Nucleoside Cyclic Phosphates by Oxidation-Reduction Condensation," J. Am. Chem. Soc. 94(24):8528-8532 (1972).
Nishimura et al., "Orally Active 1-(Cyclohexyloxycarbonyloxy)alkyl Ester Prodrugs of Cefotiam," J. Antibiotics 40(1):81-90 (1987).
Ohashi, K. et al., "Synthesis of Phosphonosphingoglycolipid Found in Marine Snail Turbo Cornutus," Tetrahedron Lett. 29(10), 1189-1192, Pergamon Press pic. (1988).
Pal, "Recent advances in glucokinase activators for the treatment of type 2 diabetes", Drug Discovery Today, 14, 784-792, (2009).
Palomo et al., "Phosphazene bases for the preparation of biaryl thioethers from aryl iodides and arenethiols," Tetrahedron Letters, 41:1283-1286 (2000).
Patois et al., "Easy preparation of alkylphosphonyl dichlorides," Bull. Soc. Chim Fr. 130:485-487 (1993).
Pelchowicz, "Organic Phosphorus Compounds. Part 1.The Reaction of Dialkyl Mthylphosphnates and Methylphosphonothionates with Inorganic Acid Chlorides," J Chern. Soc. 238-240 (1961).
Posner et al., "3-bromo-2-pyrone: an easily prepared chameleon diene and a synthetic equivalent of 2-pyrone in thermal diels-alder cycloadditions," Tetrahedron Letters 32(39):5295-5298 (1991).
Prinz et al., "Tweaking the Glucose Sensor: Adjusting Glucokinase Activity with Activator Compounds", Endocrinology 146 (9): 3693-3695, (2002).

(56) References Cited

OTHER PUBLICATIONS

Puech et al., "Intracellular delivery of nucleoside monophosphates through a reductase-mediated activation process," Antiviral Res. 22(2-3):155-174 (1993).
Quast et al., "Herstellung von Methylphosphonsaure-dichlorid," Synthesis 1974(7):490 (1974).
Rabinowitz, "The Reactions of Phosphonic Acid Esters with Acid Chlorides. A Very Mild Hydrolytic Route," J. Org. Chem. 28(11):2975-2978 (1963).
Ramachandran et al., "Efficient General Synthesis of 1,2- and 1,3-diols in High Enantiomeric Excess via the Intramolecular Asymmetric Reduction of the Corresponding Ketoalkyl Diisopinocampheylborinate Intermediates," Tetrahedron, 38(5):761-764 (1997).
Rao et al., "Studies directed towards the synthesis of immunosuppressive agent FK-506: synthesis of the entire top-half," Tetrahedron Letters 32(4):547-550 (1991).
Reddy et al., "Synthesis of Symmetrical Methylenebis(Alkyl Hydrogen Phosphonates) by Selective Cleavage of Methylenebis(DialkylPhosphonates) with Morpholine," Synth. Comm., 34(2):331-344 (2004).
Roth et al., "Optimized Stille Coupling Reactions Catalyzed by Palladiumon Carbon with CuI as Cocatalyst," Tetrahedron Letters, 36(13):2191-2194 (1995).
Rubottom et al., "An Improved Method for the Preparation of o-Quinodimethanes," Synthetic Communications, 14(6):507-513 (1984).
Sakamoto et al., "The palladium-catalyzed arylation of 4H-1,3-dioxin," Tetrahedron Lett. 33(45):6845-6848 (1992).
Sandanayaka et al., "Photoinduced Electron-Transfer Processes between [C60]Fullerene and Triphenylamine Moieties Tethered by Rotaxane Structures. Through-Space Electron Transfer via Excited Triplet States of [60]Fullerene," J. Phys. Chem. A., 108:5145-5155 (2004).
Sawa et al., "New Type of Metalloproteinase Inhibitor: Design and Synthesis of New Phosphonamide-Based HydroxamicAcids," JMed. Chem., 45:919-929(2002).
Schoeller, et al., "Measurement of energy expenditure in humans by doubly labeled water method," J. Appl Physiol., 53(4), pp. 955-959, (1982).
Schopfer et al., "A general palladium-catalyzed synthesis of aromatic and heteroaromatic thioethers," Tetrahedron, 57:3069-3070 (2001).
Scott et al., "Palladium-Catalyzed Coupling of Vinyl Triflates with Organostannanes. A Short Synthesis of Pleraplysillin-I," J. Am. Chem. Soc., 106(16):4630-4632 (1984).
Sekhon BS, "Pharmaceutical Co-Crystals", ARS Pharmaceutica, vol. 50, No. 3: 99-117 (2009).
Serafinowska et al., "Synthesis and in Vivo Evaluation of Prodrugs of 9-[2-(Phosphonomethoxy)ethoxy] adenine," J. Med. Chem. 38(8):1372-1379 (1995).
Shafer et al., "On the Mechanism of Reductive Cleavage of Aryl Phosphates," J. Am. Chem. Soc. 99(15):5118-5123 (1977).
Shaw-Ponter et al., "New synthesis of both D- and L-3-O-Carbamoyl-2-deoxy-4-thioribosides, Substrates for I)-selective Glycosylations," Tetrahedron Letters 37:1871-1874 (1981).
Shiosakietal., "Phosphorus-Containing Inhibitors of HMG-CoA Reductase. 1.4-[(2-Arylethyl)hydroxyphosphinyl]-3-hydroxybutanoicAcids: A New Class of Cell-Selective Inhibitors of Cholesterol Biosynthesis," J. Med. Chem., 33(11):2952-2956, 1990.
Shono et al., "Electroreductive Elimination of Phenolic Hydroxyl Groups and a New Synthesis of Olivetol," J. Org. Chem. 44(25):4508-4511.
Siddiqui et al., "The Presence of Substituents on the Aryl Moeity of the Aryl Phosphoramidate Derivative of d4T Enhances Anti-HIV Efficacy in Cell Culture: A Structure-Activity Relationship," J. Med. Chem. 42: 393-399 (1999).
Slavica et al., "Systhesis and Biological Activities of a New Set of Irreversibly Acting 2-(4'-Isothiocyanatobenzyl)imidazoline Analogs in Rat Thoracic Aorta," J. Med. Chem. 1994, vol. 37, No. 12, pp. 1874-1881.
Solodenkoetal., "Stereoselective Papain-Catalyzed Synthesis of Alafosfalin," Tetrahedron Letters, 30(49):6917-6918 (1989).
Starrett, Jr. et al., "Synthesis, Oral Bioavailability Determination, and in Vitro Evaluation of Prodrugs of the Antiviral Agent 9-[2-(Phosphonomethoxy)ethyl]adenine (PMEA)," J. Med, Chem 37:1857-1864 (1994).
Still et al., "Direct synthesis of Z-unsaturated esters. A useful modification of the hormer-emmons olefination," Tetrahedron Letters 24(41):4405-4408 (1983).
Stowell et al., "The Mild Preparation of Synthetically Useful Phosphonic Dichlorides: Applicationt to the Synthesis of Cyclic Phosphonic Diesters and Diamides," Tetrahedron Letters 31(23):3261-3262 (1990).
Tawfik et al., "1,8-Diazabicyclo[5.4.0]undecene Mediated Transesterification ofp-Nitrophenyl Phosphonates: A Novel Route to Phosphono Esters," Synthesis 1993(10):968-972 (1993).
Tsuchimoto et al., "Scandium(III) Triflate Catalyzed Friedel-Crafts Alkylation with Benzyl and Allyl Alcohols," Synlett, 1996:557-559 (1996).
Turner, JA, "A General Approach to the Synthesis of 1,6-,1,7-, and 1,8-Naphthyridines," J. Org. Chem. 55(15),4744-4750, American Chemical Society (1990).
Valette et al., "Decomposition Pathways and in Vitro HIV Inhibitory Effects of IsoddA Pronucleotides: Toward a Rational Approach for Intracellular Delivery of Nucleotide 5'-Monophosphates," J. Med. Chem. 39(10):1981-1990 (1996).
Villemin et al., "Rapid and Efficient Phosphonation of Aryl Halides Catalyzed by Palladium Under Microwaves Irradiation," Phosphorus, Sulfur, and Silicon and the Related Elements, 130:59-63 (1997).
Vishweshwar, et al., "Phamaceutical Co-Crystals", Journal of Phamaceutical Sciences, vol. 95, 499-516 (2006).
Waki et al., "Efficient Preparation of Nα-Formylamino Acid tert-Butyl Esters," J. Org. Chem., 42:2019-2020 (1977).
White, "Deamination of Amines. 2-Phenylethyl Benzoate via the Nitrosoamide Decomposition," Org. Synth. Collect, 5:336 (1973).
Wolff Manfred E., "Burger's Medicinal Chemistry, 5ed, Part 1", John Wiley & Sons, 1995, pp. 975-977.
Wróblewski et al., "1-Oxo-2-oxa-1-phosphabicyclo[2.2.2]octane: A New Mechanistic Probe for the Basic Hydrolysis of Phosphate Esters," J. Am. Chem. Soc., 118:10168-10174 (1996).
Xu et al., "Palladium-Catalysed Synthesis of Functionalised Alkyl Alkylarylphosphinates," Synthesis, (9):778-780 (1984).
Xu et al., "Palladium-Catalysed Synthesis of Alkyl Alkenylmethyl and Alkylarylphosphinates," Synthesis, 1986 (3):240-242 (1986).
Yamashita et al., "Direct Dexoygenation of the Hydroxy Group of Methyl 1-Hydroxyalkyl-(phenyl)-phosphinates using Diphosphorus Tetraiodide," Synthesis, 1985:896-897 (1985).
First Office Action dated Nov. 1, 2017, issued in corresponding CN Application No. 201610711385.1.

ACTIVATORS OF GLUCOKINASE

RELATED APPLICATIONS

This application is a continuation application of U.S. patent application Ser. No. 14/585,073, filed Dec. 29, 2014, which is a continuation application of U.S. patent application Ser. No. 13/115,647, filed May 25, 2011, which is a continuation application of U.S. patent application Ser. No. 12/673,743, filed Aug. 13, 2008, which is a 371 of International Application No. PCT/US2008/073026, filed Aug. 13, 2008, which claims priority to and the benefit of U.S. Provisional Application No. 60/955,522, filed Aug. 13, 2007, the entire contents of all of which are incorporated herein by reference.

FIELD OF THE INVENTION

The present invention is directed towards novel activators of glucokinase.

BRIEF SUMMARY OF THE INVENTION

The present invention relates to compounds and pharmaceutical compositions of Formulas I and II, including pharmaceutically acceptable salts or co-crystals, and prodrugs thereof which activate the enzyme glucokinase. The present invention further provides for pharmaceutical compositions comprising the same a well as methods of treating, preventing, delaying the time to onset or reducing the risk for the development or progression of a disease or condition for which one or more glucokinase activator is indicated, including Type 1 and 2 diabetes, impaired glucose tolerance, insulin resistance and hyperglycemia. Also provided are methods of making or manufacturing compounds of Formula I and II and pharmaceutically acceptable salts or co-crystals, and prodrugs thereof.

DETAILED DESCRIPTION OF THE INVENTION

Definitions

As used herein, the following terms are defined with the following meanings:

"Acyl" refers to —C(O)$R^s$ where $R^s$ is alkyl, heterocycloalkyl, or aryl.

"Acylalkyl" refers to an alkyl-C(O)-alk-, wherein "alk" is alkylene.

"Acylamino" refers to and $R^wC(O)$—$NR^w$—, wherein $R^w$ is —H, alkyl, aryl, aralkyl, and heterocycloalkyl.

"Acyloxy" refers to the ester group —O—C(O)$R^t$, where $R^t$ is H, alkyl, alkenyl, alkynyl, aryl, aralkyl, or heterocycloalkyl.

"Alicyclic" refers to a cyclic group or compound which combines the properties of aliphatic and cyclic compounds and include but are not limited to cycloalkyl and bridged cycloalkyl compounds. The cyclic compound includes heterocycles. Cyclohexenylethyl, cyclohexanylethyl, and norbornyl are suitable alicyclic groups. Such groups may be optionally substituted.

"Alkanoyl" refers to the group alkyl-C(O)—.

"Alkenyl" refers to unsaturated groups which have 2 to 12 atoms and contain at least one carbon-carbon double bond and includes straight-chain, branched-chain and cyclic groups included alkenylene and alkynylene. Alkenyl groups may be optionally substituted. Suitable alkenyl groups include allyl. "1-alkenyl" refers to alkenyl groups where the double bond is between the first and second carbon atom. If the 1-alkenyl group is attached to another group, it is attached at the first carbon.

"Alkylaminoalkyl-" refers to the group alkyl-$NR^u$-alk- wherein each "alk" is an independently selected alkylene, and $R^u$ is H or lower alkyl. "Lower alkylaminoalkyl-" refers to groups where the alkyl and the alkylene group is lower alkyl and alkylene, respectively.

"Alkylaminoalkylcarboxy" refers to the group alkyl-$NR^u$-alk-C(O)—O— where "alk" is an alkylene group, and $R^u$ is a H or lower alkyl.

"Alkylaminoaryl-" refers to the group alkyl-$NR^v$-aryl- wherein "aryl" is a divalent group and $R^v$ is —H, alkyl, aralkyl, or heterocycloalkyl. In "lower alkylaminoaryl-", the alkyl group is lower alkyl.

"Alkoxy-" or "alkyloxy-" refers to the group alkyl-O—.

"Alkoxyalkyl-" or "alkyloxyalkyl-" refers to the group alkyl-O-alk- wherein "alk" is an alkylene group. In "lower alkoxyalkyl-", each alkyl and alkylene is lower alkyl and alkylene, respectively.

"Alkoxyaryl-" refers to an aryl group substituted with an alkyloxy group. In "lower alkyloxyaryl-", the alkyl group is lower alkyl.

"Alkoxycarbonyloxy-" refers to alkyl-O—C(O)—O—.

"Alkyl" refers to a straight or branched chain or cyclic chain hydrocarbon radical with only single carbon-carbon bonds. Representative examples include methyl, ethyl, propyl, isopropyl, cyclopropyl, butyl, isobutyl, tert-butyl, cyclobutyl, pentyl, cyclopentyl, hexyl, and cyclohexyl, all of which may be optionally substituted. Alkyl groups are $C_1$-$C_{12}$.

"Alkylaryl-" refers to an aryl group substituted with an alkyl group. "Lower alkylaryl-" refers to such groups where alkyl is lower alkyl.

"Alkylene" refers to a divalent straight chain, branched chain or cyclic saturated aliphatic group. In one aspect the alkylene group contains up to and including 10 atoms. In another aspect the alkylene chain contains up to and including 6 atoms. In a further aspect the alkylene groups contains up to and including 4 atoms. The alkylene group can be either straight, branched chain or cyclic.

"Alkylthio-" and "alkylthio-" refer to the group alkyl-S—.

"Alkylthioalkyl-" refers to the group alkyl-S-alk- wherein "alk" is an alkylene group. In "lower alkylthioalkyl-" each alkyl and alkylene is lower alkyl and alkylene, respectively.

"Alkylthiocarbonyloxy-" refers to alkyl-S—C(O)—O—.

"Alkynyl" refers to unsaturated groups which have 2 to 12 atoms and contain at least one carbon-carbon triple bond and includes straight-chain, branched-chain and cyclic groups. Alkynyl groups may be optionally substituted. Suitable alkynyl groups include ethynyl. "1-alkynyl" refers to alkynyl groups where the triple bond is between the first and second carbon atom. If the 1-alkynyl group is attached to another group, e.g., it is a W substituent attached to the cyclic phosphonate, it is attached at the first carbon.

"Amido" refers to the $NR^w_2$ group next to an acyl or sulfonyl group as in $NR^w_2$—C(O)—, $R^wC(O)$—$NR^w$—, $NR^w_2$—S(=O)$_2$— and $R^wS(=O)_2$—$NR^w$—, wherein each $R^w$ independently includes —H, alkyl, aryl, aralkyl, and heterocycloalkyl.

"Amino" refers to —$NR^xR^x$ wherein each $R^x$ is independently selected from hydrogen, alkyl, aryl, aralkyl and heterocycloalkyl, all except H are optionally substituted, or wherein both $R^x$ together form a cyclic ring system.

"Aminoalkyl" refers to the group NR$^r_2$-alk- wherein "alk" is an alkylene group and R$^r$ is selected from —H, alkyl, aryl, aralkyl, and heterocycloalkyl.

"Aminocarboxamidoalkyl" refers to the group NR$^y_2$—C(O)—N(R$^y$)-alk- wherein each R$^y$ is independently an alkyl group or H and "alk" is an alkylene group. "Lower aminocarboxamidoalkyl-" refers to such groups wherein "alk" is lower alkylene.

"Animal" includes birds and mammals, in one embodiment a mammal, including rodents, livestock, companion animals/pets or humans of either gender.

"Aralkyl" refers to an alkylene group substituted with an aryl group. Suitable aralkyl groups include benzyl, picolyl, and the like, and may be optionally substituted.

"Aralkyloxyalkyl-" refers to the group aryl-alk-O-alk- wherein "alk" is an alkylene group. "Lower aralkyloxyalkyl-" refers to such groups where the alkylene groups are lower alkylene.

"Aroyl" refers to the group aryl-C(O)—.

"Aryl" refers to aromatic groups which have 5-14 ring atoms and at least one ring having a conjugated pi electron system and includes carbocyclic aryl, heterocyclic aryl, bicyclic aryl (e.g., naphthyl) and biaryl groups (e.g., biphenyl), all of which may be optionally substituted.

"Arylamino" refers to the group aryl-NH—

"Aralkylamino" refers to the group —N-alk-aryl wherein "alk" is alkylene.

"Arylene" refers to divalent aromatic ring systems which have 5-14 atoms and at least one ring having a conjugated pi electron system and includes carbocyclic arylene, heterocyclic arylene and biarylene groups, all of which may be optionally substituted.

"Arylaminoalkyl-" refers to the group aryl-N(R$^w$)-alk- wherein "alk" is an alkylene group and R$^w$ is —H, alkyl, aryl, aralkyl, or heterocycloalkyl. In "lower arylaminoalkyl-", the alkylene group is lower alkylene.

"Aryloxy" refers to aryl-O—.

"Aryloxyalkyl-" refers to an alkyl group substituted with an aryloxy group.

"Aryloxycarbonyl" refers to the group aryl-O—C(O)—O—.

"Aryloxycarbonyloxy-" refers to aryl-O—C(O)—O—.

"Atherosclerosis" refers to a condition characterized by irregularly distributed lipid deposits in the intima of large and medium-sized arteries wherein such deposits provoke fibrosis and calcification.

"Biaryl" represents aryl groups which have 5-14 atoms containing more than one aromatic ring including both fused ring systems and aryl groups substituted with other aryl groups. Such groups may be optionally substituted. Suitable biaryl groups include naphthyl and biphenyl.

"Binding" means the specific association of the compound of interest to the target of interest, e.g., a receptor.

"C$_{2-6}$-perfluoroalkyl" refers to a 2 to 6 carbon alkyl group where all of the carbon atoms are exhaustively substituted with fluorine. Non limiting examples include trifluoromethyl, pentafluoroethyl, heptafluoropropyl, pentafluorocyclopropyl, and the like.

"C$_{4-8}$-cycloalkenyl" refers to a non-aromatic, carbocyclic group having 4 to 8 carbon atoms and containing at least one double bond.

"C$_{3-8}$-cycloalkyloxy" refers to —O—C$_{3-8}$-cycloalkyl where C$_{3-8}$-cycloalkyl is an aliphatic carbocyclic group having 3 to 8 carbon atoms.

"C$_{3-8}$-cycloalkylthio" refers to —S—C$_{3-8}$-cycloalkyl where C$_{3-8}$-cycloalkyl is a 3 to 8 aliphatic carbocyclic group having 3 to 8 carbon atoms "Carboxylamido" or "carboxamido" refer to NR$^w_2$—C(O)—, wherein each R$^w$ include —H, alkyl, aryl, aralkyl, and heterocycloalkyl.

"Carboxamidoalkylaryl" refers to NR$^w_2$—C(O)-alk-aryl-, where R$^w$ includes H, alkyl, aryl, aralkyl, and heterocycloalkyl.

"Carboxamidoaryl" refers to NR$^w$—C(O)-aryl- wherein "alk" is alkylene and R$^w$ include H, alkyl, aryl, aralkyl, and heterocycloalkyl.

"Carbocyclic aryl" groups are groups which have 6-14 ring atoms wherein the ring atoms on the aromatic ring are carbon atoms, and include monocyclic carbocyclic aryl groups and polycyclic or fused compounds such as optionally substituted naphthyl groups.

"Carboxy esters" refers to —C(O)OR$^z$ where R$^z$ is alkyl, aryl, aralkyl, cyclic alkyl, or heterocycloalkyl, each optionally substituted.

"Carboxyl" refers to —C(O)OH.

"Cyano" refers to —C≡N.

"Cyclic alkyl" or "cycloalkyl" refers to alkyl groups that are cyclic of 3 to 10 carbon atoms, and, in one aspect, are 3 to 6 carbon atoms. The cycloalkyl groups include fused cyclic, bridged cyclic and spirocyclic groups. Examples of cyclic alkyl groups include but are not limited to cyclopropyl, cyclobutyl, cyclopentyl, cyclohexyl, cycloheptyl, decalin, bicycle[3.1.1]heptane, bycyclo[2.2.1]heptane, bycyclo[2.2.2]octane, bicycle[3.2.2]nonane, spiro[2.5]octane, spiro[3.5]nonane, adamantyl and the like. Such groups may be substituted.

"Cycloalkyloxy" refers to the group cycloalkyl-O—.

"Cycloalkylalkoxy" refers to the group cycloalkyl-alkyl-O—.

"Co-crystal" as used herein means a crystalline material comprised of two or more unique solids at room temperature that are H-bonded.

"Diabetes" refers to a heterogeneous group of disorders that share impaired glucose intolerance, hyperglycemia, and/or insulin resistance in common. Type I diabetes is characterized by pancreatic endocrine insufficiency or absence; and type II is characterized by insulin resistance. Diabetes refers to disorders in which carbohydrate utilization is reduced; and may be characterized by hyperglycemia, glycosuria, ketoacidosis, neuropathy or nephropathy, increased hepatic glucose production, insulin resistance in various tissues, insufficient insulin secretion and enhanced or poorly controlled glucagon secretion from the pancreas.

Several pathogenic processes are involved in the development of diabetes. These range from autoimmune destruction of the beta-cells of the pancreas with consequent insulin deficiency to abnormalities that result in resistance to insulin action. The basis of the abnormalities in carbohydrate, fat, and protein metabolism in diabetes is deficient action of insulin on target tissues. Deficient insulin action results from inadequate insulin secretion and/or diminished tissue responses to insulin at one or more points in the complex pathways of hormone action. Impairment of insulin secretion and defects in insulin action frequently coexist in the same patient.

Symptoms of marked hyperglycemia include polyuria, polydipsia, weight loss, sometimes with polyphagia, and blurred vision. The vast majority of cases of diabetes fall into two broad etiopathogenetic categories. In one category, type 1 diabetes, the cause is an absolute deficiency of insulin secretion. Individuals at increased risk of developing this type of diabetes can often be identified by scrological evidence of an autoimmune pathologic process occurring in the pancreatic islets and by genetic markers. In the other, much more prevalent category, type 2 diabetes, the cause is a combination of resistance to insulin action and an inadequate compensatory insulin secretory response. In the latter category, a degree of hyperglycemia sufficient to cause pathologic and functional changes in various target tissues, but without clinical symptoms, may be present for a long period of time before diabetes is detected. During this asymptomatic period, it is possible to demonstrate an abnormality in carbohydrate metabolism by measurement of plasma glucose in the fasting state or after a challenge with an oral glucose load.

Criteria for the diagnosis of diabetes include:
1. Symptoms of diabetes plus casual plasma glucose concentration 200 mg/dl (11.1 mmol/l). Casual is defined as any time of day without regard to time since last meal. The classic symptoms of diabetes include polyuria, polydipsia, and unexplained weight loss; or
2. Fasting Plasma Glucose equal to or greater than 126 mg/dl (7.0 mmol/1). Fasting is defined as no caloric intake for at least 8 h; or
3. 2-h post-meal or post oral glucose tolerance test (OGTT) glucose concentration of 200 mg/dl (11.1 mmol/l) during an OGTT. The test can be performed as described by WHO, using a glucose load containing the equivalent of 75 g anhydrous glucose dissolved in water.

"Energy expenditure" means basal or resting metabolic rate as defined by Schoeller et al., J Appl Physiol.; 53(4): 955-9 (1982). Increases in the resting metabolic rate can be also be measured using increases in $O_2$ consumption and/or $CO_2$ efflux and/or increases in organ or body temperature.

"Enhanced oral bioavailability" refers to an increase of at least 50% of the absorption of the dose of the parent drug, unless otherwise specified. In an additional aspect the increase in oral bioavailability of the prodrug (compared to the parent drug) is at least 100% (at least a doubling of the absorption). Measurement of oral bioavailability usually refers to measurements of the prodrug, drug, or drug metabolite in blood, plasma, tissues, or urine following oral administration compared to measurements following systemic administration of the compound administered orally.

"Enhancing" refers to increasing or improving a specific property.

"Haloalkyl" refers to an alkyl group substituted with one halo (halogen group).

"Halogen" or "halo" refers to —F, —Cl, —Br and —I.

"Heteroalicyclic" refers to an alicyclic group or compound having 1 to 4 heteroatoms selected from nitrogen, sulfur, phosphorus and oxygen.

"Heteroarylalkyl" refers to an alkylene group substituted with a heteroaryl group.

"Heteroarylene" refers to a divalent, aromatic, heterocyclic ring containing 5-14 ring atoms wherein 1 to 4 heteroatoms in the aromatic ring are ring atoms and the remainder of the ring atoms being carbon atoms.

Alternative: "Heteroarylene" refers to a divalent heterocyclic aryl or heteroaryl group.

"Heterocyclic" or "heterocyclyl" refer to cyclic groups of 3 to 10 atoms or cyclic groups of 3 to 6 atoms. These groups contain at least one heteroatom, and in some aspects contain 1 to 3 heteroatoms. Suitable heteroatoms include oxygen, sulfur, and nitrogen. Heterocyclic groups may be attached through a nitrogen or carbon atom in the ring. Heterocyclic and heterocyclyl cyclic groups include, e.g., heterocyclic alkyl or heterocycloalkyl groups. The heterocyclic alkyl groups include unsaturated cyclic, fused cyclic and spirocyclic groups. Suitable heterocyclic groups include pyrrolidinyl, morpholino, morpholinoethyl, and pyridyl.

"Heterocyclic aryl" or "heteroaryl groups" are groups which have 5-14 ring atoms wherein 1 to 4 heteroatoms are ring atoms in the aromatic ring and the remainder of the ring atoms being carbon atoms. Suitable heteroatoms include oxygen, sulfur, nitrogen, and selenium. Suitable heteroaryl groups include furanyl, thienyl, pyridyl, pyrrolyl, N-lower alkyl pyrrolyl, pyridyl-N-oxide, pyrimidyl, pyrazinyl, imidazolyl, benzimidazolyl, benzofuranyl, benzothiophenyl, and the like, all optionally substituted.

"Hydroxyalkyl" refers to an alkyl group substituted with one —OH.

"Hypercholesterolemia" refers to presence of an abnormally large amount of cholesterol in the cells and plasma of the circulating blood.

"Hyperinsulinemia" refers to a patient with a fasting serum insulin concentration of at least 12 µU/mL.

"Hyperlipidemia" or "lipemia" refers to the presence of an abnormally large amount of lipids in the circulating blood.

"Insulin resistance" is defined clinically as the impaired ability of a known quantity of exogenous or endogenous insulin to increase whole body glucose uptake and utilization.

"Impaired glucose tolerance (IGT)" refers to a condition known to precede the development of overt Type 2 diabetes. It is characterized by abnormal blood glucose excursions following a meal. The current criteria for the diagnosis of IGT are based on 2-h plasma glucose levels post a 75 g oral glucose test (144-199 mg/dL). Although variable from population to population studied, IGT progresses to full-blown NIDDM at a rate of 1.5 to 7.3% per year, with a mean of 3-4% per year. Individuals with IGT are believed to have a 6 to 10-fold increased risk in developing Type 2 diabetes. IGT is an independent risk factor for the development of cardiovascular disease.

"Increased or enhanced liver specificity" refers to an increase in the liver specificity ratio in animals treated with a compound of the present invention and a control compound.

"Lower" referred to herein in connection with organic radicals or compounds respectively defines such radicals or compounds as containing up to and including 10 carbon atoms. One aspect of this invention provides organic radicals or compounds as containing up to and including 6 carbon atoms. Yet another aspect of the invention provides organic radicals or compounds that contain one to four carbon atoms. Such groups may be straight chain, branched, or cyclic.

"Liver specificity" refers to the ratio:

$$\frac{[\text{drug or a drug metabolite in liver tissue}]}{[\text{drug or a drug metabolite in blood or another issue}]}$$

as measured in animals treated with the drug or a prodrug. The ratio can be determined by measuring tissue levels at a specific time or may represent an AUC based on values measured at three or more time points.

"Metabolic disease" includes diseases and conditions such as obesity, diabetes and lipid disorders such as hypercholesterolemia, hyperlipidemia, hypertriglyceridemia as well as disorders that are associated with abnormal levels of lipoproteins, lipids, carbohydrates and insulin such as metabolic syndrome X, diabetes, impaired glucose tolerance, atherosclerosis, coronary artery disease, cardiovascular disease, polycystic ovary syndrome (PCOS).

"Metabolic Syndrome" or "Metabolic Syndrome X" refers to a condition identified by the presence of three or more of these components:
Central obesity as measured by waist circumference:
Men: Greater than 40 inches
Women: Greater than 35 inches
Fasting blood triglycerides greater than or equal to 150 mg/dL
Blood HDL cholesterol:
Men: Less than 40 mg/dL
Women: Less than 50 mg/dL
Blood pressure greater than or equal to 130/85 mmHg
Fasting blood glucose greater than or equal to 110 mg/dL "Nitro" refers to —$NO_2$.

"Obesity" refers to the condition of being obese. Being obese is defined as a BMI of 30.0 or greater; and extreme obesity is defined at a BMI of 40 or greater. "Overweight" is defined as a body mass index of 25.0 to 29.9.

"Oxo" refers to =O in an alkyl or heterocycloalkyl group.

"Perhalo" refers to groups wherein every C—H bond has been replaced with a C-halo bond on an aliphatic or aryl group. Non-linking examples of perhaloalkyl groups include —$CF_3$ and —$CFCl_2$.

"Pharmaceutically acceptable salt" includes salts of compounds of the invention derived from the combination of a compound of this invention and an organic or inorganic acid or base. Suitable acids include acetic acid, adipic acid, benzenesulfonic acid, (+)-7,7-dimethyl-2-oxobicyclo[2.2.1] heptane-1-methanesulfonic acid, citric acid, 1,2-ethanedisulfonic acid, dodecyl sulfonic acid, fumaric acid, glucoheptonic acid, gluconic acid, glucuronic acid, hippuric acid, hydrochloride hemiethanolic acid, HBr, HCl, HI, 2-hydroxyethanesulfonic acid, lactic acid, lactobionic acid, maleic acid, methanesulfonic acid, methylbromide acid, methyl sulfuric acid, 2-naphthalenesulfonic acid, nitric acid, oleic acid, 4,4'-methylenebis [3-hydroxy-2-naphthalenecarboxylic acid], phosphoric acid, polygalacturonic acid, stearic acid, succinic acid, sulfuric acid, sulfosalicylic acid, tannic acid, tartaric acid, terphthalic acid, and p-toluenesulfonic acid.

"Patient" means an animal.

"Preventing" includes a slowing of the progress or development of a disease before onset or precluding onset of a disease.

"Prodrug" as used herein refers to any compound that when administered to a biological system generates a biologically active compound as a result of spontaneous chemical reaction(s), enzyme catalyzed chemical reaction(s), and/or metabolic chemical reaction(s), or a combination of each. Standard prodrugs are formed using groups attached to functionality, e.g., HO—, HS—, HOOC—, NHR, associated with the drug, that cleave in vivo. Standard prodrugs include but are not limited to carboxylate esters where the group is alkyl, aryl, aralkyl, acyloxyalkyl, alkoxycarbonyloxyalkyl as well as esters of hydroxyl, thiol and amines where the group attached is an acyl group, an alkoxycarbonyl, aminocarbonyl, phosphate or sulfate. The groups illustrated are exemplary, not exhaustive, and one skilled in the art could prepare other known varieties of prodrugs. Such prodrugs of the compounds of the invention, fall within this scope. Prodrugs must undergo some form of a chemical transformation to produce the compound that is biologically active or is a precursor of the biologically active compound. In some cases, the prodrug is biologically active, usually less than the drug itself, and serves to improve drug efficacy or safety through improved oral bioavailability, and/or pharmacodynamic half-life, etc. Prodrug forms of compounds may be utilized, for example, to improve bioavailability, improve subject acceptability such as by masking or reducing unpleasant characteristics such as bitter taste or gastrointestinal irritability, alter solubility such as for intravenous use, provide for prolonged or sustained release or delivery, improve ease of formulation, or provide site-specific delivery of the compound. Prodrugs are described in The Organic Chemistry of Drug Design and Drug Action, by Richard B. Silverman, Academic Press, San Diego, 1992. Chapter 8: "Prodrugs and Drug delivery Systems" pp. 352-401; Design of Prodrugs, edited by H. Bundgaard, Elsevier Science, Amsterdam, 1985; Design of Biopharmaceutical Properties through Prodrugs and Analogs, Ed. by E. B. Roche, American Pharmaceutical Association, Washington, 1977; and Drug Delivery Systems, ed. by R. L. Juliano, Oxford Univ. Press, Oxford, 1980.

"Significant" or "statistically significant" means a result (i.e. experimental assay result) where the p-value is =0.05 (i.e. the chance of a type I error is less than 5%) as determined by an art-accepted measure of statistical significance appropriate to the experimental design.

"Substituted" or "optionally substituted" includes groups substituted by one to six substituents, independently selected from lower alkyl, lower aryl, lower aralkyl, lower cyclic alkyl, lower heterocycloalkyl, hydroxy, lower alkoxy, lower aryloxy, perhaloalkoxy, aralkoxy, lower heteroaryl, lower heteroaryloxy, lower heteroarylalkyl, lower heteroaralkoxy, azido, amino, halo, lower alkylthio, oxo, lower acylalkyl, lower carboxy esters, carboxyl, -carboxamido, nitro, lower acyloxy, lower aminoalkyl, lower alkylaminoaryl, lower alkylaryl, lower alkylaminoalkyl, lower alkoxyaryl, lower arylamino, lower aralkylamino, sulfonyl, lower-carboxamidoalkylaryl, lower-carboxamidoaryl, lower hydroxyalkyl, lower haloalkyl, lower alkylaminoalkylcarboxy-, lower aminocarboxamidoalkyl-, cyano, lower alkoxyalkyl, lower perhaloalkyl, and lower arylalkyloxyalkyl. The phrase "optionally substituted" can be replaced by the phrase "substituted or unsubstituted" throughout this application.

"Substituted aryl" and "substituted heteroaryl" refers to aryl and heteroaryl groups substituted with 1-3 substituents. These substituents are selected from the group consisting of lower alkyl, lower alkoxy, lower perhaloalkyl, halo, hydroxy, and amino.

"Sulphon(yl)amido" or "sulfon(yl)amido" refer to $NR^w{}_2$—S(=O)$_2$— and $R^w$S(=O)$_2$—$NR^w$—, wherein each $R^w$ independently include alkyl, aryl, aralkyl, and heterocycloalkyl.

"Sulfonamidoalkylaryl" and "sulfonamidoaryl" refers to an aryl-alk-$NR^w$—S(=O)$_2$—, and ar-$NR^w$—S(=O)—, respectively where "ar" is aryl, "alk" is alkylene, $R^w$ includes —H, alkyl, aryl, aralkyl, and heterocycloalkyl.

"Sulphonate" or "sulfonate" refers to —$SO_2OR^w$, where $R^w$ is —H, alkyl, aryl, aralkyl, or heterocycloalkyl.

"Sulphonyl" or "sulfonyl" refers to —$SO_2R^w$, where $R^w$ is alkyl, aryl, aralkyl, or heterocycloalkyl.

"Therapeutically effective amount" means an amount of a compound or a combination of compounds that ameliorates, attenuates or eliminates one or more of the symptoms of a particular disease or condition or prevents, modifies, or delays the onset of one or more of the symptoms of a particular disease or condition.

"Treating" or "treatment" of a disease includes a slowing of the progress or development of a disease after onset or actually reversing some or all of the disease affects. Treatment also includes palliative treatment.

"Type 1 diabetes" (formerly known as "childhood." "juvenile," "insulin-dependent" diabetes) is a form of diabetes characterized by an absolute deficiency of insulin secretion. Individuals at increased risk of developing this type of diabetes can often be identified by serological evidence of an autoimmune pathologic process occurring in the pancreatic islets and by genetic markers. Type 1 diabetes may be caused by immune mediated beta-cell destruction, usually leading to absolute insulin deficiency or may be idiopathic, having no known etiologies.

"Type 2 diabetes" refers to a heterogeneous disorder characterized by impaired insulin secretion by the pancreas and insulin resistance in tissues such as the liver, muscle and adipose tissue. The manifestations of the disease include one or more of the following: impaired glucose tolerance, fasting hyperglycemia, glycosuria, decreased levels of insulin, increased levels of glucagon, increased hepatic glucose output, reduced hepatic glucose uptake and glycogen storage, reduced whole body glucose uptake and utilization, dyslipidemia, fatty liver, ketoacidosis, microvascular diseases such as retinopathy, nephropathy and neuropathy, and macrovascular diseases such as coronary heart disease.

"Phosphonate, phosphonic acid monoester and phosphinate prodrug" refers to compounds that break down chemically or enzymatically to a phosphonic acid or phosphine acid group in vivo. As employed herein the term includes, but is not limited to, the following groups and combinations of these groups:

Acyloxyalkyl esters which are well described in the literature (Farquhar et al., J. Pharm. Sci., 72: 324-325 (1983)).

Other acyloxyalkyl esters are possible in which a cyclic alkyl ring is formed. These esters have been shown to generate phosphorus-containing nucleotides inside cells through a postulated sequence of reactions beginning with deesterification and followed by a series of elimination reactions (e.g., Freed et al., Biochem. Pharm., 38: 3193-3198 (1989)).

Another class of these double esters known as alkyloxycarbonyloxymethyl esters, as shown in formula A, where $R^a$ is alkoxy, aryloxy, alkylthio, arylthio, alkylamino, or arylamino; each $R^c$ is independently —H, alkyl, aryl, alkylaryl, or heterocycloalkyl have been studied in the area of β-lactam antibiotics (Nishimura at al., J. Antibiotics, 40(1): 81-90 (1987); for a review see Ferres, H., Drugs of Today, 19: 499 (1983)). More recently Cathy, M. S., et al. (Abstract from AAPS Western Regional Meeting, April, 1997) showed that these alkyloxycarbonyloxymethyl ester prodrugs on (9-[(R)-2-phosphonomethoxy)propyl]adenine (PMPA) are bioavailable up to 30% in dogs.

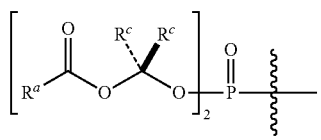

Formula A1

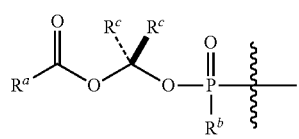

Formula A2 wherein $R^a$ and $R^c$ are independently H, alkyl, aryl, alkylaryl, and alicyclic; (see WO 90/08155; WO 90/10636) and $R^b$, for e.g., is selected from —OH, —CH$_3$, —H, —O—CH$_3$ or monoester prodrug moiety.

Other acyloxyalkyl esters are possible in which a cyclic alkyl ring is formed such as shown in formula B. These esters have been shown to generate phosphorus-containing nucleotides inside cells through a postulated sequence of reactions beginning with deesterification and followed by a series of elimination reactions (e.g., Freed et al., Biochem. Pharm., 38: 3193-3198 (1989)).

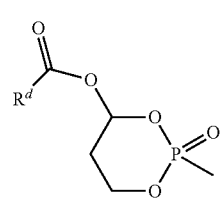

Formula B1

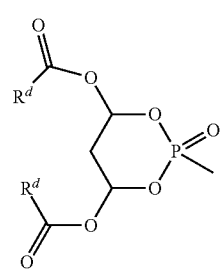

Formula B2 wherein $R^d$ is —H, alkyl, aryl, alkylaryl, alkoxy, aryloxy, alkylthio, arylthio, alkylamino, arylamino, or cycloalkyl.

Aryl esters have also been used as phosphonate prodrugs (e.g., DeLambert et al., J. Med. Chem. 37(7): 498-511 (1994); Serafinowska et al., J. Med. Chem. 38(8): 1372-9 (1995). Phenyl as well as mono and poly-substituted phenyl proesters have generated the parent phosphonio acid in studies conducted in animals and in man (Formula C). Another approach has been described where $R^e$ is a carboxylic ester ortho to the phosphate (Khamnei et al., J. Med. Chem. 39: 4109-15 (1996)).

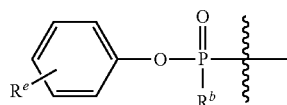

Formula C1

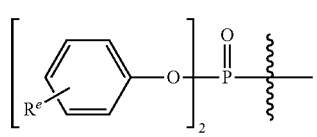

Formula C2 wherein $R^e$ is —H, alkyl, aryl, alkylaryl, alkoxy, acyloxy, halogen, amino, alkoxycarbonyl, hydroxy, cyano, or heterocycloalkyl and $R^b$ is selected, for e.g., from —OH, —CH$_3$, —H, —O—CH$_3$ or monoester prodrug moiety.

Benzyl esters have also been reported to generate the parent phosphonic acid. In some cases, using substituents at the para-position can accelerate the hydrolysis. Benzyl analogs with 4-acyloxy or 4-alkyloxy group [Formula D, X=—H, OR or O(CO)R or O(CO)OR] can generate the 4-hydroxy compound more readily through the action of enzymes, e.g., oxidases, esterases, etc. Examples of this class of prodrugs are described in Mitchell et al., J. Chem. Soc. Perkin Trans. 12345 (1992); WO 91/19721.

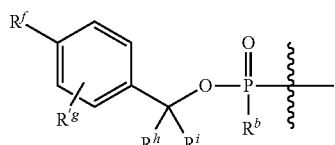

Formula D1

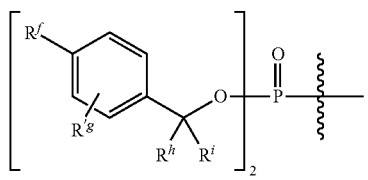

Formula D2 wherein $R^f$ and $R^g$ are independently —H, alkyl, aryl, alkylaryl, alkoxy, acyloxy, hydroxy, cyano, nitro, perhaloalkyl, halo, or alkyloxycarbonyl; $R^b$ is selected, for e.g., from —OH, —CH$_3$, —H, —O—CH$_3$ or monoester prodrug moiety, as described therein.

$R^h$ and $R^i$ are independently —H, alkyl, aryl, alkylaryl, halogen, or cyclic alkyl.

Thio-containing phosphonate proesters may also be useful in the delivery of drugs to hepatocytes. These proesters contain a protected thioethyl moiety as shown in formula E. One or more of the oxygens of the phosphonate can be esterified. Since the mechanism that results in de-esterification requires the generation of a free thiolate, a variety of thiol protecting groups are possible. For example, the disulfide is reduced by a reductase-mediated process (Puech et al., Antiviral Res. 22: 155-174 (1993)). Thioesters will also generate free thiolates after esterase-mediated hydrolysis Benzaria, et al., J. Med. Chem., 39(25): 4958-65 (1996)). Cyclic analogs are also possible and were shown to liberate phosphonate in isolated rat hepatocytes. The cyclic disulfide shown below has not been previously described and is novel.

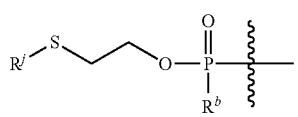

Formula E1

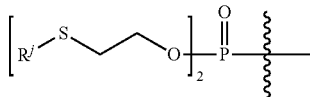

Formula E1

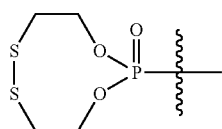

Formula E3 wherein $R^j$ is alkylcarbonyl, alkoxycarbonyl, arylcarbonyl, aryloxycarbonyl, or alkylthio and $R^b$ is selected, for e.g., from —OH, —CH$_3$, —H, —O—CH$_3$ or monoester prodrug moiety.

Other examples of suitable prodrugs include proester classes exemplified by Biller and Magnin (U.S. Pat. No. 5,157,027); Serafinowska et al., J. Med. Chem. 38(8): 1372-9 (1995); Starrett et al., J. Med. Chem. 37: 1857 (1994); Martin et al. J. Pharm. Sci. 76: 180 (1987); Alexander et al., Collect. Czech. Chem. Commun, 59: 1853 (1994); and EP 0 632 048 A1. Some of the structural classes described are optionally substituted, including fused lactones attached at the omega position (formulae E4 and E5) and optionally substituted 2-oxo-1,3-dioxolenes attached through a methylene to the phosphorus oxygen (formula E6) such as:

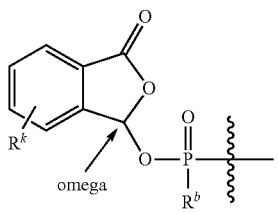

Formula E4a

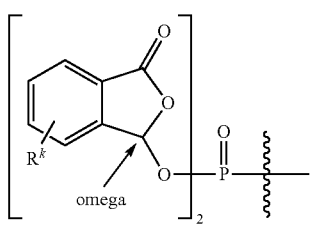

Formula E4b

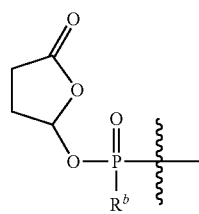

Formula E5a

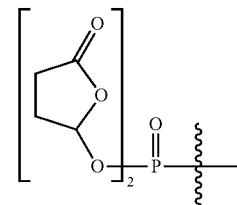

Formula E5b

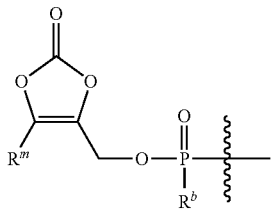

Formula E6a

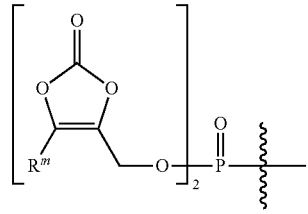

Formula E6b wherein $R^m$ is —H, alkyl, cycloalkyl, or heterocycloalkyl; $R^b$ is selected, for e.g., from —OH, —CH$_3$, —H, —O—C$_3$ or monoester prodrug moiety and $R^k$ is —H, alkyl, aryl, alkylaryl, cyano, alkoxy, acyloxy, halogen, amino, heterocycloalkyl, or alkoxycarbonyl.

The prodrugs of Formula E6 are an example of "optionally substituted heterocycloalkyl where the cyclic moiety contains a carbonate or thiocarbonate."

Propyl phosphonate proesters can also be used to deliver drugs into hepatocytes. These proesters may contain a hydroxyl and hydroxyl group derivatives at the 3-position of the propyl group as shown in formula F2. The R" and R$^p$ groups can form a cyclic ring system as shown in formula F2. One or more of the oxygens of the phosphonate can be esterified.

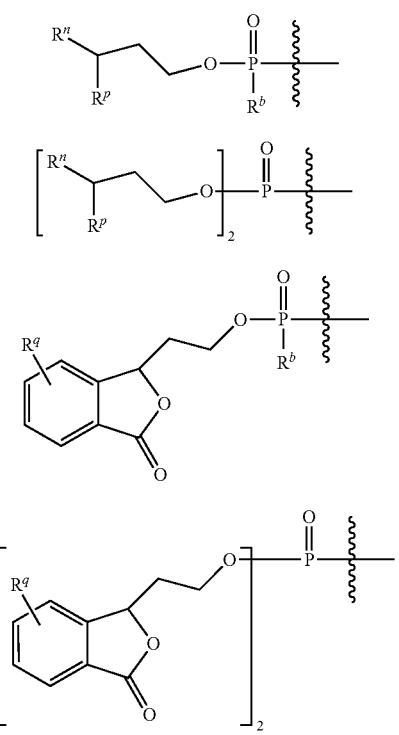

Formula F1a

Formula F1b

Formula F2a

Formula F2b wherein R" is alkyl, aryl, or heteroaryl;

R$^p$ is alkylcarbonyloxy, or alkyloxycarbonyloxy;

R$^b$ is selected, for e.g., from —OH, —CH$_3$, —H, —O—CH$_3$ or monoester prodrug moiety; and R$^q$ is alkyl, aryl, heteroaryl, alkoxy, alkylamino, alkylthio, halogen, hydrogen, hydroxy, acyloxy, or amino.

Phosphoramidate derivatives have been explored as phosphate prodrugs (e.g., McGuigan et al., J. Med. Chem., 42: 393 (1999) and references cited therein) as shown in Formula G and H, wherein R$^r$, for example, is lower alkyl, lower aryl, lower aralkyl, and as described therein.

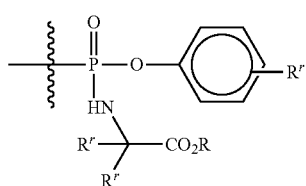

Formula G1

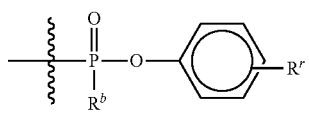

Formula G2

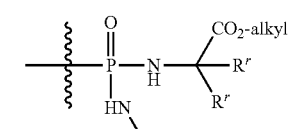

Formula H1

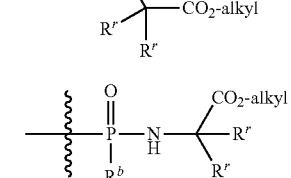

Formula H2

Cyclic phosphoramidates have also been studied as phosphonate prodrugs because of their speculated higher stability compared to non-cyclic phosphoramidates (e.g., Starrett et al, J. Med. Chem., 37: 1857 (1994)).

Another type of phosphoramidate prodrug was reported as the combination of S-acyl-2-thioethyl ester and phosphoramidate (Egron et al., Nucleosides & Nucleotides, 18, 981 (1999)) as shown in Formula J wherein R$^c$ is alkoxy, aryloxy, alkylthio, arylthio, alkylamino, or arylamino and R$^a$ is —H, alkyl, aryl, alkylaryl, or heterocycloalkyl:

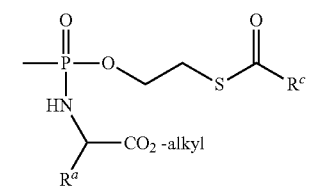

Formula J

Other prodrugs are possible based on literature reports such as substituted ethyls for example, bis(trichloroethyl) esters as disclosed by McGuigan, et al., Bioorg Med. Chem. Lett., 3:1207-1210 (1993), and the phenyl and benzyl combined nucleotide esters reported by Meier, C. et al., Bioorg. Med. Chem. Lett. 7:99-104 (1997).

The structure of formula L has a plane of symmetry running through the phosphorus-oxygen double bond when both R$^{60}$s are the same, V=W, and V and W (defined herein) are either both pointing up or both pointing down. The same is true of structures where both —NR$^{60}$s are replaced with —O—.

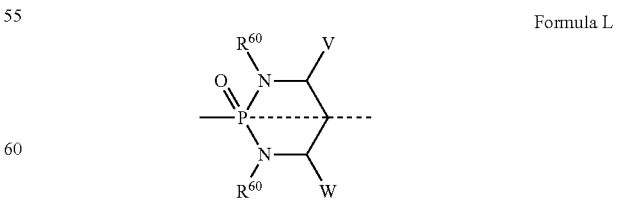

Formula L

The term "cyclic phosphonate ester of 1,3-propane diol", "cyclic phosphonate diester of 1,3-propane diol", "2 oxo 2λ$^5$ [1,3,2] dioxaphosphonane", "2 oxo [1,3,2]dioxaphosphonane", "dioxaphosphonane" refers to the following:

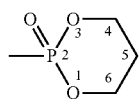

Formula M

The phrase "together V and Z are connected via an additional 3-5 atoms to form a cyclic group containing 5-7 atoms, optionally containing 1 heteroatom, substituted with hydroxy, acyloxy, alkylthiocarbonyloxy, alkoxycarbonyloxy, or aryloxycarbonyloxy attached to a carbon atom that is three atoms from both Y groups attached to the phosphorus" includes the following:

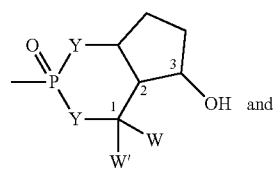

Formula N1

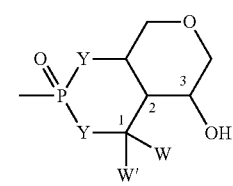

Formula N2

The structure shown above (left) has an additional 3 carbon atoms that forms a five member cyclic group. Such cyclic groups must possess the listed substitution to be oxidized.

The phrase "together V and Z are connected via an additional 3-5 atoms to form a cyclic group, optionally containing one heteroatom, that is fused to an aryl group attached at the beta and gamma position to the G attached to the phosphorus" includes the following:

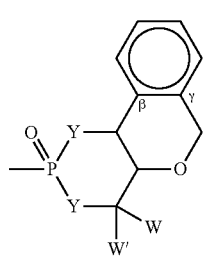

Formula O

The phrase "together V and W are connected via an additional 3 carbon atoms to form an optionally substituted cyclic group containing 6 carbon atoms and substituted with one substituent selected from the group consisting of hydroxy, acyloxy, alkoxycarbonyloxy, alkylthiocarbonyloxy, and aryloxycarbonyloxy, attached to one of said additional carbon atoms that is three atoms from a Y attached to the phosphorus" includes the following:

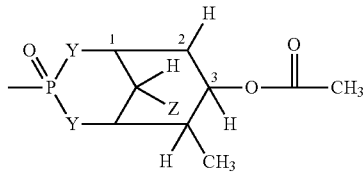

Formula P

The structure above has an acyloxy substituent that is three carbon atoms from a Y, and an optional substituent, —CH$_3$, on the new 6-membered ring. There has to be at least one hydrogen at each of the following positions: the carbon attached to Z; both carbons alpha to the carbon labeled "3"; and the carbon attached to "OC(O)CH$_3$" above.

The phrase "together W and W' are connected via an additional 2-5 atoms to form a cyclic group, optionally containing 0-2 heteroatoms, and V must be aryl, substituted aryl, heteroaryl, or substituted heteroaryl" includes the following:

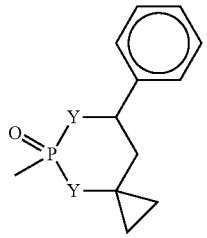

Formula Q

The structure above has V=aryl, and a spiro-fused cyclopropyl group for W and W'.

The term "cyclic phosphon(amid)ate" refers to:

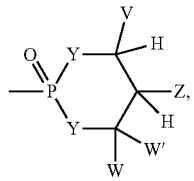

Formula R wherein Y is independently —O— or —NR$^{60}$—. The carbon attached to V must have a C—H bond. The carbon attached to Z must also have a C—H bond.

For cyclic 1,3-propanyl phosphonate prodrugs of compounds of the present invention the term "cis" stereochemistry refers to the spatial relationship of the V group and the carbon attached to the phosphorus atom on the six-membered ring. The formula below shows a cis stereochemistry.

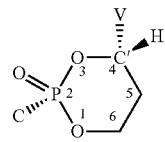

Formula S

The term "trans" stereochemistry for the same moiety refers to the spatial relationship of the V group and the carbon, attached to the phosphorus atom, on the six-membered ring. The formula below shows a trans-stereochemistry.

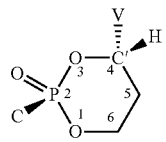

Formula T

The formula below shows another trans-stereochemistry of the same moiety.

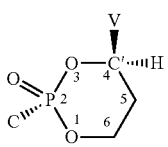

Formula U

The terms "S-configuration", "S-isomer" and "S-prodrug" of the same refers to the absolute configuration S of carbon C'. The formula below shows the S-stereochemistry.

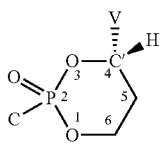

Formula W

The terms "R-configuration", "R-isomer" and "R-prodrug" of the same refers to the absolute configuration R of carbon C'. The formula below shows the R-stereochemistry.

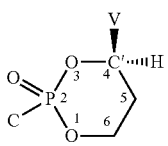

Formula Y

The term "percent enantiomeric excess (% ee)" refers to optical purity. It is obtained by using the following formula $$\frac{[R]-[S]}{[R]+[S]} \times 100 = \% \ R - \% \ S$$

where [R] is the amount of the R isomer and [S] is the amount of the S isomer. This formula provides the % ee when R is the dominant isomer.

The term "enantioenriched" or "enantiomerically enriched" refers to a sample of a chiral compound that consists of more of one enantiomer than the other. The extent to which a sample is enantiomerically enriched is quantitated by the enantiomeric ratio or the enantiomeric excess.

Compounds and Uses Thereof:

The enzyme glucokinase plays a critical role in the regulation of blood glucose levels. It is expressed in a restricted number of cell types, most notably the pancreatic beta-cell and liver parenchymal cells. Glucokinase catalyzes the rate-limiting step in glucose uptake, metabolism (glycolysis), and glucose storage (glycogenesis) in cells. In pancreatic beta cells, glucose uptake and metabolism trigger insulin secretion. Glucokinase is often referred to as a "glucose sensor" since it matches the rate of insulin secretion by pancreatic beta cells as well as the rate of glucose metabolism by liver cells to the ambient glucose concentrations.

Recent clinical data on pharmacological agents that simultaneously activate glucokinase in the pancreas and the liver have revealed a high rate of the undesirable side effect of hypoglycemia in treated patients. Development of this potentially lethal condition is attributed to the potent stimulation of insulin secretion. Compounds of the current invention were designed to safely lower blood glucose by selectively targeting glucokinase expressed in liver and thereby avoiding the activation of glucokinase in the pancreas. Treatment of diabetic rodents with compounds of the current invention resulted in significant blood glucose lowering without an increase in insulin secretion. Importantly, treatment with these agents did not result in hypoglycemia. In parallel studies with an activator of both pancreatic and hepatic glucokinase, treatment was associated with insulin secretion and a reduction of blood glucose below normal levels, i.e., hypoglycemia. Long term stimulation of insulin secretion is known to lead to pancreatic failure and an exacerbation of the diabetic condition as observed with the sulfonylurea drug class. Compounds of the current invention, by selectively targeting the liver, also provide a safe mechanism of glucose lowering that avoids insulin secretion, hypoglycemia, and pancreatic burnout.

Thus, one aspect of the present invention provides for compounds of general Formula (I),

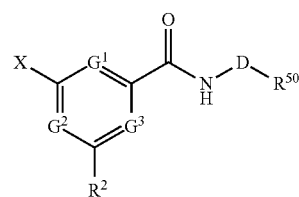

wherein:

X is selected from the group consisting of aryl, heteroaryl, alkyl, cycloalkyl, arylalkyl, aryloxy, heteroaryloxy, alkyloxy, cycloalkyloxy and arylalkyloxy;

$R^2$ is selected from the group consisting of aryl, heteroaryl, alkyl, cycloalkyl, arylalkyl, aryloxy, heteroaryloxy, alkyloxy, cycloalkyloxy, arylalkyloxy, arylthio, heteroarylthio, cycloalkylthio and arylalkylthio;

D is selected from heteroarylene and arylene, each optionally substituted;

$G^1$, $G^2$ and $G^3$ are $CR^4$ or N;

$R^4$ is H, halogen or alkyl; and $R^{50}$ is —$R^{61}$—$R^{62}$, and $R^{62}$ is selected from —P(O)($Y^2R^{51}$)$R^1$, or —P(O)($YR^{51}$)$Y^1R^{51}$:

$R^{61}$ is selected from null, arylene, heteroarylene, arylene-alkylene, alkylene-arylene, heteroarylene-alkylene, alkylene-heteroarylene, alkylene, alkenylene, alkynylene, alkylene-Q-alkylene, —$CONR^{52}$-alkylene, —COO-alkylene, —$SO_2NR^{52}$-alkylene, arylene-Q-alkylene, alkylene-Q- arylene, heteroarylene-Q-alkylene, alkylene-Q-heteroarylene, all optionally substituted;

Q is selected from O, S, SO, $SO_2$, $NR^{53}$;

With the proviso that when D is heteroarylene then $R^{50}$ is not —$(CH_2)n'$-Z'—$(CH_2)m'$-PO($OR_{63}$)($OR_{64}$), or —($CCH_2$)n'-Z'—$(CH_2)m'$-PO($OR_{63}$)$R_{65}$, or —$(CH_2)n'$-Z'—$(CH_2)m'$-O—PO($OR_{63}$)$R_{65}$, or —$(CH_2)n'$-Z'—$(CH_2)m'$-O—PO($R_{65}$)$R_{66}$, or —$(CH_2)n'$-Z'—$(CH_2)m'$-PO—($R_{65}$)$R_{66}$;

$R_{63}$ and $R_{64}$ are the same or different and are independently selected from the group consisting of hydrogen and alkyl, or $R_{63}$ and $R_{64}$ can be cyclized into a ring;

$R_{65}$ and $R_{66}$ are the same or different and are independently selected from the group consisting of alkyl, aryl, arylalkyl, heteroaryl, and heteroarylalkyl; or $R_{65}$ and $R_{66}$ can be cyclized into a ring, or $R_{63}$ and $R_{65}$ can be cyclized into a ring;

Z' is selected from the group consisting of a bond, alkylene, alkenylene, O, S, or $SO_2$;

m' is 0, 1 or 2, provided that when Z is O, S or $SO_2$, n' is 1 or 2;

n' is 0, 1, or 2;

$R^1$ is selected from the group consisting of hydrogen, optionally substituted —$C_1$-$C_6$-alkyl, —$CF_3$, —$CHF_2$, —$CH_2F$, —$CH_2OH$, optionally substituted —$C_2$-$C_6$ alkenyl, optionally substituted —$C_2$-$C_6$ alkynyl, optionally substituted —$(CR^{52}_2)_n$cycloalkyl, optionally substituted $(CR^{52}_2)_n$ heterocycloalkyl, —$(CR^{52}_2)_k$ S(=O)$R^{53}$, —$(CR^{52}_2)_k$S(=O)$_2R^{53}$;

Y, $Y^1$ and $Y^2$ are each independently selected from —O— or —$NR^{60}$—;

wherein, when $Y^2$ is —O— or when Y and $Y^1$ are both —O—, $R^{51}$ attached to —O— is independently selected from the group consisting of —H, alkyl, optionally substituted aryl, optionally substituted heterocycloalkyl, optionally substituted —$CH_2$-heterocycloakyl with a cyclic moiety containing a carbonate or thiocarbonate, optionally substituted -alkylaryl, —$C(R^{52}_2)_2OC(O)NR^{52}_2$, —$NR^{52}$—C(O)—$R^{53}$, —$C(R^{52})_2$—OC(O)$R^{53}$, —$C(R^{52})_2$—O—C(O)$OR^{53}$, —$C(R^{52})_2OC(O)SR^{53}$, -alkyl-S—C(O)$R^{53}$, -alkyl-S—S-alkylhydroxy and -alkyl-S—S—S-alkylhydroxy, or when $Y^2$ is —$NR^{60}$— or when Y and $Y^1$ are both —$NR^{60}$—, then $R^{51}$ attached to —$NR^{60}$— is independently selected from the group consisting of —H, —[C($R^{52})_2]_r$—$COOR^{53}$, —$C(R^{54})_2COOR^{53}$, —[C($R^{52})_2]_r$—C(O)$SR^{53}$, and -cycloalkylene-$COOR^{53}$; or when Y is —O— and $Y^1$ is $NR^{60}$, then $R^{51}$ attached to —O— is independently selected from —H, alkyl, optionally substituted aryl, optionally substituted heterocycloalkyl, optionally substituted $CH_2$-heterocycloakyl wherein the cyclic moiety contains a carbonate or thiocarbonate, optionally substituted -alkylaryl, —$C(R^{52})_2OC(O)NR^{52}_2$, —$NR^{52}$—C(O)—$R^{53}$, —$C(R^{52})_2$—OC(O)$R^{53}$, —$C(R^{52})_2$—O—C(O)$OR^{53}$, —$C(R^{52})_2OC(O)SR^{53}$, -alkyl-S—C(O)$R^{53}$, -alkyl-S—S-alkylhydroxy, and -alkyl-S—S—S-alkylhydroxy, and $R^{51}$ attached to —$NR^{60}$— is independently selected from —H, —[C($R^{52})_2]_r$—$COOR^{53}$, —$C(R^{54})_2COOR^{53}$, —[C($R^{52})_2]_r$—C(O)$SR^{53}$, and -cycloalkylene-$COOR^{53}$, wherein if both $R^{51}$ are alkyl, at least one is higher alkyl; or when Y and $Y^1$ are independently selected from —O— and —$NR^{60}$—, then $R^{51}$ and $R^{51}$ together form a cyclic group comprising -alkyl-S—S-alkyl-, or $R^{51}$ and $R^{51}$ together are the group

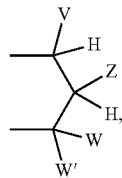

wherein,

V, W, and W' are independently selected from the group consisting of hydrogen, optionally substituted alkyl, optionally substituted aralkyl, heterocycloalkyl, aryl, substituted aryl, heteroaryl, substituted heteroaryl, optionally substituted 1-alkenyl, and optionally substituted 1-alkynyl, and Z is —$CHR^{52}OH$, —$CHR^{52}OC(O)R^{53}$, —$CHR^{52}OC(S)R^{53}$, —$CHR^{52}OC(S)OR^{53}$, —$CHR^{52}OC(O)SR^{53}$, —$CHR^{52}OCO_2R^{53}$, —$OR^{52}$, —$SR^{52}$, —$CHR^{52}N_3$, —$CH_2aryl$, —$CH(aryl)OH$, —$CH(CH=CR^{52}_2)OH$, —$CH(C≡CR^{52})OH$, —$R^{52}$, —$NR^{52}_2$, —O $COR^{53}$, —$OCO_2R^{53}$, —$SCOR^{53}$, —$SCO_2R^{53}$, —$NHCOR^{52}$, —$NHCO_2R^{53}$, —$CH_2NHaryl$, —$(CH_2)_r$—$OR^{52}$ or —$(CH_2)_r$—$SR^{52}$; or W and W' are as defined above and together V and Z are connected via an additional 3-5 atoms to form a cyclic group containing 5-7 atoms, wherein 0-1 atoms are heteroatoms and the remaining atoms are carbon; or W' and Z are as defined above and together V and W are connected via an additional 3 carbon atoms to form an optionally substituted cyclic group containing 6 carbon atoms or carbon substituted by hydrogen and substituted with one substituent selected from hydroxy, acyloxy, alkoxycarbonyloxy, alkylthiocarbonyloxy or aryloxycarbonyloxy which is attached to one of said carbon atoms that is three atoms from a Y attached to the phosphorus; or V and W' are as defined above and together Z and W are connected via an additional 3-5 atoms to form a cyclic group, wherein 0-1 atoms are heteroatoms and the remaining atoms are carbon or carbon substituted by hydrogen, and V must be aryl, substituted aryl, heteroaryl, or substituted heteroaryl; or V and Z are as defined above and together W and W' are connected via an additional 2-5 atoms to form a cyclic group, wherein 0-2 atoms are heteroatoms and the remaining atoms are carbon, where V must be aryl, substituted aryl, heteroaryl, or substituted heteroaryl;

$R^{52}$ is $R^{53}$ or —H;

$R^{53}$ is alkyl, aryl, heterocycloalkyl or aralkyl;

$R^{54}$ is independently selected from —H or alkyl, or together $R^{54}$ and $R^{54}$ form a cycloalkylene group;

$R^{60}$ is —H, lower alkyl, acyloxyalkyl, alkoxycarbonyloxyalkyl, lower acyl, $C_{1-6}$-perfluoroalkyl or NH($CR^{55}R^{55}$)$CH_3$;

r is an integer 2 or 3;

f is an integer 0, 1 or 2;

wherein, V, Z, W, W' are not all —H, and when Z is —$R^{52}$, then at least one of V, W, and W' is not —H, alkyl, aralkyl, or heterocycloalkyl; and pharmaceutically acceptable salts, co-crystals and prodrugs thereof.

One embodiment includes compounds of formula I wherein:

X is selected from the group consisting of alkyloxy, cycloalkyloxy, alkyl and cycloalkyl;

$R^2$ is -$E^1$-$E^2$-$E^3$, wherein, $E^1$ is a bond, O or S;

$E^2$ is a bond or alkylene;

wherein, when both E¹ and E² are a bond, together they form a single bond;

E³ is optionally substituted —C₁₋₄-alkyl, optionally substituted —C₃₋₈-cycloalkyl or aryl, optionally substituted with one or two groups independently selected from the group consisting of aryl, heteroaryl, halogen, —C₁₋₄-alkyl, —S(O)₂R⁵ or —OR⁵ or R² selected from the group consisting of —C₁₋₄-alkyloxy, —C₃₋₆-cycloalkyloxy, benzyloxy, 2-(2-thienyl)ethyloxy, 2-(3-thienyl)ethyloxy, and phenyloxy, each optionally substituted with one or two groups independently selected from the group consisting of halogen, —C₁₋₄-alkyl, —S(O)₂C₁₋₄-alkyl, —S(O)₂C₃₋₆-cycloalkyl, or —OC₁₋₄-alkyl;

R⁵ is alkyl or cycloalkyl;

D is heteroarylene, said heteroarylene comprising a nitrogen ring atom adjacent to a carbon ring atom, wherein said carbon ring atom is connected to the amide nitrogen atom adjacent to D, and wherein said heteroarylene has an additional 0 to 3 heteroatoms independently selected from O, S or N;

G¹ is CH;
G² is CH or N;
G³ is CH; and
R⁵⁰ is —R⁶¹—R⁶², and R⁶² is selected from —P(O)(Y²R⁵¹)R¹, or —P(O)(YR⁵¹)Y¹R⁵¹.

One embodiment includes compounds of formula I wherein D is a heteroarylene substituted with one or two groups independently selected from halogen and optionally substituted C₁₋₄-alkyl.

One embodiment includes compounds of formula I wherein, D is heteroarylene having a nitrogen as a ring atom, said nitrogen ring atom connected to a ring carbon atom, wherein said ring carbon atom is connected to the amide nitrogen atom that is adjacent to D, and wherein said heteroarylene has an additional 0 to 3 heteroatoms independently selected from O, S or N;

One embodiment includes compounds of formula I wherein:
X is isopropyloxy or benzyloxy;
R² is selected from the group consisting of n-propyloxy, isopropyloxy, 2-methylpropyloxy, cylclopentylmethyloxy, benzyloxy, 2-(2-thienyl)ethyloxy, 2-(3-thienyl)ethyloxy, 2-fluorophenylmethyloxy, 4-methylsulfonylphenyloxy, 4-ethylsulfonylphenyloxy and 4-isopropylsulfonylphenyloxy;

D is pyridine-diyl or

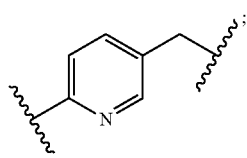

G¹ is CH;
G² is CH;
G³ is CH; and
R⁵⁰ is —R⁶¹—R⁶², and R⁶² is selected from —P(O)(Y²R⁵¹)R¹, or —P(O)(YR⁵¹)Y¹R⁵¹.

One embodiment includes compounds of formula I wherein, D is a heteroarylene selected from the group consisting of pyridine-diyl, thiazole-diyl, thiadiazole-diyl, pyrazol-diyl, pyrazine-diyl, pyridazine-diyl and pyrimidine-diyl, each optionally substituted with one or two groups independently selected from halogen and optionally substituted C₁₋₄-alkyl; wherein, when said heteroarylene is pyridino-diyl, pyrazole-diyl, pyridaze-diyl or pyrimidine-diyl, the ring atom at position 5 of said heteroarylene is connected to R⁵⁰ and when said heteroarylene is thiazole-diyl or thiadiazole-diyl, the ring atom at position 4 of said heteroarylene is connected to R⁵⁰.

Another aspect of the present invention provides for compounds of general Formula II

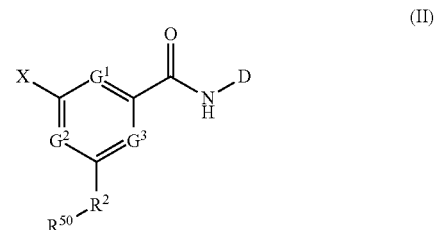

(II)

wherein:
X is selected from the group consisting of aryl, heteroaryl, alkyl, cycloalkyl, arylalkyl, aryloxy, heteroaryloxy, alkyloxy, cycloalkyloxy and arylalkyloxy, and
G² is CR⁴ or N, or
together G² and X are connected to form a cyclic group containing 5-7 atoms, wherein 0-2 ring atoms of said cyclic group are heteroatoms and the remaining ring atoms of said cyclic group are carbon atoms optionally substituted with alkyl, aryl, cycloalkyl or heteroaryl;
R² is selected from the group consisting of arylene, heteroarylene, alkylene, cycloalkylene, arylalkylene, alkylarylene, arylene-O—, heteroarylene-O—, alkylene-O—, cycloalkylene-O—, arylalkylene-O—, alkylarylene-O—, arylene-S—, arylene-SO₂, -heteroarylene-S—, heteroarylene-SO₂—, alkylene-S—, alkylene-SO₂—, cycloalkylene-S—, cycloalkylene-SO₂—; arylalkylene-S—, arylalkylene-SO₂—, alkylarylene-S—;
G¹ is CR⁴ or N;
G³ is CR⁴ or N;
R⁴ is H, halogen or optionally substituted alkyl;
D is selected from a group consisting of heteroaryl and aryl;
R⁵⁰ is —P(O)(Y²R⁵¹) R¹ or —P(O)(YR⁵¹)Y¹R⁵¹;
R¹ is selected from the group consisting of hydrogen, optionally substituted —C₁-C₆-alkyl, —CF₃, —CHF₂, —CH₂F, —CH₂OH, optionally substituted —C₂-C₆ alkenyl, optionally substituted —C₂-C₆ alkynyl, optionally substituted —(CR⁵²₂)ₙcycloalkyl, optionally substituted (CR⁵²₂)ₙheterocycloalkyl, —(CR⁵²₂)ₖ S(=O)R⁵³, —(CR⁵²₂)ₖS(=O)₂R⁵³;
Y, Y¹ and Y² are each independently selected from —O— or —NR⁶⁰—;
wherein,
when Y² is —O— or when Y and Y¹ are both —O—, R⁵¹ attached to —O— is independently selected from —H, optionally substituted aryl, optionally substituted heterocycloalkyl, optionally substituted —CH₂-heterocycloakyl wherein the cyclic moiety contains a carbonate or thiocarbonate, optionally substituted -alkylaryl, —C(R⁵²)₂OC(O)NR⁵²₂, —NR⁵²—C(O)—R⁵³, —C(R⁵²)₂—OC(O)R⁵³, —C(R⁵²)₂—O—C(O)OR⁵³, —C(R⁵²)₂OC(O)SR⁵³, -alkyl-S—C(O)R⁵³, -alkyl-S—S-alkylhydroxy, and -alkyl-S—S-S-alkylhydroxy; or
when Y² is —NR⁶⁰— or when Y and Y¹ are both —NR⁶⁰—, then R⁵¹ attached to —NR⁶⁰— is independently selected from —H, —[C(R$^{52}$)$_2$]$_r$—COOR$^{53}$, —C(R$^{54}$)$_2$COOR$^{53}$, —[C(R$^{52}$)$_2$]$_r$—C(O)SR$^{53}$,
and -cycloalkylene-COOR$^{53}$; or when Y is —O— and Y$^1$ is NR$^{60}$, then R$^{51}$ attached to —O— is independently selected from —H, alkyl, optionally substituted aryl, optionally substituted heterocycloalkyl, optionally substituted CH$_2$-heterocycloakyl wherein the cyclic moiety contains a carbonate or thiocarbonate, optionally
substituted -alkylaryl, —C(R$^{52}$)$_2$OC(O)NR$^{52}$$_2$, —NR$^{52}$—C(O)—R$^{53}$, —C(R$^{52}$)$_2$—OC(O)R$^{53}$, —C(R$^{52}$)$_2$—O—C(O)OR$^{53}$, —C(R$^{52}$)$_2$OC(O)SR$^{53}$, -alkyl-S—C(O)R$^{53}$, -alkyl-S—S-alkylhydroxy,
and -alkyl-S—S—S-alkylhydroxy, and R$^{51}$ attached to —NR$^{60}$— is independently selected from —H, —[C(R$^{52}$)$_2$]$_r$—COOR$^{53}$, —C(R$^{54}$)$_2$COOR$^{53}$, —[C(R$^{52}$)$_2$]$_r$—C(O)SR$^{53}$, and -cycloalkylene-COOR$^{53}$, wherein if both R$^{51}$ are alkyl, at least one is higher alkyl; or when Y and Y$^1$ are independently selected from —O— and —NR$^{60}$—, then R$^{51}$ and R$^{51}$ together form a cyclic group comprising -alkyl-S—S-alkyl-, or R$^{51}$ and R$^{51}$ together are the group

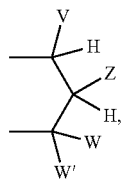

wherein,
V, W, and W' are independently selected from the group consisting of hydrogen, optionally substituted alkyl, optionally substituted aralkyl, heterocycloalkyl, aryl, substituted aryl, heteroaryl, substituted heteroaryl, optionally substituted 1-alkenyl, and optionally substituted 1-alkynyl, and Z is —CHR$^{52}$OH, —CHR$^{52}$OC(O)R$^{53}$, —CHR$^{52}$OC(S)R$^{53}$, —CHR$^{52}$OC(S)OR$^{53}$, —CHR$^{52}$OC(O)SR$^{53}$, —CHR$^{52}$OCO$_2$R$^{53}$, —OR$^{52}$, —SR$^{52}$, —CHR$^{52}$N$_3$, —CH$_2$aryl, —CH(aryl)OH, —CH(CH═CR$^{52}$$_2$)OH, —CH(C≡CR$^{52}$)OH, —R$^{52}$, —NR$^{52}$$_2$, —OCOR$^{53}$, —OCO$_2$R$^{53}$, —SCOR$^{53}$, —SCO$_2$R$^{53}$, —NHCOR$^{42}$, —NHCO$_2$R$^{53}$, —CH$_2$NHaryl, —(CH$_2$)$_r$—OR$^{52}$ or —(CH$_2$)$_r$—SR$^{52}$; or W and W are as defined above and together V and Z are connected via an additional 3-5 atoms to form a cyclic group containing 5-7 atoms, wherein 0-1 atoms are heteroatoms and the remaining atoms are carbon; or W' and Z are as defined above and together V and W are connected via an additional 3 carbon atoms to form an optionally substituted cyclic group containing 6 carbon atoms or carbon substituted by hydrogen and substituted with one substituent selected from hydroxy, acyloxy, alkoxycarbonyloxy, alkylthiocarbonyloxy or aryloxycarbonyloxy which is attached to one of said carbon atoms that is three atoms from a Y attached to the phosphorus; or V and W' are as defined above and together Z and W are connected via an additional 3-5 atoms to form a cyclic group, wherein 0-1 atoms are heteroatoms and the remaining atoms are carbon or carbon substituted by hydrogen, and V must be aryl, substituted aryl, heteroaryl, or substituted heteroaryl; or V and Z are as defined above and together W and W' are connected via an additional 2-5 atoms to form a cyclic group, wherein 0-2 atoms are heteroatoms and the remaining atoms are carbon, where V must be aryl, substituted aryl, heteroaryl, or substituted heteroaryl;

R$^{52}$ is R$^{53}$ or —H;
R$^{53}$ is alkyl, aryl, heterocycloalkyl or aralkyl;
R$^{54}$ is independently selected from —H or alkyl, or together R$^{54}$ and R$^{54}$ form a cycloalkylene group;
R$^{60}$ is —H, lower alkyl, acyloxyalkyl, alkoxycarbonyloxyalkyl, lower acyl, C$_{1-6}$-perfluoroalkyl or NH(CR$^{55}$R$^{55}$)$_f$CH$_3$;
r is an integer 2 or 3;
f is an integer 0, 1 or 2;
wherein, V, Z, W, W' are not all —H, and when Z is —R$^{52}$, then at least one of V, W, and W' is not —H, alkyl, aralkyl, or heterocycloalkyl; and
pharmaceutically acceptable salts and prodrugs thereof.

One embodiment includes compounds of formula II wherein:
X is selected from the group consisting of aryl, heteroaryl, alkyl, cycloalkyl, arylalkyl, aryloxy, alkyloxy, cycloalkyloxy and arylalkyloxy;
R$^2$ is -E$^1$-E$^2$-E$^3$-E$^4$-, wherein E$^4$ is connected to R$^{50}$;
E$^1$ is a bond, O or S;
E$^2$ is a bond or alkylene;
E$^3$ is optionally substituted C$_{1-4}$-alkylene, optionally substituted C$_{3-8}$-cycloalkylalkylene, arylene or heteroarylene optionally substituted with one or two groups independently selected from aryl, heteroaryl, cycloalkyl, cycloalkenyl, halogen, CN, CF$_3$, NR$^5$$_2$, —C$_{1-4}$-alkyl, —S(O)$_2$R$^5$ or —OR$^5$; wherein, when both E$^1$ and E$^2$ are a bond, together they form a single bond;
R$^5$ is optionally substituted alkyl or cycloalkyl;
E$^4$ is a bond or alkylene;
G$^1$ is CH;
G$^2$ is CH;
G$^3$ is CH;
D is heteroaryl having a nitrogen as a ring atom, said heteroaryl comprising a nitrogen ring atom adjacent to a carbon ring atom, wherein said carbon ring atom is connected to the amide nitrogen atom adjacent to D, and wherein said heteroaryl has an additional 0 to 3 heteroatoms independently selected from O, S or N; and
R$^{50}$ is —P(O)(Y$^2$R$^{51}$) R$^1$ or —P(O)(YR$^{51}$)Y$^1$R$^{51}$.

One embodiment includes compounds of formula II wherein:
X is selected from the group consisting of isopropyloxy, benzyloxy, 1,3-difluoroprop-2-yloxy, cyclopentyloxy, phenyloxy, 3,5-dimethylisoxazol-2-yl, phenyl and 2-methylpropyl;
R$^2$ is selected from the group consisting of phenylene-O—, methylene-phenylene-O—, phenylene-methylene-O—, furan-2-yl-5-methylene, thiophen-2-yl-5-methylene, pyridin-diyl-O—, pyrimidin-diyl-O—, pyridazin-diyl-O— and pyrazin-diyl-O—, each optionally substituted with one or two groups independently selected from aryl, heteroaryl, halogen, CN, CF$_3$, NR$^5$$_2$, —C$_{1-4}$-alkyl, —S(O)$_2$R$^5$ or —OR$^5$, wherein R$^{50}$ is connected to R$^2$ by a carbon atom.
G$^1$ is CH;
G$^2$ is CH;
G$^3$ is CH;
D is selected from the group consisting of pyridinyl, thiazolyl, 1,3,4-thiadiazolyl, 1,2,4-thiadiazolyl, oxazolyl, isoxazolyl, pyrazolyl, pyrazinyl, pyridazinyl, pyrimidinyl, benzothiazolyl and 5,6-dihydro-4H-cyclopentathiazolyl, each optionally substituted with one or two groups selected from halogen, CF$_3$, optionally substituted or C$_{1-4}$-alkyl; and,
R$^{50}$ is —P(O)(YR$^{51}$)Y$^1$R$^{51}$.

In one embodiment, compounds of the invention (formulas I and II) under the conditions of Human Enzyme Assay of Example A, at a concentration of 100 μM are able to activate 50 μg of human glucokinase by at least 150%. In other embodiments, compounds of the invention are able to activate glucokinsae by at least 160%, 170%, 180%, 190%, 200%, 210%, 220%, 230%, 240%, 250%, 260%, 270%, 280%, 290%, 300%, 310%, 320%, 330%, 340%, 350%, 360%, 370%, 380%, 390%, 400%, 410%, 420%, 430%, 440%, 450%, 460%, 470%, 480%, 490%, 500% or at least 600% as compared to glucokinase in the absence of said compound of the present invention.

In one embodiment, compounds of the invention have an $EC_{50}$ of less than or equal to 5 μM in rat hepatocyte (conditions of Example B).

In one embodiment, compounds of the invention have an $EC_{50}$ of less than or equal to 1 μM in rat hepatocyte (conditions of Example B).

In one embodiment, compounds of the invention have an $EC_{50}$ of less than or equal to 500 nM in rat hepatocyte (conditions of Example B).

One embodiment includes compounds of the invention wherein $R^{50}$ is selected from the group consisting of —$PO_3H_2$, —P(O)[—$OCR^{52}_2OC(O)R^{53}]_2$, —P(O)[—$OCR^{52}_2OC(O)OR^{53}]_2$, —P(O)[—$N(H)CR^{52}_2C(O)OR^{53}]_2$, —P(O)[—O-alk-$SC(O)R^{53}]_2$, —P(O)[—$OCR^{52}_2OC(O)R^{53}][—R^1]$, —P(O)[—$OCR^{52}_2OC(O)OR^{53}][—R^1]$, —P(O)[—$N(H)CR^{52}_2C(O)OR^{53}][—R^1]$, —P(O)[—$OCH_2CH_2SC(O)R^{53}][—R^1]$, —P(O)(OH)($YR^{51}$), —P(O)($OR^{56}$)($OR^{56}$), —P(O)(OH)(—$R^1$), —P(O)[—$OCR^{52}_2OC(O)R^{53}](OR^{56})$, —P(O)[—$OCR^{52}_2OC(O)OR^{53}](OR^{56})$, —P(O)[—$N(H)CR^{52}_2C(O)OR^{53}](OR^{56})$, P(O)(OH)($NH_2$), and —P(O)[—OCH(V)$CH_2CH_2O$—];

V is optionally substituted aryl or optionally substituted heteroaryl;

$R^{56}$ is —$C_1$-$C_{12}$ alkyl, —$C_2$-$C_{12}$ alkenyl, —$C_2$-$C_{12}$ alkynyl, —($CR^{57}_2)_n$aryl, —($CR^{57}_2)_n$cycloalkyl, or —($CR^{57}_2)_n$heterocycloalkyl, each optionally substituted;

each $R^{57}$ is independently selected from the group consisting of hydrogen, optionally substituted —$C_1$-$C_4$ alkyl, halogen, optionally substituted —O—$C_1$-$C_4$ alkyl, —$OCF_3$, optionally substituted —S—$C_1$-$C_4$ alkyl, —$NR^{58}R^{59}$, optionally substituted —$C_2$-$C_4$ alkenyl, and optionally substituted —$C_2$-$C_4$ alkynyl; with the proviso that when one $R^{57}$ is attached to C through an O, S, or N atom, then the other $R^{57}$ attached to the same C is a hydrogen, or attached via a carbon atom;

$R^{58}$ is selected from hydrogen and optionally substituted —$C_1$-$C_4$ alkyl; and, $R^{59}$ is selected from the group consisting of hydrogen and optionally substituted —$C_1$-$C_4$ alkyl, optionally substituted —C(O)—$C_1$-$C_4$ alkyl and —C(O)H.

One embodiment includes compounds of the invention wherein $R^{50}$ is selected from the group consisting of, —P(O)(OH)$_2$, —P(O)[—$OCH_2OC(O)$-t-butyl]$_2$, —P(O)[—$OCH(CH_3)OC(O)$-t-butyl]$_2$, —P(O)[—$OCH(CH_3)OC(O)O$-i-propyl]$_2$, —P(O)[—$OCH_2OC(O)O$-i-propyl]$_2$, —P(O)[—$N(H)CH(CH_3)C(O)OCH_2CH_3]_2$, —P(O)[—$N(H)C(CH_3)_2C(O)OCH_2CH_3]_2$, —P(O)[—$N(H)CH(CH_3)C(O)OCH_2CH_3$][3,4-methylene dioxyphenyl], —P(O)[—$N(H)C(CH_3)_2C(O)OCH_2CH_3$][3,4-methylenedioxyphenyl], —P(O)[—O—$CH_2CH_2S$—$C(O)CH_3]_2$, —P(O)(OH)($OCH_3$), —P(O)(OH)($OCH_2CH_3$), —P(O)(OH)($CH_3$), —P(O)[—OCH(3-chlorophenyl)$CH_2CH_2O$—], —P(O)[—OCH(pyrid-4-yl)$CH_2CH_2O$—], —P(O)[—$OCH_2OC(O)$-t-butyl]($OCH_3$), —P(O)[—$OCH_2OC(O)O$-i-propyl]($OCH_3$), —P(O)[—$OCH(CH_3)OC(O)$-t-butyl]($OCH_3$), —P(O)[—$OCH(CH_3)OC(O)O$-i-propyl]($OCH_3$), —P(O)[—$OCH_2CH_3$]($OCH_3$), —P(O)[—$OCH_2CH_3$]($CH_3$), —P(O)[—$OCH_2CH_3$]($OCH_3$), —P(O)[—$OCH_2CH_3$]($CH_3$), —P(O)[—$OCH_2OC(O)$-t-butyl]($CH_3$), —P(O)[—$OCH_2OC(O)O$-i-propyl]($CH_3$), —P(O)[—$OCH(CH_3)OC(O)$-t-butyl]($CH_3$), —P(O)[—$OCH(CH_3)OC(O)O$-i-propyl](CH), and —P(O)[—$OCH_2OC(O)O$-ethyl]$_2$.

In another embodiment, Y and $Y^1$ are each independently selected from —O— and —$NR^{60}$—; and together $R^{51}$ and $R^{51}$ are the group

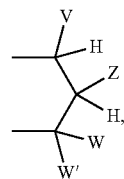

wherein, V is substituted aryl or substituted heteroaryl.

In a further embodiment, Z is —H, W is —H, and W' is —H.

In a further embodiment, V is 3-chlorophenyl, 4-chlorophenyl, 3-bromophenyl, 3-fluorophenyl, pyrid-4-yl, pyrid-3-yl or 3,5-dichlorophenyl.

In a further embodiment, the relative stereochemistry between the V-group substituent and the carbon attached to the P atom of $R^{50}$ is cis.

In a further embodiment, the relative stereochemistry between the V-group substituent and the carbon attached to the P atom of $R^{50}$ is trans.

In a further embodiment, said compound has R stereochemistry at the carbon where the V-group is attached.

In a further embodiment, the compound has S stereochemistry at the carbon where the V-group is attached.

In one aspect of the invention, the following non-limiting embodiments are provided. For example, one embodiment ("Embodiment 1") is a compound of general Formula (I),

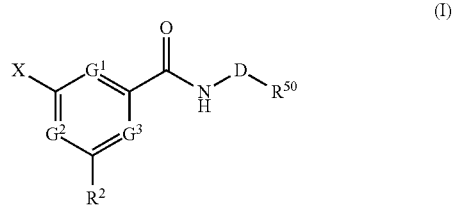

(I)

wherein:

X is selected from the group consisting of aryl, heteroaryl, alkyl, cycloalkyl, arylalkyl, aryloxy, heteroaryloxy, alkyloxy, cycloalkyloxy and arylalkyloxy;

$R^2$ is selected from the group consisting of aryl, heteroaryl, alkyl, cycloalkyl, arylalkyl, aryloxy, heteroaryloxy, alkyloxy, cycloalkyloxy, arylalkyloxy, arylthio, heteroarylthio, cycloalkylthio and arylalkylthio;

D is selected from heteroarylene and arylene, each optionally substituted;

$G^1$, $G^2$ and $G^3$ are $CR^4$ or N;

$R^4$ is H, halogen or alkyl; and $R^{50}$ is —$R^{61}$—$R^{62}$, and $R^{62}$ is selected from —P(O)($Y^2R^{51}$)$R^1$, or —P(O)($YR^{51}$)$Y^1R^{51}$;

R$^{61}$ is selected from null, arylene, heteroarylene, arylene-alkylene, alkylene-arylene, heteroarylene-alkylene, alkylene-heteroarylene, alkylene, alkenylene, alkynylene, alkylene-Q-alkylene, —CONR$^{52}$-alkylene, —COO-alkylene, —SO$_2$NR$^{52}$-alkylene, arylene-Q-alkylene, alkylene-Q-arylene, heteroarylene-Q-alkylene, alkylene-Q-heteroarylene, all optionally substituted;

Q is selected from O, S, SO, SO$_2$, NR$^{53}$;

with the proviso that when D is heteroarylene then R$^{50}$ is not —(CH$_2$)n'-Z'—(CH$_2$)m'-PO(OR$^{63}$)(OR$^{64}$), or —(CCH$_2$)n'-Z'—(CH$_2$)m'-PO(OR$^{63}$)R$^{65}$, or —(CH$_2$)n'-Z'—(CH$_2$)m'-O—PO(OR$^{63}$)R$^{65}$, or —(CH$_2$)n'-Z'—(CH$_2$)m'-O—PO(R$^{65}$)R$^{66}$, or —(CH$_2$)n'-Z'—(CH$_2$)m'-PO—(R$^{65}$)R$^{66}$;

R$^{63}$ and R$^{64}$ are the same or different and are independently selected from the group consisting of hydrogen and alkyl, or R$^{63}$ and R$^{64}$ can be cyclized into a ring;

R$^{65}$ and R$^{66}$ are the same or different and are independently selected from the group consisting of alkyl, aryl, arylalkyl, heteroaryl, and heteroarylalkyl; or R$^{65}$ and R$^{66}$ can be cyclized into a ring, or R$^{63}$ and R$^{65}$ can be cyclized into a ring;

Z' is selected from the group consisting of a bond, alkylene, alkenylene, O, S, or SO$_2$;

m' is 0, 1 or 2, provided that when Z is O, S or SO$_2$, n' is 1 or 2;

n' is 0, 1, or 2;

R$^1$ is selected from the group consisting of hydrogen, optionally substituted —C$_1$-C$_6$-alkyl, —CF$_3$, —CHF$_2$, —CH$_2$F, —CH$_2$OH, optionally substituted —C$_2$-C$_6$ alkenyl, optionally substituted —C$_2$-C$_6$ alkynyl, optionally substituted —(CR$^{52}_2$)$_n$cycloalkyl, optionally substituted (CR$^{52}_2$)$_n$heterocycloalkyl, —(CR$^{52}_2$)$_k$ S(=O)R$^{53}$, —(CR$^{52}_2$)$_k$S(=O)$_2$R$^{53}$;

Y, Y$^1$ and Y$^2$ are each independently selected from —O— or —NR$^1$—;

wherein, when Y$^2$ is —O— or when Y and Y$^1$ are both —O—, R$^{51}$ attached to —O— is independently selected from the group consisting of —H, alkyl, optionally substituted aryl, optionally substituted heterocycloalkyl, optionally substituted —CH$_2$-heterocycloakyl with a cyclic moiety containing a carbonate or thiocarbonate, optionally substituted -alkylaryl, —C(R$^{52}$)$_2$OC(O)NR$^{52}_2$, —NR$^{52}$—C(O)—R$^{53}$, —C(R$^{52}$)$_2$—OC(O)R$^{53}$, —C(R$^{52}$)$_2$—O—C(O)OR$^{53}$, —C(R$^{52}$)$_2$OC(O)SR$^{53}$, -alkyl-S—C(O)R$^{53}$, -alkyl-S—S-alkylhydroxy and -alkyl-S—S—S-alkylhydroxy; or when Y$^2$ is —NR$^{60}$— or when Y and Y$^1$ are both —NR$^{60}$—, then R$^{51}$ attached to —NR$^{50}$— is independently selected from the group consisting of —H, —[C(R$^{52}$)$_2$]$_r$—COOR$^{53}$, —C(R$^{54}$)$_2$COOR$^{53}$, —[C(R$^{52}$)$_2$]$_r$—C(O)SR$^{53}$, and -cycloalkylene-COOR$^{53}$; or when Y is —O— and Y$^1$ is NR$^{60}$, then R$^{51}$ attached to —O— is independently selected from —H, alkyl, optionally substituted aryl, optionally substituted heterocycloalkyl, optionally substituted CH$_2$-heterocycloakyl wherein the cyclic moiety contains a carbonate or thiocarbonate, optionally substituted -alkylaryl, —C(R$^{52}$)$_2$OC(O)NR$^{52}_2$, —NR$^{52}$—C(O)—R$^{53}$, —C(R$^{52}$)$_2$—OC(O)R$^{53}$, —C(R$^{52}$)$_2$—O—C(O)OR$^{53}$, —C(R$^{52}$)$_2$OC(O)SR$^{53}$, -alkyl-S—C(O)R$^{53}$, -alkyl-S—S-alkylhydroxy, and -alkyl-S—S—S-alkylhydroxy, and R$^{51}$ attached to —NR$^{60}$— is independently selected from —H, —[C(R$^{52}$)$_2$]$_r$—COOR$^{53}$, —C(R$^{54}$)$_2$COOR$^{53}$, —[C(R$^{52}$)$_2$]$_r$—C(O)SR$^{53}$, and -cycloalkylene-COOR$^{53}$, wherein if both R$^{51}$ are alkyl, at least one is higher alkyl; or when Y and Y$^1$ are independently selected from —O— and —NR$^{60}$—, then R$^{51}$ and R$^{51}$ together form a cyclic group comprising -alkyl-S—S-alkyl-, or R$^{51}$ and R$^{51}$ together are the group

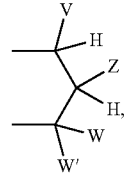

wherein,

V, W, and W' are independently selected from the group consisting of hydrogen, optionally substituted alkyl, optionally substituted aralkyl, heterocycloalkyl, aryl, substituted aryl, heteroaryl, substituted heteroaryl, optionally substituted 1-alkenyl, and optionally substituted 1-alkynyl, and Z is —CHR$^{52}$OH, —CHR$^{52}$OC(O)R$^{53}$, —CHR$^{52}$OC(S)R$^{53}$, —CHR$^{52}$OC(S)OR$^{53}$, —CHR$^{52}$OC(O)SR$^{53}$, —CHR$^{52}$OCO$_2$R$^{53}$, —OR$^{52}$, —SR$^{52}$, —CHR$^{52}$N$_3$, —CH$_2$aryl, —CH(aryl)OH, —CH(CH=CR$^{52}_2$)OH, —CH(C≡CR$^{52}$)OH, —R$^{52}$, —NR$^{52}_2$, —O COR$^{53}$, —OCO$_2$R$^{53}$, —SCOR$^{53}$, —SCO$_2$R$^{53}$, —NHCOR$^{52}$, —NHCO$_2$R$^{53}$, —CH$_2$NHaryl, —(CH$_2$)$_r$—OR$^{52}$ or —(CH$_2$)$_r$—SR$^{52}$; or W and W' are as defined above and together V and Z are connected via an additional 3-5 atoms to form a cyclic group containing 5-7 atoms, wherein 0-1 atoms are heteroatoms and the remaining atoms are carbon; or W' and Z are as defined above and together V and W are connected via an additional 3 carbon atoms to form an optionally substituted cyclic group containing 6 carbon atoms or carbon substituted by hydrogen and substituted with one substituent selected from hydroxy, acyloxy, alkoxycarbonyloxy, alkylthiocarbonyloxy or aryloxycarbonyloxy which is attached to one of said carbon atoms that is three atoms from a Y attached to the phosphorus; or V and W' are as defined above and together Z and W are connected via an additional 3-5 atoms to form a cyclic group, wherein 0-1 atoms are heteroatoms and the remaining atoms are carbon or carbon substituted by hydrogen, and V must be aryl, substituted aryl, heteroaryl, or substituted heteroaryl; or V and Z are as defined above and together W and W' are connected via an additional 2-5 atoms to form a cyclic group, wherein 0-2 atoms are heteroatoms and the remaining atoms are carbon, where V must be aryl, substituted aryl, heteroaryl, or substituted heteroaryl;

R$^{52}$ is R$^{53}$ or —H;

R$^{53}$ is alkyl, aryl, heterocycloalkyl or aralkyl;

R$^{54}$ is independently selected from —H or alkyl, or together R$^{54}$ and R$^{54}$ form a cycloalkylene group;

R$^{60}$ is —H, lower alkyl, acyloxyalkyl, alkoxycarbonyloxyalkyl, lower acyl, C$_{1-6}$-perfluoroalkyl or NH(CR$^{55}$R$^{55}$)$_f$CH$_3$;

r is an integer 2 or 3;

f is an integer 0, 1 or 2;

wherein, V, Z, W, W' are not all —H, and when Z is —R$^{52}$, then at least one of V, W, and W' is not —H, alkyl, aralkyl, or heterocycloalkyl; and pharmaceutically acceptable salts, co-crystals and prodrugs thereof.

A further embodiment ("Embodiment 2") is the compound of embodiment 1, wherein X is selected from the group consisting of alkyl, cycloalkyl, alkyloxy, cycloalkyloxy and aryloxy.

A further embodiment ("Embodiment 3") is the compound of embodiment 1, wherein X is selected from the group consisting of alkyloxy and cycloalkyloxy.

A further embodiment ("Embodiment 4") is the compound of embodiment 1, wherein $R^2$ is -$E^1$-$E^2$-$E^3$, wherein,
$E^1$ is a bond, O or S;
$E^2$ is a bond or alkylene;
wherein, when both $E^1$ and $E^2$ are a bond, together they form a single bond;
$E^1$ is optionally substituted —$C_{1-4}$-alkyl, optionally substituted —$C_{3-8}$-cycloalkyl or aryl optionally substituted with one or two groups independently selected from the group consisting of aryl, heteroaryl, halogen, —$C_{1-4}$-alkyl, —$S(O)_2R^5$ or —$OR^5$;
$R^5$ is alkyl or cycloalkyl.

A further embodiment ("Embodiment 5") is the compound of embodiment 1, wherein $R^2$ is selected from the group consisting of —$C_{1-4}$-alkyloxy, —$C_{3-6}$-cycloalkyloxy, benzyloxy, 2-(2-thienyl)ethyloxy, 2-(3-thienyl)ethyloxy, and phenyloxy, each optionally substituted with one or two groups independently selected from the group consisting of halogen, —$C_{1-4}$-alkyl, —$S(O)_2C_{1-4}$-alkyl, —$S(O)_2C_{3-6}$-cycloalkyl, or —$OC_{1-4}$-alkyl.

A further embodiment ("Embodiment 6") is the compound of embodiment 1, wherein $R^2$ is selected from the group consisting of n-propyloxy, isopropyloxy, 2-methylpropyloxy, cyclopentylmethyloxy, benzyloxy, 2-(2-thienyl)ethyloxy, 2-(3-thienyl)ethyloxy, 2-fluorophenylmethyloxy, 4-methylsulfonylphenyloxy, 4-ethylsulfonylphenyloxy and 4-isopropylsulfonylphenyloxy.

A further embodiment ("Embodiment 7") is the compound of embodiment 1, wherein D is heteroarylene, said heteroarylene comprising a nitrogen ring atom adjacent to a carbon ring atom, wherein said carbon ring atom is connected to the amide nitrogen atom adjacent to D, and wherein said heteroarylene has an additional 0 to 3 heteroatoms independently selected from O, S or N.

A further embodiment ("Embodiment 8") is the compound of embodiment 1, wherein D is a heteroarylene, optionally substituted with one or two groups independently selected from halogen and optionally substituted $C_{1-4}$-alkyl; wherein, when said heteroarylene is pyridine-diyl, pyrazole-diyl, pyridaze-diyl or pyramidine-diyl, the ring atom at position 5 of said heteroarylene is connected to $R^{50}$ and when said heteroarylene is thiazole-diyl or thiadiazole-diyl, the ring atom at position 4 of said heteroarylene is connected to $R^{50}$, and n is 0 or 1.

A further embodiment ("Embodiment 9") is the compound of embodiment 1, wherein $G^1$, $G^2$ and $G^3$ are $CR^4$ and $R^4$ is H, halogen or alkyl.

A further embodiment ("Embodiment 10") is the compound of embodiment 9, wherein $R^4$ is H.

A further embodiment ("Embodiment 11") is the compound of embodiment 1, wherein $R^{62}$ is selected from the group consisting of —$PO_3H_2$, —$P(O)[—OCR^{52}_2OC(O)R^{53}]_2$, —$P(O)[—OCR^{52}_2OC(O)OR^{53}]_2$, —$P(O)[—N(H)CR^{52}_2C(O)$ $OR^{53}]_2$, —$P(O)[—O$-alk-$SC(O)R^{53}]_2$, —$P(O)[—OCR^{52}_2OC(O)R^{53}][—R^1]$, —$P(O)[—OCR^{52}_2OC(O)OR^{53}][—R^1]$, —$P(O)[—N(H)CR^{52}C(O)OR^{53}][—R^1]$, —$P(O)[—OCH_2CH_2SC(O)R^{53}][—R^1]$, —$P(O)(OH)(YR^{51})$, —$P(O)(OR^{56})(OR^{56})$, —$P(O)(OH)(—R^1)$, —$P(O)[—OCR^{52}_2OC(O)R^{53}](OR^{56})$, —$P(O)[—OCR^{52}_2OC(O)OR^{53}](OR^{56})$, $P(O)[—N(H)CR^{52}_2C(O)OR^{53}](OR^{56})$, $P(O)(OH)(NH_2)$, and —$P(O)[—OCH(V)CH_2CH_2O—]$;
V is optionally substituted aryl or optionally substituted heteroaryl;

$R^{56}$ is —$C_1$-$C_{12}$ alkyl, —$C_2$-$C_{12}$ alkenyl, —$C_2$-$C_{12}$ alkynyl, —$(CR^{57}_2)_n$aryl, —$(CR^{57}_2)_n$cycloalkyl, or —$(CR^{57}_2)_n$heterocycloalkyl, each optionally substituted;
each $R^{57}$ is independently selected from the group consisting of hydrogen, optionally substituted —$C_1$-$C_4$ alkyl, halogen, optionally substituted —O—$C_1$-$C_4$ alkyl, —$OCF_3$, optionally substituted —S—$C_1$-$C_4$ alkyl, —$NR^{58}R^{59}$, optionally substituted —$C_2$-$C_4$ alkenyl, and optionally substituted —$C_2$-$C_4$ alkynyl; with the proviso that when one $R^{57}$ is attached to C through an O, S, or N atom, then the other $R^{57}$ attached to the same C is a hydrogen, or attached via a carbon atom;
$R^{58}$ is selected from hydrogen and optionally substituted —$C_1$-$C_4$ alkyl; and,
$R^{59}$ is selected from the group consisting of hydrogen and optionally substituted —$C_1$-$C_4$ alkyl, optionally substituted —C(O)—$C_1$-$C_4$ alkyl and —C(O)H.

A further embodiment ("Embodiment 12") is the compound of embodiment 1, wherein $R^{62}$ is selected from the group consisting of:
$P(O)(OH)_2$, —$P(O)[—OCH_2OC(O)$-t-butyl$]_2$, —$P(O)[—OCH(CH_3)OC(O)$-t-butyl$]_2$, —$P(O)[—OCH(CH_3)OC(O)O$-i-propyl$]_2$, —$P(O)[—OCH_2OC(O)O$-i-propyl$]_2$, —$P(O)[—N(H)CH(CH_3)C(O)OCH_2CH_3]_2$, —$P(O)[—N(H)C(CH_3)_2C(O)OCH_2CH_3]_2$, —$P(O)[—N(H)$ $CH(CH_3)C(O)OCH_2CH_3]$[3,4-methylenedioxyphenyl], —$P(O)[—N(H)C(CH_3)_2C(O)OCH_2CH_3]$[3,4-methylenedioxyphenyl], —$P(O)[—O—CH_2CH_2S—C(O)CH_3]_2$, —$P(O)(OH)(OCH_3)$, —$P(O)(OH)(OCH_2CH_3)$, —$P(O)(OH)(CH_3)$, —$P(O)[—OCH(3$-chlorophenyl$)CH_2CH_2O—]$, —$P(O)[—OCH($pyrid-4-yl$)CH_2CH_2O—]$, —$P(O)[—OCH_2OC(O)$-t-butyl$](OCH_3)$, —$P(O)[—OCH_2OC(O)O$-i-propyl$](OCH_3)$, —$P(O)[—OCH(CH_3)OC(O)$-t-butyl$](OCH_3)$, —$P(O)[—OCH(CH_3)OC(O)O$-i-propyl$](OCH_3)$, —$P(O)[—N(H)CH(CH_3)C(O)OCH_2CH_3](OCH_3)$, —$P(O)[—N(H)CH(CH_3)C(O)OCH_2CH_3](CH_3)$, —$P(O)[—N(H)C(CH_3)_2C(O)OCH_2CH_3](OCH_3)$, —$P(O)[—N(H)C(CH_3)_2C(O)OCH_2CH_3](CH_3)$, —$P(O)[—OCH_2OC(O)$-t-butyl$](CH_3)$, —$P(O)[—OCH_2OC(O)O$-i-propyl$](CH_3)$, —$P(O)[—OCH(CH_3)OC(O)$-t-butyl$](CH_3)$, —$P(O)[—OCH(CH_3)OC(O)O$-i-propyl$](CH_3)$, and —$P(O)[—OCH_2OC(O)O$-ethyl$]_2$.

A further embodiment ("Embodiment 13") is the compound of embodiment 1, wherein Y and $Y^1$ are each independently selected from —O— and —$NR^{60}$—; and together $R^{51}$ and $R^{51}$ are the group

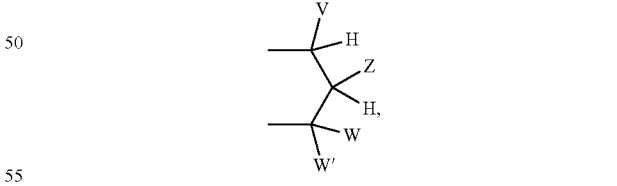

wherein, V is substituted aryl or substituted heteroaryl.

A further embodiment ("Embodiment 14") is the compound of embodiment 1, wherein said compound has one of the following combinations of substituents:

| Combination No. | Substituent No. |
|---|---|
| #1 | 1, 2 |
| #2 | 1, 3 |
| #3 | 1, 4 |

-continued

| Combination No. | Substituent No. |
|---|---|
| #4 | 1, 5 |
| #5 | 2, 3 |
| #6 | 2, 4 |
| #7 | 2, 5 |
| #8 | 3, 4 |
| #9 | 3, 5 |
| #10 | 4, 5 |
| #11 | 1, 2, 3 |
| #12 | 1, 2, 4 |
| #13 | 1, 2, 5 |
| #14 | 1, 3, 4 |
| #15 | 1, 3, 5 |
| #16 | 1, 4, 5 |
| #17 | 2, 3, 4 |
| #18 | 2, 3, 5 |
| #19 | 2, 4, 5 |
| #20 | 3, 4, 5 |
| #21 | 1, 2, 3, 4 |
| #22 | 1, 2, 3, 5 |
| #23 | 1, 2, 4, 5 |
| #24 | 1, 3, 4, 5 |
| #25 | 2, 3, 4, 5 |
| #26 | 1, 2, 3, 4, 5 | wherein:
any substituent not listed in said combination is as defined in embodiment 1; Substituent 1 is X and:

X is selected from the group consisting of aryl, heteroaryl, alkyl, cycloalkyl, arylalkyl, aryloxy, heteroaryloxy, alkyloxy, cycloalkyloxy and arylalkyloxy; or X is selected from the group consisting of alkyl, cycloalkyl, alkyloxy, cycloalkyloxy and aryloxy; or X is selected from the group consisting of alkyloxy and cycloalkyloxy; Substituent 2 is $R^2$ and:

$R^2$ is selected from the group consisting of aryl, heteroaryl, alkyl, cycloalkyl, arylalkyl, aryloxy, heteroaryloxy, alkyloxy, cycloalkyloxy, arylalkyloxy, arylthio, heteroarylthio, cycloalkylthio and arylalkylthio; or $R^2$ is $-E^1-E^2-E^3$, wherein,
$E^1$ is a bond, O or S;
$E^2$ is a bond or alkylene;
wherein, when both $E^1$ and $E^2$ are a bond, together they form a single bond;
$E^3$ is optionally substituted $-C_{1-4}$-alkyl, optionally substituted $-C_{3-8}$-cycloalkyl or aryl optionally substituted with one or two groups independently selected from the group consisting of halogen, $-C_{1-4}$-alkyl, $-S(O)_2R^5$ and $-OR^5$;
$R^5$ is alkyl or cycloalkyl; or $R^2$ is selected from the group consisting of $-C_{1-4}$-alkyloxy, $-C_{3-6}$-cycloalkyloxy, benzyloxy, 2-(2-thienyl)ethyloxy, 2-(3-thienyl)ethyloxy, and phenyloxy, each optionally substituted with one or two groups independently selected from the group consisting of halogen, $-C_{1-4}$-alkyl, $-S(O)_2C_{1-4}$-alkyl, $-S(O)_2C_{3-4}$-cycloalkyl, or $-OC_{1-4}$-alkyl; or $R^2$ is selected from the group consisting of n-propyloxy, isopropyloxy, 2-methylpropyloxy, cylclopentylmethyloxy, benzyloxy, 2-(2-thienyl)ethyloxy, 2-(3-thienyl)ethyloxy, 2-fluorophenylmethyloxy, 4-methylsulfonylphenyloxy, 4-ethylsulfonylphenyloxy and 4-isopropylsulfonylphenyloxy;
Substituent 3 is D and:
D is selected from heteroarylene or arylene, each optionally substituted; or
D is heteroarylene, said heteroarylene comprising a nitrogen ring atom adjacent to a carbon ring atom, wherein said carbon ring atom is connected to the amide nitrogen atom adjacent to D, and wherein said heteroarylene has an additional 0 to 3 heteroatoms independently selected from O, S or N; or D is a heteroarylene, optionally substituted with one or two groups independently selected from halogen and optionally substituted $C_{1-4}$-alkyl; wherein, when said heteroarylene is pyridine-diyl, pyrazole-diyl, pyridaze-diyl or pyramidine-diyl, the ring atom at position 5 of said heteroarylene is connected to $R^{50}$ and when said heteroarylene is thiazole-diyl or thiadiazole-diyl, the ring atom at position 4 of said heteroarylene is connected to $R^{50}$, and n is 0 or 1;
Substituent 4 is $G^1$, $G^2$ and $G^3$ and:
$G^1$, $G^2$ and $G^3$ are $CR^4$ or N; and $R^4$ is H, halogen or alkyl; or
$G^1$ is $CR^4$; $G^2$ is $CR^4$; $G^3$ is $CR^4$; and $R^4$ is H, halogen or alkyl; or
$G^1$ is CH; $G^2$ is CH; and $G^3$ is CH; and
Substituent 5 is $R^{50}$ and:
$R^{50}$ is $-R^{61}-R^{62}$, and $R^{62}$ is selected from $-P(O)(Y^2R^{51})R^1$, or $-P(O)(YR^{51})Y^1R^{51}$;
$R^{61}$ is selected from null, arylene, heteroarylene, arylene-alkylene, alkylene-arylene, heteroarylene-alkylene, alkylene-heteroarylene, alkylene, alkenylene, alkynylene, alkylene-Q-alkylene, $-CONR^{52}$-alkylene, $-COO$-alkylene, $-SO_2NR^{52}$-alkylene, arylene-Q-alkylene, alkylene-Q-arylene, heteroarylene-Q-alkylene, alkylene-Q-heteroarylene, all optionally substituted;
Q is selected from O, S, SO, $SO_2$, $NR^{53}$;
R is selected from the group consisting of hydrogen, optionally substituted $-C_1-C_6$-alkyl, $-CF_3$, $-CHF_2$, $-CH_2F$, $-CH_2OH$, optionally substituted $-C_2-C_6$ alkenyl, optionally substituted $-C_2-C_6$ alkynyl, optionally substituted $-(CR^{52}_2)_n$cycloalkyl, optionally substituted $(CR^{52}_2)_n$heterocycloalkyl, $-(CR^{52}_2)_k$ $S(=O)R^{53}$, $-(CR^{52}_2)_k$ $S(=O)_2R^{53}$;
Y, $Y^1$ and $Y^2$ are each independently selected from $-O-$ or $-NR^{60}-$;
wherein,
when $Y^2$ is $-O-$ or when Y and $Y^1$ are both $-O-$, $R^{51}$ attached to $-O-$ is independently selected from the group consisting of $-H$, alkyl, optionally substituted aryl, optionally substituted heterocycloalkyl, optionally substituted $-CH_2$-heterocycloalkyl with a cyclic moiety containing a carbonate or thiocarbonate, optionally substituted -alkylaryl, $-C(R^{52})_2OC(O)NR^{52}_2$, $-NR^{52}-C(O)-R^{53}$, $-C(R^{52})_2-OC(O)R^{53}$, $-C(R^{52})_2-O-C(O)OR^{53}$, $-C(R^{52})_2OC(O)SR^{53}$, -alkyl-S$-C(O)R^{53}$, -alkyl-S$-$S-alkylhydroxy and -alkyl-S$-$S$-$S-alkylhydroxy; or when $Y^2$ is $-NR^{60}-$ or when Y and $Y^1$ are both $-NR^{60}-$, then $R^{51}$ attached to $-NR^{60}-$ is independently selected from the group consisting of $-H$, $-[C(R^{52})_2]_r-COOR^{53}$, $-C(R^{54})_2COOR^{53}$, $-[C(R^{52})_2]_r-C(O)SR^{53}$,
and -cycloalkylene-$COOR^{53}$; or when Y is $-O-$ and $Y^1$ is $NR^{60}$, then $R^{51}$ attached to $-O-$ is independently selected from $-H$, alkyl, optionally substituted aryl, optionally substituted heterocycloalkyl, optionally substituted $CH_2$-heterocycloakyl wherein the cyclic moiety contains a carbonate or thiocarbonate, optionally substituted -alkylaryl, $-C(R^{52})_2OC(O)NR^{52}_2$, $-NR^{52}-C(O)-R^{53}$, $-C(R^{52})_2-OC(O)R^{53}$, $-C(R^{52})_2-O-C(O)OR^{53}$, $-C(R^{52})_2OC(O)SR^{53}$, -alkyl-S$-C(O)R^{53}$, -alkyl-S$-$S-alkylhydroxy, and -alkyl-S—S—alkylhydroxy, and $R^{51}$ attached to —$NR^{60}$— is independently selected from —H, —[C($R^{52}$)$_2$]$_r$—COO$R^{53}$, —C($R^{54}$)$_2$COO$R^{53}$, —[C($R^{52}$)$_2$]$_r$—C(O)S$R^{53}$, and -cycloalkylene-COO$R^{53}$, wherein if both $R^{51}$ are alkyl, at least one is higher alkyl; or when Y and $Y^1$ are independently selected from —O— and —$NR^{60}$—, then $R^{51}$ and $R^{51}$ together form a cyclic group comprising -alkyl-S—S-alkyl-, or $R^{51}$ and $R^{51}$ together are the group

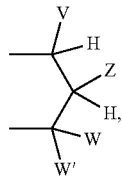

wherein,

V, W, and W' are independently selected from the group consisting of hydrogen, optionally substituted alkyl, optionally substituted aralkyl, heterocycloalkyl, aryl, substituted aryl, heteroaryl, substituted heteroaryl, optionally substituted 1-alkenyl, and optionally substituted 1-alkynyl, and Z is —CH$R^{52}$OH, —CH$R^{52}$OC(O)$R^{53}$, —CH$R^{52}$OC(S)$R^{53}$, —CH$R^{52}$OC(S)O$R^{53}$, —CH$R^{52}$OC(O)S$R^{53}$, —CH$R^{52}$OCO$_2R^{53}$, —O$R^{52}$, —S$R^{52}$, —CH$R^{52}$N$_3$, —CH$_2$aryl, —CH(aryl)OH, —CH(CH=C$R^{52}_2$)OH, —CH(C≡C$R^{52}$)OH, —$R^{52}$, —N$R^{52}_2$, —O COR$^{53}$, —OCO$_2R^{53}$, —SCO$R^{53}$, —SCO$_2R^{53}$, —NHCO$R^{52}$, —NHCO$_2R^{53}$, —CH$_2$NHaryl, —(CH$_2$)$_r$—O$R^{52}$ or —(CH$_2$)$_r$—S$R^{52}$; or W and W' are as defined above and together V and Z are connected via an additional 3-5 atoms to form a cyclic group containing 5-7 atoms, wherein 0-1 atoms are heteroatoms and the remaining atoms are carbon; or W' and Z are as defined above and together V and W are connected via an additional 3 carbon atoms to form an optionally substituted cyclic group containing 6 carbon atoms or carbon substituted by hydrogen and substituted with one substituent selected from hydroxy, acyloxy, alkoxycarbonyloxy, alkylthiocarbonyloxy or aryloxycarbonyloxy which is attached to one of said carbon atoms that is three atoms from a Y attached to the phosphorus; or V and W' are as defined above and together Z and W are connected via an additional 3-5 atoms to form a cyclic group, wherein 0-1 atoms are heteroatoms and the remaining atoms are carbon or carbon substituted by hydrogen, and V must be aryl, substituted aryl, heteroaryl, or substituted heteroaryl; or V and Z are as defined above and together W and W' are connected via an additional 2-5 atoms to form a cyclic group, wherein 0-2 atoms are heteroatoms and the remaining atoms are carbon, where V must be aryl, substituted aryl, heteroaryl, or substituted heteroaryl;

$R^{52}$ is $R^{53}$ or —H;

$R^{53}$ is alkyl, aryl, heterocycloalkyl or aralkyl;

$R^{54}$ is independently selected from —H or alkyl, or together $R^{54}$ and $R^{54}$ form a cycloalkylene group;

$R^{60}$ is —H, lower alkyl, acyloxyalkyl, alkoxycarbonyloxyalkyl, lower acyl, $C_{1-6}$-perfluoroalkyl or NH(C$R^{55}R^{55}$)$_f$CH$_3$;

r is an integer 2 or 3;

f is an integer 0, 1 or 2;

wherein, V, Z, W, W' are not all —H, and when Z is —$R^{52}$, then at least one of V, W, and W' is not —H, alkyl, aralkyl, or heterocycloalkyl; or $R^{62}$ is selected from the group consisting of:
—PO$_3$H$_2$, —P(O)[—OC$R^{52}_2$OC(O)$R^{53}$]$_2$, —P(O)[—OC$R^{52}_2$OC(O)O$R^{53}$]$_2$, —P(O)[—N(H)C$R^{52}_2$C(O)O $R^{53}$]$_2$, —P(O)[—O-alk-SC(O)$R^{53}$]$_2$, —P(O)[—OC$R^{52}_2$OC(O)$R^{53}$][—$R^1$], —P(O)[—OC$R^{52}_2$OC(O)O$R^{53}$][—$R^1$], —P(O)[—N(H)C$R^{52}_2$C(O)O$R$][—$R^1$], —P(O)[—OCH$_2$CH$_2$SC(O)$R^{53}$][—$R^1$], —P(O)(OH)(Y$R^{51}$), —P(O)(O$R^{56}$)(O$R^{56}$), —P(O)(OH)(—$R^1$), —P(O)[—OC$R^{52}_2$OC(O)$R^{53}$](O$R^{56}$), —P(O)[—OC$R^{52}_2$OC(O)O$R^{53}$](O$R^{53}$), —P(O)[—N(H)C$R^{52}_2$C(O)O$R^{53}$](O$R^{56}$), P(O)(OH)(NH$_2$), and —P(O)[—OCH(V)CH$_2$CH$_2$O—];

V is optionally substituted aryl or optionally substituted heteroaryl;

$R^{56}$ is —$C_1$-$C_{12}$ alkyl, —$C_2$-$C_{12}$ alkenyl, —$C_2$-$C_{12}$ alkynyl, —(C$R^{57}_2$)$_n$aryl, —(C$R^{57}_2$)$_n$cycloalkyl, or —(C$R^{57}_2$)$_n$heterocycloalkyl, each optionally substituted;

each $R^{57}$ is independently selected from the group consisting of hydrogen, optionally substituted —$C_1$-$C_4$ alkyl, halogen, optionally substituted —O—$C_1$-$C_4$ alkyl, —OCF$_3$, optionally substituted —S—$C_1$-$C_4$ alkyl, —N$R^{58}R^{59}$, optionally substituted —$C_2$-$C_4$ alkenyl, and optionally substituted —$C_2$-$C_4$ alkynyl; with the proviso that when one $R^{57}$ is attached to C through an O, S, or N atom, then the other $R^{57}$ attached to the same C is a hydrogen, or attached via a carbon atom;

$R^{58}$ is selected from hydrogen and optionally substituted —$C_1$-$C_4$ alkyl; and, $R^{59}$ is selected from the group consisting of hydrogen and optionally substituted —$C_1$-$C_4$ alkyl, optionally substituted —C(O)—$C_1$-$C_4$ alkyl and —C(O)H; or $R^{62}$ is selected from the group consisting of —P(O)(OH)$_2$, —P(O)[—OCH$_2$OC(O)-t-butyl]$_2$, —P(O)[—OCH(CH$_3$)OC(O)-t-butyl]$_2$, —P(O)[—OCH(CH$_3$)OC(O)-i-propyl]$_2$, —P(O)[—OCH$_2$OC(O)O-i-propyl]$_2$, —P(O)[—N(H)CH(CH$_3$)C(O)OCH$_2$CH$_3$]$_2$, —P(O)[—N(H)C(CH$_3$)$_2$C(O)OCH$_2$CH$_3$]$_2$, —P(O)[—N(H)CH(CH$_3$)C(O)OCH$_2$CH$_3$][3,4-methylenedioxyphenyl], —P(O)[—N(H)C(CH$_3$)$_2$C(O)OCH$_2$CH$_3$][3,4-methylenedioxyphenyl], —P(O)[—O—CH$_2$CH$_2$S—C(O)CH$_3$]$_2$, —P(O)(OH)(OCH$_3$), —P(O)(OH)(OCH$_2$CH$_3$), —P(O)(OH)(CH$_3$), —P(O)[—OCH(3-chlorophenyl)CH$_2$CH$_2$O—], —P(O)[—OCH(pyrid-4-yl)CH$_2$CH$_2$O—], —P(O)[—OCH$_2$OC(O)-i-butyl](OCH$_3$), —P(O)[—OCH$_2$OC(O)O-i-propyl](OCH$_3$), —P(O)[—OCH(CH$_3$)OC(O)-t-butyl](OCH$_3$), —P(O)[—OCH(CH$_3$)OC(O)O-i-propyl](OCH$_3$), —P(O)[—N(H)CH(CH$_3$)C(O)OCH$_2$CH$_3$](OCH$_3$), —P(O)[—N(H)CH(CH$_3$)C(O)OCH$_2$CH$_3$](CH$_3$), —P(O)[—N(H)C(CH$_3$)$_2$C(O)OCH$_2$CH$_3$](OCH$_3$), —P(O)[—N(H)C(CH$_3$)$_2$C(O)OCH$_2$CH$_3$](CH$_3$), —P(O)[—OCH$_2$OC(O)-t-butyl](CH$_3$), —P(O)[—OCH$_2$OC(O)O-i-propyl](CH$_3$), —P(O)[—OCH(CH$_3$)OC(O)-t-butyl](CH$_3$), —P(O)[—OCH(CH$_3$)OC(O)O-i-propyl](CH$_3$),
and —P(O)[—OCH$_2$OC(O)O-ethyl]$_2$.

A further embodiment ("Embodiment 15") is the compound of embodiment 14, wherein:

Substituent 1 is X and:

X is selected from the group consisting of aryl, heteroaryl, alkyl, cycloalkyl, arylalkyl, aryloxy, heteroaryloxy, alkyloxy, cycloalkyloxy and arylalkyloxy;

Substituent 2 is $R^2$ and:

$R^2$ is selected from the group consisting of aryl, heteroaryl, alkyl, cycloalkyl, arylalkyl, aryloxy, heteroaryloxy, alkyloxy, cycloalkyloxy, arylalkyloxy, arylthio, heteroarylthio, cycloalkylthio and arylalkylthio;

Substituent 3 is D and:
D is selected from heteroarylene or arylene, each optionally substituted;
Substituent 4 is $G^1$, $G^2$ and $G^3$ and:
$G^1$, $G^2$ and $G^3$ are $CR^4$ or N; and $R^4$ is H, halogen or alkyl;
Substituent 5 is $R^{50}$ and:
$R^{50}$ is —$R^{61}$—$R^{62}$, and $R^{62}$ is selected from —P(O)($Y^2R^{51}$)$R^1$, or —P(O)($YR^{51}$)$Y^1R^1$;
$R^{61}$ is selected from null, arylene, heteroarylene, arylene-alkylene, alkylene-arylene, heteroarylene-alkylene, alkylene-heteroarylene, alkylene, alkenylene, alkynylene, alkylene-Q-alkylene, —CONR$^{52}$-alkylene, —COO-alkylene, —SO$_2$NR$^{52}$-alkylene, arylene-Q-alkylene, alkylene-Q-arylene, heteroarylene-Q-alkylene, alkylene-Q-heteroarylene, all optionally substituted;
Q is selected from O, S, SO, SO$_2$, NR$^{53}$;
$R^1$ is selected from the group consisting of hydrogen, optionally substituted —$C_1$-$C_6$-alkyl, —$CF_3$, —$CHF_2$, —$CH_2F$, —$CH_2OH$, optionally substituted —$C_2$-$C_6$ alkenyl, optionally substituted —$C_2$-$C_6$ alkynyl, optionally substituted —$(CR^{52}_2)_n$, cycloalkyl, optionally substituted $(CR^{52}_2)_n$heterocycloalkyl, —$(CR^{52}_2)_k$ S(=O)$R^{53}$, —$(CR^{52}_2)_k$ S(=O)$_2R^{53}$;
Y, $Y^1$ and $Y^2$ are each independently selected from —O— or —NR$^{60}$—;
wherein,
when $Y^2$ is —O— or when Y and $Y^1$ are both —O—, $R^{51}$ attached to —O— is independently selected from the group consisting of —H, alkyl, optionally substituted aryl, optionally substituted heterocycloalkyl, optionally substituted —CH$_2$-heterocycloakyl with a cyclic moiety containing a carbonate or thiocarbonate, optionally substituted -alkylaryl, —C($R^{52}$)$_2$OC(O)NR$^{52}_2$, —NR$^{52}$—C(O)—$R^{53}$, —C($R^{52}$)$_2$—OC(O)$R^{53}$, —C($R^{52}$)$_2$—O—C(O)OR$^{53}$, —C($R^{52}$)$_2$OC(O)SR$^{53}$, -alkyl-S—C(O)$R^{53}$, -alkyl-S—S-alkylhydroxy
and -alkyl-S—S—S-alkylhydroxy; or
when $Y^2$ is —NR$^{60}$— or when Y and $Y^1$ are both —NR$^{60}$—, then $R^{51}$ attached to —NR$^{60}$— is independently selected from the group consisting of —H, —[C($R^{52}$)$_2$]$_r$—COOR$^{53}$, —C($R^{54}$)$_2$COOR$^{53}$, —[C($R^{52}$)$_2$]$_r$—C(O)SR$^{53}$,
and -cycloalkylene-COOR$^{53}$; or
when Y is —O— and $Y^1$ is NR$^{60}$, then $R^{51}$ attached to —O— is independently selected from —H, alkyl, optionally substituted aryl, optionally substituted heterocycloalkyl, optionally substituted CH$_2$-heterocycloakyl wherein the cyclic moiety contains a carbonate or thiocarbonate, optionally substituted -alkylaryl, —C($R^{52}$)$_2$OC(O)NR$^{52}_2$, —NR$^{52}$—C(O)—$R^{53}$, —C($R^{52}$)$_2$—OC(O)$R^{53}$, —C($R^{52}$)$_2$—O—C(O)OR$^{53}$, —C($R^{52}$)$_2$OC(O)SR$^{53}$, -alkyl-S—C(O)$R^{53}$, -alkyl-S—S-alkylhydroxy, and -alkyl-S—S—S-alkylhydroxy, and $R^{51}$ attached to —NR$^{60}$— is independently selected from —H, —[C($R^{52}$)$_2$]$_r$—COOR$^{53}$, —C($R^{54}$)$_2$COOR$^{53}$, —[C($R^{52}$)$_2$]$_r$—C(O)SR$^{53}$, and -cycloalkylene-COOR$^{53}$, wherein if both $R^{51}$ are alkyl, at least one is higher alkyl; or
when Y and $Y^1$ are independently selected from —O— and —NR$^{60}$—, then $R^{51}$ and $R^{51}$ together form a cyclic group comprising -alkyl-S—S-alkyl-, or $R^{51}$ and $R^{51}$ together are the group

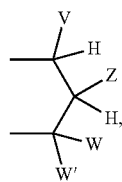

wherein,
V, W, and W' are independently selected from the group consisting of hydrogen, optionally substituted alkyl, optionally substituted aralkyl, heterocycloalkyl, aryl, substituted aryl, heteroaryl, substituted heteroaryl, optionally substituted 1-alkenyl, and optionally substituted 1-alkynyl, and
Z is —CHR$^{52}$OH, —CHR$^{52}$OC(O)$R^{53}$, —CHR$^{52}$OC(S)$R^{53}$, —CHR$^{52}$OC(S)OR$^{53}$, —CHR$^{52}$OC(O)SR$^{53}$, —CHR$^{52}$OCO$_2$R$^{53}$, —OR$^{52}$, —SR$^{52}$, —CHR$^{52}$N$_3$, —CH$_2$aryl, —CH(aryl)OH, —CH(CH=CR$^{52}_2$)OH, —CH(C≡CR$^{52}$)OH, —R$^{52}$, —NR$^{52}_2$, —O COR$^{53}$, —OCO$_2$R$^{53}$, —SCOR$^{53}$, —SCO$_2$R$^{53}$, —NHCOR$^{52}$, —NHCO$_2$R$^{53}$, —CH$_2$NHaryl, —(CH$_2$)$_r$—OR$^{52}$ or —(CH$_2$)$_r$—SR$^{52}$; or
W and W' are as defined above and together V and Z are connected via an additional 3-5 atoms to form a cyclic group containing 5-7 atoms, wherein 0-1 atoms are heteroatoms and the remaining atoms are carbon; or
W' and Z are as defined above and together V and W are connected via an additional 3 carbon atoms to form an optionally substituted cyclic group containing 6 carbon atoms or carbon substituted by hydrogen and substituted with one substituent selected from hydroxy, acyloxy, alkoxycarbonyloxy, alkylthiocarbonyloxy or aryloxycarbonyloxy which is attached to one of said carbon atoms that is three atoms from a Y attached to the phosphorus; or
V and W' are as defined above and together Z and W are connected via an additional 3-5 atoms to form a cyclic group, wherein 0-1 atoms are heteroatoms and the remaining atoms are carbon or carbon substituted by hydrogen, and V must be aryl, substituted aryl, heteroaryl, or substituted heteroaryl; or
V and Z are as defined above and together W and W' are connected via an additional 2-5 atoms to form a cyclic group, wherein 0-2 atoms are heteroatoms and the remaining atoms are carbon, where V must be aryl, substituted aryl, heteroaryl, or substituted heteroaryl;
$R^{51}$ is $R^{53}$ or —H;
$R^{53}$ is alkyl, aryl, heterocycloalkyl or aralkyl;
$R^{54}$ is independently selected from —H or alkyl, or together $R^{54}$ and $R^{54}$ form a cycloalkylene group;
$R^{60}$ is —H, lower alkyl, acyloxyalkyl, alkoxycarbonyloxyalkyl, lower acyl, $C_{1-6}$-perfluoroalkyl or NH(CR$^{55}$R$^{55}$)CH$_3$;
r is an integer 2 or 3;
f is an integer 0, 1 or 2;
wherein, V, Z, W, W' are not all —H, and when Z is —$R^{52}$, then at least one of V, W, and W' is not —H, alkyl, aralkyl, or heterocycloalkyl,
A further embodiment ("Embodiment 16") is the compound of embodiment 14, wherein:
Substituent 1 is X and:
X is selected from the group consisting of alkyl, cycloalkyl, alkyloxy, cycloalkyloxy and aryloxy;
Substituent 2 is $R^2$ and:
$R^2$ is -$E^1$-$E^2$-$E^3$, wherein,
$E^1$ is a bond, O or S;
$E^2$ is a bond or alkylene;

wherein, when both $E^1$ and $E^2$ are a bond, together they form a single bond;

$E^3$ is optionally substituted —$C_{1-4}$-alkyl, optionally substituted —$C_{3-8}$-cycloalkyl or aryl optionally substituted with one or two groups independently selected from the group consisting of halogen, —$C_{1-4}$-alkyl, —$S(O)_2R^5$ or —$OR^5$;

$R^5$ is alkyl or cycloalkyl; or $R^2$ is selected from the group consisting of —$C_{1-4}$-alkyloxy, —$C_{3-6}$-cycloalkyloxy, benzyloxy, 2-(2-thienyl)ethyloxy, 2-(3-thienyl)ethyloxy, and phenyloxy, each optionally substituted with one or two groups independently selected from the group consisting of halogen, —$C_{1-4}$-alkyl, —$S(O)_2C_{1-4}$-alkyl, —$S(O)_2C_{3-6}$-cycloalkyl, or —$OC_{1-4}$-alkyl;

Substituent 3 is D and:

D is heteroarylene, alkylene-heteroarylene, or arylene-heteroarylene, said heteroarylene comprising a nitrogen ring atom adjacent to a carbon ring atom, wherein said carbon ring atom is connected to the amide nitrogen atom adjacent to D, and wherein said heteroarylene has an additional 0 to 3 heteroatoms independently selected from O, S or N;

Substituent 4 is $G^1$, $G^2$ and $G^3$ and:

$G^1$ is $CR^4$; $G^2$ is $CR^4$; $G^3$ is $CR^4$; and $R^4$ is H, halogen or alkyl; and Substituent 5 is $R^{62}$ and:

$R^{62}$ is selected from the group consisting of:
—$PO_3H_2$, —$P(O)[—OCR^{52}_2OC(O)R^{53}]_2$, —$P(O)[—OCR^{52}_2OC(O)OR^{53}]_2$, —$P(O)[—N(H)CR^{52}_2C(O)O\ R^{53}]_2$, —$P(O)[—O-alk-SC(O)R^{53}]_2$, —$P(O)[—OCR^{52}_2OC(O)R^{53}][—R^1]$, —$P(O)[—OCR^{52}_2OC(O)OR^{53}][—R^1]$, —$P(O)[—N(H)CR^{52}_2C(O)OR^{53}][—R^1]$, —$P(O)[—OCH_2CH_2SC(O)R^{53}][—R^1]$, —$P(O)(OH)(YR^{51})$, —$P(O)(OR^{56})(OR^{56})$, —$P(O)(OH)(—R^1)$, —$P(O)[—OCR^{52}_2OC(O)R^{53}](OR^{56})$, —$P(O)[—OCR^{52}_2OC(O)OR^{53}](OR^{56})$, —$P(O)[—N(H)CR^{52}_2C(O)OR^{53}](OR^{56})$, $P(O)(OH)(NH_2)$, and —$P(O)[—OCH(V)CH_2CH_2O—]$;

V is optionally substituted aryl or optionally substituted heteroaryl;

$R^{56}$ is —$C_1$-$C_{12}$ alkyl, —$C_2$-$C_{12}$ alkenyl, —$C_2$-$C_{12}$ alkynyl, —$(CR^{57}_2)$aryl, —$(CR^{57}_2)$cycloalkyl, or —$(CR^{57}_2)$heterocycloalkyl, each optionally substituted;

each $R^{57}$ is independently selected from the group consisting of hydrogen, optionally substituted —$C_1$-$C_4$ alkyl, halogen, optionally substituted —O—$C_1$-$C_4$ alkyl, —$OCF_3$, optionally substituted —S—$C_1$-$C_4$ alkyl, —$NR^{58}R^{59}$, optionally substituted —$C_2$-$C_4$ alkenyl, and optionally substituted —$C_2$-$C_4$ alkynyl; with the proviso that when one $R^{57}$ is attached to C through an O, S, or N atom, then the other $R^{57}$ attached to the same C is a hydrogen, or attached via a carbon atom;

$R^{58}$ is selected from hydrogen and optionally substituted —$C_1$-$C_4$ alkyl; and, $R^{59}$ is selected from the group consisting of hydrogen and optionally substituted —$C_1$-$C_4$ alkyl, optionally substituted —C(O)—$C_1$-$C_4$ alkyl and —C(O)H.

A further embodiment ("Embodiment 17") is the compound of embodiment 14, wherein:

Substituent 1 is X and:

X is selected from the group consisting of alkyloxy and cycloalkyloxy;

Substituent 2 is $R^2$ and:

$R^2$ is selected from the group consisting of —$C_{1-4}$-alkyloxy, —$C_{3-6}$-cycloalkyloxy, benzyloxy, 2-(2-thienyl)ethyloxy, 2-(3-thienyl)ethyloxy, and phenyloxy, each optionally substituted with one or two groups independently selected from the group consisting of halogen, —$C_{1-4}$-alkyl, —$S(O)_2C_{1-4}$-alkyl, —$S(O)_2C_{3-6}$-cycloalkyl, or —$OC_{1-4}$-alkyl; or Substituent 3 is D and:

D is a heteroarylene, optionally substituted with one or two groups independently selected from halogen and optionally substituted $C_{1-4}$-alkyl; wherein, when said heteroarylene is pyridine-diyl, pyrazole-diyl, pyridaze-diyl or pyramidine-diyl, the ring atom at position 5 of said heteroarylene is connected to $R^{50}$ and when said heteroarylene is thiazole-diyl or thiadiazole-diyl, the ring atom at position 4 of said heteroarylene is connected to $R^{50}$, and n is 0 or 1;

Substituent 4 is $G^1$, $G^2$ and $G^3$ and:

$G^1$ is CH; $G^2$ is CH; and $G^3$ is CH; and

Substituent 5 is $R^{52}$ and:

$R^6$ is selected from the group consisting of —$P(O)(OH)_2$, —$P(O)[—OCH_2OC(O)$-t-butyl$]_2$, —$P(O)[—OCH(CH_3)OC(O)$-t-butyl$]_2$, —$P(O)[—OCH(CH_3)OC(O)O$-i-propyl$]_2$, —$P(O)[—OCH_2OC(O)O$-i-propyl$]$, —$P(O)[—N(H)CH(CH_3)C(O)OCH_2CH_3]_2$, —$P(O)[—N(H)C(CH_3)_2C(O)OCH_2CH_3]_2$, —$P(O)[—N(H)CH(CH_3)C(O)OCH_2CH_3][3,4$-methylenedioxyphenyl$]$, —$P(O)[—N(H)C(CH_3)_2C(O)OCH_2CH_3][3,4$-methylenedioxyphenyl$]$, —$P(O)[—O—CH_2CH_2S—C(O)CH_3]_2$, —$P(O)(OH)(OCH_3)$, —$P(O)(OH)(OCH_2CH_3)$, —$P(O)(OH)(CH_3)$, —$P(O)[—OCH(3$-chlorophenyl$)CH_2CH_2O—]$, —$P(O)[—OCH($pyrid-4-yl$)CH_2CH_2O—]$, —$P(O)[—OCH_2OC(O)$-t-butyl$](OCH_3)$, —$P(O)[—OCH_2OC(O)O$-i-propyl$](OCH_3)$, —$P(O)[—OCH(CH_3)OC(O)$-t-butyl$](OCH_3)$, —$P(O)[—OCH(CH_3)OC(O)O$-i-propyl$](OCH_3)$, —$P(O)[—N(H)CH(CH_3)C(O)OCH_2CH_3](OCH_3)$, —$P(O)[—N(H)CH(CH_3)C(O)OCH_2CH_3](CH_3)$, —$P(O)[—N(H)C(CH_3)_2C(O)OCH_2CH_3](OCH_3)$, —$P(O)[—N(H)C(CH_3)_2C(O)OCH_2CH_3](CH_3)$, —$P(O)[—OCH_2OC(O)$-t-butyl$](CH_3)$, —$P(O)[—OCH_2OC(O)O$-i-propyl$](CH_3)$, —$P(O)[—OCH(CH_3)OC(O)$-t-butyl$](CH_3)$, —$P(O)[—OCH(CH_3)OC(O)O$-i-propyl$](CH_3)$, and —$P(O)[—OCH_2OC(O)O$-ethyl$]_2$ A further embodiment ("Embodiment 18") is the compound of embodiments 14, 15, 16 or 17, wherein $R^2$ is selected from the group consisting of n-propyloxy, isopropyloxy, 2-methylpropyloxy, cylclopentylmethyloxy, benzyloxy, 2-(2-thienyl)ethyloxy, 2-(3-thienyl)ethyloxy, 2-fluorophenylmethyloxy, 4-methylsulfonylphenyloxy, 4-ethylsulfonylphenyloxy and 4-isopropylsulfonylphenyloxy.

A further embodiment ("Embodiment 19") is the compound according to any of embodiments 1-18, wherein $R^{61}$ is selected from null, arylene, heteroarylene, arylene-alkylene, alkylene-arylene, heteroarylene-alkylene, alkylene-heteroarylene, —$CONR^{52}$-alkylene, —COO-alkylene or —$SO_2NR^{52}$-alkylene, and all groups are optionally substituted.

A further embodiment ("Embodiment 20") is the compound according to any of embodiments 1-18, wherein $R^{61}$ is selected from null, arylene, heteroarylene, and all groups are optionally substituted.

A further embodiment ("Embodiment 21") is a compound of general Formula (II),

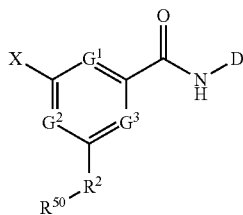

(II)

wherein:

X is selected from the group consisting of aryl, heteroaryl, alkyl, cycloalkyl, arylalkyl, aryloxy, heteroaryloxy, alkyloxy, cycloalkyloxy and arylalkyloxy, and $G^2$ is $CR^4$ or N, or together $G^2$ and X are connected to form a cyclic group containing 5-7 atoms, wherein 0-2 atoms of said cyclic group are heteroatoms and the remaining atoms of said cyclic group are carbon atoms substituted with alkyl, aryl, cycloalkyl or heteroaryl;

$R^2$ is optionally substituted and is selected from arylene, heteroarylene, alkylene, cycloalkylene, arylalkylene, alkylarylene, arylene-O—, heteroarylene-O—, alkylene-O—, cycloalkylene-O—, arylalkylene-O—, alkylarylene-O—, arylene-S—, heteroarylene-S—, alkylene-S-cycloalkylene-S—, arylalkylene-S—, or alkylarylene-S—, wherein $R^2$ is connected to $R^{50}$ by a C atom;

$G^1$ is $CR^4$ or N;

$R^4$ is H, halogen or optionally substituted alkyl;

$G^3$ is $CR^4$ or N;

$R^4$ is H, halogen or optionally substituted alkyl;

D is selected from a group consisting of heteroaryl or aryl;

$R^{50}$ is —P(O)($Y^2R^{51}$) $R^1$ or —P(O)($YR^{51}$)$Y^1R^{51}$;

$R^1$ is selected from the group consisting of hydrogen, optionally substituted —$C_1$-$C_6$-alkyl, —$CF_3$, —$CHF_2$, —$CH_2F$, —$CH_2OH$, optionally substituted —$C_2$-$C_6$ alkenyl, optionally substituted —$C_2$-$C_6$ alkynyl, optionally substituted —$(CR^{52}_2)_n$cycloalkyl, optionally substituted —$(CR^{52}_2)_n$heterocycloalkyl, —$(CR^{52}_2)_k$S(=O)$R^{53}$, —$(CR^{52}_2)_kS$(=O)$_2R^{53}$;

Y, $Y^1$ and $Y^2$ are each independently selected from —O— or —$NR^{60}$—;

wherein, when $Y^2$ is —O— or when Y and $Y^1$ are both —O—, $R^{51}$ attached to —O— is independently selected from —H, alkyl, optionally substituted aryl, optionally substituted heterocycloalkyl, optionally substituted —$CH_2$-heterocycloakyl wherein the cyclic moiety contains a carbonate or thiocarbonate, optionally substituted -alkylaryl, —$C(R^{52})_2OC(O)NR^{52}_2$, —$NR^{52}$—C(O)—$R^{53}$, —$C(R^{52})_2$—OC(O)$R^{53}$, —$C(R^{52})_2$—O—C(O)O$R^{53}$, —$C(R^{52})_2OC(O)SR^{53}$, -alkyl-S—C(O)$R^{53}$, -alkyl-S—S-alkylhydroxy, and -alkyl-S—S—S-alkylhydroxy; or when $Y^2$ is —$NR^{60}$— or when Y and $Y^1$ are both —$NR^{60}$— then $R^{51}$ attached to —$NR^{60}$— is independently selected from —H, —$[C(R^{52})_2]_r$—COOR$^{53}$, —$C(R^{54})COOR^{53}$, —$[C(R^{52})_2]_r$—C(O)SR$^{53}$, and -cycloalkylene-COOR$^{53}$; or when Y is —O— and $Y^1$ is $NR^{60}$, then $R^{51}$ attached to —O— is independently selected from —H, alkyl, optionally substituted aryl, optionally substituted heterocycloalkyl, optionally substituted $CH_2$-heterocycloakyl wherein the cyclic moiety contains a carbonate or thiocarbonate, optionally substituted -alkylaryl, —$C(R^{52})_2OC(O)NR^{52}_2$, —$NR^{52}$—C(O)—$R^{53}$, —$C(R^{52})_2$—OC(O)$R^{53}$, —$C(R^{52})_2$—O—C(O)O$R^{53}$, —$C(R^{52})_2OC(O)SR^{53}$, -alkyl-S—C(O)$R^{53}$, -alkyl-S—S-alkylhydroxy, and -alkyl-S—S—S-alkylhydroxy, and $R^{51}$ attached to —$NR^{60}$— is independently selected from —H, —$[C(R^{52})_2]_r$—COOR$^{53}$, —$C(R^{54})_2COOR^{53}$, —$[C(R^{52})_2]_r$C(O)SR$^{53}$, and -cycloalkylene-COOR$^{53}$, wherein if both $R^{51}$ are alkyl, at least one is higher alkyl; or when Y and $Y^1$ are independently selected from —O— and —$NR^{60}$—, then $R^{51}$ and $R^{51}$ together form a cyclic group comprising -alkyl-S—S-alkyl-, or $R^{51}$ and $R^{51}$ together are the group

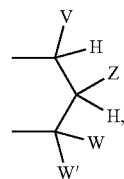

wherein,

V, W, and W' are independently selected from the group consisting of hydrogen, optionally substituted alkyl, optionally substituted aralkyl, heterocycloalkyl, aryl, substituted aryl, heteroaryl, substituted heteroaryl, optionally substituted 1-alkenyl, and optionally substituted 1-alkynyl, and Z is —CHR$^{52}$OH, —CHR$^{52}$OC(O)R$^{53}$, —CHR$^{52}$OC(S) R$^{53}$, —CHR$^{52}$OC(S)OR$^{53}$, —CHR$^{52}$OC(O)SR$^{53}$, —CHR$^{52}$OCO$_2$R$^{53}$, —OR$^{52}$, —SR$^{52}$, —CHR$^{52}$N$_3$, —CH$_2$aryl, —CH(aryl)OH, —CH(CH=CR$^{52}_2$)OH, —CH(C≡CR$^{52}$)OH, —R$^{52}$, —NR$^{52}_2$, —OC OR$^{53}$, —OCO$_2$R$^{53}$, —SCOR$^{53}$, —SCO$_2$R$^{53}$, —NHCOR$^{52}$, —NHCO$_2$R$^{53}$, —CH$_2$NHaryl, —(CH$_2$)$_r$—OR$^{52}$ or —(CH$_2$)$_r$—SR$^{52}$; or W and W are as defined above and together V and Z are connected via an additional 3-5 atoms to form a cyclic group containing 5-7 atoms, wherein 0-1 atoms are heteroatoms and the remaining atoms are carbon; or W' and Z are as defined above and together V and W are connected via an additional 3 carbon atoms to form an optionally substituted cyclic group containing 6 carbon atoms or carbon substituted by hydrogen and substituted with one substituent selected from hydroxy, acyloxy, alkoxycarbonyloxy, alkylthiocarbonyloxy or aryloxycarbonyloxy which is attached to one of said carbon atoms that is three atoms from a Y attached to the phosphorus; or V and W' are as defined above and together 7 and W are connected via an additional 3-5 atoms to form a cyclic group, wherein 0-1 atoms are heteroatoms and the remaining atoms are carbon or carbon substituted by hydrogen, and V must be aryl, substituted aryl, heteroaryl, or substituted heteroaryl; or V and Z are as defined above and together W and W' are connected via an additional 2-5 atoms to form a cyclic group, wherein 0-2 atoms are heteroatoms and the remaining atoms are carbon, where V must be aryl, substituted aryl, heteroaryl, or substituted heteroaryl;

$R^{52}$ is $R^{53}$ or —H;

$R^{53}$ is alkyl, aryl, heterocycloalkyl or aralkyl;

$R^{54}$ is independently selected from —H or alkyl, or together $R^{54}$ and $R^{54}$ form a cycloalkylene group;

$R^{60}$ is —H, lower alkyl, acyloxyalkyl, alkoxycarbonyloxyalkyl, lower acyl, $C_{1-6}$-perfluoroalkyl or NH(CR$^{53}$R$^{55}$)$_f$CH$_3$;

r is an integer 2 or 3;

f is an integer 0, 1 or 2;

wherein, V, Z, W, W' are not all —H, and when Z is —$R^{52}$, then at least one of V, W, and W' is not —H, alkyl, aralkyl, or heterocycloalkyl; and pharmaceutically acceptable salts, co-crystals and prodrugs thereof.

A further embodiment ("Embodiment 22") is the compound of embodiment 21, wherein X is selected from the group consisting of alkyl, cycloalkyl, alkyloxy, cycloalkyloxy and aryloxy.

A further embodiment ("Embodiment 23") is the compound of embodiment 21, wherein X is selected from the group consisting of alkyloxy and cycloalkyloxy.

A further embodiment ("Embodiment 24") is the compound of embodiment 21, wherein X is selected from the group consisting of aryl, heteroaryl, alkyl, cycloalkyl, arylalkyl, aryloxy, heteroaryloxy, alkyloxy, cycloalkyloxy and arylalkyloxy.

A further embodiment ("Embodiment 25") is the compound of embodiment 21, wherein $R^2$ is -$E^1$-$E^2$-$E^3$-$E^4$-, wherein $E^4$ is connected to $R^{50}$;

$E^1$ is a bond, O or S;

$E^2$ is a bond or alkylene;

$E^3$ is optionally substituted $C_{1-4}$-alkylene, optionally substituted $C_{3-8}$-cycloalkylalkylene, arylene or heteroarylene optionally substituted with one or two groups independently selected from aryl, heteroaryl, cycloalkyl, cycloalkenyl, halogen, CN, $CF_3$, $NR^5_2$, —$C_{1-4}$-alkyl, —$S(O)_2R^5$ or —$OR^5$; wherein, when both $E^1$ and $E^2$ are a bond, together they form a single bond;

$R^5$ is optionally substituted alkyl or cycloalkyl; and $E^4$ is a bond or alkylene.

A further embodiment ("Embodiment 26") is the compound of embodiment 21, wherein $R^2$ is selected from the group consisting of phenylene-O—, methylene-phenylene-O—, phenylene-methylene-O—, furan-2-yl-5-methylene, thiophen-2-yl-5-methylene, pyridin-diyl-O—, pyrimidin-diyl-O—, pyridazin-diyl-O— and pyrazin-diyl-O—, each optionally substituted with one or two groups independently selected from aryl, heteroaryl, halogen, CN, $CF_3$, $NR^5_2$, —$C_{1-4}$-alkyl, —$S(O)_2R^5$ or —$OR^5$, wherein $R^{50}$ is connected to $R^2$ by a carbon atom.

A further embodiment ("Embodiment 27") is the compound of embodiment 21, wherein $R^2$ is methylene-thiophen-2,5-diyl, phenylene-O— or thiophen-2-yl-S-methylene, wherein $R^5$ is connected to the phenylene or thiophenyl group.

A further embodiment ("Embodiment 28") is the compound of embodiment 21, wherein $R^2$ is optionally substituted and is selected from arylene, heteroarylene, alkylene, cycloalkylene, arylalkylene, alkylarylene, arylene-O—, heteroarylene-O—, alkylene-O—, cycloalkylene-O—, arylalkylene-O—, alkylarylene-O—, arylene-S—, heteroarylene-S—, alkylene-S—, cycloalkylene-S—, arylalkylene-S—, or alkylarylene-S—, wherein $R^{50}$ is connected to $R^2$ by a carbon atom.

A further embodiment ("Embodiment 29") is the compound according to embodiment 21, wherein $G^1$ and $G^2$ are $CR^4$ or N.

A further embodiment ("Embodiment 30") is the compound of embodiment 21, wherein $G^1$ and $G^2$ are $CR^4$ and $R^4$ is H, halogen or optionally substituted alkyl.

A further embodiment ("Embodiment 31") is the compound according to embodiment 30, wherein $R^4$ is H.

A further embodiment ("Embodiment 32") is the compound of embodiment 21, wherein $G^3$ is $CR^4$ or N.

A further embodiment ("Embodiment 33") is the compound of embodiment 21, wherein $G^3$ is $CR^4$ and $R^4$ is I— halogen or optionally substituted alkyl.

A further embodiment ("Embodiment 34") is the compound of embodiment 21, wherein $R^4$ is H.

A further embodiment ("Embodiment 35") is the compound of embodiment 21, wherein D is selected from a group consisting of heteroaryl or aryl.

A further embodiment ("Embodiment 36") is the compound of embodiment 21, wherein D is a heteroaryl having a nitrogen as a ring atom, said heteroaryl comprising a nitrogen ring atom adjacent to a carbon ring atom, wherein said carbon ring atom is connected to the amide nitrogen atom adjacent to D, and wherein said heteroaryl has an additional 0 to 3 heteroatoms independently selected from O, S or N.

A further embodiment ("Embodiment 37") is the compound of embodiment 21, wherein D is selected from the group consisting of pyridinyl, thiazolyl, 1,3,4-thiadiazolyl, 1,2,4-thiadiazolyl, oxazolyl, isoxazolyl, imidazolyl, pyrazolyl, pyrazinyl, pyridazinyl, pyrimidinyl, benzothiazolyl and 5,6-dihydro-4H-cyclopentathiazolyl, each optionally substituted with one or two groups selected from halogen, $CF_3$, or optionally substituted $C_{1-4}$-alkyl.

A further embodiment ("Embodiment 38") is the compound of embodiment 21, wherein D is selected from the group consisting of thiazolyl, 1,3,4-thiadiazolyl, and 1,2,4-thiadiazolyl, each optionally substituted with one or two groups selected from halogen, $CF_3$, or optionally substituted $C_{1-4}$-alkyl.

A further embodiment ("Embodiment 39") is the compound of embodiment 21, wherein $R^{50}$ is —$P(O)(Y^2R^{51})R^1$ or —$P(O)(YR^{51})Y^1R^{51}$;

$R^1$ is selected from the group consisting of hydrogen, optionally substituted —$C_1$-$C_6$-alkyl, —$CF_3$, —$CHF_2$, —$CH_2F$, —$CH_2OH$, optionally substituted —$C_2$-$C_6$ alkenyl, optionally substituted —$C_2$-$C_6$ alkynyl, optionally substituted —$(CR^{52}_2)$cycloalkyl, optionally substituted —$(CR^{52}_2)_n$heterocycloalkyl, —$(CR^{52}_2)_k$ S(=O)$R^{53}$, —$(CR^{52}_2)_k$S(=O)$_2R^{53}$;

Y, $Y^1$ and $Y^2$ are each independently selected from —O— or —$NR^{60}$—;

wherein, when $Y^2$ is —O— or when Y and $Y^1$ are both —O—, $R^{51}$ attached to —O— is independently selected from —H, alkyl, optionally substituted aryl, optionally substituted heterocycloalkyl, optionally substituted —$CH_2$-heterocycloakyl wherein the cyclic moiety contains a carbonate or thiocarbonate, optionally substituted -alkylaryl, —$C(R^{52})_2OC(O)NR^{52}_2$, —$NR^{52}$—C(O)—$R^{53}$, —$C(R^{52})_2$—OC(O)$R^{53}$, —$C(R^{52})_2$—O—C(O)OR$^{53}$, —$C(R^{52})_2OC(O)SR^{53}$, -alkyl-S—C(O)$R^{53}$, -alkyl-S—S-alkylhydroxy, and -alkyl-S—S—S-alkylhydroxy; or when $Y^2$ is —$NR^{60}$— or when Y and $Y^1$ are both —$NR^{60}$, then $R^{51}$ attached to —$NR^{60}$— is independently selected from —H, —$[C(R^{52})_2]_r$—COOR$^{53}$, —$C(R^{54})_2COOR^{53}$, —$[C(R^{52})_2]_r$—C(O)SR$^{53}$, and -cycloalkylene-COOR$^{53}$; or when Y is —O— and $Y^1$ is $NR^{60}$, then $R^{51}$ attached to —O— is independently selected from —H, alkyl, optionally substituted aryl, optionally substituted heterocycloalkyl, optionally substituted $CH_2$-heterocycloakyl wherein the cyclic moiety contains a carbonate or thiocarbonate, optionally substituted -alkylaryl, —$C(R^{52})_2OC(O)NR^{52}_2$, —$NR^{52}$—C(O)—$R^{53}$, —$C(R^{52})_2$—OC(O)$R^{53}$, —$C(R^{52})_2$—O—C(O)OR$^{53}$, —$C(R^{52})_2OC(O)SR^{53}$, -alkyl- S—C(O)R$^{53}$, -alkyl-S—S-alkylhydroxy, and -alkyl-S—S—S-alkylhydroxy, and R$^{51}$ attached to —NR$^{60}$— is independently selected from —H, —[C(R$^{52}$)$_2$]$_r$—COOR$^{53}$, —C(R$^{54}$)$_2$COOR$^{53}$, —[C(R$^{52}$)$_2$]$_r$—C(O)SR$^{53}$, and -cycloalkylene-COOR$^{53}$, wherein if both R$^{51}$ are alkyl, at least one is higher alkyl; or when Y and Y$^1$ are independently selected from —O— and —NR$^{60}$—, then R$^{51}$ and R$^{51}$ together form a cyclic group comprising -alkyl-S—S-alkyl-, or R$^{51}$ and R$^{51}$ together are the group

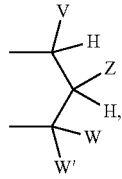

wherein,

V, W, and W' are independently selected from the group consisting of hydrogen, optionally substituted alkyl, optionally substituted aralkyl, heterocycloalkyl, aryl, substituted aryl, heteroaryl, substituted heteroaryl, optionally substituted 1-alkenyl, and optionally substituted 1-alkynyl, and Z is —CHR$^{52}$OH, —CHR$^{52}$OC(O)R$^{53}$, —CHR$^{52}$OC(S)R$^{53}$, —CHR$^{52}$OC(S)OR$^{53}$, —CHR$^{52}$OC(O)SR$^{53}$, —CHR$^{52}$OCO$_2$R$^{53}$, —OR$^{52}$, —SR$^{52}$, —CHR$^{52}$N$_3$, —CH$_2$aryl, —CH(aryl)OH, —CH(CH=CR$^{52}$$_2$)OH, —CH(C≡CR$^{52}$)OH, —R$^{52}$, —NR$^{52}$$_2$, —OC OR$^{53}$, —OCO$_2$R$^{53}$, —SCOR$^{53}$, —SCO$_2$R$^{53}$, —NHCOR$^{52}$, —NHCO$_2$R$^{53}$, —CH$_2$NHaryl, —(CH$_2$)$_r$—OR$^{52}$ or —(CH$_2$)—SR$^{52}$; or W and W are as defined above and together V and Z are connected via an additional 3-5 atoms to form a cyclic group containing 5-7 atoms, wherein 0-1 atoms are heteroatoms and the remaining atoms are carbon; or W' and Z are as defined above and together V and W are connected via an additional 3 carbon atoms to form an optionally substituted cyclic group containing 6 carbon atoms or carbon substituted by hydrogen and substituted with one substituent selected from hydroxy, acyloxy, alkoxycarbonyloxy, alkylthiocarbonyloxy or aryloxycarbonyloxy which is attached to one of said carbon atoms that is three atoms from a Y attached to the phosphorus; or V and W' are as defined above and together Z and W are connected via an additional 3-5 atoms to form a cyclic group, wherein 0-1 atoms are heteroatoms and the remaining atoms are carbon or carbon substituted by hydrogen, and V must be aryl, substituted aryl, heteroaryl, or substituted heteroaryl; or V and Z are as defined above and together W and W' are connected via an additional 2-5 atoms to form a cyclic group, wherein 0-2 atoms are heteroatoms and the remaining atoms are carbon, where V must be aryl, substituted aryl, heteroaryl, or substituted heteroaryl;

R$^{52}$ is R$^{53}$ or —H:

R$^{53}$ is alkyl, aryl, heterocycloalkyl or aralkyl;

R$^{54}$ is independently selected from —H or alkyl, or together R$^{54}$ and R$^{54}$ form a cycloalkylene group;

R$^{60}$ is —H, lower alkyl, acyloxyalkyl, alkoxycarbonyloxyalkyl, lower acyl, C$_{1-6}$-perfluoroalkyl or NH(CR$^{55}$R$^{55}$)$_f$CH$_3$;

r is an integer 2 or 3;

f is an integer 0, 1 or 2;

wherein, V, Z, W, W' are not all —H, and when Z is —R$^{52}$, then at least one of V, W, and W' is not —H, alkyl, aralkyl, or heterocycloalkyl.

A further embodiment ("Embodiment 40") is the compound of embodiment 21, wherein R$^{50}$ is selected from the group consisting of —PO$_3$H$_2$, —P(O)[—OCR$^{52}$$_2$OC(O)R$^{53}$]$_2$, —P(O)[—OCR$^{52}$$_2$OC(O)OR$^{53}$]$_2$, —P(O)[—N(H)CR$^{52}$$_2$C(O) OR$^{53}$]$_2$, —P(O)[—O-alk-SC(O)R$^{53}$]$_2$, —P(O)[—OCR$^{52}$$_2$OC(O)R$^{53}$][—R$^1$], —P(O)[—OCR$^{52}$$_2$OC(O)OR$^{53}$][—R$^1$], —P(O)[—N(H)CR$^{52}$$_2$C(O)OR$^{43}$][—R$^1$], —P(O)[—OCH$_2$CH$_2$SC(O)R$^{53}$][—R$^1$], —P(O)(OH)(YR$^{51}$), —P(O)(OR$^{56}$)(OR$^{56}$), —P(O)(OH)(—R$^1$), —P(O)[—OCR$^{52}$$_2$OC(O)R$^{53}$](OR$^{56}$), —P(O)[—OCR$^{52}$$_2$OC(O)OR$^{53}$](OR$^{56}$), —P(O)[—N(H)CR$^{52}$$_2$ C(O)OR$^{53}$](OR$^{56}$), P(O)(OH)(NH$_2$), and —P(O)[—OCH(V)CH$_2$CH$_2$O—];

V is optionally substituted aryl or optionally substituted heteroaryl;

R$^{56}$ is —C$_1$-C$_{12}$ alkyl, —C$_2$-C$_{12}$ alkenyl, —C$_2$-C$_{12}$ alkynyl, —(CR$^{72}$$_2$)$_n$aryl, —(CR$^{57}$$_2$)cycloalkyl, or —(CR$^{57}$$_2$)$_n$heterocycloalkyl, each optionally substituted;

each R$^{57}$ is independently selected from the group consisting of hydrogen, optionally substituted —C$_1$-C$_4$ alkyl, halogen, optionally substituted —O—C$_1$-C$_4$ alkyl, —OCF$_3$, optionally substituted —S—C$_1$-C$_4$ alkyl, —NR$^{58}$R$^{59}$, optionally substituted —C$_2$-C$_4$ alkenyl, and optionally substituted —C$_2$-C$_4$ alkynyl; with the proviso that when one R$^{57}$ is attached to C through an O, S, or N atom, then the other R$^{57}$ attached to the same C is a hydrogen, or attached via a carbon atom;

R$^{58}$ is selected from hydrogen and optionally substituted —C$_1$-C$_4$ alkyl; and, R$^{59}$ is selected from the group consisting of hydrogen and optionally substituted —C$_1$-C$_4$ alkyl, optionally substituted —C(O)—C$_1$-C$_4$ alkyl and —C(O)H.

A further embodiment ("Embodiment 41") is the compound of embodiment 21, wherein R$^{50}$ is selected from the group consisting of P(O)(OH)$_2$, —P(O)[—OCH$_2$OC(O)-t-butyl]$_2$, —P(O)[—OCH(CH$_3$)OC(O)-t-butyl]$_2$, —P(O)[—OCH(CH$_3$)OC(O)O-i-propyl]$_2$, —P(O)[—OCH$_2$OC(O)O-i-propyl]$_2$, —P(O)[—N(H)CH(CH$_3$)C(O)OCH$_2$ CH$_3$]$_2$, —P(O)[—N(H)C(CH$_3$)$_2$C(O)OCH$_2$CH$_3$]$_2$, —P(O)[—N(H)CH(CH$_3$)C(O)OCH$_2$CH$_3$][3,4-methylenedioxyphenyl], —P(O)[—N(H)C(CH$_3$)$_2$C(O)OCH$_2$CH$_3$][3,4-methylenedioxyphenyl], —P(O)[—O—CH$_2$CH$_2$S—C(O)CH$_3$]$_2$, —P(O)(OH)(OCH$_3$), —P(O)(OH)(OCH$_2$CH$_3$), —P(O)(OH)(CH$_3$), —P(O)[—OCH(3-chlorophenyl)CH$_2$CH$_2$O—], —P(O)[—OCH(pyrid-4-yl)CH$_2$CH$_2$O—], —P(O)[—OCH$_2$OC(O)-t-butyl](OCH$_3$), —P(O)[—OCH$_2$OC(O)O-i-propyl](OCH$_3$), —P(O)[—OCH(CH$_3$)OC(O)-t-butyl](OCH$_3$), —P(O)[—OCH(CH$_3$)OC(O)O-i-propyl](OCH$_3$), —P(O)[—N(H)CH(CH$_3$)C(O)OCH$_2$CH$_3$](OCH$_3$), —P(O)[—N(H)CH(CH$_3$)C(O)OCH$_2$CH$_3$](CH$_3$), —P(O)[—N(H)C(CH$_3$)$_2$C(O)OCH$_2$CH$_3$](OCH$_3$), —P(O)[—N(H)C(CH$_3$)$_2$C(O)OCH$_2$CH$_3$](CH$_3$), —P(O) [—OCH$_2$OC(O)-t-butyl](CH$_3$), —P(O)[—OCH$_2$OC(O)O-i-propyl](CH$_3$), —P(O)[—OCH(CH$_3$)OC(O)-t-butyl](CH$_3$), and —P(O)[—OCH(CH$_3$)OC(O)O-i-propyl](CH$_3$), and —P(O)[—OCH$_2$OC(O)O-ethyl]$_2$.

A further embodiment ("Embodiment 42") is the compound of embodiment 21, wherein Y and Y$^1$ are each independently selected from —O— and —NR$^{60}$—; and together R$^{51}$ and R$^{51}$ are the group

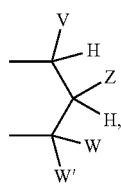

wherein, V is substituted aryl or substituted heteroaryl.

A further embodiment ("Embodiment 43") is the compound of embodiment 21, wherein $G^2$ is $CR^4$ or N, or together $G^2$ and X are connected to form a cyclic group containing 5-7 atoms, wherein 0-2 atoms of said cyclic group are heteroatoms and the remaining atoms of said cyclic group are carbon atoms substituted with alkyl, aryl, cycloalkyl or heteroaryl.

A further embodiment ("Embodiment 44") is the compound of embodiment 43, wherein $G^2$ is $CR^4$.

A further embodiment ("Embodiment 45") is the compound of embodiment 44, wherein $R^4$ is H.

A further embodiment ("Embodiment 46") is the compound of embodiment 43, wherein together $G^2$ and X are connected to form a cyclic group containing 5-7 atoms, wherein 0-2 atoms of said cyclic group are heteroatoms and the remaining atoms of said cyclic group are carbon atoms substituted with alkyl, aryl, cycloalkyl or heteroaryl.

A further embodiment ("Embodiment 47") is the compound of embodiment 43, wherein $G^2$ is N.

A further embodiment ("Embodiment 48") is the compound of embodiment 21, wherein:

X is selected from the group consisting of alkyloxy and cycloalkyloxy;

$R^2$ is selected from the group consisting of phenylene-O—, methylene-phenylene-O—, phenylene-methylene-O—, furan-2-yl-5-methylene, thiophen-2-yl-5-methylene, pyridin-diyl-O—, pyrimidin-diyl-O—, pyridazin-diyl-O— and pyrazin-diyl-O—, each optionally substituted with one or two groups independently selected from halogen, CN, $CF_3$, $NR^5_2$, —$C_{1-4}$-alkyl, —$S(O)_2R^5$ or —$OR^5$, wherein $R^2$ is connected to $R^{50}$ by a C ring atom;

$G^1$, $G^2$ and $G^3$ are $CR^4$ and $R^4$ is H;

D is selected from the group consisting of thiazolyl, 1,3,4-thiadiazolyl, 1,2,4-thiadiazolyl, each optionally substituted with one or two groups selected from halogen, $CF_3$, or optionally substituted $C_{1-4}$-alkyl; and $R^{50}$ is selected from the group consisting of: $P(O)(OH)_2$, —$P(O)[-OCH_2OC(O)$-t-butyl$]_2$, —$P(O)[-OCH(CH_3)OC(O)$-t-butyl$]_2$, —$P(O)[-OCH(CH_3)OC(O)$O-i-propyl$]_2$, —$P(O)[-OCH_2OC(O)$O-i-propyl$]_2$, —$P(O)[-OCH_2OC(O)$O-ethyl$]_2$, —$P(O)[-N(H)CH(CH_3)C(O)OCH_2CH_3]_2$, —$P(O)[-N(H)C(CH_3)_2C(O)OCH_2CH_3]_2$, —$P(O)[-OCH(3$-chlorophenyl$)CH_2CH_2O$—], —$P(O)[-OCH(pyrid-4-yl)CH_2CH_2O$—], or —$P(O)[-OCH(V)CH_2CH_2O$—];

and V is optionally substituted aryl or optionally substituted heteroaryl.

A further embodiment ("Embodiment 49") is the compound of embodiment 44, wherein $R^2$ is phenylene-O—.

A further embodiment ("Embodiment 50") is the compound of embodiment 21, wherein:

X is selected from the group consisting of alkyloxy and cycloalkyloxy;

$R^2$ is optionally substituted methylene-thiophen-2,5-diyl, phenylene-O— or thiophen-2-yl-5-methylene, wherein $R^{50}$ is attached to phenylene or thiophenyl;

$G^1$, $G^2$ and $G^3$ are CH;

D is thiazolyl, optionally substituted with one or two groups selected from halogen, $CF_3$, or optionally substituted $C_{1-4}$-alkyl;

$R^{50}$ is selected from the group consisting of —$P(O)(OH)_2$, —$P(O)[-OCH_2OC(O)$-t-butyl$]_2$, —$P(O)[-OCH(CH_3)OC(O)$-t-butyl$]_2$, —$P(O)[-OCH(CH_3)OC(O)$O-i-propyl$]_2$, —$P(O)[-OCH_2OC(O)$O-i-propyl$]_2$, —$P(O)[-OCH_2OC(O)$O-ethyl$]_2$, —$P(O)[-N(H)CH(CH_3)C(O)OCH_2CH_3]_2$, —$P(O)[-N(H)C(CH_3)_2C(O)OCH_2CH_3]_2$, —$P(O)[-OCH(3$-chlorophenyl$)CH_2CH_2O$—], —$P(O)[-OCH(pyrid-4-yl)CH_2CH_2O$—], or —$P(O)[-OCH(V)CH_2CH_2O$—];

and V is optionally substituted aryl or optionally substituted heteroaryl.

A further embodiment ("Embodiment 51") is the compound of embodiment 21, wherein said compound has one of the following combinations of substituents:

| Combination | Substituent Nos. |
|---|---|
| #1 | 1, 2 |
| #2 | 1, 3 |
| #3 | 1, 4 |
| #4 | 1, 5 |
| #5 | 1, 6 |
| #6 | 2, 3 |
| #7 | 2, 4 |
| #8 | 2, 5 |
| #9 | 2, 6 |
| #10 | 3, 4 |
| #11 | 3, 5 |
| #12 | 3, 6 |
| #13 | 4, 5 |
| #14 | 4, 6 |
| #15 | 5, 6 |
| #16 | 1, 2, 3 |
| #17 | 1, 2, 4 |
| #18 | 1, 2, 5 |
| #19 | 1, 2, 6 |
| #20 | 1, 3, 4 |
| #21 | 1, 3, 5 |
| #22 | 1, 3, 6 |
| #23 | 1, 4, 5 |
| #24 | 1, 4, 6 |
| #25 | 1, 5, 6 |
| #26 | 2, 3, 4 |
| #27 | 2, 3, 5 |
| #28 | 2, 3, 6 |
| #29 | 2, 4, 5 |
| #30 | 2, 4, 6 |
| #31 | 2, 5, 6 |
| #32 | 3, 4, 5 |
| #33 | 3, 4, 6 |
| #34 | 3, 5, 6 |
| #35 | 4, 5, 6 |
| #36 | 1, 2, 3, 4 |
| #37 | 1, 2, 3, 5 |
| #38 | 1, 2, 3, 6 |
| #39 | 1, 2, 4, 5 |
| #40 | 1, 2, 4, 6 |
| #41 | 1, 2, 5, 6 |
| #42 | 1, 3, 4, 5 |
| #43 | 1, 3, 4, 6 |
| #44 | 1, 3, 5, 6 |
| #45 | 1, 4, 5, 6 |
| #46 | 2, 3, 4, 5 |
| #47 | 2, 3, 4, 6 |
| #48 | 2, 3, 5, 6 |
| #49 | 2, 4, 5, 6 |
| #50 | 3, 4, 5, 6 |
| #51 | 1, 2, 3, 4, 5 |
| #52 | 1, 2, 3, 4, 6 |
| #53 | 1, 2, 3, 5, 6 |
| #54 | 1, 2, 4, 5, 6 |
| #55 | 1, 3, 4, 5, 6 |

| Combination | Substituent Nos. |
|---|---|
| #56 | 2, 3, 4, 5, 6 |
| #57 | 1, 2, 3, 4, 5, 6 | wherein:
substituent not listed in said combination is as defined in embodiment 21;
$G^2$ is $CR^4$ or N and $R^4$ is H, halogen or optionally substituted alkyl, or
together $G^2$ and X are connected to form a cyclic group containing 5-7 atoms, wherein 0-2 atoms of said cyclic group are heteroatoms and the remaining atoms of said cyclic group are carbon atoms substituted with alkyl, aryl, cycloalkyl or heteroaryl;
Substituent 1 is X and:
X is selected from the group consisting of aryl, heteroaryl, alkyl, cycloalkyl, arylalkyl, aryloxy, heteroaryloxy, alkyloxy, cycloalkyloxy and arylalkyloxy; or
X is selected from the group consisting of alkyl, cycloalkyl, alkyloxy, cycloalkyloxy and aryloxy; or
X is selected from the group consisting of alkyloxy and cycloalkyloxy; Substituent 2 is $R^2$ and:
$R^2$ is optionally substituted and is selected from arylene, heteroarylene, alkylene, cycloalkylene, arylalkylene, alkylarylene, arylene-O—, heteroarylene-O—, alkylene-O—, cycloalkylene-O—, arylalkylene-O—, alkylarylene-O—, arylene-S—, heteroarylene-S—, alkylene-S—, cycloalkylene-S—, arylalkylene-S—, or alkylarylene-S—, wherein $R^2$ is connected to $R^{50}$ by a C atom; or
$R^2$ is -$E^1$-$E^2$-$E^3$-$E^1$-E, wherein $E^4$ is connected to $R^{50}$;
$E^1$ is a bond, O or S;
$E^2$ is a bond or alkylene;
$E^3$ is optionally substituted $C_{1-4}$-alkylene, optionally substituted $C_{3-8}$-cycloalkylalkylene, arylene or heteroarylene optionally substituted with one or two groups independently selected from aryl, heteroaryl, cycloalkyl, cycloalkenyl, halogen, CN, $CF_3$, $NR^5_2$, —$C_{1-4}$-alkyl, —$S(O)_2R^5$ or —$OR^5$; wherein, when both $E^1$ and $E^2$ are a bond, together they form a single bond;
$R^5$ is optionally substituted alkyl or cycloalkyl; and
$E^4$ is a bond or alkylene; or
$R^2$ is selected from the group consisting of phenylene-O—, methylene-phenylene-O—, phenylene-methylene-O—, furan-2-yl-5-methylene, thiophen-2-yl-5-methylene, pyridin-diyl-O—, pyrimidin-diyl-O—, pyridazin-diyl-O— and pyrazin-diyl-O—, each optionally substituted with one or two groups independently selected from aryl, heteroaryl, halogen, CN, $CF_3$, $NR^5_2$, —$C_{1-4}$-alkyl, —$S(O)_2R^5$ or —$OR^5$, wherein $R^{50}$ is connected to $R^2$ by a carbon atom; or
$R^2$ is methylene-thiophen-2,5-diyl, phenylene-O— or thiophen-2-yl-5-methylene, wherein $R^{50}$ is connected to the phenylene or thiophenyl group;
Substituent 3 is $G^1$ and:
$G^1$ is N; or
$G^1$ is $CR^4$ and $R^4$ is H, halogen or optionally substituted alkyl;
Substituent 4 is $G^3$ and:
$G^3$ is N; or
$G^3$ is $CR^4$ and $R^4$ is H, halogen or optionally substituted alkyl;
Substituent 5 is D and:
D is selected from a group consisting of heteroaryl or aryl; or D is a heteroaryl having a nitrogen as a ring atom, said heteroaryl comprising a nitrogen ring atom adjacent to a carbon ring atom, wherein said carbon ring atom is connected to the amide nitrogen atom adjacent to D, and wherein said heteroaryl has an additional 0 to 3 heteroatoms independently selected from O, S or N; or
D is selected from the group consisting of pyridinyl, thiazolyl, 1,3,4-thiadiazolyl, 1,2,4-thiadiazolyl, oxazolyl, isoxazolyl, imidazolyl, pyrazolyl, pyrazinyl, pyridazinyl, pyrimidinyl, benzothiazolyl and 5,6-dihydro-4H-cyclopentathiazolyl, each optionally substituted with one or two groups selected from halogen, $CF_3$, or optionally substituted $C_{1-4}$-alkyl; or
D is selected from the group consisting of thiazolyl, 1,3,4-thiadiazolyl, 1,2,4-thiadiazolyl, each optionally substituted with one or two groups selected from halogen, $CF_3$, or optionally substituted $C_{1-4}$-alkyl; and
Substituent 6 is $R^{51}$ and:
$R^{50}$ is —P(O)($Y^2R^{51}$) $R^1$ or —P(O)($YR^{51}$)$Y^1R^{51}$;
$R^1$ is selected from the group consisting of hydrogen, optionally substituted —$C_1$-$C_6$-alkyl, —$CF_3$, —$CHF_2$, —$CH_2F$, —$CH_2OH$, optionally substituted —$C_2$-$C_6$ alkenyl, optionally substituted —$C_2$-$C_6$ alkynyl, optionally substituted —$(CR^{52}_2)$cycloalkyl, optionally substituted $(CR^{52}_2)_n$heterocycloalkyl, —$(CR^{52}_2)_k$ S(=O)$R^{53}$, —$(CR^{52}_2)_k$ S(=O)$_2R^{53}$;
Y, $Y^1$ and $Y^2$ are each independently selected from —O— or —$NR^{60}$—;
wherein,
when $Y^2$ is —O— or when Y and $Y^1$ are both —O—, $R^{51}$ attached to —O— is independently selected from —H, alkyl, optionally substituted aryl, optionally substituted heterocycloalkyl, optionally substituted —$CH_2$-heterocycloakyl wherein the cyclic moiety contains a carbonate or thiocarbonate, optionally substituted -alkylaryl, —C($R^{52}$)$_2$OC(O)$NR^{52}_2$, —$NR^{52}$—C(O)—$R^{53}$, —C($R^{52}$)$_2$—OC(O)$R^{53}$, —C($R^{52}$)$_2$—O—C)O$R^{53}$, —C($R^{52}$)$_2$OC(O)$SR^{53}$, -alkyl-S—C(O)$R^{53}$, -alkyl-S—S-alkylhydroxy.
and -alkyl-S—S—S-alkylhydroxy; or
when $Y^2$ is —$NR^{60}$— or when Y and $Y^1$ are both —$NR^{60}$—, then $R^{51}$ attached to —$NR^{60}$— is independently selected from —H, —[C($R^{52}$)$_2$]$_r$—COO$R^{53}$, —C($R^{54}$)$_2$COO$R^{53}$, —[C($R^{52}$)$_2$]$_r$—C(O)$SR^{53}$, and -cycloalkylene-COO$R^{53}$; or
when Y is —O— and $Y^1$ is $NR^{60}$, then $R^{61}$ attached to —O— is independently selected from —H, alkyl, optionally substituted aryl, optionally substituted heterocycloalkyl, optionally substituted $CH_2$-heterocycloakyl wherein the cyclic moiety contains a carbonate or thiocarbonate, optionally substituted -alkylaryl, —C($R^{52}$)$_2$OC(O)$NR^{52}_2$, —$NR^{52}$—C(O)—$R^{53}$, —C($R^{52}$)$_2$—OC(O)$R^{53}$, —C($R^{52}$)$_2$—O—C(O)O$R^{53}$, —C($R^{52}$)$_2$OC(O)$SR^{53}$, -alkyl-S—C(O)$R^{53}$, -alkyl-S—S-alkylhydroxy, and -alkyl-S—S—S-alkylhydroxy, and $R^{51}$ attached to —$NR^{60}$— is independently selected from —H, —[C($R^{52}$)$_2$]$_r$—COO$R^{53}$, —C($R^{54}$)$_2$COO$R^{53}$, —[C($R^{52}$)$_2$]$_r$—C(O)$SR^{53}$, and -cycloalkylene-COO$R^{53}$, wherein if both $R^{51}$ are alkyl, at least one is higher alkyl; or
when Y and $Y^1$ are independently selected from —O— and —$NR^{60}$—, then $R^{51}$ and $R^{51}$ together form a cyclic group comprising -alkyl-S—S-alkyl-, or $R^{51}$ and $R^{51}$ together are the group $$\begin{array}{c} V \\ | \\ \underline{\phantom{XX}}\!\!\diagup\!\!\diagdown\!\!\underline{\phantom{X}}\; H \\ \phantom{XXXX}\diagdown\; Z \\ \phantom{XXXX}\diagup\; H, \\ \underline{\phantom{XX}}\!\!\diagdown\!\!\diagup\!\!\underline{\phantom{X}}\; W \\ | \\ W' \end{array}$$

wherein,

V, W, and W' are independently selected from the group consisting of hydrogen, optionally substituted alkyl, optionally substituted aralkyl, heterocycloalkyl, aryl, substituted aryl, heteroaryl, substituted heteroaryl, optionally substituted 1-alkenyl, and optionally substituted 1-alkynyl, and Z is —$CHR^{52}OH$, —$CHR^{52}OC(O)R^{53}$, —$CHR^{52}OC(S)R^{53}$, —$CHR^{52}OC(S)OR^{53}$, —$CHR^{52}OC(O)SR^{53}$, —$CHR^{52}OCO_2R^{53}$, —$OR^{52}$, —$SR^{52}$, —$CHR^{52}N_3$, —$CH_2$aryl, —CH(aryl)OH, —$CH(CH=CR^{52}{}_2)OH$, —CH($C\equiv CR^{52}$)OH, —$R^{52}$, —$NR^{52}{}_2$, —O $COR^{53}$, —$OCO_2R^{53}$, —$SCOR^{53}$, —$SCO_2R^{53}$, —$NHCOR^{52}$, —$NHCO_2R^{53}$, —$CH_2NH$aryl, —$(CH_2)_r$—$OR^{52}$ or —$(CH_2)_r$—$SR^{51}$; or W and W are as defined above and together V and Z are connected via an additional 3-5 atoms to form a cyclic group containing 5-7 atoms, wherein 0-1 atoms are heteroatoms and the remaining atoms are carbon; or W' and Z are as defined above and together V and W are connected via an additional 3 carbon atoms to form an optionally substituted cyclic group containing 6 carbon atoms or carbon substituted by hydrogen and substituted with one substituent selected from hydroxy, acyloxy, alkoxycarbonyloxy, alkylthiocarbonyloxy or aryloxycarbonyloxy which is attached to one of said carbon atoms that is three atoms from a Y attached to the phosphorus; or V and W' are as defined above and together Z and W are connected via an additional 3-5 atoms to form a cyclic group, wherein 0-1 atoms are heteroatoms and the remaining atoms are carbon or carbon substituted by hydrogen, and V must be aryl, substituted aryl, heteroaryl, or substituted heteroaryl; or V and Z are as defined above and together W and W' are connected via an additional 2-5 atoms to form a cyclic group, wherein 0-2 atoms are heteroatoms and the remaining atoms are carbon, where V must be aryl, substituted aryl, heteroaryl, or substituted heteroaryl;

$R^{52}$ is $R^{53}$ or —H;

$R^{53}$ is alkyl, aryl, heterocycloalkyl or aralkyl;

$R^{54}$ is independently selected from —H or alkyl, or together $R^{54}$ and $R^{54}$ form a cycloalkylene group;

$R^{60}$ is —H, lower alkyl, acyloxyalkyl, alkoxycarbonyloxyalkyl, lower acyl, $C_{1-6}$-perfluoroalkyl or $NH(CR^{55}R^{55})CH_3$;

r is an integer 2 or 3;

f is an integer 0, 1 or 2;

wherein, V, Z, W, W' are not all —H, and when Z is —$R^{52}$, then at least one of V, W, and W' is not —H, alkyl, aralkyl, or heterocycloalkyl; or $R^{50}$ is selected from the group consisting of —$PO_3H_2$, —$P(O)[—OCR^{52}{}_2OC(O)R^{53}]_2$, —$P(O)[—OCR^{52}{}_2OC(O)OR^{53}]_2$, —$P(O)[—N(H)CR^{52}{}_2C(O)\ OR^{53}]_2$, —$P(O)[—O\text{-alk-}SC(O)R^{53}]_2$, —$P(O)[—OCR^{52}{}_2OC(O)R^{53}][—R^1]$, —$P(O)[—OCR^{52}{}_2OC(O)OR^{53}][—R^1]$, —$P(O)[—N(H)CR^{52}{}_2C(O)OR^{53}][—R^1]$, —$P(O)[—OCH_2CH_2SC(O)R^{53}][—R^1]$, —$P(O)(OH)(YR^{51})$, —$P(O)(OR^{56})(OR^{56})$, —$P(O)(OH)(—R^1)$, —$P(O)[—OCR^{52}{}_2OC(O)R^{53}](OR^{56})$, —$P(O)[—OCR^{52}{}_2OC(O)OR^{53}](OR^{56})$, —$P(O)[—N(H)CR^{52}{}_2C(O)OR^{53}](OR^{56})$, $P(O)(OH)(NH_2)$, and —$P(O)[—OCH(V)CH_2CH_2O—]$;

V is optionally substituted aryl or optionally substituted heteroaryl;

$R^{56}$ is —$C_1$-$C_{12}$ alkyl, —$C_2$-$C_{12}$ alkenyl, —$C_2$-$C_{12}$ alkynyl, —$(CR^{57}{}_2)_n$aryl, —$(CR^{57}{}_2)_n$cycloalkyl, or —$(CR^{52}{}_2)_n$heterocycloalkyl, each optionally substituted;

each $R^{57}$ is independently selected from the group consisting of hydrogen, optionally substituted —$C_1$-$C_4$ alkyl, halogen, optionally substituted —O—$C_1$-$C_4$ alkyl, —$OCF_3$, optionally substituted —S—$C_1$-$C_4$ alkyl, —$NR^{58}R^{59}$, optionally substituted —$C_2$-$C_4$ alkenyl, and optionally substituted —$C_2$-$C_4$ alkynyl; with the proviso that when one $R^{57}$ is attached to C through an O, S, or N atom, then the other $R^{57}$ attached to the same C is a hydrogen, or attached via a carbon atom;

$R^{51}$ is selected from hydrogen and optionally substituted —$C_1$-$C_4$ alkyl; and, $R^{59}$ is selected from the group consisting of hydrogen and optionally substituted —$C_1$-$C_4$ alkyl, optionally substituted —C(O)—$C_1$-$C_4$ alkyl and —C(O)H; or $R^{50}$ is —$P(O)(OH)_2$, —$P(O)[—OCH_2OC(O)\text{-r-butyl}]_2$, —$P(O)[—OCH(CH_3)OC(O)\text{-t-butyl}]_2$, —$P(O)[—OCH(CH_3)OC(O)O\text{-i-propyl}]_2$, —$P(O)[—OCH_2OC(O)O\text{-i-propyl}]_2$, —$P(O)[—OCH_2OC(O)O\text{-ethyl}]_2$, —$P(O)[—N(H)CH(CH_3)C(O)OCH_2CH_3]_2$, —$P(O)\ [—N(H)C(CH_3)_2C(O)OCH_2CH_3]_2$, —$P(O)[—OCH(3\text{-chlorophenyl})CH_2CH_2O—]$, —$P(O)[—OCH(\text{pyrid-4-yl})CH_2CH_2O—]$, or —$P(O)[—OCH(V)CH_2CH_2O—]$; and V is optionally substituted aryl or optionally substituted heteroaryl; or $R^{50}$ is selected from the group consisting of —$P(O)(OH)_2$, —$P(O)[—OCH_2OC(O)\text{-t-butyl}]_2$, —$P(O)[—OCH(CH_3)OC(O)\text{-t-butyl}]_2$, —$P(O)[—OCH(CH_3)OC(O)O\text{-i-propyl}]_2$, —$P(O)[—OCH_2OC(O)O\text{-i-propyl}]_2$, —$P(O)[—N(H)CH(CH_3)C(O)OCH_2\ CH_3]_2$, —$P(O)[—N(H)C(CH_3)_2C(O)OCH_2CH_3]_2$, —$P(O)[—N(H)CH(CH_3)C(O)OCH_2CH_3][3,4\text{-methylenedioxyphenyl}]$, —$P(O)[—N(H)C(CH_3)_2C(O)OCH_2CH_3][3,4\text{-methylenedioxyphenyl}]$, —$P(O)[—O—CH_2CH_2S—C(O)CH_3]_2$, —$P(O)(OH)(OCH_3)$, —$P(O)(OH)(OCH_2CH_3)$, —$P(O)(OH)(CH_3)$, —$P(O)[—OCH(3\text{-chlorophenyl})CH_2CH_2O—]$, —$P(O)[—OCH(\text{pyrid-4-yl})CH_2CH_2O—]$, —$P(O)[—OCH_2OC(O)\text{-t-butyl}](OCH_3)$, —$P(O)[—OCH_2OC(O)O\text{-i-propyl}](OCH_3)$, —$P(O)[—OCH(CH_3)OC(O)\text{-t-butyl}](OCH_3)$, —$P(O)[—OCH(CH_3)OC(O)O\text{-i-propyl}](OCH_3)$, —$P(O)[—N(H)CH(CH_3)C(O)OCH_2CH_3](OCH_3)$, —$P(O)[—N(H)CH(CH_3)C(O)OCH_2CH_3](CH_3)$, —$P(O)[—N(H)C(CH_3)_2C(O)OCH_2CH_3](OCH_3)$, —$P(O)[—N(H)C(CH_3)_2C(O)OCH_2CH_3](CH_3)$, —$P(O)\ [—OCH_2OC(O)\text{-t-butyl}](CH_3)$, —$P(O)[—OCH_2OC(O)O\text{-i-propyl}](CH_3)$, —$P(O)[—OCH(CH_3)OC(O)\text{-t-butyl}](CH_3)$, —$P(O)[—OCH(CH_3)OC(O)O\text{-i-propyl}](CH_3)$, and —$P(O)[—OCH_2OC(O)O\text{-ethyl}]_2$.

A further embodiment ("Embodiment 52") is the compound of embodiment 51, wherein:

Substituent 1 is X and:

X is selected from the group consisting of aryl, heteroaryl, alkyl, cycloalkyl, arylalkyl, aryloxy, heteroaryloxy, alkyloxy, cycloalkyloxy and arylalkyloxy;

Substituent 2 is $R^2$ and:

$R^2$ is optionally substituted and is selected from arylene, heteroarylene, alkylene, cycloalkylene, arylalkylene, alkylarylene, arylene-O—, heteroarylene-O—, alkylene-O—, cycloalkylene-O—, arylalkylene-O—, alkylarylene-O—, arylene-S—, heteroarylene-S—, alkylene-S—, cycloalkylene-S—, arylalkylene-S—, alkylarylene-S—, wherein $R^{50}$ is connected to $R^2$ by a carbon atom;

Substituent 3 is $G^1$ and:

$G^1$ is N; or $G^1$ is $CR^4$ and $R^4$ is H, halogen or optionally substituted alkyl;

Substituent 4 is $G^3$ and:

$G^3$ is N; or $G^3$ is $CR^1$ and $R^4$ is H, halogen or optionally substituted alkyl;

Substituent 5 is D and:

D is selected from a group consisting of heteroaryl or aryl; or and

Substituent 6 is $R^{50}$ and:

$R^{50}$ is —P(O)($Y^2R^{51}$) $R^1$ or —P(O)($YR^{51}$)$Y^1R^{51}$;

$R^1$ is selected from the group consisting of hydrogen, optionally substituted —$C_1$-$C_6$-alkyl, —$CF_3$, —$CHF_2$, —$CH_2F$, —$CH_2OH$, optionally substituted —$C_2$-$C_6$ alkenyl, optionally substituted —$C_2$-$C_6$ alkynyl, optionally substituted —$(CR^{52}_2)$cycloalkyl, optionally substituted $(CR^{52}_2)_n$heterocycloalkyl, —$(CR^{52}_2)_k$ S(=O)$R^{53}$, —$(CR^{52}_2)_kS(=O)_2R^{53}$;

Y, $Y^1$ and $Y^2$ are each independently selected from —O— or —$NR^{60}$—;

wherein, when $Y^2$ is —O— or when Y and $Y^1$ are both —O—, $R^{51}$ attached to —O— is independently selected from —H, alkyl, optionally substituted aryl, optionally substituted heterocycloalkyl, optionally substituted —$CH_2$-heterocycloakyl wherein the cyclic moiety contains a carbonate or thiocarbonate, optionally substituted -alkylaryl, —$C(R^{52})_2OC(O)NR^{52}_2$, —$NR^{52}$—C(O)—$R^{53}$, —$C(R^{52})_2$—OC(O)$R^{53}$, —$C(R^{52})_2$—O—C(O)OR$^{53}$, —$C(R^{52})_2OC(O)SR^{53}$, -alkyl-S—C(O)$R^{53}$, -alkyl-S—S-alkylhydroxy, and -alkyl-S—S—S-alkylhydroxy; or when $Y^2$ is —$NR^{60}$— or when Y and $Y^1$ are both —$NR^{60}$—, then $R^{51}$ attached to —$NR^{60}$— is independently selected from —H, —$[C(R^{52})_2]_r$—COOR$^{53}$, —$C(R^{54})_2$)COOR$^{53}$, —$[C(R^{52})_2]_r$—C(O)SR$^{53}$, and -cycloalkylene-COOR$^{53}$; or when Y is —O— and $Y^1$ is $NR^{60}$, then $R^{51}$ attached to —O— is independently selected from —H, alkyl, optionally substituted aryl, optionally substituted heterocycloalkyl, optionally substituted $CH_2$-heterocycloakyl wherein the cyclic moiety contains a carbonate or thiocarbonate, optionally substituted -alkylaryl, —$C(R^{52})_2OC(O)NR^{52}_2$, —$NR^{52}$—C(O)—$R^{53}$, —$C(R^{52})_2$—OC(O)$R^{53}$, —$C(R^{52})_2$—O—C(O)OR$^{53}$, —$C(R^{52})_2OC(O)SR^{53}$, -alkyl-S—C(O)$R^{53}$, -alkyl-S—S-alkylhydroxy, and -alkyl-S—S—S-alkylhydroxy, and $R^{51}$ attached to —$NR^{60}$— is independently selected from —H, —$[C(R^{52})_2]_r$—COOR$^{53}$, —$C(R^{54})_2$COOR$^{53}$, —$[C(R^{52})_2]_r$—C(O)SR$^{53}$, and -cycloalkylene-COOR$^{53}$, wherein if both $R^{51}$ are alkyl, at least one is higher alkyl; or when Y and $Y^1$ are independently selected from —O— and —$NR^{60}$—, then $R^{51}$ and $R^{51}$ together form a cyclic group comprising -alkyl-S—S-alkyl-, or $R^{51}$ and $R^{51}$ together are the group

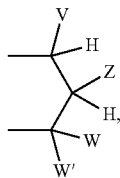

wherein,

V, W, and W' are independently selected from the group consisting of hydrogen, optionally substituted alkyl, optionally substituted aralkyl, heterocycloalkyl, aryl, substituted aryl, heteroaryl, substituted heteroaryl, optionally substituted 1-alkenyl, and optionally substituted -alkynyl, and Z is —$CHR^{52}OH$, —$CHR^{52}OC(O)R^{53}$, —$CHR^{52}OC(S)R^{53}$, —$CHR^{52}OC(S)OR^{53}$, —$CHR^{52}OC(O)SR^{53}$, —$CHR^{52}OCO_2R^{53}$, —$OR^{52}$, —$SR^{52}$, —$CHR^{52}N_3$, —$CH_2$aryl, —CH(aryl)OH, —CH(CH=$CR^{52}_2$)OH, —CH(C≡$CR^{52}$)OH, —$R^{52}$, —$NR^{52}_2$, —$OCOR^{53}$, —$OCO_2R^{53}$, —$SCOR^{53}$, —$SCO_2R^{53}$, —$NHCOR^{52}$, —$NHCO_2R^{53}$, —$CH_2NHaryl$, —$(CH_2)_r$—$OR^{52}$ or —$(CH_2)_r$—$SR^{52}$; or W and W are as defined above and together V and Z are connected via an additional 3-5 atoms to form a cyclic group containing 5-7 atoms, wherein 0-1 atoms are heteroatoms and the remaining atoms are carbon; or W' and Z are as defined above and together V and W are connected via an additional 3 carbon atoms to form an optionally substituted cyclic group containing 6 carbon atoms or carbon substituted by hydrogen and substituted with one substituent selected from hydroxy, acyloxy, alkoxycarbonyloxy, alkylthiocarbonyloxy or aryloxycarbonyloxy which is attached to one of said carbon atoms that is three atoms from a Y attached to the phosphorus; or V and W' are as defined above and together Z and W are connected via an additional 3-5 atoms to form a cyclic group, wherein 0-1 atoms are heteroatoms and the remaining atoms are carbon or carbon substituted by hydrogen, and V must be aryl, substituted aryl, heteroaryl, or substituted heteroaryl; or V and Z are as defined above and together W and W' are connected via an additional 2-5 atoms to form a cyclic group, wherein 0-2 atoms are heteroatoms and the remaining atoms are carbon, where V must be aryl, substituted aryl, heteroaryl, or substituted heteroaryl;

$R^{52}$ is $R^{53}$ or —H;

$R^{53}$ is alkyl, aryl, heterocycloalkyl or aralkyl;

$R^{54}$ is independently selected from —H or alkyl, or together $R^{54}$ and $R^{54}$ form a cycloalkylene group;

$R^{60}$ is —H, lower alkyl, acyloxyalkyl, alkoxycarbonyloxyalkyl, lower acyl, $C_{1-6}$-perfluoroalkyl or NH($CR^{55}R^{55}$)$CH_3$;

r is an integer 2 or 3;

f is an integer 0, 1 or 2;

wherein, V, Z, W, W' are not all —H, and when Z is —$R^{52}$, then at least one of V, W, and W' is not —H, alkyl, aralkyl, or heterocycloalkyl.

A further embodiment ("Embodiment 53") is the compound of embodiment 51, wherein:

Substituent 1 is X and:

X is selected from the group consisting of alkyl, cycloalkyl, alkyloxy, cycloalkyloxy and aryloxy;

Substituent 2 is $R^2$ and:

$R^2$ is -$E^1$-$E^2$-$E^3$-$E^4$-, wherein $E^4$ is connected to $R^{50}$;

$E^1$ is a bond, O or S;

$E^2$ is a bond or alkylene;

$E^3$ is optionally substituted $C_{1-4}$-alkylene, optionally substituted $C_{3-8}$-cycloalkylalkylene, arylene or heteroarylene optionally substituted with one or two groups independently selected from aryl, heteroaryl, cycloalkyl, cycloalkenyl, halogen, CN, $CF_3$, $NR^5_2$, —$C_{1-4}$-alkyl, —$S(O)_2R^5$ or —$OR^5$; wherein, when both $E^1$ and $E^2$ are a bond, together they form a single bond, $R^5$ is optionally substituted alkyl or cycloalkyl; and
$E^4$ is a bond or alkylene:
Substituent 3 is $G^1$ and:
 $G^1$ is N; or
 $G^1$ is $CR^4$ and $R^4$ is H, halogen or optionally substituted alkyl;
Substituent 4 is $G^1$ and:
 $G^3$ is N; or
 $G^3$ is $CR^4$ and $R^4$ is H, halogen or optionally substituted alkyl;
Substituent 5 is D and:
 D is a heteroaryl having a nitrogen as a ring atom, said heteroaryl comprising a nitrogen ring atom adjacent to a carbon ring atom, wherein said carbon ring atom is connected to the amide nitrogen atom adjacent to D, and wherein said heteroaryl has an additional 0 to 3 heteroatoms independently selected from O, S or N; and
Substituent 6 is $R^{50}$ and:
 $R^{50}$ is selected from the group consisting of —$PO_3H_2$, —$P(O)[-OCR^{52}_2OC(O)R^{53}]_2$, —$P(O)[-OCR^{52}_2OC(O)OR^{53}]_2$, —$P(O)[-N(H)CR^{52}_2C(O)\ OR^{53}]_2$, —$P(O)[-O\text{-alk-}SC(O)R^{53}]_2$, —$P(O)[-OCR^{52}_2OC(O)R^{53}][-R^1]$, —$P(O)[-OCR^{52}_2OC(O)OR^{53}][-R^1]$, —$P(O)[-N(H)CR^{52}_2C(O)OR^{53}][-R^1]$, —$P(O)[-OCH_2CH_2SC(O)R^{53}][-R^1]$, —$P(O)(OH)(YR^{51})$, —$P(O)(OR^{56})(OR^{56})$, —$P(O)(OH)(-R^1)$, —$P(O)[-OCR^{52}_2OC(O)R^{53}](OR^{56})$, —$P(O)[-OCR^{52}_2OC(O)OR^{53}](OR^{56})$, —$P(O)[-N(H)CR^{52}_2C(O)OR^{53}](OR^{56})$, $P(O)(OH)(NH_2)$, and —$P(O)[-OCH(V)CH_2CH_2O-]$;

V is optionally substituted aryl or optionally substituted heteroaryl;

$R^{56}$ is —$C_1$-$C_{12}$ alkyl, —$C_2$-$C_{12}$ alkenyl, —$C_2$-$C_{12}$ alkynyl, —$(CR^{57}_2)_n$aryl, —$(CR^{57}_2)_n$cycloalkyl, or —$(CR^{57}_2)_n$heterocycloalkyl, each optionally substituted;

each $R^{57}$ is independently selected from the group consisting of hydrogen, optionally substituted —$C_1$-$C_4$ alkyl, halogen, optionally substituted —O—$C_1$-$C_4$ alkyl, —$OCF_3$, optionally substituted —S—$C_1$-$C_4$ alkyl, —$NR^{58}R^{59}$, optionally substituted —$C_2$-$C_4$ alkenyl, and optionally substituted —$C_2$-$C_4$ alkynyl; with the proviso that when one $R^{57}$ is attached to C through an O, S, or N atom, then the other $R^{57}$ attached to the same C is a hydrogen, or attached via a carbon atom;

$R^{58}$ is selected from hydrogen and optionally substituted —$C_1$-$C_4$ alkyl; and, $R^{59}$ is selected from the group consisting of hydrogen and optionally substituted —$C_1$-$C_4$ alkyl, optionally substituted —C(O)—$C_1$-$C_4$ alkyl and —C(O)H.

A further embodiment ("Embodiment 54") is the compound of embodiments 51, 52 or 53, wherein $G^1$, $G^2$ and $G^3$ are $CR^4$ and $R^4$ is H, halogen or optionally substituted alkyl.

A further embodiment ("Embodiment 55") is the compound of embodiment 54, wherein $R^4$ is H.

A further embodiment ("Embodiment 56") is the compound of embodiments 51, 52, 53, 54 or 55, wherein $R^{50}$ is —$P(O)(OH)_2$, —$P(O)[-OCH_2OC(O)\text{-t-butyl}]_2$, —$P(O)[-OCH(CH_3)OC(O)\text{-t-butyl}]_2$, —$P(O)[-OCH(CH_3)OC(O)O\text{-i-propyl}]_2$, —$P(O)[-OCH_2OC(O)O\text{-i-propyl}]_2$, —$P(O)[-OCH_2OC(O)O\text{-ethyl}]_2$, —$P(O)[-N(H)CH(CH_3)C(O)OCH_2CH_3]_2$, —$P(O)[-N(H)C(CH_3)_2C(O)OCH_2CH_3]_2$, —$P(O)[-OCH(3\text{-chlorophenyl})CH_2CH_2O-]$, —$P(O)[-OCH(\text{pyrid-4-yl})CH_2CH_2O-]$, or —$P(O)[-OCH(V)CH_2CH_2O-]$; and V is optionally substituted aryl or optionally substituted heteroaryl.

A further embodiment ("Embodiment 57") is the compound of embodiments 51, 52, 53, 54, 55 or 56, wherein $R^{50}$ is selected from the group consisting of —$P(O)(OH)_2$, —$P(O)[-OCH_2OC(O)\text{-t-butyl}]_2$, —$P(O)[-OCH(CH_3)OC(O)\text{-t-butyl}]_2$, —$P(O)[-OCH(CH_3)OC(O)O\text{-i-propyl}]_2$, —$P(O)[-OCH_2OC(O)O\text{-i-propyl}]_2$, —$P(O)[-N(H)CH(CH_3)C(O)OCH_2\ CH_3]_2$, —$P(O)[-N(H)C(CH_3)_2C(O)OCH_2CH_3]_2$, —$P(O)[-N(H)CH(CH_3)C(O)OCH_2CH_3][3,4\text{-methylenedioxyphenyl}]$, —$P(O)[-N(H)C(CH_3)_2C(O)OCH_2CH_3][3,4\text{-methylenedioxyphenyl}]$, —$P(O)[-O-CH_2CH_2S-C(O)CH_3]_2$, —$P(O)(OH)(OCH_3)$, —$P(O)(OH)(OCH_2CH_3)$, —$P(O)(OH)(CH_3)$, —$P(O)[-OCH(3\text{-chlorophenyl})CH_2CH_2O-]$, —$P(O)[-OCH(\text{pyrid-4-yl})CH_2CH_2O-]$, —$P(O)[-OCH_2OC(O)\text{-t-butyl}](OCH_3)$, —$P(O)[-OCH_2OC(O)O\text{-i-propyl}](OCH_3)$, —$P(O)[-OCH(CH_3)OC(O)\text{-t-butyl}](OCH_3)$, —$P(O)[-OCH(CH_3)OC(O)O\text{-i-propyl}](OCH_3)$, —$P(O)[-N(H)CH(CH_3)C(O)OCH_2CH_3](OCH_3)$, —$P(O)[-N(H)CH(CH_3)C(O)OCH_2CH_3](CH_3)$, —$P(O)[-N(H)C(CH_3)_2C(O)OCH_2CH_3](OCH_3)$, —$P(O)[-N(H)C(CH_3)_2C(O)OCH_2CH_3](CH_3)$, —$P(O)[-OCH_2OC(O)\text{-t-butyl}](CH_3)$, —$P(O)[-OCH_2OC(O)O\text{-i-propyl}](CH_3)$, —$P(O)[-OCH(CH_3)OC(O)\text{-t-butyl}](CH_3)$, —$P(O)[-OCH(CH_3)OC(O)O\text{-i-propyl}](CH_3)$, and —$P(O)[-OCH_2OC(O)O\text{-ethyl}]_2$.

A further embodiment ("Embodiment 58") is the compound of embodiments 51, 52, 53, 54, 55, 56 or 57, wherein X is selected from the group consisting of alkyloxy and cycloalkyloxy.

A further embodiment ("Embodiment 59") is the compound of embodiments 51, 52, 53, 54, 55, 56, 57 or 58, wherein $R^2$ is selected from the group consisting of phenylene-O—, methylene-phenylene-O—, phenylene-methylene-O—, furan-2-yl-5-methylene, thiophen-2-yl-5-methylene, pyridin-diyl-O—, pyrimidin-diyl-O—, pyridazin-diyl-O— and pyrazin-diyl-O—, each optionally substituted with one or two groups independently selected from aryl, heteroaryl, halogen, CN, $CF_3$, $NR^5_2$, —$C_{1-4}$-alkyl, —$S(O)_2R^5$ or —$OR^5$, wherein $R^{50}$ is connected to $R^2$ by a carbon atom.

A further embodiment ("Embodiment 60") is the compound of embodiment 59, wherein $R^2$ is optionally substituted methylene-thiophen-2,5-diyl, phenylene-O— or thiophen-2-yl-5-methylene, wherein $R^{50}$ is connected to the phenylene or thiophenyl group.

A further embodiment ("Embodiment 61") is the compound of embodiments 51, 52, 53, 54, 55, 56, 57, 58, 59 or 60, wherein D is selected from the group consisting of pyridinyl, thiazolyl, 1,3,4-thiadiazolyl, 1,2,4-thiadiazolyl, oxazolyl, isoxazolyl, imidazolyl, pyrazolyl, pyrazinyl, pyridazinyl, pyrimidinyl, benzothiazolyl and 5,6-dihydro-4H-cyclopentathiazolyl, each optionally substituted with one or two groups selected from halogen, $CF_3$, or optionally substituted $C_{1-4}$-alkyl.

A further embodiment ("Embodiment 62") is the compound of embodiment 61, wherein D is selected from the group consisting of thiazolyl, 1,3,4-thiadiazolyl, and 1,2,4-thiadiazolyl, each optionally substituted with one or two groups selected from halogen, $CF_3$, or optionally substituted $C_{1-4}$-alkyl.

A further embodiment ("Embodiment 63") is a pharmaceutical composition comprising a compound of any one of embodiments 1-62 and a pharmaceutically acceptable excipient.

A further embodiment ("Embodiment 64") is a method of treating, preventing, delaying the time to onset or reducing the risk for the development or progression of a disease or condition for which one or more glucokinase activator is indicated, said method comprising the step of administering to an animal a therapeutically effective amount of a compound of embodiments 1-62, compositions thereof, or pharmaceutically acceptable salts or prodrugs thereof.

A further embodiment ("Embodiment 63") is the method of embodiment 64, wherein said disease or condition is Type 1 diabetes.

A further embodiment ("Embodiment 64") is the method of embodiment 64, wherein said disease or condition is Type 2 diabetes.

A further embodiment ("Embodiment 65") is the method of embodiment 64, wherein said disease or condition is impaired glucose tolerance.

A further embodiment ("Embodiment 66") is the method of embodiment 64, wherein said disease or condition is insulin resistance A further embodiment ("Embodiment 67") is the method of embodiment 64, wherein said disease or condition is hyperglycemia A further embodiment ("Embodiment 68") is the method of embodiment 64, wherein said disease or condition is postprandial hyperglycemia.

A further embodiment ("Embodiment 69") is the method of embodiment 64, wherein said disease or condition is fasting hyperglycemia.

A further embodiment ("Embodiment 70") is the method of embodiment 64, wherein said disease or condition is accelerated gluconeogenesis.

A further embodiment ("Embodiment 71") is the method of embodiment 64, wherein said disease or condition is excessive hepatic glucose output.

A further embodiment ("Embodiment 72") is the method of embodiment 64, wherein said disease or condition is hyperinsulinemia.

A further embodiment ("Embodiment 73") is the method of embodiment 64, wherein said disease or condition is Metabolic Syndrome X.

Another aspect of the present invention are pharmaceutical compositions comprising a compound of the present invention.

Another aspect of the present invention are single enantiomers or diasteromers of a compound of the present invention.

Another aspect of the present invention are enantiomerically enriched compositions comprising an enantiomer of a compound of the present invention. In one embodiment, a single enantiomer is >60%, >70%, >80%, >85%, >90%, >91%, >92%, >93%, >94%, >95%, >96%, >97%, >98% or >99% enriched as compared to the total percentage of all other enantiomers of the same compound present in the composition.

Another aspect provides for salts, including pharmaceutically acceptable salts, of compounds of the present invention and pharmaceutical compositions comprising a pharmaceutically acceptable salt of the present invention. Salts of compounds of the present invention include an inorganic base addition salt such as sodium, potassium, lithium, calcium, magnesium, ammonium, aluminum salts or organic base addition salts, or an inorganic acid addition salt such as HBr, HCl, sulfuric, nitric, or phosphoric acid addition salts or an organic acid addition salt such as acetic, propionic, pyruvic, malanic, succinic, malic, maleic, fumaric, tartaric, citric, benzoic, methanesulfonic, ethanesulforic, stearic or lactic acid addition salt.

Another aspect provides for anhydrates, hydrates and solvates of compounds of the present invention and pharmaceutical compositions comprising a pharmaceutically acceptable anhydrates, hydrates and solvates of the present invention. Included are an anhydrate, hydrate or solvate of a free form or salt of a compound of the present invention. Hydrates include, for example, a hemihydrate, monohydrate, dihydrate, trihydrate, quadrahydrate, pentahydrate, sesquihydrate.

Another aspect provides for the use of a compound of the present invention for the manufacture of a medicament for treating, preventing, delaying the time to onset or reducing the risk for the development or progression of a disease or condition for which one or more glucokinase activator is indicated.

Another aspect provides for the use of a compound of the invention for the manufacture of a medicament for treating, preventing, delaying the time to onset or reducing the risk for the development or progression of a disease or condition responsive to decreased hepatic glucose production or responsive to lowered blood glucose levels, the method comprising the step of administering to an animal a therapeutically effective amount a compound of the invention, or a pharmaceutically acceptable salt or prodrugs thereof.

Another aspect provides for methods of treating, preventing, delaying the time to onset or reducing the risk for the development or progression of a disease or condition for which one or more glucokinase activator is indicated.

Another aspect provides for methods of treating, preventing, delaying the time to onset or reducing the risk for the development or progression of a disease or condition responsive to decreased hepatic glucose production or responsive to lowered blood glucose levels, the method comprising the step of administering to an animal a therapeutically effective amount a compound of the invention, or a pharmaceutically acceptable salt or prodrugs thereof.

Another aspect provides for methods for treating, preventing, delaying the time to onset or reducing the risk for the development or progression of Type 1 diabetes, the method comprising the step of administering to an animal a therapeutically effective amount a compound of the invention.

Another aspect provides for methods for treating, preventing, delaying the time to onset or reducing the risk for the development or progression of Type 1 diabetes, the method comprising the step of administering to an animal a therapeutically effective amount a compound of the invention.

Another aspect provides for methods for treating, preventing, delaying the time to onset or reducing the risk for the development or progression of impaired glucose tolerance, the method comprising the step of administering to an animal a therapeutically effective amount a compound of the invention.

Another aspect provides for methods for treating, preventing, delaying the time to onset or reducing the risk for the development or progression of insulin resistance, the method comprising the step of administering to an animal a therapeutically effective amount a compound of the invention.

Another aspect provides for methods for treating, preventing, delaying the time to onset or reducing the risk for the development or progression of hyperglycemia, the method comprising the step of administering to an animal a therapeutically effective amount a compound of the invention. In one embodiment, the hyperglycemia is postprandial hyperglycemia. In another embodiment, the hyperglycemia is fasting hyperglycemia.

Another aspect provides for methods for treating, preventing, delaying the time to onset of or reducing the risk for the development or progression of accelerated gluconcogenesis, the method comprising the step of administering to an animal a therapeutically effective amount a compound of the invention.

Another aspect provides for methods for treating, preventing, delaying the time to onset of or reducing the risk for the development or progression of increased or excessive (greater than normal levels) hepatic glucose output, the method comprising the step of administering to an animal a therapeutically effective amount a compound of the invention.

Another aspect provides for methods for treating, preventing, delaying the time to onset of or reducing the risk for the development or progression of hyperinsulinemia, the method comprising the step of administering to an animal a therapeutically effective amount a compound of the invention.

Another aspect provides for methods for treating, preventing, delaying the time to onset of or reducing the risk for the development or progression of hyperlipidemia, the method comprising the step of administering to an animal a therapeutically effective amount a compound of the invention.

Another aspect provides for methods for treating, preventing, delaying the time to onset of or reducing the risk for the development or progression of dyslipidemia, the method comprising the step of administering to an animal a therapeutically effective amount a compound of the invention.

Another aspect provides for methods for treating, preventing, delaying the time to onset of or reducing the risk for the development or progression of hypercholesterolemia, the method comprising the step of administering to an animal a therapeutically effective amount a compound of the invention.

Other aspects provide for methods for treating, preventing, delaying the time to onset of or reducing the risk for the development or progression of atherosclerosis, obesity, or Metabolic Syndrome X, the method comprising the step of administering to an animal a therapeutically effective amount a compound of the invention.

Formulations

In one aspect, compounds of the invention are administered in a total daily dose of 0.01 to 2500 mg. In one aspect the range is about 1 mg to about 1000 mg. In one aspect the range is about 1 mg to about 500 mg. In one aspect the range is about 10 mg to about 500 mg. The dose may be administered in as many divided doses as is convenient or necessary.

In another aspect, compounds of the invention are administered in a unit dose of a range between 0.01 to 1000 mg. In one aspect the range is about 0.1 mg to about 500 mg. In one aspect the range is about 0.1 mg to about 100 mg. In one aspect the range is about 1 mg to about 1000 mg. In one aspect the range is about 1 mg to about 500 mg. In one aspect the range is about 1 mg to about 100 mg. In one aspect the range is about 1 mg to about 10 mg. In one aspect the range is about 10 mg to about 1000 mg. In one aspect the range is about 10 mg to about 500 mg. In one aspect the range is about 10 mg to about 100 mg. In one aspect, the unit dose is 10 mg. In one aspect, the unit dose is 25 mg. In one aspect, the unit dose is 50 mg. In one aspect, the unit dose is 75 mg. In one aspect, the unit dose is 100 mg. In one aspect, the unit dose is 150 mg. In one aspect, the unit dose is 200 mg. In one aspect, the unit dose is 250 mg. In one aspect, the unit dose is 300 mg. In one aspect, the unit dose is 400 mg. In one aspect, the unit dose is 500 mg. In one aspect, the unit dose is 600 mg. In one aspect, the unit dose is 700 mg. In one aspect, the unit dose is 800 mg. In one aspect, the unit dose is 900 mg. In one aspect, the unit dose is 1000 mg.

In one aspect the compound is administered QD (once a day). In another aspect the compound is administered BID (twice a day). In another aspect the compound is administered TID (three times a day). In another aspect the compound is administered QID (four times a day). In one aspect the compound is administered before a meal. In one aspect the compound is administered after a meal. In one aspect the compound is administered in the morning hours. In one aspect the compound is administered upon awaking in the morning. In one aspect the compound is administered in the evening hours. In one aspect the compound is administered at bedtime in the evening.

Compounds of this invention may be used in combination with other pharmaceutical agents. The compounds may be administered as a daily dose or an appropriate fraction of the daily dose (e.g., bid). Administration of the compound may occur at or near the time in which the other pharmaceutical agent is administered or at a different time. The compounds of this invention may be used in a multidrug regimen, also known as combination or 'cocktail' therapy, wherein, multiple agents may be administered together, may be administered separately at the same time or at different intervals, or administered sequentially. The compounds of this invention may be administered after a course of treatment by another agent, during a course of therapy with another agent, administered as part of a therapeutic regimen, or may be administered prior to therapy by another agent in a treatment program.

For the purposes of this invention, the compounds may be administered by a variety of means including orally, parenterally, by inhalation spray, topically, or rectally in formulations containing pharmaceutically acceptable carriers, adjuvants and vehicles. The term parenteral as used here includes subcutaneous, intravenous, intramuscular, and intraarterial injections with a variety of infusion techniques. Intraarterial and intravenous injection as used herein includes administration through catheters. Intravenous administration is generally preferred.

Pharmaceutically acceptable salts include acetate, adipate, besylate, bromide, camsylate, chloride, citrate, edisylate, estolate, fumarate, gluceptate, gluconate, glucoranate, hippurate, hyclate, hydrobromide, hydrochloride, iodide, isethionate, lactate, lactobionate, maleate, mesylate, methylbromide, methylsulfate, napsylate, nitrate, oleate, palmoate, phosphate, polygalacturonate, stearate, succinate, sulfate, sulfosalicylate, tannate, tartrate, terphthalate, tosylate, and triethiodide.

Pharmaceutical compositions containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. One aspect relates to the administration of a pharmaceutically acceptable composition of the present invention by controlled- or delayed-release means. Controlled-release pharmaceutical products have a common goal of improving drug therapy over that achieved by their non-controlled release counterparts.

A variety of known controlled- or extended-release dosage forms, formulations, and devices can be adapted for use with the crystalline forms of the invention. Examples include, but are not limited to, those described in U.S. Pat. Nos. 3,845,770; 3,916,899; 3,536,809; 3,598, 123; 4,008, 719; 5,674.533; 5,059,595; 5,591,767; 5,120,548; 5,073, 543; 5,639,476; 5,354,556; 5,733,566; and 6,365,185, each of which is incorporated herein by reference.

These dosage forms can be used to provide delayed or controlled-release of one or more active ingredients using, for example, hydroxypropylmethyl cellulose, other polymer matrices, gels, permeable membranes, osmotic systems (such as OROS, Alza Corporation, Mountain View, Calif. USA), multilayer coatings, microparticles, liposomes, or microspheres or a combination thereof to provide the desired release profile in varying proportions. Additionally, ion exchange materials can be used to prepare immobilized, adsorbed co-crystals and thus effect controlled delivery of the drug. Examples of specific anion exchangers include, but are not limited to, Duolite A568 and Duolite AP143 (Rohm & Haas, Spring House, Pa., USA).

One aspect of the invention encompasses a unit dosage form which comprises a pharmaceutically acceptable composition comprising a crystalline form of a compound of the present invention and one or more pharmaceutically acceptable excipients or diluents, wherein the pharmaceutical composition, medicament or dosage forms is formulated for controlled-release. In another aspect, the dosage form utilizes an osmotic drug delivery system.

A particular and well-known osmotic drug delivery system is referred to as OROS (Alza Corporation, Mountain View, Calif. USA). This technology can readily be adapted for the delivery of compounds and compositions of the invention. Various aspects of the technology are disclosed in U.S. Pat. Nos. 6,375,978; 6,368,626; 6,342,249; 6,333,050; 6,287,295; 6,283,953; 6,270,787; 6,245,357; and 6,132,420; each of which is incorporated herein by reference. Specific adaptations of OROS that can be used to administer compounds and compositions of the invention include, but are not limited to, the OROS; Push-Pull, Delayed Push-Pull, Multi-Layer Push-Pull, and Push-Stick Systems, all of which are well known. See, e.g., www.alza.com. Additional OROS systems that can be used for the controlled oral delivery of compounds and compositions of the invention include OROS-CT and L-OROS (Id.; see also, Delivery Times, vol. II, issue II (Alza Corporation).

Conventional OROS oral dosage forms are made by compressing a drug powder (e.g. a crystalline form selected from Forms A-D) into a hard tablet, coating the tablet with cellulose derivatives to form a semi-permeable membrane, and then drilling an orifice in the coating (e.g., with a laser). Kim, Cherug-ju, Controlled Release Dosage Form Design, 231-238 (Technomic Publishing, Lancaster, Pa.: 2000). The advantage of such dosage forms is that the delivery rate of the drug is not influenced by physiological or experimental conditions. Even a drug with a pH-dependent solubility can be delivered at a constant rate regardless of the pH of the delivery medium. But because these advantages are provided by a build-up of osmotic pressure within the dosage form after administration, conventional OROS drug delivery systems cannot be used to effectively deliver drugs with low water solubility. Id. at 234.

A specific dosage form of the invention comprises: a wall defining a cavity, the wall having an exit orifice formed or formable therein and at least a portion of the wall being semipermeable; an expandable layer located within the cavity remote from the exit orifice and in fluid communication with the semipermeable portion of the wall; a dry or substantially dry state drug layer located within the cavity adjacent to the exit orifice and in direct or indirect contacting relationship with the expandable layer; and a flow-promoting layer interposed between the inner surface of the wall and at least the external surface of the drug layer located within the cavity, wherein the drug layer comprises a crystalline form of a compound of the present invention. See U.S. Pat. No. 6,368,626, the entirety of which is incorporated herein by reference.

Another specific dosage form of the invention comprises: a wall defining a cavity, the wall having an exit orifice formed or formable therein and at least a portion of the wall being semipermeable; an expandable layer located within the cavity remote from the exit orifice and in fluid communication with the semipermeable portion of the wall; a drug layer located within the cavity adjacent the exit orifice and in direct or indirect contacting relationship with the expandable layer; the drug layer comprising a liquid, active agent formulation absorbed in porous particles, the porous particles being adapted to resist compaction forces sufficient to form a compacted drug layer without significant exudation of the liquid, active agent formulation, the dosage form optionally having a placebo layer between the exit orifice and the drug layer, wherein the active agent formulation comprises a crystalline form of a compound of the present invention. See U.S. Pat. No. 6,342,249, the entirety of which is incorporated herein by reference.

In another aspect, a pharmaceutical composition or medicament comprising a crystalline form of a compound of the present invention is administered transdermally. Such a transdermal (TD) delivery can avoid first-pass metabolism. Additionally, a "pill-and-patch" strategy can be taken, where only a fraction of the daily dose is delivered through the skin to generate basal systemic levels, onto which oral therapy is added.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, ethylcellulose, hydroxypropylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxy-benzoate, one or more coloring agents, one or more flavoring agents and one or more sweetening agents, such as sucrose or saccharin.

Oil suspensions may be formulated by suspending the active ingredient in a vegetable oil, such as arachid oil, olive oil sesame oil or coconut oil, or in a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules of the invention suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the invention may also be in the form of oil-in-water emulsions. The oily phase may be a vegetable oil, such as olive oil or arachid oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents.

Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

As noted above, formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet may be made by compression or molding, optionally with one or more accessory ingredients. Compressed tablets may be prepared by compressing in a suitable machine the active ingredient in a free flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein using, for example, hydroxypropyl methylcellulose in varying proportions to provide the desired release profile. Tablets may optionally be provided with an enteric coating, to provide release in parts of the gut other than the stomach. This is particularly advantageous with the compounds of Formula I when such compounds are susceptible to acid hydrolysis.

Formulations suitable for topical administration in the mouth include lozenges comprising the active ingredient in a flavored base, usually sucrose and acacia or tragacanth; pastilles comprising the active ingredient in an inert base such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous isotonic sterile injection solutions which may contain antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Injection solutions and suspensions may be prepared from sterile powders, granules and tablets of the kind previously described.

Formulations suitable for parenteral administration may be administered in a continuous infusion manner via an indwelling pump or via a hospital bag. Continuous infusion includes the infusion by an external pump. The infusions may be done through a Hickman or PICC or any other suitable means of administering a formulation either parenterally or i.v.

Preferred unit dosage formulations are those containing a daily dose or unit, daily sub-dose, or an appropriate fraction thereof, of a drug.

It will be understood, however, that the specific dose level for any particular patient will depend on a variety of factors including the activity of the specific compound employed;

the age, body weight, general health, sex and diet of the individual being treated; the time and route of administration; the rate of excretion; other drugs which have previously been administered; and the severity of the particular disease undergoing therapy, as is well understood by those skilled in the art.

Examples: Synthesis of Compounds of the Invention

Compounds of Formula I and Formula II can be prepared according to the methodology outlined in the following general synthetic schemes or with modifications of these schemes that will be evident to persons skilled in the art.
Synthesis of the Phosphonate Prodrug Compounds of the Invention
1) Preparation of a Phosphonate Prodrug Prodrugs can be introduced at different stages of the synthesis. Most often these prodrugs are made from the phosphonic acids of compounds of the invention because of their lability. Phosphonic acids of compounds of the invention can be alkylated with electrophiles such as alkyl halides and alkyl sulfonates under nucleophilic substitution conditions to give phosphonate esters. For example, acyloxyalkyl prodrugs of compounds of the invention can be prepared by direct alkylation of compounds of Formula I with an appropriate acyloxyalkyl halide (e.g., Cl, Br, I; *Phosphorus Sulfur* 54:143 (1990); *Synthesis* 62 (1988)) in the presence of a suitable base (e.g., pyridine, TEA, diisopropylethylamine) in suitable solvents such as DMF (*J. Med. Chem.* 37:1875 (1994)). The carboxylate component of these acyloxyalkyl halides includes but is not limited to acetate, propionate, isobutyrate, pivalate, benzoate, carbonate and other carboxylates.

Dimethylformamide dialkyl acetals can also be used for the alkylation of phosphonic acids (*Collect. Czech Chem. Commu.* 59:1853 (1994)). Compounds of the invention wherein the prodrug moiety comprises a cyclic carbonate, a lactone or a phthalidyl group can also be synthesized by direct alkylation of the free phosphonic acids with appropriate halides in the presence of a suitable base such as NaH or diisopropylethylamine (*J. Med. Chem.* 38:1372 (1995); *J. Med. Chem.* 37:1857 (1994); *J. Pharm. Sci.* 76:180 (1987)).

Alternatively, these phosphonate prodrugs can be synthesized by the reactions of the corresponding dichlorophosphonate and an alcohol (*Collect Czech Chem. Commun.* 59:1853 (1994)). For example, a dichlorophosphonate is reacted with substituted phenols and arylalkyl alcohols in the presence of a base such as pyridine or TEA to give the compounds of the invention wherein the prodrug moiety is an aryl group (*J. Med. Chem.* 39:4109 (1996); *J. Med. Chem.* 38:1372 (1995); *J. Med. Chem.* 37:498 (1994)) or an arylalkyl group (*J. Chem. Soc. Perkin Trans.* 1 38:2345 (1992)). The disulfide-containing prodrugs (*Antiviral Res.* 22:155 (1993)) can be prepared from a dichlorophosphonate and 2-hydroxyethyldisulfide under standard conditions. Dichlorophosphonates are also useful for the preparation of various phosphonamides as prodrugs. For example, treatment of a dichlorophosphonate with ammonia gives both a monophosphonamide and a diphosphonamide; treatment of a dichlorophosphonate with 1-amino-3-propanol gives a cyclic 1,3-propylphosphonamide; treatment of a chlorophosphonate monophenyl ester with an amino acid ester in the presence of a suitable base gives a substituted monophenyl monophosphonamidate.

Such reactive dichlorophosphonates can be generated from the corresponding phosphonic acids with a chlorinating agent (e.g., thionyl chloride, *J. Med. Chem.* 1857 (1994); oxalyl chloride, *Tetrahedron Len.* 31:3261 (1990); phosphorous pentachloride, *Synthesis* 490 (1974)). Alternatively, a dichlorophosphonate can be generated from its corresponding disilyl phosphonate esters (*Synth. Commu.* 17:1071 (1987)) or dialkyl phosphonate esters (*Tetrahedron Lett.* 24:4405 (1983); *Bull. Soc. Chim.* 130:485 (1993)). Compounds of the invention can be mixed phosphonate ester (e.g., phenyl and benzyl esters, or phenyl and acyloxyalkyl esters) including the chemically combined mixed esters such as phenyl and benzyl combined prodrugs reported in *Bioorg. Med. Chem. Lett.* 7:99 (1997).

Dichlorophosphonates are also useful for the preparation of various phosphonamides as prodrugs. For example, treatment of a dichlorophosphonate with an amine (e.g. an amino acid alkyl ester such as L-alanine ethyl ester) in the presence of a suitable base (e.g. triethylamine, pyridine, etc.) gives the corresponding bisphosphonamide; treatment of a dichlorophosphonate with 1-amino-3-propanol gives a cyclic 1,3-propylphosphonamide; treatment of a chlorophosphonate monophenyl ester with an amino acid ester in the presence of a suitable base gives a substituted monophenyl monophosphonamidate. Direct couplings of a phosphonic acid with an amine (e.g. an amino acid alkyl ester such as L-alanine ethyl ester) are also reported to give the corresponding bisamides under Mukaiyama conditions (*J. Am. Chem. Soc.,* 94:8528 (1972)).

The SATE (S-acetyl thioethyl) prodrugs can be synthesized by the coupling reaction of the phosphonic acid compounds of the invention and S-acyl-2-thioethanol in the presence of DCC, EDCI or PyBOP (*J. Med. Chem.* 39.1981 (1996)).

Cyclic phosphonate esters of substituted 1,3-propane diols can be synthesized by either reactions of the corresponding dichlorophosphonate with a substituted 1,3-propanediol or coupling reactions using suitable coupling reagents (e.g., DCC, EDCI, PyBOP; *Synthesis* 62 (1988)). The reactive dichlorophosphonate intermediates can be prepared from the corresponding acids and chlorinating agents such as thionyl chloride (*J. Med. Chem.* 1857 (1994)), oxalyl chloride (*Tetrahedron Lett.* 31:3261 (1990)) and phosphorus pentachloride (*Synthesis* 490 (1974)). Alternatively, these dichlorophosphonates can also be generated from disilyl esters (*Synth. Commun.* 17:1071 (1987)) and dialkyl esters (*Tetrahedron Lett.* 24:4405 (1983); *Bull. Soc. Chim. Fr.,* 130:485 (1993)).

Alternatively, these cyclic phosphonate esters of substituted 1,3-propane diols are prepared from phosphonic acids by coupling with diols under Mitsunobu reaction conditions (*Synthesis* 1 (1981); *J. Org. Chem.* 52:6331 (1992)), and other acid coupling reagents including, but not limited to, carbodiimides (*Collect. Czech. Chem. Commun.* 59:1853 (1994); *Bioorg. Med. Chem. Lett.* 2:145 (1992); *Tetrahedron Lett.* 29:1189 (1988)), and benzotriazolyloxytris-(dimethylamino) phosphonium salts (*Tetrahedron Lett.* 34:6743 (1993)).

Phosphonic acids also undergo cyclic prodrug formation with cyclic acetals or cyclic ortho esters of substituted propane-1,3-diols to provide prodrugs as in the case of carboxylic acid esters (*Helv. Chim. Acta.* 48:1746 (1965)). Alternatively, more reactive cyclic sulfites or sulfates are also suitable coupling precursors to react with phosphonic acid salts. These precursors can be made from the corresponding diols as described in the literature.

Alternatively, cyclic phosphonate esters of substituted 1,3-propane diols can be synthesized by trans esterification reaction with substituted 1,3-propane diol under suitable conditions. Mixed anhydrides of parent phosphonic acids generated in situ under appropriate conditions react with diols to give prodrugs as in the case of carboxylic acid esters (*Bull. Chem. Soc. Jpn.* 52:1989 (1979)). Aryl esters of phosphonates are also known to undergo transesterification with alkoxy intermediates (*Tetrahedron Lett.* 38:2597 (1997); *Synthesis* 968 (1993)).

One aspect of the present invention provides methods to synthesize and isolate single isomers of prodrugs of compounds of the invention that are phosphonic acids. Because phosphorus is a stereogenic atom, formation of a prodrug with a substituted-1,3-propane-diol will produce a mixture of isomers. For example, formation of a prodrug with a racemic 1-(V)-substituted-1,3-propane diol gives a racemic mixture of cis-prodrugs and a racemic mixture of trans-prodrugs. In an other aspect, the use of the enantioenriched substituted-1,3-propane diol with the R-configuration gives enantioenriched R-cis- and R-trans-prodrugs. These compounds can be separated by a combination of column chromatography and/or fractional crystallization.

The compounds of the invention can be mixed phosphonate esters (e.g. phenyl benzyl phosphonate esters, phenyl acyloxyalkyl phosphonate esters, phenyl aminoacid esters etc). For example, the chemically combined phenyl-benzyl prodrugs are reported by Meier, et al. *Bioorg. Med. Chem. Lett.*, 1997, 7: 99.

The substituted cyclic propyl phosphonate esters compounds of the invention, can be synthesized by reaction of the corresponding dichlorophosphonate and the substituted 1,3-propane diol. The following are non-limiting methods to prepare the substituted 1,3-propane diols.

Synthesis of the 1,3-Propane Diols Used in the Preparation of Certain Prodrugs

The discussion of this step includes various synthetic methods for the preparation of the following types of propane-1,3-diols: i) 1-substituted; ii) 2-substituted; and iii) 1,2- or 1,3-annulated. Different groups on the prodrug part of the molecule i.e., on the propane diol moiety can be introduced or modified either during the synthesis of the diols or after the synthesis of the prodrugs.

i) 1-Substituted 1,3-propanediols 1,3-Propanediols useful in the synthesis of compounds in the present invention can be prepared using various synthetic methods. As described in Scheme A, additions of an aryl Grignard to a 1-hydroxy-propan-3-al give 1-aryl-substituted 1,3-propanediols (path a). This method is suitable for the conversion of various aryl halides to 1-arylsubstituted-1,3-propanediols (*J. Org. Chem.* 1988, 53, 911). Conversions of aryl halides to 1-substituted 1,3-propanediols can also be achieved using Heck reactions (e.g., couplings with a 1,3-diox-4-ene) followed by reductions and subsequent hydrolysis reactions (*Tetrahedron Lett.* 1992, 33, 6845). Various aromatic aldehydes can also be converted to 1-substituted-1,3-propanediols using alkenyl Grignard addition reactions followed by hydroboration-oxidation reactions (path b).

Scheme A

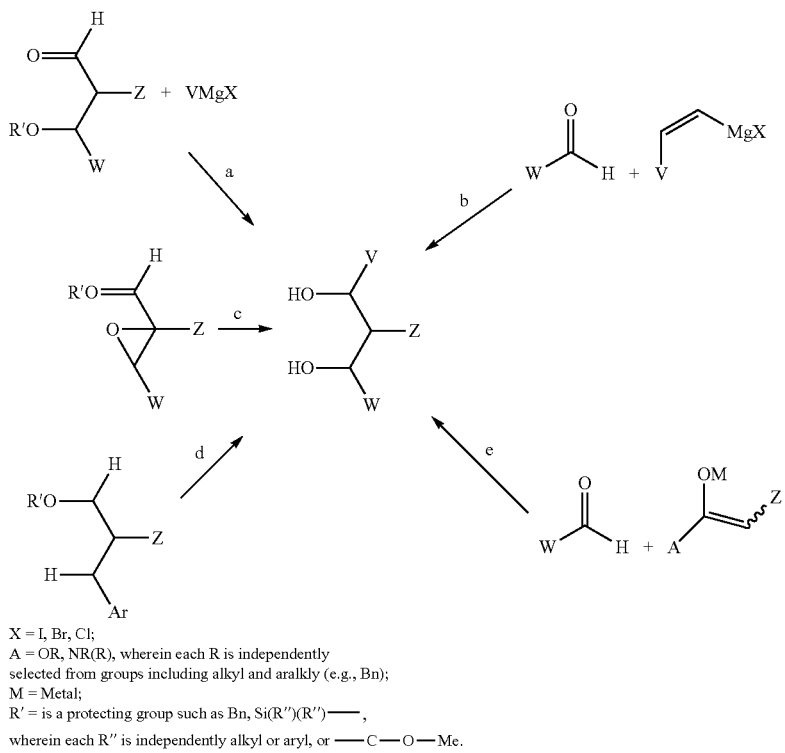

X = I, Br, Cl;
A = OR, NR(R), wherein each R is independently selected from groups including alkyl and aralkly (e.g., Bn);
M = Metal;
R' = is a protecting group such as Bn, Si(R″)(R″)——,
wherein each R″ is independently alkyl or aryl, or ——C—O—Me.

Aldol reactions between an enolate (e.g., lithium, boron, tin enolates) of a carboxylic acid derivative (e.g., tert-butyl acetate) and an aldehyde (e.g., the Evans's aldol reactions) are especially useful for the asymmetric synthesis of enantioenriched 1,3-propanediols. For example, reaction of a metal enolate of t-butyl acetate with an aromatic aldehyde followed by reduction of the ester (path e) gives a 1,3-propanediol (*J. Org. Chem.* 1990, 55 4744). Alternatively, epoxidation of cinnamyl alcohols using known methods (e.g., Sharpless epoxidations and other asymmetric epoxidation reactions) followed by reduction reactions (e.g., using Red-Al) give various 1,3-propanediols (path c). Enantioenriched 1,3-propanediols can be obtained via asymmetric reduction reactions (e.g., enantioselective borane reductions) of 3-hydroxy-ketones (*Tetrahedron Lett.* 1997, 38 of one the hydroxymethyl groups in a 2-(hydroxymethyl)-1,3-propanediol to an aldehyde followed by addition reactions with an aryl Grignard (path c). Aldehydes can also be converted to alkyl amines via reductive amination reactions (path e).

Scheme B

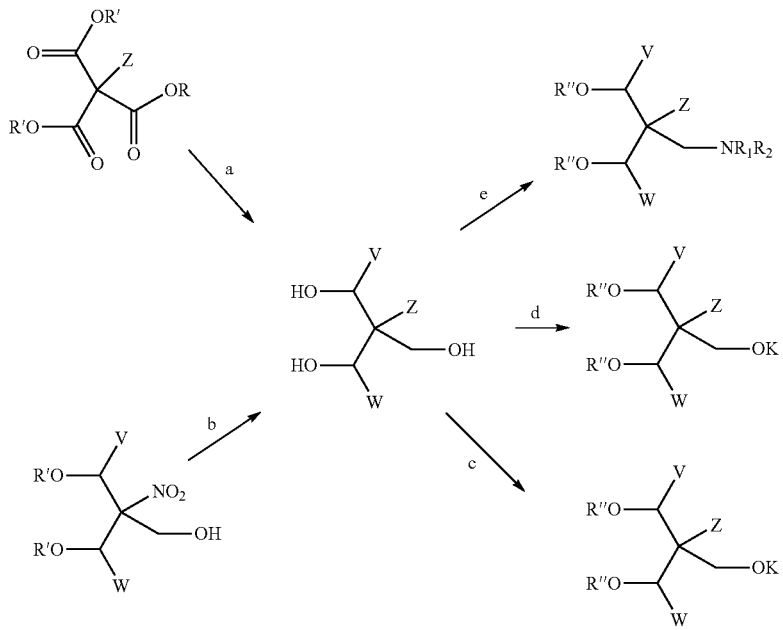

K = COR or OCOR, wherein R is alkyl or aryl;
R' = is a protecting group such as Bn, Si(R")(R") ——
wherin each R" is independently alkyl or aryl, or ——C——O——Me;
R" = H if final compound or standard protecting group if intermediate.

761). Alternatively, resolution of racemic 1,3-propanediols using various methods (e.g., enzymatic or chemical methods) can also give enantioenriched 1,3-propanediol. Propan-3-ols with a 1-heteroaryl substituent (e.g., a pyridyl, a quinolinyl or an isoquinolinyl) can be oxygenated to give 1-substituted 1,3-propanediols using N-oxide formation reactions followed by a rearrangement reaction in acetic anhydride conditions (path d) (*Tetrahedron* 1981, 37, 1871).

ii) 2-Substituted 1,3-propanediols

A variety of 2-substituted 1,3-propanediols useful for the synthesis of compounds of Formula I can be prepared from various other 1,3-propanediols (e.g., 2-(hydroxymethyl)-1, 3-propanediols) using conventional chemistry (*Comprehensive Organic Transformations*, VCH, New York, 1989). For example, as described in Scheme B, reductions of a trialkoxycarbonylmethane under known conditions give a triol via complete reduction (path a) or a bis(hydroxymethyl) acetic acid via selective hydrolysis of one of the ester groups followed by reduction of the remaining two other ester groups. Nitrotriols are also known to give triols via reductive elimination (path b) (*Synthesis* 1987, 8, 742). Furthermore, a 2-(hydroxymethyl)-1,3-propanediol can be converted to a mono acylated derivative (e.g., acetyl, methoxycarbonyl) using an acyl chloride or an alkyl chloroformate (e.g., acetyl chloride or methyl chloroformate) (path d) using known chemistry (*Protective Groups In Organic Synthesis*; Wiley, New York, 1990). Other functional group manipulations can also be used to prepare 1,3-propanediols such as oxidation iii) Annulated 1,3-Propane Diols Compounds of invention wherein V and Z or V and W are connected by four carbons to form a ring can be prepared from a 1,3-cyclohexanediol. For example, cis, cis-1,3,5-cyclohexanetriol can be modified to give various other 1,3,5-cyclohexanetriols which are useful for the preparations of compounds of Formula I wherein $R^{51}$ and $R^{51}$ together are

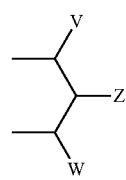

wherein together V and W are connected via 3 atoms to form a cyclic group containing 6 carbon atoms substituted with a hydroxy group. It is envisioned that these modifications can be performed either before or after formation of a cyclic phosphonate 1,3-propanediol ester. Various 1,3-cyclohexanediols can also be prepared using Diels-Alder reactions (e.g., using a pyrone as the diene: *Tetrahedron Lett.* 1991, 32, 5295). 2-Hydroxymethylcyclohexanol and 2-hydroxymethylcyclopentanols are useful for the preparations of compounds of the invention wherein $R^{51}$ and $R^{51}$ together are

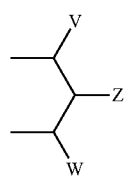

wherein together V and Z are connected via 2 or 3 atoms to form a cyclic group containing 5 or 6 carbon atoms. 1,3-Cyclohexanediol derivatives are also prepared via other cycloaddition reaction methodologies. For example, cycloadducts from the cycloaddition reactions of a nitrile oxide and an olefin can be converted to a 2-ketoethanol derivative which can be further converted to a 1,3-propanediol (including 1,3-cyclohexanediol, 2-hydroxymethylcyclohexanol and 2-hydroxymethylcyclopentanol) using known chemistry (*J. Am. Chem. Soc.* 1985, 107, 6023). Alternatively, precursors to 1,3-cyclohexanediol can be made from quinic acid (*Tetrahedron Lett.* 1991, 32, 547.)

Generation of Phosphonic Acid

Select compounds may be prepared from phosphonate esters using known phosphate and phosphonate ester cleavage conditions. In general, silyl halides have been used to cleave the various phosphonate esters, followed by mild hydrolysis of the resulting silyl phosphonate esters to give the desired phosphonic acids. Depending on the stability of the products, these reactions are usually accomplished in the presence of acid scavengers such as 1,1,1,3,3,3-hexamethyldisilazane, 2,6-lutidine, etc. Such silyl halides include, chlorotrimethylsilane (Rabinowitz, *J. Org. Chem.,* 1963, 28: 2975), bromotrimethylsilane (McKenna, et al, *Tetrahedron Lett.*, 1977, 155), iodotrimethylsilane (Blackburn, et al, *J. Chem. Soc., Chem. Commun.,* 1978, 870). Alternately, phosphonate esters can be cleaved under strong acid conditions, (e.g HBr, HCl, etc.) in polar solvents, preferably acetic acid (Moffatt, et al, U.S. Pat. No. 3,524,846, 1970) or water. These esters can also be cleaved via dichlorophosphonates, prepared by treating the esters with halogenating agents e.g. phosphorus pentachloride, thionyl chloride, $BBr_3$, etc. (Pelchowicz, et al, *J. Chem. Soc.,* 1961, 238) followed by aqueous hydrolysis to give phosphonic acids. Aryl and benzyl phosphonate esters can be cleaved under hydrogenolysis conditions (Lejczak, et al, *Synthesis,* 1982, 412; Elliott, et al, *J. Med. Chem.,* 1985, 28: 1208; Baddiley, et al, *Nature,* 1953, 171: 76) or dissolving metal reduction conditions (Shafer, et al, *J. Am. Chem. Soc.,* 1977, 99: 5118). Electrochemical (Shono, et al, *J. Org. Chem.,* 1979, 44: 4508) and pyrolysis (Gupta, et al, *Synth. Commun.,* 1980, 10: 299) conditions have also been used to cleave various phosphonate esters.

Synthesis of the Phosphinate and Phosphonate Monoester Prodrug Compounds of the Invention 1) Preparation of Phosphinate and Phosphonate Monoester Prodrug Phosphinic acids and phosphonic acid monoesters can be alkylated with electrophiles such as alkyl halides and alkyl sulfonates under nucleophilic substitution conditions to give phosphinate and phosphonate ester prodrugs. For example, compounds of Formulas I and II wherein $Y^2R^{51}$ is an acyloxyalkyl group can be prepared by direct alkylation of compounds of Formulas I and II wherein $Y^2R^{51}$ is OH with an appropriate acyloxyalkyl halide (e.g., Cl, Br, I; *Phosphorus Sulfur* 54:143 (1990); *Synthesis* 62 (1988)) in the presence of a suitable base (e.g., pyridine, TEA, diisopropylethylamine) in suitable solvents such as DMF (*J. Med. Chem.* 37:1875 (1994)). The carboxylate component of these acyloxyalkyl halides includes but is not limited to acetate, propionate, isobutyrate, pivalate, benzoate, carbonate and other carboxylates.

Dimethylformamide dialkyl acetals can also be used for the alkylation of phosphinic acids and phosphonic acid monoesters (*Collect. Czech Chem. Commu.* 59:1853 (1994)). Compounds of Formulas I and II wherein $Y^2R^{51}$ is a cyclic carbonate, a lactone or a phthalidyl group can also be synthesized by direct alkylation of the free phosphonic acids with appropriate halides in the presence of a suitable base such as NaH or diisopropylethylamine (*J. Med. Chem.* 38:1372 (1995); *J. Med. Chem.* 37:1857 (1994); *J. Pharm. Sci.* 76:180 (1987)).

Alternatively, these phosphinate and phosphonate monoester prodrugs can be synthesized by the reactions of the corresponding chlorophospho(i)nate and an alcohol (*Collect Czech Chem. Commun.* 59:1853 (1994)). For example, a chlorophospho(i)nate is reacted with substituted phenols and arylalkyl alcohols in the presence of a base such as pyridine or TEA to give the compounds of Formula I wherein $YR^{51}$ is an aryl group (*J. Med. Chem.* 39:4109 (1996): *J. Med. Chem.* 38:1372 (1995); *J. Med. Chem.* 37:498 (1994)) or an arylalkyl group (*J. Chem. Soc. Perkin Trans.* 1 38:2345 (1992)). The disulfide-containing prodrugs (*Antiviral Res.* 22:155 (1993)) can be prepared from a chlorophospho(i)nate and 2-hydroxyethyldisulfide under standard conditions. Chlorophospho(i)nates are also useful for the preparation of various phospho(i)namides as prodrugs. For example, treatment of a chlorophospho(i)nate with ammonia gives the phospho(i)namide.

Such reactive chlorophospho(i)nates can be generated from the corresponding phosphinic acids and phosphonic acid monoesters with a chlorinating agent (e.g., thionyl chloride, *J. Med. Chem.* 1857 (1994); oxalyl chloride, *Tetrahedron Len.* 31:3261 (1990); phosphorous pentachloride, *Synthesis* 490 (1974)). Alternatively, a chlorophospho(i)nate can be generated from its corresponding silyl phosphinate ester or phosphonic acid monester (*Synth. Commu.* 17:1071 (1987)) or alkyl phosphinate esters (*Tetrahedron Lett.* 24:4405 (1983); *Bull Soc. Chim.* 130:485 (1993)).

Chlorophospho(i)nates are also useful for the preparation of various phosphonamides as prodrugs. For example, treatment of a chlorophospho(i)nate with an amine (e.g. an amino acid alkyl ester such as L-alanine ethyl ester) in the presence of a suitable base (e.g. triethylamine, pyridine, etc.) gives the corresponding phospho(i)namide. Direct couplings of phosphinic acids or phosphonic acid monoesters with an amine (e.g. an amino acid alkyl ester such as L-alanine ethyl ester) are also reported to give the corresponding amidate under Mukaiyama conditions (*J. Am. Chem. Soc.* 94:8528 (1972)).

The SATE (S-acetyl thioethyl) prodrugs can be synthesized by the coupling reaction of the phosphinic acids or phosphonic acid monoesters of Formulas I and II and S-acyl-2-thioethanol in the presence of DCC, EDCI or PyBOP (*J. Med. Chem.* 39:1981 (1996)).

2) Generation of Phosphonic Acid Monoesters

Compounds of Formulas I and II wherein $R^{50}$ is —P(O)($Y^2R^{51}$)($OR^3$) and $R^3$ is $C_1$-$C_6$alkyl may be prepared from the diester intermediate, used for the synthesis of phosphonic acid, by monosaponification. Monohydrolysis of one of the ester groups on the phosphonate may be accomplished by treatment of phosphonate diesters with aqueous alkaline solution such as NaOH, KOH or LiOH at rt or while heating. Sodium azide can also be used in DMF (*Bioorg. Med. Chem. Lett* 14(13), 3559-62 (2004)) to accomplished the monosaponification. Alternatively, organic bases such as morpholine or N-methyl-piperazine can be used to hydrolyze one of the phosphonate ester groups (*Synth. Comm.* 34(2):331-344 (2004)).

3) Generation of Phosphinic Acids

The introduction of a phosphinic acid group can generally be accomplished according to known methods. An efficient way to synthesize phosphinic acid is to convert a phosphonate diester to its corresponding monochloridate-monoester using one of many chlorinating agents such as $PCl_5$ (*Can. J. Chem.* 76(3):313-18 (1998)), oxalyl chloride (*Tetrahedron Lett.* 44(12):1445-48 (2003)), thionyl chloride (*J. Med. Chem.* 45(4):919-29 (2002)) or phosgene (*Redcl. Trav. Chim. Pays-Bas* 78:59-61 (1959)) and to introduce the carbon-based substituent on the phosphorus atom via a Grignard reagent (*J. Chem. Soc. Perkin Trans.* 1 17:2179-86 (1996)), a lithium anion (*J. Med. Chem.* 33(11):2952-56 (1990)) or an enolate (*Bioorg Med. Chem.* 5(7):1327-38 (1997)) to produce the desired phosphinate ester. The phosphinic acid is then generated by saponification with aqueous NaOH, KOH or LiOH or using one of the many methods known to deprotect phosphonic acids such as TMSBr or TMSCl/KI. Alternatively, phosphinic acids can be generated from phosphonic acid monoesters by making the monochloridate-monoester with chlorinating reagents such as thionyl chloride or oxalyl chloride, and introducing the substituent on the phosphorus as above.

Other methods include palladium-catalyzed cross-coupling of alkyl phosphinates to form H-phosphinate esters (*Tetrhedron* 61(26):6315-6329 (2005)), based-promoted alkylation of H-phosphinate esters with electrophiles (*J. Org. Chem.* 72(8):2851-2856(2007)), and palladium-catalyzed cross-coupling of (low alkyl)phosphinic acid ester with aryl halides and aryl triflates (*J. Org. Chem.* 63(10): 3463-3467(1998); *Synthesis* (14):2216-2220(2003); *Synthesis* (9):778-780(1984)).

Cyclic phosphinic acids can be synthesized starting from a 1,2-dicarboxylate-benzene precursor (*J. Am. Chem. Soc.* 101:7001-08 (1979)) which is reduced to the di-benzylic alcohol and brominated with $PBr_3$ to give the di-benzylic bromide precursor (*Synth. Commun.* 14(6):507-514 (1984)). Double Arbuzov condensation of the di-benzylic bromide with bis(trimethylsilyloxy)phosphine, made from the reaction of ammonium hypophosphite and hexamethyldisilazane, provides the cyclic phosphinate ester (*J. Org. Chem.* 60:6076-81 (1995)) which can be converted to the phosphinic acid by saponification with NaOH or TMSBr. Alternatively, the di-benzyl bromide precursor can be obtained by bromination of a substituted 1,2-dimethyl benzene with bromine or N-bromosuccinimide (*J. Chem. Soc.* 3358-61 (1959)) or direct bromomethylation by reacting formaldehyde and HBr in presence of acetic acid (*J. Phys. Chem.* 108(4):5145-55 (2004)).

The following examples are provided so that the invention can be more fully understood and should not be construed as limiting the invention in any way.

Hydrogen atoms on both carbon and heteroatoms may be implied on chemical structures within.

Examples: Synthesis of Compounds of Formula I

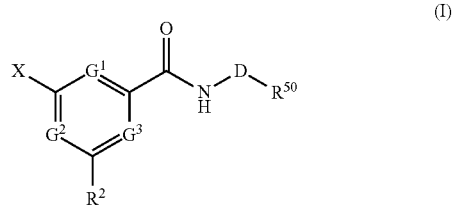

Compounds of Formula I can be prepared according to the processes described in the following representative Schemes. Reagents and conditions given are only for illustration purposes and alternative methods may be employed by those skilled in the art. It should be understood that the following Schemes do not limit the invention which is defined by the claims. Typically the synthesis of a compound of Formula I includes the following general steps: (1) deprotection of a phosphonate or phosphinate ester; (2) introduction of a phosphonate or phosphinate; (3) formation of the amide bond; (4) preparation of the aryl or heteroaryl carboxylic acid; (5) construction of the aryl or heteroaryl carboxylic ester. The order of introduction of a phosphonate or phosphinate group and the formation of the amide bond in the synthesis of compounds of Formula I can be freely decided by those skilled in the art based on the structure of the substrate. Variable groups in Schemes have the same meanings defined for Formula I unless stated otherwise. In all applicable structures contained in the Schemes described in this invention, $P^1$ is a protecting group such as $C_{1-4}$-alkyl; $P^2$ is alkyl or cycloalkyl; $P^3$ is a leaving group such as F, Cl, Br, I, or triflate; $P^4$ is $P^3$, $-P(O)(OP^1)_2$, or $-P(O)(OP^1)P^2$; $P^5$ is aryl, heteroaryl, alkyl, cycloalkyl, or arylalkyl; X' is X or a functional group that can be transformed into X; and Y' is R or a functional group that can be transformed into $R^2$. Protection and deprotection in the Schemes may be carried out according to the procedures generally known in the art (e.g., T. W. Greene and P. G. M. Wuts, "Protecting Groups in Organic Synthesis", $3^{rd}$ edition, John Wiley & Sons, 1999).

Deprotection of a Phosphonate or Phosphinate Ester

Compounds of Formula I wherein $R^{50}$ is $-P(O)(OH)_2$ or $-P(O)(OH)P^2$ may be prepared from phosphonate or phosphinate esters using the known cleavage methods. Silyl halides are generally used to cleave various phosphonate or phosphinate esters and give the desired phosphonic or phosphinic acid upon mild hydrolysis of the resulting phosphonate or phosphinate silyl esters. When needed, acid scavengers (e.g., HMDS) can be used for the acid sensitive compounds. Representative conditions can be found in the Generation of phospho(i)nic acid section in this publication. Methods to form phosphonate monoesters can be found in the Generation of Phosphonic Acid Monoesters section in this publication.

Scheme 1

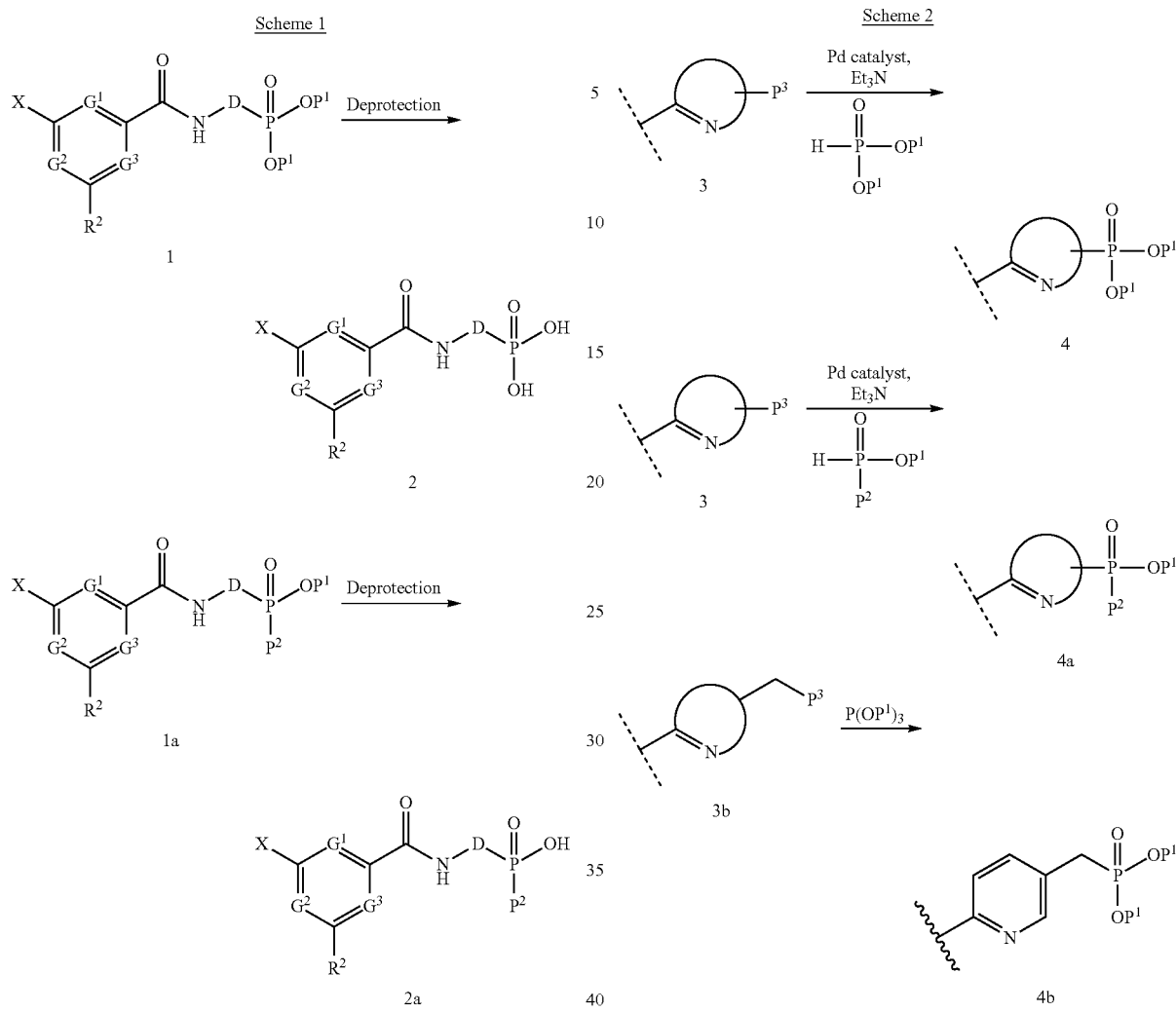

Scheme 2

Introduction of a Phosphonate or Phosphinate Estr

The introduction of a phosphonate or phosphinate group generally can be accomplished according to known procedures. Compounds of Formula I wherein D is nitrogen-containing heteroarylene may be prepared by a number of known methods (Scheme 2). For example, the coupling reaction of a phenyl bromide (*J. Org. Chem.* 1999, 64, 120), iodide (*Phosphorus Sulfur* 1997, 130, 59) or triflate (*J. Org. Chem.* 2001, 66, 348) with diethyl phosphite or diisopropyl phosphite in the presence of a palladium catalyst is widely used within the art. Alkylphosphinic acid isopropyl ester or alkylphosphinic acid ethyl ester may be used in the aforementioned procedures to afford the desired alkylphosphinate esters. Other methods such as Michaelis-Arbuzov reaction (*Chem. Rev.* 1981, 81, 415) can also be used to introduce the phosphonate group by coupling a benzyl, arylalkyl, or heteroarylalkyl halide/triflate with triethyl phosphite or triisopropyl phosphite. Lithiated heteroaryl ring carbon can react with dialklyl chlorophosphate to attach the phosphonate group to the corresponding heteroaryl ring.

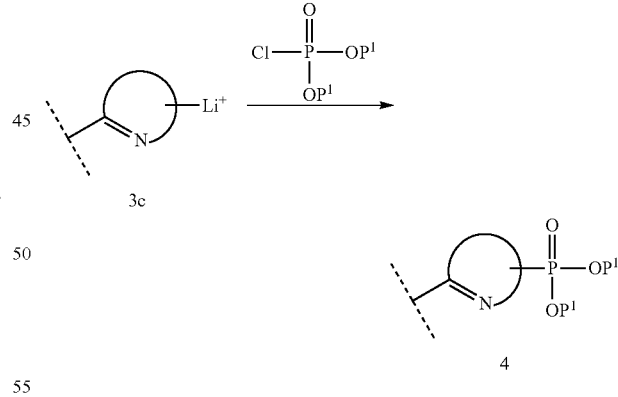

Formation of an Amide Bond

Standard amide bond formation methods can be used to couple amino groups with carboxylic acids or activated derivatives thereof. For example, (i) reactions of an amine with a carboxylic acid in the presence of DCC or EDC according to the known methods (e.g., *J. Org. Chem.* 1977, 42, 2019); (ii) conversion of a carboxylic group to an acid chloride by reaction with oxalyl chloride, followed by coupling the acid chloride with an amine in the presence of a base (e.g. triethyl amine or pyridine) in chloroform or DCM (*Org. Synth., Collect Vol. V,* 1973, 336); (iii) other known procedures (*Tetrahedron Lett.* 1990, 31, 7119; *Tetrahedron Lett.* 1989, 30, 6917; *J. Org. Chem.* 1993, 58, 618).

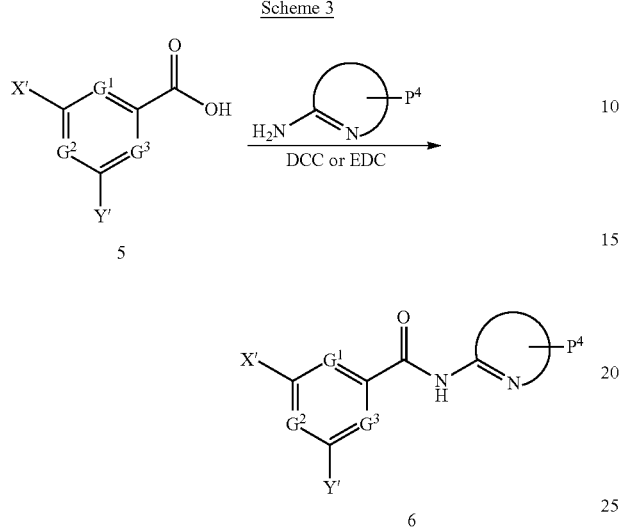

Scheme 3

Preparation of the Aryl or Heteroaryl Carboxylic Acid

Deprotection reactions of carboxylic esters are well known in the art. Methyl or ethyl ester is deprotected in the presence of sodium hydroxide or lithium hydroxide in a mixture of THF/EtOH/water (e.g., *Tetrahedron Lett.* 1977, 3529). Benzyl ester is removed using hydrogenolysis conditions (e.g., *Org. React.* 1953, VII, 263).

Scheme 4

Construction of the Aryl or Heteroaryl Carboxylic Ester

Processes for the synthesis of compounds 7 are provided according to their substitution patterns. Syntheses of compounds 7a generally follow similar synthetic processes as those of compounds 7.

Compounds 7 wherein $G^1=G^2=G^3=CH$ can be prepared by a number of known methods:

(i) When X is aryl, heteroaryl, alkyl, cycloalkyl, or arylalkyl, the installation of X' can be accomplished by Stille couplings (*J. Am. Chem. Soc.* 1984, 106, 4630; *Tetrahedron Lett.* 1995, 36, 2191), Suzuki couplings (*Chem. Rev.* 1995, 95, 2457), Friedel-Crafts alkylations (*Synlett* 1996, 557), or Negishi couplings (*Org. Lett.,* 2003, 5, 423) as described in Scheme 5.

Scheme 5

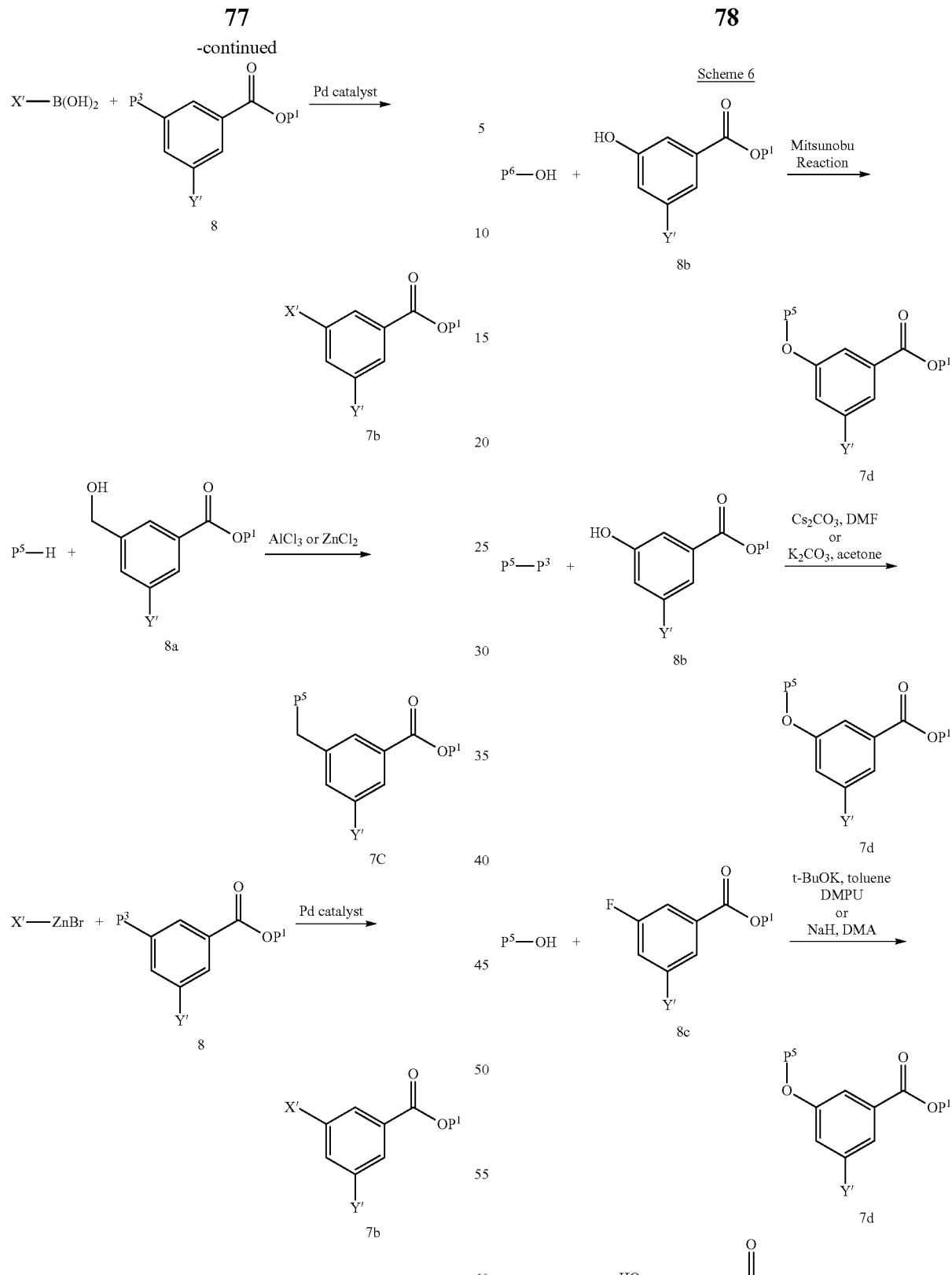
(ii) When X is aryloxy, heteroaryloxy, alkyloxy, cycloalkyloxy or arylalkyloxy, the installation of O—P⁵ can be accomplished by Mitsunobu reactions (*Org. Prep. Proceed. Int.* 1996, 28, 127), displacement reactions (*J. Org. Chem.* 2006, 71, 2170; *Synthesis* 2004, 2625), or coupling reactions (*J. Am. Chem. Soc.* 2003, 125, 9032) as described in Scheme 6.

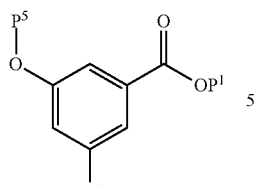

7d

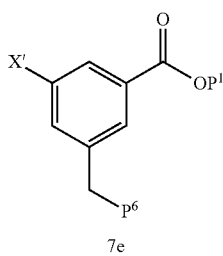

7e (iii) When $R^2$ is the group $-E^2-E^3$, wherein $E^2$ is a direct bond or an alkylene, the installation of Y' can be accomplished by Stille couplings (*J. Am. Chem. Soc.* 1984, 106, 4630; *Tetrahedron Lett.* 1995, 36, 2191), Suzuki couplings (*Chem. Rev.* 1995, 95, 2457), Friedel-Crafts alkylations (*Synlett* 1996, 557), or Negishi couplings (*Org. Lett.*, 2003, 5, 423) as described in Scheme 7.

(iv) When $R^2$ is the group $-E^1-E^2-E^3$, wherein $E^1$ is O, the installation of O—$P^5$ can be accomplished by Mitsunobn reactions (*Org. Prep. Proceed, km* 1996, 28, 127), displacement, reactions (*J. Org. Chem,* 2006, 71, 2170; *Synthesis* 2004, 2625), or coupling reactions (*J. Am. Chem. Soc.* 2003, 125, 9032) as described in Scheme 8.

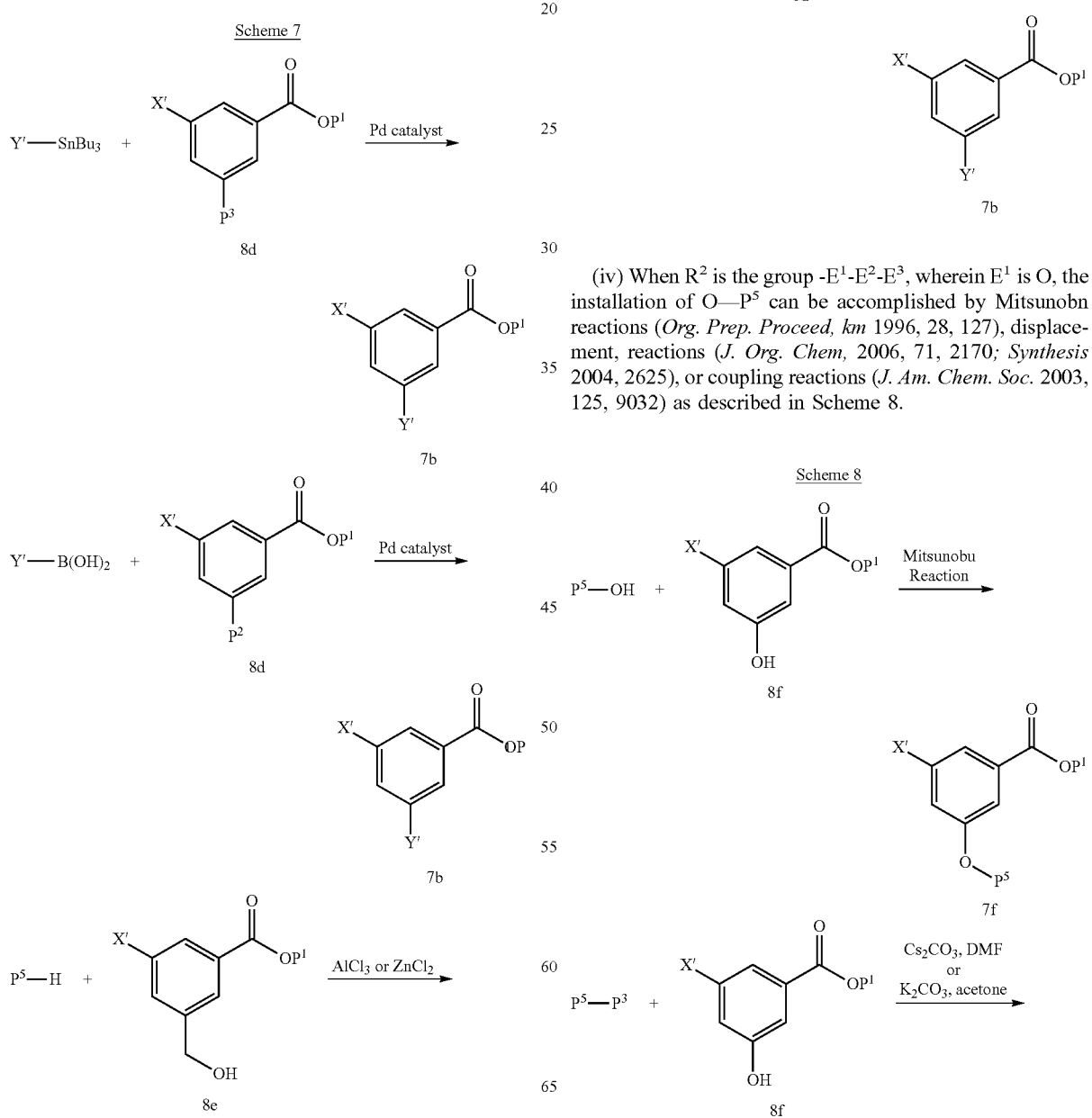

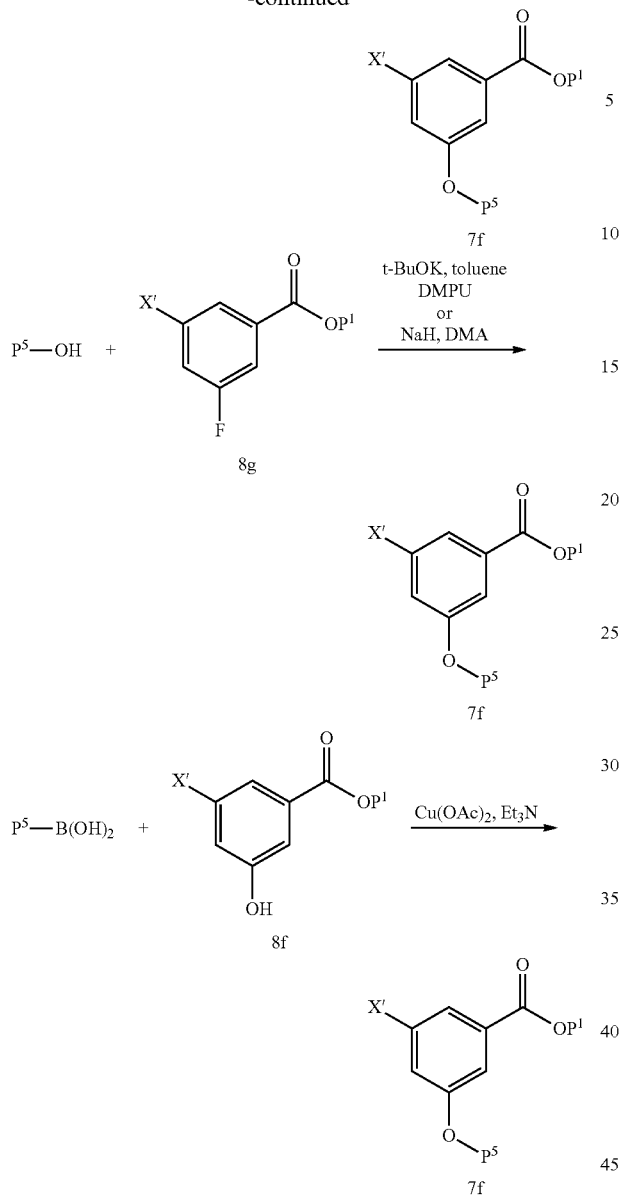

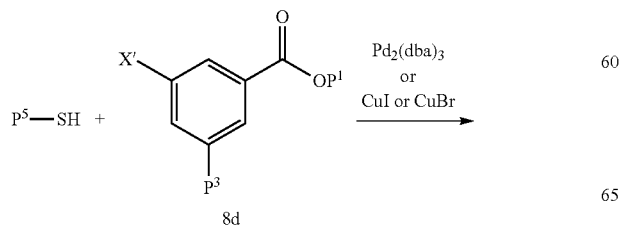

(v) When R² is the group -E¹-E²-E³, wherein E¹ is S, the installation of S—P⁵ can be accomplished by Pd₂(dba)₃, CuBr, or CuI catalyzed reactions (*Tetrahedron* 2001, 57, 3069; *Tetrahedron Lett.* 2000, 41, 1283; *Synlett* 2004, 1254; *Org. Let.* 2002, 4, 3517), or displacement reactions as described in Scheme 9.

Scheme 9

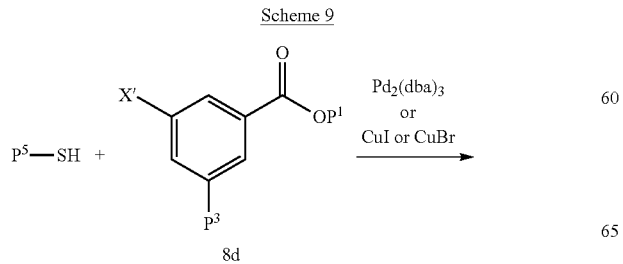

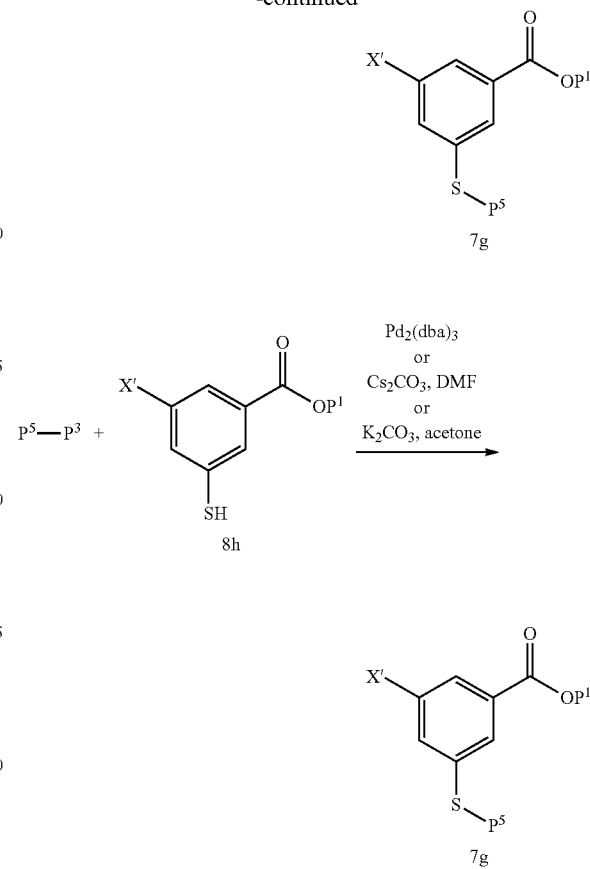

Compounds 7 wherein G²=N and G¹=G³=CH can be prepared by a number of known methods:

(i) When X is aryl, heteroaryl, alkyl, cycloalkyl, or arylalkyl, the installation of X' can be accomplished by either Stille couplings (*J. Am. Chem. Soc.* 1984, 106, 4630; *Tetrahedron Lett.* 1995, 36, 2191) or Suzuki couplings (*Chem. Rev.* 1995, 95, 2457) as described in Scheme 10.

Scheme 10

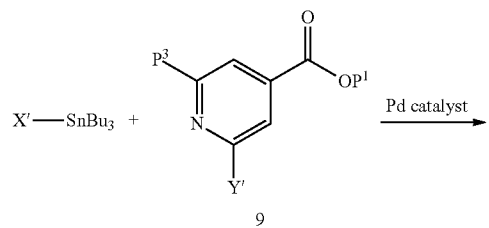

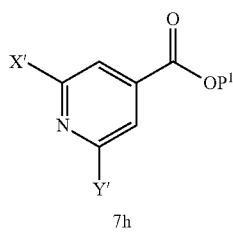

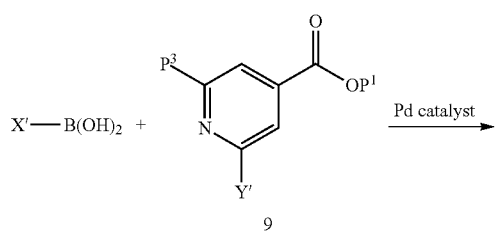

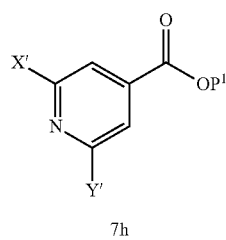

(ii) When X is aryloxy, heteroaryloxy, alkyloxy, cycloalkyloxy or arylalkyloxy, the installation of O—P$^5$ can be accomplished by displacement reaction as described in Scheme 11.

Scheme 11

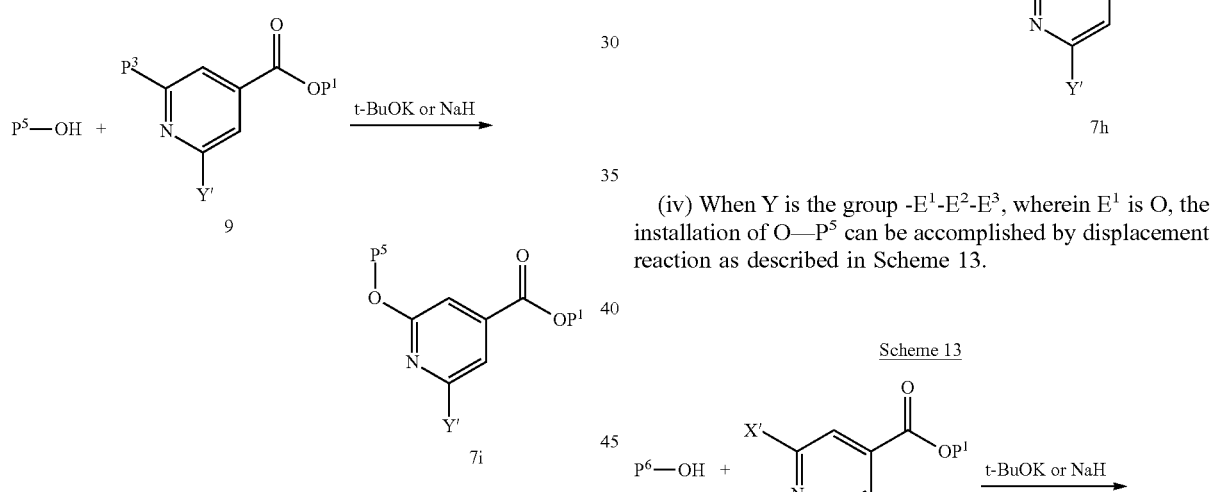

(iii) When Y is the group -E$^2$-E$^3$, wherein E$^2$ is a direct bond or an alkylene, the installation of Y' can be accomplished by either Stille couplings (*J. Am. Chem. Soc.* 1984, 106, 4630; *Tetrahedron Lett.* 1995, 36, 2191) or Suzuki couplings (*Chem. Rev.* 1995, 95, 2457) as described in Scheme 12.

Scheme 12

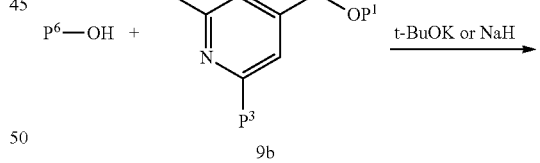

(iv) When Y is the group -E$^1$-E$^2$-E$^3$, wherein E$^1$ is O, the installation of O—P$^5$ can be accomplished by displacement reaction as described in Scheme 13.

Scheme 13

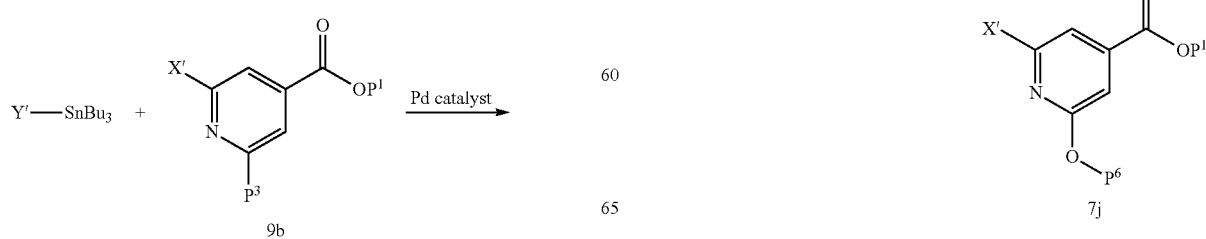

Examples: Synthesis of Compounds of Formula II

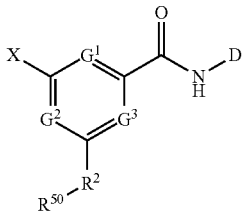

(II)

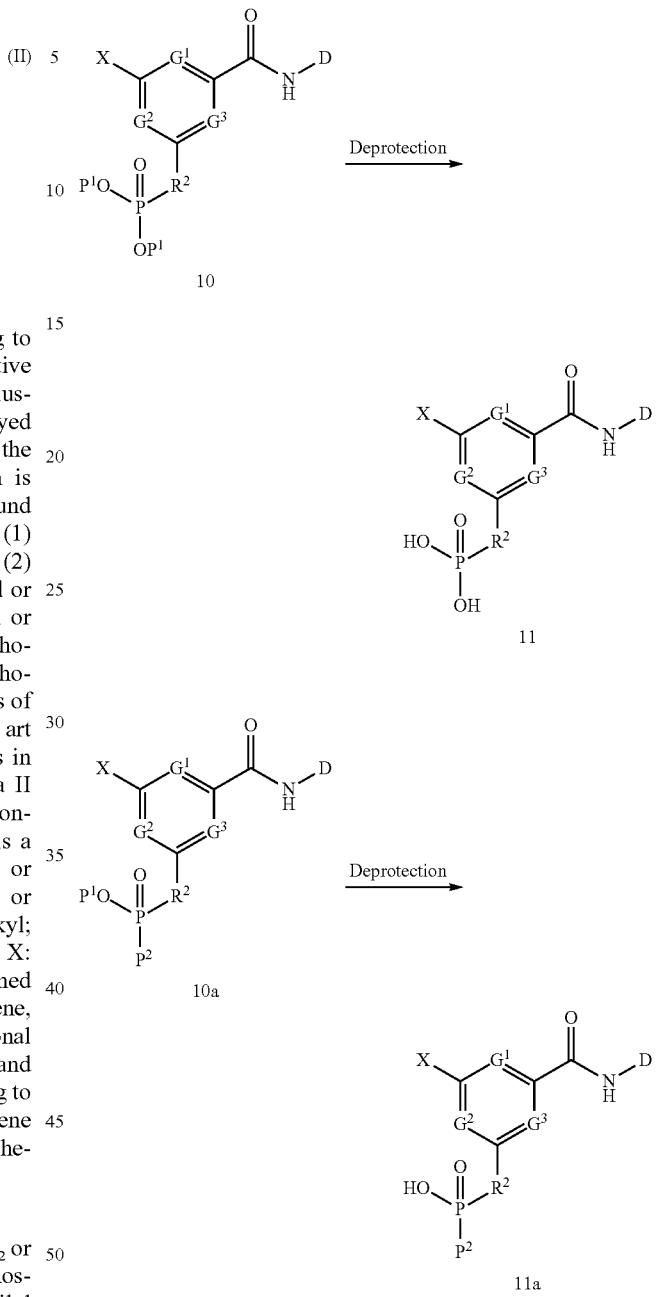

Scheme 14

Compounds of Formula II can be prepared according to the processes described in the following representative Schemes. Reagents and conditions given are only for illustration purposes and alternative methods may be employed by those skilled in the art. It should be understood that the following Schemes do not limit the invention which is defined by the claims. Typically the synthesis of a compound of Formula II includes the following general steps: (1) deprotection of a phosphonate or phosphinate ester; (2) formation of the amide bond; (3) preparation of the aryl or heteroaryl carboxylic acid; (4) construction of the aryl or heteroaryl carboxylic ester; (5) introduction of a phosphonate or phosphinate. The timing of introducing a phosphonate or phosphinate group in the synthesis of compounds of Formula II can be freely decided by those skilled in the art based on the structure of the substrate. Variable groups in Schemes have the same meanings defined for Formula II unless stated otherwise. In all applicable structures contained in the Schemes described in this invention, $P^1$ is a protecting group such as $C_{1-4}$-alkyl; $P^2$ is alkyl or cycloalkyl; $P^3$ is a leaving group such as F, Cl, Br, I, or triflate; $P^5$ is aryl, heteroaryl, alkyl, cycloalkyl, or arylalkyl; X' is X or a functional group that can be transformed into X: Y" is $R^2$—$R^{50}$ or a functional group that can be transformed into $R^2$—$R^{50}$; Y1 is arylene, alkylene, heteroarylene, cycloalkylene, or arylalkylene; Y1' is Y1-$R^{50}$ or a functional group that can be transformed into Y1-$R^{50}$. Protection and deprotection in the Schemes may be carried out according to the procedures generally known in the art (e.g., T. W. Greene and P. G. M. Wuts, "Protecting Groups in Organic Synthesis", $3^{rd}$ edition, John Wiley & Sons, 1999).

Deprotection of a Phosphonate or Phosphinate Ester

Compounds of Formula II wherein $R^{50}$ is —P(O)(OH)$_2$ or —P(O)(OH)P$^2$ may be prepared from phosphonate or phosphinate esters using the known cleavage methods. Silyl halides are generally used to cleave various phosphonate or phosphinate esters and give the desired phosphonic or phosphinic acid upon mild hydrolysis of the resulting phosphonate or phosphinate silyl esters. When needed, acid scavengers (e.g., HMDS) can be used for the acid sensitive compounds. Such silyl halides include TMSCl (*J. Org. Chem.* 1963, 28, 2975), TMSBr (*Tetrahedron Lett.* 1977, 155) and TMSI (*J. Chem. Soc., Chem. Commun.* 1978, 870). Aryl and benzyl phosphonate or phosphinate esters can be cleaved under hydrogenolysis conditions (*Synthesis* 1982, 412; *J. Med. Chem.* 1985, 28, 1208) or metal reduction conditions (*J. Chem. Soc.* 1977, 99, 5188). Electrochemical (*J. Org. Chem.* 1979, 44, 4508) and pyrolysis (*Synth. Commun.* 1980, 10, 299) conditions have been used to cleave various phosphonate esters.

Formation of an Amide Bond

Standard amide bond formation methods can be used to couple amino groups with carboxylic acids or activated derivatives thereof. For example, (i) reactions of an amine with a carboxylic acid in the presence of DCC or EDC according to the known methods (e.g., *J. Org. Chem.* 1977, 42, 2019); (ii) conversion of a carboxylic group to an acid chloride by reaction with oxalyl chloride, followed by coupling the acid chloride with amine in the presence of a base (e.g. triethyl amine or pyridine) in chloroform or DCM (*Org. Synth., Collect Vol. V,* 1973, 336); (iii) other known procedures (*Tetrahedron Lett.* 1990, 31, 7119; *Tetrahedron Lett.* 1989, 30, 6917; *J Org. Chem.* 1993, 58, 618).

Scheme 15

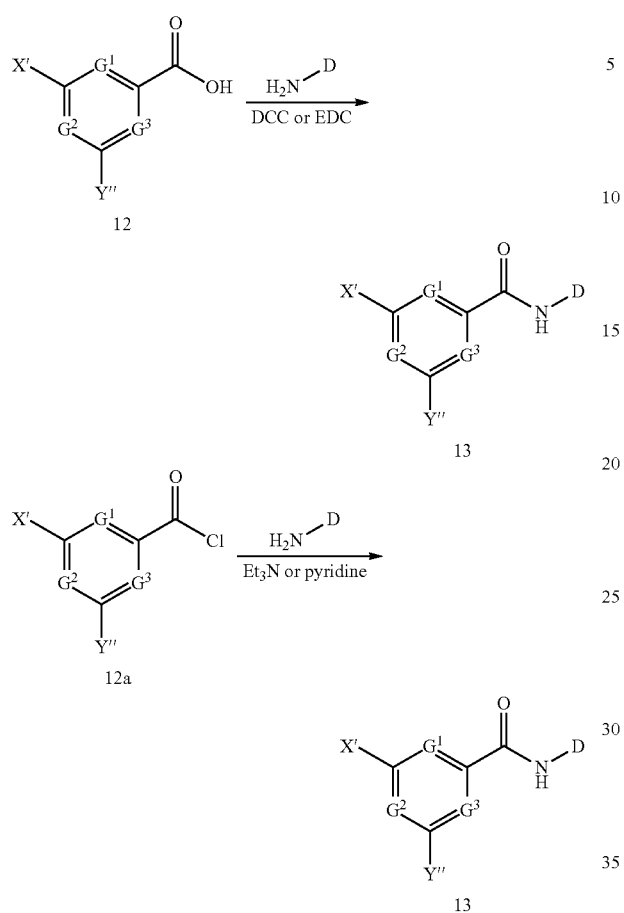

Preparation of the Aryl or Heteroaryl Carboxylic Acid

Deprotection reactions of esters are well known in the art. Methyl or ethyl ester is deprotected in the presence of sodium hydroxide or lithium hydroxide in a mixture of THF/EtOH/water (e.g., *Tetrahedron Lett.* 1977, 3529). Benzyl ester is removed using hydrogenolysis condition (e.g., *Org. React* 1953, VII, 263).

Scheme 16

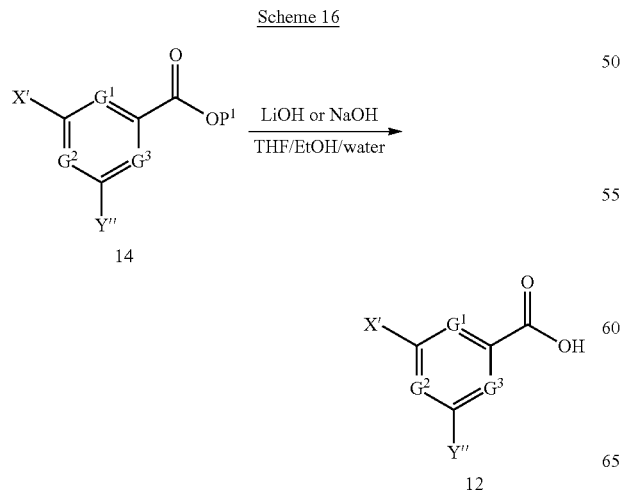

-continued

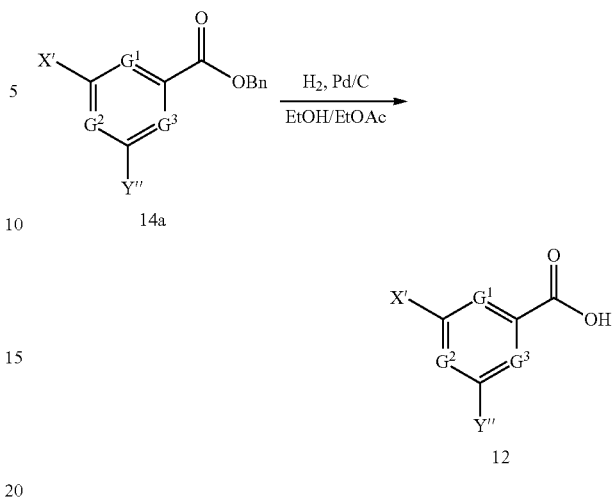

Construction of the Aryl or Heteroaryl Carboxylic Ester

Processes for the synthesis of compounds 14 are provided according to their substitution patterns. Syntheses of compounds 14a generally follow similar synthetic processes as those of compounds 14.

Compounds 14 wherein $G^1=G^2=G^3=CH$ can be prepared by a number of known methods:

(i) When X is aryl, heteroaryl, alkyl, cycloalkyl, or arylalkyl, the installation of X' can be accomplished by Stille couplings (*J. Am. Chem. Soc.* 1984, 106, 4630; *Tetrahedron Lett.* 1995, 36, 2191), Suzuki couplings (*Chem. Rev.* 1995, 95, 2457), Friedel-Crafts alkylations (*Synlett* 1996, 557), or Negishi couplings (*Org. Lett.*, 2003, 5, 423) as described in Scheme 17.

Scheme 17

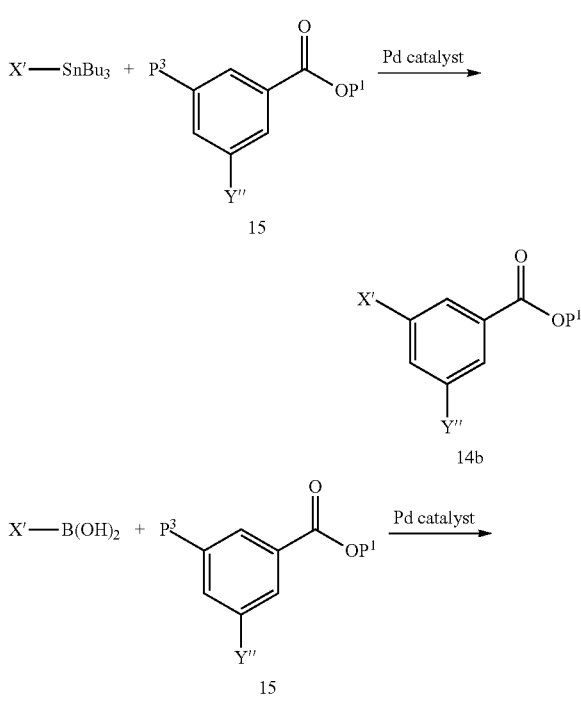

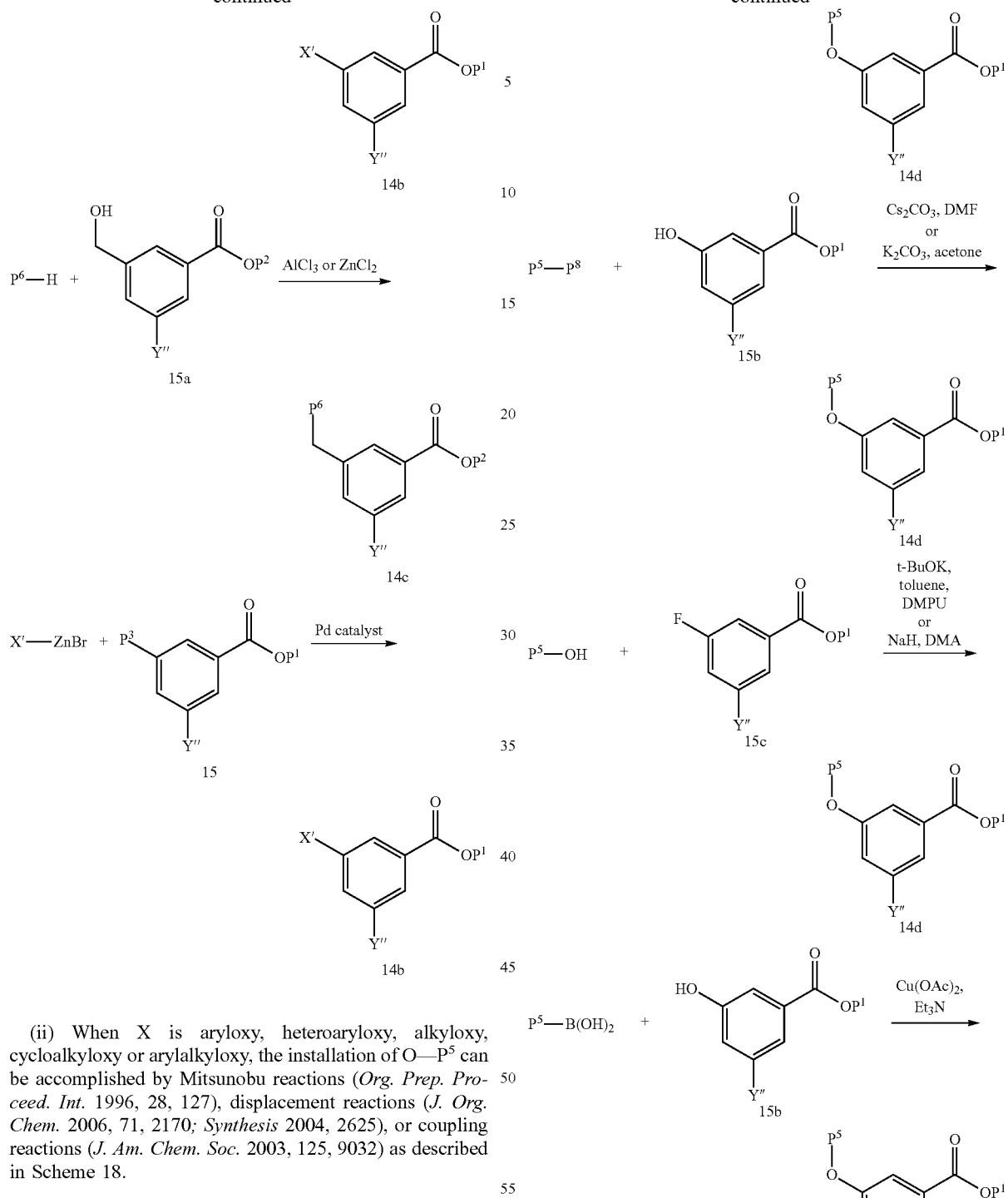

(ii) When X is aryloxy, heteroaryloxy, alkyloxy, cycloalkyloxy or arylalkyloxy, the installation of O—P⁵ can be accomplished by Mitsunobu reactions (*Org. Prep. Proceed. Int.* 1996, 28, 127), displacement reactions (*J. Org. Chem.* 2006, 71, 2170; *Synthesis* 2004, 2625), or coupling reactions (*J. Am. Chem. Soc.* 2003, 125, 9032) as described in Scheme 18.

Scheme 18

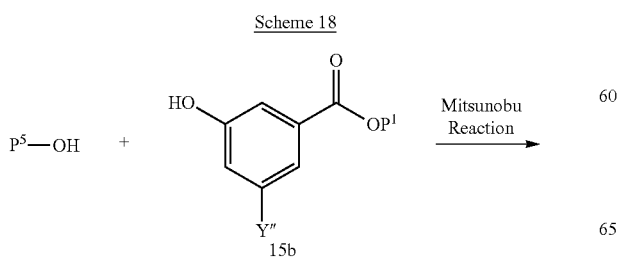

(iii) When R² is the group -E³-E⁴-, wherein E³ is arylene, heteroarylene, alkylene, or cycloalkylene, the installation of Y″ can be accomplished by Stille couplings (*J. Am. Chem. Soc.* 1984, 106, 4630; *Tetrahedron Len.* 1995, 36, 2191), Suzuki couplings (*Chem. Rev.* 1995, 95, 2457), Friedel- Crafts alkylations (*Synlett* 1996, 557), or Negishi couplings (*Org. Lett.,* 2003, 5, 423) as described in Scheme 19.
(iv) When R² is the group -E¹-E²-E³-E⁴-, wherein E¹ is O, the installation of O—Y1' can be accomplished by Mitsunobu reactions (*Org. Prep. Proceed Int.* 1996, 28, 127), displacement reactions (*J. Org. Chem.* 2006, 71, 2170; *Synthesis* 2004, 2625), or coupling reactions (*J. Am. Chem. Soc.* 2003, 125, 9032) as described in Scheme 20.
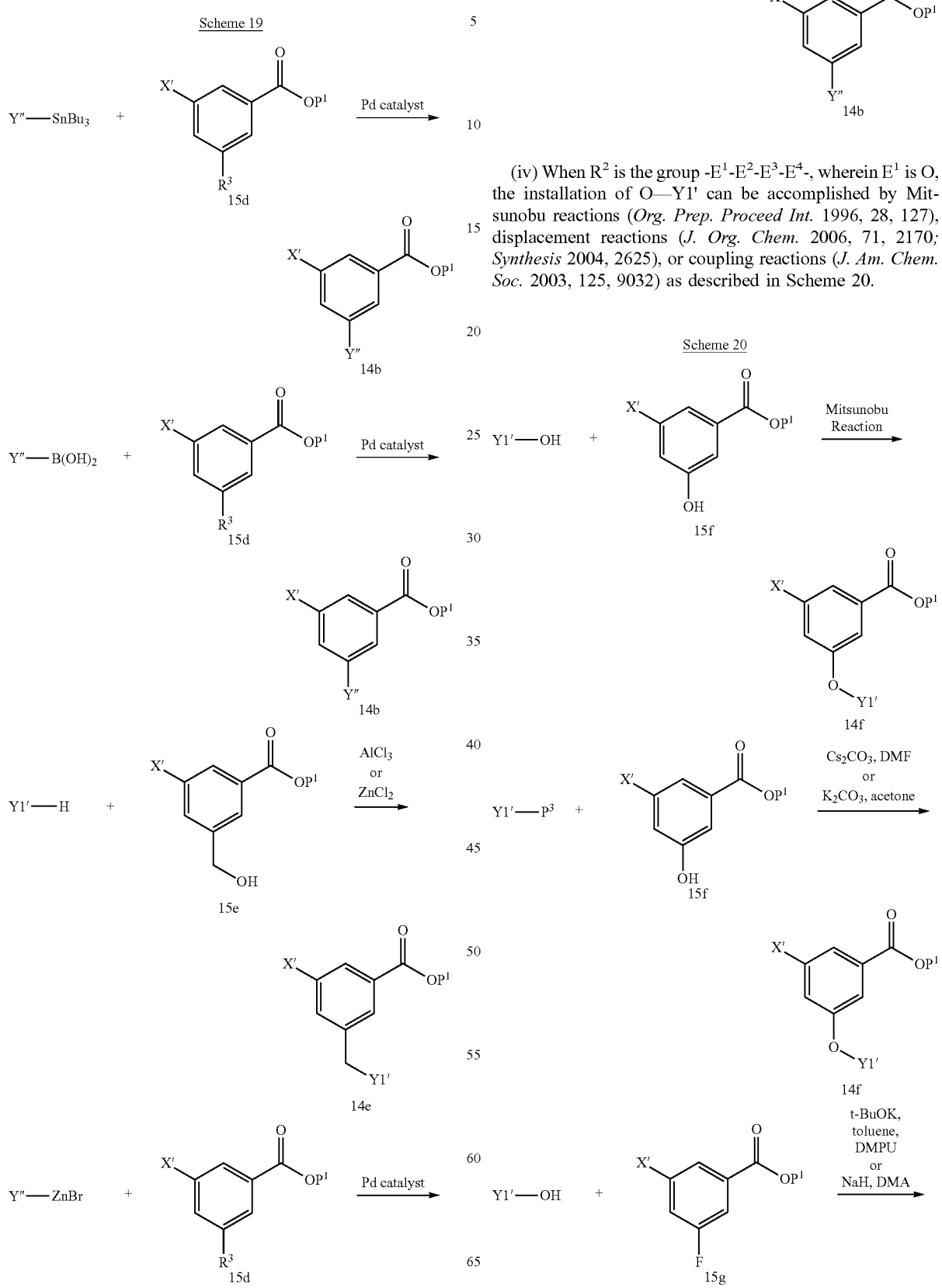

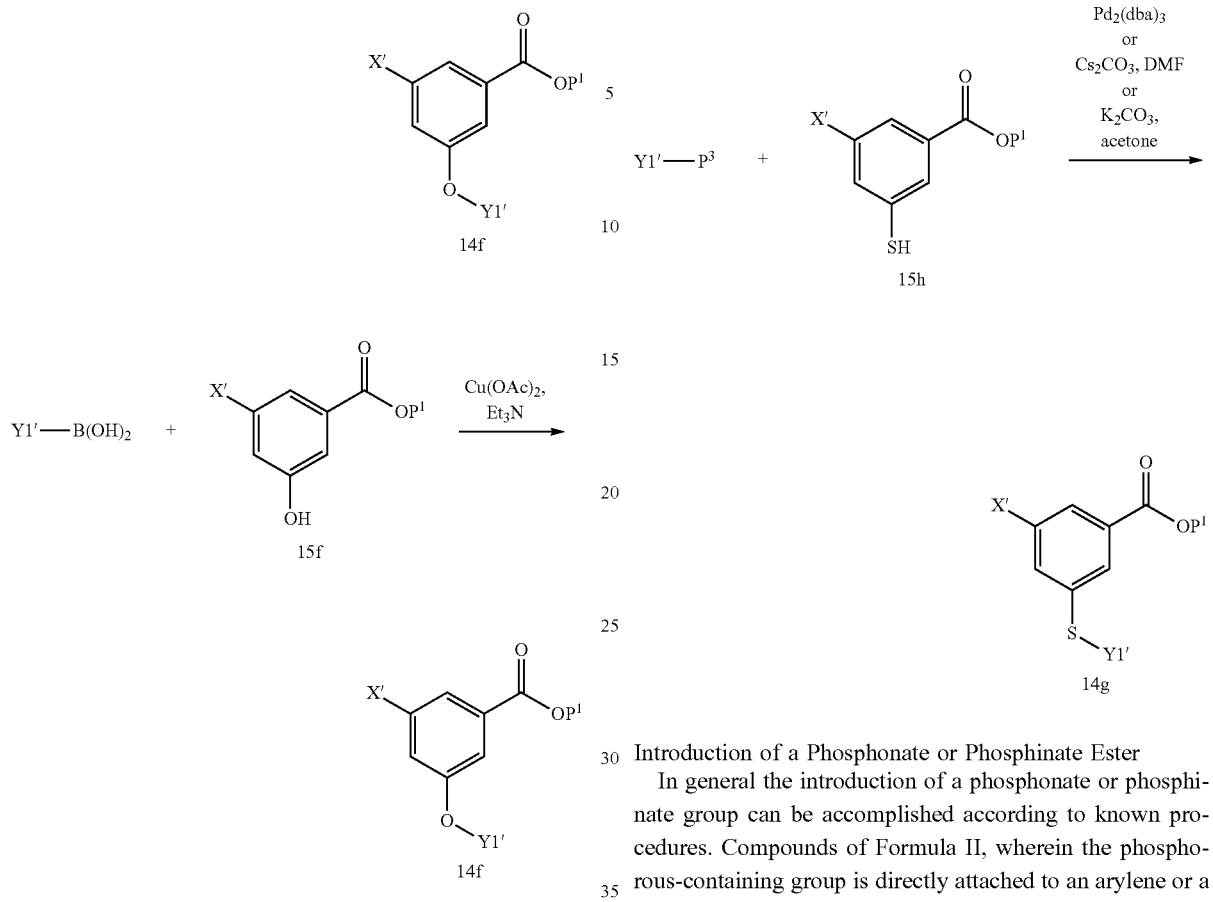

(v) When Y is the group -E$^1$-E$^2$-E$^3$-E$^4$-, wherein E$^1$ is S, the installation of S—Y1' can be accomplished by either Pd$_2$(dba)$_3$, CuBr, or CuI catalyzed reactions (*Tetrahedron* 2001, 57, 3069; *Tetrahedron Let.* 2000, 41, 1283; *Synlett* 2004, 1254; *Org. Let.* 2002, 4, 3517) or displacement reactions as described in Scheme 21.

Scheme 21

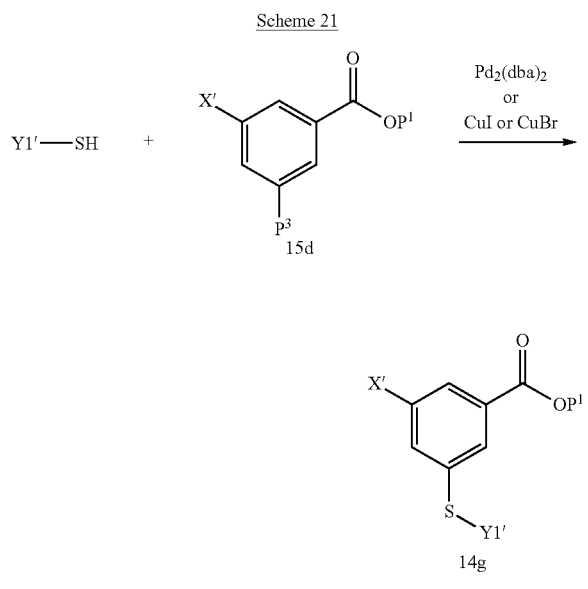

Introduction of a Phosphonate or Phosphinate Ester

In general the introduction of a phosphonate or phosphinate group can be accomplished according to known procedures. Compounds of Formula II, wherein the phosphorous-containing group is directly attached to an arylene or a nitrogen-containing heteroarylene, may be prepared by a number of known methods. For example, the coupling reaction of a phenyl bromide (*J. Org. Chem.* 1999, 64, 120), iodide (*Phosphorus Sulfur* 1997, 130, 59) or triflate (*J. Org. Chem.* 2001, 66, 348) with diethyl phosphite or diisopropyl phosphite in the presence of a palladium catalyst is widely used within the art. Alkylphosphinic acid isopropyl ester or alkylphosphinic acid ethyl ester may be used in the aforementioned procedures to afford the desired alkylphosphinate esters. Functionalized arylphosphinates may be prepared according to a known procedure (*Tetrahedron Lent.* 1996, 37, 1651)

Compounds of Formula II, wherein the phosphonate is directly attached to an alkylene linker, may be prepared by a number of known methods. For example, Michaelis-Arbuzov reaction (*Chem. Rev.* 1981, 81, 415) can also be used to introduce the phosphonate group by coupling an alkyl, benzyl, arylalkyl, or heteroarylalkyl halide/triflate with triethyl phosphite or triisopropyl phosphite.

Compounds of Formula II, wherein the phosphorous-containing group is an H-phosphinic acid can be formed according to literature procedures (*Tetrahedron Lett.* 1992, 33, 813; *J. Orgnomet. Chem* 2005, 690, 2388; *Tetrahedron* 2005, 61, 6315). These H-phosphinic acid derivatives can be alkylated to give the corresponding alkylphosphonates according to known procedures (*Synthesis* 1985, 896; *Synthesis* 1986, 240; *Phosphorus Sulfur* 1996, 115, 255; *J. Am. Chem. Soc.* 1996, 118, 10168; *J. Am. Chem. Soc.* 2002, 124, 3842).

Example 1

{6-[3-Isopropoxy-5-(2-thiophen-3-yl-ethoxy)-benzoylamino]-pyridin-3-yl}-methylphosphinic acid

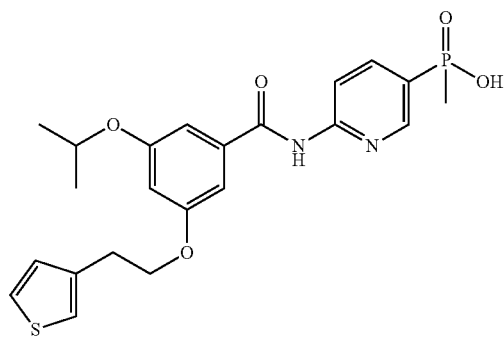 [SMILES: CC(C)Oc1cc(OCCc2ccsc2)cc(C(=O)Nc2ccc(P(C)(=O)O)cn2)c1]

To a solution of {6-[3-isopropoxy-5-(2-thiophen-3-yl-ethoxy)-benzoylamino]-pyridin-3-yl}-methyl-phosphinic acid ethyl ester (469 mg, 0.960 mmol) in DCM (10 mL) was added HMDS (1.62 mL, 7.68 mmol) and TMSBr (0.51 mL, 3.84 mmol) at rt. Stirred at rt overnight. TMSI (0.07 mL, 0.480 mmol) was added to the milky mixture on the second day. Stirred at rt for 1.5 hr. The mixture was concentrated, re-dissolved in EtOAc (10 mL), and filtered through a 0.4 µm syringe filter to remove insoluble NH$_4$Br. The filtrate was concentrated and the residue was dissolved in MeOH (10 mL), stirred at rt for 3 hr, and concentrated again. The resulting residue was partitioned between EtOAc and water. After layers were separated, the aqueous layer was extracted with EtOAc (2×). Combined EtOAc layers were washed with brine (1×), dried with anhydrous MgSO4, filtered, and concentrated to give {6-[3-Isopropoxy-5-(2-thiophen-3-yl-ethoxy)-benzoylamino]-pyridin-3-yl}-methylphosphinic acid (242 mg, 53%) as a yellow foam. $^1$H NMR (300 MHz, DMSO-d$_6$): δ 11.08 (br, 1H), 8.68 (ddd, J=6, 2, 1 Hz, 1H), 8.32 (m, 1H), 8.14 (m, 1H), 7.51 (dd, J=5, 3 Hz, 1H), 7.36 (dd, J=3, 2 Hz, 1H), 7.24 (m, 1H), 7.20 (m, 1H), 7.15 (dd, J=5, 1 Hz, 1H), 6.71 (m, 1H), 4.77 (m, 1H), 4.28 (m, 2H), 3.11 (m, 2H), 1.58 (d, J=15 Hz, 3H), 1.30 (d, J=6 Hz, 6H); LC-MS (m/z): 461.3 [C23H25N2O5PS+H]$^+$. Anal. Calcd. for (C23H25N2O5PS+1.1H$_2$O): C, 55.02; H, 5.71; N, 5.83. Found: C, 55.02; H, 5.31; N, 5.44.

Intermediates for the preparation of Example 1 were prepared according to Route 1, as described below.

Route 1

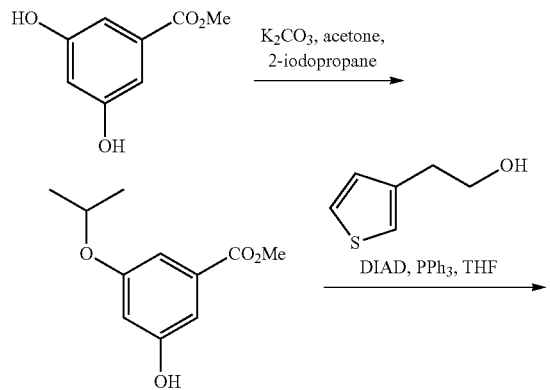

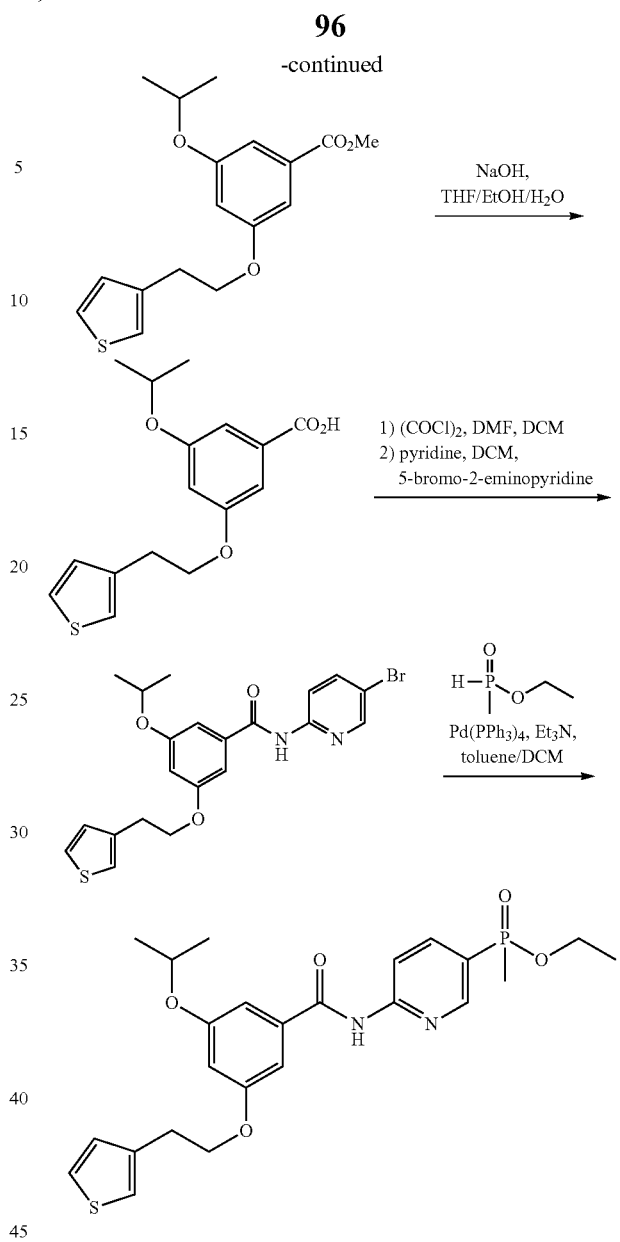

Step A

3-Hydroxy-5-isopropoxy-benzoic acid methyl ester

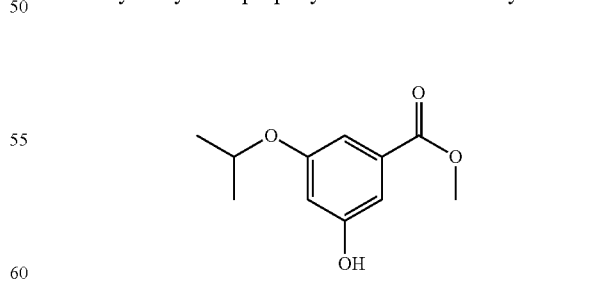

To a stirred solution of methyl 3,5-dihydroxybenzoate (20.0 g, 119 mmol) in acetone (500 mL) was added K$_2$CO$_3$ (19.7 g, 143 mmol) and 2-iodopropane (13.1 mL, 131 mmol) at rt. The resulting mixture was refluxed for 12 hr. Then the mixture was filtered through a pad of Celite to remove insoluble salts and the cake was rinsed with acetone. Combined filtrates were concentrated under vacuum to afford a residue which was purified by silica gel flash chromatography (7.5×30 cm, hexane/EtOAc, v/v 10:1, 5:1). Fractions containing the mono-alkylation product were pooled and concentrated to give 3-hydroxy-5-isopropoxy-benzoic acid methyl ester (11.1 g, 44%) as a white solid. $^1$H NMR (300 MHz, CDCl$_3$): δ 7.11-7.14 (m, 2H), 6.60 (m, 1H), 4.56 (m, 1H), 3.89 (s, 3H), 1.32 (d, J=6 Hz, 6H).

Step B

3-Isopropoxy-5-(2-thiophen-3-yl-ethoxy)-benzoic acid methyl ester

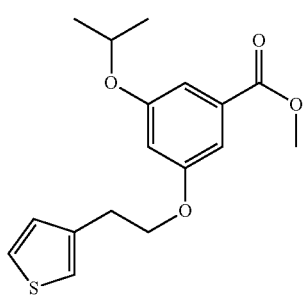 [SMILES: COC(=O)c1cc(OCCc2ccsc2)cc(OC(C)C)c1]

To a stirred solution of 3-hydroxy-5-isopropoxy-benzoic acid methyl ester (3.76 g, 17.9 mmol) in THF (100 mL) at rt was added PPh$_3$ (4.93 g, 18.8 mmol) and 2-(3-thienyl)ethanol (2.10 mL, 18.8 mmol). DIAD (3.71 mL, 18.8 mmol) was added dropwise at rt with external cooling to keep the solvent from boiling off. The resulting mixture was stirred at rt for 3 hr and concentrated to give a residue which was purified by silica gel chromatography (5×25 cm, hexane/EtOAc, v/v=10:1, 5:1). Fractions containing the product were pooled and concentrated to give 3-isopropoxy-5-(2-thiophen-3-yl-ethoxy)-benzoic acid methyl ester (5.24 g, 91%) as a yellow oil. $^1$H NMR (300 MHz, CDCl$_3$): δ 7.28 (dd, J=5, 3 Hz, 1H), 7.15-7.18 (m, 2H), 7.08-7.09 (m, 1), 7.03 (dd, J=5, 1 Hz, 1H), 6.63 (m, 1H), 4.58 (m, 1H), 4.19 (t, J=7 Hz, 2H), 3.89 (s, 3H), 3.12 (t, J=7 Hz, 2H), 1.33 (d, J=6 Hz, 6H).

Step C

3-Isopropoxy-5-(2-thiophen-3-yl-ethoxy)-benzoic acid

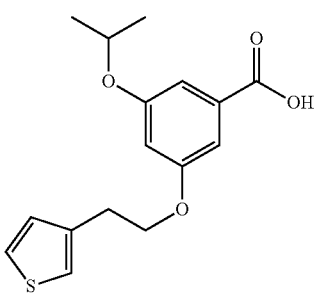 [SMILES: CC(C)Oc1cc(OCCc2ccsc2)cc(C(=O)O)c1]

To a solution of 3-isopropoxy-5-(2-thiophen-3-yl-ethoxy)-benzoic acid methyl ester (5.24 g, 16.4 mmol) in THF (120 mL) was added EtOH (80 mL) and water (40 mL) at rt. Sodium hydroxide solution (1.0 M, 49.1 mL) was added slowly with some external cooling if needed. The mixture was stirred at rt overnight. On the second day organic solvents were removed by evaporation. The residue was partitioned between ether and water. After the ether layer was discarded, the aqueous layer was acidified with HCl (6.0 M, ~8.2 mL) to pH<1, and extracted with EtOAc (3×). Combined EtOAc layers were washed with brine (1×), dried with anhydrous MgSO$_4$, filtered, and concentrated to give 3-isopropoxy-5-(2-thiophen-3-yl-ethoxy)-benzoic acid (4.54 g, 90%) as a white solid. $^1$H NMR (300 MHz, CDCl$_3$): δ 7.29 (dd, J=5, 3 Hz, 1H), 7.22-7.24 (m, 2H), 7.09-7.10 (m, 1H), 7.04 (dd, J=5, 1 Hz, 1H), 6.69 (m, 1H), 4.59 (m, 1H), 4.21 (t, J=7 Hz, 2H), 3.14 (t, J=7 Hz, 2H), 1.35 (d, J=6 Hz, 6H).

Step D

N-(5-Bromo-pyridin-2-yl)-3-isopropoxy-5-(2-thiophen-3-yl-ethoxy)-benzamide

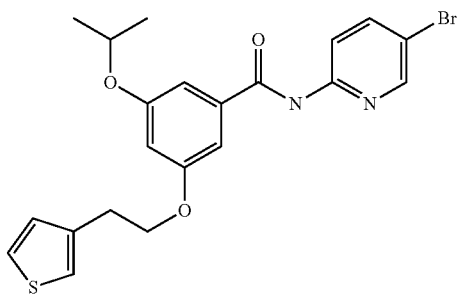 [SMILES: CC(C)Oc1cc(OCCc2ccsc2)cc(C(=O)Nc2ccc(Br)cn2)c1]

To a solution of 3-isopropoxy-5-(2-thiophen-3-yl-ethoxy)-benzoic acid (2.5 g, 8.16 mmol) in DCM (50 mL) was added (COCl)$_2$ (1.42 mL, 16.3 mmol) and DMF (0.06 mL, 0.816 mmol) at rt. After stirring at rt for 1.5 hr, the mixture was concentrated. The resulting residue was azeotroped with 50 mL anhydrous toluene and then re-dissolved in DCM (40 mL), cooled to 0° C. A solution of pyridine and 2-amino-5-bromo-pyridine in DCM (10 mL) was added slowly to the reaction flask. The resulting mixture was stirred at rt overnight. On second day solvents were removed and the residue was partitioned between EtOAc and water. The organic layer was separated, washed with brine (1×), dried with anhydrous MgSO$_4$, filtered, and concentrated. The residue was purified by silica gel flash chromatography (6×25 cm, hexane/EtOAc, v/v=10:1, 5:1, 3:1). Fractions containing the coupling product were pooled and concentrated to give N-(5-bromo-pyridin-2-yl)-3-isopropoxy-5-(2-thiophen-3-yl-ethoxy)-benzamide (3.78 g, 90%) as a yellow foam. $^1$H NMR (300 MHz, CDCl$_3$): δ 8.56 (br, 1H), 8.30-8.33 (m, 2H), 7.85 (dd, J=9, 3 Hz, 1H), 7.29 (dd, J=5, 3 Hz, 1H), 7.09-7.10 (m, 1H), 7.03 (dd, J=5, 1 Hz, 1H), 6.97-7.00 (m, 2H), 6.63 (m, 1H), 4.59 (m, 1H), 4.21 (t, J=7 Hz, 2H), 3.14 (t, J=7 Hz, 2H), 1.35 (d, J=6 Hz, 6H).

Step E

{6-[3-Isopropoxy-5-(2-thiophen-3-yl-ethoxy)-benzoylamino]-pyridin-3-yl}-methyl-phosphinic acid ethyl ester

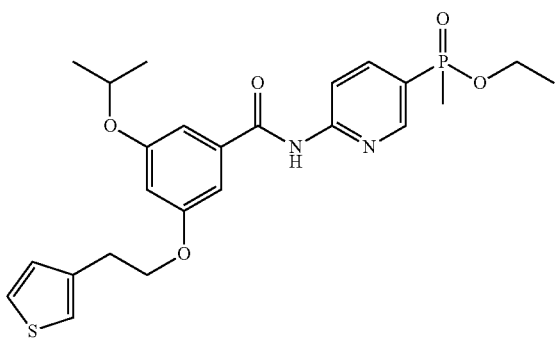 [SMILES: CCOP(C)(=O)c1ccc(NC(=O)c2cc(OCCc3ccsc3)cc(OC(C)C)c2)nc1]

To a stirred solution of N-(5-bromo-pyridin-2-yl)-3-isopropoxy-5-(2-thiophen-3-yl-ethoxy)-benzamide (1.69 g, 3.66 mmol) in toluene (40 mL) was added a solution of methylphosphinic acid ethyl ester (0.475 g, 4.40 mmol), palladium tetrakis(triphenylphosphine) (0.846 g, 0.733 mmol), and Et$_3$N (1.54 mL, 10.9 mmol) in DCM (5.0 mL) at rt. The mixture was heated at 90° C. overnight. Cooled to rt and concentrated. EtOAc and water were added and the mixture was filtered through a pad of Celite to remove the insoluble solids. The organic layer was separated, washed with brine (1×), dried with anhydrous MgSO$_4$, filtered, and concentrated. The residue was purified by silica gel flash chromatography (6×25 cm, hexane/EtOAc, v/v=1:3, EtOAc, 1% MeOH in EtOAc). Fractions containing the product were pooled and concentrated to give {6-[3-Isopropoxy-5-(2-thiophen-3-yl-ethoxy)-benzoylamino]-pyridin-3-yl}-methyl-phosphinic acid ethyl ester (1.65 g, 92%) as a yellow oil. $^1$H NMR (300 MHz, CDCl$_3$): δ 8.74 (br, 1H), 8.68 (ddd, J=6, 2, 1 Hz, 1H), 8.49 (ddd, J=9, 2, 1 Hz, 1H), 8.10 (ddd, J=11, 9, 2 Hz, 1H), 7.63-7.70 (m, 1H), 7.43-7.47 (m, 1H), 7.29 (dd, J=5, 3 Hz, 1H), 7.09-7.10 (m, 1H), 7.04 (dd, J=5.1 Hz, 1H), 6.99-7.03 (m, 2H), 6.64 (m, 1H), 4.60 (m, 1H), 4.22 (t, J=7 Hz, 2H), 4.07-4.15 (m, 1H), 3.84-3.92 (m, 1H), 3.14 (t, J=7 Hz, 2H), 1.70 (d, J=15 Hz, 3H), 1.35 (d, J=6 Hz, 6H), 1.23-1.31 (m, 3H).

Example 2

{6-[3-isopropoxy-5-(2-thiophen-3-yl-ethoxy)-benzoylamino]-pyridin-3-ylmethyl}-phosphonic acid hydrochloride

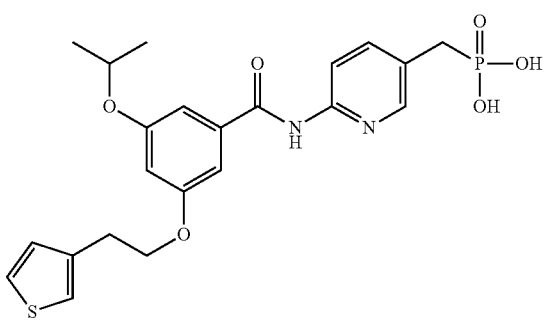 [SMILES: CC(C)Oc1cc(OCCc2ccsc2)cc(C(=O)Nc2ccc(CP(=O)(O)O)cn2)c1]

{6-[3-Isopropoxy-5-(2-thiophen-3-yl-ethoxy)-benzoylamino]-pyridin-3-ylmethyl}-phosphonic acid diethyl ester (86.0 mg, 0.166 mmol) was dissolved in DCM (0.8 mL) and cooled to −78° C. TMSBr (0.21 mL, 1.61 mmol) was added and the reaction mixture was allowed to warm to rt over 24 hours. The reaction mixture was concentrated under reduced pressure and partitioned in diethyl ether (5 mL) and 1N aqueous sodium hydroxide (5 mL). The aqueous layer was rinsed twice with diethyl ether (5 mL), then acidified to pH=1 with concentrated hydrochloric acid and extracted with EtOAc (3×5 mL). The organic layer dried over sodium sulfate, filtered, and concentrated to give the title compound, {6-[3-isopropoxy-5-(2-thiophen-3-yl-ethoxy)-benzoylamino]-pyridin-3-ylmethyl}-phosphonic acid hydrochloride (16.6 mg, 21.6% yield), as a pale brown foam. $^1$H NMR (300 MHz, DMSO-d$_6$): δ 10.70 (s, 1H), 8.20 (s, 1H), 8.05 (d, J=6.0 Hz, 1H), 7.70 (d, J=6.0 Hz, 1H), 7.45 (d, J=3.0 Hz, 1H), 7.30 (s, 1H), 7.20 (s, 1H), 7.15 (s, 1H), 7.10 (d, J=3.0 Hz, 1H), 6.65 (s, 1H), 4.70 (m, 1H), 4.25 (t, 2H), 3.10 (t, 2H), 2.95 (d, J=12.0 Hz, 2H), 1.25 (s, 6H); LCMS (m/z): 477.1 [C22H25N2O6PS+H]$^+$. Anal. Calcd. for (C22H25N2O6PS+1.2 HCl): C, 50.79; H, 5.08; N, 5.38. Found: C, 50.72; H, 4.91; N, 4.80.

Intermediates for the preparation of Example 2 were prepared according to Route 2, as described below.

Route 2

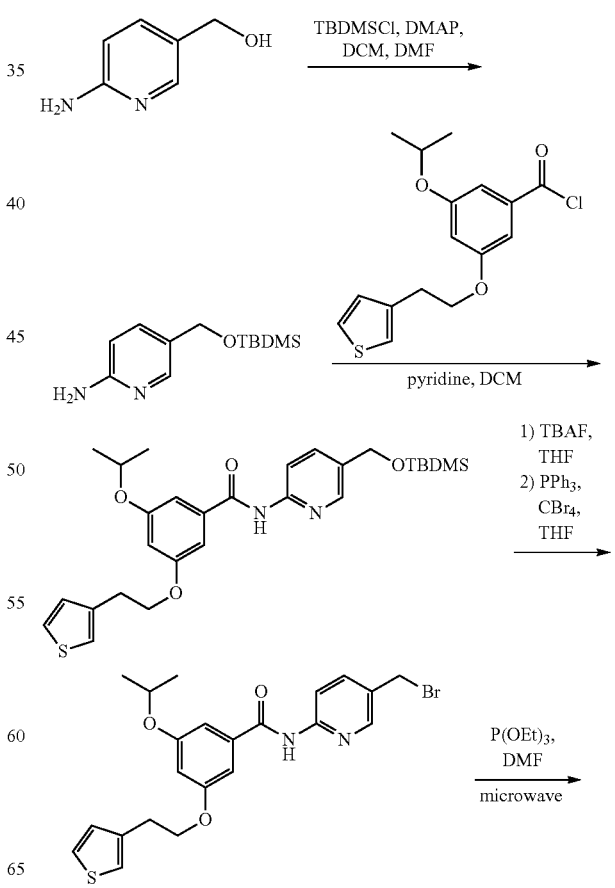

-continued

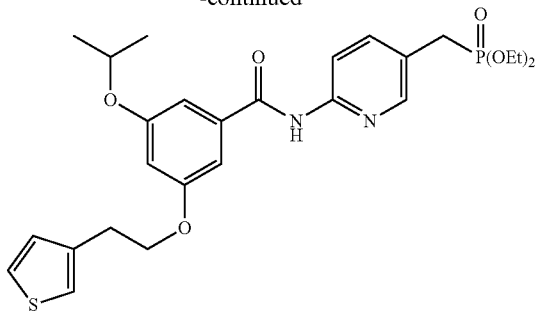

Step A 5-(tert-Butyl-dimethyl-silanyloxymethyl)-pyridin-2-ylamine

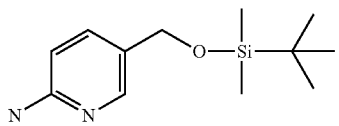 [SMILES: CC(C)(C)[Si](C)(C)OCc1ccc(N)nc1]

(6-Amino-pyridin-3-yl)-methanol (1.00 g, 8.06 mmol) was dissolved in a mixture of DCM DMF (v/v 4:1, 50 mL) with stirring, and cooled to 0° C. N,N-diisopropylethylamine (1.99 mL, 12.09 mmol), tert-butyl-chloro-dimethyl-silane (1.67 g, 11.1 mmol) and 4-dimethylaminopyridine (0.02 g, 0.16 mmol) were added. Stirred at rt for 20 hours. The reaction mixture was concentrated under rotary evaporation and partitioned in EtOAc (30 mL) and water (30 mL). The organic layer was rinsed with water (20 mL), and then a saturated sodium chloride solution (20 mL), dried over sodium sulfate, filtered, and concentrated to yellow oil. After chromatography on silica gel with a gradient from 10-100% ethyl acetate-hexanes, 5-(tert-butyl-dimethyl-silanyloxymethyl)-pyridin-2-ylamine (1.71 g, 89.0% yield) was obtained as white crystals. $^1$H NMR (300 MHz, DMSO-d$_6$): δ 7.78 (s, 1H), 7.35 (d, J=6.0 Hz, 1H), 6.35 (d, J=6.0 Hz, 1H), 5.80 (s, 2H), 4.45 (s, 2H), 0.80 (s, 9H), 0.00 (s, 6H); LCMS (m/z): 239.4 [C12H22N2OSi+H]$^+$.

Step B

N-[5-(tert-Butyl-dimethyl-silanyloxymethyl)-pyridin-2-yl]-3-isopropoxy-5-(2-thiophen-3-yl-ethoxy)-benzamide

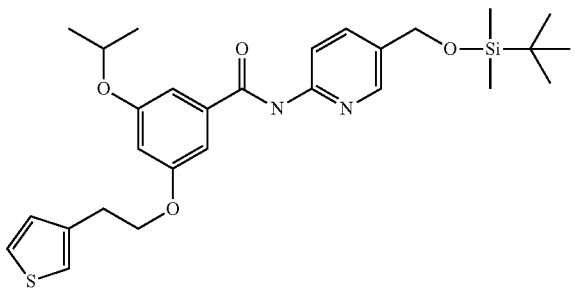 [SMILES: CC(C)Oc1cc(OCCc2ccsc2)cc(C(=O)Nc2ccc(CO[Si](C)(C)C(C)(C)C)cn2)c1]

3-Isopropoxy-5-(2-thiophen-3-yl-ethoxy)-benzoic acid (2.03 g, 6.61 mmol) was dissolved in DCM (33 mL) with DMF (0.05 mL), and cooled to 0° C. Oxalyl chloride (1.16 mL, 13.22 mmol) was added dropwise and the mixture was allowed to stir for 1.5 hours. The reaction mixture was concentrated under reduced pressure to remove residual oxalyl chloride. The yellow oil was re-dissolved in DCM (33 mL), and 5-(tert-butyl-dimethyl-silanyloxymethyl)-pyridin-2-ylamine (1.71 g, 7.17 mmol) and pyridine (0.86 mL, 10.5 mmol) were added. After 16 hours, the reaction mixture was concentrated under reduced pressure and partitioned in EtOAc (50 mL) and water (50 mL). The organic layer was rinsed with water (30 mL), and then a saturated sodium chloride solution (30 mL), dried over sodium sulfate, filtered, and concentrated to brown oil. After chromatography on silica gel with a gradient from 5-30% ethyl acetate-hexanes, N-[5-(tert-butyl-dimethyl-silanyloxymethyl)-pyridin-2-yl]-3-isopropoxy-5-(2-thiophen-3-yl-ethoxy)-benzamide (1.25 g, 36.0% yield) was obtained. $^1$H NMR (300 MHz, DMSO-d$_6$): δ 10.65 (s, 1H), 8.25 (s, 1H), 8.05 (d, J=6.0 Hz, 1H), 7.65 (d, J=6.0 Hz, 1H), 7.40 (d, J=3.0 Hz, 1H), 7.25 (s, 1H), 7.15 (s, 1H), 7.10 (s, 1H), 7.05 (d, J=3.0 Hz, 1H), 6.60 (s, 1H), 4.65 (s, 2H), 4.60 (m, 1H), 4.15 (t, 2H), 2.95 (t, 2H), 1.05 (s, 3H), 1.0 (s, 3H), 0.85 (s, 9H), 0.00 (s, 6H); LCMS (m/z): 527.3 [C28H38N2O4SSi+H]$^+$.

Step C

N-(5-Hydroxymethyl-pyridin-2-yl)-3-isopropoxy-5-(2-thiophen-3-yl-ethoxy)-benzamide

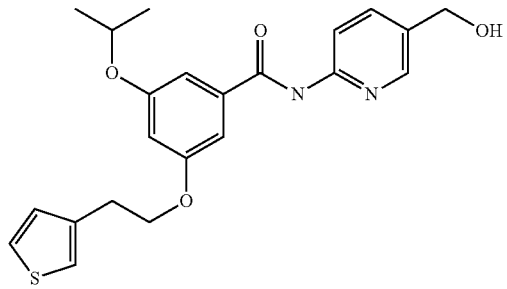 [SMILES: CC(C)Oc1cc(OCCc2ccsc2)cc(C(=O)Nc2ccc(CO)cn2)c1]

N-[5-(tert-Butyl-dimethyl-silanyloxymethyl)-pyridin-2-yl]-3-isopropoxy-5-(2-thiophen-3-yl-ethoxy)-benzamide (1.25 g, 2.37 mmol) was dissolved in THF (12 mL) and cooled to 0° C. Tetrabutylammonium fluoride (1.0 M solution in THF, 3.08 mL, 3.08 mmol) was added dropwise and the mixture was allowed to warm to rt over 24 hours. The reaction mixture was concentrated under reduced pressure and partitioned in EtOAc (30 mL) and water (30 mL). The organic layer was rinsed with water (20 mL), and then a saturated sodium chloride solution (20 mL), dried over sodium sulfate, filtered, and concentrated to yellow oil. After chromatography on silica gel with a gradient from 15-100% ethyl acetate-hexanes, N-(5-hydroxymethyl-pyridin-2-yl)-3-isopropoxy-5-(2-thiophen-3-yl-ethoxy)-benzamide (0.73 g, 74.9% yield) was obtained as a colorless oil. 1H NMR (300 MHz, DMSO-d$_6$): δ 10.75 (s, 1H), 8.30 (s, 1H), 8.10 (d, J=6.0 Hz, 1H), 7.75 (d, J=6.0 Hz, 1H), 7.45 (d, J=3.0 Hz, 1H), 7.30 (s, 1H), 7.20 (s, 1H), 7.15 (s, 1H), 7.10 (d, J=3.0 Hz, 1H), 6.65 (s, 1H), 5.25 (t, 1H), 4.70 (m, 1H), 4.50 (d, J=3.0 Hz, 2H), 4.25 (t, 2H), 3.05 (t, 2H), 1.25 (s, 6H); LCMS (m/z): 413.1 [C22H24N2O4S+H]$^+$.

Step D

N-(5-Bromomethyl-pyridin-2-yl)-3-isopropoxy-5-(2-thiophen-3-yl-ethoxy)-benzamide

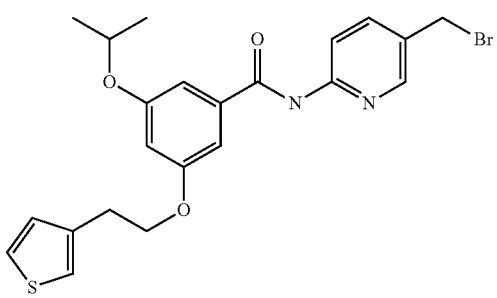 [SMILES: CC(C)Oc1cc(OCCc2ccsc2)cc(C(=O)Nc2ccc(CBr)cn2)c1]

N-(5-Hydroxymethyl-pyridin-2-yl)-3-isopropoxy-5-(2-thiophen-3-yl-ethoxy)-benzamide (0.79 g, 1.92 mmol) in THF (10 mL) was added to a solution of triphenylphosphine (1.03 g, 3.84 mmol) and carbon tetrabromide (1.27 g, 3.84 mmol) in diethyl ether (10 mL). After 16 hours, the reaction mixture was concentrated under reduced pressure and partitioned in EtOAc (30 mL) and water (30 mL). The organic layer was rinsed with water (20 mL), and then a saturated sodium chloride solution (20 mL), dried over sodium sulfate, filtered, and concentrated to yellow oil. After chromatography on silica gel with a gradient from 5-100% ethyl acetate-hexanes, N-(5-bromomethyl-pyridin-2-yl)-3-isopropoxy-5-(2-thiophen-3-yl-ethoxy)-benzamide (0.92 g, 101.3% yield) was obtained, including some impurity, but was used as-is. 1H NMR (300 MHz, DMSO-$d_6$): δ 10.85 (s, 1H), 8.45 (s, 1H), 8.15 (d, J=6.0 Hz, 1H), 7.90 (d, J=6.0 Hz, 1H), 7.45 (d, J=3.0 Hz, 1H), 7.30 (s, 1H), 7.20 (s, 1H), 7.15 (s, 1H), 7.10 (d, J=3.0 Hz, 1H), 6.65 (s, 1H), 4.75 (s, 2H), 4.70 (m, 1H), 4.25 (t, 2H), 3.05 (t, 2H), 1.25 (s, 6H); LCMS (m/z): 477.1 [C22H23BrN2O3S+H]$^+$.

Step E

{6-[3-Isopropoxy-5-(2-thiophen-3-yl-ethoxy)-benzoylamino]-pyridin-3-ylmethyl}-phosphonic acid diethyl ester

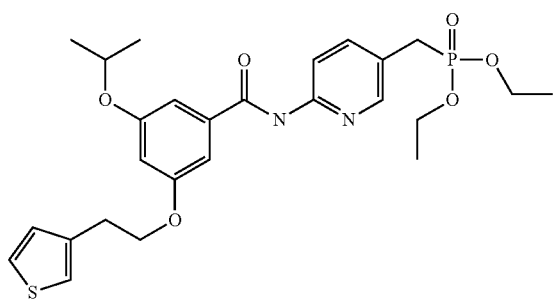 [SMILES: CCOP(=O)(Cc1ccc(NC(=O)c2cc(OCCc3ccsc3)cc(OC(C)C)c2)nc1)OCC]

N-(5-Bromomethyl-pyridin-2-yl)-3-isopropoxy-5-(2-thiophen-3-yl-ethoxy)-benzamide (0.46 g, 0.97 mmol) was dissolved in DMF (5 mL). Triethyl phosphite (0.51 mL, 2.91 mmol) was added and the reaction mixture was subjected to microwave radiation at 180° C. for 30 minutes. The reaction mixture was concentrated under reduced pressure and partitioned in EtOAc (20 mL) and water (20 mL). The organic layer was rinsed with water (10 mL), and then a saturated sodium chloride solution (10 mL), dried over sodium sulfate, filtered, and concentrated to dark brown oil. After chromatography on silica gel with a gradient from 50-100% ethyl acetate-hexanes to 10% methanol-ethyl acetate, {6-[3-isopropoxy-5-(2-thiophen-3-yl-ethoxy)-benzoylamino]-pyridin-3-ylmethyl}-phosphonic acid diethyl ester (86.0 mg, 16.6% yield) was obtained. 1H NMR (300 MHz, DMSO-$d_6$): δ 10.85 (s, 1H), 8.25 (s, 1H), 8.10 (d, J=6.0 Hz, 1H), 7.70 (d, J=6.0 Hz, 1H), 7.45 (d, J=3.0 Hz, 1H), 7.30 (s, 1H), 7.20 (s, 1H), 7.15 (s, 1H), 7.10 (d, J=3.0 Hz, 1H), 6.65 (s, 1H), 4.70 (m, 1H), 4.25 (t, 2H), 3.95 (m, 4H), 3.25 (d, J=12.0 Hz, 2H), 3.05 (t, 2H), 1.25 (s, 6H), 1.15 (m, 6H); LCMS (m/z): 533.2 [C26H33N2O6PS+H]$^+$.

Example 3

{4-[3-Isopropoxy-5-(thiazol-2-ylcarbamoyl)-phenoxy]-phenyl}-phosphonic acid

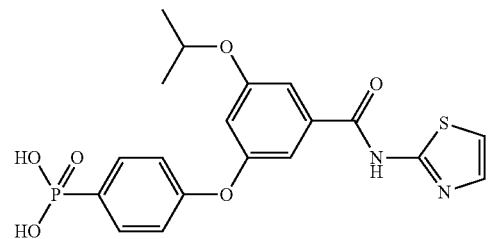 [SMILES: CC(C)Oc1cc(Oc2ccc(P(=O)(O)O)cc2)cc(C(=O)Nc2nccs2)c1]

Starting from {4-[3-isopropoxy-5-(thiazol-2-ylcarbamoyl)-phenoxy]-phenyl}-phosphonic acid diisopropyl ester (1.92 g, 3.78 mmol), {4-[3-isopropoxy-5-(thiazol-2-ylcarbamoyl)-phenoxy]-phenyl}-phosphonic acid was synthesized as a white solid (1.38 g, 3.11 mmol) according to the TMSBr deprotection procedure in Example 1. 1H NMR (300 MHz, DMSO-$d_6$): δ 7.73-7.77 (m, 2H), 7.61 (m, 1H), 7.54 (s, 1H), 7.33-7.35 (m, 2H), 7.13 (s, 1H), 7.12 (m, 1H), 6.87 (m, 1H), 4.77-4.82 (m, 1H), 1.35 (d, J=6 Hz, 6H); LC-MS (m/z): 435.4 [C19H19N2O6PS+H]$^+$. Anal. Calcd. for (C19H19N2O6PS+0.7H2O): C, 51.05; H, 4.60; N, 6.27. Found: C, 50.90; H, 4.88; N, 6.67.

Intermediates for the preparation of Example 3 were prepared according to Route 3, as described below.

Route 3

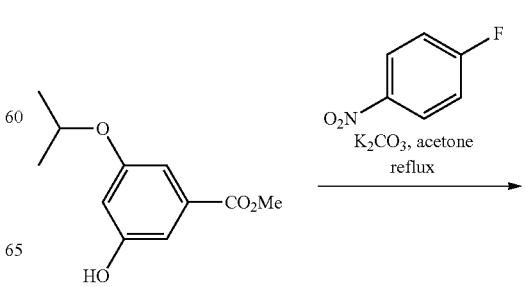

-continued

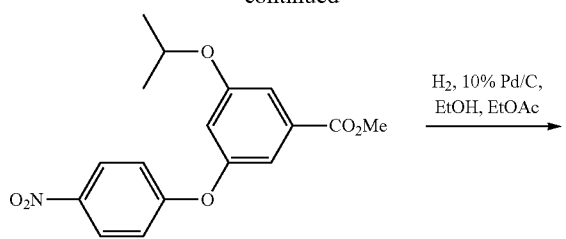
H₂, 10% Pd/C, EtOH, EtOAc

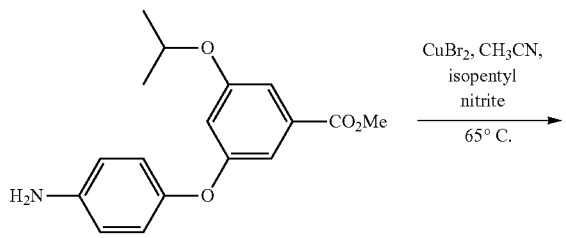
CuBr₂, CH₃CN, isopentyl nitrite
65° C.

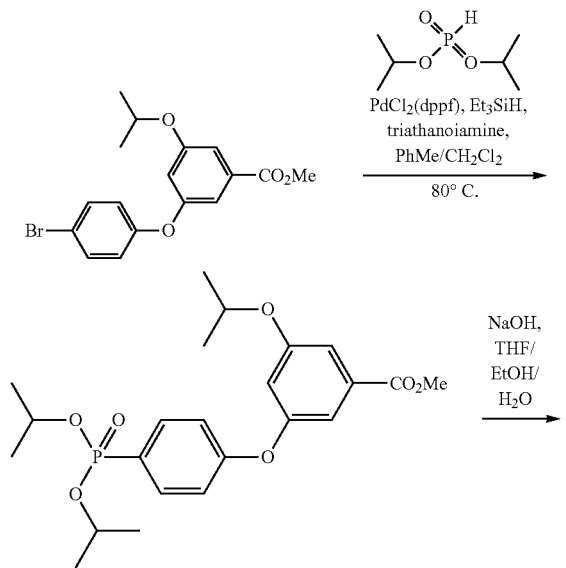
PdCl₂(dppf), Et₃SiH, triethanolamine, PhMe/CH₂Cl₂
80° C.

NaOH, THF/EtOH/H₂O 1) (COCl)₂, DMF, DCM
2) pyridine, DCM, 2-amino-thiazole

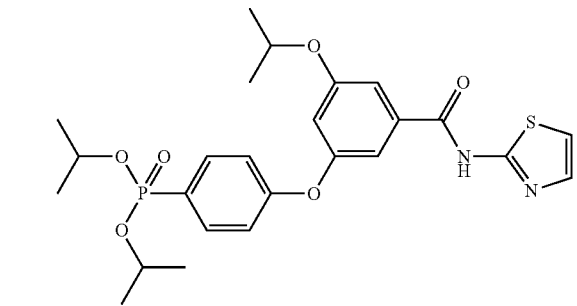 [SMILES: CC(C)Oc1cc(Oc2ccc(P(=O)(OC(C)C)OC(C)C)cc2)cc(C(=O)Nc2nccs2)c1]

Step A

3-Isopropoxy-5-(4-nitro-phenoxy)-benzoic acid methyl ester

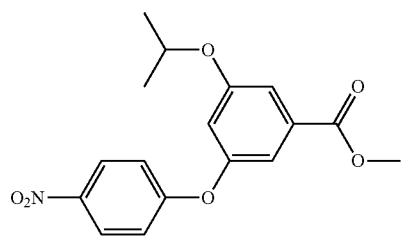 [SMILES: COC(=O)c1cc(Oc2ccc([N+](=O)[O-])cc2)cc(OC(C)C)c1]

To a solution of 3-hydroxy-5-isopropoxy-benzoic acid methyl ester (7.00 g, 33.3 mmol) in acetone (80 mL) was added K₂CO₃ (5.06 g, 36.6 mmol) and 1-fluoro-4-nitrobenzene (3.53 mL, 33.3 mmol) at rt. The resulting mixture was refluxed for 12 hr. Then the mixture was filtered through a pad of Celite to remove insoluble salts and the cake was rinsed with acetone. Combined filtrates were concentrated under vacuum to afford a residue which was purified by silica gel flash chromatography (7.5×30 cm, hexane/EtOAc, v/v 10:1, 5:1). Fractions containing the mono-alkylation product were pooled and concentrated to give 3-isopropoxy-5-(4-nitro-phenoxy)-benzoic acid methyl ester (11.0 g, 44%) as a brown oil. ¹H NMR (300 MHz, CDCl₃): δ 8.22 (d, J=9 Hz, 2H), 7.43 (dd, J=1, 2 Hz, 1H), 7.29 (dd, J=1, 2 Hz, 1H), 7.04 (d, J=9 Hz, 2H), 6.80 (dd, J=2, 2 Hz, 1H), 4.56-4.64 (m, 1H), 3.90 (s, 3H), 1.35 (d, J=6 Hz, 6H).

Step B

3-Isopropoxy-5-(4-nitro-phenoxy)-benzoic acid methyl ester

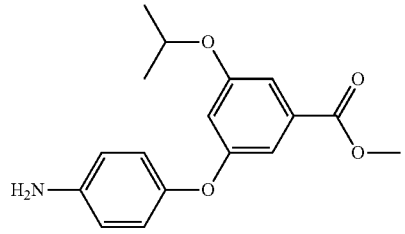

A mixture of 3-isopropoxy-5-(4-nitro-phenoxy)-benzoic acid methyl ester (11.0 g, 33.3 mmol) and Pd/C (3.50 g, 10% wt, 3.33 mmol) catalyst in EtOH/EtOAc (v/v 1:10, 44 mL) was hydrogenated using Parr apparatus at 50 psi H₂ for 3 hr. The mixture was filtered through a pad of Celite and the cake was washed with EtOAc. The combined filtrates were concentrated, azeotroped with toluene (1×) to give 3-isopropoxy-5-(4-nitro-phenoxy)-benzoic acid methyl ester (8.94 g, 29.7 mmol) as yellow oil. ¹H NMR (300 MHz, CDCl₃): δ 7.21 (dd, J=1, 2 Hz, 1H), 7.13 (dd, J=1, 2 Hz, 1H), 6.86 (d, J=9 Hz, 2H), 6.68 (d, J=9 Hz, 2H), 6.65 (dd, J=2, 2 Hz, 1H), 4.51-4.59 (m, 1H), 3.86 (s, 3H), 1.31 (d, J=6 Hz, 6H).

Step C 3-(4-Bromo-phenoxy)-5-isopropoxy-benzoic acid methyl ester

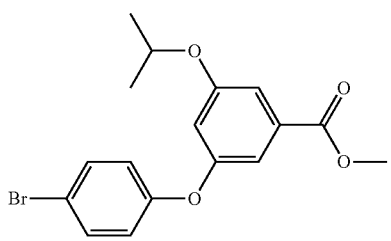 [SMILES: COC(=O)c1cc(Oc2ccc(Br)cc2)cc(OC(C)C)c1]

To a flask containing CuBr$_2$ (8.28 g, 37.1 mmol) in CH$_3$CN (100 mL) was added t-butyl nitrite (8.06 mL, 50.4 mmol) rt. The mixture was heated to 65° C. Then a solution of 3-isopropoxy-5-(4-nitro-phenoxy)-benzoic acid methyl ester in DMF (50 mL) was added slowly in 10 min. After the addition was complete, the solution was left at 65° C. for 1 h. Cooled to rt. The mixture was concentrated and the residue was partitioned between HCl (1 N) and EtOAc. The organic layer was separated and washed with brine (1×), dried and concentrated to give a residue, which was purified by silica gel column (6×25 cm, hexane/EtOAc, v/v 10:1, 5:1). Fractions containing the product were pooled and concentrated to give 3-(4-bromo-phenoxy)-5-isopropoxy-benzoic acid methyl ester as yellow oil (8.69 g, 71%). $^1$H NMR (300 MHz, CDCl$_3$): δ 7.45 (d, J=9 Hz, 2H), 7.31 (dd, J=1, 2 Hz, 1H), 7.19 (dd, J=1, 2 Hz, 1H), 6.90 (d, J=9 Hz, 2H), 6.70 (dd, J=2, 2 Hz, 1H), 4.53-4.61 (m, 1H), 3.88 (s, 3H), 1.33 (d, J=6 Hz, 6H).

Step D

3-[4-(Diisopropoxy-phosphoryl)-phenoxy]-5-isopropoxy-benzoic acid methyl ester

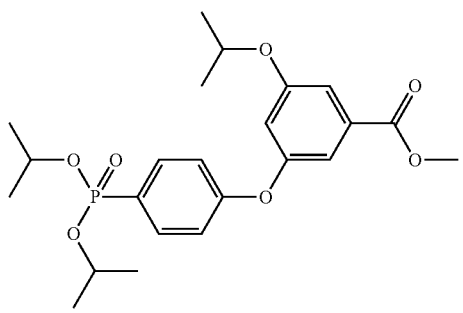 [SMILES: COC(=O)c1cc(Oc2ccc(P(=O)(OC(C)C)OC(C)C)cc2)cc(OC(C)C)c1]

To a stirred solution of 3-(4-bromo-phenoxy)-5-isopropoxy-benzoic acid methyl ester (5.00 g) in toluene (120 mL) was added diisopropyl phosphite (2.80 mL), dichloro[1,1'-bis(diphenylphosphino)-ferrocene]palladium (II) dichloromethane adduct (1.00 g, 1.37 mmol), triethylsilane (0.44 mL, 2.74 mmol), and Et$_3$N (5.72 mL, 41.1 mmol) at rt. DCM (12 mL) was added to the reaction flask which was purged with nitrogen. The mixture was heated at 90° C. overnight. Cooled to rt and concentrated. EtOAc and water were added and the mixture was filtered through a pad of Celite to remove the insoluble. The organic layer was separated, washed with brine (1×), dried with anhydrous MgSO4, filtered, and concentrated. The residue was purified by silica gel column (6×25 cm, hexane/EtOAc, v/v=5:1, 1:1). Fractions containing the product were pooled and concentrated to give 3-[4-(Diisopropoxy-phosphoryl)-phenoxy]-5-isopropoxy-benzoic acid methyl ester (4.0 g, 65%) as yellow oil. $^1$H NMR (300 MHz, CDCl$_3$): δ 7.77 (dd, J=9, 13 Hz, 2H), 7.36 (dd, J=1, 2 Hz, 1H), 7.26 (m, 1H), 7.02 (dd, J=4, 9 Hz, 2H), 6.76 (dd, J=2, 2 Hz, 1H), 4.63-4.74 (m, 2H), 4.54-4.62 (m, 1H), 1.37 (d, J=6 Hz, 6H), 1.33 (d, J=6 Hz, 6H) 1.24 (d, J=6 Hz, 6H).

Step E

3-[4-(Diisopropoxy-phosphoryl)-phenoxy]-5-isopropoxy-benzoic acid

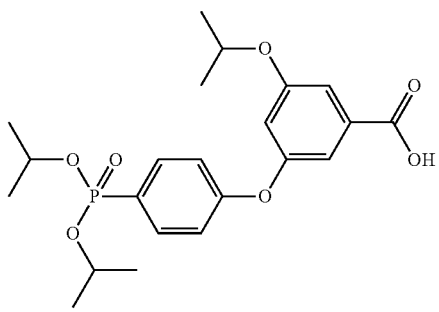 [SMILES: CC(C)Oc1cc(Oc2ccc(P(=O)(OC(C)C)OC(C)C)cc2)cc(C(=O)O)c1]

Starting from 3-[4-(Diisopropoxy-phosphoryl)-phenoxy]-5-isopropoxy-benzoic acid methyl ester (8.00 g, 17.8 mmol), 3-[4-(diisopropoxy-phosphoryl)-phenoxy]-5-isopropoxy-benzoic acid was synthesized as yellow oil (7.64 g, 17.6 mmol) according to Step C in Example 1. $^1$H NMR (300 MHz, CDCl$_3$): δ 7.80 (dd, J=9, 13 Hz, 2H), 7.44 (dd, J=1, 2 Hz, 1H), 7.33 (dd, J=1, 2 Hz, 1H), 7.05 (dd, J=4, 9 Hz, 2H), 6.81 (dd, J=2, 2 Hz, 1H), 4.67-4.78 (m, 2H), 4.56-4.64 (m, 1H), 1.39 (d, J=6 Hz, 6H), 1.35 (d, J=6 Hz, 6H) 1.25 (d, J=6 Hz, 6H).

Step F

{4-[3-isopropoxy-5-(thiazol-2-ylcarbamoyl)-phenoxy]-phenyl}-phosphonic acid diisopropyl ester

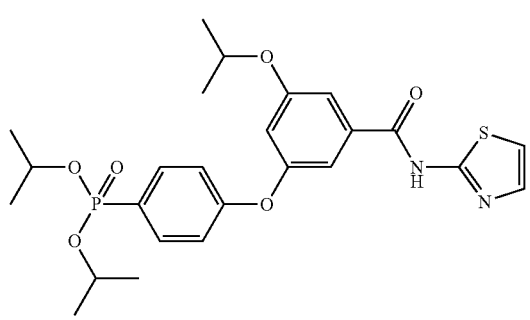 [SMILES: CC(C)Oc1cc(Oc2ccc(P(=O)(OC(C)C)OC(C)C)cc2)cc(C(=O)Nc2nccs2)c1]

Starting from 3-[4-(diisopropoxy-phosphoryl)-phenoxy]-5-isopropoxy-benzoic acid (7.64 g, 17.6 mmol) and 2-aminothiazole (1.84 g, 18.4 mmol), {4-[3-isopropoxy-5-(thiazol-2-ylcarbamoyl)-phenoxy]-phenyl}-phosphonic acid was synthesized as yellow gum (8.80 g, 17.0 mmol) according to Step D in Example 1. ¹H NMR (300 MHz, CDCl₃): δ 7.78 (dd, J=9, 13 Hz, 2H), 7.29-7.30 (m, 1H), 7.18-7.20 (m, 2H), 7.04 (dd, J=4, 9 Hz, 2H), 6.94 (d J=4 Hz, 1H), 6.78 (dd, J=2, 2 Hz, 1H), 4.63-4.74 (m, 2H), 4.51-4.59 (m, 1H), 1.36 (d, J=6 Hz, 6H), 1.33 (d, J=6 Hz, 6H) 1.24 (d, J=6 Hz, 6H).

Example 4

{4-[3-Isobutyl-5-(thiazol-2-ylcarbamoyl)phenoxy]phenyl}phosphonic acid

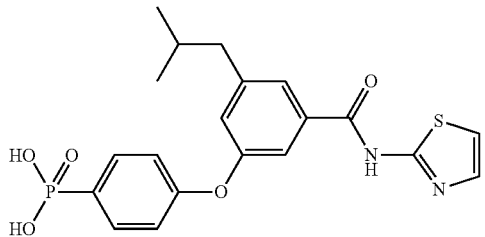

The title compound was prepared from 3-hydroxy-5-isobutylbenzoic acid methyl ester in the same manner as described in Example 3 with modifications evident to an individual skilled in the art. ¹H NMR (500 MHz, DMSO-d₆) δ 0.89 (d, 6H, J=7 Hz), 1.92 (m, 1H), 2.54 (d, 2H, J=7 Hz), 7.10 (dd, 1H, J=8, 3 Hz), 7.17 (s, 1H), 7.28 (d, 1H, J=3 Hz), 7.55 (d, 1H, J=3 Hz), 7.58 (t, 1H, J=2 Hz), 7.70 (dd, 2H, J=12, 8 Hz), 7.79 (s, 1H); LCMS m/z=433.1 [C₂₀H₂₁N₂O₅PS+H]⁺.

Step A

3-Benzyloxy-5-hydroxy-benzoic acid methyl ester

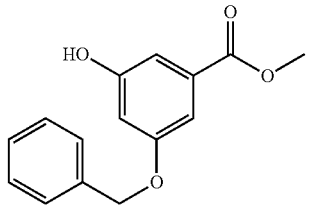 [SMILES: COC(=O)c1cc(O)cc(OCc2ccccc2)c1]

To a solution of methyl 3,5-dihydroxybenzoate (15.0 g, 89.21 mmol) in 350 mL of acetone was added potassium carbonate (13.56 g, 98.13 mmol) followed by benzyl bromide (11.2 mL, 93.6 mmol). And the mixture refluxed for 3 h. After cooling to rt the solids were filtered and the filtrate was evaporated. The residue was chromatographed on silica gel using an EtOAc-hexane gradient to afford 7.08 g (31%) of 3-benzyloxy-5-hydroxybenzoic acid methyl ester. ¹H NMR (300 MHz, DMSO-d₆) δ 3.81 (s, 3H), 5.10 (s, 2H), 6.64-6.66 (m, 1H), 6.97-7.01 (m, 2H), 7.35-7.45 (m, 5H), 9.89 (br s, 1H).

Step B

3-Benzyloxy-5-trifluoromethanesulfonyloxybenzoic acid methyl ester

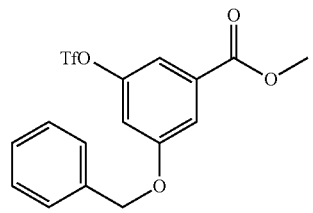 [SMILES: COC(=O)c1cc(OCc2ccccc2)cc(OS(=O)(=O)C(F)(F)F)c1]

To a solution of 3-benzyloxy-5-hydroxybenzoic acid methyl ester (1.50 g, 5.81 mmol) in DCM (60 mL) at −78° C. was added diisopropylethylamine (1.05 mL, 6.39 mmol). After stirring at −78° C. for 20 min, trifluoromethanesulfonic anhydride (1.07 mL, 6.39 mmol) was added and the mixture stirred at room temperature for 30 min. The reaction mixture was diluted with 150 ml of diethyl ether and the organic layer washed with 1N HCl, brine, dried (MgSO₄) and evaporated to afford 2.28 g (100%) of 3-Benzyloxy-5-trifluoromethanesulfonyloxybenzoic acid methyl ester. ¹H NMR (500 MHz, DMSO-d₆) δ 3.87 (s, 3H), 5.25 (s, 2H), 7.35-7.37 (m, 1H), 7.39-7.41 (m, 2H), 7.47-7.49 (m, 2H), 7.52-7.56 (m, 2H), 7.65-7.66 (m, 1H).

Step C

3-Benzyloxy-5-isobutylbenzoic acid methyl ester

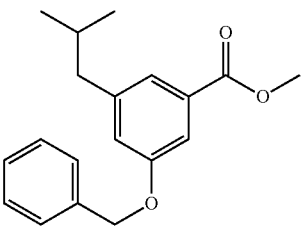 [SMILES: COC(=O)c1cc(CC(C)C)cc(OCc2ccccc2)c1]

To a microwave reaction vial was added 3-benzyloxy-5-trifluoromethanesulfonyloxybenzoic acid methyl ester (70 mg, 0.179 mmol), lithium chloride (23 mg, 0.537 mmol), Pd(PPh₃)₄ (10 mg, 0.009 mmol) and 3 ml of THF. Isobutylzinc bromide (0.5 M in THF) (0.537 mL, 0.269 mmol) was added and the vial sealed. After heating in microwave reactor at 1300 for 5 min the reaction mixture was adsorbed onto silica gel and purified by silica gel chromatography using an ethyl acetate-hexane gradient to afford 36 mg (68%) of 3-benzyloxy-5-isobutylbenzoic acid methyl ester. ¹H NMR (300 MHz. DMSO-d₆) δ 0.850 (d, 6H, J=6 Hz), 1.78-1.92 (m, 1H), 3.84 (s, 3H), 5.16 (s, 2H), 7.11 (d, 1H, J=2 Hz), 7.33-7.48 (m, 7H).

Step D

3-Hydroxy-5-isobutylbenzoic acid methyl ester

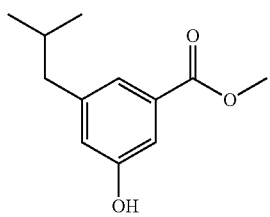

To a solution of 3-benzyloxy-5-isobutylbenzoic acid methyl ester (388 mg, 1.30 mmol) in ethanol (20 mL) was added palladium hydroxide (80 mg, 20 wt % on carbon). After shaking on Parr hydrogenation apparatus for 3 h at 45 psi, the catalyst was filtered through a pad of Celite and the solvent evaporated to afford 271 mg (100%) of 3-hydroxy-5-isobutylbenzoic acid methyl ester. $^1$H NMR (300 MHz, DMSO-$d_6$) δ 0.850 (d, 6H, J=6 Hz), 1.77-1.84 (m, 1H), 2.42 (d, 2H, J=7 Hz), 3.81 (s, 3H), 6.81-6.82 (m, 1H), 7.17-7.19 (m, 2H), 9.70 (s, 1H).

Example 5

{4-[3-(5-Chlorothiazol-2-ylcarbamoyl)-5-cyclopentyloxyphenoxy]phenyl}phosphonic acid

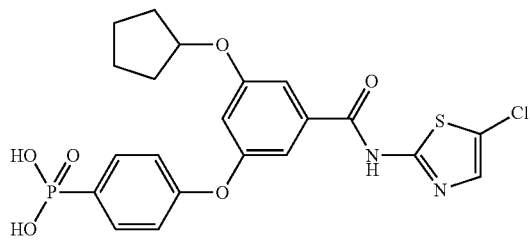 [SMILES: O=C(Nc1ncc(Cl)s1)c1cc(Oc2ccc(P(=O)(O)O)cc2)cc(OC2CCCC2)c1]

The title compound was prepared from 3-(4-bromophenoxy)-5-hydroxybenzoic acid methyl ester in a similar manner to Example 3 with modifications evident to an individual skilled in the art. $^1$H NMR (500 MHz, DMSO-$d_6$) δ 1.58-1.61 (m, 2H), 1.69-1.74 (m, 4H), 1.91-1.96 (m, 2H), 4.94 (m, 1H), 6.87 (t, 1H, J=2 Hz), 7.13 (dd, 2H, J=9, 2 Hz), 7.28 (t, 1H, J=2 Hz), 7.48 (t, 1H, J=2 Hz), 7.61 (s, 1H), 7.71 (dd, 2H, J=12, 9 Hz); LCMS m/z=495.4 [C$_{21}$H$_{20}$ClN$_2$O$_6$PS+H]$^+$; Anal. Calcd. for C$_{21}$H$_{20}$ClN$_2$O$_6$PS: C, 50.97; H, 4.07; N, 5.66. Found: C, 50.61; H, 3.70; N, 5.54.

Step A 3-(4-Bromo-phenoxy)-5-hydroxybenzoic acid methyl ester

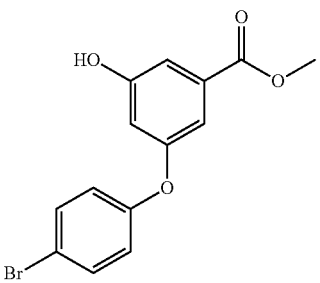 [SMILES: COC(=O)c1cc(O)cc(Oc2ccc(Br)cc2)c1]

To a solution of methyl 3,5-dihydroxybenzoate (8.0 g, 47.6 mmol) in DCM (800 mL) was added 4-bromophenylboronic acid (9.56 g, 47.6 mmol), copper(II)acetate (8.6 g, 47.6 mmol), 4 A molecular sieves (4 g), and pyridine (19.4 mL, 238.0 mmol). After stirring at rt for 72 h, more 4-bromophenylboronic acid (7 g, 35 mmol) was added and stirring continued for another 16 h. The solvent was evaporated and the reaction mixture was re-dissolved in diethyl ether. Washed with 1N HCl, brine, dried (MgSO$_4$) and evaporated. The residue was subjected to silica gel chromatography using an ethyl acetate-hexane gradient to afford 3.4 g (22%) of 3-(4-Bromophenoxy)-5-hydroxybenzoic acid methyl ester. $^1$H NMR (300 MHz, DMSO-$d_6$) δ 3.78 (s, 3H), 6.64-6.66 (m, 1H), 6.89 (dd, 1H, J=2, 1 Hz), 7.02 (dd, 2H, J=7, 2 Hz), 7.12 (dd, 1H, J=2, 1 Hz), 7.57 (dd, 2H, J=7, 2 Hz).

Example 6

{6-[3-Isopropoxy-5-(4-methanesulfonyl-phenoxy)-benzoylamino]-pyridin-3-yl}-methyl-phosphinic acid

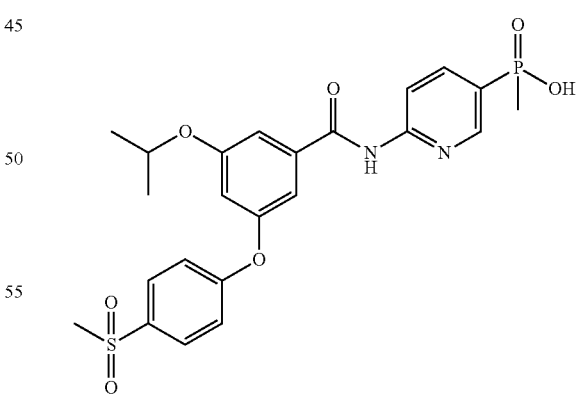

The title compound was prepared from 3-isopropoxy-5-(4-methanesulfonyl-phenoxy)-benzoic acid methyl ester in a similar manner to Example 1 with modifications evident to an individual skilled in the art. $^1$H NMR (500 MHz, DMSO-$d_6$) δ 10.99 (br, 1H), 8.58 (m, 1H), 8.12 (m, 1H), 8.02 (m, 1H), 7.91 (d, J=9 Hz, 2H), 7.47 (m, 1H), 7.30 (m, 1H), 7.21 (d, J=9 Hz, 2H), 6.90 (m, 1H), 4.72-4.79 (m, 1H), 3.18 (s, 3H), 1.27 (d, J=6 Hz, 6H). LC-MS (m/z): 507.4 [C22H23N2O8PS+H]+. Anal. Calcd. for (C22H23N2O8PS+0.5 HBr): C, 47.38; H, 4.67; N, 5.53. Found: C, 47.65; H, 4.47; N, 5.28.

Step A

3-Isopropoxy-5-(4-methanesulfonyl-phenoxy)-benzoic acid methyl ester

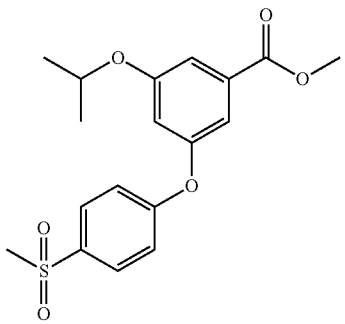

To a solution of 3-hydroxy-5-isopropoxy-benzoic acid methyl ester (3.20 g, 15.2 mmol) in DMF (80 mL) was added Cs$_2$CO$_3$ (5.45 g, 16.7 mmol) and 4-fluorophenyl methyl sulfone (2.65 g, 15.2 mmol) at rt. The resulting mixture was heated at 115° C. for 12 hr. Then the mixture was concentrated. The resulting residue was partitioned between EtOAc and water. The aqueous layer was separated and extracted with EtOAc (2×). Combined organic layers were washed with water (1×), dried and concentrated to a residue, which was purified by silica gel flash chromatography (7.5×30 cm, hexane/EtOAc, v/v 5:1, 2:1, 1:1). Fractions containing the mono-alkylation product were pooled and concentrated to give 3-isopropoxy-5-(4-methanesulfonyl-phenoxy)-benzoic acid methyl ester (5.60 g, 100%) as a yellow oil. $^1$H NMR (300 MHz, CDCl$_3$): δ 8.90 (d, J=9 Hz, 2H), 7.41 (m, 1H), 7.26 (m, 1H), 7.10 (d, J=9 Hz, 2H), 6.79 (m, 1H), 4.56-4.63 (m, 1H), 3.90 (s, 3H), 3.06 (s, 3H), 1.35 (d, J=6 Hz, 6H).

Example 7

{6-[(2-Isobutoxy-6-isopropoxy-pyridine-4-carbonyl)-amino]-pyridin-3-yl}-phosphonic acid

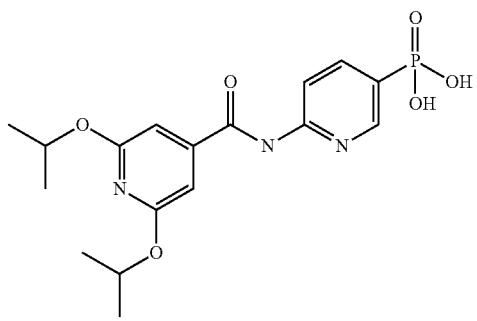 [SMILES: CC(C)Oc1cc(C(=O)Nc2ccc(P(=O)(O)O)cn2)cc(OC(C)C)n1]

The title compound was prepared from 2-isobutoxy-6-isopropoxyisonicotinic acid in a similar manner to Example 1 with modifications evident to an individual skilled in the art. $^1$H NMR (300 MHz, DMSO-d$_6$) δ 0.98 (d, 6H, J=7 Hz), 1.32 (d, 6H, J=6 Hz), 2.00-2.09 (m, 1H), 4.05 (d, 2H, J=6 Hz), 5.13-5.22 (m, 1H), 6.79 (d, 1H, J=1 Hz), 6.86 (d, 1H, J=1 Hz), 8.02-8.09 (m, 1H), 8.20-8.24 (m, 1H), 8.57-8.61 (m, 1H), 11.10 (s, 1H). LCMS m/z 410.4 [C$_{18}$H$_{24}$N$_3$O$_6$P+H]+. Anal. Calcd. for C$_{18}$H$_{24}$N$_3$O$_6$P+0.7H$_2$O: C, 51.23; H, 6.07; N, 9.96. Found: C, 51.26; H, 6.00; N, 9.86.

Step A

2-Chloro-6-isopropoxyisonicotinic acid

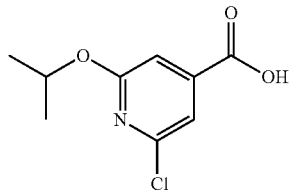

To a solution of 2,6-dichloroisonicotinic acid (1.26 g, 6.56 mmol) in isopropanol (20 mL) was added 27 mL (16.40 mmol) of freshly made sodium isopropoxide (0.61 M in isopropanol). This mixture was split evenly into four 20 mL microwave vials and each vial was heated under microwave irradiation at 150° C. for 10 min. The combined reaction solutions were eluted through a column of Dianion HP-20 PS resin eluting first with water followed by 100% acetonitrile to provide 770 mg (54%) of 2-chloro-6-isopropoxyisonicotinic acid. $^1$H NMR (300 MHz, DMSO-d$_6$) δ 1.27 (d, 6H, J=6 Hz), 5.08-5.14 (m, 1H), 6.95 (s, 1H), 7.23 (s, 1H)

Step B 2,6-Diisopropoxy-isonicotinic acid

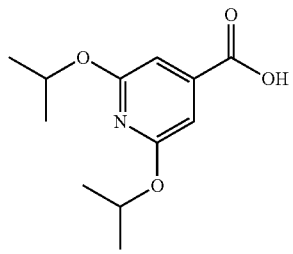 [SMILES: CC(C)Oc1cc(C(=O)O)cc(OC(C)C)n1]

To a flask containing 2-chloro-6-isopropoxyisonicotinic acid (1.05 g, 4.83 mmol) was added 28 mL (9.66 mmol) of freshly prepared sodium isobutoxide (0.35 M in isobutanol). This mixture was split evenly into two 20 mL microwave vials and each vial was heated under microwave irradiation at 210° C. for 20 min. The reaction mixture was purified by C18 medium pressure chromatography using a gradient of acetonitrile in water to afford 310 mg (25%) of 2-isobutoxy-6-isopropoxyisonicotinic acid. $^1$H NMR (300 MHz, DMSO-d$_6$) δ 0.95 (d, 6H, J=7 Hz), 1.27 (d, 6H, J=6 Hz), 1.96-2.05 (m, 1H), 3.96 (d, 2H, J=7 Hz), 5.05-5.13 (m, 1H), 6.59 (s, 1H), 6.63 (s, 1H).

Example 8

{4-[5-(Thiazol-2-ylcarbamoyl)-biphenyl-3-yloxy]-phenyl}-phosphonic acid

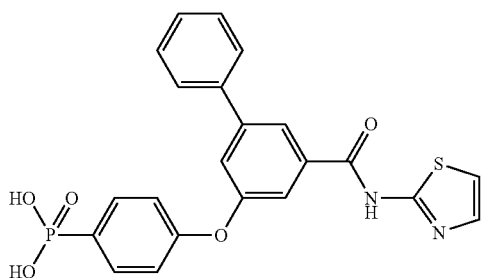 [SMILES: O=C(Nc1nccs1)c1cc(Oc2ccc(P(=O)(O)O)cc2)cc(-c2ccccc2)c1]

The title compound was prepared from 5-benzyloxybiphenyl-3-carboxylic acid methyl ester in a similar manner to Example 4 with modifications evident to an individual skilled in the art. $^1$H NMR (300 MHz, DMSO-$d_6$) δ 7.02-7.04 (m, 2H), 7.14 (d, 1H, J=3 Hz), 7.26-7.29 (m, 1H), 7.34-7.37 (m, 2H), 7.42 (d, 1H, J=3 Hz), 7.49-7.59 (m, 4H), 7.67-7.69 (m, 2H), 8.16 (t, 1H, J=2 Hz); LCMS m/z=453.4 $[C_{22}H_{17}N_2O_5PS+H]^+$. Anal. Calcd. for $C_{22}H_{17}N_2O_5PS$: C, 58.41; H, 3.79; N, 6.19. Found: C, 58.24, H, 3.78; N, 5.99.

Step A

5-Benzyloxybiphenyl-3-carboxylic acid methyl ester

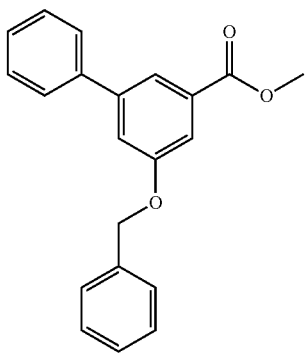 [SMILES: COC(=O)c1cc(OCc2ccccc2)cc(-c2ccccc2)c1]

To a mixture of THF/H$_2$O (5 mL, v/v=4:1) in a microwave vial was added 3-benzyloxy-5-trifluoromethanesulfonyloxy-benzoic acid methyl ester (100 mg, 0.256 mmol), phenylboronic acid (34 mg, 0.281 mmol), potassium carbonate (71 mg, 0.512 mmol), and Pd(PPh$_3$)$_4$ (15 mg, 0.02 mmol). The reaction vessel was sealed and subjected to microwave heating for 5 min at 130° C. After cooling, it was diluted with diethyl ether and washed with brine, dried (MgSO$_4$), and evaporated. The residue was subjected to chromatography on silica gel using an ethyl acetate-hexane gradient to afford 74 mg (90%) of 5-benzyloxybiphenyl-3-carboxylic acid methyl ester: LCMS m/z=319.4 $[C_{21}H_{18}O_3+H]^+$.

Example 9

{4-[3-(4-Chloro-thiazol-2-ylcarbamoyl)-5-(3,5-dimethyl-isoxazol-4-yl)-phenoxy]-phenyl}-phosphonic acid

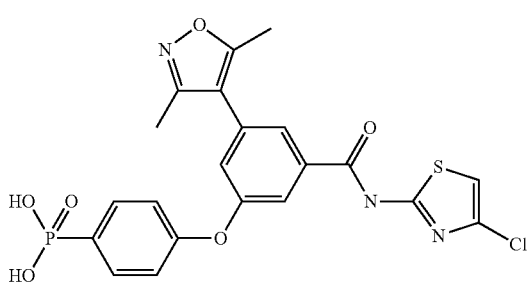 [SMILES: Cc1noc(C)c1-c1cc(Oc2ccc(P(=O)(O)O)cc2)cc(C(=O)Nc2nc(Cl)cs2)c1]

The title compound was prepared from 3-benzyloxy-5-trifluoromethanesulfonyloxy-benzoic acid methyl ester in a similar manner to Example 8 with modifications evident to an individual skilled in the art. $^1$H NMR (500 MHz, DMSO-$d_6$) δ 2.27 (s, 3H), 2.46 (s, 3H), 7.18 (dd, 2H, J=9, 3 Hz), 7.45 (dd, 1H, J=2, 2 Hz), 7.62 (s, 1H), 7.71-7.75 (m, 3H), 7.91 (t, 1H, J=2 Hz); LCMS m/z=506.1 $[C_{21}H_{17}ClN_3O_6PS+H]^+$. Anal. Calcd. for $(C_{21}H_{17}ClN_3O_6PS+0.75\ HBr)$: C, 44.52: H, 3.16; N, 7.42. Found: C, 44.61; H, 3.28; N, 7.15.

Example 10

{4-[3-(5-Chloro-thiazol-2-ylcarbamoyl)-5-phenoxy-phenoxy]-phenyl}-phosphonic acid

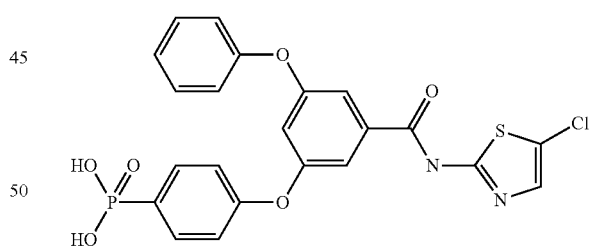

The title compound was prepared from 3-(4-bromo-phenoxy)-5-hydroxybenzoic acid methyl ester in a similar manner to Example 3 with modifications evident to an individual skilled in the art. $^1$H NMR (500 MHz, DMSO-$d_6$) δ 7.02 (t, 1H, J=2 Hz), 7.14-7.25 (m, 5H), 7.44-7.52 (m, 4H), 7.60 (s, 1H), 7.70-7.74 (m, 2H). LCMS m/z=503.4 $[C_{22}H_{16}ClN_2O_6PS+H]^+$; Anal. Calcd. for $C_{22}H_{16}ClN_2O_6PS$: C, 52.55; H, 3.21; N, 5.57. Found: C, 52.37; H, 3.08; N, 5.29.

Step A

3-(4-Bromophenoxy)-5-phenoxybenzoic acid methyl ester

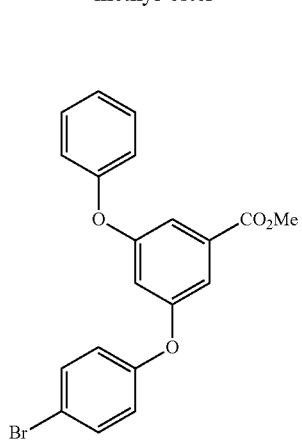

To a solution of 3-(4-bromophenoxy)-5-hydroxybenzoic acid methyl ester (200 mg, 0.619 mmol) in 10 mL of acetonitrile was added iodobenzene (189 mg, 0.928 mmol), cesium carbonate (403 mg, 1.24 mmol), copper(I)oxide (5 mg, 0.03 mmol), magnesium sulfate (185 mg), and dimethylglyoxime (14 mg, 0.124 mmol). The mixture was stirred at reflux for 16 h. Then the mixture was filtered through a pad of Celite and the filtrate was evaporated. The residue was chromatographied on silica gel using an ethyl acetate-hexane gradient afforded 58 mg (23%) of 3-(4-bromophenoxy)-5-phenoxybenzoic acid methyl ester: $^1$H NMR (300 MHz, DMSO-d$_6$) δ 3.79 (s, 3-1), 7.00-7.02 (m, 1H), 7.08-7.18 (m, 6H), 7.20-7.26 (m, 1H), 7.43-7.46 (m, 2H), 7.61 (d, 2H, J=9 Hz).

Example 11

{5-[3-Isopropoxy-5-(thiazol-2-ylcarbamoyl)-benzyl]-thiophen-2-yl}-phosphonic acid

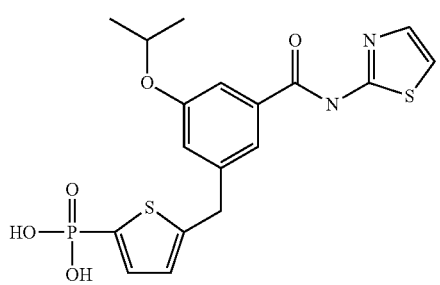 [SMILES: CC(C)Oc1cc(Cc2ccc(P(=O)(O)O)s2)cc(C(=O)Nc2nccs2)c1]

The title compound was prepared from 3-[5-(diethoxyphosphoryl)-thiophen-2-ylmethyl]-5-isopropoxy-benzoic acid in a similar manner to Example 3 with modifications evident to an individual skilled in the art. $^1$H NMR (300 MHz, DMSO-d$_6$): δ 7.57 (m, 3H), 7.28 (m, 2H), 7.07 (m, 1H), 7.00 (m, 1H), 4.74 (m, 1H), 4.21 (m, 2H), 1.31 (m, 6H). LC-MS m/z=439.4 [C18H19N2O5PS2+H]$^+$; Anal Calcd for (C18H19N2O5PS2+0.15 HBr): C, 47.98H, 4.28; N, 6.22. Found: C, 47.95; H, 4.29; N, 5.98.

Intermediates for the preparation of Example 11 were prepared according to Route 4, as described below.

Route 4

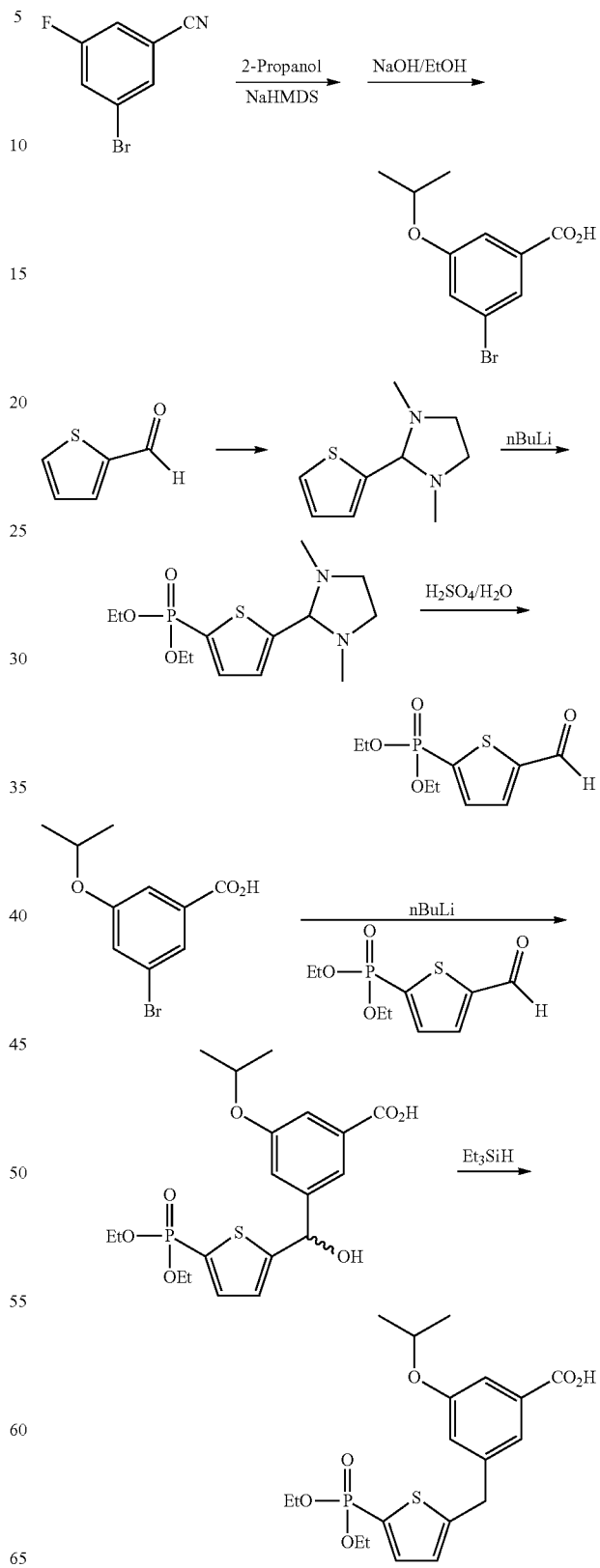

Step A

3-Bromo-5-isopropoxy-benzonitrile

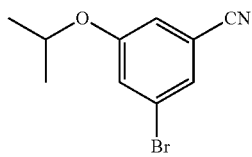

To a solution of 1M NaHMDS (74.26 ml, 74.26 mmol) in DMF was added 2-propanal (5.69 ml, 74.26 mmol) at r.t. After stirring for 5 min 3-bromo-5-fluoro-benzonitrile was added. The reaction mixture was stirred at r.t. for 2 hrs, concentrated down. The residue was then partitioned between EtOAc and water. The organic layer was collected and the water layer was back-extracted with EtOAc once. The combined organic layers were dried over MgSO$_4$, filtrated, concentrated, purified by Biotage (5% EtOAc) to afford the final product 3-bromo-5-isopropoxy-benzonitrile (9.46 g, 79.0%). $^1$H NMR (300 MHz, DMSO-d$_6$): δ 7.62 (m, 1H), 7.47 (m, 1H), 7.44 (m, 1H), 4.73 (m, 2H), 1.24 (d, J=6.3 Hz, 6H). LC-MS m/z=241.4 [C10H10BrNO+H]$^+$.

Step B

3-Bromo-5-isopropoxy-benzoic acid

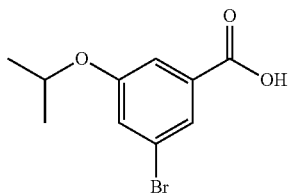

To a solution of 3-bromo-5-isopropoxy-benzonitrile (6.0 g, 24.78 mmol) in EtOH (80 ml) was added water (8.0 ml), followed by 50% NaOH (6.52 ml, 123.91 mmol). The reaction mixture was then refluxed for 2 hrs, concentrated down, re-dissolved in water, acidified with HCl, extracted with EtOAc. The EtOAc layer was separated, dried over MgSO$_4$, filtrated, and concentrated to afford the final product 3-bromo-5-isopropoxy-benzoic acid (6.36 g, 100%). $^1$H NMR (300 MHz, DMSO-d$_6$): δ 13.31 (s, 1H), 7.56 (s, 1H), 7.36 (m, 2H), 4.70 (m, 2H), 1.25 (d, J=6.0 Hz, 6H). LC-MS m/z=260.4 [C10H11BrO3+H]$^+$.

Step C 1, 3-Dimethyl-2-thiophen-2-yl-imidazolidine

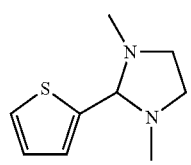

To a solution of 2-thiophenecarboxaldehyde (8.6 ml, 104 mmol) in toluene was added N,N'-dimethylethylene amine (11.0 ml, 104 mmol) at 0° C. The reaction mixture was heated to reflux after the addition was complete. After 3 h at reflux, the mixture was cooled to rt, concentrated down to afford the final product 1, 3-dimethyl-2-thiophen-2-yl-imidazolidine (20 g, 100%). $^1$H NMR (300 MHz, DMSO-d$_6$): δ 7.47 (d, J=5.4 Hz, 1H), 7.09 (d, J=3.3 Hz, 1H), 6.94 (m, 1H), 3.60 (s, 1H), 3.18 (m, 4H), 2.11 (s, 6H).

Step D

[5-(1, 3-Dimethyl-imidazolidin-2-yl)-thiophen-2-yl]-phosphonic acid diethyl ester

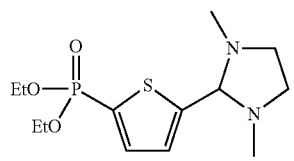 [SMILES: CCOP(=O)(OCC)c1ccc(C2N(C)CCN2C)s1]

To a solution of 1,3-Dimethyl-2-thiophen-2-yl-imidazolidine (10 g, 60.17 mmol) in THF was added TMEDA (9.1 ml, 60.17 mmol), cooled to −78° C., then added 1.6 M nBuLi (47 m, 75.21 mmol). After stirring at −78° C. for 30 min the mixture was warmed up to 0° C. in 1 hr and treated with diethyl chlorophosphonate (10.4 ml, 72.2 mmol). The reaction mixture was stirred at 0° C. for another 30 min. The reaction was then quenched by adding EtOAc and water. The EtOAc layer was separated and the water layer was further extracted with EtOAc once. The combined EtOAc layers were dried over MgSO$_4$, filtrated and concentrated to afford the crude product [5-(1, 3-dimethyl-imidazolidin-2-yl)-thiophen-2-yl]-phosphonic acid diethyl ester (17 g). $^1$H NMR (300 MHz, DMSO-d$_6$): δ 7.44 (m, 1H), 7.24 (m, 1H), 4.01 (m, 4H), 3.18 (m, 2H), 2.53 (m, 2H), 1.22 (m, 9H).

Step E (5-Formyl-thiophen-2-yl)-phosphonic acid diethyl ester

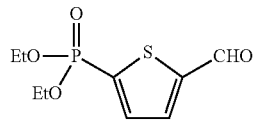 [SMILES: CCOP(=O)(OCC)c1ccc(C=O)s1]

To a solution of [5-(1, 3-dimethyl-imidazolidin-2-yl)-thiophen-2-yl]-phosphonic acid diethyl ester (17.2 g, 60.17 mmol) in water (20 ml) was added sulfuric acid (3 ml) over 5 mins. The reaction was stirred at r.t. for 20 min, diluted with water, extracted with EtOAc. The organic layer was washed with sat. NaHCO$_3$, dried over MgSO$_4$, filtrated, concentrated, purified by Biotage (80% EtOAc) to give (5-formyl-thiophen-2-yl)-phosphonic acid diethyl ester (7.2 g, 48.3%). $^1$H NMR (300 MHz, DMSO-d$_6$): δ 10.02 (d, J=2.4 Hz, 1H), 8.09 (m, 1H), 7.75 (m, 1H), 4.05 (m, 4H), 1.24 (m, 6H). LC-MS m/z=249.4 [C9H13O4PS+H]+.

Step F

3-{[5-(Diethoxy-phosphoryl)-thiophen-2-yl]-hydroxy-methyl}-5-isopropoxy-benzoic acid

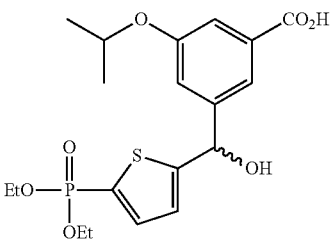 [SMILES: CCOP(=O)(OCC)c1ccc(C(O)c2cc(OC(C)C)cc(C(=O)O)c2)s1]

To a solution of 3-bromo-5-isopropoxy-benzoic acid (2.0 g, 8.26 mmol) in THF (30 ml) was added 1.6 M nBuLi (10.6 mL 16.94 mmol) at −78° C. The reaction was stirred at −78° C. for 1 h and treated with a solution of (5-formyl-thiophen-2-yl)-phosphonic acid diethyl ester (2.5 g, 9.91 mmol) in THF. After stirring at −78° C. for 30 min, the reaction mixture was warmed up to r.t. and quenched by water, diluted with EtOAc. The aqueous layer was separated, acidified with 2N HCl to pH<1, and extracted with EtOAc (3×). The combined EtOAc layers were dried over MgSO4, filtered, concentrated to give the crude product 3-{[5-(diethoxy-phosphoryl)-thiophen-2-yl]-hydroxy-methyl}-5-isopropoxy-benzoic acid.

Step G

3-[5-(Diethoxy-phosphoryl)-thiophen-2-ylmethyl]-5-isopropoxy-benzoic acid

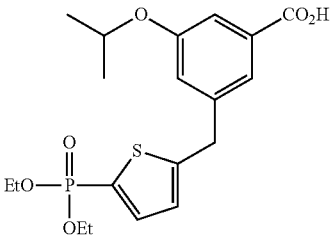 [SMILES: CCOP(=O)(OCC)c1ccc(Cc2cc(OC(C)C)cc(C(=O)O)c2)s1]

To a solution of 3-{[5-(diethoxy-phosphoryl)-thiophen-2-yl]-hydroxy-methyl}-5-isopropoxy-benzoic acid (700 m g, 1.64 mmol) in CH2Cl2 (10 ml) was added TFA (1.1 ml), followed by triethylsilane (0.92 ml, 5.72 mmol). The reaction mixture was then stirred at r.t. for 30 min, concentrated down, re-dissolved in water, extracted with EtOAc. The EtOAc layer was separated, dried over MgSO4, filtrated, and concentrated to afford the crude product 3-[5-(diethoxy-phosphoryl)-thiophen-2-ylmethyl]-5-isopropoxy-benzoic acid.

Example 12

{4-[2-(5-Chloro-thiazol-2-ylcarbamoyl)-quinolin-4-yloxy]-phenyl}-phosphonic acid

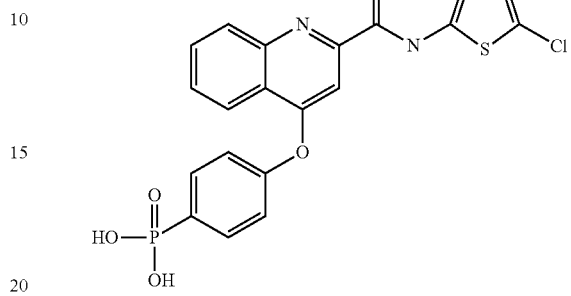

The title compound was prepared from 4-chloro-quinoline-2-carboxylic acid ethyl ester in a similar manner to Example 3 with modifications evident to an individual skilled in the art. 1H NMR (300 MHz, DMSO-d6): δ 8.48 (d, J=8.1 Hz), 8.36 (d, J=8.7 Hz), 8.08 (m, 1H), 7.94 (m, 3H), 7.72 (s, 1H), 7.54 (m, 2H), 7.32 (s, 1H). LC-MS m/z=462.4 [C19H13ClN3O5PS+H]+; Anal Calcd for (C19H13ClN3O5PS+0.8H2O): C, 47.92H, 3.09; N, 8.82. Found: C, 47.77; H, 3.12; N, 9.10.

Step A 4-(4-Bromo-phenoxy)-quinoline-2-carboxylic acid ethyl ester

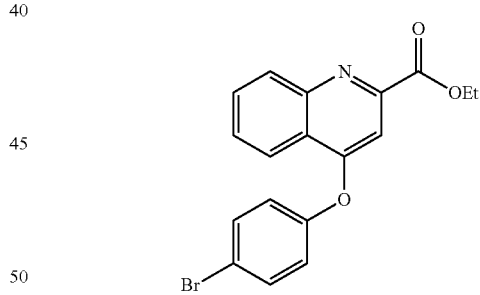

To a solution of 4-chloro-quinoline-2-carboxylic acid ethyl ester (910 mg, 3.87 mmol) in DMF (15 ml) was added 4-bromophenol (737 mg, 4.26 mmol), followed by Cs2CO3 (1.89 g, 5.81 mmol). The reaction mixture was then heated to 60° C. for 16 hrs. On the second day the mixture was cooled to r.t. and concentrated down. The residue was partitioned between EtOAc (10 ml) and water (20 ml). The EtOAc layer was separated, dried over MgSO4, filtrated, concentrated, and purified by Biotage with EtOAc/Hexane (15%, 4 CV) to afford 4-(4-bromo-phenoxy)-quinoline-2-carboxylic acid ethyl ester (609 mg, 42.3%). 1H NMR (300 MHz, DMSO-d6): δ 8.36 (m, 1H), 8.18 (m, 1H), 7.93 (m, 1H), 7.80 (m, 1H), 7.75 (m, 2H), 7.34 (m, 2H), 7.14 (s, 1H), 4.34 (m, 2H), 1.30 (m, 3H). LC-MS m/z=373 [C18H14BrNO3+H]+.

Example 13

{4-[2-(5-Fluoro-thiazol-2-ylcarbamoyl)-quinolin-4-yloxy]-phenyl}-phosphonic acid

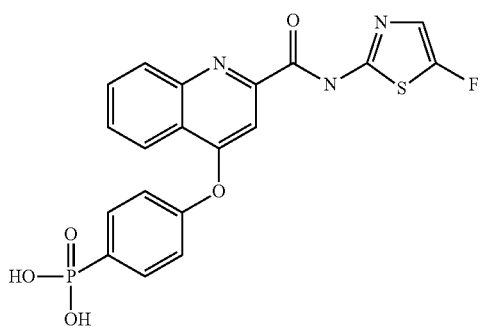 [SMILES: O=C(Nc1ncc(F)s1)c1cc(Oc2ccc(P(=O)(O)O)cc2)c2ccccc2n1]

The title compound was prepared from 4-Chloro-quinoline-2-carboxylic acid ethyl ester in a similar manner to Example 12 with modifications evident to an individual skilled in the art. $^1$H NMR (300 MHz, DMSO-$d_6$): δ 8.35 (d, J=7.8 Hz), 8.23 (d, J=7.8 Hz), 7.96 (m, 1H), 7.82 (m, 3H), 7.41 (m, 3H), 7.19 (s, 1H). LC-MS m/z=446.4 [C19H13FN3O5PS+H]$^+$; Anal Calcd for (C19H13FN3O5PS+0.1 HBr+0.5H2O): C, 49.35H, 3.07; N, 9.09. Found: C, 49.07; H, 3.27; N, 9.49.

Example 14

(5-{2-[3-Isopropoxy-5-(4-methanesulfonyl-phenoxy)-benzoylamino]-thiazol-4-yl}-thiophen-2-yl)-phosphonic acid

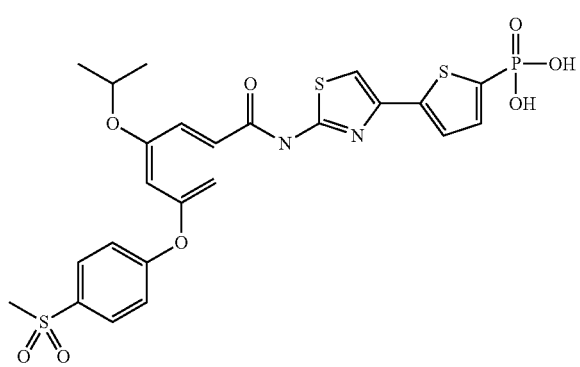 [SMILES: C=C(/C=C(\C=C\C(=O)Nc1nc(-c2ccc(P(=O)(O)O)s2)cs1)OC(C)C)Oc1ccc(S(C)(=O)=O)cc1]

The title compound was prepared from [5-(2-amino-thiazol-5-yl)-thiophen-2-yl]-phosphonic acid diethyl ester in a similar manner to Example 6 with modifications evident to an individual skilled in the art. $^1$H NMR (300 MHz, DMSO-$d_6$): δ 12.93 (s, 1H), 8.02 (m, 2H), 7.75 (s, 1H), 7.66 (m, 2H), 7.47 (m, 2H), 7.33 (m, 2H), 7.06 (m, 1H), 4.86 (m, 1H), 3.29 (s, 3H), 1.38 (d, J=6.3 Hz, 6H). LC-MS m/z=625.6 [C24H23N2O8PS3+H]$^+$; Anal Calcd for (C24H23N2O8PS3+0.2 HBr): C, 47.19H, 3.83; N, 4.59. Found: C, 47.40; H, 3.91; N, 4.26.

Step A (5-Acetyl-thiophen-2-yl)-phosphonic acid diethyl ester

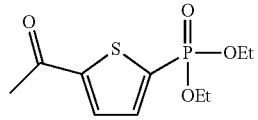 [SMILES: CCOP(=O)(OCC)c1ccc(C(C)=O)s1]

(5-Acetyl-thiophen-2-yl)-phosphonic acid diethyl ester was made according to Mu, X. J.; Zou. J. P.; Qian, Q. F.; Zhang, W. Org. Lett., 2006, 8, 5291-5293: $^1$H NMR (300 MHz, DMSO-$d_6$): δ 7.99 (m, 1H), 7.68 (m, 1H), 4.06 (m, 4H), 1.24 (m, 6H).

Step B

[5-(2-Amino-thiazol-5-yl)-thiophen-2-yl]-phosphonic acid diethyl ester

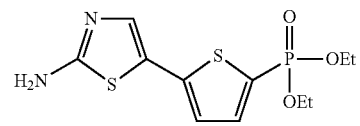 [SMILES: CCOP(=O)(OCC)c1ccc(-c2cnc(N)s2)s1]

To a solution of (5-acetyl-thiophen-2-yl)-phosphonic acid diethyl ester (1.13 g, 4.31 mmol) in EtOH (80 ml) was added CuBr$_2$ (959 mg, 8.62 mmol). The reaction mixture was then refluxed for 3 hr, diluted with EtOAc, quenched by adding sat. NaHCO$_3$. After layers were separated, the org, layer was collected and the aqueous layer was further extracted with EtOAc once. Combined organic layers were dried over MgSO$_4$, filtrated, and concentrated. The residue was then dissolved in EtOH/EtOAc (4 ml/16 ml) and treated with thiourea (394 mg, 5.17 mmol). The reaction mixture was then heated to reflux for 1 hr, cooled to r.t., and concentrated down. The residue was partitioned between EtOAc and water. The organic layer was collected, dried over MgSO$_4$, filtrated, concentrated, and purified by Biotage to give the final compound (218 mg, 15.9%). $^1$H NMR (300 MHz, DMSO-$d_6$): δ 7.50 (m, 2H), 7.23 (s, 2H), 7.10 (s, 1H), 4.02 (m, 4H), 1.21 (m, 6H). LC-MS m/z=263.4 [C7H7N2O3PS2+H]$^+$.

Example 15

{6-[2-Amino-4-fluoro-5-(1-methyl-1H-imidazol-2-ylsulfanyl)-benzoylamino]-pyridin-3-yl}-methyl-phosphinic acid hydroiodide salt

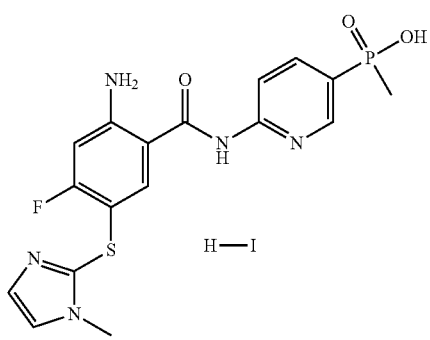

In a similar manner to Example 1, a mixture of isopropyl 2-amino-N-(5-bromo-pyridin-2-yl)-4-fluoro-5-(1-methyl-1H-imidazol-2-ylsulfanyl)-benzamide (57 mg, 0.12 mmol) and iodotrimethylsilane (0.07 mL, 0.49 mmol) in 2 mL of CH$_2$Cl$_2$ was stirred for 90 min at rt and the solvents evaporated. The residue was sonicated in 1 mL of CH$_3$CN, the solvent evaporated, the residue sonicated in 1 mL CH$_3$CN and 0.1 mL water, the solvent evaporated and the residue suspended in CH$_3$CN and the resulting solid collected by filtration. It was dissolved in 1:1 CH$_3$CN/water and subjected to MPLC purification through a 25 g C18 column eluting with % acetonitrile in water (time): 10 (3 min), 15 (15 min). Lyophilization of the eluent containing the desired product provided 31 mg (46%) of the title compound as an amorphous solid: $^1$H NMR (500 MHz, DMSO-d$_6$): δ 1.57 (d, 3H, J=15 Hz), 3.79 (s, 3H), 6.64 (d, 1H, J=12 Hz), 7.15 (br s, 2H), 7.37 (br s, 1H), 7.57 (s, 1H), 8.11 (ddd, 1H, J=10, 8, 2 Hz), 8.16 (d, 1H, J=8 Hz), 8.17 (dd, 1H, J=8, 2 Hz), 8.65 (dq, 1H, J=6, 1 Hz); LCMS (m/z): 422.1 [C$_{17}$H$_{17}$FN$_5$O$_3$PS+H]$^+$. Anal. calcd. for (C$_{17}$H$_{17}$FN$_5$O$_3$PS+HI+H$_2$O): C, 36.06; H, 3.38; N, 12.37. Found: C, 36.22; H, 3.39; N, 12.18.

Intermediates for the preparation of Example 15 were prepared according to Route 5, as described below.

Route 5

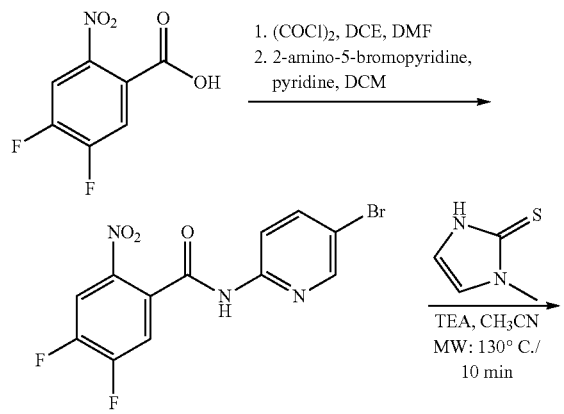

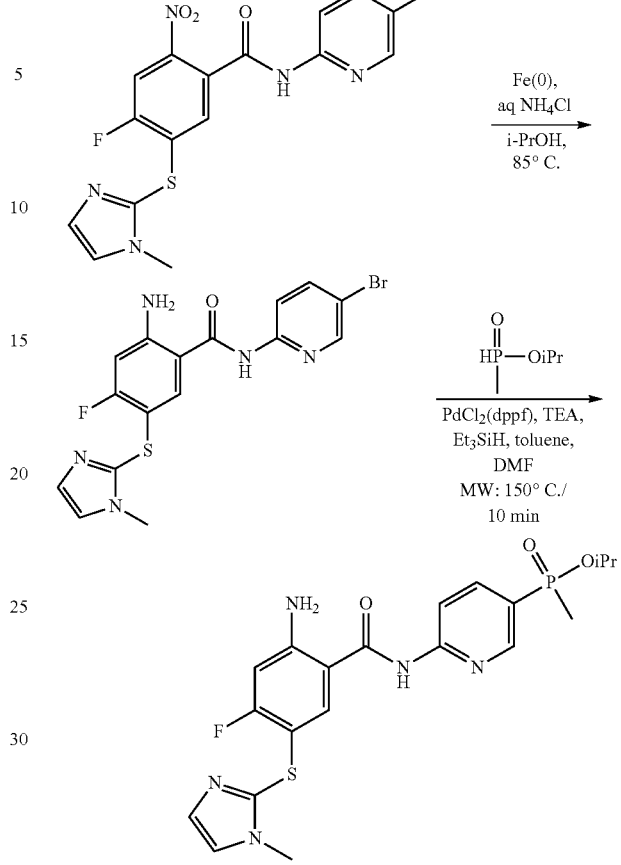

Step A

N-(5-Bromo-pyridin-2-yl)-4,5-difluoro-2-nitro-benzamide

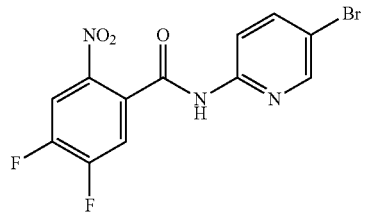 [SMILES: O=C(Nc1ccc(Br)cn1)c1cc(F)c(F)cc1[N+](=O)[O-]]

Conducted as described for Step D of Example 1 using 4,4-difluoro-2-nitrobenzoic acid (2500 mg, 12.3 mmol) and 2-amino-5-bromopyridine (2340 mg, 13.5 mmol) and substituting dichloroethane for CH$_2$Cl$_2$ in the acid chloride forming step. The solid residue obtained after extractive isolation was recrystallized from EtOAc to provide 2.43 g of the title compound. A second crop from the filtrate provided a further 549 mg to make a total of 2.98 g (68%) of the title compound as a yellow crystalline solid. $^1$H NMR (500 MHz, DMSO-d$_6$): δ 8.07 (dd, 1H, J=10, 8 Hz), 8.11 (dd, 1H, J=9, 2 Hz), 8.14 (d, 1H, J=9 Hz), 8.46 (dd, 1H, J=10, 7 Hz), 8.50 (br s, 1H), 11.45 (s, 1H); LCMS (m/z): 358/360 [C$_{12}$H$_6$BrF$_2$N$_3$O$_3$+H]$^+$.

Step B

N-(5-Bromo-pyridin-2-yl)-4-fluoro-5-(1-methyl-1H-imidazol-2-ylsulfanyl)-2-nitro-benzamide

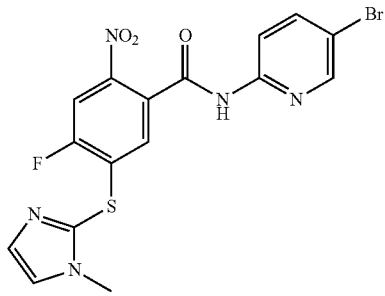 [SMILES: Cn1ccnc1Sc1cc(C(=O)Nc2ccc(Br)cn2)c([N+](=O)[O-])cc1F]

A mixture of N-(5-bromo-pyridin-2-yl)-4,5-difluoro-2-nitro-benzamide (236 mg, 0.66 mmol), 2-mercapto-1-methylimidazole (83 mg, 0.73 mmol) and triethylamine (0.18 mL, 1.32 mmol) in 2 mL $CH_3CN$ was microwave heated to 130° C. for 10 min and the resulting solid was collected by filtration, rinsed with $CH_3CN$, and dried under high vacuum to provide 214 mg (72%) of the title compound as a yellow solid. $^1H$ NMR (500 MHz, DMSO-$d_6$): δ 3.70 (s, 3H), 6.91 (d, 1H, J=7 Hz), 7.20 (d, 1H, J=1 Hz), 7.58 (d, 1H, J=1 Hz), 8.07 (br s, 2H), 8.24 (d, 1H, J=10 Hz), 8.47 (br s, 1H), 11.39 (s, 1H); LCMS (m/z): 452/454 $[C_{16}H_{11}BrFN_5O_3S+H]^+$.

Step C

2-Amino-N-(5-bromo-pyridin-2-yl)-4-fluoro-5-(1-methyl-1H-imidazol-2-ylsulfanyl)-benzamide

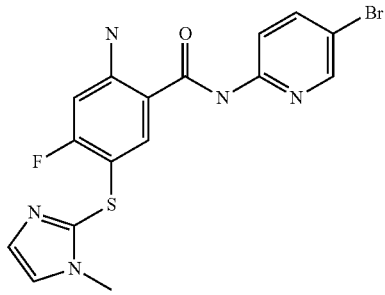 [SMILES: Cn1ccnc1Sc1cc(C(=O)Nc2ccc(Br)cn2)c(N)cc1F]

A mixture of N-(5-bromo-pyridin-2-yl)-4-fluoro-5-(1-methyl-1H-imidazol-2-ylsulfanyl)-2-nitro-benzamide (1.42 g, 3.14 mmol), 325 mesh iron dust (7.1 g, 127 mmol), 6 mL of 4 M aqueous $NH_4Cl$ and 60 mL of isopropanol were mechanically stirred at 85° C. for 4 h, then slurried hot with Celite and filtered. The filtrate was diluted with EtOAc, washed with brine, dried ($MgSO_4$) and evaporated. The residue obtained was triturated in boiling methanol. After cooling, the resulting solid was collected by filtration and dried under high vacuum to provide 692 mg (52%) of the title compound as a light-green solid. $^1H$ NMR (500 MHz, DMSO-$d_6$): δ 3.67 (s, 3H), 6.58 (d, 1H, J=12 Hz), 6.89 (s, 1H), 6.95 (br s, 2H), 7.26 (s, 1H), 7.99 (d, 1H, J=8 Hz), 8.03 (d, 1H, J=8 Hz), 8.04 (d, 1H, J=8 Hz), 8.50 (s, 1H), 10.86 (s, 1H); LCMS (m/z): 422/424 $[C_{16}H_{13}BrFN_5OS+H]^+$.

Step D

{6-[2-Amino-4-fluoro-5-(1-methyl-1H-imidazol-2-ylsulfanyl)-benzoylamino]-pyridin-3-yl}-methyl-phosphinic acid isopropyl ester

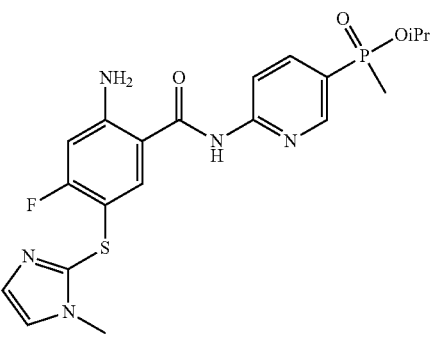 [SMILES: CC(C)OP(C)(=O)c1ccc(NC(=O)c2cc(Sc3nccn3C)c(F)cc2N)nc1]

A mixture of 2-amino-N-(5-bromo-pyridin-2-yl)-4-fluoro-5-(1-methyl-1H-imidazol-2-ylsulfanyl)-benzamide (346 mg, 0.82 mmol), isopropyl methylphosphinate (0.256 mL, 2.05 mmol), [1,1'-bis(diphenylphosphino)ferrocene] palladium (II) dichloride (60 mg, 0.082 mmol) and 8 mL of toluene was degassed by bubbling $N_2$ through it for 2 min, then triethylamine (0.285 mL, 2.05 mmol) and triethylsilane (0.033 mL, 0.205 mmol) were added and the mixture microwave heated at 150° C. for 10 min. The solvent was evaporated and the residue dissolved in $CH_2Cl_2$, washed with brine, dried ($MgSO_4$) and evaporated. The residue was adsorbed to $SiO_2$ and subjected to MPLC on a 12 g $SiO_2$ column eluting with % EtOAc in hexanes (time): 75 (8 min), 85 (10 min), 90 (10 min), 100 (20 min), then % MeOH in EtOAc (time): 1 (10 min), 2 (10 min) to provide 60 mg (16%) of the title compound. $^1H$ NMR (500 MHz, DMSO-$d_6$): δ 1.11 (d, 3H, J=6 Hz), 1.29 (d, 3H, J=6 Hz), 1.69 (d, 3H, J=15 Hz), 3.68 (s, 3H), 4.40 (septet, 1H, J=6 Hz), 6.60 (d, 1H, J=12 Hz), 6.90 (d, 1H J=1 Hz), 6.98 (s, 2H), 7.27 (d, 1H, J=1 Hz), 8.02 (d, 1H, J=8 Hz), 8.12 (td, 1H, J=7, 3 Hz), 8.17 (dd, 1H, J=7, 2 Hz), 8.67 (dt, 1H, J=5, 1 Hz), 11.02 (s, 1H); LCMS (m/z): 464.1 $[C_{20}H_{23}FN_5O_3PS+H]^+$.

Example 16

{5-[3-Isopropoxy-5-(4-methanesulfonyl-phenoxy)-benzoylamino]-pyrazin-2-ylmethyl}-phosphonic acid hydrobromide salt

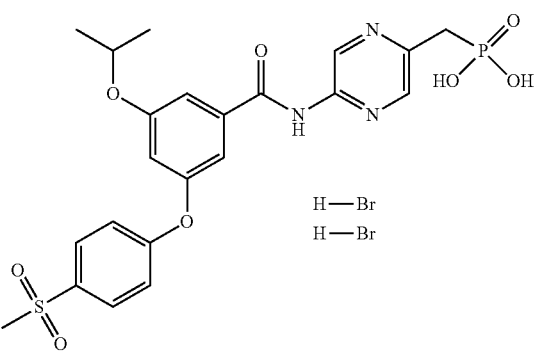

In a similar manner to Example 1, a mixture of diethyl {2-[3-isopropoxy-5-(4-methanesulfonyl-phenoxy)-benzoylamino]-pyrazin-5-ylmethyl}phosphonate (29 mg, 0.05 mmol) and bromotrimethylsilane (0.13 mL, 1.0 mmol) in 1 mL of $CH_2Cl_2$ was stirred for 16 h at rt and the solvents evaporated. The residue was sonicated in 1 mL of $CH_3CN$, the solvent evaporated, the residue sonicated in 1 mL $CH_3CN$ and 2 mL water, the solution concentrated by evaporation followed by lyophilization to provide 28 mg (76%) of the title compound as an amorphous solid. $^1H$ NMR (500 MHz, DMSO-$d_6$): δ 1.31 (d, 6H1, J=6 Hz), 3.21 (s, 3H), 3.23 (d, 2H, J=22 Hz), 4.78 (septet, 1H, J=6 Hz), 6.97 (t, 1H, J=2 Hz), 7.25 (d, 2H, J=8 Hz), 7.36 (t, 1H, J=2 Hz), 7.52 (t, 1H, J=2 Hz), 7.95 (d, 2H, J=8 Hz), 8.39 (t, 1H, J=2 Hz), 9.25 (d, 1H, J=1 Hz), 11.13 (s, 1H); LCMS (m/z): 522.4 $[C_{22}H_{24}N_3O_8PS+H]^+$. Anal. calcd. for ($C_{22}H_{24}N_3O_8PS+2HBr+3H_2O$): C, 35.84; H, 4.37; N, 5.70. Found: C, 35.59; H, 4.19: N, 5.41.

Intermediates for the preparation of Example 16 were prepared according to Route 6, as described below.

Route 6

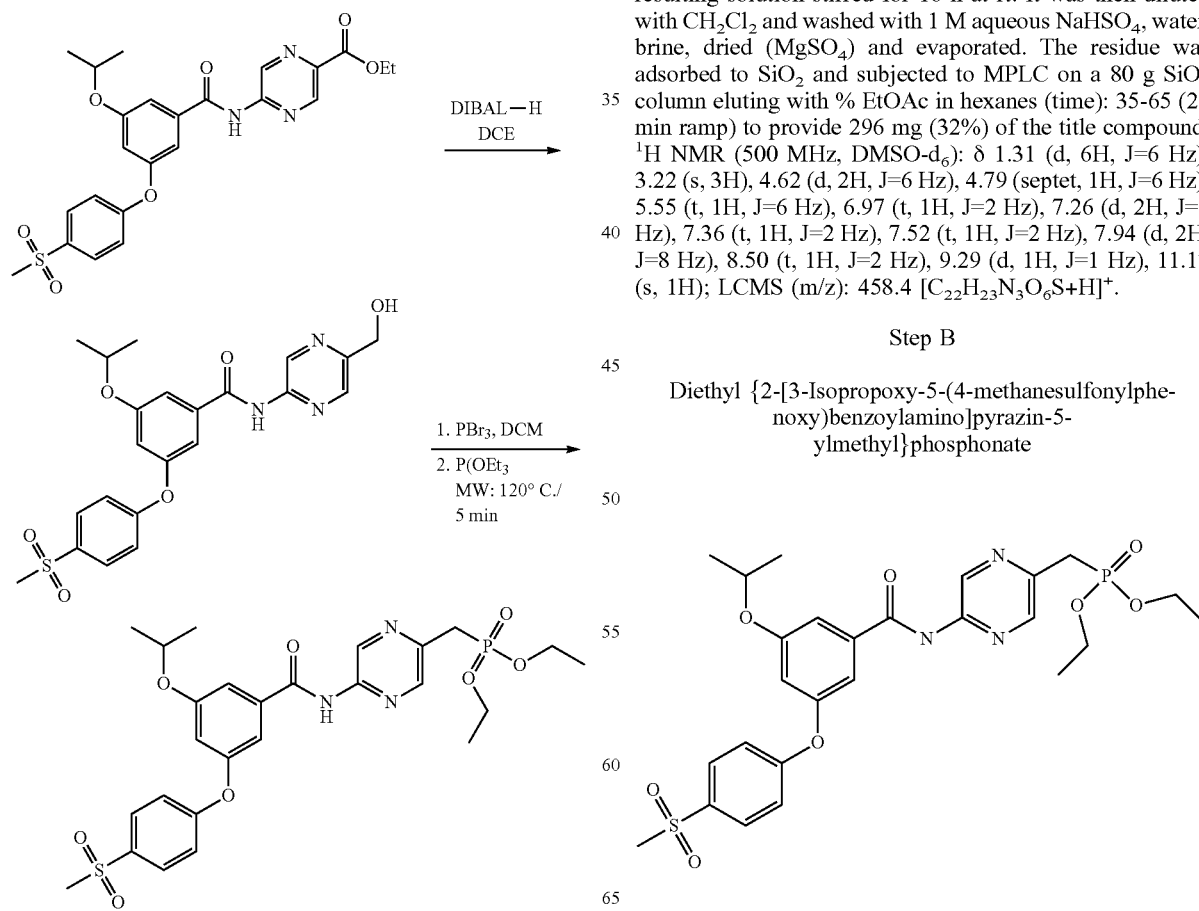

Step A

N-(5-Hydroxymethyl-pyrazin-2-yl)-3-isopropoxy-5-(4-methanesulfonylphenoxy)-benzamide

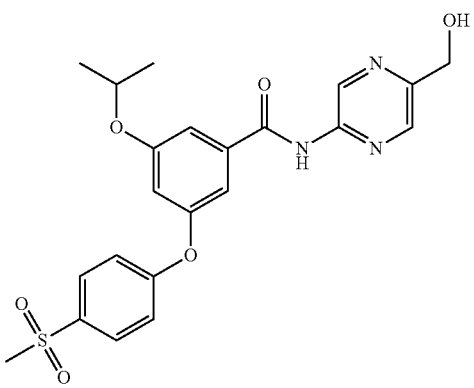 [SMILES: CC(C)Oc1cc(Oc2ccc(S(C)(=O)=O)cc2)cc(C(=O)Nc2cnc(CO)cn2)c1]

To a solution of ethyl 5-[3-isopropoxy-5-(4-methanesulfonyl-1-phenoxy)-benzoylamino]-pyrazine-2-carboxylic acid ethyl ester (1.00 g, 2 mmol, prepared in a similar manner to Example 6 from the appropriate intermediates with modifications evident to an individual skilled in the art) in 20 mL of dichloroethane at 0° C. was added 8 mL of a 1 M solution of diisobutylaluminum hydride in hexane and the resulting solution stirred for 16 h at rt. It was then diluted with $CH_2Cl_2$ and washed with 1 M aqueous $NaHSO_4$, water, brine, dried ($MgSO_4$) and evaporated. The residue was adsorbed to $SiO_2$ and subjected to MPLC on a 80 g $SiO_2$ column eluting with % EtOAc in hexanes (time): 35-65 (25 min ramp) to provide 296 mg (32%) of the title compound. $^1H$ NMR (500 MHz, DMSO-$d_6$): δ 1.31 (d, 6H, J=6 Hz), 3.22 (s, 3H), 4.62 (d, 2H, J=6 Hz), 4.79 (septet, 1H, J=6 Hz), 5.55 (t, 1H, J=6 Hz), 6.97 (t, 1H, J=2 Hz), 7.26 (d, 2H, J=8 Hz), 7.36 (t, 1H, J=2 Hz), 7.52 (t, 1H, J=2 Hz), 7.94 (d, 2H, J=8 Hz), 8.50 (t, 1H, J=2 Hz), 9.29 (d, 1H, J=1 Hz), 11.17 (s, 1H); LCMS (m/z): 458.4 $[C_{22}H_{23}N_3O_6S+H]^+$.

Step B

Diethyl {2-[3-Isopropoxy-5-(4-methanesulfonylphenoxy)benzoylamino]pyrazin-5-ylmethyl}phosphonate

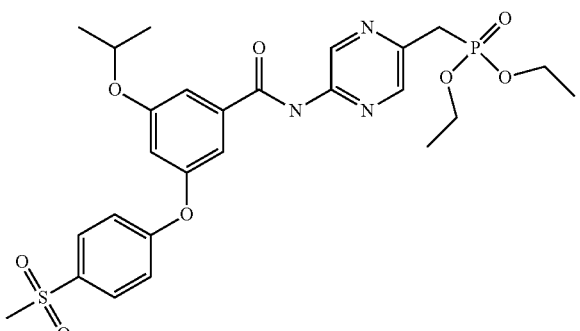

To a solution of N-(5-hydroxymethyl-pyrazin-2-yl)-3-isopropoxy-5-(4-methanesulfonyl-phenoxy)-benzamide (130 mg, 0.28 mmol) in 2.8 mL of dichloroethane was added 0.56 mL of a 1 M solution of $PBr_3$ in $CH_2Cl_2$ and the solution stirred for 4 h at rt. Then triethylphosphite (0.5 mL, 2.8 mmol) was added and the resulting solution microwave heated at 120° C. for 5 min. Then the mixture was diluted with $CH_2Cl_2$ and washed with aqueous $NaHCO_3$, brine, dried ($MgSO_4$) and evaporated. The residue was adsorbed to $SiO_2$ and subjected to MPLC on a 12 g $SiO_2$ column eluting with % EtOAc in hexanes (time): 65-95 (30 min ramp) to provide 33 mg (20%) of the title compound. $^1$H NMR (500 MHz, DMSO-$d_6$): δ 1.19 (t, 6H, J=6 Hz), 1.30 (d, 6H, J=6 Hz), 3.22 (s, 3H), 3.50 (d, 2H, J=21 Hz), 4.02 (m, 4H), 4.78 (septet, 1H, J=6 Hz), 6.97 (t, 1H, J=2 Hz), 7.25 (d, 2H, J=8 Hz), 7.35 (t, 1H, J=2 Hz), 7.51 (t, 1H, J=2 Hz), 7.95 (d, 2H, J=8 Hz), 8.41 (dd, 1H, J=1, 2 Hz), 9.29 (d, 1H, J=1 Hz), 11.17 (s, 1H); LCMS (m/z): 578.6 $[C_{26}H_{32}N_3O_8PS+H]^+$.

Example 17

{4-[3-(1-Methyl-1H-imidazol-2-ylsulfanyl)-5-(thiazol-2-ylcarbamoyl)-phenoxy]-phenyl}-phosphonic acid hydrobromide salt

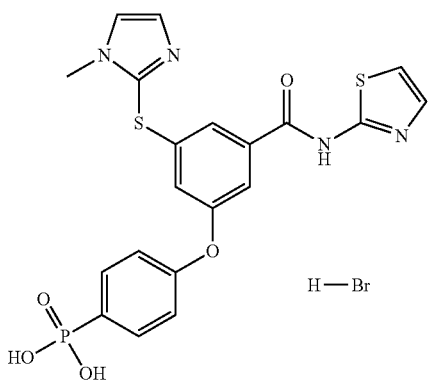 [SMILES: Cn1ccnc1Sc1cc(Oc2ccc(P(=O)(O)O)cc2)cc(C(=O)Nc2nccs2)c1 ; Br]

In a manner similar to Example 1, a mixture of {4-[3-(1-methyl-1H-imidazol-2-ylsulfanyl)-5-(thiazol-2-ylcarbamoyl)-phenoxy]-phenyl}-phosphonic acid diisopropyl ester (58 mg, 0.10 mmol) and bromotrimethylsilane (0.27 mL, 2.03 mmol) in 2 mL $CH_2Cl_2$ was stirred for 16 h at rt. The solvent evaporated, the residue dissolved in $CH_3CN$ and then the solvent evaporated, and the residue sonicated in a mixture of 1 mL $CH_3CN$ and 0.1 mL water. The resulting white solid was collected by filtration and dried under high vacuum to provide 30 mg (61%) of the title compound. $^1$H NMR (500 MHz, DMSO-$d_6$): δ 3.84 (s, 3H), 7.14 (dd, 2H, J=8, 3 Hz), 7.30 (d, 1H, J=4 Hz), 7.38 (br s, 1H), 7.55 (d, 1H, J=4 Hz), 7.72 (d, 1H, J=1 Hz), 7.72 (dd, 2H, J=12, 8 Hz), 7.76 (br s, 1H), 7.80 (t, 1H, J=2 Hz), 7.88 (d, 1H, J=1 Hz); LCMS (m/z): 489.5 $[C_{20}H_{17}N_4O_5PS_2+H]^+$. Anal. calcd. for ($C_{20}H_{17}N_4O_5PS_2$+1.5 HBr+1.5$H_2O$): C, 37.72; H, 3.40; N, 8.80. Found: C, 37.94; H, 3.44; N, 8.58.

Intermediates for the preparation of Example 17 were prepared according to Route 7, as described below.

Route 7

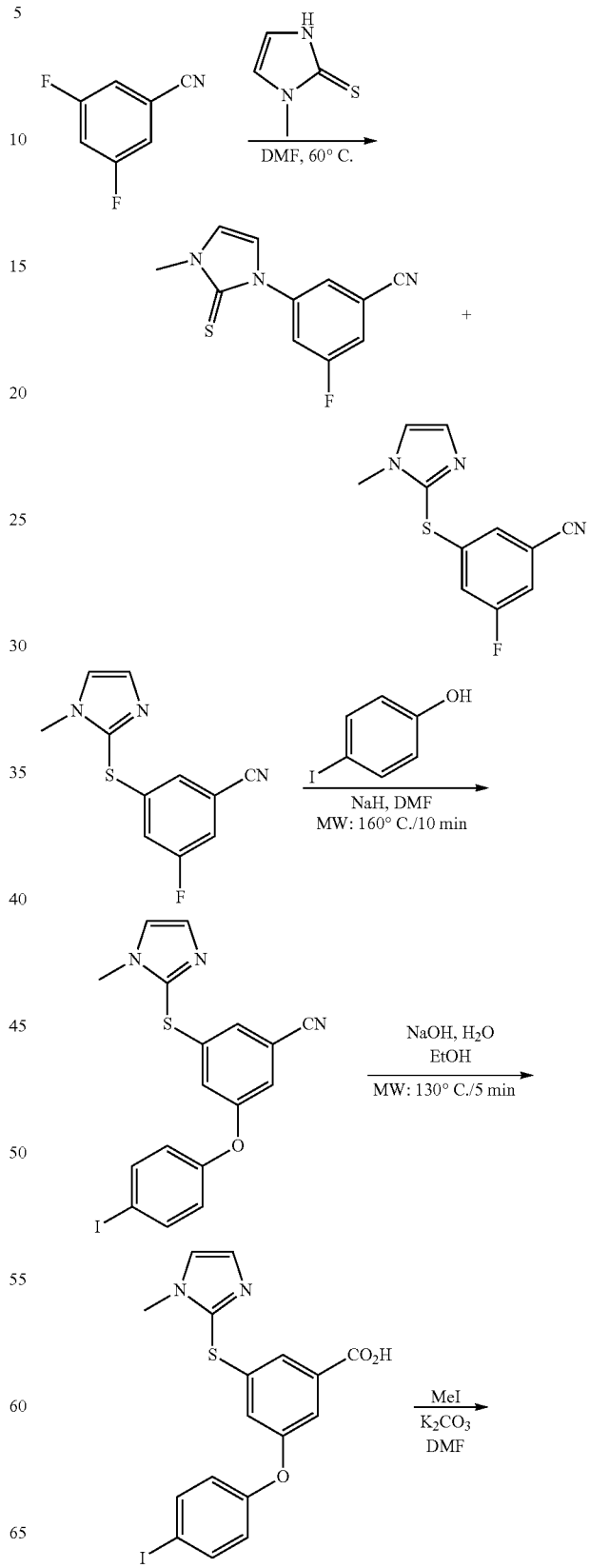

133
-continued

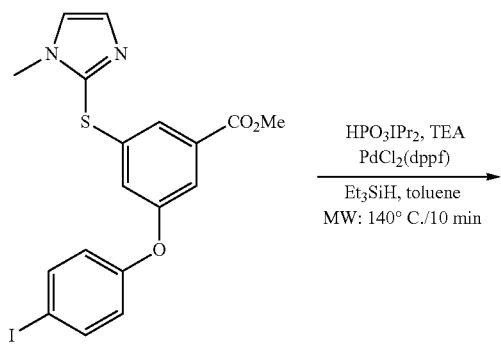

HPO₃IPr₂, TEA
PdCl₂(dppf)
───────────────
Et₃SiH, toluene
MW: 140° C./10 min

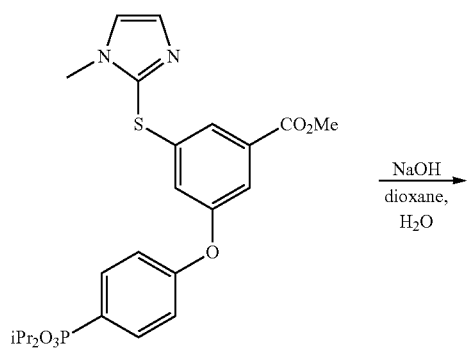

NaOH
─────
dioxane,
H₂O

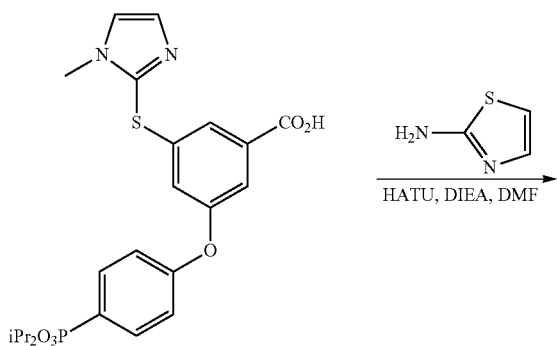

HATU, DIEA, DMF

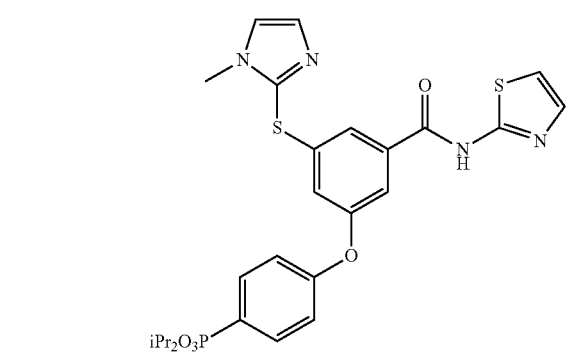

134

Step A

3-Fluoro-5-(1-methyl-1H-imidazol-2-ylsulfanyl)-benzonitrile

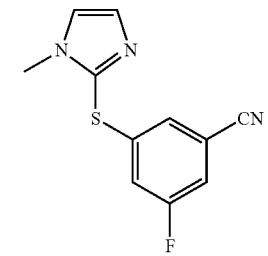 [SMILES: Cn1ccnc1Sc1cc(F)cc(C#N)c1]

A mixture of NaH (60%, 3.16 g, 79 mmol) in oil was rinsed with dry pentane by syringe (3×10 mL) and excess solvent removed under a steam of N₂. Solid 2-mercapto-1-methylimidazole (9.03 g, 79 mmol) was added followed by 200 mL of DMF under ice-bath cooling which resulted in a vigorous evolution of gas. After 15 min, solid 3,5-difluorobenzonitrile (10.00 g, 71.9 mmol) was added and the resulting mixture stirred for 5 days at 60° C. After cooling to rt the mixture was diluted with 500 mL ether and 500 mL water. The resulting white solid was collected by filtration and triturated in 50 mL of boiling ethanol which after cooling to rt was collected by filtration and dried under high vacuum to provide 1.54 g (9%) of 3-fluoro-5-(1-methyl-1H-imidazol-2-ylsulfanyl)-benzonitrile: $^1$H NMR (500 MHz, DMSO-$d_6$): δ 3.54 (s, 3H), 7.40 (d, 1H, J=2 Hz), 7.52 (d, 1H, J=2 Hz), 7.96 (dt, 1H, J=8, 2 Hz), 8.13 (m, 1H), 8.15 (dt, 1H, J=8, 2 Hz); LCMS (m/z): 234.1 $[C_{11}H_8FN_3S+H]^+$. The ether layer was separated from the filtrate and washed with water, brine, dried (MgSO₄) and evaporated. The residue was recrystallized from 30 mL of boiling ethanol to provided after filtration and drying a further 1.57 g (9%) which by HPLC was 75% enriched in 3-fluoro-5-(1-methyl-1H-imidazol-2-ylsulfanyl)-benzonitrile. The filtrate was evaporated to provide 5 g of crude product enriched in the title compound. This was adsorbed to 15 g of SiO₂ from CH₂Cl₂ and subjected to MPLC on a 120 g column of SiO₂ eluting with % EtOAc in hexanes (time): 35% (10 min), 35-50% (5 min ramp), 50% (20 min) which provided 1.2 g (7%) of 90% HPLC pure title compound as well as 1.96 g (12%) of 98% HPLC pure title compound: $^1$H NMR (500 MHz, DMSO-$d_6$): δ 3.66 (s, 3H), 7.20 (d, 1H, J=1 Hz), 7.22 (ddd, 1H, J=8, 3, 2 Hz), 7.34 (t, 1H, J=2 Hz), 7.55 (d, 1H, J=1 Hz), 7.72 (ddd, 1H, J=8, 3, 2 Hz); LCMS (m/z): 234.1 $[C_{11}H_8FN_3S+H]^+$.

Step B 3-(4-Iodo-phenoxy)-5-(1-methyl-1H-imidazol-2-ylsulfanyl)-benzonitrile

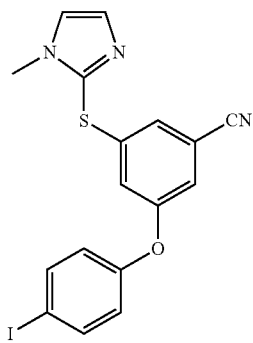 [SMILES: Cn1ccnc1Sc1cc(C#N)cc(Oc2ccc(I)cc2)c1]

A mixture of NaH (60%, 312 mg, 7.8 mmol) in oil was rinsed with dry pentane by syringe (3×3 mL) and excess solvent removed under a steam of N₂. Solid 4-iodophenol (1.72 g, 7.8 mmol) was added followed by 16 mL of DMF under ice-bath cooling which resulted in a vigorous evolution of gas. After 15 min, solid 3-fluoro-5-(1-methyl-1H-imidazol-2-ylsulfanyl)-benzonitrile (910 mg, 3.9 mmol) was added and the resulting mixture microwave heated at 160° C. for 10 min. After cooling to rt, the mixture was diluted with ether and 3 M aqueous NaOH and shaken. The organic layer was washed with water, brine, dried (MgSO₄) and evaporated. The resulting 1.8 g of residue was adsorbed to 4.5 g SiO₂ from CH₂Cl₂ and subjected to MPLC on a 40 g column of SiO₂ eluting with % EtOAc in hexanes (time): 33% (10 min), 35-50% (20 min ramp) which provided 1.60 g (95%) of the title compound: $^1$H NMR (500 MHz, DMSO-d₆): δ 3.63 (s, 3H), 6.82 (dd, 1H, J=2, 1 Hz), 6.90 (d, 2H, J=8 Hz), 7.13 (d, 1H, J=1 Hz), 7.26 (t, 1H, J=2 Hz), 7.37 (dd, 1H, J=2, 1 Hz), 7.50 (d, 1H, J=1 Hz), 7.75 (d, 2H, J=8 Hz); LCMS (m/z): 434.3 [C₁₇H₁₂IN₃OS+H]⁺.

Step C 3-(4-Iodo-phenoxy)-5-(1-methyl-1H-imidazol-2-ylsulfanyl)-benzoic acid

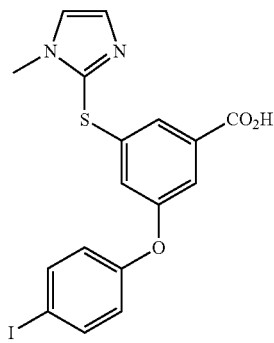 [SMILES: Cn1ccnc1Sc1cc(Oc2ccc(I)cc2)cc(C(=O)O)c1]

A mixture of 3-(4-iodo-phenoxy)-5-(1-methyl-1H-imidazol-2-ylsulfanyl)-benzonitrile (1.60 g, 3.69 mmol), 12 mL of ethanol, 1.2 mL of water and 1 mL of 50% w/w NaOH in water (18.45 mmol) was microwave heated at 130° C. for 5 min and then cooled to rt. The mixture was concentrated by evaporation and diluted with 20 mL of water, then with stirring, 20 mL of 1 M aqueous NaHSO₄ was added. The resulting solid was collected by filtration and dried at 0.1 mm/23° C. for 16 h to provide 1.5 g (90%) of the title compound as a white solid: $^1$H NMR (500 MHz, DMSO-d₆): δ 3.63 (s, 3H), 6.91 (d, 2H, J=8 Hz), 6.94 (t, 1H, J=2 Hz), 7.14 (d, 1H, J=1 Hz), 7.21 (dd, 1H, J=2, 1 Hz), 7.28 (dd, 1H, J=2, 1 Hz), 7.51 (d, 1H, J=1 Hz), 7.75 (d, 2H, J=8 Hz); LCMS (m/z): 453.5 [C₁₇H₁₃IN₂O₃S+H]⁺, Step D 3-(4-Iodo-phenoxy)-5-(1-methyl-1H-imidazol-2-ylsulfanyl)-benzoic acid methyl ester

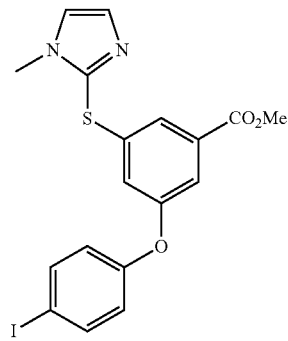 [SMILES: COC(=O)c1cc(Oc2ccc(I)cc2)cc(Sc2nccn2C)c1]

A mixture of 3-(4-iodo-phenoxy)-5-(1-methyl-1H-imidazol-2-ylsulfanyl)-benzoic acid (1.4 g, 3.1 mmol), K₂CO₃ (856 mg, 6.2 mmol), iodomethane (0.29 mL, 4.65 mmol) and 16 mL of DMF were stirred for 2 h at rt. Then the mixture was diluted with ether and washed with water, brine, dried (MgSO₄) and evaporated. The residue was adsorbed to SiO₂ from CH₂Cl₂ and subjected to MPLC on a 40 g column of SiO₂ eluting with % EtOAc in hexanes (time): 33% (10 min), 35-50% (20 min ramp) which provided 1.32 g (91%) of the title compound: $^1$H NMR (500 MHz, DMSO-d₆): δ 3.63 (s, 3H), 3.79 (s, 3H), 6.91 (d, 2H, J=8 Hz), 6.96 (dd, 1H, J=2, 1 Hz), 7.14 (d, 1H, J=1 Hz), 7.23 (dd, 1H, J=2, 1 Hz), 7.32 (t, 1H, J=1 Hz), 7.51 (d, 1H, J=1 Hz), 7.75 (d, 2H, J=8 Hz); LCMS (m/z): 467.4 [C₁₈H₁₅N₂O₃S+H]⁺.

Step E

3-[4-(Diisopropoxy-phosphoryl)-phenoxy]-5-(1-methyl-1H-imidazol-2-ylsulfanyl)-benzoic acid methyl ester

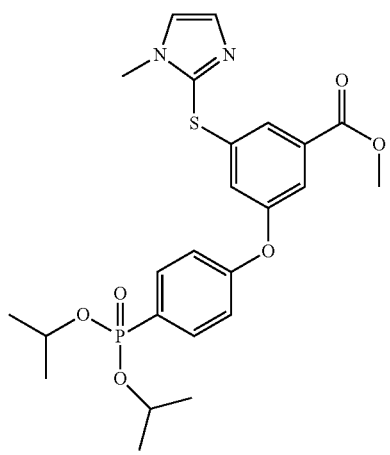 [SMILES: COC(=O)c1cc(Oc2ccc(P(=O)(OC(C)C)OC(C)C)cc2)cc(Sc2nccn2C)c1]

Conducted as described for STEP D, Example 15 only substituting diisopropyl phosphite for isopropyl methylphosphinate. From 3-(4-iodo-phenoxy)-5-(1-methyl-1H-imidazol-2-ylsulfanyl)-benzoic acid methyl ester (650 mg, 1.39 mmol), 292 mg (42%) of the title compound was isolated: $^1$H NMR (500 MHz, DMSO-d$_6$): δ 1.19 (d, 6H, J=6 Hz), 1.28 (d, 6H, J=6 Hz), 3.64 (s, 3H), 3.80 (s, 3H), 4.56 (m, 2H), 7.05 (t, 1H, J=2 Hz), 7.13 (d, 1H, J=1 Hz), 7.15 (dd, 2H, J=8, 3 Hz), 7.33 (dd, 1H, J=2, 1 Hz), 7.38 (t, 1H, J=1 Hz), 7.50 (d, 1H, J=1 Hz), 7.73 (dd, 2H, J=12, 8 Hz); LCMS (m/z): 505.7 [C$_{24}$H$_{29}$N$_2$O$_6$PS+H]$^+$.

Step F

3-[4-(Diisopropoxy-phosphoryl)-phenoxy]-5-(1-methyl-1H-imidazol-2-ylsulfanyl)-benzoic acid

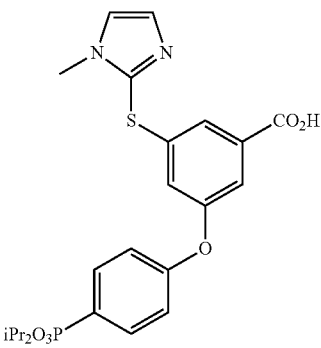

A mixture of 3-[4-(diisopropoxy-phosphoryl)-phenoxy]-5-(1-methyl-1H-imidazol-2-ylsulfanyl)-benzoic acid methyl ester (292 mg, 0.58 mmol), 3 mL of dioxane, 3 mL of water and 1.2 mL of 1 M aqueous NaOH was stirred for 2 h at rt, diluted with water, washed with EtOAc, the aqueous layer pH lowered to 4 with 1 M NaHSO$_4$, the aqueous layer extracted with 4:1 CH$_2$Cl$_2$/MeOH. The organic extract dried (MgSO$_4$) and evaporated to provide 234 mg (82%) of the title compound: $^1$H NMR (500 MHz, DMSO-d$_6$): δ 1.18 (d, 6H, J=6 Hz), 1.28 (d, 6H, J=6 Hz), 3.64 (s, 3H), 4.55 (m, 2H), 7.03 (t, 1H, J=2 Hz), 7.13 (s, 1H), 7.15 (dd, 2H, J=8, 3 Hz), 7.31 (dd, 1H, J=2, 1 Hz), 7.35 (t, 1H, J=1 Hz), 7.50 (s, 1H), 7.72 (dd, 2H, J=12, 8 Hz); LCMS (m/z): 491.9 [C$_{23}$H$_{27}$N$_2$O$_6$PS+H]$^+$.

Step G

{4-[3-(1-Methyl-1H-imidazol-2-ylsulfanyl)-5-(thiazol-2-ylcarbamoyl)-phenoxy]-phenyl}-phosphonic acid diisopropyl ester

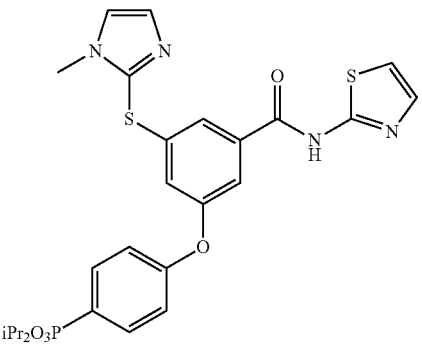

A mixture of diisopropyl 3-[4-(diisopropoxy-phosphoryl)-phenoxy]-5-(1-methyl-1H-imidazol-2-ylsulfanyl)-benzoic acid (68 mg, 0.139 mmol), 2-aminothiazole (28 mg, 0.277 mmol), HATU (66 mg, 0.174 mmol), DIEA (0.058 mL, 0.35 mmol) and 0.7 mL of DMF were stirred for 16 h ant rt, diluted with CH$_2$Cl$_2$, washed with water, brine, dried and evaporated. The residue was adsorbed to SiO$_2$ and subjected to MPLC on a 12 g column of SiO$_2$ eluting with % MeOH in CH$_2$Cl$_2$ (time): 1% (5 min), 2.5% (10 min), 5% (10 min) which provided 50 mg (63%) of the title compound: $^1$H NMR (500 MHz, DMSO-d$_6$): δ 1.20 (d, 6H, J=6 Hz), 1.28 (d, 6H, J=6 Hz), 3.66 (s, 3H), 4.56 (m, 2H), 6.95 (t, 1H, J=2 Hz), 7.13 (d, 1H, J=1 Hz), 7.15 (dd, 2H, J=8, 3 Hz), 7.30 (br s, 1H), 7.50 (d, 1H, J=1 Hz), 7.55 (d, 1H, J=3 Hz), 7.60 (br s, 1H), 7.67 (br s, 1H), 7.73 (dd, 2H, J=12, 8 Hz); LCMS (m/z): 573.7 [C$_{26}$H$_{29}$N$_4$O$_5$PS$_2$+H]$^+$.

Example 18

{4-[3-(5-Chloro-thiazol-2-ylcarbamoyl)-5-(1-methyl-1H-imidazol-2-ylsulfanyl)-phenoxy]-phenyl}-phosphonic acid hydrobromide salt

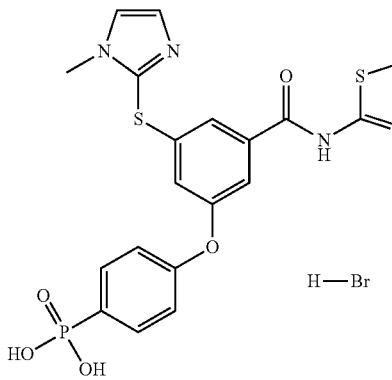

Prepared as described in Example 17, Route 6, with modifications evident to an individual skilled in the art. $^1$H NMR (500 MHz, DMSO-d$_6$): δ 3.78 (s, 3H), 7.14 (dd, 2H, J=8, 3 Hz), 7.25 (br s, 1H), 7.57 (br s, 1H), 7.62 (s, 1H), 7.68 (t, 1H, J=1 Hz), 7.72 (br s, 1H), 7.72 (dd, 2H, J=12, 8 Hz), 7.76 (br s, 1H); LCMS (m/z): 489.5 [C$_{20}$H$_{16}$ClN$_4$O$_5$PS$_2$+H]$^+$. Anal. calcd. for (C$_{20}$H$_{16}$ClN$_4$O$_5$PS$_2$+1 HBr+0.6H$_2$O): C, 39.08; H, 2.98; N, 9.12. Found: C, 39.08; H, 3.16; N, 9.12.

Example 19

{4-[3-(1-Methyl-1H-imidazol-2-ylsulfanyl)-5-(thiazol-2-ylcarbamoyl)-phenoxy]-phenyl}-phosphinic acid bis-sodium salt

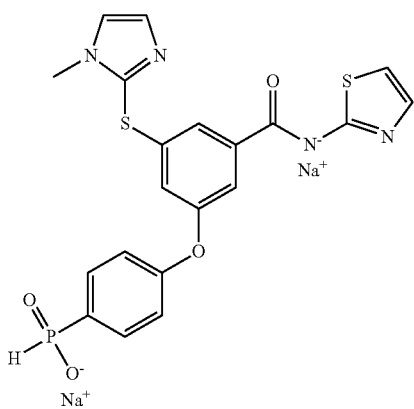 [SMILES: Cn1ccnc1Sc1cc(Oc2ccc([PH](=O)[O-])cc2)cc(C(=O)[N-]c2nccs2)c1 ; [Na+] ; [Na+]]

A mixture of 3-(4-iodo-phenoxy)-5-(1-methyl-1H-imidazol-2-ylsulfanyl)-N-thiazol-2-yl-benzamide (140 mg, 0.26 mmol), anilinium hypophosphite (83 mg, 0.52 mmol), [1,1'-bis(diphenylphosphino)ferrocene]palladium (II) dichloride (10 mg, 0.013 mmol) and 2.6 mL of CH$_3$CN was degassed by bubbling N$_2$ through it for 2 min, then triethylamine (0.11 mL, 0.78 mmol) was added and the mixture microwave heated at 140° C. for 10 min. The mixture was diluted with water and concentrated to a suspension by evaporation. Aqueous 3 M NaOH was added until the solution was pH 12. Then 1 M aqueous NaHSO$_4$ was added until the solution was pH 3 and the resulting tan solid collected. The solid was dissolved in water with the addition of 3 M NaOH and subjected to MPLC on a 25 g C18 reverse phase SiO$_2$ column. Elution with % CH$_3$CN in water (time): 5% (5 min), 5-75% (15 min ramp) provided 11 mg (7%) of the title compound: $^1$H NMR (500 MHz, DMSO-d$_6$): δ 3.65 (s, 3H), 6.79 (t, 1H, J=2 Hz), 6.99 (dd, 2H, J=8, 2 Hz), 7.13 (d, 2H, J=1 Hz), 7.25 (br s, 1H), 7.39 (d, 1H, J=467 Hz), 7.50 (d, 1H, J=1 Hz), 7.52-7.54 (m, 3H), 7.56 (dd, 2H, J=11, 8 H1); LCMS (m/z): 473.6 [C$_{20}$H$_{17}$N$_4$O$_4$PS$_2$+H]$^+$. Anal. calcd. for (C$_{20}$H$_{15}$N$_4$Na$_2$O$_4$PS$_2$+2H$_2$O): C, 43.48; H, 3.47; N, 10.14. Found: C, 43.85; H, 3.47; N, 9.97.

The intermediate for the preparation of Example 19 were prepared according to the following procedure.

Step A 4-(3-(1-Methylimidazol-2-ylthio)-5-(triazol-2-ylcarbamoyl)phenoxy)phenyliodine

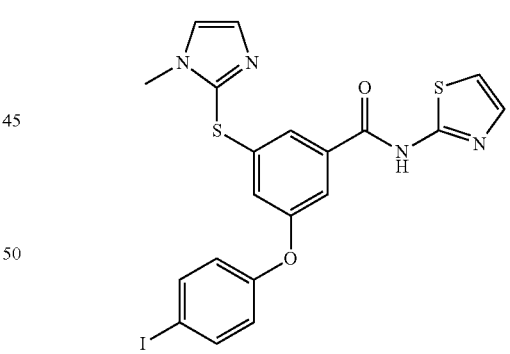

The title compound was prepared from 3-(4-Iodo-phenoxy)-5-(1-methyl-1H-imidazol-2-ylsulfanyl)-benzoic acid (Example 17, STEP C) according to the method described in Example 17, STEP G. $^1$H NMR (300 MHz, DMSO-d$_6$): δ 3.65 (s, 3H), 6.85 (t, 1H, J=2 Hz), 6.92 (d, 2H, J=8 Hz), 7.14 (d, 1H, J=1 Hz), 7.29 (d, 1H, J=3 Hz), 7.51 (m, 1H), 7.51 (d, 1H, J=1 Hz), 7.53 (m, 1H), 7.54 (d, 1H, J=3 Hz), 7.74 (d, 2H, J=8 Hz), 12.75 (s, 1H); LCMS (m/z): 535.4 [C$_{20}$H$_{15}$N$_4$O$_2$S$_2$+H]$^+$.

Example 20

{4-[3-(5-Chloro-thiazol-2-ylcarbamoyl)-5-(1-methyl-1H-imidazol-2-ylsulfanyl)-phenoxy]-phenyl}-phosphinic acid bis-sodium salt

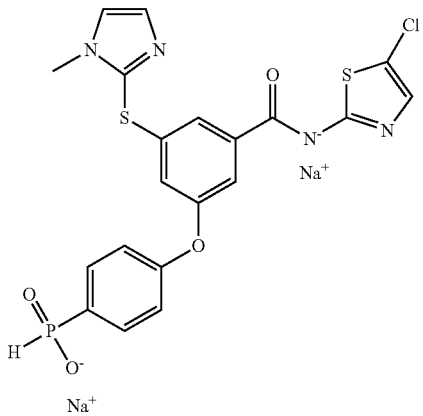 [SMILES: Cn1ccnc1Sc1cc(Oc2ccc([PH](=O)[O-])cc2)cc(C(=O)[N-]c2ncc(Cl)s2)c1 ; [Na+] ; [Na+]]

Prepared according to the method described in Example 19 with modifications evident to an individual skilled in the art. $^1$H NMR (500 MHz, DMSO-$d_6$): δ 3.63 (s, 3H), 6.64 (t, 1H, J=2 Hz), 6.96 (dd, 2H, J=8, 2 Hz), 7.09 (s, 1H), 7.11 (d, 2H, J=1 Hz), 7.39 (d, 1H, J=469 Hz), 7.44 (dd, 1H, J=2, 1 Hz), 7.47 (d, 1H, J=1 Hz), 7.56 (dd, 2H, J=11, 8 Hz), 7.58 (t, 1H, J=2 Hz); LCMS (m/z): 507.7 [$C_{20}H_{16}ClN_4O_4PS_2H$]+. Anal. calcd. for ($C_{20}H_{14}ClN_4Na_2O_4PS_2$+5H$_2$O); C, 37.48; H, 3.77; N, 8.74. Found: C, 37.71; H, 2.99; N, 8.43.

Example 21

[({2-[3-Isopropoxy-5-(4-methanesulfonyl-phenoxy)-benzoylamino]-thiazole-4-carbonyl}-amino)-methyl]-phosphonic acid

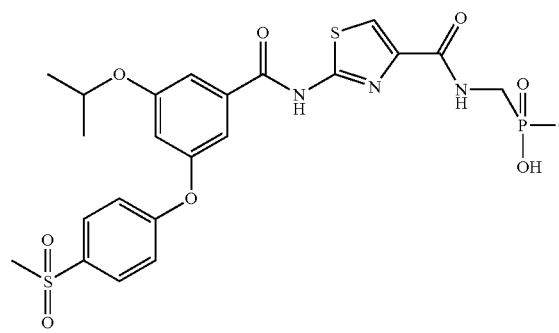

{[(2-Amino-thiazole-4-carbonyl)-amino]-methyl}-phosphonic acid diethyl ester is prepared according to Route 7, as described below.

Route 7

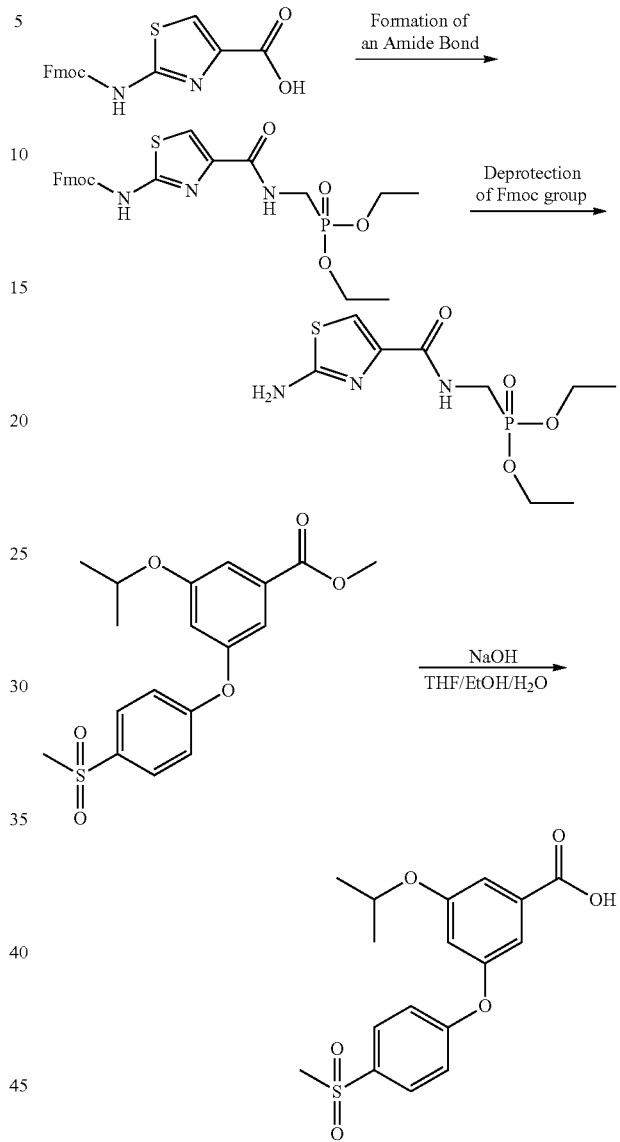

To a solution of 3-isopropoxy-5-(4-methanesulfonyl-phenoxy)-benzoic acid methyl ester (prepared as in Example 6 Step A) (6.50 g, 17.8 mmol) in THF (120 mL) was added EtOH (80 mL) and water (40 mL) at room temperature. Sodium hydroxide solution (1.0 M, 36.0 mL) was added slowly with some external cooling, if needed. The mixture was stirred at room temperature overnight. On the second day organic solvents were removed by evaporation. The residue was partitioned between ether and water. After the ether layer was discarded, the aqueous layer was acidified with HCl (6.0 M, ~6.0 mL) to pH<2, and extracted with EtOAc three times. Combined EtOAc layers were washed with brine, dried with anhydrous MgSO$_4$, filtered, and concentrated to give 3-isopropoxy-5-(4-methanesulfonyl-phenoxy)-benzoic acid (6.40 g, 100%) as a white solid. $^1$H NMR (300 MHz, CDCl$_3$): δ 9.91 (s, 1H), 7.93 (d, J=9 Hz, 2H), 7.23 (m, 1H), 7.14 (d, J=9 Hz, 2H), 7.10 (m, 1H), 6.85 (m, 1H), 4.57-4.65 (m, 1H), 3.01 (s, 3H), 1.37 (d, J=6 Hz, 6H).

The above prepared 3-isopropoxy-5-(4-methanesulfonyl-phenoxy)-benzoic acid is coupled with {[(2-amino-thiazole-4-carbonyl)-amino]-methyl}-phosphonic acid diethyl ester following the procedure described in Example 1, Step D to give [({2-[3-isopropoxy-5-(4-methanesulfonyl-phenoxy)-benzoylamino]-thiazole-4-carbonyl}-amino)-methyl]-phosphonic acid diethyl ester.

The above [({2-[3-isopropoxy-5-(4-methanesulfonyl-phenoxy)-benzoylamino]-thiazole-4-carbonyl}-amino)-methyl]-phosphonic acid diethyl ester is converted to the title compound following the procedure described in Example 2.

Example 22

[({2-[3-Isopropoxy-5-(4-methanesulfonyl-phenoxy)-benzoylamino]-4-methyl-thiazole-5-carbonyl}-amino)-methyl]-phosphonic acid

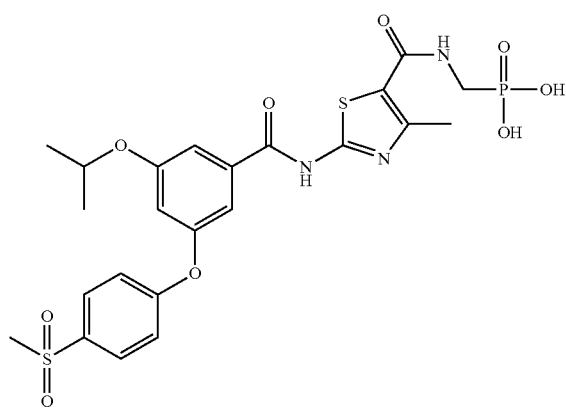 [SMILES: Cc1nc(NC(=O)c2cc(Oc3ccc(S(C)(=O)=O)cc3)cc(OC(C)C)c2)sc1C(=O)NCP(=O)(O)O]

{[(2-Amino-4-methyl-thiazole-5-carbonyl)-amino]-methyl}-phosphonic acid diethyl ester is prepared according to Route 8, as described below.

Route 8

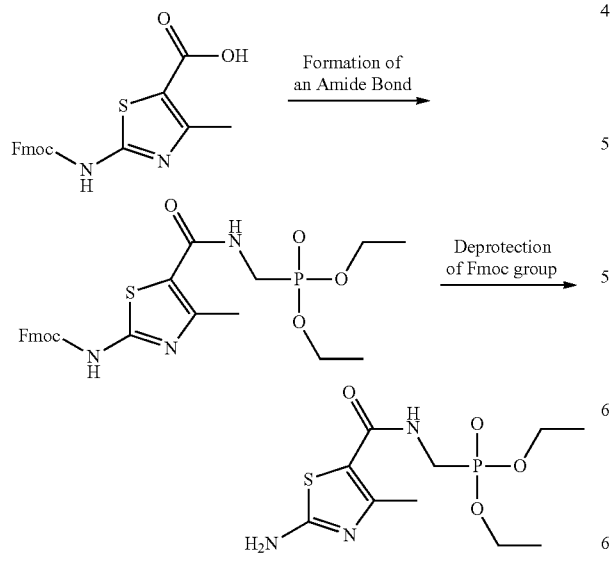

The title compound is prepared from {[(2-amino-4-methyl-thiazole-5-carbonyl)-amino]-methyl}-phosphonic acid diethyl ester and 3-isopropoxy-5-(4-methanesulfonyl-phenoxy)-benzoic acid in a similar manner to Example 21.

Example 23

{4-[3-Isopropoxy-5-(thiazol-2-ylcarbamoyl)-benzyl]-phenyl}-phosphonic acid

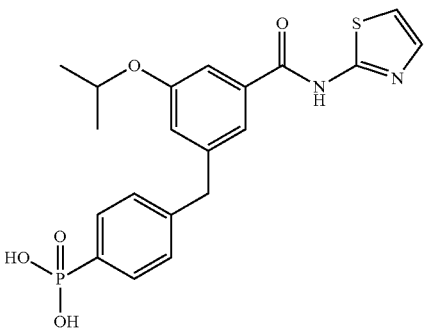 [SMILES: CC(C)Oc1cc(Cc2ccc(P(=O)(O)O)cc2)cc(C(=O)Nc2nccs2)c1]

The title compound was prepared from {4-[3-isopropoxy-5-(thiazol-2-ylcarbamoyl)-benzyl]-phenyl}-phosphonic acid diisopropyl ester according to the method described in Example 3. $^1$H NMR (300 MHz, DMSO-$d_6$): δ 7.62 (dd, J=8, 13 Hz, 2H), 7.56 (d, J=4 Hz, 1H), 7.54 (m, 1H), 7.50 (m, 1H), 7.37 (dd, J=3, 8 Hz, 2H), 7.27 (d, J=4 Hz, 1H), 7.02 (m, 1H), 4.68-4.76 (m, 1H), 4.00 (s, 2H), 1.28 (d, J=6 Hz, 6H); LC-MS (m/z): 433.6 [C20H21N2O5PS+H]$^+$. Anal. Calcd. for (C20H21N2O5PS): C, 55.55; H, 4.89; N, 6.48. Found: C, 55.49; H, 4.82; N, 6.38.

Intermediates for the preparation of Example 23 were prepared according to Route 10, as described below, and Route 3, with modifications evident to an individual skilled in the art.

Route 10

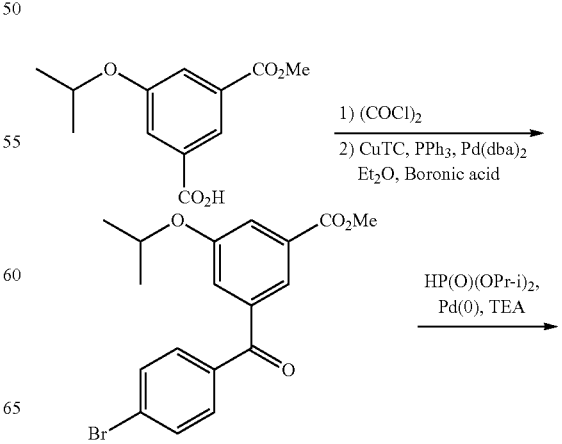

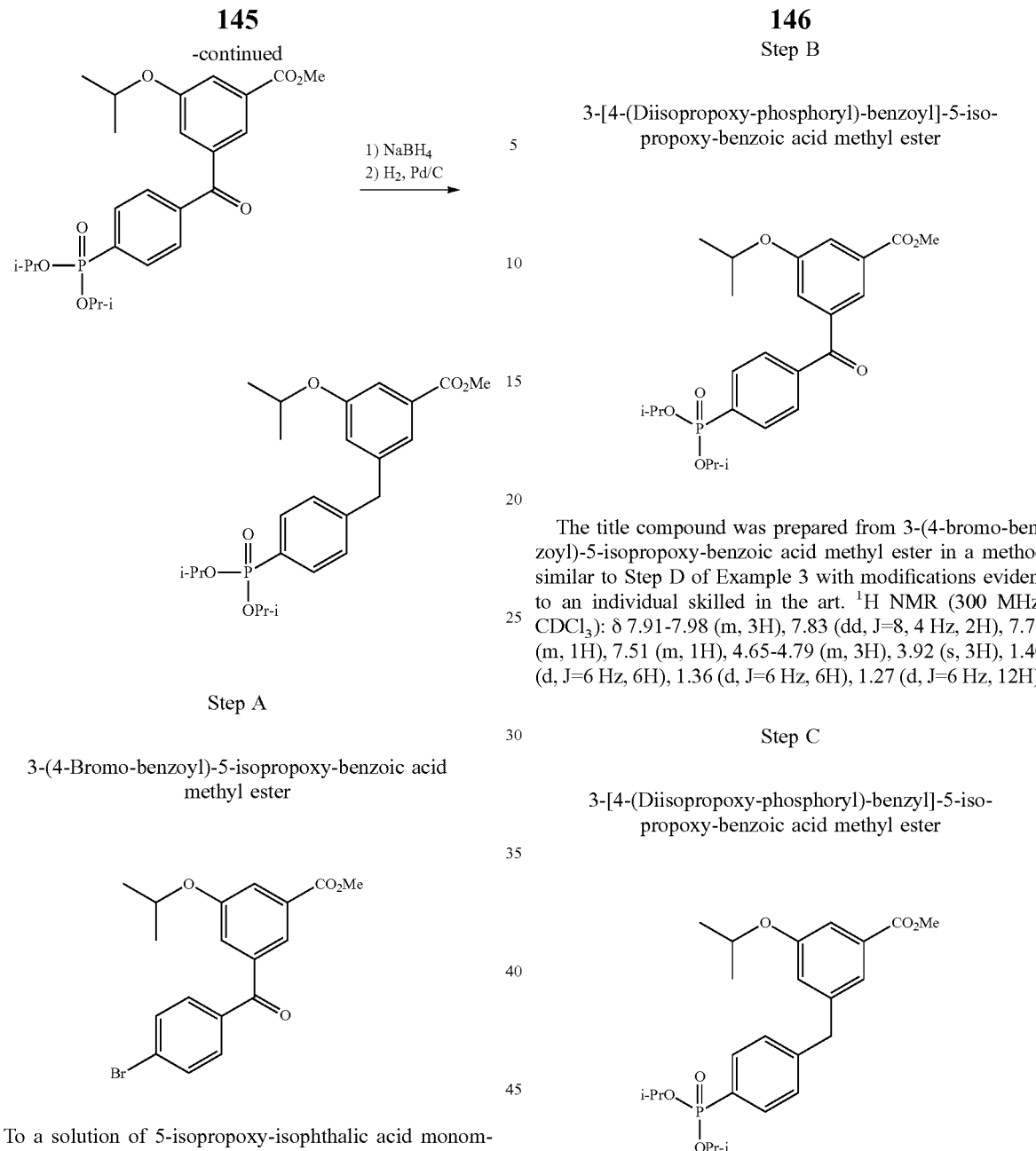

Step A 3-(4-Bromo-benzoyl)-5-isopropoxy-benzoic acid methyl ester

To a solution of 5-isopropoxy-isophthalic acid monomethyl ester (1.90 g, 7.98 mmol) in DCM (50 mL) was added (COCl)₂ (1.39 mL, 16.9 mmol) and DMF (0.03 mL, 0.400 mmol) at rt. After stirring at rt for 2 hr, the mixture was concentrated. The resulting residue was azeotroped with 50 mL anhydrous toluene and then re-dissolved in Et₂O (40 mL). Palladium bis(dibenzylideneacetone) (229 mg, 0.400 mmol), copper (I) thiophene-2-carboxylate (1.52 g, 7.98 mmol), triphenylphosphine (209 mg, 0.798 mmol), and 4-bromophenylboronic acid (3.20 g, 16.0 mmol) were added to the reaction flask. The resulting mixture was stirred at rt for 3 hr, filtered through a pad of Celite, rinsed with Et₂O. The combined Et₂O layers were concentrated. The residue was purified by silica gel flash chromatography (6×25 cm, hexane/EtOAc, v/v=5:1, 3:1). Fractions containing the coupling product were pooled and concentrated to give the title compound (2.60 g, 86%) as a yellow oil. ¹H NMR (300 MHz, CDCl₃): δ 7.91 (m, 1H), 7.77 (m, 1H), 7.63-7.69 (m, 3H), 7.48 (m, 1H), 7.38-7.43 (m, 1H), 4.57 (m, 1H), 3.92 (s, 3H), 1.35 (d, J=6 Hz, 6H).

Step B

3-[4-(Diisopropoxy-phosphoryl)-benzoyl]-5-isopropoxy-benzoic acid methyl ester

The title compound was prepared from 3-(4-bromo-benzoyl)-5-isopropoxy-benzoic acid methyl ester in a method similar to Step D of Example 3 with modifications evident to an individual skilled in the art. ¹H NMR (300 MHz, CDCl₃): δ 7.91-7.98 (m, 3H), 7.83 (dd, J=8, 4 Hz, 2H), 7.78 (m, 1H), 7.51 (m, 1H), 4.65-4.79 (m, 3H), 3.92 (s, 3H), 1.40 (d, J=6 Hz, 6H), 1.36 (d, J=6 Hz, 6H), 1.27 (d, J=6 Hz, 12H).

Step C

3-[4-(Diisopropoxy-phosphoryl)-benzyl]-5-isopropoxy-benzoic acid methyl ester

To a solution of 3-[4-(diisopropoxy-phosphoryl)-benzoyl]-5-isopropoxy-benzoic acid methyl ester (750 mg, 1.62 mmol) in MeOH (30 mL) was added NaBH₄ (120 mg, 3.17 mmol) at rt. Stirred at rt overnight. On the second day, the mixture was concentrated. The residue was partitioned between EtOAc/HCl (0.1 M) and the organic layer was separated, washed with brine, dried, and concentrated. The resulting residue was dissolved in a mixture of EtOAc/EtOH (20 mL, v/v=10:1) and hydrogenated over Pd/C (10%, 200 mg) using a Parr apparatus overnight. Then the mixture was filtered through a Celite plug. The filtrate was concentrated, azeotroped with CH₂Cl₂ to give the title compound (720 mg, 100%). ¹H NMR (300 MHz, CDCl₃): δ 7.72 (dd, J=13, 8 Hz, 2H), 7.45 (m, 1H), 7.40 (m, 1H), 7.25 (dd, J=8, 4 Hz, 2H), 6.87 (m, 1H), 4.62-4.70 (m, 2H), 4.53-4.61 (m, 1H), 3.88 (s, 3H), 1.36 (d J=6 Hz, 6H), 1.32 (d J=6 Hz, 6H), 1.22 (d, J=6 Hz, 12H).

Example 24

2,2-Dimethyl-propionic acid hydroxy-{4-[3-isopropoxy-5-(thiazol-2-ylcarbamoyl)-phenoxy]-phenyl}-phosphinoyloxymethyl ester, sodium salt

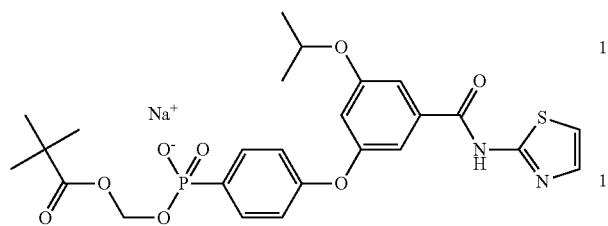

A mixture of {4-[3-isopropoxy-5-(thiazol-2-ylcarbamoyl-)phenoxy]-phenyl}-phosphonic acid (250 mg, 0.58 mmol) and 0.7 mL of saturated aqueous $NaHCO_3$ in 4 mL of DMF were stirred at rt for 15 min and then iodomethyl pivalate (0.088 mL, 0.58 mmol) was added. The mixture was stirred at rt for 3 h, then 0.46 mL of saturated aqueous $NaHCO_3$ was added. After a further 2 h, more iodomethyl pivalate (0.044 mL, 0.29 mmol) was added. After stirring at rt a further 16 h, and 0.1 mL of 5 M NaOH was added. The solvents were evaporated under high vacuum and the residue dissolved in 1:1 acetonitrile/water and subjected to MPLC purification through a 25 g C18 column eluting with % acetonitrile in water (time): 10 (5 min), 10-30 (6 min), 30 (6 min). Lyophilization of the eluent containing the desired product provided 81 mg (23%) of the title compound as an amorphous solid: $^1H$ NMR (500 MHz, DMSO-$d_6$): δ 0.91 (s, 9H), 1.29 (d, 6H, J=6 Hz), 4.73 (septet, 1H, J=6 Hz), 5.43 (d, 2H, J=13 Hz), 6.72 (t, 1H, J=2 Hz), 6.98 (dd, 2H, J=8, 2 Hz), 7.22 (t, 1H, J=2 Hz), 7.27 (d, 1H, J=3.5 Hz), 7.44 (d, 1H, J=2 Hz), 7.55 (d, 1H, J=3.5 Hz), 7.64 (dd, 2H, J=11, 8 Hz); LCMS (m/z): 549.4 $[C_{25}H_{28}N_2NaO_8PS+H]^+$. Anal. calcd. for ($C_{25}H_{28}N_2NaO_8PS+1.5H_2O$): C, 50.25; H, 5.23; N, 4.69. Found: C, 50.29; H, 5.16; N, 4.69.

Example 25

{5-[3-Isopropoxy-5-(4-methanesulfonyl-phenoxy)-benzoylamino]-pyrazin-2-ylmethyl}-methyl-phosphinic acid hydrobromide salt

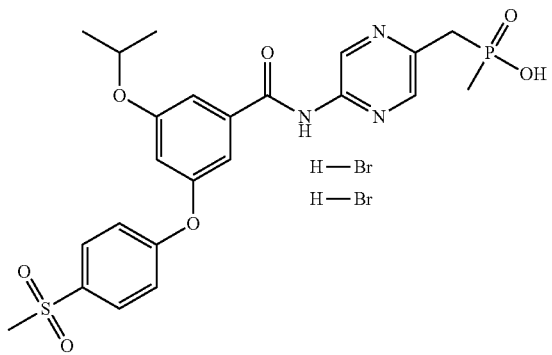

Prepared as described for Example 16 with substitution of diethyl methylphosphonite for the triethylphosphite used in Step B, Route 10. $^1H$ NMR (500 MHz, DMSO-$d_6$): δ 1.31 (d, 6H, J=6 Hz), 1.36 (d, 3H, J=15 Hz), 3.21 (s, 3H), 3.30 (d, 2H, J=17 Hz), 4.78 (septet, 1H, J=6 Hz), 6.97 (t, 1H, J=2 Hz), 7.25 (d, 2H, J=8 Hz), 7.35 (t, 1H, J=2 Hz), 7.51 (t, 1H, J=2 Hz), 7.95 (d, 2H, J=8 Hz), 8.39 (t, 1H, J=1 Hz), 9.28 (d, 1H, J=1 Hz), 11.14 (s, 1H); LCMS (m/z): 520.6 $[C_{23}H_{26}N_3O_7PS+H]^+$. Anal. calcd. for ($C_{23}H_{26}N_3O_7PS+2$ HBr+$4H_2O$): C, 36.67; H, 4.82; N, 5.58. Found: C, 37.04; H, 4.72; N, 5.18.

Example 26

{4-[3-Isopropoxy-5-(thiazol-2-ylcarbamoyl)phenoxy]phenyl}phosphonic acid monomethyl ester

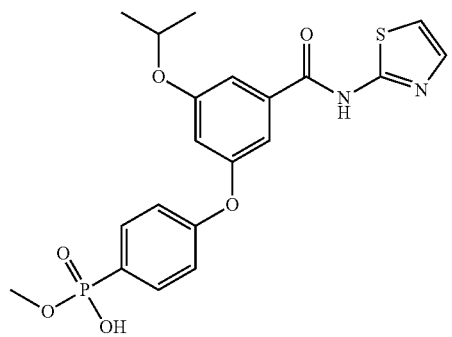 [SMILES: COP(=O)(O)c1ccc(Oc2cc(OC(C)C)cc(C(=O)Nc3nccs3)c2)cc1]

To a solution of {4-[3-isopropoxy-5-(thiazol-2-ylcarbamoyl)-phenoxy]-phenyl}-phosphonic acid (Example 3) (100 mg, 0.225 mmol) in DMF (2 mL) and pyridine (300 μL) was added methanol (91 μL, 2.25 mmol) and EDCI (47 mg, 0.247 mmol). The resulting mixture was subjected to microwave heating at 130° C. for 5 min. Then NaOH (2 mL) was added and the resulting mixture was stirred at rt for 10 min. The residue was partitioned between EtOAc and $H_2O$. The aqueous layer was acidified with HCl (6N) to pH 2 and extracted into EtOAc. The organic layer was washed with brine (2×), dried and concentrated to give an oil. Water was added (10 mL) until a precipitate formed which was filtered and dried to afford 25 mg (25%) of {4-[3-isopropoxy-5-(thiazol-2-ylcarbamoyl)phenoxy]phenyl}phosphonic acid monomethyl ester. $^1H$ NMR (500 MHz, DMSO-$d_6$): δ 7.71 (dd, J=12, 9 Hz, 2H), 7.53 (m, 2H), 7.32 (m, 2H), 7.15 (dd, J=9, 3 Hz, 2H), 6.89 (t, J=3 Hz, 1H), 4.76 (m, 1H), 3.52 (d, J=11 Hz, 3H), 1.30 (d, J=6 Hz, 6H); LCMS m/z=449.6 $[C_{20}H_{21}N_2O_6PS+H]^+$; Anal. Calcd. for ($C_{20}H_{21}N_2O_6PS+$ $0.5H_2O$): C, 52.51; H, 4.85; N, 6.12. Found: C, 52.54; H, 4.93; N, 6.15.

Example 27

{4-[3-Isopropoxy-5-(thiazol-2-ylcarbamoyl)-phenoxy]-phenyl}-phosphinic acid

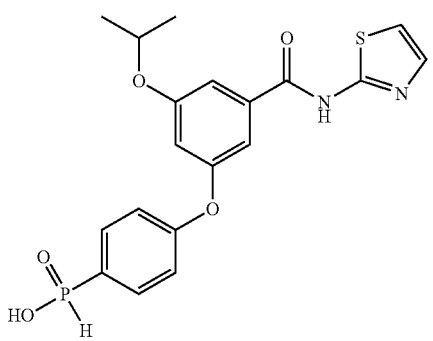 [SMILES: CC(C)Oc1cc(Oc2ccc([PH](=O)O)cc2)cc(C(=O)Nc2nccs2)c1]

Prepared from 3-hydroxy-5-isopropoxy-benzoic acid methyl ester (Example 1, Route 1, STEP A) in a similar manner to Example 19 from the appropriate intermediates with modifications evident to an individual skilled in the art: $^1$H NMR (300 MHz, DMSO-$d_6$): δ 7.74 (dd J=13, 9 Hz, 2H), 7.54 (dd, J=8, 3 Hz, 1H), 7.52 (s, 1H), 7.49 (d, J=547 Hz, 1H), 7.31 (m, 2H), 7.20 (dd, J=9, 2 Hz, 2H), 6.90 (t, J=2 Hz, 1H), 4.76 (m, 1H), 1.30 (d, J=6 Hz, 6H); LCMS m/z=419.4 [$C_{19}H_{19}N_2O_5PS+H$]$^+$; Anal. Calcd. for ($C_{19}H_{19}N_2O_5PS$): C, 54.54; H, 4.58; N, 6.70. Found: C, 54.72; H, 4.57; N, 6.46.

Examples 28-54

The following examples were prepared in a similar manner to Example 1 from the appropriate intermediates with modifications evident to an individual skilled in the art:

| Example | Structure | Mass Spect. (Mode) | 1H NMR δ (DMSO-$d_6$) & Elemental Analysis |
|---|---|---|---|
| 28 | 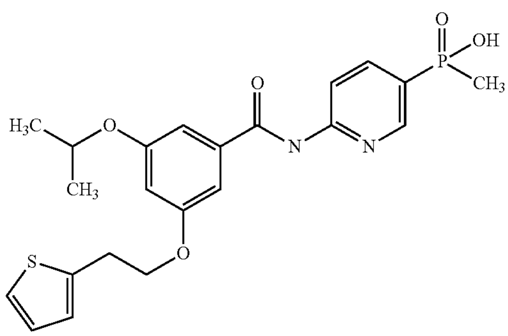 [SMILES: CC(C)Oc1cc(OCCc2cccs2)cc(C(=O)Nc2ccc(P(C)(=O)O)cn2)c1] | 461.3 (+) | 11.05 (br, 1 H), 8.64 (m, 1 H), 8.27 (m 1 H), 8.07-8.14 (m, 1 H), 7.35 (dd, J = 5, 2 Hz, 1 H), 7.17-720 (m, 2 H), 7.95-6.98 (m, 2 H), 6.67 (m, 1 H), 4.67-4.75 (m, 1 H), 4.25 (t, J = 6 Hz, 2 H), 3.25 (t, J = 6 Hz, 2 H), 1.54 (d, J = 15 Hz, 3 H), 1.26 (d, J = 6 Hz, 6 H) Anal. Calcd. for (C22H25N2O5PS + 0.9 H2O): C, 55.43; H, 5.67; N, 5.88. Found: C, 55.67; H, 5.28, N, 5.62. |
| 29 | 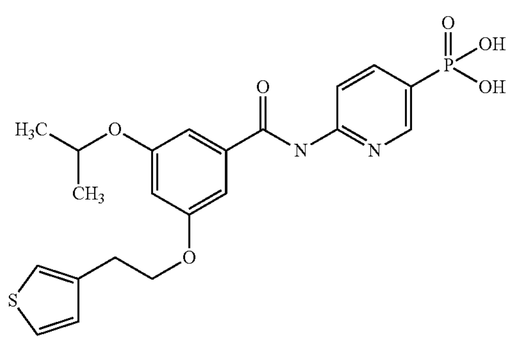 [SMILES: CC(C)Oc1cc(OCCc2ccsc2)cc(C(=O)Nc2ccc(P(=O)(O)O)cn2)c1] | 463.3 (+) | 10.90 (br, 1H), 8.62 (m, 1H), 8.18 (m 1 H), 8.01-8.09 (m, 1 H), 7.47 (dd, J = 5, 3 Hz, 1 H), 7.31-7.33 (m, 1 H), 7.21 (m, 1 H), 7.17 (m, 1 H), 6.66 (m, 1 H), 4.66-4.74 (m, 1 H), 4.24 (t, J = 7 Hz, 2H), 3.05 (t, J = 6 Hz, 2 H), 1.27 (d, J = 6 Hz, 6 H). Anal. Calcd. for (C21H23N2O6PS + 0.5 H2O − 0.4 HBr): C, 50.06; H, 4.88; N, 5.56. Found: C, 49.95; H, 4.92; N, 5.37. |
| 30 | 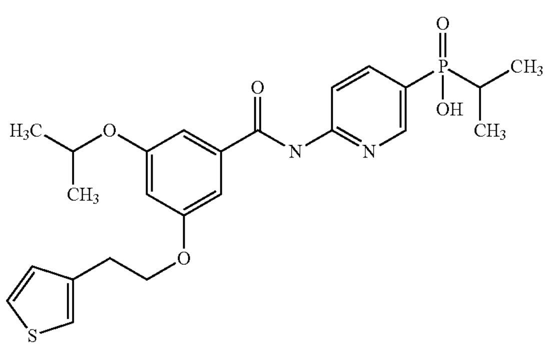 [SMILES: CC(C)Oc1cc(OCCc2ccsc2)cc(C(=O)Nc2ccc(P(=O)(O)C(C)C)cn2)c1] | 489.6 (+) | 11.05 (br, 1 H), 8.57 (dd, J = 6.2 Hz, 1 H). 8.28 (d, J = 9 Hz, 1H), 8.05 (m, 1 H), 7.47 (dd, J = 5, 3 Hz, 1 H). 7.31 (dd. J = 3, 1 Hz, 1 H), 7.20 (m, 1 H), 7.16 (m, 1 H), 7.11 (dd. J = 5, 1 Hz, 1 H), 6.67 (m, 1 H), 4.70-4.72 (m, 1 H), 4.24 (t, J = 7 Hz, 2 H), 3.05 (1, J = 7 Hz, 2 H), 1.92-1.95 (m, 1 H), 1.26 (d, J = 6 Hz, 6 H), 0.98 (dd, J = 17, 8 Hz, 6 H), Anal. Calcd. for (C24H29N2O5PS +0.5 HBr): C, 54.49; H, 5.62; N, 5.30. Found: C, 54.44; H, 5.43; N. 4.92. |

| Example | Structure | Mass Spect. (Mode) | 1H NMR δ (DMSO-d₆) & Elemental Analysis |
|---|---|---|---|
| 31 | 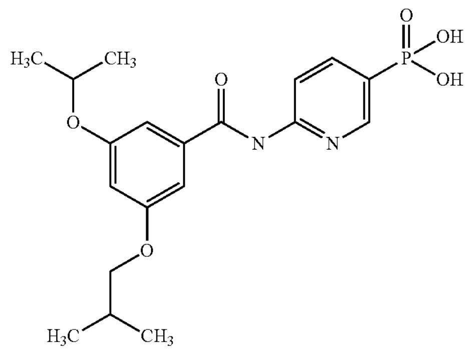 [SMILES: CC(C)COc1cc(OC(C)C)cc(C(=O)Nc2ccc(P(=O)(O)O)cn2)c1] | 409.1 (+) | 11.00 (s, 1 H), 8.57 (m, 1 H), 8.23 (m, 1 H), 8.03 (m, 1H), 7.16 (d, J = 1.2 Hz, 2 H), 6.63 (m, 1H), 4.70 (m, 1 H), 3.78 (d, J = 6.6 Hz, 2 H), 2.00 (m, 1 H), 1.25 (d, J = 6.3 Hz, 6 H), 0.96 (d, J = 6.9 Hz, 6 H). Anal. Calcd. for (C19H25N2O6P + 0.3 HI): C, 51.08; H, 5.71; N, 6.27. Found: C, 50.75; H, 5.59; N, 6.13. |
| 32 | 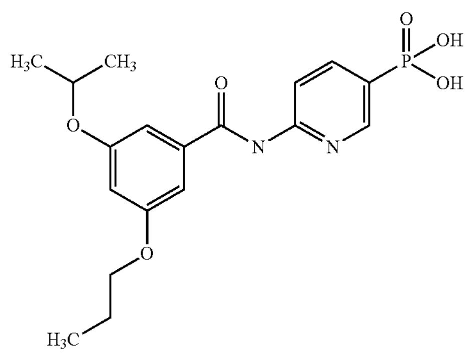 [SMILES: CCCOc1cc(OC(C)C)cc(C(=O)Nc2ccc(P(=O)(O)O)cn2)c1] | 395.4 (+) | 10.99 (s, 1 H), 8.5= (m, 1 H), 8.25 (m, 1 H), 8.02 (m, 1H), 7.15 (d, J = 1.8 Hz, 2 H), 6.63 (s, 1H), 4.71 (m, 1 H), 3.96 (m, 2 H), 1.70 (m, 2 H), 1.25 (d, J = 6.0 Hz, 6 H), 0.96 (m, 3H). Anal. Calcd. for (C18H123N2O6P + 0.12 HI): C, 52.77; H, 5.69; N, 6.84, Found: C, 52.70; H, 5.44; N, 6.66. |
| 33 | 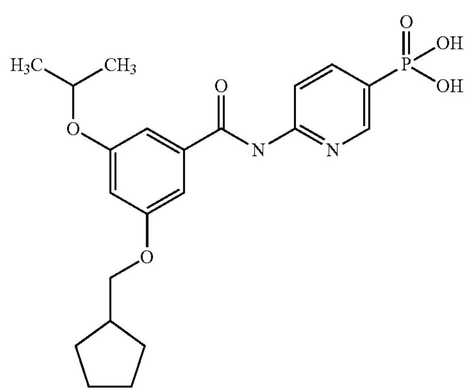 [SMILES: CC(C)Oc1cc(OCC2CCCC2)cc(C(=O)Nc2ccc(P(=O)(O)O)cn2)c1] | 435.4 (+) | 10.98 (s, 1 H), 8.56 (m, 1 H), 8.23 (m, 1 H), 8.02 (m, 1H), 7.15 (d, J = 1.2 Hz, 2 H), 6.63 (m, 1H), 4.70 (m, 1H) 3.88 (d, J = 6.9 Hz, 2 H), 2.28 (m, 1H), 1.75 (m, 2 H), 1.56 (m. 4H), 1.33 (m, 2H), 1.25 (d, J = 6.0 Hz, 6 H). Anal. Calcd. for (C21H27N2O6P +0.18 HI): C, 55.14; H, 5.98; N, 6.12. Found: C, 55.32; H, .5.98; N, 6.06, |
| 34 | 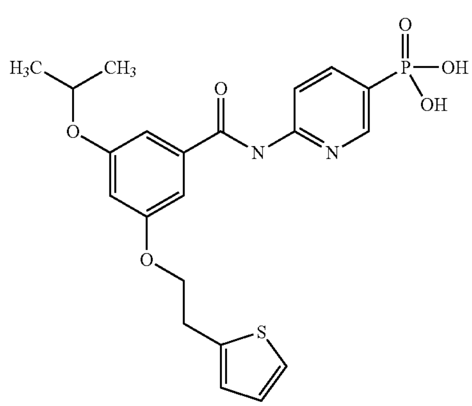 [SMILES: CC(C)Oc1cc(OCCc2cccs2)cc(C(=O)Nc2ccc(P(=O)(O)O)cn2)c1] | 463.5 (+) | 11.03 (s, 1 H), 8.56 on, 1H), 8.23 (m, 1 H), 8.03 (m, 1 H), 7.46 (m, 7.31 (m, 1H), 7.18 (m, 2H), 7.11 (m, 1H), 6.66 (m, 1H), 4.70 (m, 1 H), 4.24 (m, 2H), 3.04 (m, 2H), 1.25 (d, J = 6.3 Hz, 6 H). Anal. Calcd. for (C21H23N2O6PS + 0.5 HI): C, 47.91 H, 4.50; N, 5.32 Found: C, 48.07; H., 4.69; N, 4.97. |

-continued

| Example | Structure | Mass Spect. (Mode) | 1H NMR δ (DMSO-d$_6$) & Elemental Analysis |
|---|---|---|---|
| 35 | 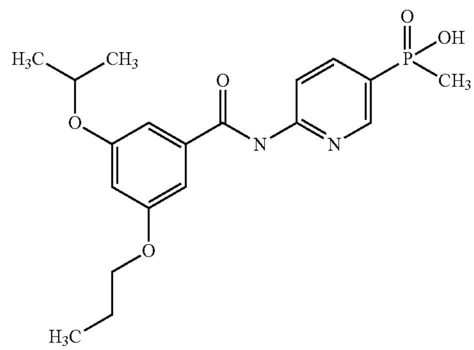 [SMILES: CCCOc1cc(OC(C)C)cc(C(=O)Nc2ccc(P(C)(=O)O)cn2)c1] | 393.4 (+) | 11.01 (s, 1 H), 8.58 (m, 1 H), 8.21 (m, 1 H), 8.06 (m, 1H), 7.12 (d, J = 1.4 Hz, 2H), 6.60 (m, 1H), 4.67 (m, 1 H), 3.93 (m, 2H), 1.67 (m, 2 H), 1.51 (d, J = 14.6 Hz, 3 H), 1.22 (d, J = 6.0 Hz, 6H), 0.92 (m, 3H). Anal. Calcd. for (C19H25N2O5P + 0.3 HI): C, 52.98; H, 5.92; N, 6.50. Found: C, 52.74; H, 6.11; N, 6.56. |
| 36 | 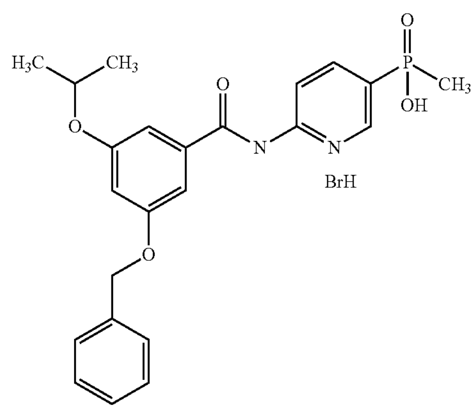 [SMILES: CC(C)Oc1cc(OCc2ccccc2)cc(C(=O)Nc2ccc(P(C)(=O)O)cn2)c1 ; Br] | 441.4 (+) | 11.11 (s, 1 H), 8.67 (m, 1 H), 8.30 (m, 1 H), 8.13 (m, 1H), 7.35 (m, 7H), 6.79(s, 1H), 5.20 (s, 2H), 4.71 (m, 1 H), 1.58 (d, J = 14.6 Hz, 3H), 1.23 (d, J = 6.0 Hz, 6H). Anal. Calcd. for (C23H25N2O5P + 1.1 HBr): C, 52.18; H, 4.97; N, 5.29. Found: C, 51.82; H, 4.97; N, 5.60. |
| 37 | 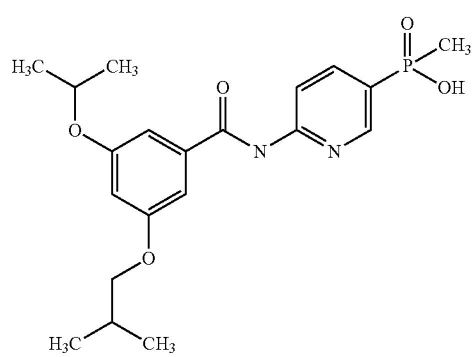 [SMILES: CC(C)COc1cc(OC(C)C)cc(C(=O)Nc2ccc(P(C)(=O)O)cn2)c1] | 407.4 (+) | 10.98 (s, 1 H), 8.58 (m, 1 H), 8.20 (m, 1 H), 8.04 (m, 1H), 7.09 (d, J = 1.8 Hz, 2H), 6.58 (m, 1H), 4.64 (m, 1 H), 3.72 (d, J = 6.6 Hz, 2H), 1.94 (m, 1 H), 1.49 (d, J = 15.0 Hz. 3 H), 1.19 (d, J = 6.0 Hz, 6H), 0.90 (d, J = 6.6 Hz, 6H). Anal. Calcd. for (C20H27N2O5P + 0.15 HBr): C, 57.39; H, 6.54; N, 6.69. Found: C, 57.46; H, 6.23; N, 6.55. |
| 38 | 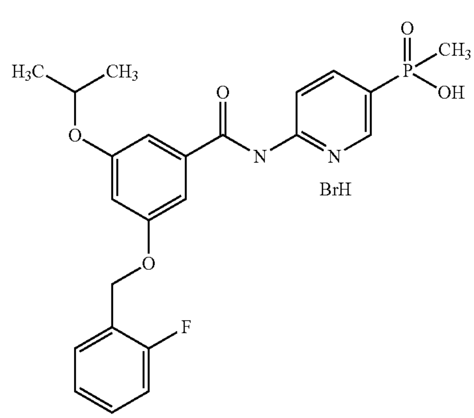 [SMILES: CC(C)Oc1cc(OCc2ccccc2F)cc(C(=O)Nc2ccc(P(C)(=O)O)cn2)c1 ; Br] | 459.4 (+) | δ 10.92 (s, 1 H), 8.46 (m, 1 H) 8.05 (m, 1 H), 7.92 (m, 1H), 7.22 (m, 6H), 6.57 (m, 1H), 5.02 (s, 2H), 4.54 (m, 1 H), 1.36 (d, J = 15.2 Hz, 3H), 1.07 (d, J = 6.0 Hz, 6H) = Anal. Calcd. for (C23H24FN2O5P + 1.0 HBr): C, 51.22; H, 4.67; N, 5.19. Found: C, 51.15; H, 4.47; N, 5.25. |

-continued

| Example | Structure | Mass Spect. (Mode) | 1H NMR δ (DMSO-d₆) & Elemental Analysis |
|---|---|---|---|
| 39 | 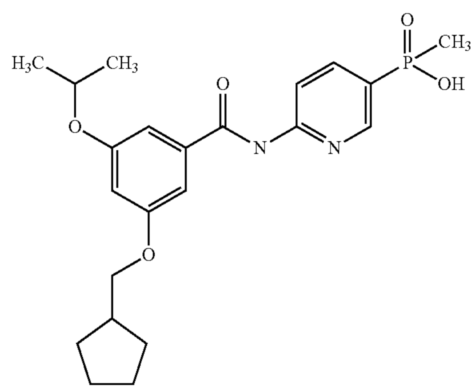 [SMILES: CC(C)Oc1cc(OCC2CCCC2)cc(C(=O)Nc2ccc(P(C)(=O)O)cn2)c1] | 433.4 (+) | 11.03 (s, 1 H), 8.64 (m, 1 H), 8.26 (m, 1 H), 8.13 (m, HI), 7.16 (m, 2 H), 6.64 (m, 1H), 4.71 (m, 1 H), 3.89 (d, J = 6.6 Hz, 2 H), 2.29 (m, 1H), 1.75 (m, 2 H), 1.56 (m, 2H), 1.33 (m, 4H), 1.25 (d, J = 6.0 Hz, 6 H). Anal. Calcd. for (C22H29N2O5P +0.35 HBr): C, 57.35; H, 6.42; N, 6.08. Found: C, 57.11; H, 6.31; N, 6.38 |
| 40 | 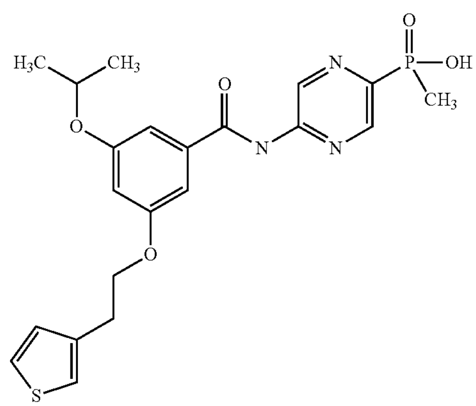 [SMILES: CC(C)Oc1cc(OCCc2ccsc2)cc(C(=O)Nc2cnc(P(C)(=O)O)cn2)c1] | 462.3 (+) | 1.28 (d, 6, JH = 6 Hz), 1.60 (d, 3H, J = 15 Hz), 3.07 (t, 2H, J = 7 Hz), 4.26 (t, 2H, J? 7 Hz). 4.69-4.77 (m, 1H), 6.71 (t, 1H, J = 2 Hz), 7.13 (dd, 1H, J = 5, 2 Hz), 7.23 (dd, 1H, J = 9, 2 Hz), 7.33-7.34 (m, 1H), 7.49 (dd, 1H, J = 5. Hz), 8.78 (s, 1H), 9.54 (d, 1H, J = 1 Hz). 11.36 (s, 1H). Anal. Calcd. for (C₂₁H₂₄N₃O₅PS + 0.3H₂0): C, 54.02; H, 5.31; N. 9.00. Found: C, 53.96; H, 5.24; N, 8.73. |
| 41 | 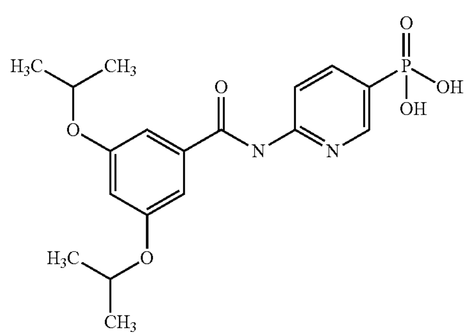 [SMILES: CC(C)Oc1cc(OC(C)C)cc(C(=O)Nc2ccc(P(=O)(O)O)cn2)c1] | 395.4 (+) | 10.99 (s, 1 H), 8.59 (d, J = 3.0 Hz, 1 H), 8.23 (d, J = 6.0 Hz, 1 H), 8.02 (t, J = 6.0 Hz, 1 H), 7.16 (s, 2 H), 6.60 (s, 1 H), 4.69 (m, 2 H), 1.25 (s, 12 H). Anal. Calcd, for (C18H23N2O6P + 0.7 eq H2O) C, 53.12; H, 6.04; N, 6.88. Found: C, 53.07; H, 5.66; N, 6.73. |
| 42 | 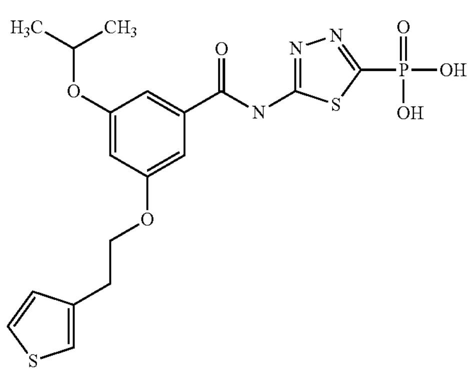 [SMILES: CC(C)Oc1cc(OCCc2ccsc2)cc(C(=O)Nc2nnc(P(=O)(O)O)s2)c1] | 470.5 (+) | 7.43 (m, 1 H), 7.27 (m, 3H), 7.08 (m, 2H), 6.70 (m, 1H), 4.67 (m, 1 H), 4.21 (m, 2H), 3.02 (m, 2H), 1.23 (d, J = 6.0 Hz, 6 H). Anal. Calcd. for (C18H2ON3O6PS + 1.0 H2O): C, 44.35 H, 4.55; N, 8.62. Found: C, 44.56; H, 4.41; N, 8.27. |

| Example | Structure | Mass Spect. (Mode) | 1H NMR δ (DMSO-d$_6$) & Elemental Analysis |
|---|---|---|---|
| 43 | 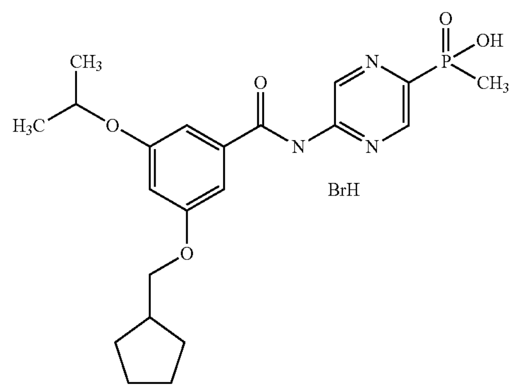 [SMILES: CC(C)Oc1cc(OCC2CCCC2)cc(C(=O)Nc2cnc(P(C)(=O)O)cn2)c1 ; Br] | 434.6 (+) | 1.28 (d, 6H, J = 6 Hz), 1.32-1.36 (m, 2H), 1.53-1.58 (m, 2H), 1.61 (d, 3H, J = 15 Hz), 1.76-1.80 (m, 2H), 2.29-2.33 (m, 1H), 3.91 (d, 2H, J = 7 Hz), 4.71-4.74 (m, 1H), 6.68 (dd, 1H, J = 5, 3 Hz), 7.20-7.22 (m, 2H), 8.79 (s, 1H), 9.54 (s, 1H), 11.35 (s, 1H). Anal. (Calcd. for C$_{21}$H$_{28}$N$_3$O$_5$P + 1.1 HBr): C, 48.28; H, 5.61; N, 8.04. Found: C, 48.55; H, 5.81: N, 7.76. |
| 44 | 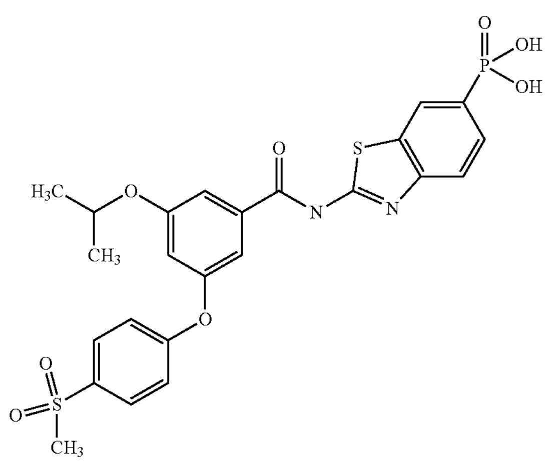 | 563.4 (+) | 8.32 (d, J = 13 Hz, 1H), 7.96 (dd, J = 7, 2 Hz, 2 H), 7.78 (m, 2H), 7.61 (s, 1 H), 7.44 (d, J = 2 Hz, 1 H), 7.27 (dd, J = 7, 2 Hz, 2 H), 7.01 (t, J = 2 Hz, 1 H), 4.79 (m, 1 H), 3.22 (s, 3 H), 1.32 (d, J = 6 Hz, 6 H). Anal. Calcd. for (C$_{24}$H$_{23}$N$_2$O$_8$PS$_2$ + 1.0 H$_2$O): C, 49.65; H, 4.34: N, 4.83. Found: C, 49.78; H, 4.62; N, 4.57, |
| 45 | 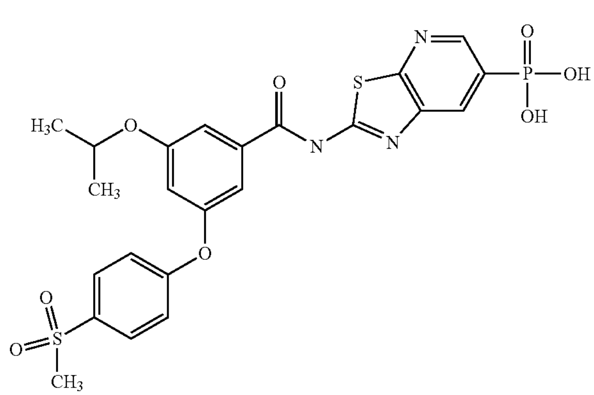 [SMILES: CC(C)Oc1cc(Oc2ccc(S(C)(=O)=O)cc2)cc(C(=O)Nc2nc3cc(P(=O)(O)O)cnc3s2)c1] | 564.4 (+) | 8.70 (dd, J = 6. 2 Hz, 1 H), 8.24 (dd, J = 13, 2 Hz, 1 H), 7.96 (dd, J = 7, 2 Hz, 2H), 7.62 (m, 1 H), 7.45 (m, 1 H), 7.28 (dd, J = 7, 2 Hz, 2 H), 7.02 (t, J = 2 Hz, 1 H), 4.80 (m, 1 H), 3.22 (s, 3 H), 1.32 (d, J = 6 Hz, 6 H). Anal. Calcd. for (C$_{23}$H$_{22}$N$_3$O$_8$PS$_2$ + 0.3 H$_2$O): C, 48.55; H, 4.00; N, 7.39. Found: C. 48.44; H, 3.96; N, 7.28. |

-continued

| Example | Structure | Mass Spect. (Mode) | 1H NMR δ (DMSO-d₆) & Elemental Analysis |
|---|---|---|---|
| 46 | 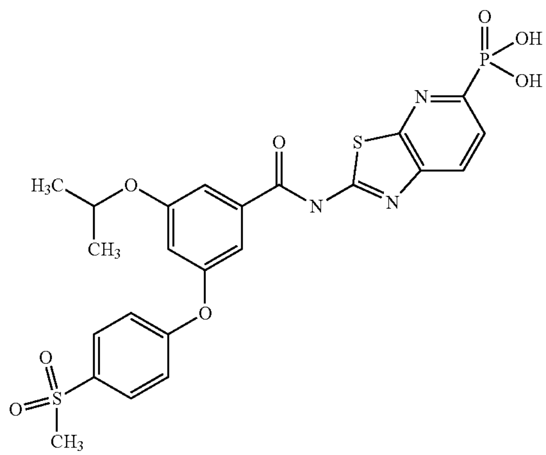 [SMILES: CC(C)Oc1cc(Oc2ccc(S(C)(=O)=O)cc2)cc(C(=O)Nc2nc3ccc(P(=O)(O)O)nc3s2)c1] | 564.4 (+) | 8.19 (dd, J = 9, 5 Hz, 1 H), 7.94 (m, 3 H), 7.63 (d, J = 1 Hz, 1H), 7.45 (m, 1 H), 7.28 (dd, J = 7, 2 Hz, 2 H), 7.03 (t, J = 2 Hz, 1 H), 4.80 (m, 1 H), 3.23 (s, 3 H), 1.32 (d, J = 6 Hz, 6 H), Anal. Calcd. for ($C_{23}H_{22}N_3O_8PS_2$ +1.2 $H_2O$): C, 47.21; H. 4.20; N, 7.18. Found: C, 47.28; H, 4.60; N, 6.89, |
| 47 | 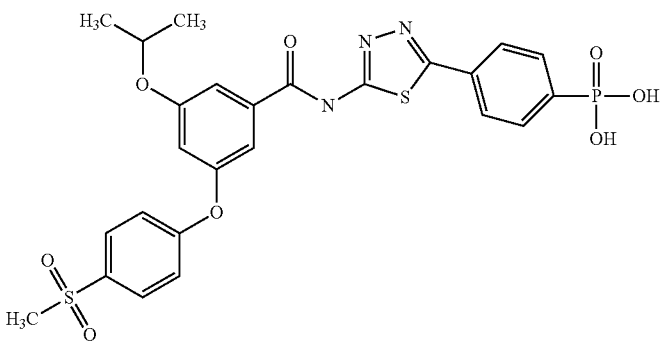 [SMILES: CC(C)Oc1cc(Oc2ccc(S(C)(=O)=O)cc2)cc(C(=O)Nc2nnc(-c3ccc(P(=O)(O)O)cc3)s2)c1] | 590.4 (+) | 8.05 (m, 2H), 7.94 (d, J = 5.7 Hz. 2 H), 7.80 (m, 2H), 7.59 (s, 1H), 7.42 (s, 1H), 7.25 (d, J = 9.0 Hz, 2H), 7.01 (m, 1H), 4.76 (m, 1 H), 3.20 (s, 3H), 1.30 (d, J = 5.7 Hz, 6 H). Anal Calcd for ($C_{25}H_{24}N_3O_8PS_2$ + 1.5 H2O): C, 48.70 H, 4.41; N, 6.81. Found: C, 48.67; H, 4.46; N, 6.72. |
| 48 | 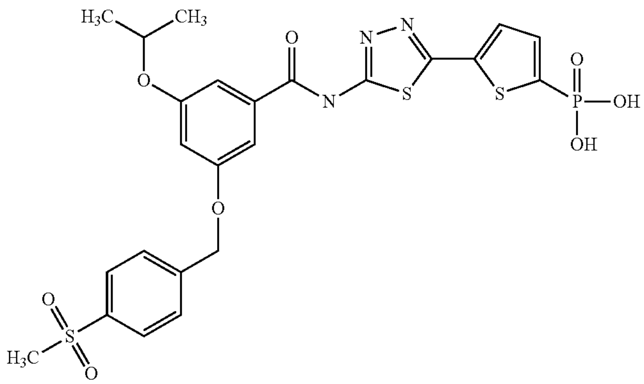 [SMILES: CC(C)Oc1cc(OCc2ccc(S(C)(=O)=O)cc2)cc(C(=O)Nc2nnc(-c3ccc(P(=O)(O)O)s3)s2)c1] | 596.6 (+) | 7.94 (m, 2H) 7.72 (m, 1H), 7.58 (d, J = 1.8 Hz, 1 H), 7.42 (m, 3H), 7.25 (m, 2H), 7.01 (m, 1H), 4.77 (m, 1 H), 3.15 (s, 3H), 1.30 (d, J = 6.0 Hz, 6 H). Anal Calcd for ($C_{23}H_{22}N_3O_8PS_3$): C, 46.38 H, 3.72; N, 7.05. Found: C, 46.41; H, 3.71; N, 6.04. |
| 49 | 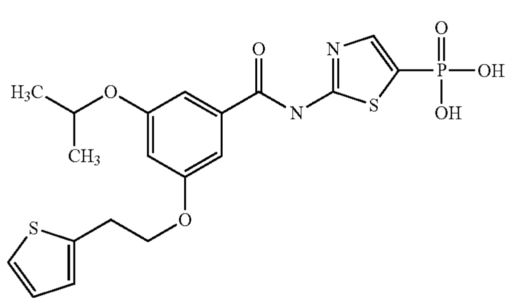 [SMILES: CC(C)Oc1cc(OCCc2cccs2)cc(C(=O)Nc2ncc(P(=O)(O)O)s2)c1] | 469.3 (+) | 7.72 (d, J = 5 Hz, 1 H), 7.35 (dd, J = 5, 2 Hz, 1 H), 7.28 (m, 1 H), 7.25 (m, 1 H), 6.95-6.98 (m, 1 H), 6.70 (m, 1 H), 5.74 (m, 1 H), 4.67-4.75 (m, 1 H), 4.25 (t, J = 6 Hz, 2 H), 3.26 (t, J = 6 Hz, 2H), 1.27 (d, J = 6 Hz, 6 H). Anal. Calcd. for ($C_{20}H_{23}N_2O_5PS_2$ + 0.5 HBr): C, 47.38; H, 4.67; N, 5.53. Found: C, 47.65; H, 4.47; N, 5.28. |

| Example | Structure | Mass Spect. (Mode) | 1H NMR δ (DMSO-d₆) & Elemental Analysis |
|---|---|---|---|
| 50 | 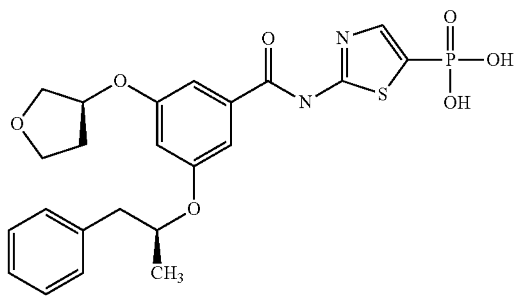 [SMILES: C[C@@H](Cc1ccccc1)Oc1cc(O[C@H]2CCOC2)cc(C(=O)Nc2ncc(P(=O)(O)O)s2)c1] | 505.3 (+) | 7.75 (d, J = 5 Hz, 1 H), 7.25-7.32 (m, 5 H), 7.28 (m, 1 H), 7.20-7.24 (m, 2 H), 6.70 (m, 1 H), 5.13 (m, 1 H), 4.81-4.87 (m, 1 H), 3.74-3.93 (m, 4 H), 2.98-3.04 (m, 1 H), 2.86-2.93 (m, 1 H), 2.19-2.28 (m, 1 H), 1.92-2.02 (m, 1 H), 1.26 (d, J = 6 Hz, 3 H), Anal. Calcd. far (C23H25N2O7PS + 1.4 H2O): C, 52.15: H, 5.29; N, 5.29. Found: C, 52.01: H, 5.35; N, 4.90 |
| 51 | 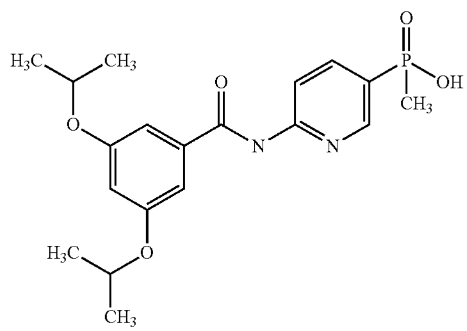 [SMILES: CC(C)Oc1cc(OC(C)C)cc(C(=O)Nc2ccc(P(C)(=O)O)cn2)c1] | 393.3 (+) | 11.02 (s, 1 H), 8.62 (d, J = 3.0 Hz, 1 H), 8.27 (d, J = 6.0 Hz, 1 H), 8.11 (t, J = 6.0 Hz, 1 H), 7.15 (s, 2 H), 6.61 (s, 1 H), 4.68 (m, 2 H), 1.57 (d, J = 30 Hz, 3 H), 1.22 (s, 12 H). Anal. Calcd. for (C19H25N2O5P + 0.6 CH3COOH): C, 56.63; H, 6.45; N, 6.54. Found: C, 56.55; H, 6.12; N, 6.48. |
| 52 | 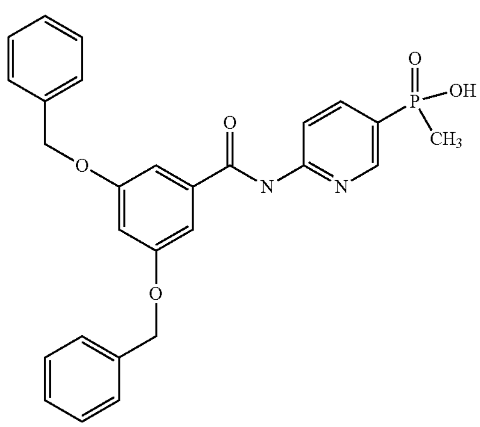 [SMILES: CP(=O)(O)c1ccc(NC(=O)c2cc(OCc3ccccc3)cc(OCc3ccccc3)c2)nc1] | 489.1 (+) | 1.56 (d, 3H, J = 14 Hz), 5.19 (s, 4H), 6.88-6.90 (m, 2H), 7.31-7.48 (m, 11H), 8.12-8.16 (m, 1H), 8.29 (d, 1H, J = 8 Hz), 8.67 (d, 1H, J = 4 Hz), 11.07 (s, 1H), Anal. Calcd, for (C₂₇H₂₅N₂O₅P + 1.0 H20 + 0.2 AcOH): C, 63.47; H, 5.40; N, 5.40. Found: C, 63.70; H, 5.40; N, 5.25. |
| 53 | 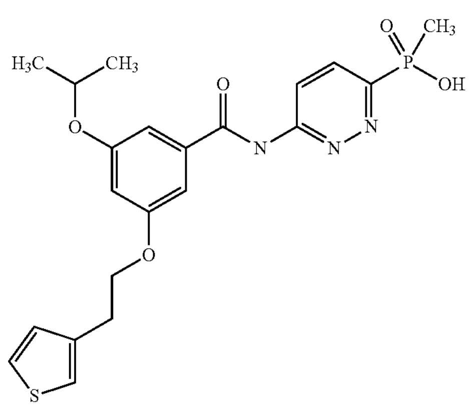 [SMILES: CC(C)Oc1cc(OCCc2ccsc2)cc(C(=O)Nc2ccc(P(C)(=O)O)nn2)c1] | 462.1 (+) | δ 1.28 (d, 6H, J = 6 Hz), 1.68 (d, 3H, J = 15 Hz), 3.07 (t, 2H, J = 7 Hz), 4.27 (t, 2H, J = 7 Hz), 4.69-4.77 (m, 1H,), 6.72 (t, 1H, J = 2 Hz), 7.13 (dd, 1H, J = 5, 1 Hz), 7.24 (d, 2H, J = 12 Hz), 7.33-7.34 (m, 1H), 7.49 (dd, 1H, J = 5, 3 Hz), 8.07 (br s, 1H), 8.47 (br s, 1H), 11.63 (br s, 1H). Anal. Calcd. for (C₂₁H₂₄N₃O₅PS + 1.0 H₂O + 0.3 AcOH): C, 52.15; H, 5.51; N, 8.45. Found: C, 52.27; H, 5.22; N, 8.01. |

| Example | Structure | Mass Spect. (Mode) | 1H NMR δ (DMSO-d$_6$) & Elemental Analysis |
|---|---|---|---|
| 54 | 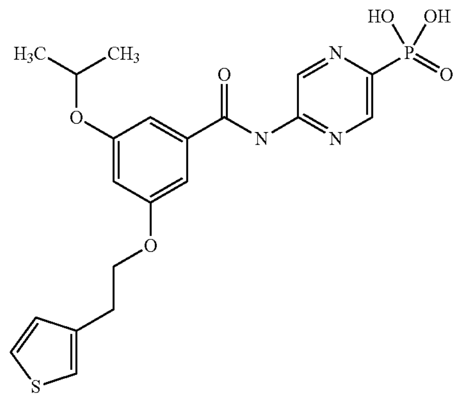 [SMILES: CC(C)Oc1cc(OCCc2ccsc2)cc(C(=O)Nc2cnc(P(=O)(O)O)cn2)c1] | 464.0 (+) | 1.28 (d, 6H, J = 6 Hz), 3.07 (t, 2H, J = 7 Hz), 4.26 (t, 2H, J = 7 Hz), 4.71-4.75 (m, 1H), 6.71-6.72 (m, 1H), 7.12-7.14 (m, 1H), 7.21-7.25 (m. 2H), 7.33 (d, 1H, J = 2 Hz), 7.47-7.50 (m, 1H), 8.70 (s, 1H), 9.54 (s, 1H), 11.31 (s, 1H). Anal. Calcd. for C$_{20}$H$_{22}$N$_3$O$_6$PS: C, 51.83; H, 4.78; N, 9.07. Found: C, 51.78: H. 4.69: N, 8.98. |

Examples 55-143

The following examples were prepared in a similar manner to Example 3 from the appropriate intermediates with modifications evident to an individual skilled in the art:

| Example | Structure | Mass Spect. (Mode) | 1H NMR δ (DMSO-d$_6$) & Elemental Analysis |
|---|---|---|---|
| 55 | 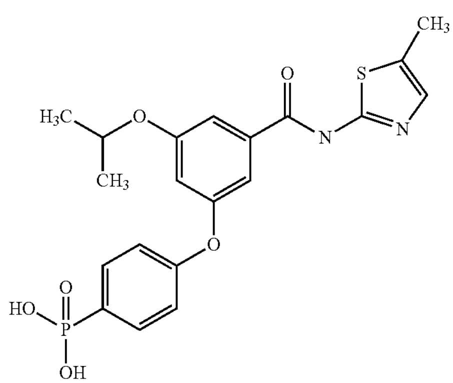 [SMILES: Cc1cnc(NC(=O)c2cc(Oc3ccc(P(=O)(O)O)cc3)cc(OC(C)C)c2)s1] | 449.0 (+) | 7.71 (dd, J = 12, 8 Hz, 2 H), 7.49 (m, 1 H), 7.26 (dd, J = 2, 1 H), 7.21 (d, J = 1 Hz, 1H) 7.12 (dd, J = 8, 3 Hz, 2 H), 6.85 (m, 1 H), 4.71-4.79 (m, 1H), 2.36 (d, J = 1 Hz, 3 H), 1.30 (d, J = 6 Hz, 6H) Anal. Calcd, for C20H21N2O6PS: C, 53.57; H, 4.72; N, 6.25, Found: C, 53.47; H, 4.48; N, 6.16. |
| 56 | 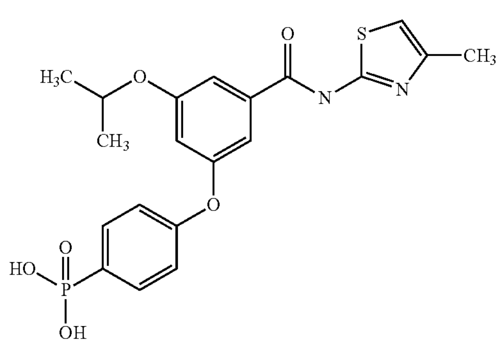 [SMILES: Cc1csc(NC(=O)c2cc(Oc3ccc(P(=O)(O)O)cc3)cc(OC(C)C)c2)n1] | 449.0 (+) | 7.71 (dd, J = 12, 9 Hz, 2 H), 7.50 (m, 1 H), 7.26 (dd, J = 2, 1 Hz, 1 H), 7.13 (dd, J = 9, 3 Hz, 2 H), 6.85 (m, 1 H), 6.82 (d, J = 1 Hz, 1 H), 4.71-4.79 (m, 1 H), 2.30 (d, J = 1 Hz, 3 H), 1.30 (d, J = 6 Hz, 6 H). Anal. Calcd. for (C20H21N2O6PS + 0.11 HBr): C, 52.53; H, 4.65; N, 6.13, Found: C, 52.77; H, 4.25; N, 6.41. |

-continued

| Example | Structure | Mass Spect. (Mode) | 1H NMR δ (DMSO-d₆) & Elemental Analysis |
|---|---|---|---|
| 57 | 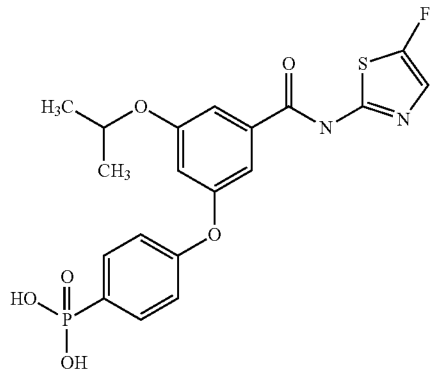 [SMILES: CC(C)Oc1cc(Oc2ccc(P(=O)(O)O)cc2)cc(C(=O)Nc2ncc(F)s2)c1] | 453.1 (+) | 7.69 (dd, J = 12, 8 Hz, 2 H), 7.45 (m, 1 H), 7.38 (d, J = 3 Hz, 1 H), 7.25 (m, 1 H), 7.07 (dd, J = 8, 3 Hz, 2 H), 6.83 (m, 1 H), 4.69-4.77 (m, 1 H), 1.29 (d, J = 6 Hz, 6 H). Anal. Calcd. for (C19H18FN2O6PS + 0.5 HCl): C, 48.49; H, 3.96; N, 5.95. Found: C, 48.40; H, 4.09; N, 6.08. |
| 58 | 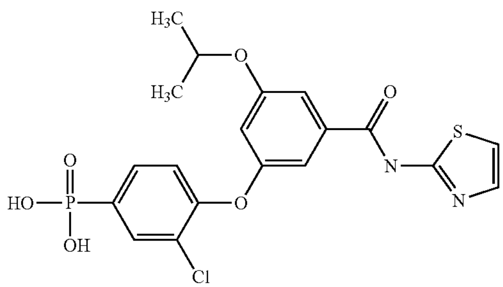 [SMILES: CC(C)Oc1cc(Oc2ccc(P(=O)(O)O)cc2Cl)cc(C(=O)Nc2nccs2)c1] | 469.1 (+) | 7.77 (dd, J = 13, 1 Hz, 1 H), 7.64 (ddd, J = 12, 8, 2 Hz, 1 H), 7.55 (d, J = 4 Hz, 1 H), 7.50 (m, 1 H), 7.28 (d, J = 3 Hz, 1 H), 7.23 (d, J = 3 Hz, 1 H), 7.20 (m, 1H), 6.85 (m, 1 H), 4.72-4.80 (m, 1 H), 1.30 (d, J = 6 Hz, 6 H). Anal. Calcd. for (C19H18ClN2O6PS + 0.3 HCl + 0.1 NH4Cl): C, 47.04: H, 3.98; N, 6.06. Found: C, 46.84; H, 3.62; N, 5.90. |
| 59 | 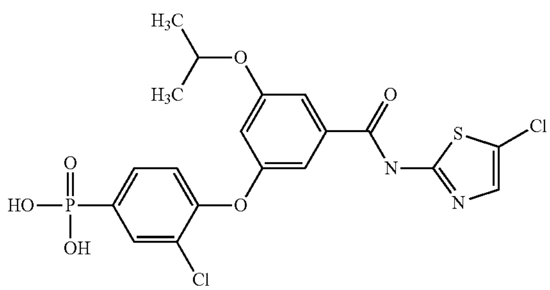 [SMILES: CC(C)Oc1cc(Oc2ccc(P(=O)(O)O)cc2Cl)cc(C(=O)Nc2ncc(Cl)s2)c1] | 503.4 (+) | 7.73 (dd, J = 12, 2 Hz, 1 H), 7.58-7.62 (m, 1 H), 7.56 (s, 1 H), 7.44 (m, 1 H), 7.14 (m 1 H), 7.11 (d, J = 3 Hz, 1 H), 6.74 (m, 1 H. 4.68-4.76 (m, 1 H), 1.28 (d, J = 6 Hz, 6 H). Anal. Calcd. for (C19H17Cl2N2O6PS + 0.2 H2O + 0.1 acetone): C, 42.52; H, 3.99; N, 5.14. Found: C, 42.36; H, 3.63; N, 5.08. |
| 60 | 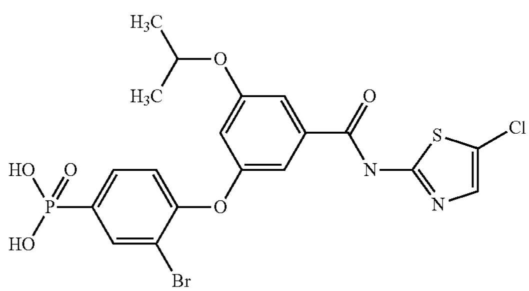 [SMILES: CC(C)Oc1cc(Oc2ccc(P(=O)(O)O)cc2Br)cc(C(=O)Nc2ncc(Cl)s2)c1] | 547.4, 549.1, 551.4 (+) | 7.89-7.94 (m, 1 H), 7.63-7.70 (m, 1 H), 7.59 (m, 1 H), 7.49 1 (m, 1 H), 7.16-7.19 (m, 2 H), 6.85 (m, 1 H), 4.70-4.78 (m, 1 H), 1.28 (d, J = 6 Hz, 6 H). Anal. Calcd. for (C19H17BrClN2O6PS + 0.2 HBr + 0.05 acetone): C, 40.58; H, 3.11; N, 4.94. Found: C, 40.40 H, 3.23; N, 4.87. |
| 61 | 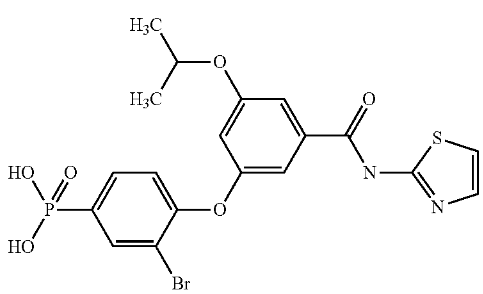 [SMILES: CC(C)Oc1cc(Oc2ccc(P(=O)(O)O)cc2Br)cc(C(=O)Nc2nccs2)c1] | 513.4, 515.4 (+) | 7.92 (dd, J = 13, 2 Hz, 1 H), 7.68 (ddd, J = 12, 8, 2 Hz, 1 H), 7.54 (d, J = 4 Hz, 1 H), 7.51 (m, 1 H), 7.28 (d, J = 4 Hz, 1 H), 7.17-7.21 (m, 2 H), 6.84 (m, 1 H), 4.68-4.76 (m, 1 1 H), 1.28 (d, J = 6 Hz, 6 H). Anal. Calcd. for (C19H18BrN2O6PS + 0.05 HBr): C, 44.11; H, 3.52; N, 5.41. Found: C, 44.08; H, 3.25; N, 5.25. |

-continued

| Example | Mass Spect. (Mode) | 1H NMR δ (DMSO-d$_6$) & Elemental Analysis |
|---|---|---|
| 62 | 531.1, 533.1 (+) | 7.91 (dd, J = 13, 2 Hz, 1 H), 7.67 (ddd, J = 12, 8. 2 Hz, 1 H), 7.47 (m, 1 H), 7.38 (d, J = 2 Hz, 1 H), 7.17 (dd, J = 8, 3 Hz, 1 H), 7.14 (dd, J = 2, 1 Hz, 1 H), 6.84 (m, 1 H), 4.70-4.78 (m, 1 H), 1.28 (d, J = 6 Hz, 6 H). Anal. Calcd. for C19H17BrFN2O6P: C, 42.95; H, 3.23; N, 5.27. Found: C, 42.83; H, 2.98; N, 5.16. |
| 63 | 483.0 (+) | 7.00-7.01 (m, 1H), 7.12 (dd, 2H, J = 9, 3 Hz), 7.29 (d, 1H, J = 4 Hz), 7.33-7.37 (m, 2H), 7.41 (t, 2H, J = 8 Hz), 7.47-7.48 (m, 2H), 7.56 (dd, 1H, J = 4, 1 Hz), 7.65 (s, 1H), 7.68-7.73 (m, 2H). Anal. Calcd. for C$_{23}$H$_{19}$N$_2$O$_6$PS + 0.1 HBr + 0.1 H$_2$O: C, 56.11; H, 3.95; N, 5.69. Found: C, 56.07; H, 3.66; N. 5.58. |
| 64 | 429.4 (+) | 10.94 (s, 1H), 8.44 (d, J = 3.3 Hz, 1H), 8.19 (d, J = 6.4 Hz, 1H), 7.90 (m, 1 H), 7.77 (m, 2H), 7.50 (s, 1H), 7.21 (m, 4H), 6.89 (s, 1H), 4.83 (m, 1 H), 1.36 (d, J = 5.7 Hz, 6H). Anal. Calcd. for (C21H21N2O6P + 0.15 HBr + 0.4 H2O): C, 56.34 H, 4.94; N, 6.26. Found: C, 56.74; H, 4.92; N, 5.81 |
| 65 | 497.4 (+) | 11.31 (s, 1H), 8.76 (s, 1H), 8.34 (d, J = 9.0 Hz, 1H), 8.22 (m, 1H), 7.69 (m, 2 H), 7.43 (d, J = 1.8 Hz, 1H), 7.21 (d, J = 1.8 Hz, 1H), 7.11 (d, J = 6.6 , Hz, 2H), 6.83 (m, 1H), 4.75 (m, 1 H), 1.28 (d, J = 6.0 Hz, 6H). Anal. Calcd. for (C22H20F3N2O6P + 0.7 H2O): C, 51.91 H, 4.24; N, 5.50. Found: C. 51.84; H, 4.13; N, 5.42. |

| Example | Structure | Mass Spect. (Mode) | 1H NMR δ (DMSO-d$_6$) & Elemental Analysis |
|---|---|---|---|
| 66 | 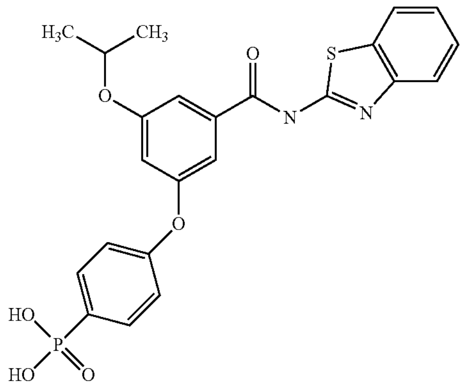 [SMILES: CC(C)Oc1cc(Oc2ccc(P(=O)(O)O)cc2)cc(C(=O)Nc2nc3ccccc3s2)c1] | 434.6 (+) | 1.29 (d, 6H, J = 6 Hz). 4.71-4.74 (m, 1H), 6.77 (s, 1H), 7.01 (d, 2H, J = 8 Hz), 7.26-7.29 (m, 2H), 7.42 (t, 1H, J = 8 Hz), 7.49 (s, 1H), 7.65-7.72 (m, 3H), 7.95 (d, 1H, J = 8 Hz); Anal. Calcd. for C$_{21}$H$_{28}$N$_3$O$_5$P + 1.1 HBr: C, 48.28; H, 5.61; N, 8.04. Found: C, 48.55; H, 5.81; N, 7.76. |
| 67 | 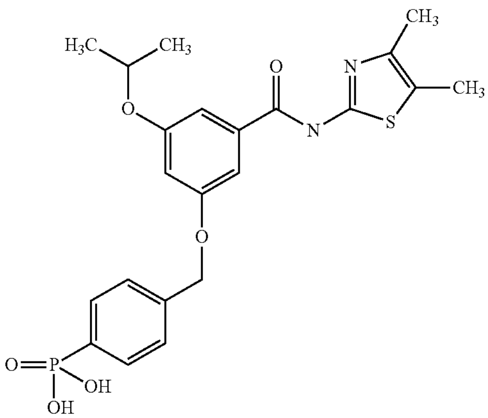 [SMILES: Cc1nc(NC(=O)c2cc(OCc3ccc(P(=O)(O)O)cc3)cc(OC(C)C)c2)sc1C] | 463.5 (+) | 7.69 (m, 2 H), 7.47 (s, 1H), 7.23 (s, 1H), 7.21 (m, 2H), 6.82 (m, 1H), 4.73 (m, 1 H), 2.23 (s, 3H), 2.17 (s. 3H), 1.28 (d, J = 6.0 Hz, 6H). Anal. Calcd. for (C21H23N2O6PS): C, 54.54 H, 5.01; N, 6.06. Found: C, 54.28; H, 4.82; N, 5.87. |
| 68 | 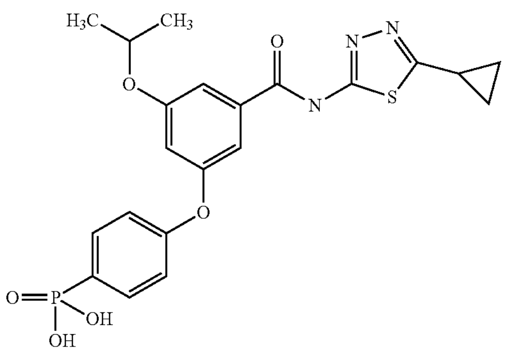 [SMILES: CC(C)Oc1cc(Oc2ccc(P(=O)(O)O)cc2)cc(C(=O)Nc2nnc(C3CC3)s2)c1] | 476.5 (+) | 7.69 (m, 2 H), 7.48 (m, 1H), 7.26 (m, 1H), 7.10 (m, 2H), 6.86 (m, 1H), 4.73 (m, 1 H), 2.39 (m, 1H), 1.28 (d. J = 6.0 Hz, 6H), 1.13 (m, 2H), 0.98 (m, 2H). Anal. Calcd. for (C21H22N3O6PS + 0.8 MeOH): C, 52.25 H, 5.07; N, 8.39. Found: C, 52.15; H, 4.94; N, 8.58. |
| 69 | 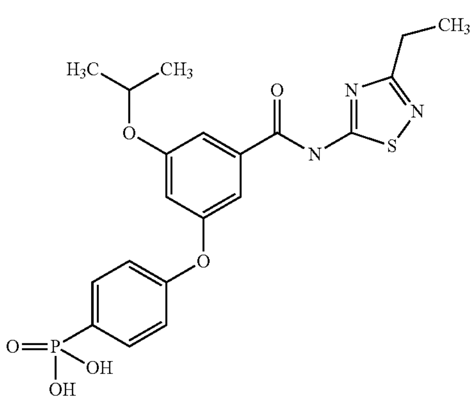 [SMILES: CCc1nsc(NC(=O)c2cc(Oc3ccc(P(=O)(O)O)cc3)cc(OC(C)C)c2)n1] | 464.4 (+) | 7.27 (m, 2 H), 7.60 (m, 1H), 7.38 (m, 1H), 7.18 (m, 2H), 6.95 (m, 1H). 4.81 (m, 1 H), 2.88 (m, 2H), 1.29 (m. 9H). Anal. Calcd. for (C20H22N3O6PS + 0.1 HBr): C, 50.94 H, 4.72; N, 8.91. Found: C, 50.96; H, 4.37; N, 8.73. |

| Example | Structure | Mass Spect. (Mode) | 1H NMR δ (DMSO-d₆) & Elemental Analysis |
|---|---|---|---|
| 70 | 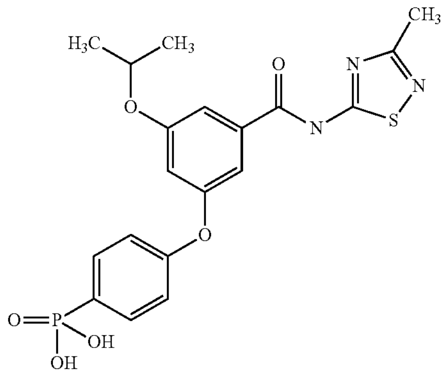 [SMILES: Cc1nsc(NC(=O)c2cc(Oc3ccc(P(=O)(O)O)cc3)cc(OC(C)C)c2)n1] | 450.4 (+) | 7.78 (m, 2 H), 7.60 (s, 1H), 7.37 (s, 1H), 7.20 (d, J = 7.5 Hz, 2H), 6.98 (s, 1H), 4.82 (m, 1 H), 2.5 (s, 3H), 1.37 (d, J = 6.3 Hz, 6H). Anal. Calcd. for (C19H20N3O6PS + 0.1 HBr + 0.23 H2O): C, 49.43 H, 4.49; N, 9.10. Found: C, 49.83; H, 4.53; N, 8.68. |
| 71 | 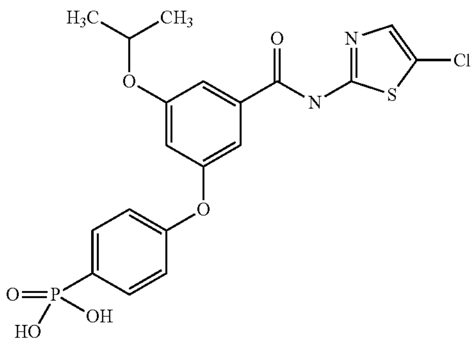 [SMILES: CC(C)Oc1cc(Oc2ccc(P(=O)(O)O)cc2)cc(C(=O)Nc2ncc(Cl)s2)c1] | 469.8 (+) | 7.78 (m, 2 H), 7.67 (s, 1H), 7.56 (s, 1H), 7.19 (m, 2H), 6.94 (s, 1H), 4.81 (m, 1 H). 1.36 (d, J = 5.7 Hz. 6H), Anal. Calcd. for (C19H18ClN2O6PS): C, 48.67 H, 3.87; N, 5.97. Found: C, 48.44; H, 3.61; N, 5.78. |
| 72 | 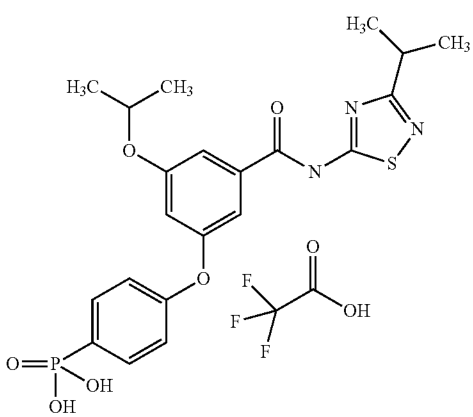 | 478.5 (+) | 7.70 (m, 2 H), 7.53 (m, 1H), 7.30 (m, 1H), 7.12 (m, 2H), 6.88 (m, 1H), 4.74 (m, 1 H), 3.10 (m, 1H), 1.28 (m, 12H). LC-MS m/z = 478.5 [C21H24N3O6PS + H]⁺; Anal. Calcd. for (C21H24N3O6PS + 0.9 TFA): C, 47.21 H. 4.33; N, 7.24. Found: C, 47.21; H, 4.55; N, 7.20. |
| 73 | 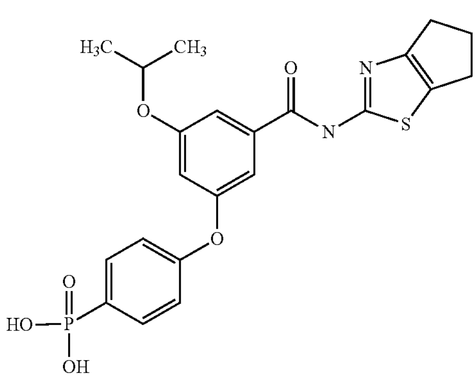 [SMILES: CC(C)Oc1cc(Oc2ccc(P(=O)(O)O)cc2)cc(C(=O)Nc2nc3c(s2)CCC3)c1] | 475.5 (+) | 7.68 (m, 2H), 7.46 (s, 1H), 7.22 (s, 1H), 7.10 (m, 2H), 6.81 (m, 1H), 4.72 (m, 1 H), 2.81(m, 2H), 2.67 (m, 2H), 2.35 (m, 2H), 1.27 (d, J = 5.7 Hz, 6H). Anal. Calcd. for (C22H23N2O6PS + 0.3 HBr): C, 52.98; H, 4.71; N, 5.62 Found: C, 53.20; H, 4.39; N, 5.79 |

-continued

| Example | Structure | Mass Spect. (Mode) | 1H NMR δ (DMSO-d$_6$) & Elemental Analysis |
|---|---|---|---|
| 74 | 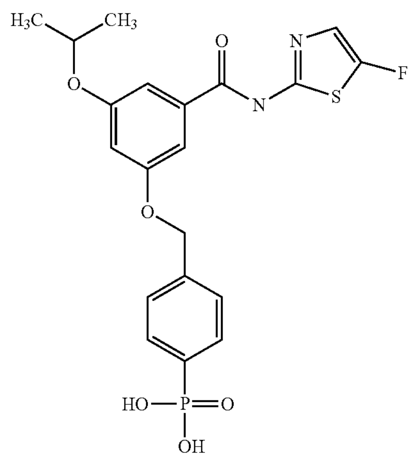 [SMILES: CC(C)Oc1cc(OCc2ccc(P(=O)(O)O)cc2)cc(C(=O)Nc2ncc(F)s2)c1] | 467.4 (+) | 7.76 (m, 2 H), 7.60 (m, 2H), 7.46 (d, J = 2.4 Hz, 1H), 7.38 (s, 1H), 7.32 (s, 1H), 6.85 (s, 1H), 5.28 (s, 2H), 4.78 (m, 1 H), 1.34 (d, J = 6.0 Hz, 6H). Anal. Calcd. for (C20H20FN2O6PS + 0.1 HBr): C, 50.62 H. 4.27; N. 5.90, Found: C, 50.72; H, 4.40; N, 5.67. |
| 75 | 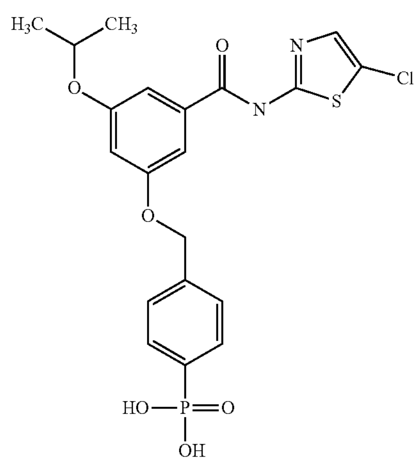 [SMILES: CC(C)Oc1cc(OCc2ccc(P(=O)(O)O)cc2)cc(C(=O)Nc2ncc(Cl)s2)c1] | 483.9 (+) | 7.71 (m, 2 H), 7.63 (s, 1H), 7.56 (m, 2H). 7.35 (s, 1H), 7.29 (s, 1H), 6.81 (s, 1H), 5.24 (s, 2H), 4.73 (m, 1 H), 1.29 (d, J = 6.0 Hz, 6H). Anal. Calcd. for (C20H20ClN2O6PS): C, 49.75 H, 4.17; N, 5.80. Found: C, 49.48; H, 4.13; N. 5.81. |
| 76 | 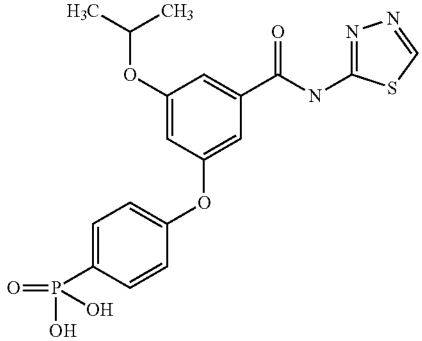 [SMILES: CC(C)Oc1cc(Oc2ccc(P(=O)(O)O)cc2)cc(C(=O)Nc2nncs2)c1] | 436.4 (+) | 9.21 (s, 1H), 7.70 (m, 2 H), 7.52 (m, 1H), 7.28 (m, 1H), 7.12 (m, 2H), 6.88 (m, 1H), 4.74 (m, 1 H), 1.29 (d, J = 6.3 Hz, 6H). Anal. Calcd. for (C18H18N3O6PS): C, 48.75 H, 4.11; N, 9.47. Found: C, 48.91; H, 4.02; N, 9.35. |

-continued

| Example | Structure | Mass Spect. (Mode) | 1H NMR δ (DMSO-d₆) & Elemental Analysis |
|---------|-----------|--------------------|-----------------------------------------|
| 77 | 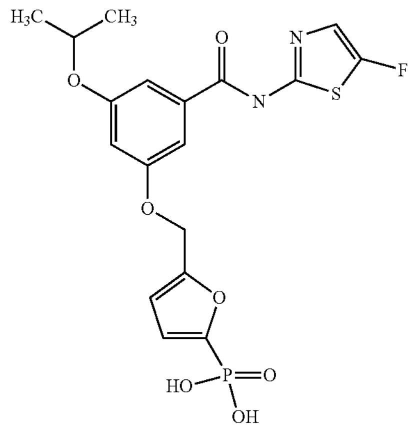 [SMILES: CC(C)Oc1cc(OCc2ccc(P(=O)(O)O)o2)cc(C(=O)Nc2ncc(F)s2)c1] | 457.4 (+) | 7.41 (s, 1 H), 7.40 (s, 1H), 7.26 (s, 1H), 6.85 (m, 2H), 6.66 (m, 1H), 5.17 (s, 2H), 4.73 (m, 1 H), 1.29 (d, J = 5.7 Hz, 6H). Anal. Calcd. for (C18H18FN2O7PS + 0.15 HBr): C, 46.14 H, 3.90; N, 5.98. Found: C, 46.17; H, 4.13; N, 5.79. |
| 78 | 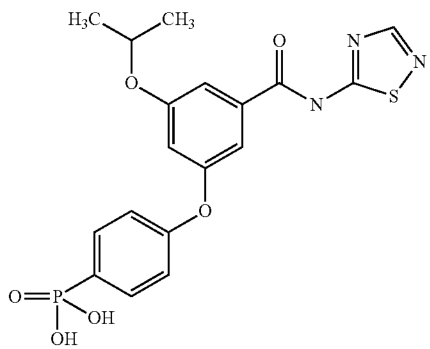 [SMILES: CC(C)Oc1cc(Oc2ccc(P(=O)(O)O)cc2)cc(C(=O)Nc2ncns2)c1] | 436.4 (+) | 7.72 (m, 2 H), 7.57 (m, 1H), 7.34 (m, 1H), 7.14 (m, 2H), 6.93 (m, 1H), 4.77 (m, 1 H), 1.32 (d, J = 6.0 Hz, 6H). Anal. Calcd. for (C18H18N3O6PS + 0.2 HBr): C, 47.88 H, 4.06; N, 9.31. Found: C, 8.00; H, 3.79; N, 9.43. |
| 79 | 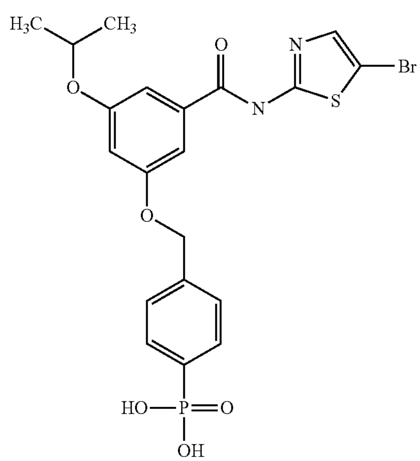 [SMILES: CC(C)Oc1cc(OCc2ccc(P(=O)(O)O)cc2)cc(C(=O)Nc2ncc(Br)s2)c1] | 528.3 (+) | 7.68 (m. 3 H), 7.52 (m, 2H), 7.32 (m, 1H), 7.26 (s, 1H), 6.78 (m, 1H), 5.21 (s, 2H), 4.70 (m, 1 H), 1.26 (d, J = 3.6 Hz, 6H). Anal. Calcd. for (C20H20BrN2O6PS): C, 45.55 H, 3.82; N, 5.31. Found: C, 45.73; H, 3.66; N, 5.18. |
| 80 | 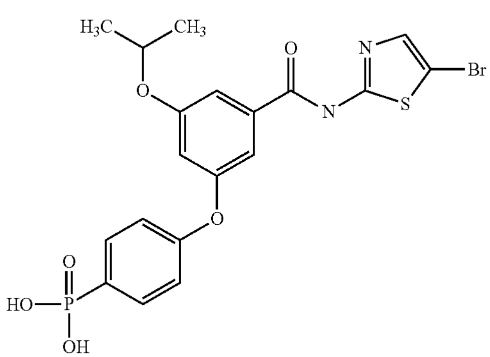 [SMILES: CC(C)Oc1cc(Oc2ccc(P(=O)(O)O)cc2)cc(C(=O)Nc2ncc(Br)s2)c1] | 514.3 (+) | δ 7.70 (m, 2 H), 7.65 (s, 1H), 7.49 (m, 1H), 7.26 (m, 1H), 7.12 (m, 2H), 6.87 (m, 1H), 4.74 (m, 1H), 1.29 (d, J = 3.6 Hz, 6H). Anal. Calcd, for (C19H18BrN2O6PS); C, 44.46 H, 3.53; N, 5.46. Found: C, 44.45; H, 3.66; N, 5.18. |

| Example | Structure | Mass Spect. (Mode) | 1H NMR δ (DMSO-d$_6$) & Elemental Analysis |
|---|---|---|---|
| 81 | 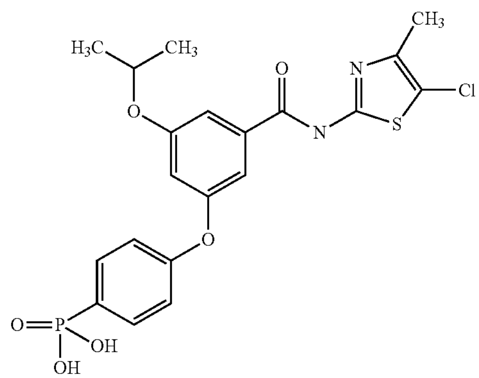 [SMILES: Cc1nc(NC(=O)c2cc(Oc3ccc(P(=O)(O)O)cc3)cc(OC(C)C)c2)sc1Cl] | 483.9 (+) | 7.66 (m, 2 H), 7.44 (s; 1H), 7.21 (s, 1H), 7.07 (m, 2H), 6.81 (m, 1H), 4.69 (m, 1 H), 2.20 (s, 3H), 1.24 (d, J = 6.0 Hz, 6H). Anal. Calcd. for (C20H20ClN2O6PS): C, 49.75 H, 4.17; N, 5.80. Found: C. 50.03; H, 3.92; N, 5.64. |
| 82 | 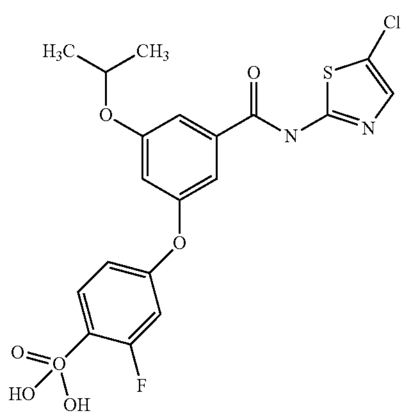 | 487.4 (+) | 1.30 (d, 6H, J = 6 Hz), 4.73-4.78 (m, 1H), 6.89-7.01 (m, 3H), 7.33 (t, 1H, J = 2 Hz), 7.52 (t, 1H, J = 2 Hz), 7.61 (s, 1H), 7.65-7.75 (m, 1H). Anal. Calcd, for C$_{19}$H$_{17}$ClFN$_2$O$_6$PS: C, 46.88; H, 3.52; N, 5.75. Found: C. 47.04; H, 2.86; N, 5.58. |
| 83 | 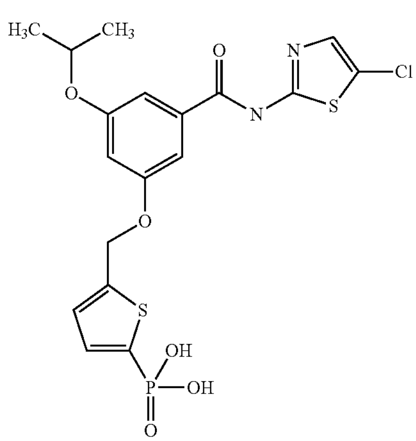 [SMILES: CC(C)Oc1cc(OCc2ccc(P(=O)(O)O)s2)cc(C(=O)Nc2ncc(Cl)s2)c1] | 489.4 (+) | 7.61 (s, 1 H), 7.30 (m, 4H), 6.80 (m, 1H), 5.39 (s, 2H), 4.72 (m, 1 H), 1.28 (d, J = 6.0 Hz, 6H). Anal Calcd for (C18H18ClN2O6PS2); C, 44.22 H, 3.71; N, 5.73. Found: C, 44.16; H, 3.79; N, 5.61. |

-continued

| Example | Structure | Mass Spect. (Mode) | 1H NMR δ (DMSO-d$_6$) & Elemental Analysis |
|---|---|---|---|
| 84 | 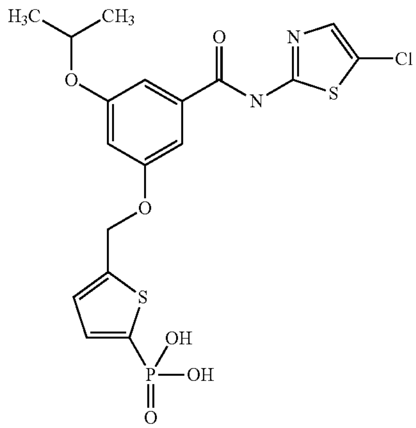 [SMILES: CC(C)Oc1cc(OCc2ccc(P(=O)(O)O)s2)cc(C(=O)Nc2ncc(Cl)s2)c1] | 473.4 (+) | 7.39 (d, J = 2.7 Hz, 1 H), 7.32 (m, 2H), 7.23 (m, 2H), 6.79 (m, 1H), 5.39 (s, 2H), 4.71 (m, 1 H), 1.27 (d, J = 6.3 Hz, 6H), Anal Calcd for (C18H18FN2O6PS2): C, 45.76 H, 3.84; N, 5.93. Found: C. 45.67; H, 3.93; N, 6.12, |
| 85 | 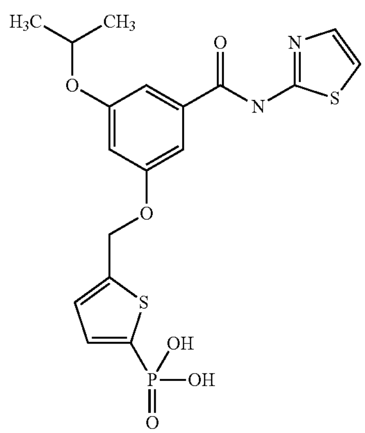 [SMILES: CC(C)Oc1cc(OCc2ccc(P(=O)(O)O)s2)cc(C(=O)Nc2nccs2)c1] | 455.1 (+) | 7.59 (d, J = 3.6 Hz, 1 H), 7.34 (m, 5H), 6.82 (s, 1H), 5.43 (s, 2H), 4.76 (m, 1 H), 1.31 (d, J = 5.7 Hz, 6H). Anal Calcd for (C18H19N2O6PS2 + 1.0 H2O): C, 45.76, 4.48; N, 5.93. Found: C, 46.12; H, 4.40; N, 5.54. |
| 86 | 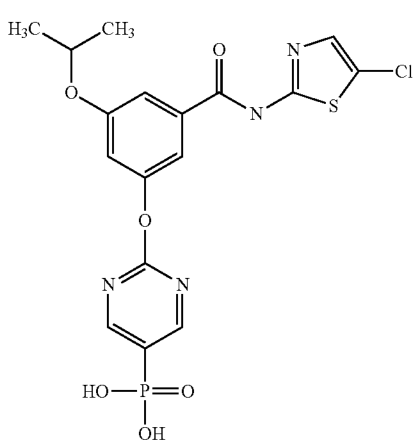 [SMILES: CC(C)Oc1cc(Oc2ncc(P(=O)(O)O)cn2)cc(C(=O)Nc2ncc(Cl)s2)c1] | 471.4 (+) | 8.63 (d, J = 6.0 Hz, 2H), 7.58 (d, J = 1.2 Hz, 1 H), 7.50 (m, 1H), 7.46 (m, 1H), 7.06 (m, 1H), 4.72 (m, 1 H), 1.28 (d, J = 6.3 Hz, 6H), Anal Calcd for (C17H16ClN4O6PS + 0.5 NH3 + 1.2 H2O): C, 40.76; H, 4.00; N, 12.58. Found: C, 40.59; H, 4.22; N, 12.73. |

| Example | Structure | Mass Spect. (Mode) | 1H NMR δ (DMSO-d₆) & Elemental Analysis |
|---|---|---|---|
| 87 | (isopropoxy-benzamide-thiazolopyridine with fluoro-phosphonophenoxy, 2 BrH salt) | 504.6 (+) | 8.50 (m, 1 H), 8.14 (dd, J = 8, 1 Hz, 1 H), 7.65-7.75 (m, 1 H), 7.56 (m, 1 H), 7.51 (dd, J = 8, 5 Hz, 1 H), 7.36 (m, 1H) 6.91-7.02 (m, 3 H), 4.72-4.80 (m, 1 H), 1.29 (d, J = 6 Hz, 6 H). Anal. Calcd, for (C22H19FN3O6PS + 2.0 HBr + 2.0 H2O): C. 37.68; H, 3.59; N, 5.99. Found: C, 37.65; H, 3.64; N, 5.59. |
| 88 | (isopropoxy-benzamide-thiazolopyridine with phosphonophenoxy) | 486.6 (+) | 8.48 (dd, J = 5, 1 Hz, 1H), 8.12 (dd, J = 8, 1 Hz, 1H), 7.10 (dd, J = 12, 9 Hz, 2H), 7.54 (m, 1 H), 7.50 (dd, J = 8, 5 Hz, 1H), 7.31 (m, 1 H), 7.14 (dd, J = 9, 3 Hz, 2H), 6.89 (m, 1H), 4.75-4.81 (m, 1 H), 1.32 (d, J = 6 Hz, 6 H). Anal. Calcd. for (C20H20N3O6PS + 0.5 H2O): C, 53.44; H, 4.28; N, 8.50. Found: C. 53.55; H, 4.07; N, 8.43. |
| 89 | (isopropoxy-benzamide-chlorothiazole with methyl-phosphonophenoxy) | 483.1 (+) | ¹H NMR (300 MHz, DMSO-d₆) δ 1.29 (d, 6H), 4.72-4.77 (m, 1H), 6.84 (t, 1H), 6.89 (d, 1H), 6.95 (s, 1H), 7.24 (t, 1H), 7.47 (s, 1H), 7.60 (s, 1H), 7.76 (dd, 1H); Anal. Calcd. for (C20H20ClN2O6PS + 0.6 H2O): C, 48.66; H, 4.33; N, 5.67. Found: C. 48.98; H, 4.03; N, 5.39. |
| 90 | (isopropoxy-benzamide-chlorothiazole with phosphonopyridinyloxy) | 470.4 (+) | ¹H NMR (300 MHz, DMSO-d₆) δ 1.31 (d, 6H), 4.72-4.78 (m, 1H), 6.99 (t, 1H), 7.32 (t, 1H), 7.50-7.61 (m, 2H), 7.61 (s, 1H), 7.83 (dd, 1H), 8.58 (d, 1H); Anal. Calcd. for (C₁₈H₁₇ClN₃O₆PS): C, 46.02; H, 3.65; N, 8.94. Found: C, 45.75; H, 3.82; N, 8.72. |

-continued

| Example | Structure | Mass Spect. (Mode) | 1H NMR δ (DMSO-d$_6$) & Elemental Analysis |
|---|---|---|---|
| 91 | 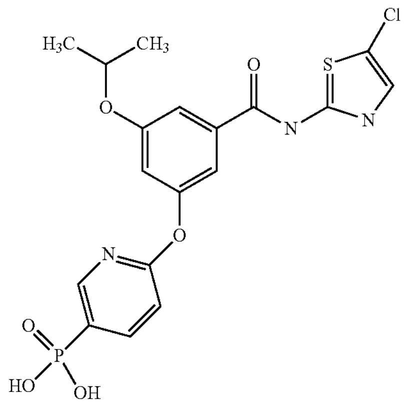 | 470.4 (+) | $^1$H NMR (300 MHz, DMSO-d$_6$) δ 1.30 (d, 6H), 4.72-4.77 (m, 1H), 7.02 (t, 1H), 7.15 (dd, 1H), 7.42 (s, 1H), 7.54 (S. 1H), 7.61 (s, 1H), 8.02-8.10 (m, 1H), 8.38 (dd, 1H); Anal. Calcd. for (C$_{18}$H$_{17}$ClN$_3$O$_6$PS), C, 45.15; H, 3.79; N, 8.78. Found: C, 45.46; H, 3.52; N, 8.73. |
| 92 | 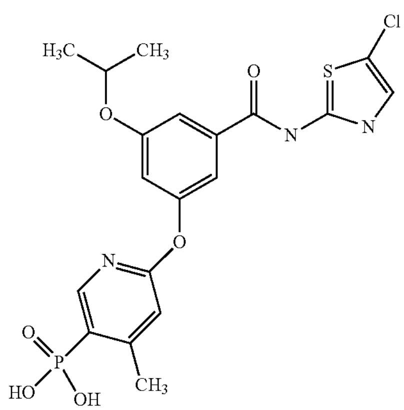 | 484.1 (+) | $^1$H NMR (300 MHz, DMSO-(d$_6$) δ 1.30 (d, 6H), 2.53 (s, 3H), 4.72-4.77 (m, 1H), 6.98-7.01 (m, 2H), 7.39 (s, 1H), 7.53 (s. 1H), 7.61 (s, 1H), 8.35 (d, 1H), Anal. Calcd. for (C$_{19}$H$_{19}$ClN$_3$O$_6$PS + 1.0 H2O): C, 45.47; H, 4.22; N, 8.37. Found: C, 45.63; H, 3.89; N. 7.97. |
| 93 | 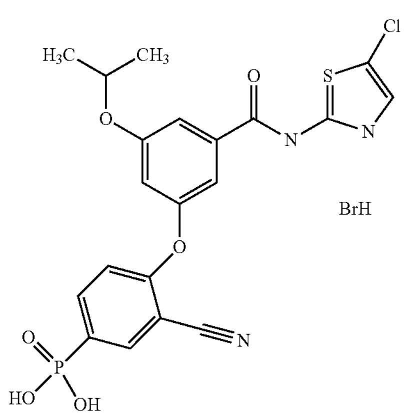 | 494.4 (+) | $^1$H NMR (300 MHz, DMSO-(d$_6$) δ 1.30 (d, 6H), 4.75-4.80 (m, 1H), 7.12-7.13 (m, 2H), 7.42 (s, 1H), 7.57 (s, 1H), 7.61 (s, 1H), 7.88-7.95 (m, 1H), 8.04 (d, 1H); Anal. Calcd. for (C$_{20}$H$_{17}$ClN$_3$O$_6$PS + 1.1 HBr): C, 41.21, H, 3.13, N, 7.21. Found: C, 41.29; H, 3.05; N, 6.89. |

-continued

| Example | Structure | Mass Spect. (Mode) | 1H NMR δ (DMSO-$d_6$) & Elemental Analysis |
|---|---|---|---|
| 94 | 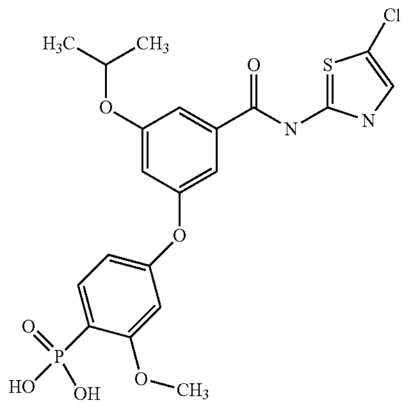 | 499.6 (+) | $^1$H NMR (300 MHz, DMSO-$d_6$) δ 1.29-1.31 (m, 6H), 3.77 (s, 3H), 4.71-4.79 (m, 1H), 6.59 (d, 1H), 6.80 (d, 1H), 6.87 (d, 1H), 7.29 (s, 1H), 7.50 (s, 1H), 7.61 (d, 1H), 7.64-7.69 (m, 2H); Anal. Calcd. for ($C_{20}H_{20}ClN_2O_7PS$ + 0.9 $H_2O$): C, 46.64; H, 4.27; N, 5.44, Found: C, 45.76; H, 4.27; N, 5.27. |
| 95 | 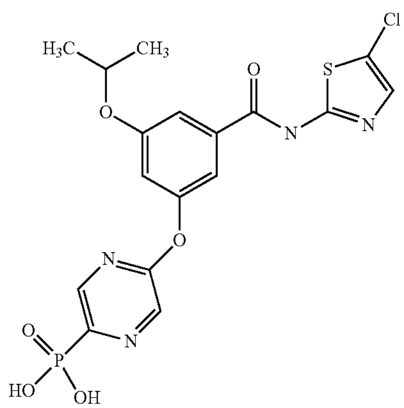 [SMILES: CC(C)Oc1cc(Oc2cnc(P(=O)(O)O)cn2)cc(C(=O)Nc2ncc(Cl)s2)c1] | 471.4 (+) | $^1$H NMR (300 MHz, DMSO-$d_6$) δ 1.30 (d, 6H), 4.72-4.77 (m, 1H), 7.14 (t, 1H), 7.50 (s, 1H), 7.57 (d, 1H), 7.62 (d, 1H), 8.46 (s, 1H), 8.72 (d, 1H); Anal. Calcd. for ($C_{17}H_{16}ClN_4O_6PS$): C, 43.37; H, 3.43; N, 11.90. Found: C, 43.62; H, 3.47; N, 11.61. |
| 96 | 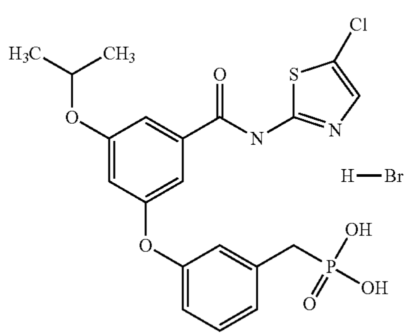 | 483.1 (+) | 7.61 (s, 1 H), 7.43 (m, 1H), 7.28 (m, 1H), 7.08 (d, J = 7.5 Hz, 1H), 6.99 (d, J = 1.5 Hz, 1H), 6.91 (d, J = 8.0 Hz, 1H), 6.76 (m, 1H), 4.72 (m, 1 H), 2.98 (d, J = 21.5 Hz, 2H) 1.28 (d, J = 6.0 Hz, 6H). Anal Calcd for (C20H20ClN2O6PS + 0.2 $H_2O$): C, 49.38 H, 4.23; N, 5.76. Found: C, 49.25; H, 4.02; N, 5.50. |
| 97 | 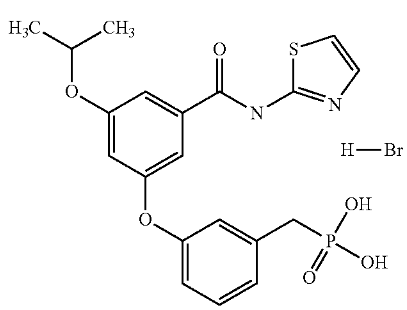 | 449.4 (+) | 7.74 (d, J = 4.0 Hz, 1 H), 7.52 (d, J = 4.5 Hz, 1H), 7.37 (m, 1H), 7.33 (d, J = 2.0 Hz, 1H), 7.16 (m, 3H), 6.99 (d, J = 7.5 Hz, 1H), 6.92 (m, 1H), 4.70 (m, 1 H), 3.18 (d, J = 21.5 Hz, 2H) 1.36 (d, J = 6.0 Hz, 6H). Anal Calcd for (C20H21N2O6PS + 1.5 HBr + 0.4 $H_2O$): C, 41.63 H, 4.07; N, 4.85. Found: C, 41.70; H, 4.29; N, 4.65. |

| Example | Structure | Mass Spect. (Mode) | 1H NMR δ (DMSO-d$_6$) & Elemental Analysis |
|---|---|---|---|
| 98 | 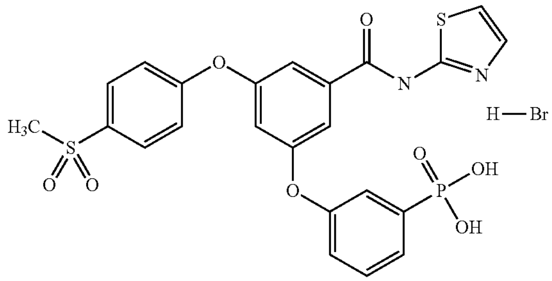 | 547.6 (+) | 800 (d, J = 4.0 Hz, 2 H), 7.57 (m, 5H), 7.51 (m, 2H), 7.31 (m, 3H), 7.08 (s, 1H), 3.14 (s, 3H). Anal Calcd for (C23H19N2O8PS2 + 1.3 HBr + 0.3 H$_2$O): C, 42.04 H. 3.21; N, 4.26. Found: C, 41.86; H, 3.49; N. 4.00. |
| 99 | 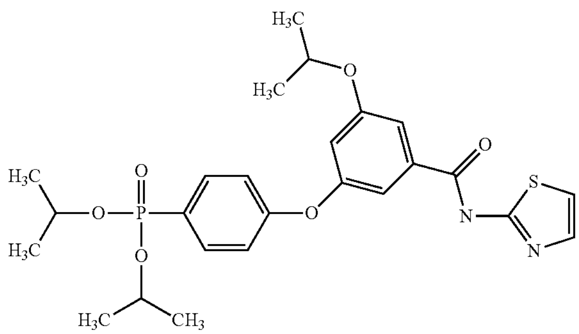 [SMILES: CC(C)Oc1cc(Oc2ccc(P(=O)(OC(C)C)OC(C)C)cc2)cc(C(=O)Nc2nccs2)c1] | 519.6 (+) | 12.68 (bs, 1 H), 7.73 (m, 2 H), 7.54 (m, 2 H), 7.36 (t, J = 2 Hz, 1 H), 7.28 (d, J = 4 Hz, 1H), 7.16 (m, 2 H), 6.93 (t, J = 4 Hz, 1 H), 4.76 (m, 1 H), 4.55 (m, 2 H), 1.29 (m, 12 H), 1.18 (d, J = 6 Hz, 6 H). Anal. Calcd. for (C$_{25}$H$_{31}$N$_2$O$_6$PS): C, 57.90: H, 6.03; N, 5.40. Found: C, 57.73; H, 5.99; N, 5.37. |
| 100 | 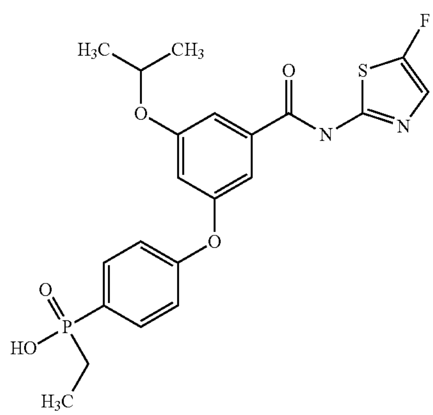 [SMILES: CCP(=O)(O)c1ccc(Oc2cc(OC(C)C)cc(C(=O)Nc3ncc(F)s3)c2)cc1] | 465.6 (+) | 7.69 (t, J = 9 Hz, 2 H), 7.44 (s, 1 H), 7.29 (d, J = 2 Hz, 1H), 7.04 (dd, J = 7.1 Hz, 2 H), 6.78 (s, 1 H), 4.70 (m, 1 H), 1.50 (m, 2 H), 1.25 (m, 6 H) 0.86 (m, 3 H). |
| 101 | 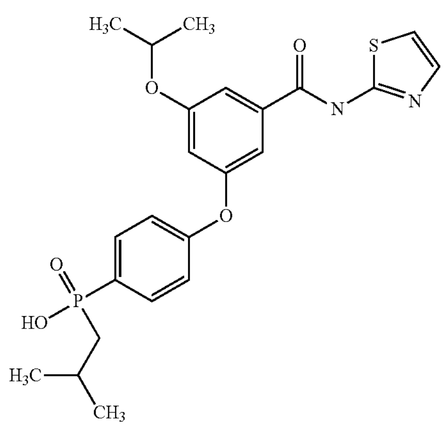 [SMILES: CC(C)CP(=O)(O)c1ccc(Oc2cc(OC(C)C)cc(C(=O)Nc3nccs3)c2)cc1] | 475.6 (+) | 7.72 (t, J = 10 Hz, 2 H), 7.55 (d, J = 4 Hz, 1 H), 7.50 (s, 1H), 7.28 (dd, J = 8, 4 Hz, 2 H), 7.10 (d, J = 8 Hz, 2 H), 6.83 (s, 1 H), 4.74 (m, 1 H), 1.81 (m, 1 H), 1.60 (m, 2 H), 1.28 (m, 6 H), 0.90 (d, J = 6 Hz, 6 H). Anal. Calc. for (C$_{23}$H$_{27}$N$_2$O$_5$PS): C, 58.22; H, 5.74; N, 5.90. Found: C, 58.01; H, 5.58; N, 5.75. |

-continued

| Example | Structure | Mass Spect. (Mode) | 1H NMR δ (DMSO-d$_6$) & Elemental Analysis |
|---|---|---|---|
| 102 | 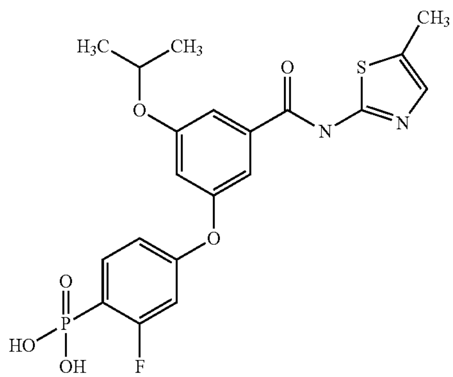 [SMILES: Cc1cnc(NC(=O)c2cc(Oc3ccc(P(=O)(O)O)c(F)c3)cc(OC(C)C)c2)s1] | 467.4 (+) | 7.69 (m, 1 H), 7.51 (d, 1= 2 Hz, 1 H), 7.32 (dd, J = 3.2 Hz, 1H), 7.22 (d, J = 2 Hz, 1 H), 6.98 (m, 1 H), 6.90 (m, 2 H), 4.75 (m, 1 H), 2.36 (d, 1= 1 Hz, 3 H), 1.30 (d, J = 6 Hz, 6 H). Anal. Calcd. for (C$_{20}$H$_{20}$FN$_2$O$_6$PS): C, 51.50; H, 4.32; N, 6.01. Found: C, 51.25; H, 4.28; N, 5.71. |
| 103 | 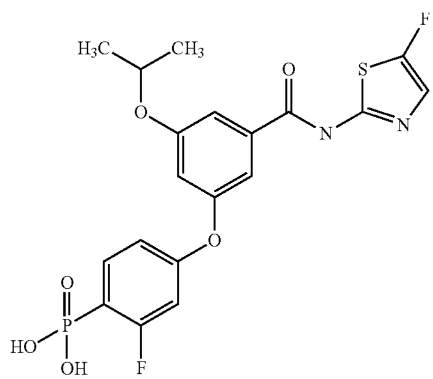 [SMILES: CC(C)Oc1cc(Oc2ccc(P(=O)(O)O)c(F)c2)cc(C(=O)Nc2ncc(F)s2)c1] | 471.6 (+) | 7.69 (m, 1 H), 7.51 (t, J = 2 Hz, 1 H), 7.39 (d, J = 2 Hz, 1H), 7.31 (dd, J = 3, 2 Hz, 1 H), 6.92 (m, 3 H), 4.76 (m, 1 H), 1.30 (d, J = 6 Hz, 6 H). Anal. Calcd. for (C$_{19}$H$_{17}$F$_2$N$_2$O$_6$PS): C, 47.78; H, 3.76; N, 5.87. Found C, 47.77; H, 3.65; N, 6.04. |
| 104 | 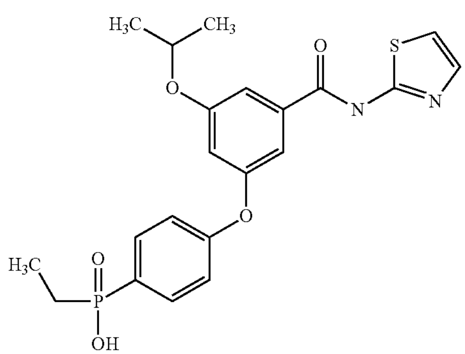 [SMILES: CCP(=O)(O)c1ccc(Oc2cc(OC(C)C)cc(C(=O)Nc3nccs3)c2)cc1] | 447.9 (+) | 7.73 (m, 2 H), 7.56 (s, 1 H), 7.53 (dd, J = 3, 1 Hz, 1H), 7.31 (m, 2 H), 7.15 (dd, J = 9, 2 Hz, 2 H), 6.88 (t, J = 2 Hz, 1 H). 4.76 (m, 1 H), 1.74 (m, 2 H), 1.30 (d, J = 6 Hz, 6 H), 0.95 (m, 3 H). Anal. Calcd, for (C21H23N2O5PS +0.5 HCl): C, 54.28; H, 5.10; N. 6.03. Found: C, 54.03; H, 4.76; N, 5.89. |
| 105 | 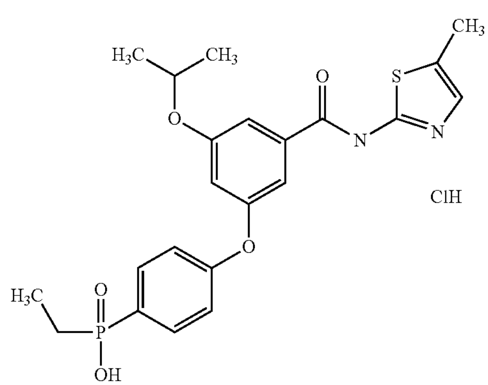 [SMILES: CCP(=O)(O)c1ccc(Oc2cc(OC(C)C)cc(C(=O)Nc3ncc(C)s3)c2)cc1 ; Cl] | 461.6 (+) | 7.73 (m, 2H), 7.51 (t, J = 2 Hz, 1 H), 7.29 (t, J = 1 Hz, 1H), 7.28 (d, J = 1 Hz, 1 H), 7.15 (m, 2 H), 6.87 (t, J = 3 Hz, 1 H), 4.76 (m, 1 H), 2.36 (s, 3 H). 1.74 (m, 2 H), 1.30 (d, J = 6 Hz, 6 H), 0.95 (m, 3 H). Anal. Calcd, for (C$_{22}$H$_{25}$N$_2$O$_5$PS +0.7 HCl) C, 54.37; H, 5.33; N, 5.76. Found: C, 54.65; H, 4.91; N, 5.71. |

-continued

| Example | Structure | Mass Spect. (Mode) | 1H NMR δ (DMSO-d$_6$) & Elemental Analysis |
|---|---|---|---|
| 106 | 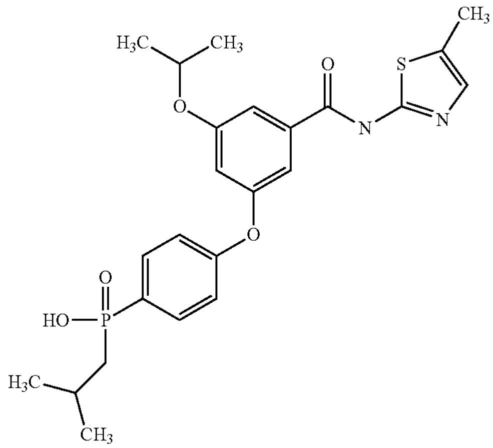 [SMILES: Cc1cnc(NC(=O)c2cc(Oc3ccc(P(=O)(O)CC(C)C)cc3)cc(OC(C)C)c2)s1] | 489.6 (+) | 7.74 (t, J = 8 Hz, 2 H), 7.50 (s, 1 H), 7.28 (s, 1H), 7.22 (s, 1 H), 7.13 (d, J = 7 Hz, 2 H) 6.85 (s, 1 H), 4.75 (m, 1 H), 2.36 (s, 3 H), 1.83 (m, 1 H), 1.68 (m, 2 H), 1.30 (d, J = 6 Hz, 6 H), 0.92 (d, J =3Hz, 6 H), Anal. Calcd. for (C$_{24}$H$_{29}$N$_2$O$_5$ +LPS): C, 59.01; H, 5.98; N, 5.73, Found: C, 58.82; H, 5.91; N, 5.46, |
| 107 | 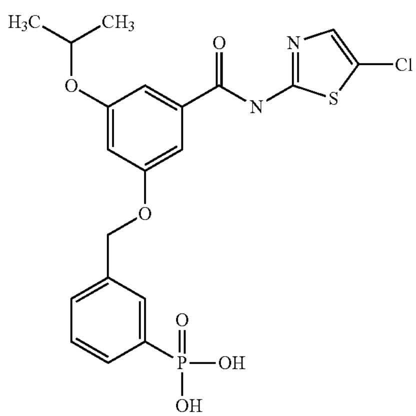 [SMILES: CC(C)Oc1cc(OCc2cccc(P(=O)(O)O)c2)cc(C(=O)Nc2ncc(Cl)s2)c1] | 483.1 (+) | 7.79 (d, J = 13.2 Hz. 1H), 7.65 (m, 2H), 7.63 (s, 1H). 7.51 (m, 1H), 7.36 (m, 1H), 7.29 (m, 1H), 6.82 (m, 1H), 5.23 (s, 2H), 4.74 (m, 1 H), 1.29 (d, J = 6.0 Hz, 6H). Anal Calcd for (C20H20ClN2O6PS + 0.8 H$_2$O): C, 48.31 H, 4.38; N, 5.63, Found: C, 48.41; H, 4.47; N, 5.33. |
| 108 | 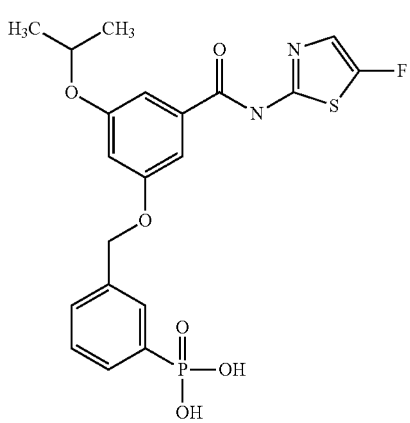 [SMILES: CC(C)Oc1cc(OCc2cccc(P(=O)(O)O)c2)cc(C(=O)Nc2ncc(F)s2)c1] | 467.4 (+) | 7.77 (d, J = 13.2 Hz, 1 H), 7.63 (m, 2H), 7.50 (m, 1H). 7.39 (d, J = 2,4 Hz, 1H), 7.32 (m, 1H), 7.25 (m, 1H), 6.79 (m, 1H), 5.21 (s, 2H), 4.71 (m, 1 H), 1.27 (d, J = 6.0 Hz, 6H). Anal Calcd for (C20H20FN2O6PS + 0.3 H$_2$O): C, 50.91 H, 4.40; N, 5.94, Found: C, 50.85; H, 4.39; N, 5.74. |

-continued

| Example | Structure | Mass Spect. (Mode) | 1H NMR δ (DMSO-d$_6$) & Elemental Analysis |
|---|---|---|---|
| 109 | 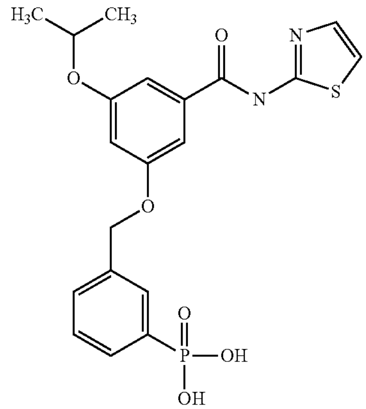 [SMILES: CC(C)Oc1cc(OCc2cccc(P(=O)(O)O)c2)cc(C(=O)Nc2nccs2)c1] | 449.4 (+) | 7.78 (d, J = 13.2 Hz, 1 H), 7.53 (m, 4H), 7.36 (s, 1H), 7.28 (m, 2H), 6.79 (m, 1H), 5.22 (s, 2H), 4.73 (m, 1 H), 1.29 (d, J = 6.0 Hz, 6H). Anal Calcd for (C20H21N2O6PS): C, 53.57 H, 4.72; N, 6.25. Found: C, 53.49; H, 4.76: N, 5.98. |
| 110 | 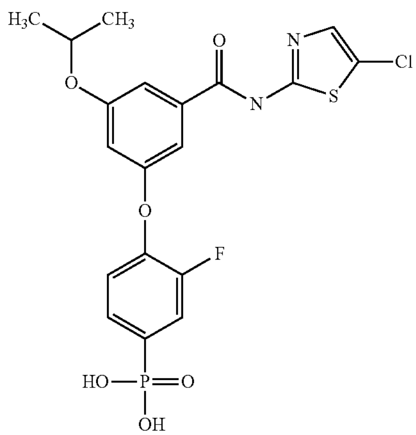 [SMILES: CC(C)Oc1cc(Oc2ccc(P(=O)(O)O)cc2F)cc(C(=O)Nc2ncc(Cl)s2)c1] | 487.4 (+) +32 | 7.59 (s, 1 H), 7.53 (d, J = 12.3 Hz, 1H), 7.48 (s, 2H), 7.27 (m, 2H), 7.18 (s, 1H), 6.88 (s, 1H), 4.74 (m, 1 H), 1.28 (d, J 6.0 Hz, 6H). Anal Calcd for (C19H17ClFN2O6PS): C, 46.88 H, 3.52; N, 5.75. Found: C, 46.83; H. 3.80; N, 5.53. |
| 111 | 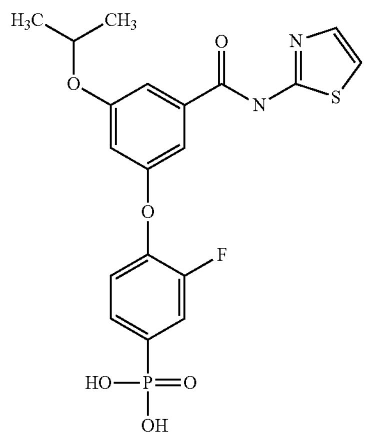 [SMILES: CC(C)Oc1cc(Oc2ccc(P(=O)(O)O)cc2F)cc(C(=O)Nc2nccs2)c1] | 453.4 (+) | δ 7.54 (m, 4H), 7.29 (m, 2H), 7.19 (s, 1H), 6.86 (s, 1H), 4.75 (m, 1 H), 1.29 (d, J = 6.0 Hz, 6H). Anal Calcd for (C19H18FN2O6PS + 0.8 H2O): C, 48.89 H, 4.23; N, 6.00, Found: C, 48.75; H, 4.05; N, 5.83. |

-continued

| Example | Structure | Mass Spect. (Mode) | 1H NMR δ (DMSO-d$_6$) & Elemental Analysis |
|---|---|---|---|
| 112 | 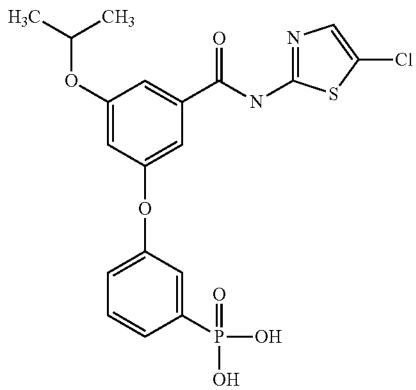 [SMILES: CC(C)Oc1cc(Oc2cccc(P(=O)(O)O)c2)cc(C(=O)Nc2ncc(Cl)s2)c1] | 469.4 (+) | 7.59 (s, 1 H), 7.48 (m, 3H), 7.25 (m, 3H), 6.82 (s, 1H), 4.73 (m, 1 H), 1.28 (d, J = 6.0 Hz, 6H). Anal Calcd for (C19H18ClN2O6PS + 0.2 H2O): C, 48.30 H. 3.93; N. 5.93. Found: C, 48.51; H, 5.88; N, 4.29. |
| 113 | 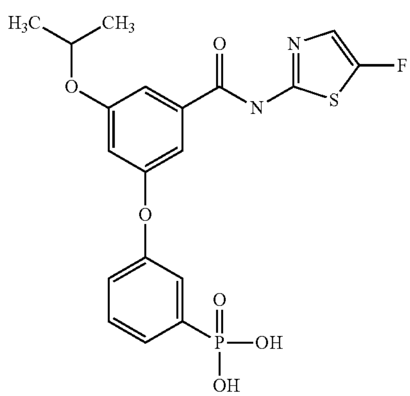 [SMILES: CC(C)Oc1cc(Oc2cccc(P(=O)(O)O)c2)cc(C(=O)Nc2ncc(F)s2)c1] | 453.4 (+) | 7.48 (m, 3H), 7.37 (m, 1 H), 7.23 (m, 3H), 6.81 (s, 1H), 4.73 (m, 1 H), 1.28 (d, J = 6.0 Hz, 6H). Anal Calcd for (C19H18FN2O6PS + 0.6 H2O): C, 49.27 H, 4.18; N, 6.05. Found: C, 49.73, H, 4.65; N, 6.14. |
| 114 | 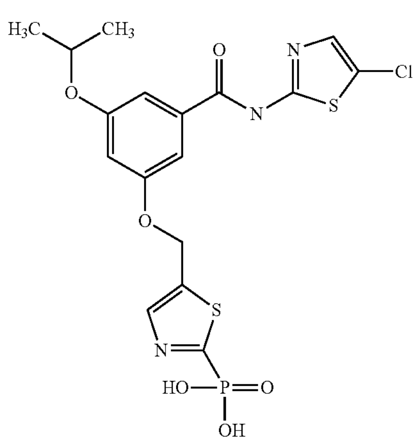 [SMILES: CC(C)Oc1cc(OCc2cnc(P(=O)(O)O)s2)cc(C(=O)Nc2ncc(Cl)s2)c1] | 490.4 (+) | 8.14 (s, 1 H), 7.63 (s, 1H), 7.37 (m, 1H), 7.31 (m, 1H), 6.84 (m, 1H), 5.51 (s, 2H), 4.74 (m, 1 H), 1.30 (d, J = 6.0 Hz, 6H). Anal Calcd for (C17H17ClN3O6PS2 + 1.6 H2O): C, 39.36 H, 3.93; N, 8.10, Found: C, 42.70; H, 402; N, 7.65 |

-continued

| Example | Structure | Mass Spect. (Mode) | 1H NMR δ (DMSO-d₆) & Elemental Analysis |
|---|---|---|---|
| 115 | 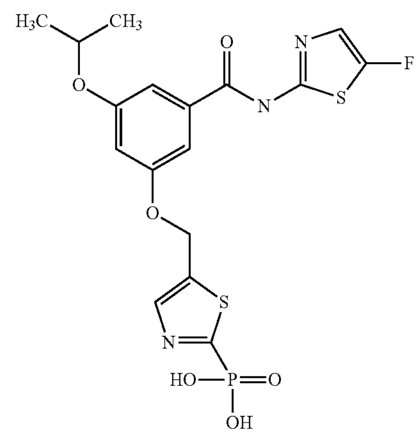 [SMILES: CC(C)Oc1cc(OCc2cnc(P(=O)(O)O)s2)cc(C(=O)Nc2ncc(F)s2)c1] | 474.6 (+) | 8.11 (s, 1 H), 7.38 (d, J = 2.7 Hz), 7.32 (s, 1H), 7.26 (s, 1H), 6.81 (m, 1H), 5.48 (s, 2H), 4.71 (m, 1 H), 1.27 (d, J = 6.3 Hz, 6H), Anal Calcd for (C17H17FN3O6PS2): C, 43.13 H, 3.62; N, 8.88. Found: C, 42.89; H, 3.75; N, 8.48. |
| 116 | 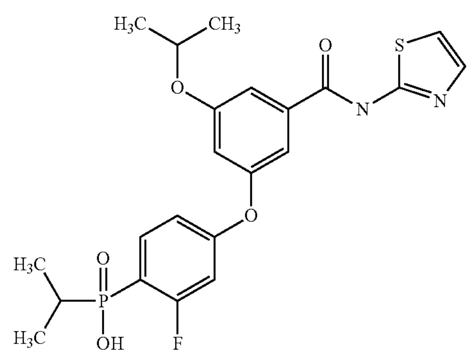 [SMILES: CC(C)Oc1cc(Oc2ccc(P(=O)(O)C(C)C)c(F)c2)cc(C(=O)Nc2nccs2)c1] | 479.1 (+) | 7.68-7.77 (m, 1 H), 7.55 (d, J = 4 Hz, 1H), 7.54 (m, 1 H), Hz, 1 H), 7.02 (m, 1 H), 6.98 (m, 1 H), 6.95 (m, 1 H), 4.72-4.80 (m, 1 H), 1.90-2.04 (m, 1 H), 1.30 (d, J = 6 Hz, 6H), 1.00 (dd, J = 18, 7 Hz, 6 H), Anal Calcd for (C22H24FN2O5PS + 0.9 H2O): C, 43.13 H, 3.62; N, 8.88. Found: C, 42.89; H, 3.75; N, 8.48. |
| 117 | 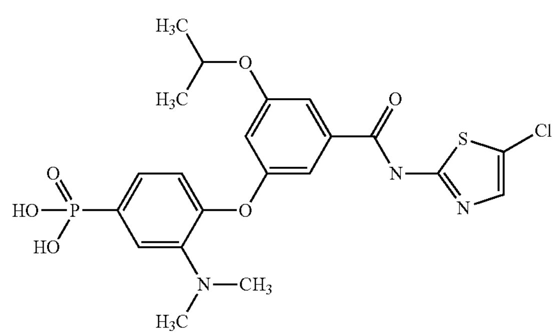 [SMILES: CC(C)Oc1cc(Oc2ccc(P(=O)(O)O)cc2N(C)C)cc(C(=O)Nc2ncc(Cl)s2)c1] | 512.4 (+) | 7.60 (s, 1 H), 7.40 (m, 1 H), 7.31(dd, J = 14, 2 Hz, 1 H), 7.24 (ddd, J = 12, 8, 2 Hz, 1 H), 7.09 (m, 1 H), 7.01 (dd, J = 8, 4 Hz, 1 H), 6.66 (m, 1 H) 4.65-4.75 (m, 1 H), 2.73 (s, 3 H), 1.27 (d, J = 6 Hz, 6 H). Anal. Calcd. for (C21H23ClN3O6PS + 0.1 HBr): C, 48.50; H, 4.48; N, 8.08. Found: C, 48.60; H, 4.70; N, 8.08. |
| 118 | 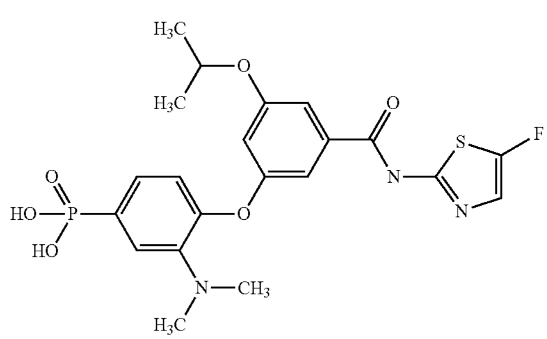 [SMILES: CC(C)Oc1cc(Oc2ccc(P(=O)(O)O)cc2N(C)C)cc(C(=O)Nc2ncc(F)s2)c1] | 496.1 (+) | 7.30-7.36 (m, 3 H), 7.24 (dd, J = 12, 9 Hz, 1 H), 7.09 (m, 1 H), 6.96 (dd, J = 8, 4 Hz, 1 H), 6.61 (m, 1H), 4.65-4.72 (m, 1 H), 2.69 (s, 3 H), 1.25(d, J = 6 Hz, 6H), Anal. Calcd. for (C21H231FN3O6PS + 0.1 HBr + 0.1 NH4Br): C, 49.13; H, 4.61; N, 8.46. Found: C, 48.90; H, 4.76; N, 8.75. |

-continued

| Example | Structure | Mass Spect. (Mode) | 1H NMR δ (DMSO-d₆) & Elemental Analysis |
|---|---|---|---|
| 119 | 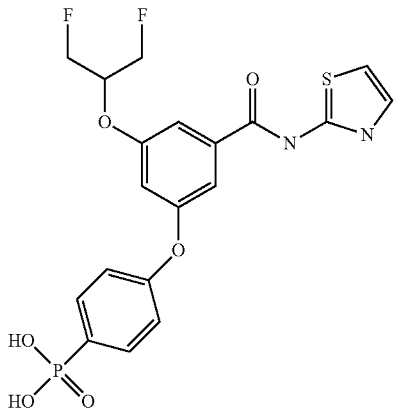 | 471.4 (+) | 4.65-4.68 (m, 1H), 4.74-4.78 (m, 2H), 4.83-4.84 (m, 1H), 5.05-5.20 (m, 1H), 7.03 (d, 1H, J = 2 Hz), 7.16 (dd, 2H, J = 9.3 Hz), 7.29 (d, 1H, J = 4 Hz), 7.63 (s, 1H), 7.56 (d, 1H, J = 4 Hz), 7.63 (s, 1H), 7.72 (dd, 2H, J = 13, 8 Hz) Anal. Calcd. for (C$_{19}$H$_{17}$F$_2$N$_2$O$_6$PS + 0.7 H$_2$O): C, 47.25; H, 3.84; N, 5.80. Found: C, 47.35; H, 3.52; N, 5.71. |
| 120 | 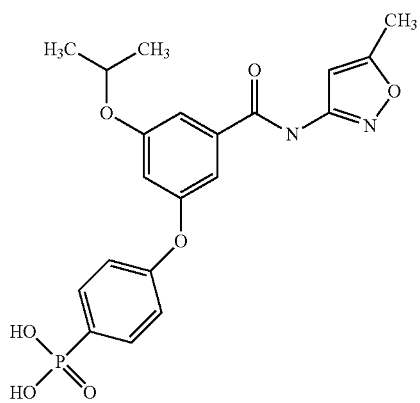 [SMILES: Cc1cc(NC(=O)c2cc(Oc3ccc(P(=O)(O)O)cc3)cc(OC(C)C)c2)no1] | 433.4 (+) | 1.27 (d, 6H, J = 6 Hz), 2.39 (s, 3H), 4.68-4.73 (m, 1H), 6.71 (s, 1H), 6.75 (t, 1H, J = 2 Hz), 6.97 (d, 2H, J = 8 Hz), 7.15 (dd, 1H, J = 2, 1 Hz). 7.35 (dd, 1H, J = 4, 1 Hz), 7.58-7.74 (m, 2H). Anal. Calcd. for C$_{20}$H$_{21}$N$_2$O$_7$P + 0.5 HBr + 1.1 NH$_3$: C, 48.87; H, 5.09; N, 8.83. Found: C, 48.71; H, 5.02; N, 8.71 |
| 121 | 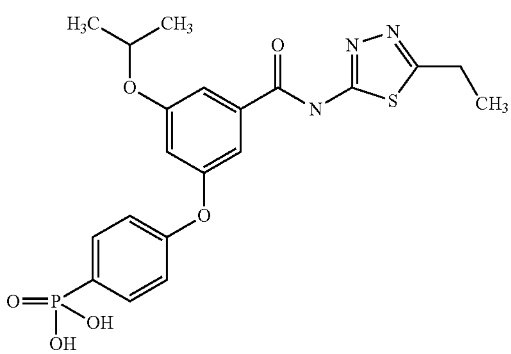 [SMILES: CCc1nnc(NC(=O)c2cc(Oc3ccc(P(=O)(O)O)cc3)cc(OC(C)C)c2)s1] | 464.4 (+) | 7.70 (m, 2 H), 7.50 (s, 1H), 7.27 (s, 1H), 7.11 (d, J = 7.5 Hz, 2H), 6.87 (s, 1H), 4.74 (m, 1 H), 2.99 (m, 2H), 1.29 (m, 9H). Anal. Calcd. for (C20H22N3O6PS + 0.1 HBr + 0.2 H2O): C, 50.56 H, 4.77; N. 8.84. Found: C, 50.91; H, 4.46; N, 8.45. |

-continued

| Example | Structure | Mass Spect. (Mode) | 1H NMR δ (DMSO-d$_6$) & Elemental Analysis |
|---|---|---|---|
| 122 | 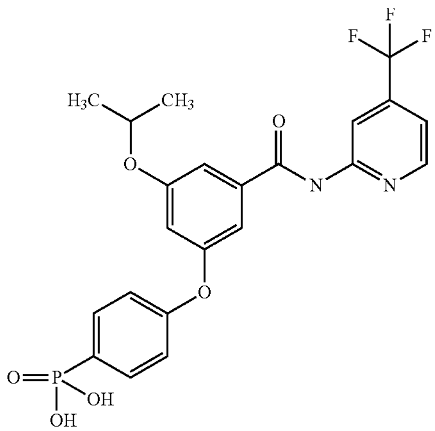 [SMILES: CC(C)Oc1cc(Oc2ccc(P(=O)(O)O)cc2)cc(C(=O)Nc2cc(C(F)(F)F)ccn2)c1] | 497.4 (+) | 11.33 (s, 1H), 8.65 (d, J = 4.8 Hz, 1H), 8.48 (s, 1H), 7.70 (m, 2 H), 7.52 (d, J = 5.1 Hz, 1H), 7.44 (s, 1H), 7.22 (m, 1H), 7.11 (m, 2H), 6.84 (m, 1H), 4.75 (m, 1 H), 1.28 (d, J = 6.3 Hz, 6H). Anal. Calcd. for (C22H20F3N2O6P + 0.1 HBr): C, 52.38 H, 4.02; N, 5.55. Found: C, 52.58; H, 3.83; N, 5.52, |
| 123 | 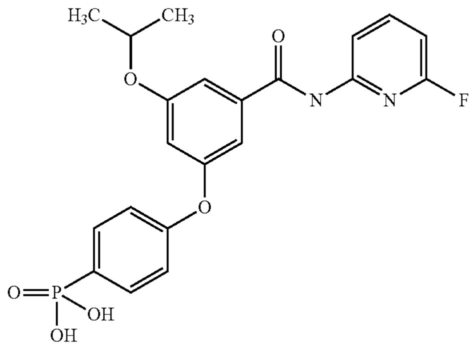 [SMILES: CC(C)Oc1cc(Oc2ccc(P(=O)(O)O)cc2)cc(C(=O)Nc2cccc(F)n2)c1] | 447.4 (+) | 11.02 (s, 1H), 8.09 (m, 1H), 8.00 (m, 1H), 7.70 (m, 2H), 7.41 (m, 1H), 7.19 (m, 1H), 7.10 (d, J = 7.5 Hz, 2H), 6.90 (m, 1H), 6.81 (m, 1H), 4.75 (m, 1 H), 1.28 (d, J = 6.0 Hz, 6H). Anal. Calcd, for (C21H20FN2O6P + 0.2 HBr): C, 54.53 H, 4.40; N, 6.06. Found: C, 54.74; H, 4.35; N, 5.88. |
| 124 | 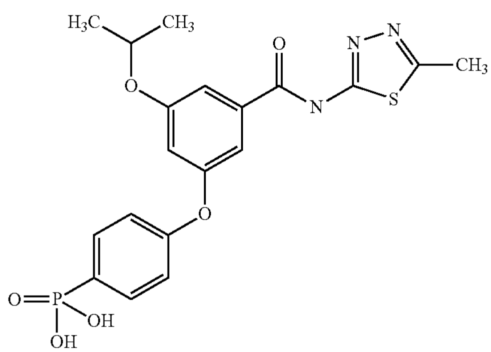 [SMILES: Cc1nnc(NC(=O)c2cc(Oc3ccc(P(=O)(O)O)cc3)cc(OC(C)C)c2)s1] | 450.4 (+) | 7.70 (m, 2 H), 7.50 (m, 1H), 7.27 (m, 1H), 7.12 (m, 2H), 6.87 (m, 1H), 4.74 (m, 1 H), 2.62 (s, 3H), 1.29 (d, J = 6.3 Hz, 6H). Anal. Calcd. for (C19H20N3O6PS): C, 50.78 H, 4.49; N, 9.35. Found: C, 50.56; H, 4.43; N, 9.23. |
| 125 | 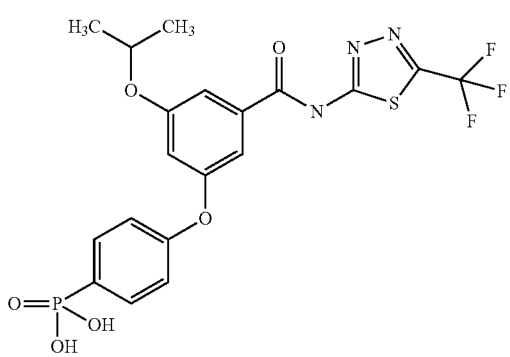 [SMILES: CC(C)Oc1cc(Oc2ccc(P(=O)(O)O)cc2)cc(C(=O)Nc2nnc(C(F)(F)F)s2)c1] | 504.4 (+) | 7.71 (m, 2 H), 7.54 (m, 1 H), 7.31 (m, 1 H), 7.13 (m, 2 H). 6.93 (m, 1 H), 4.75 (m, 1 H), 1.30 (d, J = 6 Hz, 6 H). Anal. Calcd. for (C19H17F3N3O6PS + 0.8 H2O): C, 44.07; H, 3.62; N, 8.12. Found: C, 44.38; H, 8.11. |

-continued

| Example | Structure | Mass Spect. (Mode) | 1H NMR δ (DMSO-d$_6$) & Elemental Analysis |
|---|---|---|---|
| 126 | 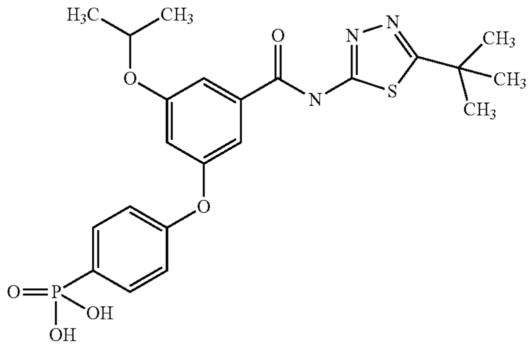 [SMILES: CC(C)Oc1cc(Oc2ccc(P(=O)(O)O)cc2)cc(C(=O)Nc2nnc(C(C)(C)C)s2)c1] | 492.4 (+) | 7.70 (m, 2 H), 7.49 (m, 1 H), 7.27 (m, 1 H), 7.12 (m, 2 H), 6.87 (m, 1 H), 4.73 (m, 1 H), 1.39 (s, 9 H), 1.28 (d, J = 6 Hz, 6 H). Anal. Calcd. for (C22H26N3O6PS + 1.0 MeOH): C, 52,77; H, 5.78; N, 8.03. Found: C, 53.00; H, 5.78; N, 7.65. |
| 127 | 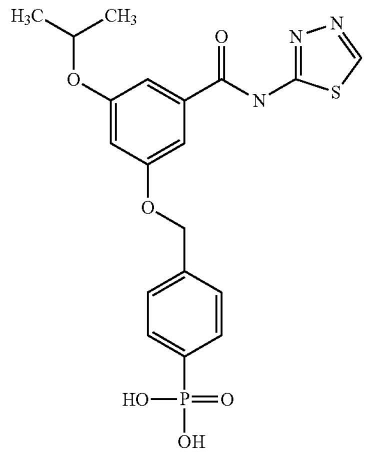 [SMILES: CC(C)Oc1cc(OCc2ccc(P(=O)(O)O)cc2)cc(C(=O)Nc2nncs2)c1] | 449.4 (+) | 7.68 (m, 2 H), 7.52 (m, 3H), 7.33 (m, 1H), 7.26 (m, 2H), 6.75 (s, 1H), 5.21 (s 2H), 4.70 (m, 1 H), 1.26 (d, J = 6.0 Hz, 6H), Anal Calcd for (C20H21N2O6PS + 0.25 HBr): C, 51.26 H, 4.57; N. 5.98. Found: C, 51.19; H, 4.54; N, 5.69. |
| 128 | 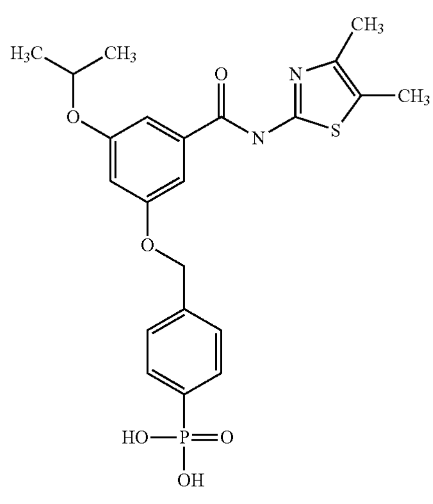 [SMILES: Cc1nc(NC(=O)c2cc(OCc3ccc(P(=O)(O)O)cc3)cc(OC(C)C)c2)sc1C] | 477.4 (+) | 7.70 (m, 2 H), 7.53 (m, 2 7.32 (s, 1H), 7.26 (s, 1H), 6.75 (m, 1H), 5.22 (s, 2H), 4.71 (m, 1 H), 2.62 (s, 3H 2.20 (s, 3H), 1.27 (d, J = 5.7 Hz, 6H). Anal Calcd for (C22H25N2O6PS + 0.15 HBr): C, 54.08 H, 5.19; N, 5.73 Found: C, 54.32; H, 5.03; N, 5.33. |

-continued

| Example | Structure | Mass Spect. (Mode) | 1H NMR δ (DMSO-d₆) & Elemental Analysis |
|---|---|---|---|
| 129 | 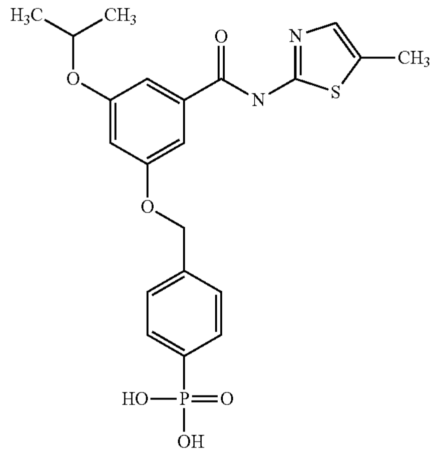 [SMILES: Cc1cnc(NC(=O)c2cc(OCc3ccc(P(=O)(O)O)cc3)cc(OC(C)C)c2)s1] | 463.0 (+) | 7.71 (m, 2 H), 7.54 (m, 2H), 7.33 (d, J = 1.8 Hz, 1H), 7.27 (d, J = 1.8 Hz, 1H), 7.23 (d, J = 1.2 Hz, 1H), 6.77 (m, 1H), 5.23 (s, 2H), 4.72 (m, 1 H), 2.38 (d, J = 1.2 Hz, 3H), 1.28 (d, J = 5.7 Hz, 6H), Anal Calcd for (C21H23N2O6PS + 0.1 HBr): C, 53.60 H. 4.95; N. 5.95. Found: C, 53.79; H, 5.07; N, 5.68. |
| 130 | 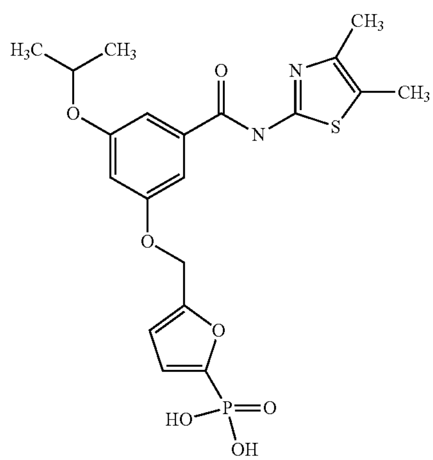 [SMILES: Cc1nc(NC(=O)c2cc(OCc3ccc(P(=O)(O)O)o3)cc(OC(C)C)c2)sc1C] | 467.4 (+) | 7.34 (m, 1 H), 7.26 (m, 1H), 6.86 (m, 1H), 6.79 (m, 1H), 6.66 (m, 1H), 5.17 (s, 2H), 4.72 (m, 1 H), 2.27 (d, J = 0.3 Hz, 3H), 2.20 (d, J = 0.3 Hz, 3H), 1.28 (d, J = 3.3 Hz, 6H). Anal Calcd for (C20H23N2O7PS + 1.4 H2O): C, 48.86 H, 5.29; N, 5.70, Found: C, 49.26; H, 5.55; N, 5.11. |
| 131 | 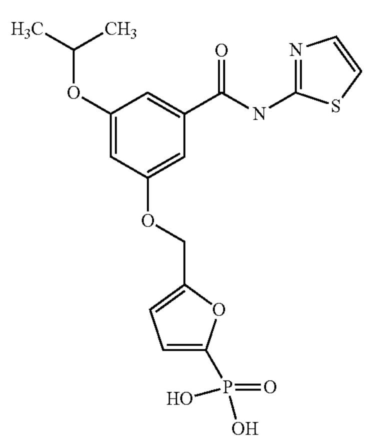 [SMILES: CC(C)Oc1cc(OCc2ccc(P(=O)(O)O)o2)cc(C(=O)Nc2nccs2)c1] | 439.4 (+) | 7.57 (d, J = 2.1 Hz, 1 H), 7.36 (m, 1H), 7.29 (m, 2H), 6.86 (d, J = 1.5 Hz, 1H), 6.82 (m, 1H), 6.66 (d, J = 1.2 Hz, 1H), 5.18 (s, 2H), 4.74 (m, 1 H), 1.29 (d, J = 3.6 Hz, 6H). Anal Calcd for (C18H19N2O7PS + 0.1 HBr): C, 48.42 H, 4.31; N, 6.27. Found: C, 48.52; H 4.25; N, 6.09. |

-continued

| Example | Structure | Mass Spect. (Mode) | 1H NMR δ (DMSO-d₆) & Elemental Analysis |
|---|---|---|---|
| 132 | 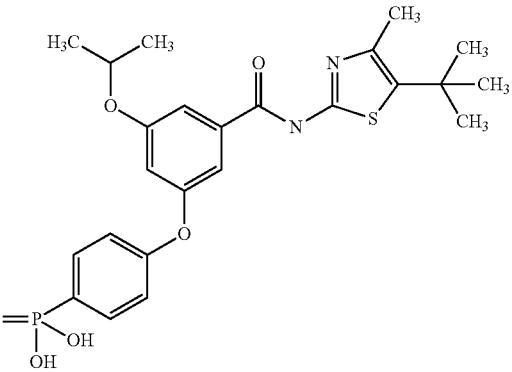 | 505.4 (+) | 7.77 (m, 2 H), 7.54 (m, 1H), 7.31 (m, 1H), 7.19 (m, 2H), 6.89 (m, 1H), 4.80 (m, 1 H), 2.41 (s, 3H), 1.44 (s, 9H), 1.36 (d, J = 6.0 Hz, 6H). Anal Calcd for (C24H29N2O6PS): C, 57.13 H, 5.79; N, 5.55. Found: C, 56.92; H, 5.85; N, 5.29. |
| 133 | 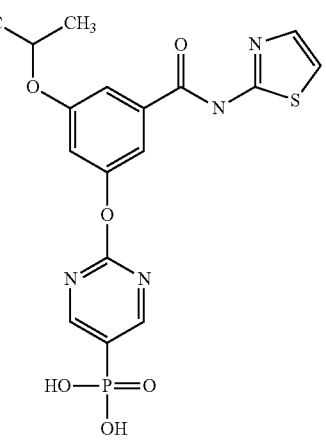 | 437.4 (+) | 8.65 (d, J = 5.7 Hz, 2H), 7.52 (m, 3 H), 7.26 (m, 1H), 7.05 (m, 1H), 4.72 (m, 1 H), 1.28 (d, J = 6.3 Hz, 6H). Anal Calcd for (C17H17N4O6PS + 0.2 NH4Br + 0.3 NH3 + 1.0 H2O): C, 42.62 H, 4.35; N, 13.16. Found: C, 42.71; H, 4.66; N, 13.36, |
| 134 | 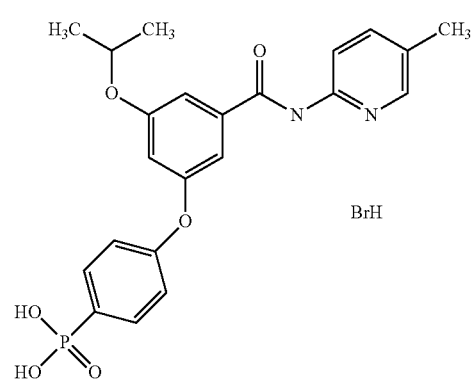 [SMILES: Cc1ccc(NC(=O)c2cc(Oc3ccc(P(=O)(O)O)cc3)cc(OC(C)C)c2)nc1 ; Br] | 443.3 (+) | $^1$H NMR (500 MHz, DMSO-d₆) δ 1.29 (d, 6H, J = 6 Hz), 2.31 (s, 3H), 4.75-4.77 (m, 1H), 6.87 (t, 1H, J = 2 Hz), 7.12 (dd, 2H, J = 9, 3 Hz), 7.21 (s, 1H), 7.43 (s, 1H), 7.72 (dd, 2H, J = 13, 9 Hz), 7.83 (d, 1H, J = 8 Hz), 7.96 (d, 1H, J = 9 Hz), 8.25 (s, 1H), 11.09 (s, 1H); Anal. Calcd. for (C22H23N2O6P + 1.7HB)r: C, 45.56; H, 4.29; N, 4.83. Found: C, 45.83; H, 4.05; N, 4.63. |
| 135 | 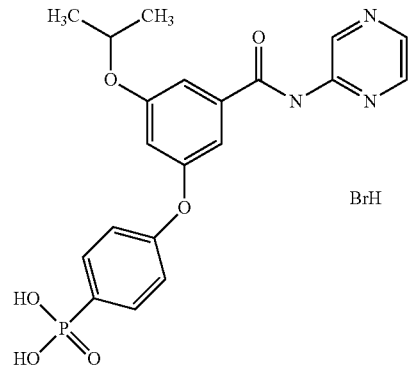 [SMILES: CC(C)Oc1cc(Oc2ccc(P(=O)(O)O)cc2)cc(C(=O)Nc2cnccn2)c1 ; Br] | 430.1 (−) | $^1$H NMR (500 MHz, DMSO-d₆) δ 1.29 (d, 6H), 4.75-4.77 (m, 1H), 6.86 (t, 1H), 7.13 (dd, 2H), 7.14 (s, 1H), 7.46 (s, 1H), 7.71 (dd, 2H), 8.42 (d, 1H), 8.47 (s, 1H), 9.37 (s, 1H), 11.18 (s, 1H); Anal. Calcd, for (C20H20N3O6P + 1.4HBr + 0.2 Et2O): C, 44.81; H, 4.23; N, 7.54. Found: C. 45.16; H, 4.28N, 6.75. |

-continued

| Example | Structure | Mass Spect. (Mode) | 1H NMR δ (DMSO-d$_6$) & Elemental Analysis |
|---|---|---|---|
| 136 | (structure) BrH | 432.4 (+) | $^1$H NMR (500 MHz, DMSO-d$_6$) δ 1.29 (d, 6H), 3.77 (s, 3H), 4.75-4.77 (m, 1H), 6.55 (d, 1H), 6.78 (t, 1H), 7.11 (dd, 2H), 7.17 (s, 1H). 7.41 (s, 1H), 7.59 (d, 1H), 7.70 (dd, 2H), 10.88 (s, 1H); Anal. Calcd. for (C$_{20}$H$_{22}$N$_3$O$_6$P + 1.4HBr); C, 44.10; H, 4.33; N, 7.71, Found: C, 44.08; H, 4.29; N, 7.46. |
| 137 | (structure) BrH | 447.6 (+) | $^1$H NMR (500 MHz, DMSO-d$_6$) δ 1.29 (d, 6H), 4.74-4.77 (m, 1H), 6.83 (d, 1H), 7.12 (dd, 2H), 7.20 (d, 1H), 7.43 (s, 1H), 7.41 (s, 1H), 7.70 (dd, 2H), 7.77-7.81(m, 1H), 8.16 (dd, 1H), 8.39 (d, 1H), 10.98 (s, 1H); Anal. Calcd. for (C$_{21}$H$_{20}$FN$_2$O$_6$P +1.4HBr): C, 45.07; H, 3.85; N. 5.01, Found: C, 45.26; H, 3.76; N, 4.82. |
| 138 | (structure) BrH | 446.6 (+) | $^1$H NMR (300 MHz, DMSO-d$_6$) δ 1.29 (d, 6H), 1.36 (t, 3H), 4.05 (q, 2H), 4.72-4.77 (m, 1H), 6.55 (d, 1H), 6.78 (d, 1H), 7.12 (dd, 2H), 7.18 (t. 1H), 7.42 (t, 1H), 7.64 (d. 1H), 7.70(dd, 2H), 10.90 (s, 1H); Anal. Calcd. for (C$_{21}$H$_{24}$N$_3$O$_6$P + 1.4HBr): C, 45.15; H, 4.58; N, 7.52. Found: C, 45,39; H, 4.58; N, 7.30. |
| 139 | (structure) | 465.4 (+) | $^1$H NMR (500 MHz, DMSO-d$_6$) δ 1.25 (d, 3H), 3.47-3.53 (m, 3H), 4.75-4.78 (m, 1H), 6.89 (t, 1H), 7.14 (dd, 2H), 7.28 (t, 2H), 7.55 (t, 2H). 7.72 (dd, 2H); Anal. Calcd. for (C$_{20}$H$_{21}$N$_2$O$_7$PS + 0.5 H$_2$O): C, 50.74; H, 4.68; N. 5.92. Found: C, 50.74; H, 4.59; N, 5.56. |

| Example | Structure | Mass Spect. (Mode) | 1H NMR δ (DMSO-d₆) & Elemental Analysis |
|---|---|---|---|
| 140 | 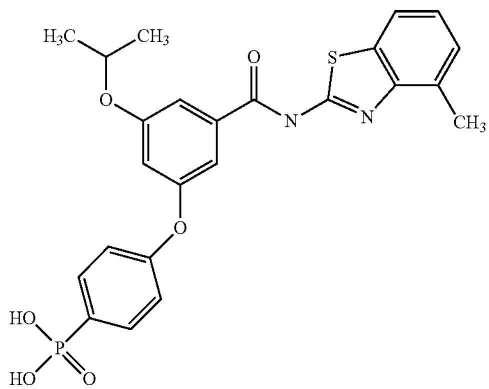 [SMILES: Cc1cccc2sc(NC(=O)c3cc(Oc4ccc(P(=O)(O)O)cc4)cc(OC(C)C)c3)nc12] | 499.6 (+) | ¹H NMR (300 MHz,DMSO-d₆) δ 1.31 (d, 6H), 2.61 (s, 3H), 4.76-4.81 (m, 1H), 6.87 (s, 1H), 7.13 (m. 2H), 7.25 (m, 2H), 7.33 (s, 1H), 7.56 (s, 1H), 7.71 (bs, 2H), 7.81(d, 1H); Anal. Calcd. for (C₂₄H₂₃N₂O₆PS + 0.8 H₂O): C, 56.20; H, 4.83; N, 5.46. Found: C, 56.22; H, 4.55; N. 5.52. |
| 141 | 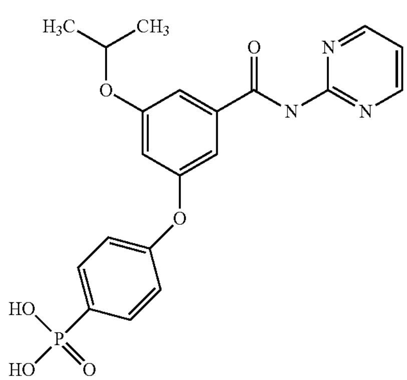 [SMILES: CC(C)Oc1cc(Oc2ccc(P(=O)(O)O)cc2)cc(C(=O)Nc2ncccn2)c1] | 430.1 (+) | ¹H NMR (500 MHz, DMSO-d₆) δ 1.27 (d, 6H), 4.69-4.72 (m, 1H), 6.75 (s, 1H). 6.99 (d, 2H), 7.11 (s, 1H), 7.25 (t, 1H), 7.30 (s, 1H). 7.66 (dd, 214), 8.72 (d, 2H); Anal Calcd, for (C₂₀H₂₀N₃O₆P + 0.9 HBr + 1.2 NH3): C, 45.96; H, 4.73; N, 11.26. Found: C, 45.65; H, 4.88; N, 11.25. |
| 142 | 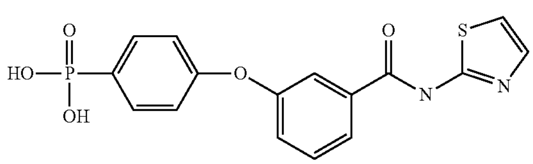 [SMILES: O=C(Nc1nccs1)c1cccc(Oc2ccc(P(=O)(O)O)cc2)c1] | 377.1 (+) | ¹H NMR (500 MHz, DMSO-d₆) δ 7.11-7.14 (m, 2H), 7.29 (d, 1H), 7.35-7.37 (m, 1H), 7.55 (d, 2H), 7.60 (t, 1H), 7.69-7.77 (m, 2H), 7.92-7.94 (m, 1H); Anal. Calcd, for (C₁₆H₁₃N₂O₅PS): C, 51.07; H, 3.48; N, 7.44. Found: C. 51.29; H, 3.70; N, 7.29. |
| 143 | 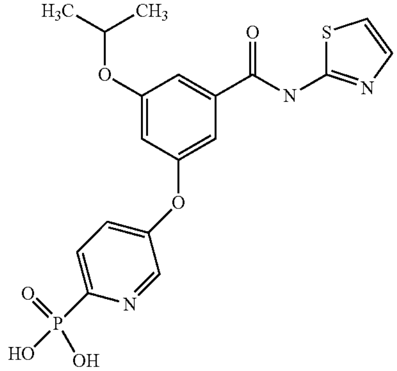 [SMILES: CC(C)Oc1cc(Oc2ccc(P(=O)(O)O)nc2)cc(C(=O)Nc2nccs2)c1] | 436.4 (+) | ¹H NMR (300 MHz, DMSO-d₆) δ 1.32 (d, 6H), 4.74-4.79 (m, 1H), 6.96 (t, 1H), 7.29 (d. 1H), 7.33 (s, 1H), 7.50-7.56 (m, 3H), 7.83 (dd, 1H), 8.58 (d, 1H); Anal. Calcd. for (C₁₈H₁₈N₃O₆PS): C, 49.66; H, 4.17; N, 9.65. Found: C, 49.39; H, 4.21; N, 9.38. |

Examples 144-145

The following examples were prepared in a similar manner to Example 4 from the appropriate intermediates with modifications evident to an individual skilled in the art:

| Example | Structure | Mass Spect. (Mode) | 1H NMR δ (DMSO-d$_6$) & Elemental Analysis |
|---|---|---|---|
| 144 | (structure) | 451.4 (+) | 7.93 (s, 1 H), 7.59-7.63 (m, 3 H), 7.38-7.42 (m, 3 H), 7.27-730 (m, 1 H), 4.78-4.84 (m, 1 H), 3.06 (d, J = 21 Hz, 2 H), 1.34 (d, J = 6 Hz, 6 H). Anal. Calcd. for (C$_{20}$H$_{20}$FN$_2$O$_5$PS + 0.5 H$_2$O): C, 52.29; H, 4.61; N, 6.10. Found: C, 52.13; H, 4,44; N, 6.05. |
| 145 | (structure) | 467.4 (+) | 7.78 (s , 1 H), 7.70 (dd J = 13,9 Hz, 2 H), 7.61 (s, 1 H), 7.57 (t, J = 2 Hz, 1 H), 7.18 (s, 1H), 7.10 (dd, J = 6, 3 Hz, 2 H), 2.54 (d, J = 7 Hz, 2 H), 1.91 (m, 1 H), 0.88 (d, J = 7 Hz, 6 H). Anal. Calcd. for (C$_{20}$H$_{20}$ClN$_2$O$_5$PS): C, 51.45; H, 4.32; N, 6.00. Found: C, 51.55; H, 4.63; N, 5.86. |

Examples 146-157

The following examples were prepared in a similar manner to Example 6 from the appropriate intermediates with modifications evident to an individual skilled in the art:

| Example | Structure | Mass Spect. (Mode) | 1H NMR δ (DMSO-d$_6$) & Elemental Analysis |
|---|---|---|---|
| 146 | (structure) | 506.1 (+) | 1.30 (d, 6H, J = 6 Hz), 1.61 (d, 3H, J = 15 Hz), 3.21 (s, 3H), 4.65-4.74 (m, 1H), 6.98 (t, 1H, J = 2 Hz), 7.23-7.26 (m, 2H); 7.36-7.37 (m, 1H), 7.52-7.54 (m, 1H), 7.93-7.96 (m, 2H), 8.78 (t, 1H, J = 1 Hz), 9.52 (t, 1H, J = 1 Hz), 11.47 (s, 1H). Anal. Calcd. for (C$_{22}$H$_{24}$N$_3$O$_7$PS + 1.3HBr + 1.0 H$_2$O): C, 42.03; H, 4.38; N, 6.68. Found: C, 41.88; H, 4.35; N, 6.32. |

-continued

| Example | Structure | Mass Spect. (Mode) | 1H NMR δ (DMSO-d$_6$) & Elemental Analysis |
|---|---|---|---|
| 147 | 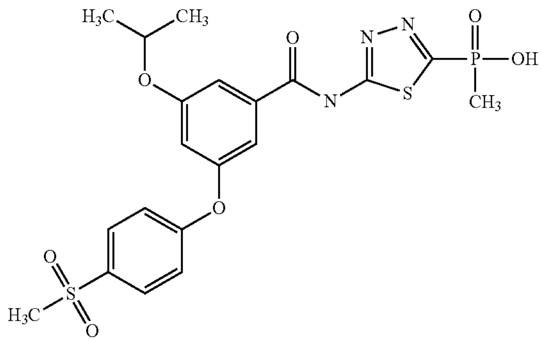 [SMILES: CC(C)Oc1cc(Oc2ccc(S(C)(=O)=O)cc2)cc(C(=O)Nc2nnc(P(C)(=O)O)s2)c1] | 512.5 (+) | 7.96 (m, 2 H), 7,61 (m, 1H), 7.44 (m, 1H), 7.28 (m, 2H), 7.03 (m, 1H), 4.80 (m, 1 H), 3.20 (s, 3H), 1.73 (d, J = 15.6 Hz, 3H), 1.32 (d, J = 6.0 Hz, 6 H). Anal. Calcd. for (C20H22N3O7PS2 + 0.6 H2O): C, 45.99 H, 4.48; N, 8.04. Found: C, 45.99; H, 4.27; N, 7.93. |
| 148 | 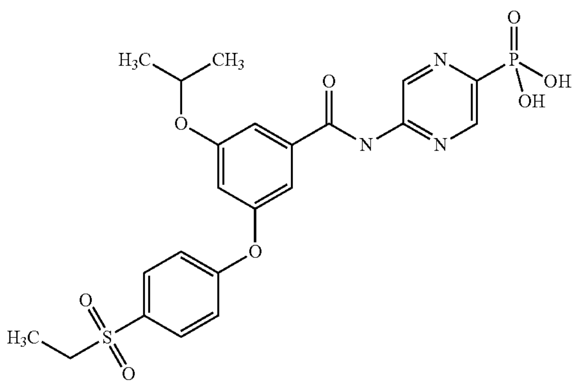 [SMILES: CCS(=O)(=O)c1ccc(Oc2cc(OC(C)C)cc(C(=O)Nc3cnc(P(=O)(O)O)cn3)c2)cc1] | 521.5 (+) | 11.26 (s, 1H), 9.41 (s, 1H), 8.61 (s, 1H), 7.86 (m, 2H), 7.50 (m, 1H), 7.35 (m, 1H), 7.22 (m, 2H), 6.94 (m, 1H), 4.75 (m, 1 H), 3.26 (m, 2H), 1.28 (d, J = 6.0 Hz, 6 H), 1.09 (m, 3H). Anal. Calcd. for (C22H24N3O8PS + 0.1 NH4I + 0.2 NH4OH): C, 48.66 H, 4.71; N, 8.51. Found: C, 48.56; H, 4.82; N, 8.80. |
| 149 | 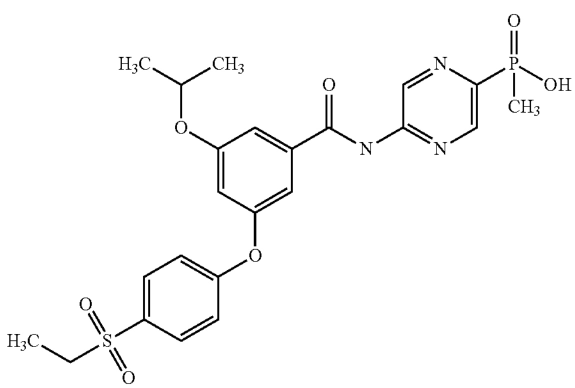 [SMILES: CCS(=O)(=O)c1ccc(Oc2cc(OC(C)C)cc(C(=O)Nc3cnc(P(C)(=O)O)cn3)c2)cc1] | 520.5 (+) | 11.26 (s, 1H), 9.40 (s, 1H), 8.61 (s, 1H), 7.87 (m, 2 H), 7.50 (m, 1H), 7.35 (m, 1H), 7.22 (m, 2H), 6.94 (m, 1H), 4.75 (m, 1 H), 3.25 (m, 2H), 1.28 (d, J = 6.0 Hz, 6 H), 1.09 (m, 3H). Anal. Calcd. for (C23H26N3O7PS + 0.8 H2O): C, 51.74 H, 5.21; N, 7.87. Found: C, 51.79; H, 5.05; N, 8.13. |
| 150 | 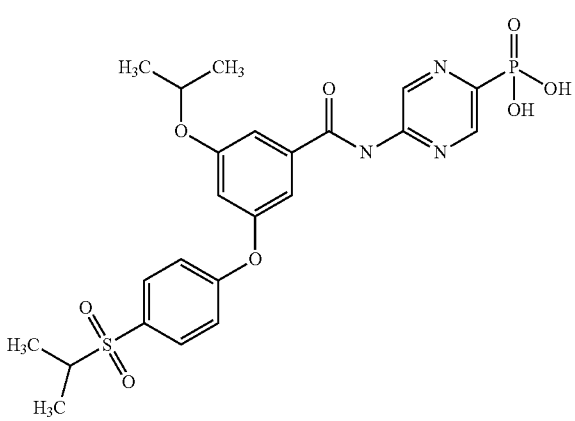 [SMILES: CC(C)Oc1cc(Oc2ccc(S(=O)(=O)C(C)C)cc2)cc(C(=O)Nc2cnc(P(=O)(O)O)cn2)c1] | 536.5 (+) | 11.31 (s, 1H), 9.45 (s, 1H), 8.64 (s, 1H), 7.84 (m, 2 H), 7.52 (m, 1H), 7.37 (m, 1H), 7.23 (m, 2H), 6.96 (m, 1H), 4.76 (m, 1 H), 3.37 (m, 1H), 1.29 (d, J = 6.0 Hz, 6H), 1.15 (d, J = 6.6 Hz, 6H). Anal. Calcd. for (C23H26N3O8PS + 0.1 NH4I + 0.1 HI): C, 49.09 H, 4.75; N, 7.72. Found: C, 48.82; H, 4.37; N, 8.10. |

| Example | Structure | Mass Spect. (Mode) | 1H NMR δ (DMSO-d$_6$) & Elemental Analysis |
|---------|-----------|--------------------|---------------------------------------------|
| 151 | 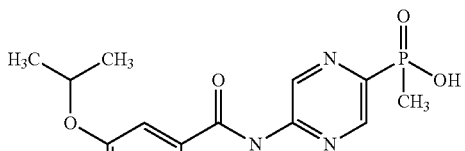 | 534.5 (+) | 11.42 (s, 1H), 9.49 (s, 1H), 8.75 (s, 1H), 7.84 (m, 2 H), 7.52 (m, 1H), 7.37 (m, 1H), 7.24 (m, 2H), 6.98 (m, 1H), 4.77 (m, 1 H), 3.37 (m, 1H), 1.55 (d, J = 15.0 Hz, 3H), 1.29 (d, J = 6.3 Hz, 6 H), 1.14 (d, J = 6.9 Hz, 6H). Anal. Calcd. for (C24H28N3O7PS + 0.5 H2O): C, 53.13 H, 5.39; N, 7.74. Found: C, 52.94; H, 5.08; N, 7.85. |
| 152 | 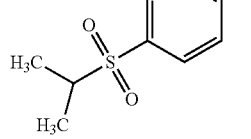 | 535.5 (+) | 11.05 (s, 1H), 8.55 (d, J = 5.5 Hz, 1H), 8.17 (d, J = 8.0 Hz, 1H), 7.98 (m, 1H), 7.83 (d, J = 8.5 Hz, 2 H), 7.49 (s, 1H), 7.35 (s, 1H), 7.22 (d, J = 8.5 Hz, 2H), 6.93 (m, 1H), 4.77 (m, 1 H), 3.37 (m, 1H), 1.28 (d, J = 6.0 Hz, 6H), 1.14 (d, J = 6.5 Hz, 6H). Anal. Calcd. for (C24H27N2O8PS + 0.2 NH4I): C, 51.15 H, 4.97; N, 5.47. Found: C, 51.44; H, 5.09; N, 5.48. |
| 153 | 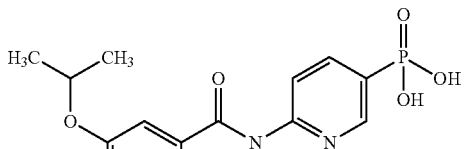 | 533.5 (+) | 11.14 (s, 1H), 8.63 (s, 1H), 8.24 (d, J = 8.0 Hz, 1H), 8.09 (m, 1H), 7.84 (d, J = 9 Hz, 2 H), 7.49 (s, 1H), 7.35 (s, 1H), 7.23 (d, J = 9 Hz, 2H), 6.95 (m, 1H), 4.77 (m, 1 H), 3.37 (m, 1H), 1.52 (d, J = 14.5 Hz, 3H), 1.28 (d, J = 6 Hz, 6H), 1.14 (d, J = 7.0 Hz, 6H). Anal. Calcd. for (C25H29N2O7PS + 0.2 HI + 0.2 H2O): C, 53.11 H, 5.35; N, 4.96. Found: C, 53.13 H, 4.96; N, 4.93. |

| Example | Structure | Mass Spect. (Mode) | 1H NMR δ (DMSO-d$_6$) & Elemental Analysis |
|---|---|---|---|
| 154 | 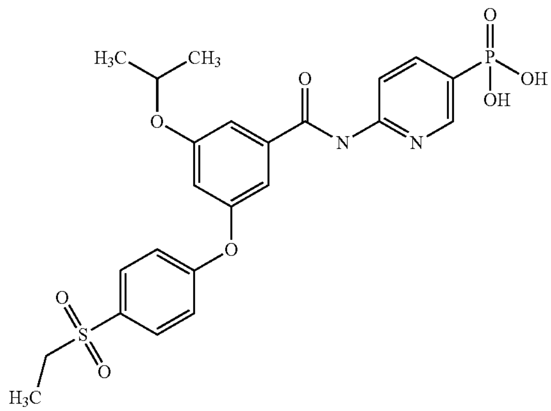 [SMILES: CCS(=O)(=O)c1ccc(Oc2cc(OC(C)C)cc(C(=O)Nc3ccc(P(=O)(O)O)cn3)c2)cc1] | 521.5 (+) | 11.10 (s, 1H), 8.56 (s, 1H), 8.22 (d, J = 8.5 Hz, 1H), 8.02 (m, 1H), 7.87 (m, 2 H), 7.49 (s, 1H), 7.34 (s, 1H), 7.23 (m, 2H), 6.94 (m, 1H), 4.77 (m, 1 H), 3.26 (m, 2H), 1.28 (d, J = 6.0 Hz, 6 H), 1.09 (m, 3H). Anal. Calcd. for (C23H25N2O8PS + 0.1 HI): C, 51.80 H, 4.74; N, 5.25. Found: C, 51.80; H, 4.76; N, 5.11. |
| 155 | 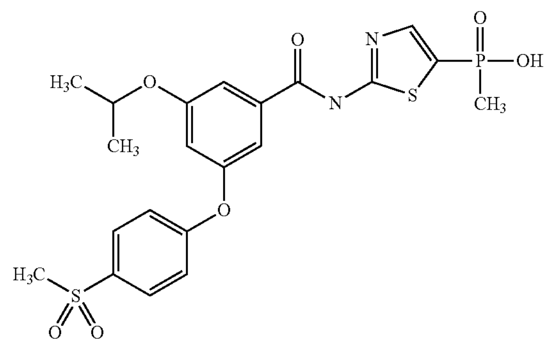 [SMILES: CC(C)Oc1cc(Oc2ccc(S(C)(=O)=O)cc2)cc(C(=O)Nc2ncc(P(C)(=O)O)s2)c1] | 511.0 (+) | 7.95 (d, J = 9 Hz, 2 H), 7.85 (d, J = 5 Hz, 1 H), 7.57 (m, 1 H), 7.40 (m, 1H), 7.25 (d, J = 9 Hz, 2 H), 7.00 (m, 1 H), 4.77-4.80 (m, 1 H), 3.22 (s, 3 H), 1.59 (d, J = 15 Hz, 3 H), 1.31 (d, J = 6 Hz, 6 H). Anal. Calcd. for (C22H23N2O8PS + 0.5 HBr): C, 47.38; H, 4.67; N, 5.53. Found: C, 47.65; H, 4.47; N, 5.28. |
| 156 | 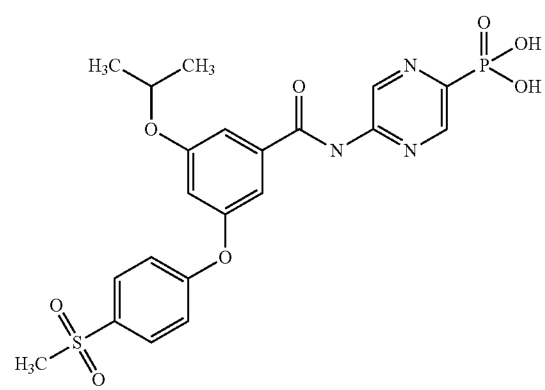 [SMILES: CC(C)Oc1cc(Oc2ccc(S(C)(=O)=O)cc2)cc(C(=O)Nc2cnc(P(=O)(O)O)cn2)c1] | 508.4 (+) | 1.31 (d, 6H, J = 6 Hz), 3.21 (s, 3H), 4.76-4.81 (m, 1H), 6.98 (t, 1H, J = 2 Hz), 7.25 (dd, 2H, J = 7, 2 Hz), 7.36-7.37 (m, 1H), 7.53-7.54 (m, 1H), 7.95 (dd, 2H, J = 7, 2 Hz), 8.70 (t, 1H, J = 1 Hz), 9.52 (t, 1H, J = 1 Hz), 11.42 (s, 1H). Anal. Calcd. for C$_{21}$H$_{22}$N$_3$O$_8$PS: C, 49.70; H, 4.37; N, 8.28. Found: C, 49.72; H, 4.26; N, 8.30. |
| 157 | 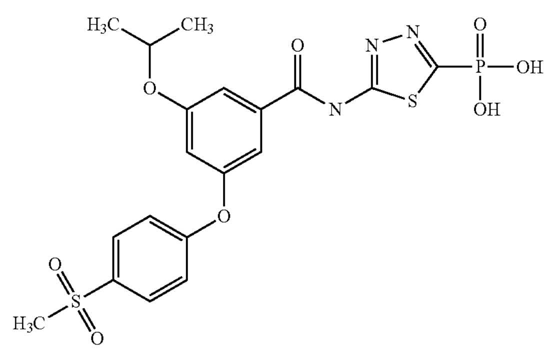 [SMILES: CC(C)Oc1cc(Oc2ccc(S(C)(=O)=O)cc2)cc(C(=O)Nc2nnc(P(=O)(O)O)s2)c1] | 514.5 (+) | 7.94 (m, 2 H), 7.58 (m, 1H), 7.40 (m, 1H), 7.26 (m, 2H), 6.99 (m, 1H), 4.76 (m, 1 H), 3.20 (s, 3H), 1.31 (d, J = 6.0 Hz, 6H). Anal. Calcd. for (C19H20N3O8PS2 + 0.2 NH4Br + 0.5 H2O): C, 42.10 H, 4.05; N, 8.27. Found: C, 42.47; H, 4.40; N, 8.64. |

Examples 158-163

The following examples were prepared in a similar manner to Example 10 from the appropriate intermediates with modifications evident to an individual skilled in the art:

| Example | Structure | Mass Spect. (Mode) | 1H NMR δ (DMSO-$d_6$) & Elemental Analysis |
|---|---|---|---|
| 158 | 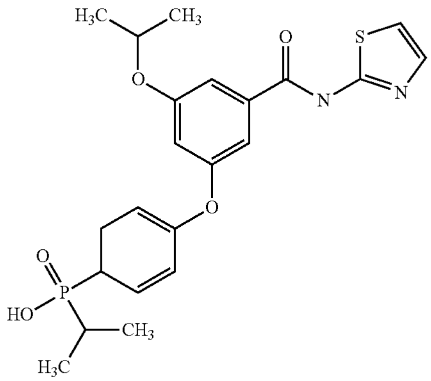 [SMILES: CC(C)Oc1cc(OC2=CCC(P(=O)(O)C(C)C)C=C2)cc(C(=O)Nc2nccs2)c1] | 461.6 (+) | 0.96 (d, 3H, J = 7 Hz), 1.01 (d, 3H, J = 7 Hz), 1.31 (d, 6H, J = 6 Hz), 1.91 (septet, 1H, J = 7 Hz), 4.77 (septet, 1H, J = 6 Hz), 6.89 (t, 1H, J = 2 Hz), 7.16 (dd, 2H, J = 9, 2 Hz), 7.32 (t, 1H, J = 2 Hz), 7.29 (d, 1H, J = 4 Hz), 7.32 (t, 1H, J = 2 Hz), 7.53 (t, 1H, J = 2 Hz), 7.56 (d, 1H, J = 4 Hz), 7.72 (dd, 2H, J = 10, 9 Hz). Anal. calcd. for ($C_{22}H_{25}N_2O_5PS$): C, 57.38; H, 5.47; N, 6.08. Found: C, 57.24; H, 5.40; N, 6.01. |
| 159 | 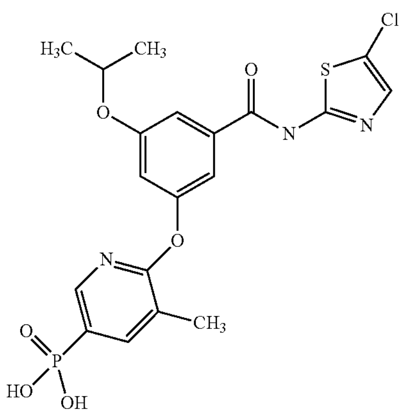 [SMILES: Cc1cc(P(=O)(O)O)cnc1Oc1cc(OC(C)C)cc(C(=O)Nc2ncc(Cl)s2)c1] | 484.1 (+) | 8.18 (dd, J = 5, 2 Hz, 1 H), 7.92 (d, J = 11 Hz, 1 H), 7.61 (s, 1 H), 7.53 (s, 1 H), 7.40 (s, 1 H), 6.99 (m, 1 H), 4.75 (m, 1 H), 2.36 (s, 3H), 1.31 (d, J = 6 Hz, 6H). Anal. Calcd. for ($C_{19}H_{19}ClN_3O_6PS$ + 1.2 $H_2O$): C, 45.15; H, 4.27; N, 8.31. Found: C, 44.97; H, 4.14; N, 8.16. |
| 160 | 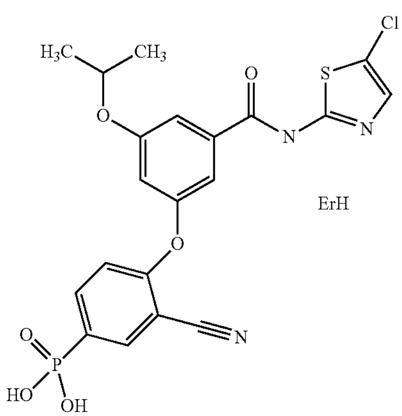 | 494.4 (+) | 8.04 (m, 1 H), 7.91 (m, 1 H), 7.61 (s, 1 H), 7.57 (s, 1 H), 7.42 (s, 1 H), 7.12 (m, 2H), 4.78 (m, 1 H), 1.31 (d, J = 6 Hz, 6 H). Anal. Calcd. for ($C_{20}H_{17}ClN_3O_6PS$ + 1.1 HBr): C, 41.21; H, 3.13; N, 7.21. Found: C, 41.29; H, 3.05; N, 6.89. |

-continued
| Example | Structure | Mass Spect. (Mode) | 1H NMR δ (DMSO-d$_6$) & Elemental Analysis |
|---|---|---|---|
| 161 | 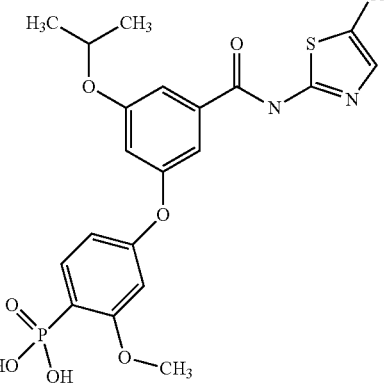 | 499.6 (+) | 7.67 (m, 1 H), 7.61 (d, J = 2 Hz, 1 H), 7.50 (s, 1 H), 7.29 (s, 1 H), 6.87 (d, J = 2 Hz, 1 H), 6.80 (d, J = 5 Hz; 1H), 6.59 (d, J = 8 Hz, 1 H), 4.75 (m, 1H), 3.78 (s, 3H), 1.29 (m, 6 H). Anal. Calcd. for (C$_{20}$H$_{20}$ClN$_2$O$_7$PS + 0.9 H$_2$O): C, 46.64; H, 4.27; N, 5.44. Found: C, 46.76; H, 4.27; N, 5.27. |
| 162 | 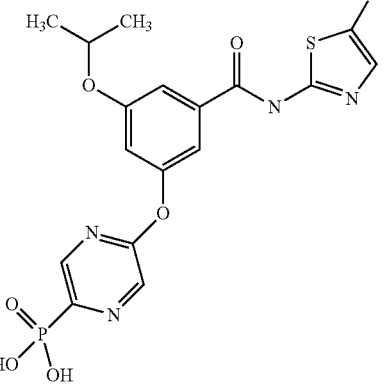 | 471.4 (+) | 8.72 (d, J = 1 Hz, 1 H), 8.46 (s, 1 H), 7.62 (d, J = 1 Hz, 1 H), 7.57 (d, J = 1 Hz, 1 H), 7.50 (s, 1 H), 7.14 (t, J = 2 Hz, 1H), 4.75 (m, 1H), 1.30 (d, J = 6 Hz, 6 H). Anal Calcd. for (C$_{17}$H$_{16}$ClN$_4$O$_6$PS): C, 43.37; H, 3.43; N, 11.90. Found: C, 43.62; H, 3.47; N, 11.61. |
| 163 | 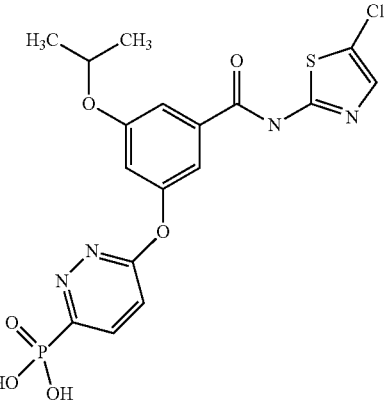 | 471.1 (+) | 8.01 (dd, J = 9, 5 Hz, 1 H), 7.62 (s, 1 H), 7.4-7.6 (m, 3 H), 7.16 (t, J = 2 Hz, 1 H), 4.7-4.8 (m, 1 H), 1.32 (d, J = 6 Hz, 6 H). Anal. Calcd. for (C$_{17}$H$_{16}$ClN$_4$O$_6$PS + 0.3 H$_2$O): C, 42.88; H, 3.51; N, 11.76. Found: C, 42.85; H, 3.21; N, 11.56. |

Examples 164-165

The following examples were prepared in a similar manner to Example 11 from the appropriate intermediates with modifications evident to an individual skilled in the art:

| Example | Structure | Mass Spect. (Mode) | 1H NMR δ (DMSO-d$_6$) & Elemental Analysis |
|---|---|---|---|
| 164 | 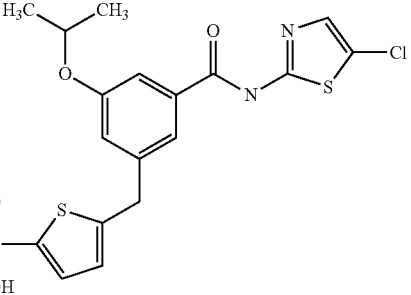 | 473.4 (+) | δ 7.57 (m, 3 H), 7.25 (m, 1H), 7.07 (m, 1H), 6.97 (m, 1H), 4.70 (m, 1 H), 4.19 (s, 2H), 1.27 (m, 6H). Anal Calcd for (C18H18ClN2O5PS2 + 0.1 HBr): C, 44.95 H, 3.79; N, 5.82. Found: C, 45.05; H, 3.75; N, 5.88. |
| 165 | 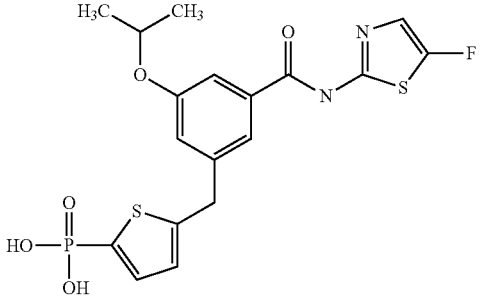 [SMILES: CC(C)Oc1cc(Cc2ccc(P(=O)(O)O)s2)cc(C(=O)Nc2ncc(F)s2)c1] | 457.1 (+) | 7.51 (d, J = 7.2 Hz, 2 H), 7.37 (d, J = 2.4 Hz, 1H), 7.23 (m, 1H), 7.06 (s, 1H), 6.96 (s, 1H), 4.70 (m, 1 H), 4.18 (s, 2H), 1.27 (d, J = 6.0 Hz, 6H). Anal Calcd for (C18H18FN2O5PS2 + 0.1 HBr): C, 46.54 H, 3.93; N, 6.03. Found: C, 46.40; H, 4.14; N, 5.93. |

Examples 166-167

The following examples were prepared in a similar manner to Example 14 from the appropriate intermediates with modifications evident to an individual skilled in the art:

| Example | Structure | Mass Spect. (Mode) | 1H NMR δ (DMSO-d$_6$) & Elemental Analysis |
|---|---|---|---|
| 166 | 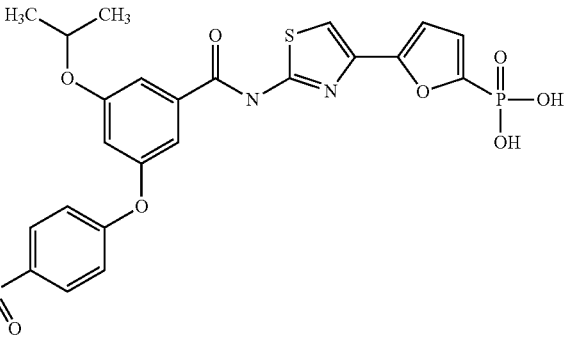 | 579.6 (+) | 12.93 (s, 1 H), 7.95 (m, 2H), 7.58 (d, J = 1.8 Hz, 1 H), 7.51 (s, 1H), 7.40(m, 1H), 7.25 (m, 2H), 6.94 (m, 2H), 6.77 (m, 1H), 4.78 (m, 1 H), 3.21 (s, 3H), 1.30 (d, J = 5.7 Hz, 6 H). Anal Calcd for (C24H23N2O9PS2 + 0.1 HBr): C, 49.14 H, 3.97; N, 4.78. Found: C, 48.96; H, 3.94; N, 4.59. |

| Example | Structure | Mass Spect. (Mode) | 1H NMR δ (DMSO-d$_6$) & Elemental Analysis |
|---|---|---|---|
| 167 | 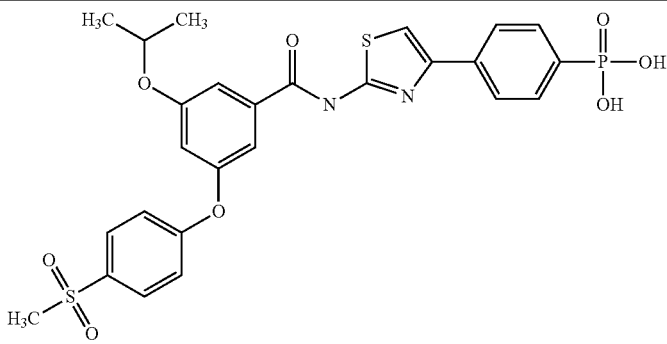 | 589.4 (+) | 8.00 (m, 2H), 7.94 (m, 2 H), 7.80 (s, 1H), 7.73 (m, 2H), 7.60 (m, 1H), 7.41 (m, 1H), 7.25 (m, 2H), 6.97 (m, 1H), 4.79 (m, 1 H), 3.20 (s, 3H), 1.30 (d, J = 6.0 Hz, 6 H). Anal Calcd for (C26H25N2O8PS2 + 0.6 HBr): C, 49.01 H, 4.05; N, 4.40. Found: C, 49.09; H, 3.72; N, 4.13. |

Examples 168-171

The following examples were prepared in a similar manner to Example 16 from the appropriate intermediates with modifications evident to an individual skilled in the art:

| Example | Structure | Mass Spect. (Mode) | 1H NMR δ (DMSO-d$_6$) & Elemental Analysis |
|---|---|---|---|
| 168 | 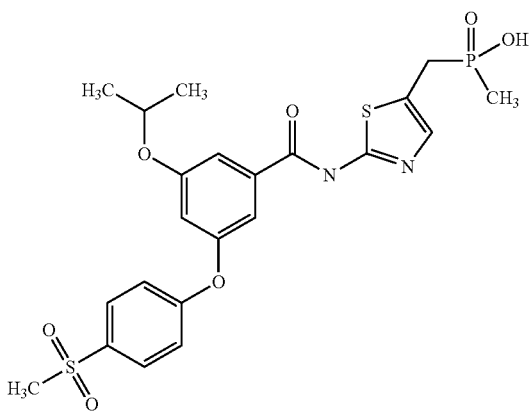 [SMILES: CC(C)Oc1cc(Oc2ccc(S(C)(=O)=O)cc2)cc(C(=O)Nc2ncc(CP(C)(=O)O)s2)c1] | 525.6 (+) | 7.95 (dd, J = 7.2 Hz, 2 H), 7.54 (s, 1 H), 7.37 (t, J = 2 Hz, 1 H), 7.26 (m, 4H), 6.96 (t, J = 2 Hz, 1 H), 4.77 (m, 1 H), 3.20 (m, 5 H), 1.30 (m, 9 H). Anal. Calcd. for (C$_{22}$H$_{25}$N$_2$O$_7$PS$_2$): C, 50.38; H, 4.80; N, 5.34. Found: C, 50.24; H, 4.94; N, 5.11. |
| 169 | 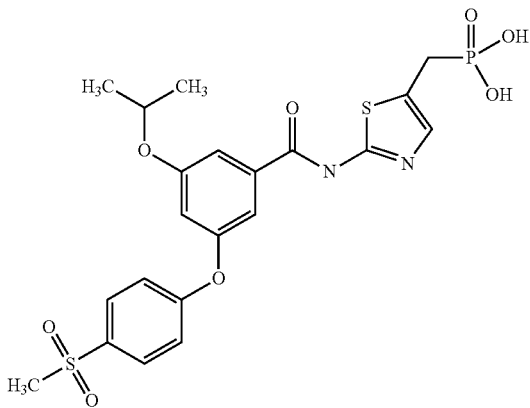 [SMILES: CC(C)Oc1cc(Oc2ccc(S(C)(=O)=O)cc2)cc(C(=O)Nc2ncc(CP(=O)(O)O)s2)c1] | 527.6 (+) | 7.94 (dd, J = 7, 2 Hz, 2 H), 7.54 (d, J = 2 Hz, 1H), 7.37 (t, J = 2 Hz, 1 H), 7.26 (m, 3H), 6.96 (t, J = 2 Hz, 1H), 4.77 (m, 1 H), 3.21 (s, 3 H), 3.10 (d, J = 20 Hz, 2 H), 1.30 (d, J = 6 Hz, 2 H). Anal. Calcd. for (C$_{21}$H$_{23}$N$_2$O$_8$PS$_2$ + 0.2 H$_2$O): C, 47.58; H, 4.45; N, 5.28. Found: C, 47.61; H, 4.40; N, 5.01. |

| Example | Structure | Mass Spect. (Mode) | 1H NMR δ (DMSO-$d_6$) & Elemental Analysis |
|---|---|---|---|
| 170 | 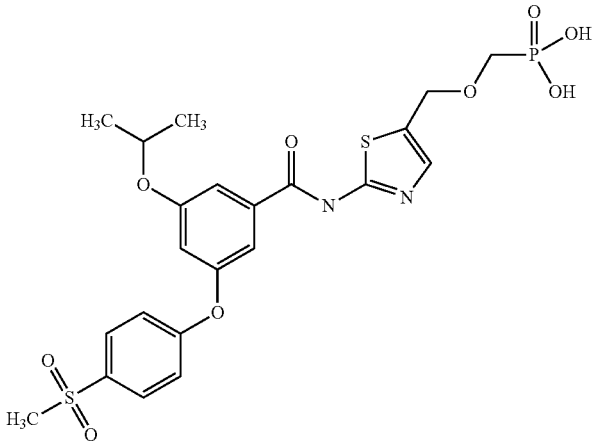 [SMILES: CC(C)Oc1cc(Oc2ccc(S(C)(=O)=O)cc2)cc(C(=O)Nc2ncc(COCP(=O)(O)O)s2)c1] | 557.6 (+) | δ 7.95 (dd, J = 7, 2 Hz, 2 H), 7.55 (d, J = 2 Hz, 1 H), 7.51 (s, 1H), 7.38 (t, J = 2 Hz, 1 H), 7.25 (dd, J = 7, 2 Hz, 2 H), 6.97 (t, J = 2 Hz, 1 H), 4.77 (m, 1 H), 4.73 (s, 2 H), 3.54 (d, J = 9 Hz, 2 H), 3.21 (s, 3 H), 1.30 (d, J = 6 Hz, 2 H). Anal. Calcd. for ($C_{22}H_{25}N_2O_9PS_2$ + 0.2 $H_2O$ + 0.3 TMS-OH): C, 46.84; H, 4.87; N, 4.77. Found: C, 46.89; H, 4.51; N, 4.36. |
| 171 | 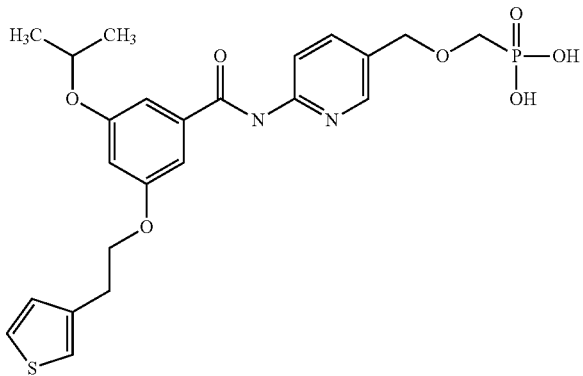 [SMILES: CC(C)Oc1cc(OCCc2ccsc2)cc(C(=O)Nc2ccc(COCP(=O)(O)O)cn2)c1] | 507.4 (+) | 10.78 (s, 1 H), 8.32 (d, J = 1.5 Hz, 1H), 8.13 (d, J = 6.8 Hz, 1 H), 7.79 (m, 1 H), 7.46 (m, 1H), 7.31(m, 1H), 7.18 (m, 2H), 7.11 (m, 1H), 6.63 (m, 1H), 4.70 (m, 1 H), 4.52 (s, 2H), 4.24 (m, 2H), 3.35 (d, J = 8.4 Hz, 2H), 3.04 (m, 2H), 1.25 (d, J = 6.0 Hz, 6 H). Anal Calcd for (C23H27N2O7PS + 0.1 NH4Br + 0.7 NH3): C, 52.30 H, 5.63; N, 7.42. Found: C, 52.36: H, 5.58; N, 7.37. |

Examples 172-173

The following examples were prepared in a similar manner to Example 23 from the appropriate intermediates with modifications evident to an individual skilled in the art:

| Example | Structure | Mass Spect. (Mode) | 1H NMR δ (DMSO-$d_6$) & Elemental Analysis |
|---|---|---|---|
| 172 | 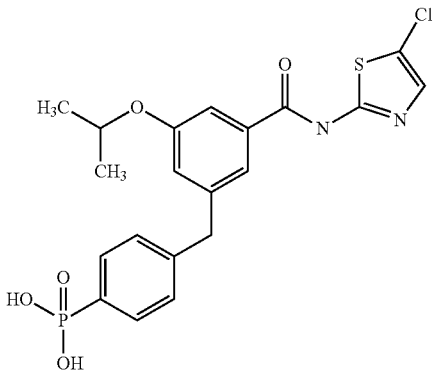 [SMILES: CC(C)Oc1cc(Cc2ccc(P(=O)(O)O)cc2)cc(C(=O)Nc2ncc(Cl)s2)c1] | 467.4 (+) | 7.57 (s, 1 H), 7.53 (dd, J = 8, 5 Hz, 2 H), 7.52 (m, 1 H), 7.46 (m, 1H), 7.24 (dd, J = 8, 3 Hz, 2 H), 6.99 (m, 1 H), 6.65-4.71 (m, 1 H), 3.94 (s, 2 H), 1.25 (d, J = 6 Hz, 6 H). Anal, calcd. for ($C_{20}H_{20}ClN_2O_5PS$ + 0.3 $NH_4Cl$): C, 49.74; H, 4.76; N, 6.67. Found: C, 49.68; H, 4.74; N, 6.83. |

| Example | Structure | Mass Spect. (Mode) | 1H NMR δ (DMSO-d$_6$) & Elemental Analysis |
|---|---|---|---|
| 173 | 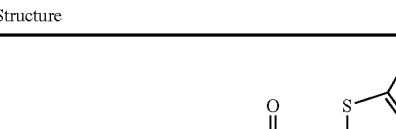 | 451.4 (+) | 7.59 (dd, J = 12, 8 Hz, 2 H), 7.49 (m, 1 H), 7.46 (m, 1 H), 7.37 (d, J = 3 Hz, 1 H), 7.35 (dd, J = 8, 3 Hz, 2 H), 7.02 (m, 1 H), 4.66-4.71 (m, 1 H), 3.98 (s, 2 H), 1.26 (d, J = 6 Hz). Anal. calcd. for (C$_{20}$H$_{20}$FN$_2$O$_5$PS + 0.4 H$_2$O): C, 52.49: H, 4.58; N, 6.12. Found: C, 52.45; H, 4.56; N, 5.91. |

Examples 174-176

The following examples were prepared in a similar manner to Example 26 from the appropriate intermediates with modifications evident to an individual skilled in the art:

| Example | Structure | Mass Spect. (Mode) | 1H NMR δ (DMSO-d$_6$) & Elemental Analysis |
|---|---|---|---|
| 174 | 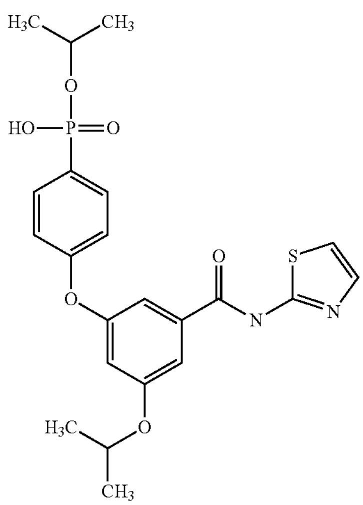 [SMILES: CC(C)Oc1cc(Oc2ccc(P(=O)(O)OC(C)C)cc2)cc(C(=O)Nc2nccs2)c1] | 477.4 (+) | 7.70 (dd, J = 12, 8 Hz, 2 H), 7.55 (d, J = 4 Hz, 1 H), 7.50 (d, J = 1 Hz, 1H), 730 (m, 2 H), 7.10 (d, J = 8 Hz, 1 H), 6.85 (s, 1 H), 4.75 (m, 1 H), 1.29 (d, J = 6 Hz, 6 H), 1.14 (d, J = 6 Hz, 6 H). Anal Calcd. for (C$_{22}$H$_{25}$N$_2$O$_6$PS + 0.8 H$_2$O); C, 53.83; H, 5.46; N, 5.71. Found: C, 53.67; H, 5.02; N, 5.23. |
| 175 | 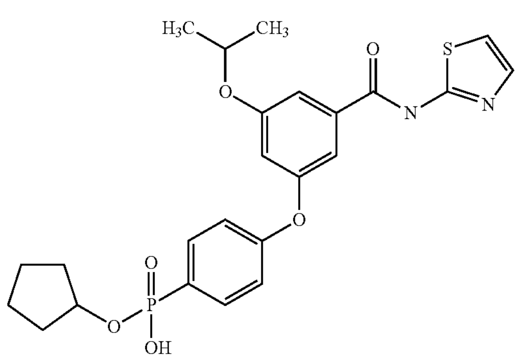 [SMILES: CC(C)Oc1cc(Oc2ccc(P(=O)(O)OC3CCCC3)cc2)cc(C(=O)Nc2nccs2)c1] | 503.6 (+) | 7.71 (m, 2 H), 7.56 (s, 1 H), 7.52 (t, J = 2 Hz, 1H), 7.32 (dd, J = 2, 1 Hz, 2 H), 7.15 (m, 2 H), 6.89 (t, J = 2 Hz, 1 H), 4.76 (m, 1 H), 4.69 (m, 1 H), 1.65 (m, 6 H), 1.51 (m, 2 H), 1.30 (d, J = 6 Hz, 6H). Anal. Calcd. for (C$_{24}$H$_{27}$N$_2$O$_6$PS): C, 57.36; H, 5.42: N, 5.57. Found: C, 57.22; H, 5.38; N, 5.54. |

| Example | Structure | Mass Spect. (Mode) | 1H NMR δ (DMSO-d$_6$) & Elemental Analysis |
|---|---|---|---|
| 176 | 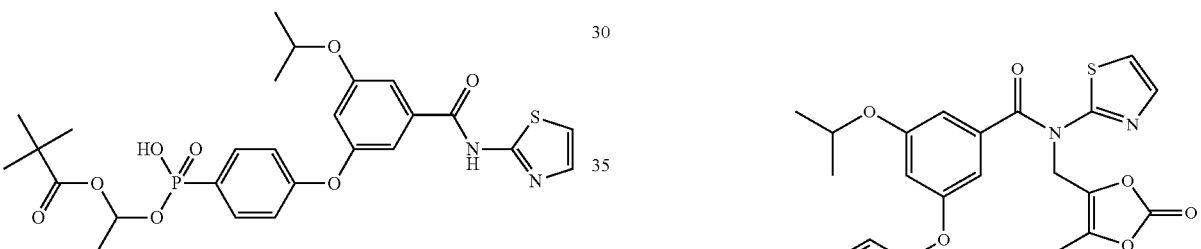 | 493.6 (+) | 7,72(dd, J = 13, 9 Hz, 2 H), 7.56 (s, 1 H), 7.53 (d, J = 1 Hz, 1H), 7.32 (d, J = 2, Hz, 1 H), 7.28 (d, J = 3 Hz, 1 H), 7.15 (m, 2 H), 6.89 (t, J = 2 Hz, 1 H), 4.76 (m, 1 H), 3.92 (m, 2 H), 3.46 (t, J = 5 Hz, 2 H), 3.21 (s, 3H), 1.30 (d, J = 6 Hz, 6H); LCMS m/z = 493.6 [C$_{22}$H$_{25}$N$_2$O$_7$PS + H]$^+$; Anal. Calcd. for (C$_{22}$H$_{25}$N$_2$O$_7$PS): C, 53.65; H, 5.12; N, 5.69. Found: C, 53.56; H, 5.06; N, 5.59. |

Example 177

2,2-Dimnethyl-propionic acid 1-(hydroxy-{4-[3-isopropoxy-5-(thiazol-2-ylcarbamoyl)-phenoxy]-phenyl}-phosphinoyloxy)-ethyl ester A mixture of {4-[3-isopropoxy-5-(thiazol-2-ylcarbamoyl-)phenoxy]-phenyl}-phosphonic acid (250 mg, 0.58 mmol) and DIEA (0.193 mL, 1.16 mmol) in 6 mL of acetonitrile was stirred for 15 min and then 1-iodoethyl pivalate (177 mg, 0.69 mmol) was added. The resulting mixture was stirred for 2 h at rt, then diluted with CH$_2$Cl$_2$, washed with 1 M aqueous NaHSO$_4$, dried (MgSO$_4$) and evaporated. The residue was dissolved in 3:1 acetonitrile/water and subjected to MPLC purification through a 25 g C18 column eluting with % acetonitrile in water (time): 15-50 (15 min). Lyophilization of the eluent containing the desired product provided 31 mg (10%) of the title compound as an amorphous solid: $^1$H NMR (500 MHz, DMSO-d$_6$): δ 0.91 (s, 9H), 1.29 (d, 6H, J=6 Hz), 1.30 (d, 3H, J=6 Hz), 4.73 (septet, 1H, J=6 Hz), 6.34 (br s, 1H), 6.75 (s, 1H), 7.01 (d, 2H, J=7 Hz), 7.24 (s, 1H), 7.28 (d, 1H, J=3 Hz), 7.45 (s, 1H), 7.56 (d, 1H, J=3 Hz), 7.63 (br s, 2H), 12.61 (br s, 1H); LCMS (m/z): 563.4 [C$_{26}$H$_{31}$N$_2$O$_8$PS+H]$^+$. Anal. calcd. for (C$_{26}$H$_{31}$N$_2$O$_8$PS+1H$_2$O): C, 53.79; H, 5.73; N, 4.82. Found: C, 52.93; H, 5.93; N, 5.92.

Example 178

(4-{3-Isopropoxy-5-[(5-methyl-2-oxo-[1,3]dioxol-4-ylmethyl)-thiazol-2-yl-carbamoyl]-phenoxy}-phenyl)-phosphonic acid mono-(5-methyl-2-oxo-[1,3]dioxol-4-ylmethyl) ester The title compound was prepared from {4-[3-isopropoxy-5-(thiazol-2-ylcarbamoyl-)phenoxy]-phenyl}-phosphonic acid and 5-methyl-2-oxo-1,3-dioxolen-4-yl)methylbromide according to the method described in Example 177 with modifications evident to an individual skilled in the art. $^1$H NMR (500 MHz, DMSO-d$_6$): δ 1.29 (d, 6H, J=6 Hz), 2.07 (s 3H), 2.14 (s, 3H), 4.71 (septet, 1H, J=6 Hz), 4.76 (d, 2H, J=10 Hz), 5.40 (s, 2H), 6.84 (t, 1H J=2 Hz), 7.11 (dd, 2H, J=8, 3 Hz), 7.12 (d, 1H, J=5 Hz), 7.43 (dd, 1H, J=2, 1 Hz), 7.59 (dd, 2H, J=2, 1 Hz), 7.61 (d, 1H, J=5 Hz), 7.70 (dd, 2H, J=12, 8 Hz); LCMS (m/z): 658.8 [C$_{29}$H$_{27}$N$_2$O$_{12}$PS+H]$^+$. Anal. calcd. for (C$_{29}$H$_{27}$N$_2$O$_{12}$PS): C, 52.89; H, 4.13; N, 4.25. Found: C, 52.83; H, 4.43; N, 4.10.

Example 179

3-Methyl-thiobutyric acid 2-{{4-[3-isopropoxy-5-(thiazol-2-ylcarbamoyl)phenoxy]phenyl}[2(3methyl-butyrylsulfanyl)ethoxy]phosphinoyloxy}ethyl ester

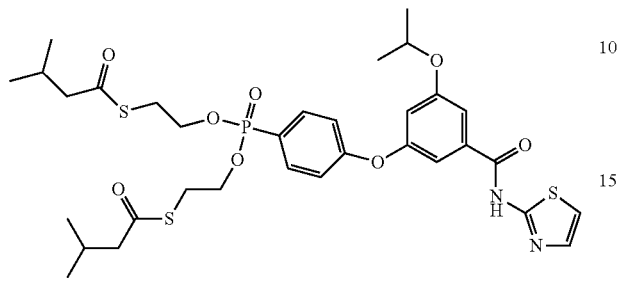

To a solution of {4-[3-isopropoxy-5-(thiazol-2-ylcarbamoyl)-phenoxy]-phenyl}-phosphonic acid (Example 3) (800 mg, 1.84 mmol) in THF (20 mL) was added triphenylphosphine (1.21 g, 4.60 mmol), 3-methyl-thiobutyric acid S-(2-hydroxy-ethyl) ester (746 mg, 4.60 mmol) and diisopropylazodicarboxylate (906 μL, 4.60 mmol). The resulting mixture was stirred at rt for 3 hr. The crude reaction mixture was concentrated under vacuum. The residue was chromatographed on silica gel using an ethyl acetate-hexanes gradient to afford 82 mg (6%) of the title compound: $^1$H NMR (300 MHz, DMSO-$d_6$): δ 12.70 (bs, 1H), 7.73 (dd, J=13, 9 Hz, 2H), 7.55 (t, 2H), 7.36 (d, J=2 Hz, 1H), 7.28 (s, 1H), 7.18 (t, J=4 Hz, 2H), 6.91 (d, J=2 Hz, 1H), 4.76 (m, 1H), 4.06 (m, 4H), 3.15 (m, 4H), 4.95 (m, 4H), 2.01 (m, 2H), 1.30 (d, J=6 Hz, 6H), 0.87 (d, J=7 Hz, 12H); LCMS m/z=723.4 $[C_{33}H_{43}N_2O_8PS_3+H]^+$; Anal. Calcd. for $(C_{33}H_{43}N_2O_8PS_3)$: C, 54.83; H, 6.00; N, 3.88. Found: C, 55.49; H, 5.36; N, 3.92.

Example 180

2,2-Dimethyl-propionic acid (2,2-dimethyl-propionyloxymethoxy){4-[3-isopropoxy-5-(thiazol-2-ylcarbamoyl)phenoxy]phenyl}phosphinoyloxymethyl ester

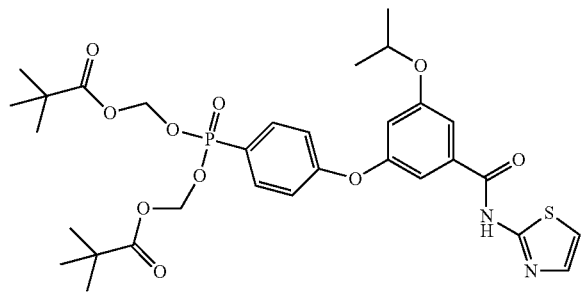 [SMILES: CC(C)Oc1cc(Oc2ccc(P(=O)(OCOC(=O)C(C)(C)C)OCOC(=O)C(C)(C)C)cc2)cc(C(=O)Nc2nccs2)c1]

To a solution of {4-[3-isopropoxy-5-(thiazol-2-ylcarbamoyl)-phenoxy]-phenyl}-phosphonic acid (Example 3) (200 mg, 0.459 mmol) in acetonitrile (10 mL) was added diisopropylethylamine (155 μL, 0.941 mmol). Let stir until mixture goes into solution. Add 2,2-dimethyl-propionic acid iodomethylester and stir at rt for 16 h. The residue was adsorbed onto SiO$_2$ and chromatographed on silica gel using an ethyl acetate-hexanes gradient to afford 50 mg (16%) of the title compound as an oil: $^1$H NMR (300 MHz, DMSO-$d_6$): δ 12.68 (bs, 1H), 7.74 (dd J=13, 9 Hz, 2H), 7.55 (d, J=4 Hz, 2H), 7.29 (m, 4H), 6.85 (s, 1H), 5.66 (m, 4H), 4.76 (m, 1H), 1.31 (d, J=6 Hz, 6H), 1.07 (s, 18H); LCMS m/z=663.9 $[C_{31}H_{39}N_2O_1PS+H]^+$; Anal. Calcd. for $(C_{31}H_{39}N_2O_{10}PS)$: C, 56.19; H, 5.93; N, 4.23. Found: C, 56.41; H, 6.08; N, 4.00.

Example 181

2,2-Dimethylpropionic acid 1-([1-(2,2-dimethyl-propionyloxy)ethoxy]{4-[3-isopropoxy-5-(thiazol-2-ylcarbamoyl)phenoxy]phenyl}phosphinoyloxy)ethyl ester

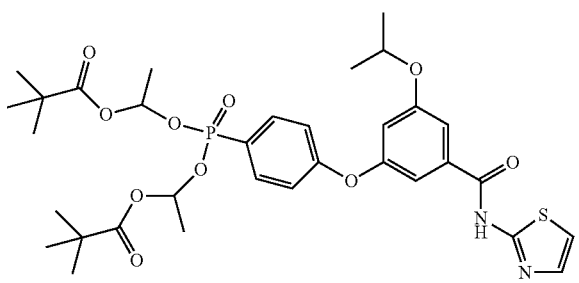 [SMILES: CC(C)Oc1cc(Oc2ccc(P(=O)(OC(C)OC(=O)C(C)(C)C)OC(C)OC(=O)C(C)(C)C)cc2)cc(C(=O)Nc2nccs2)c1]

Prepared from {4-[3-isopropoxy-5-(thiazol-2-ylcarbamoyl)-phenoxy]-phenyl}-phosphonic acid (Example 3) in a similar manner to Example 177 from the appropriate intermediates with modifications evident to an individual skilled in the art: $^1$H NMR (300 MHz, DMSO-$d_6$): δ 12.68 (bs, 1H), 7.72 (m, 2H), 7.54 (m, 2H), 6.86 (d, J=24 Hz, 1H), 6.48 (m, 2H), 4.75 (m, 1H), 1.49 (dd, J=14, S Hz, 6H), 1.31 (d, J=6 Hz, 6H), 1.01 (m, 18H); LCMS m/z=691.9 $[C_{33}H_{43}N_2O_{10}PS+H]^+$; Anal. Calcd. for $(C_{33}H_{43}N_2O_{10}PS)$: C, 57.38; H, 6.27; N, 4.06. Found: C, 57.16; H, 6.32; N, 3.89.

Example 182

{4-[3-Isopropoxy-5-(thiazol-2-ylcarbamoyl)phenoxy]phenyl}phosphonic acid bis-(1-isopropoxycarbonyloxymethyl) ester

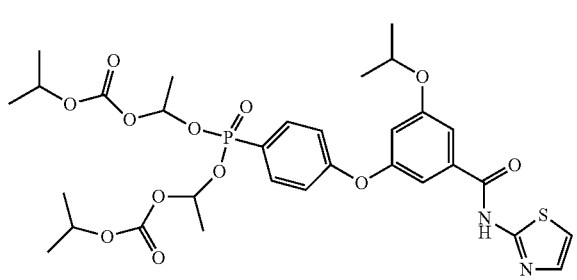 [SMILES: CC(C)OC(=O)OC(C)OP(=O)(OC(C)OC(=O)OC(C)C)c1ccc(Oc2cc(OC(C)C)cc(C(=O)Nc3nccs3)c2)cc1]

Prepared from {4-[3-isopropoxy-5-(thiazol-2-ylcarbamoyl)-phenoxy]-phenyl}-phosphonic acid (Example 3) in a similar manner to Example 177 from the appropriate intermediates with modifications evident to an individual skilled in the art: $^1$H NMR (300 MHz, DMSO-$d_6$): δ 12.70 (bs, 1H), 7.71 (m, 2H), 7.55 (d, J=3 Hz, 2H), 7.33 (m, 2H), 7.17 (m, 2H), 6.87 (m, 1H), 6.40 (m, 2H), 4.77 (m, 2H), 4.60 (m, 1H), 1.52 (m, 6H), 1.15 (m, 18H); LCMS ml: =695.4 $[C_{31}H_{39}N_2O_{12}PS+H]^+$; Anal. Calcd. for $(C_{31}H_{39}N_2O_{12}PS)$: C, 53.60; H, 5.66; N, 4.03. Found: C, 53.67; H, 5.75; N, 3.77.

Example 183

(4-{3-[(3-Fluoro-4-methoxybenzyl)thiazol-2-yl-carbamoyl]-5-isopropoxyphenoxy}phenyl)-phosphonic acid bis-(3-fluoro-4-methoxy-benzyl) ester

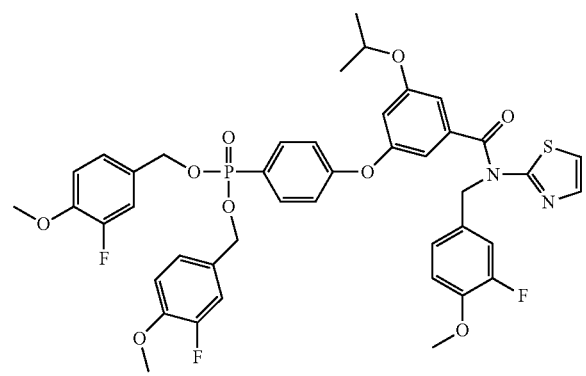 [SMILES: COc1ccc(COP(=O)(OCc2ccc(OC)c(F)c2)c2ccc(Oc3cc(OC(C)C)cc(C(=O)N(Cc4ccc(OC)c(F)c4)c4nccs4)c3)cc2)cc1F]

Prepared from {4-[3-isopropoxy-5-(thiazol-2-ylcarbamoyl)-phenoxy]-phenyl}-phosphonic acid (Example 3) in a similar manner to Example 177 from the appropriate intermediates with modifications evident to an individual skilled in the art: $^1$H NMR (300 MHz, DMSO-$d_6$): δ 7.75 (m, 3H), 7.57 (dd, J=2, 1 Hz, 1H), 7.42 (dd, J=2, 1 Hz, 1H), 7.28 (dd, J=12, 2 Hz, 1H), 7.13 (m, 11H), 6.87 (t, J=3 Hz, 1H), 5.36 (s, 2H), 4.93 (m, 4H), 4.70 (m, 1H), 3.80 (s, 6H), 3.77 (s, 3H), 1.29 (d, J=6 Hz, 6H); LCMS m/z=849.9 $[C_{43}H_{40}F_3N_2O_9PS+H]^+$; Anal. Calcd. for $(C_{43}H_{40}F_3N_2O_9PS)$: C, 60.85; H, 4.75; N, 3.30. Found: C, 60.70; H, 4.59; N, 3.16.

Example 184

{4-[3-Isopropoxy-5-(thiazol-2-ylcarbamoyl)phenoxy]phenyl}phosphonic acid bis-(3-fluoro-4-methoxybenzyl) ester

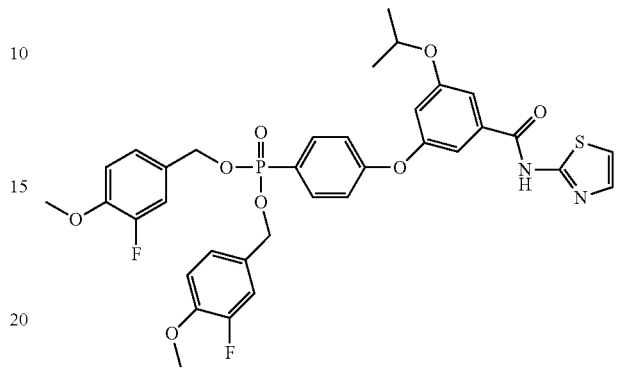

To a solution of 3-{4-[bis-(3-fluoro-4-methoxy-benzyloxy)-phosphoryl]-phenoxy}-5-isopropoxy-benzoic acid (350 mg, 0.557 mmol) in DMF (6 mL) was added 2-aminothiazole (70 mg, 0.696 mmol), HATU (265 mg, 0.696 mmol), and diisopropylethylamine (368 μL, 2.23 mmol). Stirred at rt for 16 h. The reaction mixture was diluted with EtOAc and washed with H2O (2×) and brine (2×). Dried with MgSO$_4$, filtered, and concentrated. The residue was chromatographed on silica gel using an ethyl acetate-hexanes gradient to provide 164 mg (42%) of the title compound: $^1$H NMR (300 MHz, DMSO-$d_6$): δ 12.68 (bs, 1H), 7.75 (dd, J=13, 9 Hz, 2H), 7.55 (d, J=4 Hz, 2H), 7.35 (s, 1H), 7.16 (m, 9H), 6.91 (s, 1H), 4.97 (dd, J=8, 2 Hz, 4H), 4.76 (m, 1H), 3.82 (s, 6H), 1.30 (d, J=6 Hz, 6H); LCMS m/z=711.6 $[C_{33}H_{33}F_2N_2O_8PS+H]^+$; Anal. Calcd. for $(C_{35}H_{33}F_2N_2O_8PS+1.2H_2O)$: C, 57.41; H, 4.87; N, 3.83. Found: C, 57.06; H, 4.24; N, 3.91.

Intermediates for the preparation of Example 184 were prepared according to Route 11, as described below.

Route 11

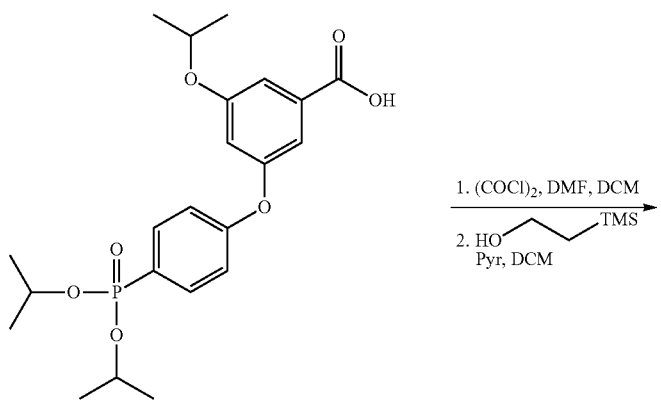

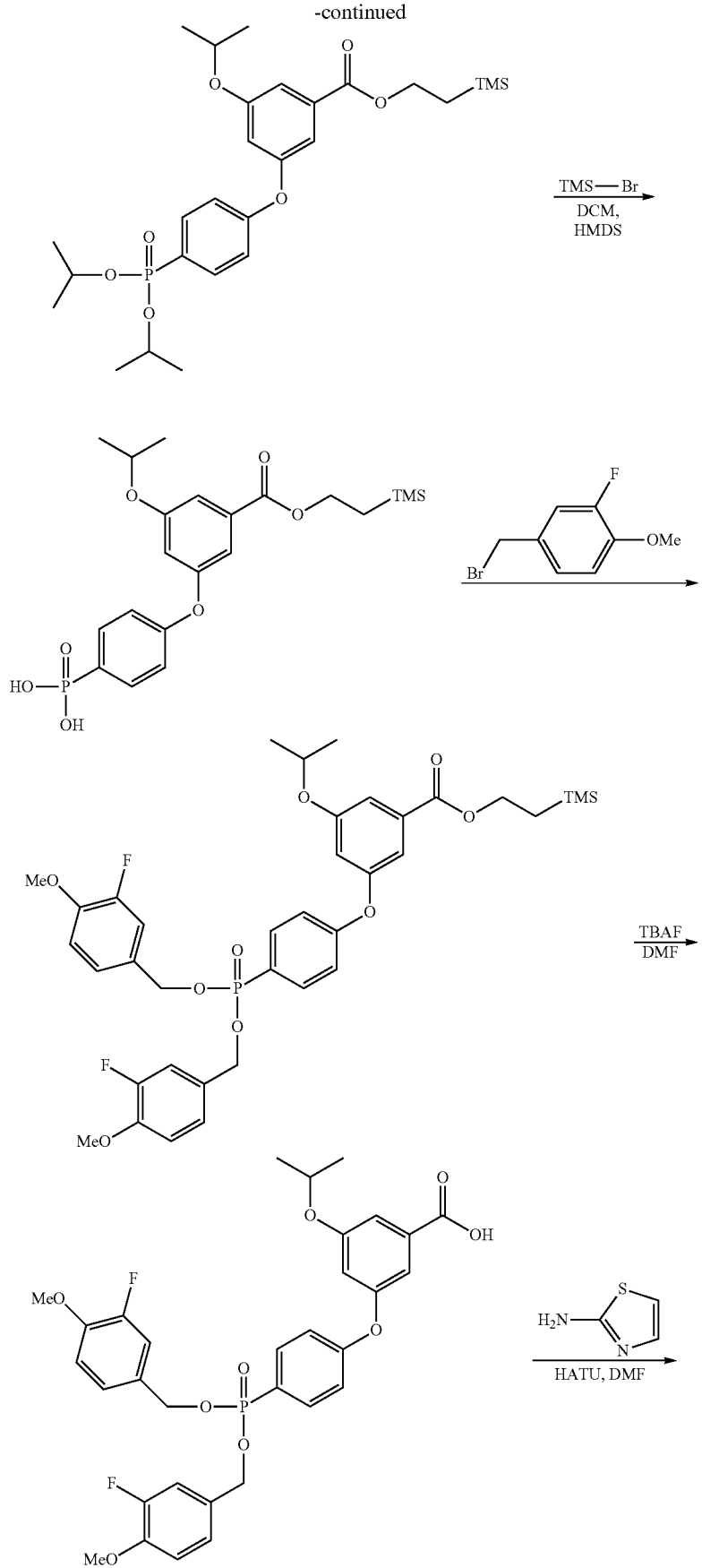

-continued

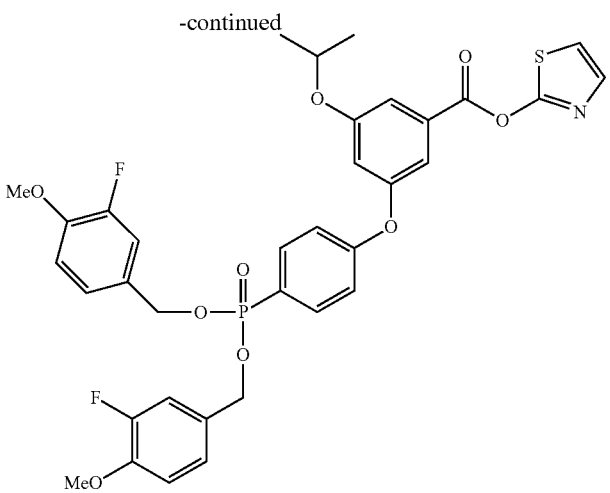

Step A

3-[4-(Diisopropoxy-phosphoryl)-phenoxy]-5-isopropoxy-benzoic acid 2-trimethylsilanyl-ethyl ester

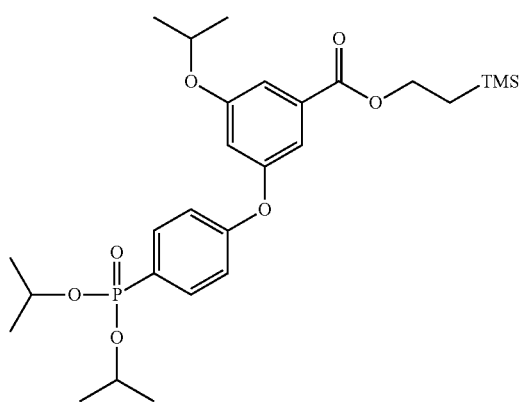 [SMILES: CC(C)Oc1cc(Oc2ccc(P(=O)(OC(C)C)OC(C)C)cc2)cc(C(=O)OCC[Si](C)(C)C)c1]

To a solution of 3-[4-(diisopropoxy-phosphoryl)-phenoxy]-5-isopropoxy-benzoic acid (Example 3, route 3, step E) (10 g, 22.9 mmol) in DCM (115 mL) was added DMF (0.09 mL, 1.15 mmol) and oxalyl chloride (4.0 mL, 45.8 mmol). The resulting mixture was stirred at rt for 2 h. The mixture was concentrated. The resulting residue was azeotroped with 50 mL anhydrous toluene and then re-dissolved in DCM (40 mL), cooled to 0° C. A solution of pyridine (3.1 mL, 36.6 mmol) in DCM (10 mL) was added slowly to the reaction flask followed by 2-trimethylsilanylethanol (3.6 mL, 25.2 mmol). The resulting mixture was stirred at rt overnight. On second day solvents were removed and the residue was partitioned between EtOAc and saturated sodium bicarbonate. The organic layer was separated, washed with brine (1x), dried with anhydrous MgSO$_4$, filtered, and concentrated. The residue was chromatographed on silica gel using an ethyl acetate-hexanes gradient to afford 5.0 g (41%) of 3-[4-(diisopropoxy-phosphoryl)-phenoxy]-5-isopropoxy-benzoic acid 2-trimethylsilanyl-ethyl ester. $^1$H NMR (500 MHz, DMSO-d$_6$): δ 7.72 (dd, J=13, 9 Hz, 2H), 7.26 (dd, J=3, 2 Hz, 1H), 7.16 (dd, J=9, 3 Hz, 2H), 7.06 (dd, J=3, 2 Hz, 1H), 6.99 (t, J=3 Hz, 1H), 4.69 (m, 1H), 4.54 (m, 2H), 3.48 (t, 2H), 1.28 (dd, J=8, 3 Hz, 12H), 1.18 (d, J=6 Hz, 6H), 1.04 (t, 2H), −0.16 (s, 9H).

Step B

3-Isopropoxy-5-(4-phosphono-phenoxy)-benzoic acid 2-trimethylsilanyl-ethyl ester

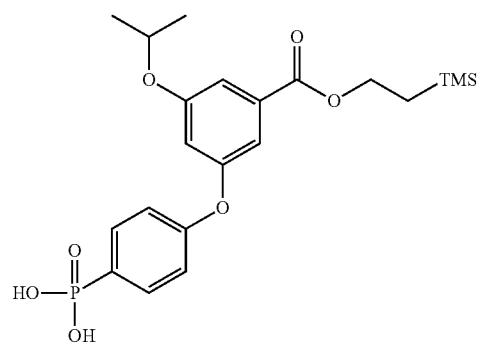 [SMILES: CC(C)Oc1cc(Oc2ccc(P(=O)(O)O)cc2)cc(C(=O)OCC[Si](C)(C)C)c1]

To a solution of 3-[4-(diisopropoxy-phosphoryl)-phenoxy]-5-isopropoxy-benzoic acid 2-trimethylsilanyl-ethyl ester (5.0 g, 9.30 mmol) in CH$_2$Cl$_2$ (100 mL) was added HMDS (31.7 Ml, 149 mmol), and TMS-Br (9.8 mL, 74.5 mmol). The mixture was stirred at rt for 16 h. The solvent was evaporated and the residue was diluted with water and acidified to pH 2-3 with aqueous HCl. Extracted into EtOAc (2x). The extract was washed with dilute HC, water, and brine. Dried (MgSO$_4$) and evaporated to provide 2.74 g of 3-Isopropoxy-5-(4-phosphono-phenoxy)-benzoic acid 2-trimethylsilanyl-ethyl ester. $^1$H NMR (500 MHz, DMSO-d$_6$): δ 7.71 (dd, J=13, 9 Hz, 2H), 7.22 (dd, J=3, 2 Hz, 1H), 7.11 (dd, J=9, 3 Hz, 2H), 7.03 (dd, J=3, 2 Hz, 1H), 6.92 (t, J=3 Hz, 1H), 4.67 (m, 1H), 4.34 (t, 2H), 1.27 (d, J=6 Hz, 6H), 1.05 (t, 2H), 0.01 (s, 9H).

Step C

3-{4-[Bis-(3-fluoro-4-methoxy-benzyloxy)-phosphoryl]-phenoxy}-5-isopropoxy-benzoic acid 2-trimethylsilanyl-ethyl ester

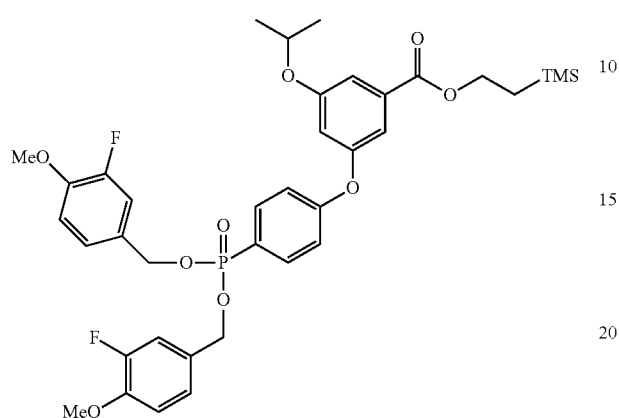

To a solution of 3-isopropoxy-5-(4-phosphono-phenoxy)-benzoic acid 2-trimethylsilanyl-ethyl ester (532 mg, 1.17 mmol) in ACN (15 mL) was added diisopropylethylamine (425 μL, 2.57 mmol), and benzyl bromide (640 mg, 2.92 mmol). Stirred at 55° C. for 16 h. The reaction mixture was cooled to rt and adsorbed onto SiO₂ and chromatographed on silica gel using an ethyl acetate-hexanes gradient to provide 536 mg (63%) of 3-{4-[bis-(3-fluoro-4-methoxy-benzyloxy)-phosphoryl]-phenoxy}-5-isopropoxy-benzoic acid 2-trimethylsilanyl-ethyl ester. ¹H NMR (300 MHz, DMSO-d₆): δ 7.74 (dd, J=13, 9 Hz, 2H), 7.26 (dd, J=2, 1 Hz, 1H), 7.20 (s, 1H), 7.15 (m, 7H), 7.07 (m, 1H), 6.98 (m, 1H), 4.97 (dd, J=8, 2 Hz, 4H), 4.67 (m, 1H), 4.34 (t, J=8 Hz, 2H), 3.82 (s, 6H), 1.27 (d, J=6 Hz, 6H), 1.03 (t, J=9 Hz, 2H), 0.01 (s, 9H).

Step D

3-{4-[Bis-(3-fluoro-4-methoxy-benzyloxy)-phosphoryl]-phenoxy}-5-isopropoxy-benzoic acid

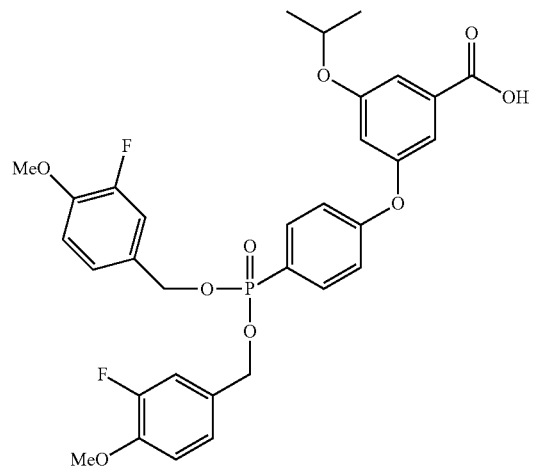 [SMILES: COc1ccc(COP(=O)(OCc2ccc(OC)c(F)c2)c2ccc(Oc3cc(OC(C)C)cc(C(=O)O)c3)cc2)cc1F]

To a solution of 3-{4-[bis-(3-fluoro-4-methoxy-benzyloxy)-phosphoryl]-phenoxy}-5-isopropoxy-benzoic acid 2-trimethylsilanyl-ethyl ester (536 mg, 0.735 mmol) in DMF (10 mL) was added tetrabutylammonium fluoride (1.0 M solution in THF) (1.84 mL, 1.84 mmol). Stirred at rt for 16 h. The reaction mixture was diluted with EtOAc and washed with H2O (2×) and brine (2×). Dried with MgSO₄ and evaporated solvent to provide 462 mg (100%) of 3-{4-[bis-(3-fluoro-4-methoxy-benzyloxy)-phosphoryl]-phenoxy}-5-isopropoxy-benzoic acid. ¹H NMR (300 MHz, DMSO-d₆): δ 13.20 (bs, 1H), 7.74 (dd, J=13, 9 Hz, 2H), 7.27 (dd, J=2, 1 Hz, 1H), 7.13 (m, 9H), 6.94 (t, J=2 Hz, 1H), 4.97 (dd, J=9, 2 Hz, 4H), 4.67 (m, 1H), 3.82 (s, 6H), 1.27 (s, J=6 Hz, 6H).

Examples 185-212

The following examples were prepared according to methods used for Example 177-184 from the appropriate intermediates with modifications evident to an individual skilled in the art:

| Example | Structure | Mass Spect. (Mode) | 1H NMR δ (DMSO-d₆) & Elemental Analysis |
|---|---|---|---|
| 185 | 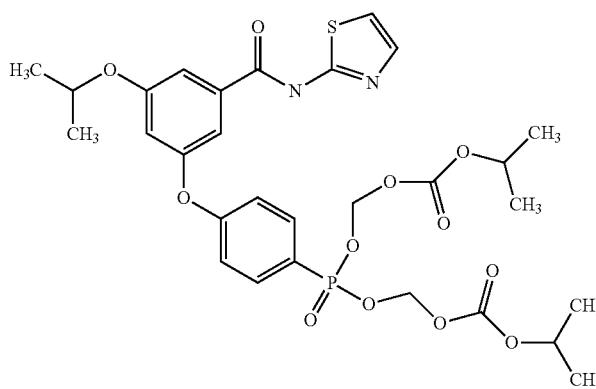 | 667.6 (+) | 7.82 (m, 2H), 7.49 (d, J = 4.0 Hz, 1H), 7.44 (m, 1H), 7.29 (m, 1H), 7.17 (m, 3H), 6.89 (m, 1H), 5.74 (m, 4H), 4.85 (m, 2H), 4.74 (m, 1H), 1.36 (d, J = 5.5 Hz, 6H) 1.25 (m, 12H). Anal Calcd for (C29H35N2O12PS): C, 52.25; H, 5.29: N, 4.20. Found: C, 52.06: H, 5.51; N, 4.17. |

| Example | Structure | Mass Spect. (Mode) | 1H NMR δ (DMSO-d₆) & Elemental Analysis |
|---|---|---|---|
| 186 | 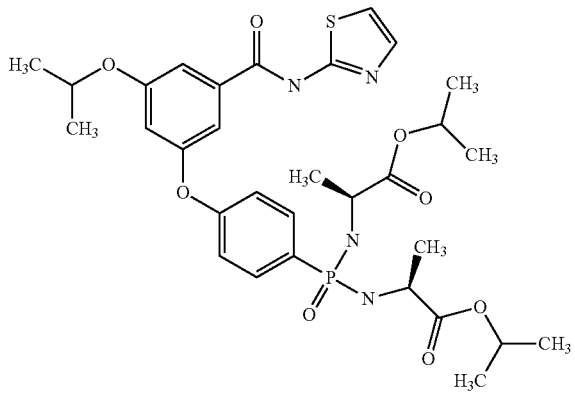 [SMILES: CC(C)OC(=O)[C@H](C)NP(=O)(N[C@@H](C)C(=O)OC(C)C)c1ccc(Oc2cc(OC(C)C)cc(C(=O)Nc3nccs3)c2)cc1] | 661.9 (+) | 7.86 (m, 2H), 7.49 (d, J = 4.0 Hz, 1H), 7.39 (m, 1H), 7.24 (m, 1H), 7.16 (d, J = 4.0 Hz, 1H), 7.13 (m, 2H), 6.84 (m, 1H), 5.00 (m, 1H), 4.69 (m, 1H), 3.97 (m, 1H), 3.85 (m, 1H), 1.35 (m, 12 H), 1.26 (m, 6H), 1.14 (m, 6H). Anal Calcd for (C31H41N4O8PS): C, 56.35; H, 6.25; N, 8.48. Found: C, 56.17; H, 6.04; N, 8.51. |
| 187 | 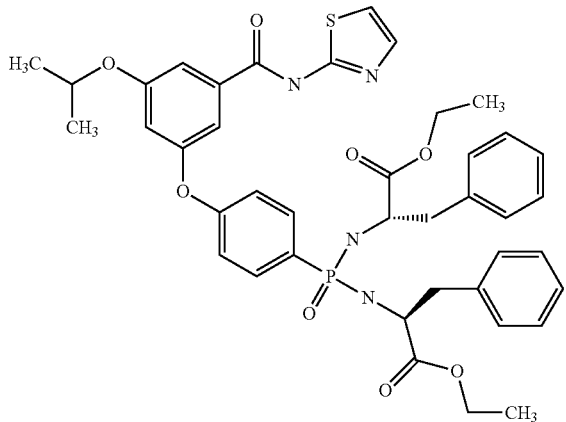 [SMILES: CCOC(=O)[C@H](Cc1ccccc1)NP(=O)(N[C@@H](Cc1ccccc1)C(=O)OCC)c1ccc(Oc2cc(OC(C)C)cc(C(=O)Nc3nccs3)c2)cc1] | 785.9 (+) | 7.48 (m, 3H), 7.40 (m, 1H), 7.28 (m, 10H), 7.04 (m, 2H), 6.97 (m, 2H), 6.81 (m, 1H), 4.71 (m, 1H), 4.02 (m, 2H), 4.13 (m, 3H), 3.91 (m, 1H), 3.16 (m, 1H), 2.92 (m, 2H), 2.72 (m, 1H), 1.36 (d, J = 6.0 Hz, 6 H), 1.23 (m, 3H), 1.11 (m, 3H). Anal Calcd for (C41H45N2O8PS): C, 62.74; H, 5.78; N, 7.14. Found: C, 62.55; H, 5.55; N, 6.92. |
| 188 | 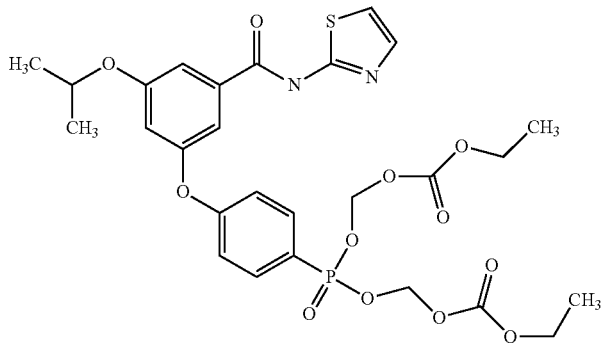 [SMILES: CCOC(=O)OCOP(=O)(OCOC(=O)OCC)c1ccc(Oc2cc(OC(C)C)cc(C(=O)Nc3nccs3)c2)cc1] | 639.6 (+) | 7.82 (m, 2H), 7.50 (d, J = 3.5 Hz, 1H), 7.45 (m, 1H), 7.30 (m, 1H), 7.18 (m, 3H), 6.89 (m, 1H), 5.74 (m, 4H), 4.86 (m, 1H), 4.19 (m, 4H), 1.36 (m, 6H) 1.27 (m, 12H). Anal Calcd for (C27H31N2O12PS): C, 50.78: H, 4.89; N, 4.39. Found: C, 50.70; H, 5.13; N, 4.28. |

| Example | Structure | Mass Spect. (Mode) | 1H NMR δ (DMSO-$d_6$) & Elemental Analysis |
|---|---|---|---|
| 189 | 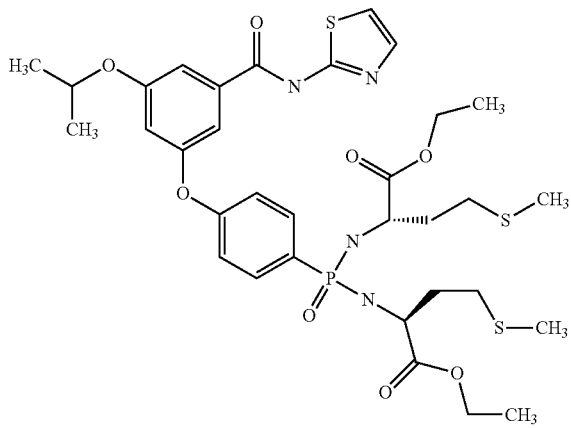 [SMILES: CCOC(=O)[C@H](CCSC)NP(=O)(N[C@@H](CCSC)C(=O)OCC)c1ccc(Oc2cc(OC(C)C)cc(C(=O)Nc3nccs3)c2)cc1] | 753.4 (+) | 7.87 (m, 2H), 7.49 (d, J = 3.5 Hz, 1H), 7.39 (m, 1H), 7.24 (m, 1H), 7.16 (m, 3H), 6.84 (m, 1H), 4.70 (m, 1H), 4.20 (m, 2H), 4.06 (m, 3H), 3.98 (m, 1H), 2.63 (m, 3H), 2.51(m, 2H), 2.05 (m, 9H), 1.90 (m, 2H), 1.32 (m, 12 H), 1.16 (m, 3H). Anal Calcd for (C33H45N4O8PS3): C, 52.64; H, 6.02; N, 7.44. Found: C, 53.20; H, 6.31; N, 7.38. |
| 190 | 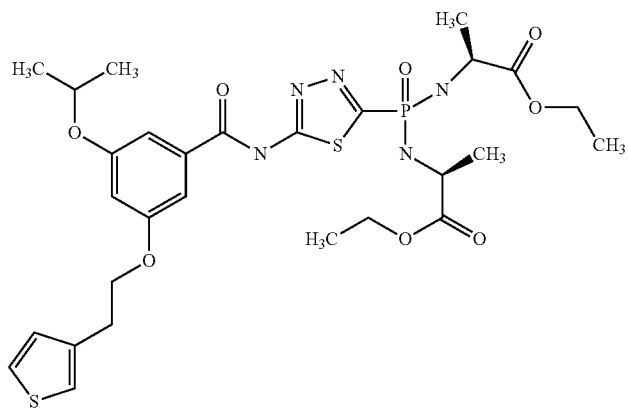 [SMILES: CCOC(=O)[C@H](C)NP(=O)(N[C@@H](C)C(=O)OCC)c1nnc(NC(=O)c2cc(OCCc3ccsc3)cc(OC(C)C)c2)s1] | 668.3 (+) | 13.20 (s, 1H), 7.51 (m, 1H), 7.35 (m, 3H), 7.15 (m, 1H), 6.76 (m, 1H), 5.57 (m, 1H), 4.75 (m, 1H), 4.26 (m, 1H), 3.98 (m, 6H), 3.10 (m, 2H), 1.31 (m, 12H), 1.16 (m, 6H). Anal Calcd for (C28H38N5O8PS2); C, 50.37; H, 5.74; N, 10.49. Found: C, 50.42; H, 6.02; N, 10.24. |
| 191 | 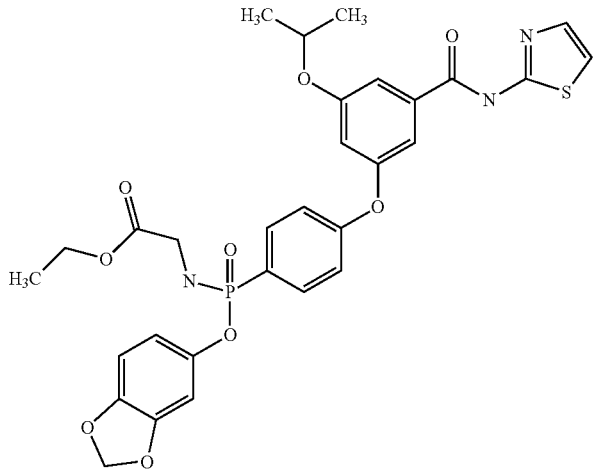 [SMILES: CCOC(=O)CNP(=O)(Oc1ccc2c(c1)OCO2)c1ccc(Oc2cc(OC(C)C)cc(C(=O)Nc3nccs3)c2)cc1] | 640.4 (+) | 12.67 (s, 1H), 7.85(m, 2H), 7.53(m, 2H), 7.28 (m, 2H), 7.15 (m, 2H), 6.85 (m, 3H), 6.65 (m, 1H), 5.99 (s, 2H), 5.89 (m, 1H), 4.74 (m, 1H), 3.99 (m, 2H), 3.66 (m, 2H), 1.28 (d, J = 6.3 Hz, 6H) 1.10 (m, 3H). LC-MS m/z = 640.4 [C30H30N3O9PS + H]$^+$; Anal Calcd for (C30H30N3O9PS + 0.4 CH2Cl2): C, 54.21; H, 4.61; N, 6.24. Found; C, 54.10: H, 4.49; N, 6.20. |

| Example | Structure | Mass Spect. (Mode) | 1H NMR δ (DMSO-d$_6$) & Elemental Analysis |
|---|---|---|---|
| 192 | 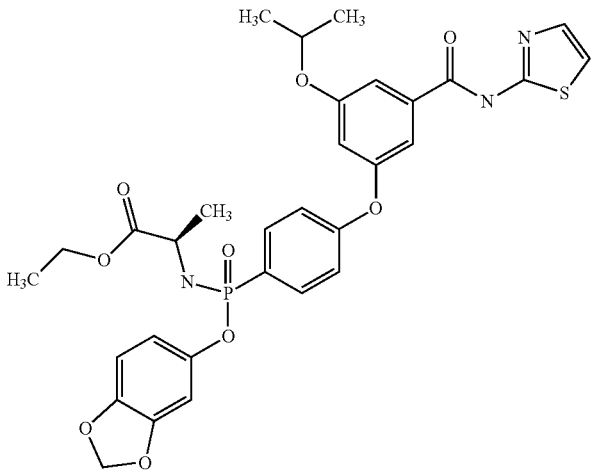 [SMILES: CCOC(=O)[C@@H](C)NP(=O)(Oc1ccc2c(c1)OCO2)c1ccc(Oc2cc(OC(C)C)cc(C(=O)Nc3nccs3)c2)cc1] | 654.6 (+) | 12.67 (s, 1H), 7.83(m, 2H), 7.53(m, 2H), 7.29 (m, 2H), 7.15 (m, 2H), 6.83 (m, 3H), 6.65 (m, 1H), 5.99 (s, 2H), 5.92 (m, 1H), 4.74 (m, 1H), 3.92 (m, 3H), 1.28 (d, J = 6.3 Hz, 6H) 1.17(m, 3H), 1.02 (m, 3H). Anal Calcd for (C31H32N3O9PS + 0.1 CH2Cl2): C, 56.41: H, 4.90: N, 6.35. Found: C, 56.19; H, 4.92; N, 6.26. |
| 193 | 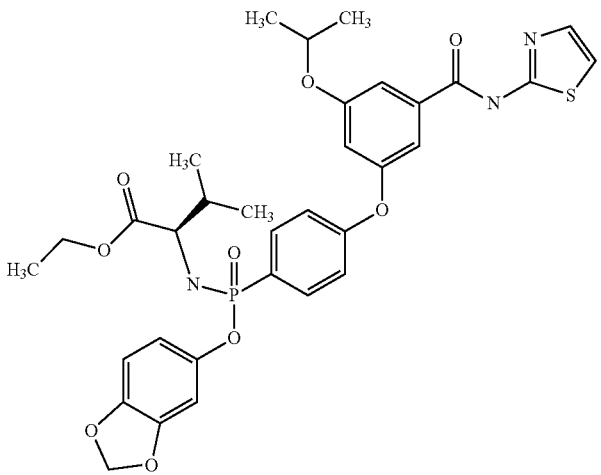 [SMILES: CCOC(=O)[C@H](NP(=O)(Oc1ccc2c(c1)OCO2)c1ccc(Oc2cc(OC(C)C)cc(C(=O)Nc3nccs3)c2)cc1)C(C)C] | 682.6 (+) | 12.66 (s, 1H), 7.84 (m, 2H), 7.52(m, 2H), 7.27 (m, 2H), 7.17 (m, 2H), 6.82 (m, 3H), 6.65 (m, 1H), 5.98 (s, 2H), 5.79 (m, 1H), 4.73 (m, 1H), 3.94 (m, 2H), 3.56 (m, 1H), 1.86 (m, 1H), 1.27 (d, J = 6.3 Hz, 6H), 1.02 (m, 3H), 0.71 (m, 6H). Anal Calcd for (C33H36N3O9PS): C, 58.14; H, 5.32; N, 6.16. Found: C, 58.13; H, 5.39; N, 5.88. |
| 194 | 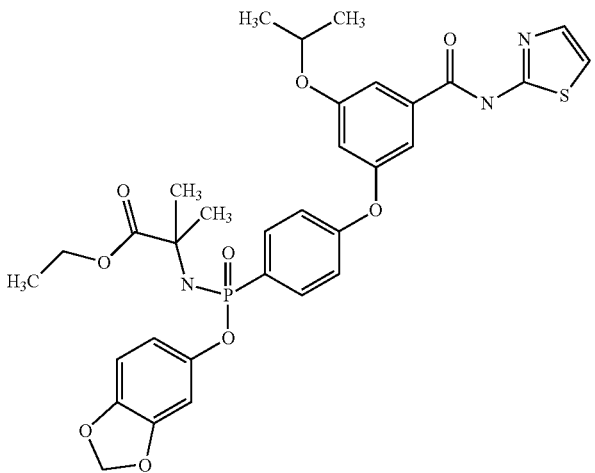 [SMILES: CCOC(=O)C(C)(C)NP(=O)(Oc1ccc2c(c1)OCO2)c1ccc(Oc2cc(OC(C)C)cc(C(=O)Nc3nccs3)c2)cc1] | 668.4 (+) | 12.66 (s, 1H), 7.84(m, 2H), 7.53(m, 2H), 7.28 (m, 2H), 7.15 (m, 2H), 6.81 (m, 3H), 6.60 (m, 1H), 5.98 (s, 2H), 5.74 (m, 1H), 4.73 (m, 1H), 3.97 (m, 2H), 1.28 (m, 12H), 1.02 (m, 3H). Anal Calcd for (C32H34N3O9PS): C, 57.57; H, 5.13; N, 6.28. Found: C, 57.28; H, 5.05; N, 6.08. |

-continued

| Example | Structure | Mass Spect. (Mode) | 1H NMR δ (DMSO-d₆) & Elemental Analysis |
|---|---|---|---|
| 195 | 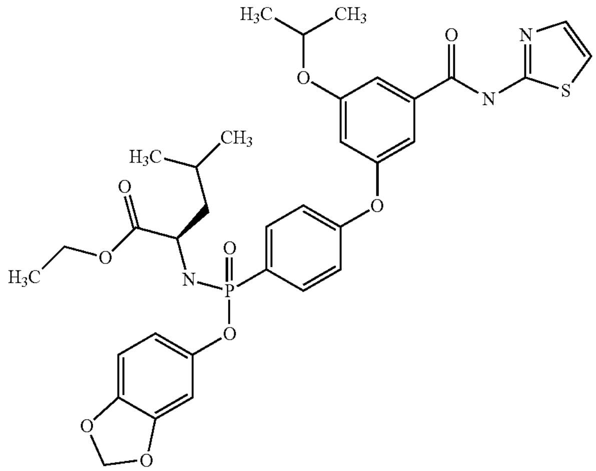 [SMILES: CCOC(=O)[C@@H](CC(C)C)NP(=O)(Oc1ccc2c(c1)OCO2)c1ccc(Oc2cc(OC(C)C)cc(C(=O)Nc3nccs3)c2)cc1] | 696.4 (+) | 12.67 (s, 1H), 7.83 (m, 2H), 7.52(m, 2H), 7.27 (m, 2H), 7.17 (m, 2H), 6.83 (m, 3H), 6.64 (m, 1H), 5.98 (s, 2H), 5.86 (m, 1H), 4.74 (m, 1H), 3.86 (m, 2H), 3.78 (m, 1H), 1.28 (d, J = 6.0 Hz, 6H), 1.04 (m, 6H), 0.72 (m, 5H). Anal Calcd for (C.34H38N3O9PS): C, 58.70; H, 5.51; N, 6.04. Found: C, 58.45; H, 5.63; N, 5.78. |
| 196 | 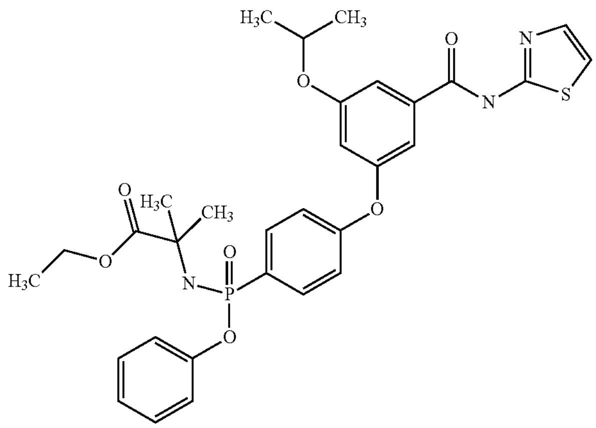 [SMILES: CCOC(=O)C(C)(C)NP(=O)(Oc1ccccc1)c1ccc(Oc2cc(OC(C)C)cc(C(=O)Nc3nccs3)c2)cc1] | 624.6 (+) | 12.67 (s, 1H), 7.86 (m, 2H), 7.52 (m, 2H), 7.33 (m, 4H), 7.17 (m, 4H), 6.85 (m, 1H), 5.84 (d, J = 11.4 Hz, 1H), 4.73 (m, 1H), 3.92 (m, 2H), 1.30 (m, 12H), 1.03 (m, 3H). Anal Calcd for (C31H34N3O7PS + 3.2 H2O + 0.1 EtOAc): C, 54.65; H, 6.02; N, 6.17. Found: C, 54.34; H, 5.23; N, 5.94. |
| 197 | 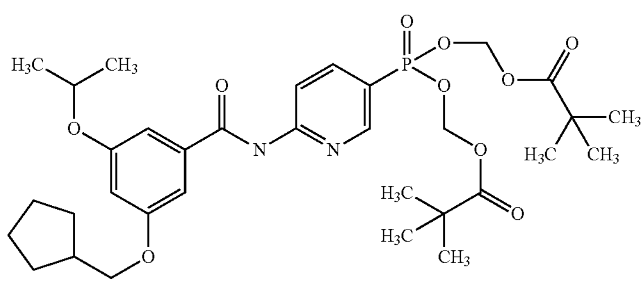 [SMILES: CC(C)Oc1cc(OCC2CCCC2)cc(C(=O)Nc2ccc(P(=O)(OCOC(=O)C(C)(C)C)OCOC(=O)C(C)(C)C)cn2)c1] | 663.9 (+) | 8.95 (s, 1 H), 8.66-8.69 (m, 1 H), 8.47-8.51 (m, 1 H), 8.11 (ddd, J = 13, 8, 2 Hz, 1 H), 7.01-7.03 (m, 2 H), 6.64 (m, 1 H), 5.72-5.81 (m, 4 H), 4.58-4.66 (m, 1 H), 3.87 (d, J = 7 Hz, 2 H), 2.32-2.42 (m, 1 H), 1.64-1.88 (m, 2 H), 1.54-1.63 (m, 4 H), 1.35 (d, J = 6 Hz, 6 H), 1.30-1.45 (m, 2H), 1.15 (s, 18 H). Anal Calcd for (C33H47N2O10P): C, 59.81; H, 7.15; N, 4.23. Found; C, 59.98; H, 7.07; N, 4.01. |
| 198 | 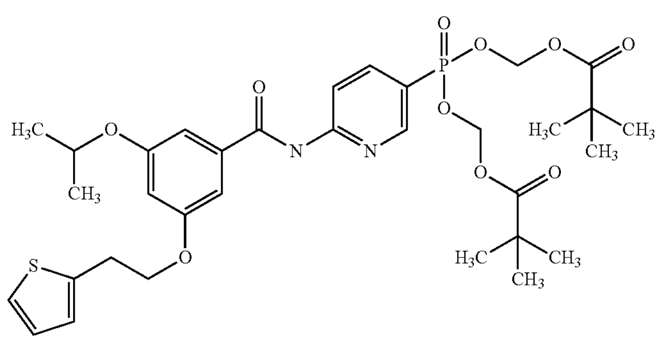 [SMILES: CC(C)Oc1cc(OCCc2cccs2)cc(C(=O)Nc2ccc(P(=O)(OCOC(=O)C(C)(C)C)OCOC(=O)C(C)(C)C)cn2)c1] | 691.3 (+) | 8.91 (s, 1 H), 8.68 (dd, J = 7, 2 Hz, 1 H), 8.48 (dd, J = 9, 3 Hz, 1 H), 8.11 (ddd, J = 13, 9, 2 Hz, 1 H), 7.17-7.19 (m, 1 H), 7.03-7.05 (m, 2 H), 6.92-6.97 (m, 2 H), 6.66 (m, 1 H), 5.72-5.81 (m, 4 H), 4.58-4.66 (m, 1 H), 4.24 (m, 2 H), 3.33 (m, 2 H), 1.35 (d, J = 5 Hz, 6 H), 1.15 (s, 18 H). Anal Calcd for (C33H43N2O10PS + 1.0 H2O): C, 55.92; H, 6.40: N, 3.95. Found: C, 55.76; H, 6.02; N, 4.09. |

| Example | Structure | Mass Spect. (Mode) | 1H NMR δ (DMSO-d$_6$) & Elemental Analysis |
|---|---|---|---|
| 199 | 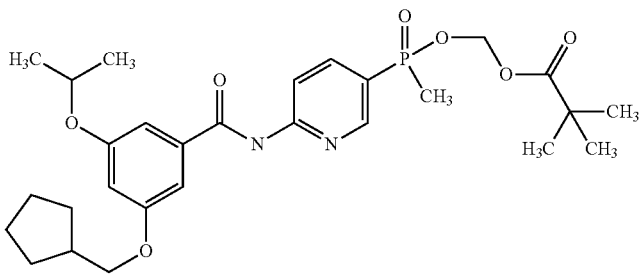 [SMILES: CC(C)Oc1cc(OCC2CCCC2)cc(C(=O)Nc2ccc(P(C)(=O)OCOC(=O)C(C)(C)C)cn2)c1] | 547.3 (+) | 8.68-8.72 (m, 2 H), 8.48 (dd, J = 9, 2 Hz, 1 H), 8.10 (ddd, J = 11, 9, 2 Hz, 1 H), 7.00 (m, 2 H), 6.64 (m, 1 H), 5.64-5.74 (m, 2 H), 4.57-4.65 (m, 1 H), 3.85 (d, J = 7 Hz, 2 H), 2.32-2.39 (m, 1 H), 1.80-1.87 (m, 2 H), 1.77 (d, J = 12 Hz, 3 H), 1.55-1.70 (m, 4 H), 1.35 (d, J = 6 Hz, 6 H), 1.30-1.41 (m, 2 H), 1.09 (s, 9 H). Anal Calcd for (C28H39N2O7P + 1.5 H2O): C, 58.63; H, 7.38; N, 4.88. Found: C, 58.51; H, 7.26; N, 5.01. |
| 200 | 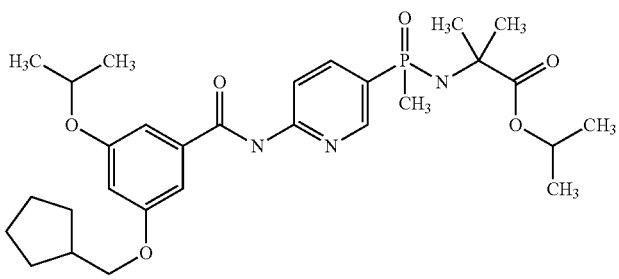 [SMILES: CC(C)OC(=O)C(C)(C)NP(C)(=O)c1ccc(NC(=O)c2cc(OCC3CCCC3)cc(OC(C)C)c2)nc1] | 560.3 (+) | 8.72-8.75 (m, 2 H), 8.44-8.47 (m, 1 H), 8.10-8.17 (m, 1 H), 6.99-7.26 (m, 2 H), 6.63-6.64 (m, 1 H), 4.98-5.06 (m, 1 H), 4.57-4.65 (m, 1 H), 3.85-3.90 (m, 1 H), 3.86 (d, J = 7 Hz, 2 H), 2.34-2.39 (m, 1 H), 1.71-1.87 (m, 2 H), 1.68 (d, J = 14 Hz, 3 H), 1.56-1.66 (m, 7 H), 1.35 (d, J = 6 Hz, 6 H), 1.31-1.41 (m, 5 H), 1.23-1.29 (m, 6 H). Anal Calcd for (C29H42N3O6P + 1.0 H2O): C, 60.30; H, 7.68; N, 7.27. Found: C, 60.48; H, 7.64; N, 7.45. |
| 201 | 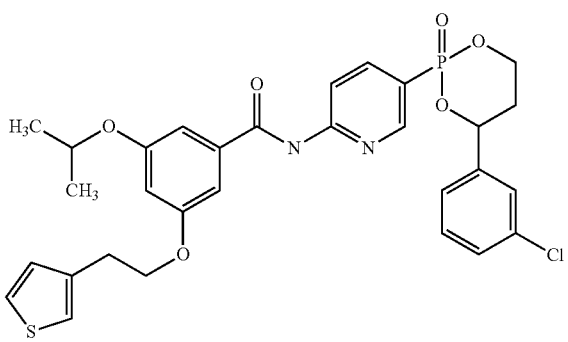 [SMILES: CC(C)Oc1cc(OCCc2ccsc2)cc(C(=O)Nc2ccc(P3(=O)OCCC(c4cccc(Cl)c4)O3)cn2)c1] | 613.2, 615.2 (+) | 11.23 (s, 1 H), 8.82 (d, J = 7 Hz, 1 H), 8.30-8.42 (m, 2 H), 7.54 (m, 1 H), 7.51 (dd, J = 5, 3 Hz, 1 H), 7.45 (m, 3 H), 7.35 (m, 1 H), 7.25 (m, 1 H), 7.20 (m, 1 H), 7.15 (dd, J = 2, 1 Hz, 1 H), 6.72 (m, 1 H), 5.86 (m, 1 H), 4.70-4.79 (m, 2 H), 4.40-4.56 (m, 2 H), 4.29 (m, 2 H), 3.09 (m, 2 H), 2.18-2.23 (m, 1 H), 1.90-1.95 (m, 1 H), 1.30 (d, J = 6 Hz, 6 H). Anal Calcd for (C30H30ClN2O6PS + 0.6 H2O): C, 57.76; H, 5.04; N, 4,49. Found: C, 57.88; H, 5.04; N, 4.37. |
| 202 | 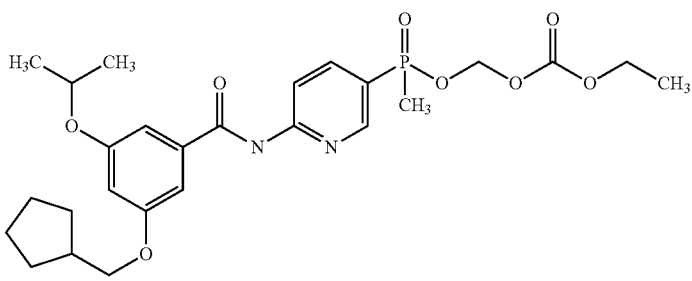 [SMILES: CCOC(=O)OCOP(C)(=O)c1ccc(NC(=O)c2cc(OCC3CCCC3)cc(OC(C)C)c2)nc1] | 535.3 (+) | 11.18 (s, 1 H), 8.70-8.73 (m, 1 H), 8.32-8.36 (m, 1 H), 8.14-8.22 (m, 1 H), 7.20 (s, 2 H), 6.68 (m, 1 H), 5.57-5.63 (m, 2 H), 4.71-4.79 (m, 1 H), 4.08 (q, J = 7 Hz, 2 H), 3.93 (d, J = 7 Hz, 2 H), 2.28-2.38 (m, 1 H), 1.86 (d, J = 15 Hz, 3 H), 1.75-1.83 (m, 2 H), 1.52-1.67 (m, 4 H), 1.30 (d, J = 6 Hz, 6 H), 1.29-1.40 (m, 2 H), 1.16 (t, J = 7 Hz, 3 H). Anal Calcd for (C26H35N2O8P + 0.4 H2O): C, 57.64; H, 6.66; N, 5.17. Found: C, 57.31; H, 6.27; N, 5.06. |

| Example | Structure | Mass Spect. (Mode) | 1H NMR δ (DMSO-$d_6$) & Elemental Analysis |
|---|---|---|---|
| 203 | 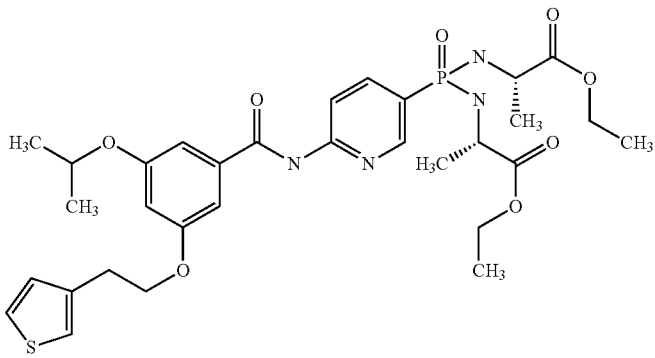 [SMILES: CCOC(=O)[C@H](C)NP(=O)(N[C@@H](C)C(=O)OCC)c1ccc(NC(=O)c2cc(OCCc3ccsc3)cc(OC(C)C)c2)nc1] | 661.3 (+) | 8.76 (m, 1 H), 8.61 (m, 1 H), 8.29 (m, 1 H), 7.31-7.34 (m, 2 H0, 7.15 (s, 2 H), 7.09 (d, J = 5 Hz, 1 H), 6.69 (m, 1 H), 4.64-4.72 (m, 1 H), 4.08-4.28 (m, 5 H), 3.99-4.04 (m, 1 H), 3.60-3.63 (m, 1 H), 3.34-3.38 (m, 1 H), 3.18 (m, 2 H), 1.44-1.49 (m, 6 H), 1.39 (d, J = 6 Hz, 6 H), 1.21-1.35 (m, 6 H). Anal Calcd for (C31H41N4O8PS + 0.4 H2O): C, 55-75; H, 6.31; N, 8.39. Found: C, 55.87; H, 6.61; N, 8.65. |
| 204 | 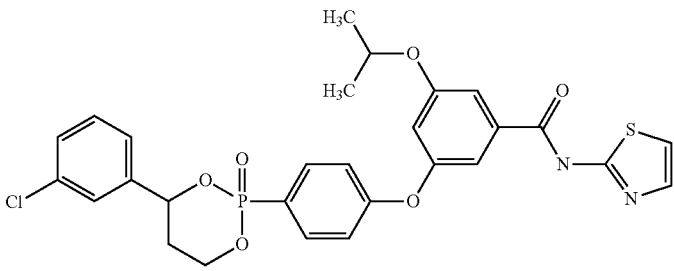 [SMILES: CC(C)Oc1cc(Oc2ccc(P3(=O)OCCC(c4cccc(Cl)c4)O3)cc2)cc(C(=O)Nc2nccs2)c1] | 585.4 (+) | 12.66 (s, 1 H), 7.91 (dd, J = 13, 9 Hz, 2 H), 7.52-7.54 (m, 2 H), 7.47 (m, 1 H), 7.37-7.42 (m, 2 H), 7.27 (m, 1 H), 7.19 (dd, J = 9, 4 Hz, 2 H), 6.94 (m, 1 H), 5.77-5.80 (m, 1 H), 4.63-4.79 (m, 3 H), 4.35-3.45 (m, 1 H), 2.30-2.40 (m, 1 H), 2.13-2.17 (m, 1 H), 1.29 (d, J = 6 Hz, 6 H). Anal Calcd for (C28H26ClN2O8PS + 0.1 EtOAc + 0.1 CH2Cl2): C, 56.83; H, 4.52; N, 4.65. Found: C, 56.90; H, 4.89; N, 4.37. |
| 205 | 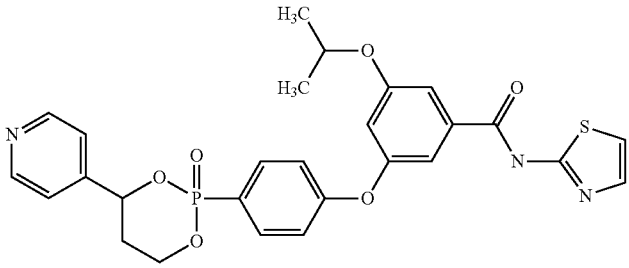 [SMILES: CC(C)Oc1cc(Oc2ccc(P3(=O)OCCC(c4ccncc4)O3)cc2)cc(C(=O)Nc2nccs2)c1] | 552.6 (+) | 8.58 (m, 2 H), 7.91 (dd, J = 13, 9 Hz, 2 H), 7.53-7.54 (m, 2 H), 7.37-7.41 (m, 3 H), 7.27 (d, J = 4 Hz, 1 H), 7.19 (dd, J = 9, 2 Hz, 2 H), 6.94 (m, 1 H), 5.80-5.84 (m, 1 H), 4.65-4.80 (m, 2H), 4.37-4.47 (m, 1 H), 2.24-2.30 (m, 2 H), 1.29 (d, J = 6 Hz, 6 H). Anal Calcd for (C27H26N3O6PS + 0.2 CH2Cl2): C, 57.46; H, 4.68; N, 7.39. Found: C, 57.12; H, 4.79; N, 7.18. |
| 206 | 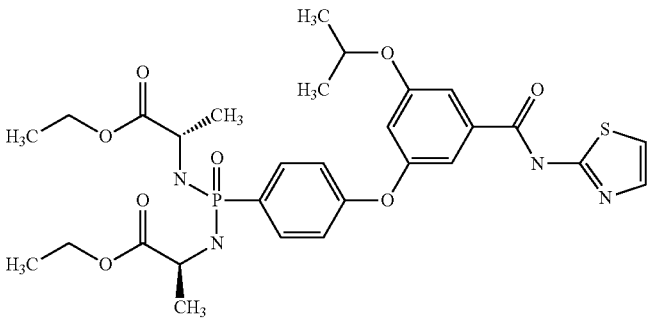 [SMILES: CCOC(=O)[C@H](C)NP(=O)(N[C@@H](C)C(=O)OCC)c1ccc(Oc2cc(OC(C)C)cc(C(=O)Nc3nccs3)c2)cc1] | 633.6 (+) | 7.76 (dd, J = 12, 9 Hz, 2 H), 7.56 (d, J = 4 Hz, 1 H), 7.52 (m, 1 H), 7.26-7.29 (m, 2 H), 7.14 (dd, J = 9, 2 Hz, 2 H), 6.82 (m, 1 H), 4.90 (m, 1 H), 4.70-4.77 (m, 2 H), 3.93-4.09 (m, 4 H), 3.79-3.85 (m, 2 H), 1.30 (d, J = 6 Hz, 6 H), 1.06-1.27 (m, 12 H). Anal Calcd for (C29H37N4O8PS): C, 55.05; H, 5.89; N, 8.86. Found: C, 54.89; H, 6.16; N, 8.71. |

| Example | Structure | Mass Spect. (Mode) | 1H NMR δ (DMSO-d6) & Elemental Analysis |
|---|---|---|---|
| 207 | 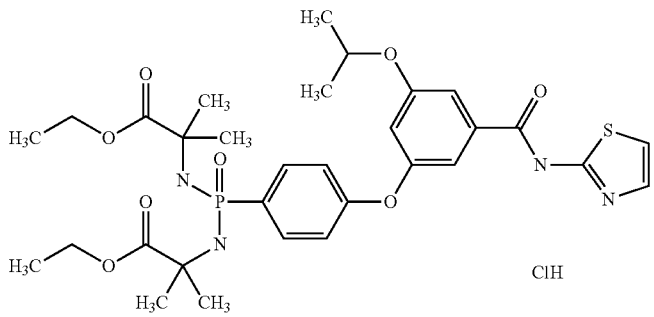 [SMILES: CCOC(=O)C(C)(C)NP(=O)(NC(C)(C)C(=O)OCC)c1ccc(Oc2cc(OC(C)C)cc(C(=O)Nc3nccs3)c2)cc1 ; Cl] ClH | 661.9 (+) | 7.76 (dd, J = 12, 9 Hz, 2 H), 7.56 (d, J = 4 Hz, 1 H), 7.53 (m, 1 H), 7.28-7.29 (m, 2 H), 7.34 (dd, J = 9, 2 Hz, 2 H), 6.82 (m, 1 H), 4.76 (m, 1 H), 4.63 (d, J = 11 Hz, 2 H), 4.03 (q, J = 7 Hz, 4 H), 1.41 (s, 3 H), 1.33 (s, 3 H), 1.30 (d, J = 6 Hz, 6 H), 1.16 (t, J = 7 Hz, 12 H). Anal Calcd for (C31H41N4O8PS + 0.1 HCl + 0.80 H2O): C, 52.32; H, 6.18; N, 7.87. Found: C, 52.02; H, 5.84; N, 8.27. |
| 208 | 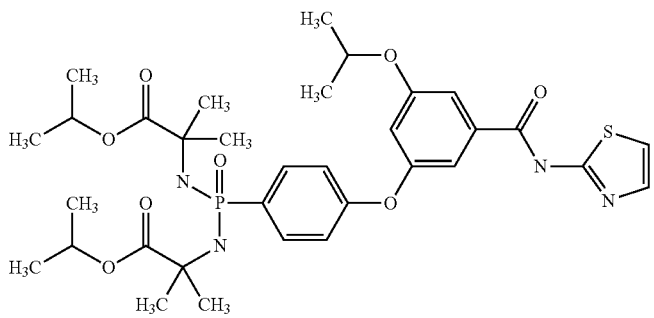 [SMILES: CC(C)OC(=O)C(C)(C)NP(=O)(NC(C)(C)C(=O)OC(C)C)c1ccc(Oc2cc(OC(C)C)cc(C(=O)Nc3nccs3)c2)cc1] | 689.9 (+) | 7.76 (dd, J = 12, 9 Hz, 2 H), 7.54 (d, J = 4 Hz, 1 H), 7.51 (m, 1 H), 7.26-7.27 (m, 2 H), 7.11 (dd, J = 9, 2 Hz, 2 H), 6.79 (m, 1 H), 4.76 (m, 1 H), 4.83 (m, 2 H), 4.74 (m, 1 H), 4.58 (d, J = 11 Hz, 2 H), 1.29 (d, J = 6 Hz, 6 H), 1.17 (s, 6 H), 1.16 (d, J = 6 Hz, 12 H). Anal Calcd for (C33H45N4O8PS − 0.5 H2O): C, 56.80; H, 6,64; N, 8.03. Found: C, 56.82; H, 6.53; N, 8.01. |
| 209 | 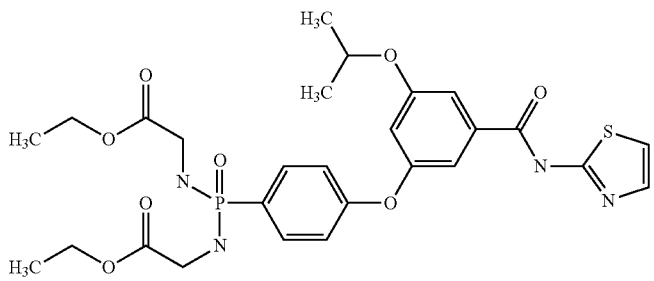 [SMILES: CCOC(=O)CNP(=O)(NCC(=O)OCC)c1ccc(Oc2cc(OC(C)C)cc(C(=O)Nc3nccs3)c2)cc1] | 605.9 (+) | 7.77 (dd, J = 12, 9 Hz, 2 H), 7.54 (d, J = 4 Hz, 1 H), 7.51 (m, 1 H), 7.26-7.27 (m, 2 H), 7.13 (dd, J = 9, 2 Hz, 2 H), 6.82 (m, 1 H), 4.74-4.83 (m, 3 H), 4.04 (q, J = 7 Hz, 4 H), 3.56-3.65 (m, 4 H), 1.29 (d, J = 6 Hz, 6 H), 1.14 (t, J = 7 Hz, 12 H). Anal Calcd for (C27H33N4O8PS): C, 53.64; H, 5.50; N, 9.27. Found: C, 53.42; H, 5.41; N, 9.08. |
| 210 | 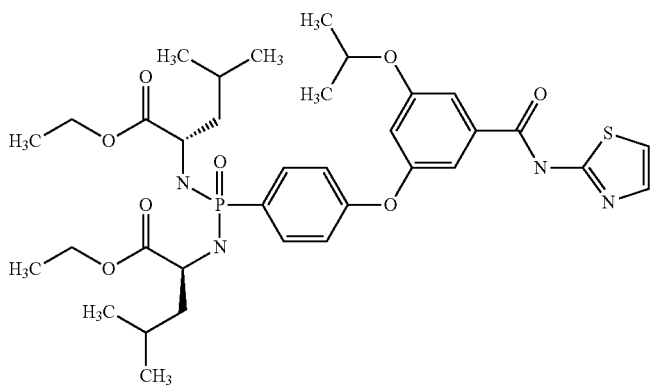 [SMILES: CCOC(=O)[C@H](CC(C)C)NP(=O)(N[C@@H](CC(C)C)C(=O)OCC)c1ccc(Oc2cc(OC(C)C)cc(C(=O)Nc3nccs3)c2)cc1] | 718.1 (+) | 7.74 (dd, J = 12, 9 Hz, 2 H), 7.53 (d, J = 4 Hz, 1 H), 7.49 (m, 1 H), 7.26 (d, J = 4 Hz, 1 H), 7.21 (m, 1 H), 7.12 (dd, J = 9, 2 Hz, 2 H), 6.74 (m, 1 H), 4.71-4.81 (m, 2 H), 4.49 (m, 1 H), 4.06 (m, 2 H), 3.88 (m, 2 H), 3.72 (m, 2 H), 1.29-1.73 (m, 6 H), 1.28 (d, J = 6 Hz, 6 H), 1.18 (m, 3 H), 1.00 (m, 3 H), 0.72-0.88 (m, 12 H). Anal Calcd for (C35H49N4O8PS): C, 58.64; H, 6.89; N, 7.82. Found: C, 58.84; H, 6.98; N, 7.53. |

| Example | Structure | Mass Spect. (Mode) | 1H NMR δ (DMSO-d6) & Elemental Analysis |
|---|---|---|---|
| 211 | (structure) | 690.1 (+) | 7.73 (dd, J = 12, 9 Hz, 2 H), 7.54 (d, J = 4 Hz, 1 H), 7.50 (m, 1 H), 7.27 (d, J = 4 Hz, 1 H), 7.23 (m, 1 H), 7.11 (dd, J = 9, 2 Hz, 2 H), 6.77 (m, 1 H), 4.73 (m, 1 H), 4.61 (m, 1 H), 4.45 (m, 1 H), 4.03-4.14 (m, 2 H), 3.83-3.95 (m, 2 H), 3.52-3.60 (m, 1 H), 3.35-3.44 (m, 1 H), 1.90 (m, 2 H), 1.28 (d, J = 6 Hz, 6 H), 1.18 (t, 3 H), 1.02 (t, 3 H), 0.89 (t, 6 H), 0.77 (t, 6 H). Anal Calcd for (C33H45N4O8PS + 1.0 HCl, + 0.7 H2O); C, 53.72; H, 6.48; N, 7.58. Found: C, 53.63; H, 6.23; N, 7.58. |
| 212 | (structure) | 695.4 (+) | 7.73 (dd, J = 12, 7 Hz, 2 H), 7.54 (m, 2 H), 7.35 (m, 1 H), 7.27 (d, J = 4 Hz, 1 H), 7.17 (dd, J = 7, 2 Hz, 2 H), 6.89 (m, 1 H), 5.67 (m, 4 H), 4.75 (m, 1 H), 3.87 (d, J = 7 Hz, 4 H), 1.85 (m, 2 H), 1.29 (d, J = 6 Hz, 6 H), 0.83 (d, J = 7 Hz, 6 H). Anal. Calcd. for (C31H39N2O12PS): C, 53.60; H, 5.66; N, 4.03. Found: C, 53.32; H, 5.69; N, 3.96. |

Example 213

{4-[3-(2-Fluoro-phenylcarbamoyl)-5-isopropoxy-phenoxy]-phenyl}-phosphonic acid

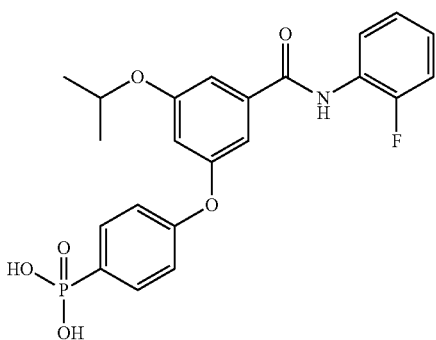 [SMILES: CC(C)Oc1cc(Oc2ccc(P(=O)(O)O)cc2)cc(C(=O)Nc2ccccc2F)c1]

To a solution of 3-[4-(diisopropoxy-phosphoryl)-phenoxy]-5-isopropoxy-benzoic acid (prepared as in Example 3 Step E) (530 mg, 1.2 mmol) in toluene (10 mL) was added thionyl chloride (0.22 mL, 3.0 mmol). The reaction was heated to 110° C. for 1 h and allowed to cool to room temperature. The solvents were removed by rotary evaporation, and the crude product was re-dissolved in toluene and treated with 2-fluoroaniline (0.11 mL, 1.2 mmol), diisopropylethylamine (0.6 mL, 3.6 mmol), and catalytic DMAP. The reaction was then heated to 110° C. for 1 hour, at which point TLC analysis indicated that the reaction was complete. The reaction was cooled to room temperature and preloaded on silica. The desired product, {4-[3-(2-fluoro-phenylcarbamoyl)-5-isopropoxy-phenoxy]-phenyl}-phosphonic acid diisopropyl ester, (350 mg, 54%) was obtained after chromatography on silica gel eluting with ethyl acetate in hexanes. LC-MS m/z=530 $[C_2H_{33}FNO_6P+H]^+$.

The above prepared {4-[3-(2-fluoro-phenylcarbamoyl)-5-isopropoxy-phenoxy]-phenyl}-phosphonic acid diisopropyl ester was converted to the title compound following the procedure described in Example 2. $^1$H NMR (300 MHz, DMSO-d$_6$): δ 10.11 (s, 1H), 7.80-7.70 (q, 2H), 7.50 (t, 1H), 7.39 (s, 1H), 7.38-7.08 (m, 6H), 6.83 (s, 1H), 4.65 (m, 1H), 1.30 (d, 6H). $^{31}$P NMR (300 MHz, DMSO-d$_6$): δ 13.45. $^{19}$F NMR (300 MHz, DMSO-d$_6$): δ -121.25. LC-MS m/z=446 $[C_{22}H_{21}FN_3O_6P+H]^+$. Anal. Calcd for $(C_{22}H_{21}FN_3O_6P+1.3H_2O)$: C, 56.37; H, 5.07; N, 2.99. Found: C, 56.40; H, 4.85; N, 2.83.

Examples: Biological Examples

The assays below can be used to test compounds of the present invention. Compounds set forth in the chemistry Examples above were assayed using the Human Enzyme Assay below (compounds may have been tested in additional assays as well). The compounds of the above Examples were tested in the Human Enzyme Assay at a concentration of 100 M and were able to activate 50 &g of human glucokinase by at least 150%.

Example A. Human Enzyme Assay

Biochemical activation of GK is accomplished with assays that utilize purified recombinant human GK (isoform 1/variant 2) and purified recombinant *Leuconostoc mes-*

*enteroides* glucose-6-phosphate dehydrogenase (Sigma-Aldrich, Inc.). In these assays, glucose is acted upon by GK to form glucose-6-phosphate. Subsequently, glucose-6-phosphate is acted upon by glucose-6-phosphate dehydrogenase to form 6-phospho-D-gluconate and beta-NADPH, which can be quantified spectrophotometrically. Specifically, compounds are serially diluted to 100× the final concentration in DMSO. After dilution, 3 uL of the compound solution and 277 uL of Reaction Buffer (25 mM HEPES-pH 7.4, 25 mM KCl, 2 mM $MgCl_2$, and 10 mM ATP, 0.5 mM beta-NADP, 1 mM DTT, 0.1% bovine serum albumin) are added to each well of a UV/Visible transparent 96-well microtiter plates (Falcon Inc.). The microtiter plates are then placed on wet ice for 10 min. The enzymatic reactions are initiated by the addition of 10 uL glucose-6-phosphate dehydrogenase (~40 ug/well) and 10 uL of GK (~50 ug/well). After initiation, the microtiter plate is immediately placed into a microtiter plate reader (SpectraMax 190; Molecular Devices Inc.) and the generation of beta-NADPH is monitored at 340 nm for 20 min at 30° C.

Example B. Rat Hepatocyte Assay

Cellular activation of OK is accomplished with assays that utilized [$2-^3H$] glucose (G.E. Healthcare Inc.) and primary hepatocytes isolated from fed adult male Sprague-Dawley rats (Harlan Inc.). All animal procedures are conducted in accordance with the National Institutes of Health Guidelines for the Care and Use of Laboratory Animals and are approved by the Institutional Animal Care and Use Committee. In these assays, [$2-^3H$] glucose is taken up into the hepatocytes and acted upon by endogenous GK to form [2-3H] glucose-6-phosphate. Subsequently, [$2-^3H$] glucose-6-phosphate is acted upon by endogenous phosphoglucose isomerase to form fructose-6-phosphate and $^3H_3O^-$, which diffuses out of the hepatocyte into the culture media. Specifically, rats (~300 g) are anaesthetized with pentobarbital (Savemart Inc.) administered at concentration of 2 uL/gram body weight. After confirming no response to deep pain stimuli, the abdominal cavity is exposed. The livers are perfused at ~25 ml/min through the portal vein with Perfusion Buffer [Krebs-Ringer bicarbonate buffer supplemented with 2.5 mM $CaCl_2$ and 1% fatty acid free BSA (Calbiochem Inc.)] and drained through the supra vena cava during the procedure. The buffer is prepared by equilibrating at 37° C. and aerating with a 95% oxygen/5 % carbon dioxide mixture. After, 2 to 3 min the Perfusion Buffer is supplemented with 1 mg/ml collagenase (Sigma-Aldrich Inc.). Following perfusion viable cells are isolated will 70% Percoll gradient in aerated Perfusion Buffer. After isolation, hepatocytes are resuspended (700,000 cells/mL) in Dulbecco's minimal essential medium (DMEM, Invitrogen Inc.) supplemented with 5.6 mM glucose, 10% fetal bovine serum (FBS), 1 U/mL penicillin, 0.1 mg/mL streptomycin, and 2 mM L-glutamine. The resuspended hepatocytes are plated 500 uL/well on a 24-well plate (Becton Dickenson Labware Inc.) and incubated at 37° C. in 95% $O_2$/5% $CO_2$ in a water-jacketed incubator (Forma Scientific Inc.). After attachment to the plate (~2 hr), media is removed and 500 uL of serum-free DMEM supplemented with 5.6 mM glucose, 1 U/mL penicillin, 0.1 mg/mL streptomycin, and 2 mM L-glutamine is added. After 16-20 hr, 2 uCi/mL [$2-^3H$] glucose and compound solutions are added to the media. Compounds are first serially diluted to 100× the final concentration in DMSO and are added in a 5 uL volume. After 3 hrs, 500 uL of media is removed and $^3H_3O^+$ is isolated by strong anion exchange chromatography using AG 1-X8 columns (Bio Rad Laboratories Inc.) according to the manufacture's recommendations. Quantification of the isolated $^3H_3O^+$ is accomplished by scintillation counting using scintillation cocktail (Packard BioScience Inc.) and a scintillation counter (LS6000IC; Palo Beckman Inc.).

Example C. Fasting Blood Glucose Test

Effects on fasting blood glucose after administration of compounds are determined in conscious overnight fasted male Zucker fa/fa rats (Harlan Inc.) that range from 8 to 0 weeks in age. All animal procedures are conducted in accordance with the National Institutes of Health Guidelines for the Care and Use of Laboratory Animals and are approved by the Institutional Animal Care and Use Committee. Whole blood glucose levels are determined by a glucose meter (OneTouch Ultra, Life Scan Inc.) and whole blood is collected by a tail vein nick method. Prior to administration, compounds are formulated in phosphate buffered saline pH ~7.4 (PBS). Before and after administration of either compound formulation or PBS, glucose levels are measured at regular time intervals.

Example D. Oral Glucose Tolerance Test (OGTT)

Effects on OGTT after administration of compounds are determined in conscious overnight fasted male Zucker fa/fa rats (Harlan Inc.) that range from 8 to 20 weeks in age. All animal procedures are conducted in accordance with the National Institutes of Health Guidelines for the Care and Use of Laboratory Animals and are approved by the Institutional Animal Care and Use Committee. Whole blood glucose levels are determined by a glucose meter (OneTouch Ultra, Life Scan Inc.) and whole blood is isolated by a tail vein nick method. Prior to administration, compounds are formulated in phosphate buffered saline pH~7.4 (PBS). Thirty min after administration of either compound formulation or PBS, an aqueous solution of D-glucose is orally administered at dosage of 2 g/kg body weight. Before and after administration of either compound formulation or PBS, blood samples for glucose and insulin levels determinations are collected at regular time intervals.

Example D. Insulin Secretion Test

Effects on insulin secretion after administration of compound is determined in conscious overnight fasted adult male Sprague-Dawley (Harlan Inc.) rats that are cannulated through the jugular vein. All animal procedures are conducted in accordance with the National Institutes of Health Guidelines for the Care and Use of Laboratory Animals and are approved by the Institutional Animal Care and Use Committee. Whole blood glucose levels are determined by a glucose meter (OneTouch Ultra, Life Scan Inc.) and whole blood is isolated from the cannula. Plasma is isolated from whole blood by centrifugation in Heparinized plasma separator tubes (BD Microtainer Inc.) and plasma insulin levels are determined by insulin specific radioimmunoassay detection (Linco Inc.). Prior to administration, compounds are formulated in phosphate buffered saline pH ~7.4 (PBS). Before and after administration of either compound formulation or PBS, glucose and insulin levels are measured at regular time intervals.

The invention claimed is:
1. A compound of Formula (II),

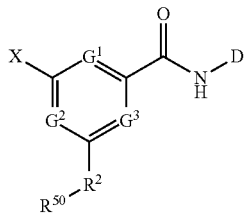

(II)

wherein:
X is selected from the group consisting of aryl, heteroaryl, alkyl, cycloalkyl, arylalkyl, aryloxy, heteroaryloxy, alkyloxy, cycloalkyloxy, and arylalkyloxy, and
$G^2$ is $CR^4$ or N, or
together $G^2$ and X are connected to form a cyclic group containing 5-7 atoms, wherein 0-2 atoms of said cyclic group are heteroatoms and the remaining atoms of said cyclic group are carbon atoms substituted with alkyl, aryl, cycloalkyl or heteroaryl;
$R^2$ is optionally substituted and is selected from alkylene, cycloalkylene, arylene-O—, heteroarylene-O—, arylalkylene-O—, alkylarylene-O—, arylene-S—, heteroarylene-S—,
alkylene-S—, cycloalkylene-S—, arylalkylene-S—, alkylarylene-S—, furan-2-yl-5-methylene or thiophen-2-yl-5-methylene, wherein $R^2$ is connected to $R^{50}$ by a carbon atom;
$G^1$ is $CR^4$ or N;
$R^4$ is H, halogen, or optionally substituted alkyl
$G^3$ is $CR^4$ or N;
$R^4$ is H, halogen, or optionally substituted alkyl;
D is selected from a group consisting of heteroaryl, aryl, optionally substituted heteroaryl, and optionally substituted aryl;
$R^{50}$ is —P(O)($Y^2R^{51}$) $R^1$ or —P(O)($YR^{51}$)$Y^1R^{51}$;
$R^1$ is selected from the group consisting of hydrogen, optionally substituted —$C_1$-$C_6$-alkyl, —$CF_3$, —$CHF_2$, —$CH_2F$, —$CH_2OH$, optionally substituted —$C_2$-$C_6$ alkenyl, optionally substituted —$C_2$-$C_6$ alkynyl, optionally substituted —$(CR^{52}{}_2)_n$cycloalkyl, and optionally substituted $(CR^{52}{}_2)_n$heterocycloalkyl;
Y, $Y^1$, and $Y^2$ are each independently selected from —O— or —$NR^{60}$,
wherein,
when $Y^2$ is —O— or when Y and $Y^1$ are both —O—, $R^{51}$ attached to —O— is independently selected from —H, alkyl, optionally substituted aryl, optionally substituted heterocycloalkyl, optionally substituted —$CH_2$-heterocycloakyl wherein the cyclic moiety contains a carbonate or thiocarbonate, optionally substituted -alkylaryl, —$C(R^{52})_2OC(O)NR^{52}{}_2$, —$NR^{52}$—C(O)—$R^{53}$, —$C(R^{52})_2$—OC(O)$R^{53}$, —$C(R^{52})_2$—O—C(O)O$R^{53}$, —$C(R^{52})_2OC(O)SR^{53}$, -alkyl-S—C(O)$R^{53}$, -alkyl-S—S-alkylhydroxy, and -alkyl-S—S—S-alkylhydroxy; or
when $Y^2$ is —$NR^{60}$— or when Y and $Y^1$ are both —$NR^{60}$—, then $R^{51}$ attached to —$NR^{60}$— is independently selected from —H, —$[C(R^{52})_2]_r$—COOR$^{53}$, —$C(R^{54})_2COOR^{53}$, —$[C(R^{52})_2]_r$—C(O)SR$^{53}$, and -cycloalkylene-COOR$^{53}$; or
when Y is —O— and $Y^1$ is $NR^{60}$, then $R^{51}$ attached to —O— is independently selected from —H, alkyl, optionally substituted aryl, optionally substituted heterocycloalkyl, optionally substituted —$CH_2$-heterocycloakyl wherein the cyclic moiety contains a carbonate or thiocarbonate, optionally substituted -alkylaryl, —$C(R^{52})_2OC(O)NR^{52}{}_2$, —$NR^{52}$—C(O)—$R^{53}$, —$C(R^{52})_2$—OC(O)$R^{53}$, —$C(R^{52})_2$—O—C(O)O$R^{53}$, —$C(R^{52})_2OC(O)SR^{53}$, -alkyl-S—C(O)$R^{53}$, -alkyl-S—S-alkylhydroxy, and -alkyl-S—S—S-alkylhydroxy, and $R^{51}$ attached to —$NR^{60}$— is independently selected from —H, —$[C(R^{52})_2]_r$—COOR$^{53}$, —$C(R^{54})_2COOR^{53}$, —$[C(R^{52})_2]_r$—C(O)SR$^{53}$, and -cycloalkylene-COOR$^{53}$, wherein if both $R^{51}$ are alkyl, at least one is higher alkyl; or
when Y and $Y^1$ are independently selected from —O— and —$NR^{60}$—, then $R^{51}$ and $R^{51}$ together form a cyclic group comprising -alkyl-S—S-alkyl-, or $R^{51}$ and $R^{51}$ together are the group

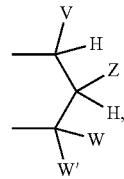

wherein,
V, W, and W' are independently selected from the group consisting of hydrogen, optionally substituted alkyl, optionally substituted aralkyl, heterocycloalkyl, aryl, substituted aryl, heteroaryl, substituted heteroaryl, optionally substituted 1-alkenyl, and optionally substituted 1-alkynyl; and
Z is —$CHR^{52}OH$, —$CHR^{52}OC(O)R^{53}$, —$CHR^{52}OC(S)R^{53}$, —$CHR^{52}OC(S)OR^{53}$, —$CHR^{52}OC(O)SR^{53}$, —$CHR^{52}OCO_2R^{53}$, —$OR^{52}$, —$SR^{52}$, —$CHR^{52}N_3$, —$CH_2aryl$, —$CH(aryl)OH$, —$CH(CH=CR^{52}{}_2)OH$, —$CH(C≡CR^{52})OH$, —$R^{52}$, —$NR^{52}{}_2$, —$OCOR^{53}$, —$OCO_2R^{53}$, —$SCOR^{53}$, —$SCO_2R^{53}$, —$NHCOR^{52}$, —$NHCO_2R^{53}$, —$CH_2NHaryl$, —$(CH_2)_r$—$OR^{52}$ or —$(CH_2)_r$—$SR^{52}$; or
W and W' are as defined above and together V and Z are connected via an additional 3-5 atoms to form a cyclic group containing 5-7 atoms, wherein 0-1 atoms are heteroatoms and the remaining atoms are carbon; or
W' and Z are as defined above and together V and W are connected via an additional 3 carbon atoms to form an optionally substituted cyclic group containing 6 carbon atoms or carbon substituted by hydrogen and substituted with one substituent selected from hydroxy, acyloxy, alkoxycarbonyloxy, alkylthiocarbonyloxy or aryloxycarbonyloxy which is attached to one of said carbon atoms that is three atoms from a Y attached to the phosphorus; or
V and W' are as defined above and together Z and W are connected via an additional 3-5 atoms to form a cyclic group, wherein 0-1 atoms are heteroatoms and the remaining atoms are carbon or carbon substituted by hydrogen, and V must be aryl, substituted aryl, heteroaryl, or substituted heteroaryl; or
V and Z are as defined above and together W and W' are connected via an additional 2-5 atoms to form a cyclic group, wherein 0-2 atoms are heteroatoms and the remaining atoms are carbon, where V must be aryl, substituted aryl, heteroaryl, or substituted heteroaryl;
$R^{52}$ is $R^{53}$ or —H;

$R^{53}$ is alkyl, aryl, heterocycloalkyl or aralkyl;

$R^{54}$ is independently selected from —H or alkyl, or together $R^{54}$ and $R^{54}$ form a cycloalkylene group;

$R^{60}$ is —H, lower alkyl, acyloxyalkyl, alkoxycarbonyloxyalkyl, lower acyl, or $C_{1-6}$-perfluoroalkyl;

r is an integer 2 or 3;

n is 0 to 1;

wherein, V, Z, W, W' are not all —H, and when Z is —$R^{52}$, then at least one of V, W, and W' is not —H, alkyl, aralkyl, or heterocycloalkyl;

wherein one of $G^1$, $G^2$, $G^3$ is N and the other two are $CR^4$; and wherein $G^2$ and X do not form an isomeric pyridine compound or pharmaceutically acceptable salts thereof.

2. The compound of claim 1, wherein X is selected from the group consisting of alkyl, cycloalkyl, alkyloxy, cycloalkyloxy, and aryloxy.

3. The compound of claim 1, wherein X is selected from the group consisting of alkyloxy and cycloalkyloxy.

4. The compound of claim 1, wherein X is selected from the group consisting of aryl, heteroaryl, alkyl, cycloalkyl, arylalkyl, aryloxy, heteroaryloxy, alkyloxy, cycloalkyloxy, and arylalkyloxy.

5. The compound of claim 1, wherein $R^2$ is arylene-O—.

6. The compound of claim 1, wherein $R^2$ is selected from the group consisting of phenylene-O—, methylene-phenylene-O—, phenylene-methylene-O—, furan-2-yl-5-methylene, thiophen-2-yl-5-methylene, pyridin-diyl-O—, pyrimidin-diyl-O—, pyridazin-diyl-O— and pyrazin-diyl-O—, each optionally substituted with one or two groups independently selected from aryl, heteroaryl, halogen, CN, $CF_3$, $NR^5_2$, —$C_{1-4}$-alkyl, —$S(O)_2R^5$, or —$OR^5$, wherein $R^{50}$ is connected to $R^2$ by a carbon atom; and wherein $R^5$ is optionally substituted alkyl or cycloalkyl.

7. The compound of claim 1, wherein $R^2$ is phenylene-O— or thiophen-2-yl-5-methylene, wherein $R^{50}$ is connected to the phenylene or thiophenyl group.

8. The compound of claim 1, wherein $R^2$ is optionally substituted and is selected from alkylene, cycloalkylene, arylene-O—, heteroarylene-O—, arylalkylene-O—, alkylarylene-O—, arylene-S—, heteroarylene-S—, alkylene-S—, cycloalkylene-S—, arylalkylene-S—, or alkylarylene-S—, wherein $R^{50}$ is connected to $R^2$ by a carbon atom.

9. The compound of claim 1, wherein $G^1$ and $G^2$ are $CR^4$ or N.

10. The compound of claim 1, wherein $G^1$ and $G^2$ are $CR^4$ and $R^4$ is H, halogen or optionally substituted alkyl.

11. The compound of claim 10, wherein $R^4$ is H.

12. The compound of claim 1, wherein $G^3$ is $CR^4$ or N.

13. The compound of claim 1, wherein $G^3$ is $CR^4$ and $R^4$ is H, halogen or optionally substituted alkyl.

14. The compound of claim 1, wherein $R^4$ is H.

15. The compound of claim 1, wherein D is selected from a group consisting of heteroaryl and aryl.

16. The compound of claim 1, wherein D is a heteroaryl having a nitrogen as a ring atom, said heteroaryl comprising a nitrogen ring atom adjacent to a carbon ring atom, wherein said carbon ring atom is connected to the amide nitrogen atom adjacent to D, and wherein said heteroaryl has an additional 0 to 3 heteroatoms independently selected from O, S or N.

17. The compound of claim 1, wherein D is selected from the group consisting of pyridinyl, thiazolyl, 1,3,4-thiadiazolyl, 1,2,4-thiadiazolyl, oxazolyl, isoxazolyl, imidazolyl, pyrazolyl, pyrazinyl, pyridazinyl, pyrimidinyl, benzothiazolyl, and 5,6-dihydro-4H-cyclopentathiazolyl, each optionally substituted with one or two groups selected from halogen, $CF_3$, or optionally substituted $C_{1-4}$-alkyl.

18. The compound of claim 1, wherein D is selected from the group consisting of thiazolyl, 1,3,4-thiadiazolyl, and 1,2,4-thiadiazolyl, each optionally substituted with one or two groups selected from halogen, $CF_3$, or optionally substituted $C_{1-4}$-alkyl.

19. The compound of claim 1, wherein $R^{50}$ is —P(O)($Y^2R^{51}$) $R^1$ or —P(O)($YR^{51}$)$Y^1R^{51}$;

$R^1$ is selected from the group consisting of hydrogen, optionally substituted —$C_1$-$C_6$-alkyl, —$CF_3$, —$CHF_2$, —$CH_2F$, —$CH_2OH$, optionally substituted —$C_2$-$C_6$ alkenyl, optionally substituted —$C_2$-$C_6$ alkynyl, optionally substituted —$(CR^{52}_2)_n$cycloalkyl, or optionally substituted $(CR^{52}_2)_n$heterocycloalkyl;

Y, $Y^1$ and $Y^2$ are each independently selected from —O— or —$NR^{60}$—;

wherein, when $Y^2$ is —O— or when Y and $Y^1$ are both —O—, $R^{51}$ attached to —O— is independently selected from —H, alkyl, optionally substituted aryl, optionally substituted heterocycloalkyl, optionally substituted —$CH_2$-heterocycloakyl wherein the cyclic moiety contains a carbonate or thiocarbonate, optionally substituted -alkylaryl, —$C(R^{52})_2OC(O)NR^{52}_2$, —$NR^{52}$—$C(O)$—$R^{53}$, —$C(R^{52})_2$—$OC(O)R^{53}$, —$C(R^{52})_2$—O—$C(O)OR^{53}$, —$C(R^{52})_2OC(O)SR^{53}$, -alkyl-S—$C(O)R^{53}$, -alkyl-S—S-alkylhydroxy, and -alkyl-S—S—S-alkylhydroxy;

when $Y^2$ is —$NR^{60}$— or when Y and $Y^1$ are both —$NR^{60}$—, then $R^{51}$ attached to —$NR^{60}$— is independently selected from —H, —$[C(R^{52})_2]_r$—$COOR^{53}$, —$C(R^{54})_2COOR^{53}$, —$[C(R^{52})_2]_r$—$C(O)SR^{53}$, and -cycloalkylene-$COOR^{53}$; or when Y is —O— and $Y^1$ is $NR^{60}$, then $R^{51}$ attached to —O— is independently selected from —H, alkyl, optionally substituted aryl, optionally substituted heterocycloalkyl, optionally substituted $CH_2$-heterocycloakyl wherein the cyclic moiety contains a carbonate or thiocarbonate, optionally substituted -alkylaryl, —$C(R^{52})_2OC(O)NR^{52}_2$, —$NR^{52}$—$C(O)$—$R^{53}$, —$C(R^{52})_2$—$OC(O)R^{53}$, —$C(R^{52})_2$—O—$C(O)OR^{53}$, —$C(R^{52})_2OC(O)SR^{53}$, -alkyl-S—$C(O)R^{53}$, -alkyl-S—S-alkylhydroxy, and -alkyl-S—S—S-alkylhydroxy, and $R^{51}$ attached to —$NR^{60}$— is independently selected from —H, —$[C(R^{52})_2]_r$—$COOR^{53}$, —$C(R^{54})_2COOR^{53}$, —$[C(R^{54})_2]_r$—$C(O)SR^{53}$, and -cycloalkylene-$COOR^{53}$, wherein if both $R^{51}$ are alkyl, at least one is higher alkyl; or when Y and $Y^1$ are independently selected from —O— and —$NR^{60}$—, then $R^{51}$ and $R^{51}$ together form a cyclic group comprising -alkyl-S—S-alkyl-, or $R^{51}$ and $R^{51}$ together are the group

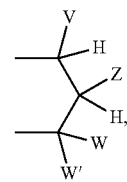

wherein,

V, W, and W' are independently selected from the group consisting of hydrogen, optionally substituted alkyl, optionally substituted aralkyl, heterocycloalkyl, aryl, substituted aryl, heteroaryl, substituted heteroaryl, optionally substituted 1-alkenyl, and optionally substituted 1-alkynyl; and Z is —CHR$^{52}$OH, —CHR$^{52}$OC(O)R$^{53}$, —CHR$^{52}$OC(S)R$^{53}$, —CHR$^{52}$OC(S)OR$^{53}$, —CHR$^{52}$OC(O)SR$^{53}$, —CHR$^{52}$OCO$_2$R$^{53}$, —OR$^{52}$, —SR$^{52}$, —CHR$^{52}$N$_3$, —CH$_2$aryl, —CH(aryl)OH, —CH(CH=CR$^{52}$$_2$)OH, —CH(C=CR$^{52}$)OH, —R$^{52}$, —NR$^{52}$$_2$, —OCOR$^{53}$, —OCO$_2$R$^{53}$, —SCOR$^{53}$, —SCO$_2$R$^{53}$, —NHCOR$^{52}$, —NHCO$_2$R$^{53}$, —CH$_2$NHaryl, —(CH$_2$)$_r$—OR$^{52}$ or —(CH$_2$)$_r$—SR$^{52}$; or W and W' are as defined above and together V and Z are connected via an additional 3-5 atoms to form a cyclic group containing 5-7 atoms, wherein 0-1 atoms are heteroatoms and the remaining atoms are carbon; or W' and Z are as defined above and together V and W are connected via an additional 3 carbon atoms to form an optionally substituted cyclic group containing 6 carbon atoms or carbon substituted by hydrogen and substituted with one substituent selected from hydroxy, acyloxy, alkoxycarbonyloxy, alkylthiocarbonyloxy or aryloxycarbonyloxy which is attached to one of said carbon atoms that is three atoms from a Y attached to the phosphorus; or V and W' are as defined above and together Z and W are connected via an additional 3-5 atoms to form a cyclic group, wherein 0-1 atoms are heteroatoms and the remaining atoms are carbon or carbon substituted by hydrogen, and V must be aryl, substituted aryl, heteroaryl, or substituted heteroaryl; or V and Z are as defined above and together W and W' are connected via an additional 2-5 atoms to form a cyclic group, wherein 0-2 atoms are heteroatoms and the remaining atoms are carbon, where V must be aryl, substituted aryl, heteroaryl, or substituted heteroaryl;

R$^{52}$ is R$^{53}$ or —H;

R$^{53}$ is alkyl, aryl, heterocycloalkyl or aralkyl;

R$^{54}$ is independently selected from —H or alkyl, or together R$^{54}$ and R$^{54}$ form a cycloalkylene group;

R$^{60}$ is —H, lower alkyl, acyloxyalkyl, alkoxycarbonyloxyalkyl, lower acyl, or C$_{1-6}$-perfluoroalkyl;

r is an integer 2 or 3;

n is 0 or 1;

wherein, V, Z, W, W' are not all —H, and when Z is —R$^{52}$, then at least one of V, W, and W' is not —H, alkyl, aralkyl, or heterocycloalkyl; and pharmaceutically acceptable salt thereof.

20. The compound of claim 1, wherein R$^{50}$ is selected from the group consisting of —PO$_3$H$_2$, —P(O)[—OCR$^{52}$$_2$OC(O)R$^{53}$]$_2$, —P(O)[—OCR$^{52}$$_2$OC(O)OR$^{53}$]$_2$, —P(O)[—N(H)CR$^{52}$$_2$C(O)OR$^{53}$]$_2$, —P(O)[—O-alk-SC(O)R$^{53}$]$_2$, —P(O)[—OCR$^{52}$$_2$OC(O)R$^{53}$][—R$^1$], —P(O)[—OCR$^{52}$$_2$OC(O)OR$^{53}$][—R$^1$], —P(O)[—N(H)CR$^{52}$$_2$C(O)OR$^{53}$][—R$^1$], —P(O)[—OCH$_2$CH$_2$SC(O)R$^{53}$][—R$^1$], —P(O)(OH)(YR$^{51}$), —P(O)(OR$^{56}$)(OR$^{56}$), —P(O)(OH)(—R$^1$—P(O)[—OCR$^{52}$$_2$OC(O)R$^{53}$](OR$^{56}$), —P(O)[—OCR$^{52}$$_2$OC(O)OR$^{53}$](OR$^{56}$), —P(O)[—N(H)CR$^{52}$$_2$C(O)OR$^{53}$](OR$^{56}$), P(O)(OH)(NH$_2$), and P(O)[—OCH(V)CH$_2$CH$_2$O—];

V is optionally substituted aryl or optionally substituted heteroaryl;

R$^{56}$ is —C$_1$-C$_{12}$ alkyl, —C$_2$-C$_{12}$ alkenyl, —C$_2$-C$_{12}$ alkynyl, —(CR$^{57}$$_2$)$_n$aryl, —CR$^{57}$$_2$)$_n$cycloalkyl, or —(CR$^{57}$$_2$)$_n$heterocycloalkyl, each optionally substituted;

each R$^{57}$ is independently selected from the group consisting of hydrogen, optionally substituted —C$_1$-C$_4$ alkyl, halogen, optionally substituted —O—C$_1$-C$_4$ alkyl, —OCF$_3$, optionally substituted —S—C$_1$-C$_4$ alkyl, —NR$^{58}$R$^{59}$, optionally substituted —C$_2$-C$_4$ alkenyl, and optionally substituted —C$_2$-C$_4$ alkynyl;

with the proviso that when one R$^{57}$ is attached to C through an O, S, or N atom, then the other R$^{57}$ attached to the same C is a hydrogen, or attached via a carbon atom;

R$^{58}$ is selected from hydrogen and optionally substituted —C$_1$-C$_4$ alkyl; and, R$^{59}$ is selected from the group consisting of hydrogen and optionally substituted —C$_1$-C$_4$ alkyl, optionally substituted —C(O)—C$_1$-C$_4$ alkyl, and —C(O)H.

21. The compound of claim 1, wherein R$^{50}$ is selected from the group consisting of P(O)(OH)$_2$, —P(O)[—OCH$_2$OC(O)-t-butyl]$_2$, —P(O)[—OCH(CH$_3$)OC(O)-t-butyl]$_2$, —P(O) [—OCH(CH3)OC(O)O-i-propyl]$_2$, —P(O)[—OCH$_2$OC(O)O-i-propyl]$_2$, —P(O)[—N(H)CH(CH$_3$)C(O)OCH$_2$CH$_3$]$_2$, —P(O)[—N(H)C(CH$_3$)$_2$C(O)OCH$_2$CH$_3$]$_2$, —P(O)[—N(H)CH(CH3)C(O)OCH$_2$CH$_3$] [3,4-methylenedioxyphenyl], —P(O)[—N(H)C(CH3)2C(O)OCH$_2$CH$_3$][3,4-methylenedioxyphenyl], —P(O)[—O—CH$_2$CH$_2$S—C(O)CH$_3$]$_2$, —P(O)(OH)(OCH$_3$), —P(O)(OH)(OCH$_2$CH$_3$), —P(O)(OH)(CH$_3$), —P(O)[—OCH(3-chlorophenyl)CH$_2$CH$_2$O—], —P(O)[—OCH(pyrid-4-yl)CH$_2$CH$_2$O—], —P(O)[—OCH$_2$OC(O)-t-butyl](OCH$_3$), —P(O)[—OCH$_2$OC(O)O-i-propyl](OCH$_3$), —P(O)[—OCH(CH$_3$)OC(O)-t-butyl](OCH$_3$), —P(O)[—OCH(CH$_3$)OC(O)O-i-propyl](OCH$_3$),

—P(O)[—N(H)CH(CH$_3$)C(O)OCH$_2$CH$_3$](OCH$_3$),

—P(O)[—N(H)CH(CH$_3$)C(O)OCH$_2$CH$_3$](CH$_3$),

—P(O)[—N(H)C(CH$_3$)$_2$C(O)OCH$_2$CH$_3$](OCH$_3$),

—P(O)[—N(H)C(CH$_3$)$_2$C(O)OCH$_2$CH$_3$](CH$_3$), —P(O)[—OCH$_2$OC(O)-t-butyl](CH$_3$), —P(O)[—OCH$_2$OC(O)O-i-propyl](CH$_3$), —P(O)[—OCH(CH$_3$)OC(O)-t-butyl](CH$_3$), and —P(O)[—OCH(CH$_3$)OC(O)O-i-propyl](CH$_3$), and —P(O)[—OCH$_2$OC(O)O-ethyl]$_2$.

22. The compound of claim 1, wherein Y and Y$^1$ are each independently selected from —O— and —NR$^{60}$—; and together R$^{51}$ and R$^{51}$ are the group

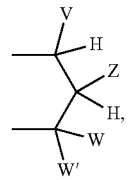

wherein, V is substituted aryl or substituted heteroaryl.

23. The compound of claim 1, wherein G$^2$ is CR$^4$ or N, or together G$^2$ and X are connected to form a cyclic group containing 5-7 atoms, wherein 0-2 atoms of said cyclic group are heteroatoms and the remaining atoms of said cyclic group are carbon atoms substituted with alkyl, aryl, cycloalkyl or heteroaryl.

24. The compound of claim 23, wherein $G^2$ is $CR^4$.

25. The compound of claim 24, wherein $R^4$ is H.

26. The compound of claim 23, wherein $G^2$ is N.

27. The compound of claim 1, wherein:

X is selected from the group consisting of alkyloxy and cycloalkyloxy;

$R^2$ is selected from the group consisting of phenylene-O—, methylene-phenylene-O—, phenylene-methylene-O—, furan-2-yl-5-methylene, thiophen-2-yl-5-methylene, pyridin-diyl-O—, pyrimidin-diyl-O—, pyridazin-diyl-O— and pyrazin-diyl-O—, each optionally substituted with one or two groups independently selected from halogen, CN, $CF_3$, $NR^5{}_2$, —$C_{1-4}$-alkyl, —$S(O)_2R^5$, or —$OR^5$, wherein $R^2$ is connected to $R^{50}$ by a C ring atom; and wherein $R^5$ is optionally substituted alkyl or cycloalkyl;

$G^1$, $G^2$, and $G^3$ are $CR^4$ and $R^4$ is H;

D is selected from the group consisting of thiazolyl, 1,3,4-thiadiazolyl, 1,2,4-thiadiazolyl, each optionally substituted with one or two groups selected from the group consisting of halogen, $CF_3$, and optionally substituted $C_{1-4}$-alkyl; and $R^{50}$ is selected from the group consisting of: $P(O)(OH)_2$, —$P(O)[—OCH_2OC(O)$-t-butyl$]_2$, —$P(O)[—OCH(CH_3)OC(O)$-t-butyl$]_2$, —$P(O)[—OCH(CH_3)OC(O)O$-i-propyl$]_2$, —$P(O)[—OCH_2OC(O)O$-i-propyl$]_2$, —$P(O)[—OCH_2OC(O)O$-ethyl$]_2$, —$P(O)[—N(H)CH(CH_3)C(O)OCH_2CH_3]_2$, —$P(O)[—N(H)C(CH_3)_2C(O)OCH_2CH_3]_2$, —$P(O)[—OCH(3$-chlorophenyl$)CH_2CH_2O—]$, —$P(O)[—OCH(pyrid-4-yl)CH_2CH_2O—]$, and —$P(O)[—OCH(V)CH_2CH_2O—]$;

and V is optionally substituted aryl or optionally substituted heteroaryl.

28. The compound of claim 24, wherein $R^2$ is phenylene-O—.

29. A compound of Formula (I),

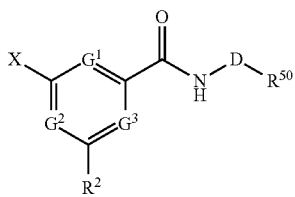

wherein:

X is selected from the group consisting of aryl, heteroaryl, alkyl, cycloalkyl, arylalkyl, aryloxy, heteroaryloxy, alkyloxy, cycloalkyloxy, and arylalkyloxy;

$R^2$ is selected from the group consisting of alkyl, cycloalkyl, arylalkyl, aryloxy, heteroaryloxy, arylalkyloxy, arylthio, heteroarylthio, cycloalkylthio, and arylalkylthio;

D is selected from heteroarylene and arylene, each optionally substituted;

$G^1$, $G^2$, and $G^3$ are $CR^4$ or N;

$R^4$ is H, halogen, or alkyl; and $R^{50}$ is —$R^{61}$-$R^{62}$, and $R^{62}$ is selected from —$P(O)(Y^2R^{51})R^1$, or —$P(O)(YR^{51})Y^1R^{51}$;

$R^{61}$ is selected from null, arylene, heteroarylene, arylene-alkylene, alkylene-arylene, heteroarylene-alkylene, alkylene-heteroarylene, alkylene, alkenylene, alkynylene, alkylene-Q-alkylene, —$CONR^{52}$-alkylene, —COO-alkylene, —$SO_2NR^{52}$— alkylene, arylene-Q-alkylene, alkylene-Q-arylene, heteroarylene-Q-alkylene, or alkylene-Q-heteroarylene, all optionally substituted;

Q is selected from O, S, SO, $SO_2$, $NR^{53}$;

with the proviso that when D is heteroarylene then $R^{50}$ is not —$(CH_2)_{n'}$—$Z'$—$(CH_2)_{m'}$-$PO(OR^{63})(OR^{64})$, —$(CH_2)_{n'}$—$Z'$—$(CH_2)_{m'}$-$PO(OR^{63})R^{65}$, —$(CH_2)_{n'}$—$Z'$—$(CH_2)_{m'}$-$PO(OR^{63})R^{65}(CH2)_{n'}$—$Z'$—$(CH_2)_{m'}$—O—$PO(OR^{63})R^{65}$; —$(CH_2)_{n'}$—$Z'$—$(CH_2)_{m'}$—O—$PO(R^{65})R^{66}$, or —$(CH_2)_{n'}$—$Z'$—$(CH_2)_{n'}$—$Z'$—$(CH_2)_{m'}$—$PO$—$(R^{65})R^{66}$, $R^{63}$ and $R^{64}$ are the same or different and are independently selected from the group consisting of hydrogen and alkyl, or $R^{63}$ and $R^{64}$ can be cyclized into a ring;

$R^{65}$ and $R^{66}$ are the same or different and are independently selected from the group consisting of alkyl, aryl, arylalkyl, heteroaryl, and heteroarylalkyl; or $R^{65}$ and $R^{66}$ can be cyclized into a ring; or $R^{63}$ and $R^{65}$ can be cyclized into a ring;

Z' is selected from the group consisting of a bond, alkylene, alkenylene, O, S, and $SO_2$;

m' is 0, 1, or 2, provided that when Z is O, S or $SO_2$, n' is 1 or 2;

n' is 0, 1, or 2;

$R^1$ is selected from the group consisting of hydrogen, optionally substituted —$C_1$-$C_6$-alkyl, —$CF_3$, —$CHF_2$, —$CH_2F$, —$CH_2OH$, optionally substituted —$C_2$-$C_6$ alkenyl, optionally substituted —$C_2$-$C_6$ alkynyl, optionally substituted —$(CR^{52}{}_2)_n$cycloalkyl, or optionally substituted $(CR^{52}{}_2)_n$heterocycloalkyl;

Y, $Y^1$, and $Y^2$ are each independently selected from —O— or —$NR^{60}$—;

wherein, when $Y^2$ is —O— or when Y and $Y^1$ are both —O—, $R^{51}$ attached to —O— is independently selected from the group consisting of —H, alkyl, optionally substituted aryl, optionally substituted heterocycloalkyl, optionally substituted —$CH_2$-heterocycloakyl with a cyclic moiety containing a carbonate or thiocarbonate, optionally substituted -alkylaryl, —$C(R^{52})_2OC(O)NR^{52}{}_2$, —$NR^{52}$—$C(O)$—$R^{53}$, —$C(R^{52})_2$—$OC(O)R^{53}$, —$C(R^{52})$—O—$C(O)OR^{53}$, —$C(R^{52})_2OC(O)SR^{53}$, -alkyl-S—$C(O)R^{53}$, -alkyl-S—S-alkylhydroxy, and -alkyl-S—S—S-alkylhydroxy; or when $Y^2$ is —$NR^{60}$— or when Y and $Y^1$ are both —$NR^{60}$—, then $R^{51}$ attached to —$NR^{60}$— is independently selected from the group consisting of —H, —$[C(R^{52})_2]_r$—$COOR^{53}$, —$C(R^{54})_2COOR^{53}$, —$[C(R^{52})_2]_r$—$C(O)SR^{53}$, and -cycloalkylene-$COOR^{53}$; or when Y is —O— and $Y^1$ is $NR^{60}$, then $R^{51}$ attached to —O— is independently selected from —H, alkyl, optionally substituted aryl, optionally substituted heterocycloalkyl, optionally substituted $CH_2$-heterocycloakyl wherein the cyclic moiety contains a carbonate or thiocarbonate, optionally substituted -alkylaryl, —$C(R^{52})_2OC(O)NR^{52}{}_2$, —$NR^{52}$—$C(O)$—$R^{53}$, —$C(R^{52})_2$—$OC(O)R^{53}$, —$C(R^{52})_2$—O—$C(O)OR^{53}$, —$C(R^{52})_2OC(O)SR^{53}$, -alkyl-S—$C(O)R^{53}$, -alkyl-S—S-alkylhydroxy, or -alkyl-S—S—S-alkylhydroxy, and $R^{51}$ attached to —$NR^{60}$— is independently selected from —H, —$[C(R^{52})_2]_r$—$COOR^{53}$, —$C(R^{54})_2COOR^{53}$, —$[C(R^{52})_2]_r$—$C(O)SR^{53}$, or -cycloalkylene-$COOR^{53}$, wherein if both $R^{51}$ are alkyl, at least one is higher alkyl; or when Y and Y$^1$ are independently selected from —O— and —NR$^{60}$—, then R$^{51}$ and R$^{51}$ together form a cyclic group comprising -alkyl-S—S-alkyl-, or R$^{51}$ and R$^{51}$ together are the group

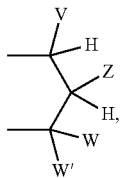

wherein,
V, W, and W' are independently selected from the group consisting of hydrogen, optionally substituted alkyl, optionally substituted aralkyl, heterocycloalkyl, aryl, substituted aryl, heteroaryl, substituted heteroaryl, optionally substituted 1-alkenyl, and optionally substituted 1-alkynyl; and Z is —CHR$^{52}$OH, —CHR$^{52}$OC(O)R$^{53}$, —CHR$^{52}$OC(S) R$^{53}$, —CHR$^{52}$OC(S)OR$^{53}$, —CHR$^{52}$OC(O)SR$^{53}$, —CHR$^{52}$OCO$_2$R$^{53}$, —OR$^{52}$, —SR$^{52}$, —CHR$^{52}$N$_3$, —CH$_2$aryl, —CH(aryl)OH, —CH(CH=CR$^{52}$$_2$)OH, —CH(C≡CR$^{52}$)OH, —R$^{52}$, —NR$^{52}$$_2$, —OCOR$^{53}$, —OCO$_2$R$^{53}$, —SCOR$^{53}$, —SCO$_2$R$^{53}$, —NHCOR$^{52}$, —NHCO$_2$R$^{53}$, —CH$_2$NHaryl, —(CH$_2$)$_r$—OR$^{52}$, or —(CH$_2$)$_r$—SR$^{52}$; or W and W' are as defined above and together V and Z are connected via an additional 3-5 atoms to form a cyclic group containing 5-7 atoms, wherein 0-1 atoms are heteroatoms and the remaining atoms are carbon; or W' and Z are as defined above and together V and W are connected via an additional 3 carbon atoms to form an optionally substituted cyclic group containing 6 carbon atoms or carbon substituted by hydrogen and substituted with one substituent selected from hydroxy, acyloxy, alkoxycarbonyloxy, alkylthiocarbonyloxy, or aryloxycarbonyloxy which is attached to one of said carbon atoms that is three atoms from a Y attached to the phosphorus; or V and W' are as defined above and together Z and W are connected via an additional 3-5 atoms to form a cyclic group, wherein 0-1 atoms are heteroatoms and the remaining atoms are carbon or carbon substituted by hydrogen, and V must be aryl, substituted aryl, heteroaryl, or substituted heteroaryl; or V and Z are as defined above and together W and W' are connected via an additional 2-5 atoms to form a cyclic group, wherein 0-2 atoms are heteroatoms and the remaining atoms are carbon, where V must be aryl, substituted aryl, heteroaryl, or substituted heteroaryl;

R$^{52}$ is R$^{53}$ or —H;
R$^{53}$ is alkyl, aryl, heterocycloalkyl, or aralkyl;
R$^{54}$ is independently selected from —H or alkyl, or together R$^{54}$ and R$^{54}$ form a cycloalkylene group;
R$^{60}$ is —H, lower alkyl, acyloxyalkyl, alkoxycarbonyloxyalkyl, lower acyl, C$_{1-6}$-perfluoroalkyl;

r is an integer 2 or 3;
n is 0 or 1;
wherein, V, Z, W, W' are not all —H, and when Z is —R$^{52}$, then at least one of V, W, and W' is not —H, alkyl, aralkyl, or heterocycloalkyl; wherein one of G$^1$, G$^2$, G$^3$ is N and the other two are CR$^4$; and wherein G$^2$ and X do not form an isomeric pyridine compound or pharmaceutically acceptable salts thereof.

30. A pharmaceutical composition comprising a compound of claim 1 and a pharmaceutically acceptable excipient.

31. A pharmaceutical composition comprising a compound of claim 29 and a pharmaceutically acceptable excipient.

32. A method of treating a disease or condition selected from the group consisting of Type 1 diabetes, Type 2 diabetes, impaired glucose tolerance, insulin resistance, hyperglycemia, accelerated gluconeogenesis, hyperinsulinemia, excessive hepatic glucose output, and Metabolic Syndrome X, said method comprising the step of administering to an animal in need thereof a therapeutically effective amount of a compound of claim 1, a composition thereof including at least one pharmaceutically acceptable excipient, or a pharmaceutically acceptable salt thereof.

33. A method of treating a disease or condition selected from the group consisting of Type 1 diabetes, Type 2 diabetes, impaired glucose tolerance, insulin resistance, hyperglycemia, accelerated gluconeogenesis, hyperinsulinemia, excessive hepatic glucose output, and Metabolic Syndrome X, said method comprising the step of administering to an animal in need thereof a therapeutically effective amount of a compound of claim 29, a composition thereof including at least one pharmaceutically acceptable excipient, or a pharmaceutically acceptable salt thereof.

34. The compound of claim 1, wherein R$^1$ is selected from the group consisting of hydrogen, optionally substituted —C$_1$—C$_6$-alkyl, —CF$_3$, —CHF$_2$, —CH$_2$F, —CH$_2$OH, optionally substituted —C$_2$—C$_6$ alkenyl, and optionally substituted —C$_2$—C$_6$ alkynyl.

35. A compound having the structure:

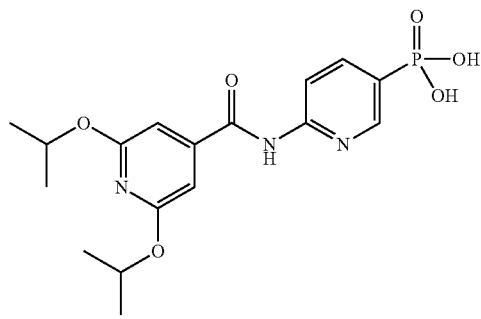 [SMILES: CC(C)Oc1cc(C(=O)Nc2ccc(P(=O)(O)O)cn2)cc(OC(C)C)n1]

or a pharmaceutically acceptable salt thereof.

* * * * *